US008114960B2

(12) United States Patent
Arico et al.

(10) Patent No.: US 8,114,960 B2
(45) Date of Patent: Feb. 14, 2012

(54) HETEROLOGOUS EXPRESSION OF NEISSERIAL PROTEINS

(75) Inventors: Maria Beatrice Arico, Siena (IT); Maurizio Comanducci, Siena (IT); Cesira Galeotti, Montegriggioni (IT); Vega Masignani, Siena (IT); Marzia Monica Guiliani, Siena (IT); Mariagrazia Pizza, Siena (IT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/825,210

(22) Filed: Jun. 28, 2010

(65) Prior Publication Data

US 2010/0267931 A1 Oct. 21, 2010

Related U.S. Application Data

(62) Division of application No. 10/220,481, filed as application No. PCT/IB01/00452 on Feb. 28, 2001, now Pat. No. 7,803,387.

(30) Foreign Application Priority Data

Feb. 28, 2000 (GB) .................................. 0004695.3
Nov. 13, 2000 (GB) .................................. 0027675.8

(51) Int. Cl.
*A61K 38/00* (2006.01)
*A61K 38/095* (2006.01)

(52) U.S. Cl. .................. 530/324; 530/300; 424/249.1; 424/250.1

(58) Field of Classification Search .................. None
See application file for complete search history.

(56) References Cited

U.S. PATENT DOCUMENTS

| | | |
|---|---|---|
| 4,239,749 A | 12/1980 | Buchanan |
| 5,547,670 A | 8/1996 | Goldstein et al. |
| 5,914,254 A | 6/1999 | Mascarenhas et al. |
| 6,013,267 A | 1/2000 | Blake et al. |
| 6,028,049 A | 2/2000 | Jacobs et al. |
| 6,197,312 B1 | 3/2001 | Peak et al. |
| 6,248,329 B1 | 6/2001 | Chandrashekar et al. |
| 6,709,660 B1 | 3/2004 | Scarlato et al. |
| 6,914,131 B1 | 7/2005 | Scarlato et al. |
| 7,368,261 B1 | 5/2008 | Rappuoli et al. |
| 7,504,111 B2 | 3/2009 | Fontana et al. |
| 7,576,176 B1 | 8/2009 | Fraser et al. |
| 7,604,810 B2 | 10/2009 | Rappuoli et al. |
| 7,612,192 B2 | 11/2009 | Fraser et al. |
| 2002/0160016 A1 | 10/2002 | Peak et al. |
| 2004/0092711 A1 | 5/2004 | Arico et al. |
| 2004/0110670 A1 | 6/2004 | Arico et al. |
| 2005/0222385 A1 | 10/2005 | Pizza |
| 2006/0051840 A1 | 3/2006 | Arico et al. |
| 2006/0171957 A1 | 8/2006 | Pizza |
| 2007/0082014 A1 | 4/2007 | Costantino |
| 2008/0241180 A1 | 10/2008 | Contorni |
| 2009/0232820 A1 | 9/2009 | Fraser et al. |
| 2009/0285845 A1 | 11/2009 | Masignani et al. |

FOREIGN PATENT DOCUMENTS

| | | |
|---|---|---|
| EP | 0273116 | 7/1988 |
| EP | 0467714 A1 | 1/1992 |
| EP | 1790660 | 5/2007 |
| FR | 2720408 | 12/1995 |
| JP | 2003525050 | 8/2003 |
| NL | 8901612 | 7/1990 |
| WO | WO-90/06696 | 6/1990 |
| WO | WO-9006696 | 6/1990 |
| WO | WO-9216643 | 10/1992 |
| WO | WO-9503413 | 2/1995 |
| WO | WO-95/33049 A2 | 12/1995 |
| WO | WO-9533049 | 12/1995 |
| WO | WO-96/29412 | 9/1996 |
| WO | WO-9629412 | 9/1996 |
| WO | WO-9710844 | 3/1997 |
| WO | WO-9713860 | 4/1997 |
| WO | WO-9728273 | 8/1997 |
| WO | WO-9924578 | 5/1999 |
| WO | WO-9936544 | 7/1999 |
| WO | WO-9957280 | 11/1999 |
| WO | WO-0022430 | 4/2000 |
| WO | WO-0050075 | 8/2000 |
| WO | WO-00/71574 | 11/2000 |
| WO | WO-0066791 | 11/2000 |
| WO | WO-0071574 | 11/2000 |
| WO | WO-0071725 | 11/2000 |
| WO | WO-0131019 | 5/2001 |
| WO | WO-0152885 | 7/2001 |
| WO | WO-0164920 | 9/2001 |
| WO | WO-0164922 | 9/2001 |
| WO | WO-03010194 | 2/2003 |
| WO | WO-03020756 | 3/2003 |
| WO | WO-2004032958 | 4/2004 |
| WO | WO-2004048404 | 6/2004 |
| WO | WO-2004067030 | 8/2004 |
| WO | WO-2004112832 | 12/2004 |

(Continued)

OTHER PUBLICATIONS

Abad et al. (2008). "PorB2/3 Protein Hybrid in *Neisseria meningitidis*," Emerging Infectious Diseases, 14(4):688-689.
Ala'aldeen et al. (1996). "The Meningococcal Transferrin-binding Proteins 1 and 2 are Both Surface Exposed and Generate Bactericidal Antibodies Capable of Killing Homologous and Heterologous Strains," Vaccine 14(1):49-53.
Bartsevich et al. (Mar. 7, 1997). "Molecular Identification of a Novel Protein That Regulates Biogenesis of Photosystem I, a Membrane Protein Complex," The Journal of Biological Chemistry 272(10):6382-6387.
Bethell et al. (2002). "Meningococcal vaccines," Expert Review of Vaccines 1(1):75-84.

(Continued)

*Primary Examiner* — Vanessa L. Ford
(74) *Attorney, Agent, or Firm* — Amy Hessler; Otis Littlefield; Robert Gorman

(57) ABSTRACT

Alternative and improved approaches to the heterologous expression of the proteins of *Neisseria meningitidis* and *Neisseria gonorrhoeae*. These approaches typically affect the level of expression, the ease of purification, the cellular localization, and/or the immunological properties of the expressed protein.

13 Claims, 13 Drawing Sheets

FOREIGN PATENT DOCUMENTS

| | | |
|---|---|---|
| WO | WO-2005032583 | 4/2005 |
| WO | WO-2005033148 | 4/2005 |
| WO | WO-2005102384 | 11/2005 |
| WO | WO-2005106009 | 11/2005 |
| WO | WO-2008001224 | 1/2008 |

OTHER PUBLICATIONS

Blythe et al. (2005). "Benchmarking B cell epitope prediction: underperformance of existing methods," Protein Sci. 14:246-248.

Boslego et al. (1991). "Gonorrhea Vaccines" Chapter 17 in Vaccines and Immunotherapy, S. Cryz (Ed.). pp. 211-223.

Bowie, J. et al. (1990). "Deciphering the Message in Protein Sequences: Tolerance to Amino Acid Substitutions," Science 247: 1306-1310.

Brandhorst et al. (1995). "Effects of leader Sequences upon the Heterologous Expression of Restriction in *Aspergillus nidulans* and *Aspergillus niger*," CJM 41(7):601-611.

Bygraves et al. (1992). "Analysis of the Clonal Relationships Between Strains of *Neisseria meningitidis* by Pulsed Field Gel Electrophoresis," Journal of General Microbiology 138:523-531.

Cann et al. (1989). "Detection of Antibodies to Common Antigens of Pathogenic and Commensal *Neisseria* Species," Journal of Medical Microbiology 30:23-30.

Caugant et al. (1987). "Genetic Structure of *Neisseria meningitidis* Populations in Relation to Serogroup, Serotype, and Outer Membrane Protein Pattern," Journal of Bacteriology 169(6):2781-2792.

Christodoulides et al. (1994). "Immunization with a Multiple Antigen Peptide Containing Defined B- and T-Cell Epitopes: Production of Bacterial Antibodies Group B *Neisseria meningitidis*," Microbiology 140:2951-2960.

Comanducci, M. (2002). "NadA, a Novel Vaccine Candidate of *Neisseria meningitides*," Journal of Experimental Medicine 195(11): 1445-1454.

Cooney et al. (1993). "Three Contiguous Lipoprotein Genes in *Pasteurella haemolytica* A1 which are Homologous to a Lipoprotein Gene in Haemophilus Influenza Type B," Infection and Immunity 61 (11):4682-4688.

Cruse et al. Illustrated Dict. of Immunology, 2nd ed., CRC Press, 2003. pp. 46, 166, and 382.

Dempsey et al. (1991). "Physical Map of the Chromosome of *Neisseria gonorrhoeae* FA1090 with Locations of Genetic Markers, including *Opa* and *Pil* Genes," Journal of Bacteriology 173(17):5476-5486.

Devries et al. (Aug. 1996). "Invasion of Primary Nasopharyngeal Epithelial Cells by *Neisseria meningitidis* is Controlled by Phase Variation of Multiple Surface Antigens," Infection and Immunity 64(8):2998-3006.

Ellis (1988). "New Technologies for Making Vaccines" in Vaccines. Plotkin et al. (Eds.) pp. 568-575.

Feng et al. (1996). "P55, an Immunogenic but Nonprotective 55-Kilodalton *Borrelia burgdorferi* Protein in Murine Lyme Disease," Infection and Immunity. 64(1):363-365.

Gervais et al. (1992). "Putative Lipoprotein Yaec Precursor," Database Swissport Acc No. p28635.

Greenspan et al. (1999). "Defining epitopes: It's not as easy as it seems," Nature Biotechnology, 17:936-937.

Grifantini, R. et al. (2002). "Previously Unrecognized Vaccine Candidates against Group B Meningococcus Identified by DNA Microarrays," Nature Biotechnology 20(9): 914-921.

Guillen et al. (1996). "Expression in *Escherichia coli* and immunological characterization of a hybrid class I-P64K protein from *Neisseria meningitidis*," Biotechnologia Aplicada 13(4):271-275.

Herbert et al. (1985). The Dictionary of Immunology. Academic Press: London 3$^{rd}$ edition, pp. 58-59.

Herbert et al. (1995). The Dictionary of Immunology. Academic Press: London 4$^{th}$ edition, 3 pages.

Holmes, E. (2001). "PSMA Specific Antibodies and their Diagnostic and Therapeutic Use," Expert Opinion on Investigational Drugs 10(3): 511-519.

Jacobsson et al. (2009). Vaccine. 27:1579-1584.

Jolley et al. (2007). "Molecular typing of meningococci: recommendations for target choice and nomenclature," FEMS Microbiol. Rev. 31:89-96.

Legrain, M. et al. (1995). "Production of lipidated meningococcal transferrin binding protein 2 in *Escherichia coli*," Protein Expression and Purification 6:570-578.

Maiden et al. (1998). "Multilocus Sequence Typing: a Portable Approach to the Identification of Clones within Populations of Pathogenic Microorganisms," Proceedings of the National Academy of Sciences USA 95:3140-3145.

McGuinness et al. (1993). "Class 1 outer membrane protein of *Neisseria meningitidis*: epitope analysis of the antigenic diversity between strains, implications for subtype definition and molecular epidemiology," Mol Microbiol. 7:505-514.

Morley et al. (2002). "Vaccine prevention of meningococcal disease, coming soon?" Vaccine 20:666-687.

Moudallai et al. (1982). "Monoclonal anti bodies as probes of the antigenic structure of tobacco mosaic virus," EMBO Journal 1:1005-1010.

Ni et al. (1992). "Phylogenetic and Epidemiological Analysis of *Neisseria meningitidis* Using DNA Probes," Epidemiology and Infection 109:227-239.

Nosoh et al. (1991). Protein Stability and Stabilization through Protein Engineering. Chapter 7, p. 197, second paragraph.

Parkhill et al. (Mar. 2000) "Complete DNA sequence of a serogroup A strain of *Neisseria meningitides* Z2491" 404: 502-505.

Perkins et al. (1998). "Immunogenicity of two efficacious outer membrane protein-based serogroup B meningococcal vaccines among young adults in Iceland," The Journal of Infectious Disease 177:683-691.

Perrett et al. (2005). "Towards an improved serogroup B *Neisseria meningitidis* vaccine," Expert Opinion on Biological Therapy 5(12):1611-1625.

Pettersson et al. (1999). "Sequence Variability of the Meningococcal Lactoferrin-binding Protein LbpB," Gene 231:105-110.

Pizza et al. (Mar. 10, 2000). "Identification of Vaccine Candidates Against Serogroup B Meningococcus by Whole-Genome Sequencing," Science 287(5459):1816-1820.

Poolman (1995). "Development of a Meningococcal Vaccine," Infectious Agents and Disease 4:13-28.

Poolman et al. (1985). "Colony Variants of *Neisseria meningitidis* Strain 2996 (B:2b:P1.2): Influence of Class-5 Out Membrane Proteins and Lipolysaccharides," J. Med. Microbiol 19:203-209.

Poolman et al. (1988). "Outer membrane protein serosubtyping of *Neisseria meningitidis*," European Journal of Clinical Microbiology and Infectious Diseases 7(2):291-292.

Renauld-Mongenie et al. (1997). "Identification of human transferrin-binding sites within meningococcal transferrin-binding protein B," J. Bacteriology 179(20):6400-6407.

Roitt, I. et al. (1993). Immunology. Mosby: St. Louis, 4$^{th}$ edition, pp. 7, 7-7,8.

Rosenqvist et al. (1995). "Human Antibody Response to Meningococcal Outer Membrane Antigens after Three Doses of the Norwegian Group B Meningococcal Vaccine," Infection and Immunity 63(12):4642-4652.

Seiler et al. (1996). "Allelic polymorphism and site-specific recombination in the opc locus of *Neisseria meningitidis*," Molecular Microbiology 19(4):841-856.

Telford (Jun. 2008). "Bacterial Genome Variability and Its Impact on Vaccine Design," Cell Host & Microbe 3(6):408-416.

Tettelin et al. (2006). "Towards a universal group B Streptococcus vaccine using multistrain genome analysis," Expert Rev Vaccines 25:687-694.

Tettelin et al. (Mar. 10, 2000). "Complete Genome Sequence of *Neisseria meningitidis* Serogroup B Strain MC58," Science 287(5459):1809-1815.

Thompson et al. (1994). "Clustal W: Improving the Sensitivity of Progressive Multiple Sequence Alignment through Sequence Weighting, Position-specific Gap Penalties and Weight Matrix Choice," Nucleic Acids Research 22(22):4673-4680.

Thompson et al. (1998). "Multiple Sequence Alignment with Clustal X," Trends in Biochemical Sciences 23:403-405.

Thomas E. Creighton (1984). Proteins: Structures and Molecular Properties. pp. 314-315.

Thomas E. Creighton (1989). Protein Structure: A Practical Approach. pp. 184-186.

Van Der Lay et al. (1992). "Construction of a Multivalent Meningococcal Vaccine Strain Based on the Class I Outer Membrane Protein," Infection and Immunity 60(8): 3516-3161.

Van Der Lay et al. (1995). "Construction of Neisseria meningitidis Strains Carrying Multiple Chromosomal Copies of the PorA Gene for Use in Production of a Multivalent Outer Membrane Vesicle Vaccine," Vaccine 13(4): 401-107.

Virji et al. (1992). Variations in the Expression of Pili: the Effect on Adherence of Neisseria.

Capecchi B. et al. "Neisseria meningitidis NadA is a new invasin which promotes bacterial adhesion to and penetration into human epithelial cells," Molecular Microbiology, vol. 55, No. 3, 2005, pp. 687-698.

Tavano. R. et al. "The membrane expression of Neisseria meningitidis adhesin A (NadA) increases the proimmune effects of MenB OMVs on human macrophages, compared with NadA-OMVs, without further stimulating their proinflammatory activity on circulating monocytes," Journal of Leukocyte Biology, vol. 86, 2009, pp. 143-153.

Poolman. (1995). "Development of a Meningococcal Vaccine," Infectious Agents and Disease 4:13-28.

Wolff et al. (1992). "Phylogeny and Nucleotide Sequence of a 23S rRNA Gene from Neisseria gonorrhea and Neisseria meningitidis" Nucleic Acids Research 20(17):4657.

FIGURE 3
PURIFICATION
WESTERN BLOT
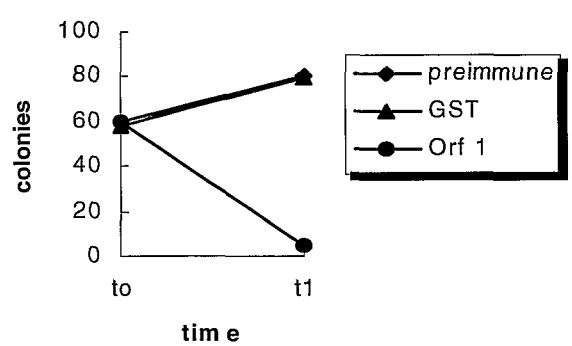
BACTERICIDAL ASSAY
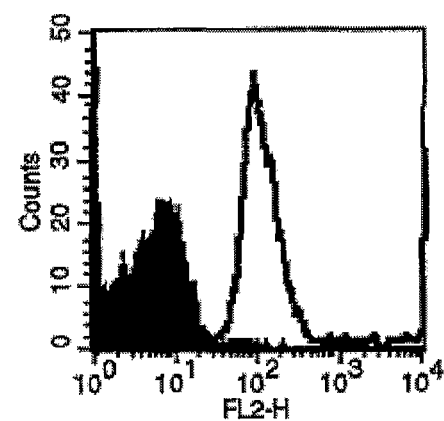
FACS
*ELISA:* *POSITIVE*

FIGURE 4
PURIFICATION    WESTERN BLOT
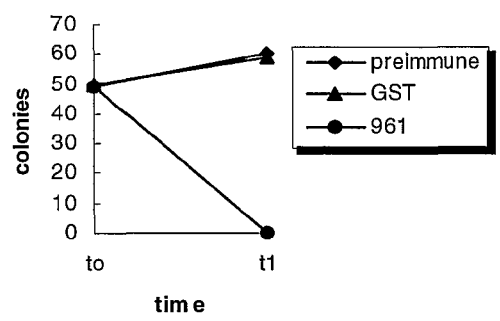
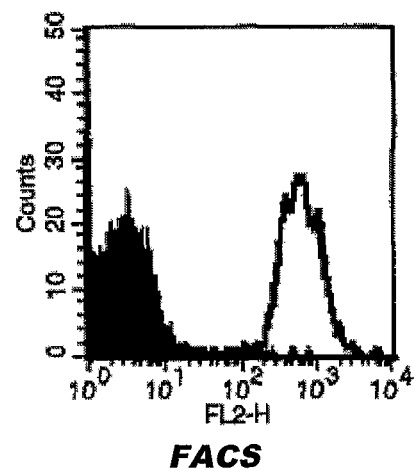
BACTERICIDAL ASSAY    FACS
ELISA: *POSITIVE*

FIGURE 7

```
           <A------------------------<Δ1-----------------------------
MC58    1  MFKRSVIAMACIFALSACGGGGGGSPDVKSADTLSKPAAPVVSEKETEAKEDAPQAGSQG
2996    1  MFERSVIAMACIFALSACGGGGGGSPDVKSADTLSKPAAPVVAEKETEVKEDAPQAGSQG

---------<Δ2------------------------------
MC58   61  QGAPSAQGSQDMAAVSEENTGNGGAVLADNPKNEDEVAQNDMPQNAAGTDSSTPNHTPDP
2996   61  QGAPSTQGSQDMAAVSAENTGNGGAATTDKPKNEDEGPQNDMPQN...............

----------<Δ3--------
MC58  121  NMLAGNMENQATDAGESSQPANQPDMANAADGMQGDDPSAGGQNAGNTAAQGANQAGNNQ
2996  106  ...............................................SAESANQTGNNQ

-------------------A><B----------------------------------
MC58  181  AAGSSDPIPASNPAPANGGSNFGRVDLANGVLIDGPSQNITLTHCKGDSCSGNNFLDEEV
2996  118  PADSSDSAPASNPAPANGGSNFGRVDLANGVLIDGPSQNITLTHCKGDSCNGDNLLDEEA

---------------------------------------------------B>----
MC58  241  QLKSEFEKLSDADKISNYKKDGKNDKFVGLVADSVQMKGINQYIIFYKPK..PTSFARFR
2996  178  PSKSEFENLNESERIEKYKKDGKSDKFTNLVATAVQANGTNKYVIIYKDKSASSSSARFR

<C-------------------------------------------------
MC58  299  RSARSRRSLPAEMPLIPVNQADTLIVDGEAVSLTGHSGNIFAPEGNYRYLTYGAEKLPGG
2996  238  RSARSRRSLPAEMPLIPVNQADTLIVDGEAVSLTGHSGNIFAPEGNYRYLTYGAEKLPGG

MC58  359  SYALRVQGEPAKGEMLAGAAVYNGEVLHFHTENGRPYPTRGRFAAKVDFGSKSVDGIIDS
2996  298  SYALRVQGEPAKGEMLAGTAVYNGEVLHFHTENGRPYPTRGRFAAKVDFGSKSVDGIIDS

MC58  419  GDDLHMGTQKFKAAIDGNGFKGTWTENGSGDVSGKFYGPAGEEVAGKYSYRPTDAEKGGF
2996  358  GDDLHMGTQKFKAAIDGNGFKGTWTENGGGDVSGRFYGPAGEEVAGKYSYRPTDAEKGGF

--------C>
MC58  479  GVFAGKKEQD*
2996  418  GVFAGKKEQD*
```

FIGURE 11A
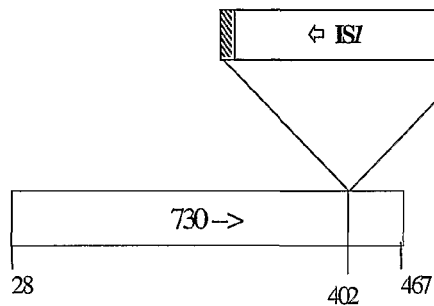
FIGURE 11B
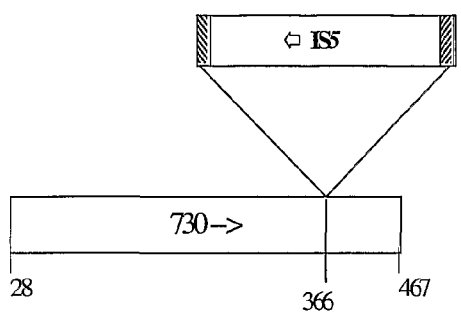
FIGURE 12
961 (2996)
961 L (2996)  ☐
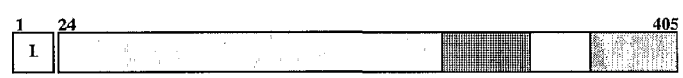
961 (MC58)
961 L (MC58)  ☐
961a (2996=MC58)
961b (2996)
961c (2996)
961c-L (2996)  ☐
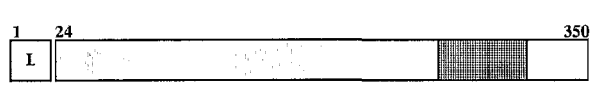
961c (MC58)
961c-L (MC58)  ☐
961d (2996)
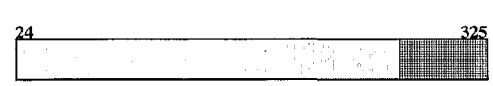
961-Δ1 (2996)
961Δ1-L  ☐
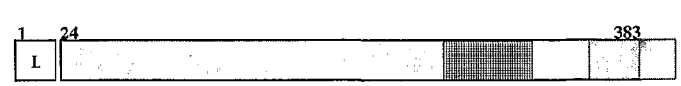
☐ Leader Peptide    ▓ Region present in 2996, not in MC58    ☐ Coil-coiled segment    ▓ Membrane anchor

FIGURE 13
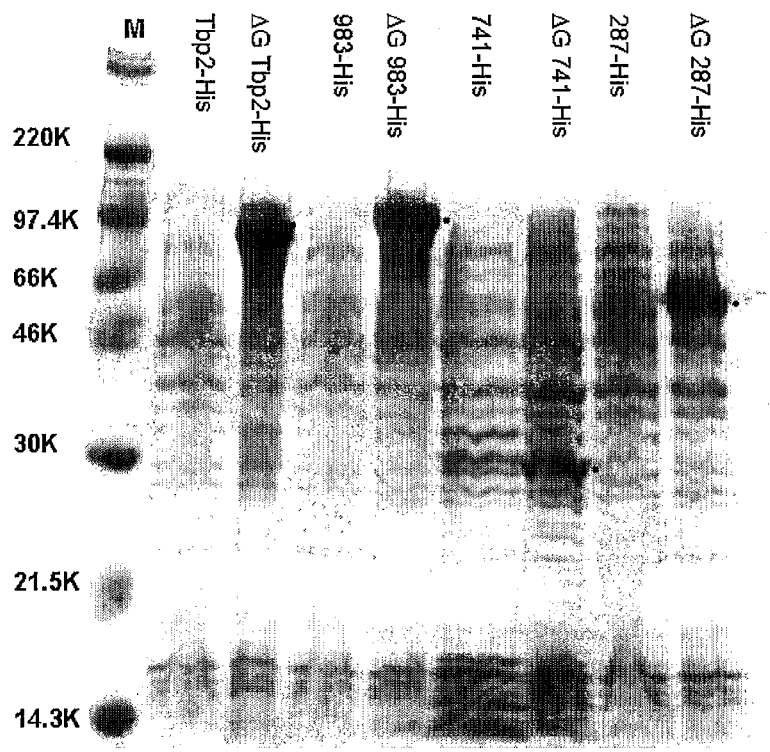
FIGURE 14
FIGURE 14A — ΔG287—919
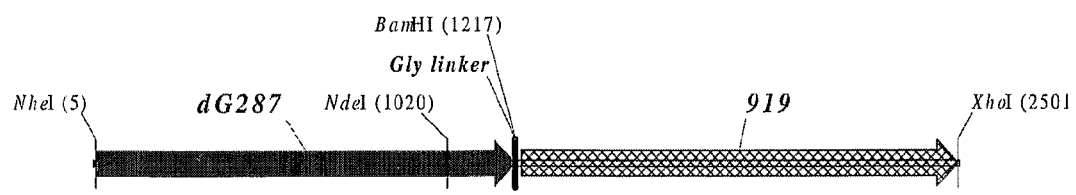
FIGURE 14B — ΔG287—953
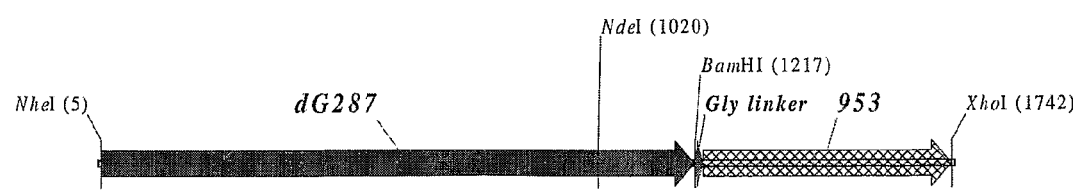

FIGURE 14C — ΔG287—961
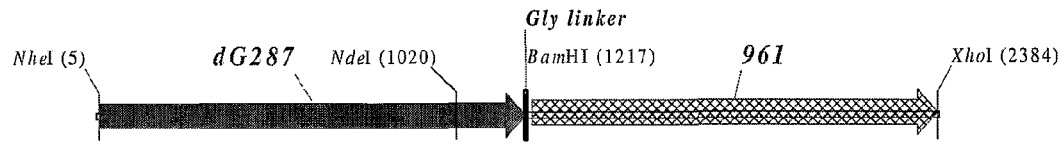
FIGURE 14D — ΔG287NZ—919
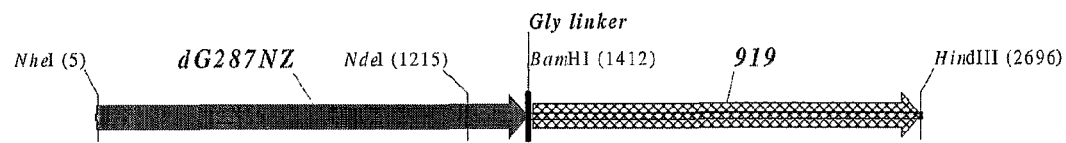
FIGURE 14E — ΔG287NZ—953
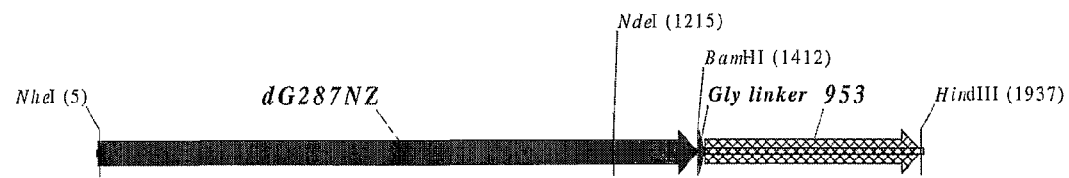
FIGURE 14F — ΔG287NZ—961
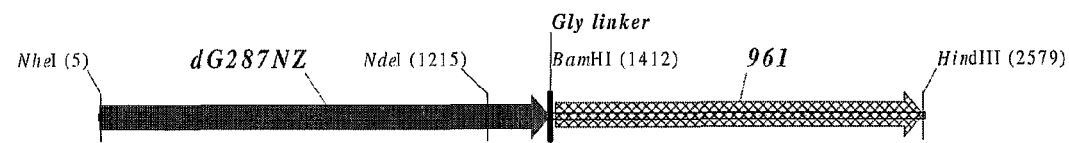
FIGURE 14G — ΔG983-ORF46.1
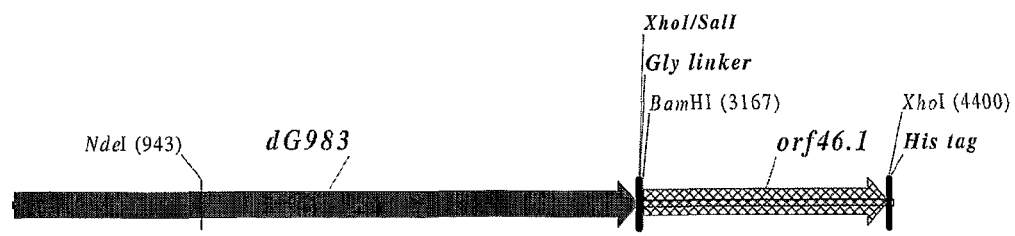

FIGURE 14H — ΔG983-741
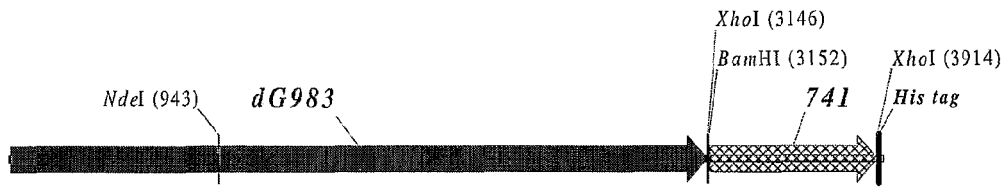
FIGURE 14I — ΔG983-961
FIGURE 14J — ΔG983-961c
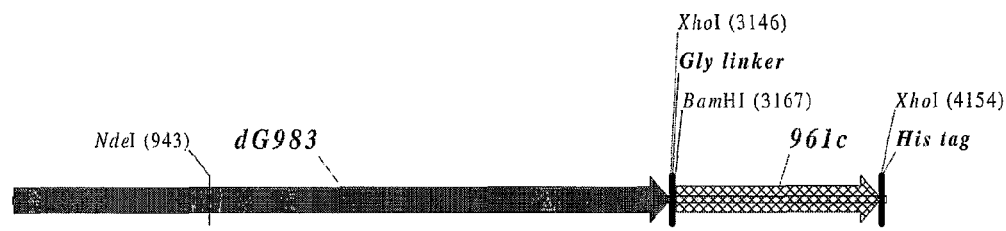
FIGURE 14K — ΔG741-961
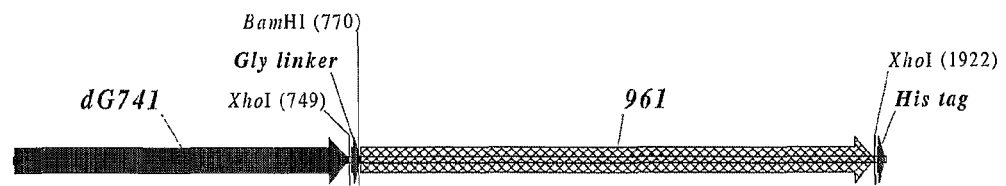
FIGURE 14L — ΔG741-961c
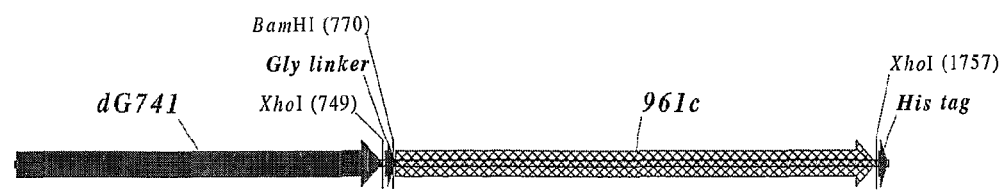

FIGURE 14M — ΔG741-983
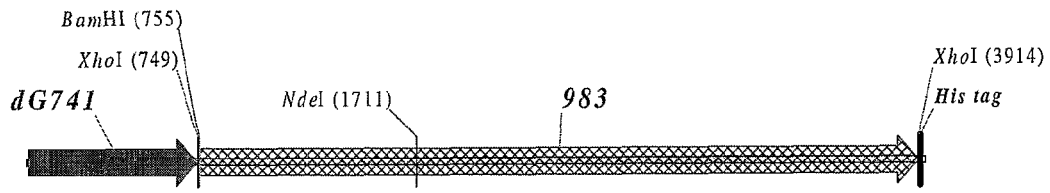
FIGURE 14N — ΔG741-ORF46.1
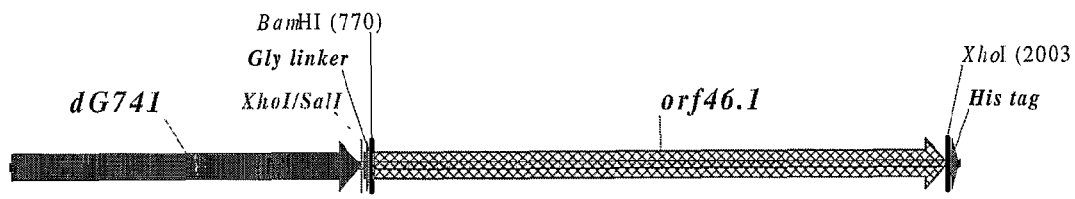
FIGURE 14O — ORF46.1-741
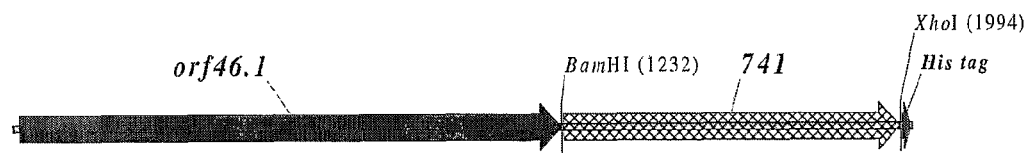
FIGURE 14P — ORF46.1-961
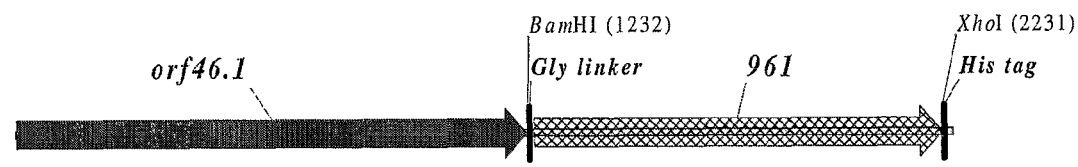
FIGURE 14Q — ORF46.1—961c
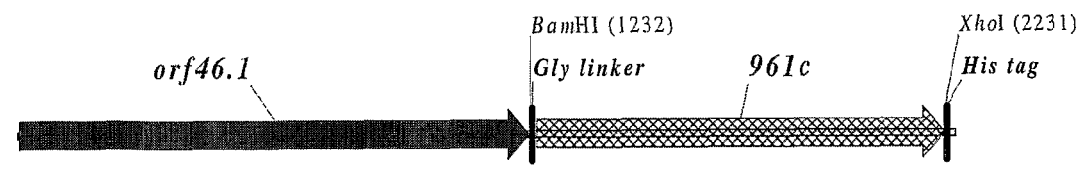

FIGURE 14R — 961-ORF46.1
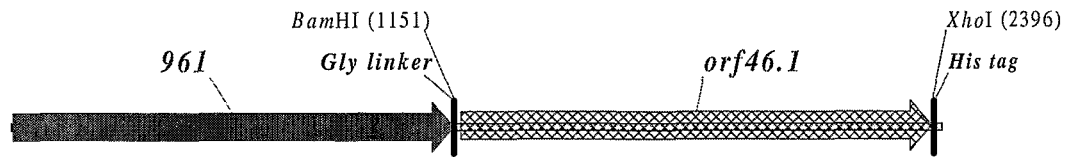
FIGURE 14S — 961-741
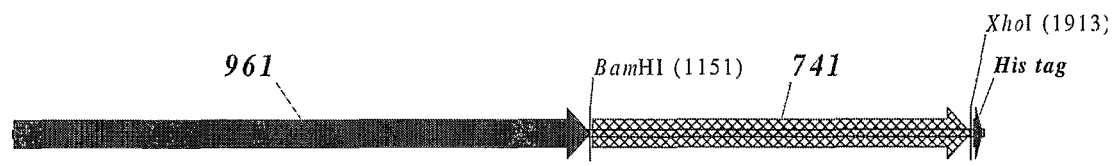
FIGURE 14T — 961-983
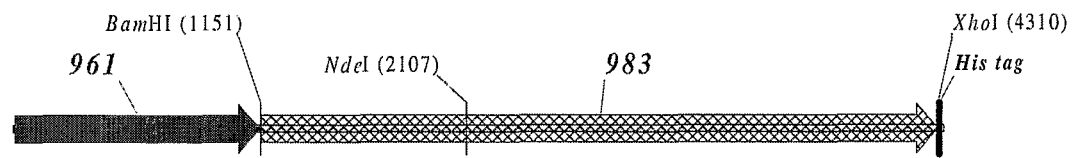
FIGURE 14U — 961c-ORF46.1
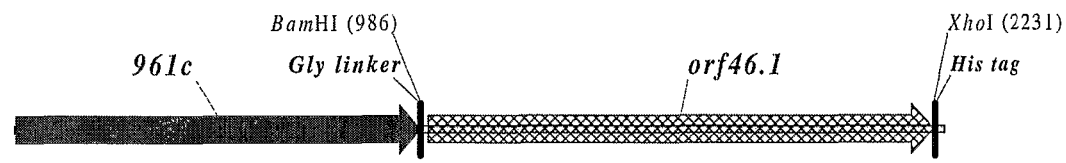
FIGURE 14V — 961c-741
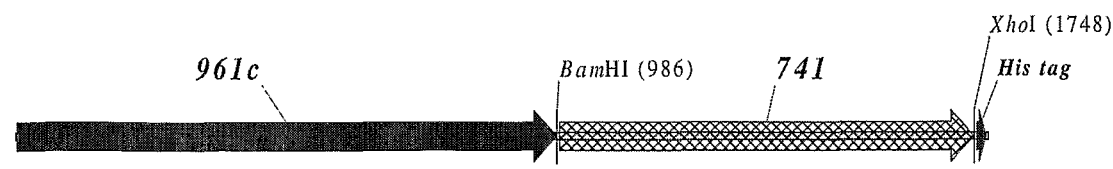

FIGURE 14W — 961c-983
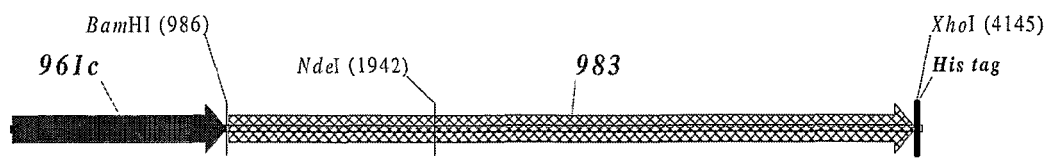
FIGURE 14X — 961cL-ORF46.1
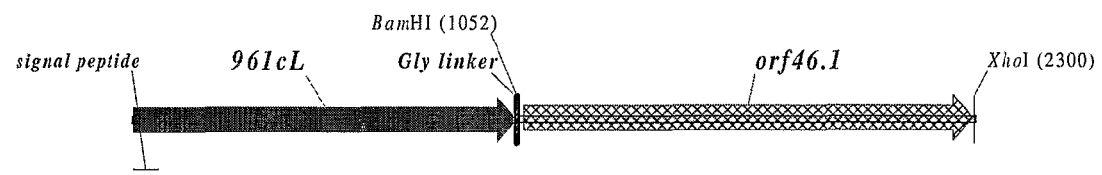
FIGURE 14Y — 961cL-741
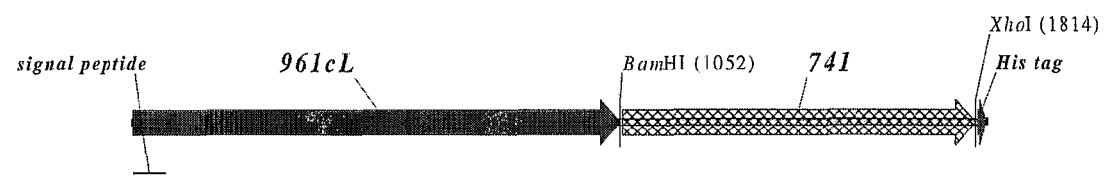
FIGURE 14Z — 961cL-983
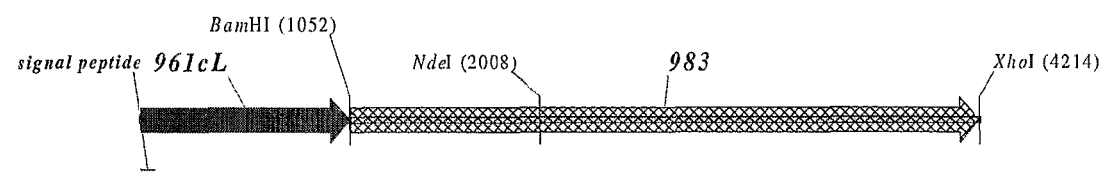

HETEROLOGOUS EXPRESSION OF NEISSERIAL PROTEINS

All documents cited herein are incorporated by reference in their entirety.

CROSS-REFERENCE TO RELATED APPLICATION

This application is a divisional patent application of U.S. Ser. No. 10/220,481, which is the National Stage filing of International Patent Application No. PCT/IB01/00452, filed Feb. 28, 2001, which claims the benefit of two Great Britain patent applications GB0004695.3, filed Feb. 28, 2000, and GB0027675.8, filed Nov. 13, 2000, all of which is incorporated herein by reference in its entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 223002099810SeqList.txt, date recorded: Jun. 25, 2010, size: 501 KB).

TECHNICAL FIELD

This invention is in the field of protein expression. In particular, it relates to the heterologous expression of proteins from Neisseria (e.g. N. gonorrhoeae or, preferably, N. meningitidis).

BACKGROUND ART

International patent applications WO99/24578, WO99/36544, WO99/57280 and WO00/22430 disclose proteins from Neisseria meningitidis and Neisseria gonorrhoeae. These proteins are typically described as being expressed in E. coli (i.e. heterologous expression) as either N-terminal GST-fusions or C-terminal His-tag fusions, although other expression systems, including expression in native Neisseria, are also disclosed.

It is an object of the present invention to provide alternative and improved approaches for the heterologous expression of these proteins. These approaches will typically affect the level of expression, the ease of purification, the cellular localisation of expression, and/or the immunological properties of the expressed protein.

DISCLOSURE OF THE INVENTION

Nomenclature Herein

The 2166 protein sequences disclosed in WO99/24578, WO99/36544 and WO99/57280 are referred to herein by the following SEQ# numbers:

| Application | Protein sequences | SEQ# herein |
|---|---|---|
| WO99/24578 | Even SEQ IDs 2-892 | SEQ#s 1-446 |
| WO99/36544 | Even SEQ IDs 2-90 | SEQ#s 447-491 |
| WO99/57280 | Even SEQ IDs 2-3020 | SEQ#s 492-2001 |
| | Even SEQ IDs 3040-3114 | SEQ#s 2002-2039 |
| | SEQ IDs 3115-3241 | SEQ#s 2040-2166 |

In addition to this SEQ# numbering, the naming conventions used in WO99/24578, WO99/36544 and WO99/57280 are also used (e.g. 'ORF4', 'ORF40', 'ORF40-1' etc. as used in WO99/24578 and WO99/36544; 'm919', 'g919' and 'a919' etc. as used in WO99/57280).

The 2160 proteins NMB0001 to NMB2160 from Tettelin et al. [*Science* (2000) 287:1809-1815] are referred to herein as SEQ#s 2167-4326 [see also WO00/66791].

The term 'protein of the invention' as used herein refers to a protein comprising:

(a) one of sequences SEQ#s 1-4326; or
(b) a sequence having sequence identity to one of SEQ#s 1-4326; or
(c) a fragment of one of SEQ#s 1-4326.

The degree of 'sequence identity' referred to in (b) is preferably greater than 50% (eg. 60%, 70%, 80%, 90%, 95%, 99% or more). This includes mutants and allelic variants [e.g. see WO00/66741]. Identity is preferably determined by the Smith-Waterman homology search algorithm as implemented in the MPSRCH program (Oxford Molecular), using an affine gap search with parameters gap open penalty=12 and gap extension penalty=1. Typically, 50% identity or more between two proteins is considered to be an indication of functional equivalence.

The 'fragment' referred to in (c) should comprise at least n consecutive amino acids from one of SEQ#s 1-4326 and, depending on the particular sequence, n is 7 or more (eg. 8, 10, 12, 14, 16, 18, 20, 25, 30, 35, 40, 50, 60, 70, 80, 90, 100 or more). Preferably the fragment comprises an epitope from one of SEQ#s 1-4326. Preferred fragments are those disclosed in WO00/71574 and WO01/04316.

Preferred proteins of the invention are found in N. meningitidis serogroup B.

Preferred proteins for use according to the invention are those of serogroup B N. meningitidis strain 2996 or strain 394/98 (a New Zealand strain). Unless otherwise stated, proteins mentioned herein are from N. meningitidis strain 2996. It will be appreciated, however, that the invention is not in general limited by strain. References to a particular protein (e.g. '287', '919' etc.) may be taken to include that protein from any strain.

Non-Fusion Expression

In a first approach to heterologous expression, no fusion partner is used, and the native leader peptide (if present) is used. This will typically prevent any 'interference' from fusion partners and may alter cellular localisation and/or post-translational modification and/or folding in the heterologous host.

Thus the invention provides a method for the heterologous expression of a protein of the invention, in which (a) no fusion partner is used, and (b) the protein's native leader peptide (if present) is used.

The method will typically involve the step of preparing an vector for expressing a protein of the invention, such that the first expressed amino acid is the first amino acid (methionine) of said protein, and last expressed amino acid is the last amino acid of said protein (i.e. the codon preceding the native STOP codon).

This approach is preferably used for the expression of the following proteins using the native leader peptide: 111, 149, 206, 225-1, 235, 247-1, 274, 283, 286, 292, 401, 406, 502-1, 503, 519-1, 525-1, 552, 556, 557, 570, 576-1, 580, 583, 664, 759, 907, 913, 920-1, 936-1, 953, 961, 983, 989, Orf4, Orf7-1, Orf9-1, Orf23, Orf25, Orf37, Orf38, Orf40, Orf40.1, Orf40.2, Orf72-1, Orf76-1, Orf85-2, Orf91, Orf97-1, Orf119, Orf143.1, NMB0109 and NMB2050. The suffix 'L' used herein in the name of a protein indicates expression in this manner using the native leader peptide.

Proteins which are preferably expressed using this approach using no fusion partner and which have no native leader peptide include: 008, 105, 117-1, 121-1, 122-1, 128-1, 148, 216, 243, 308, 593, 652, 726, 926, 982, Orf83-1 and Orf143-1.

Advantageously, it is used for the expression of ORF25 or ORF40, resulting in a protein which induces better anti-bactericidal antibodies than GST- or His-fusions.

This approach is particularly suited for expressing lipoproteins.

Leader-Peptide Substitution

In a second approach to heterologous expression, the native leader peptide of a protein of the invention is replaced by that of a different protein. In addition, it is preferred that no fusion partner is used. Whilst using a protein's own leader peptide in heterologous hosts can often localise the protein to its 'natural' cellular location, in some cases the leader sequence is not efficiently recognised by the heterologous host. In such cases, a leader peptide known to drive protein targeting efficiently can be used instead.

Thus the invention provides a method for the heterologous expression of a protein of the invention, in which (a) the protein's leader peptide is replaced by the leader peptide from a different protein and, optionally, (b) no fusion partner is used.

The method will typically involve the steps of: obtaining nucleic acid encoding a protein of the invention; manipulating said nucleic acid to remove nucleotides that encode the protein's leader peptide and to introduce nucleotides that encode a different protein's leader peptide. The resulting nucleic acid may be inserted into an expression vector, or may already be part of an expression vector. The expressed protein will consist of the replacement leader peptide at the N-terminus, followed by the protein of the invention minus its leader peptide.

The leader peptide is preferably from another protein of the invention (e.g. one of SEQ#s 1-4326), but may also be from an *E. coli* protein (e.g. the OmpA leader peptide) or an *Erwinia carotovora* protein (e.g. the PelB leader peptide), for instance.

A particularly useful replacement leader peptide is that of ORF4. This leader is able to direct lipidation in *E. coli*, improving cellular localisation, and is particularly useful for the expression of proteins 287, 919 and ΔG287. The leader peptide and N-terminal domains of 961 are also particularly useful.

Another useful replacement leader peptide is that of *E. coli* OmpA. This leader is able to direct membrane localisation of *E. coli*. It is particularly advantageous for the expression of ORF1, resulting in a protein which induces better anti-bactericidal antibodies than both fusions and protein expressed from its own leader peptide.

Another useful replacement leader peptide is MKKYLF-SAA (SEQ ID NO:621). This can direct secretion into culture medium, and is extremely short and active. The use of this leader peptide is not restricted to the expression of Neisserial proteins—it may be used to direct the expression of any protein (particularly bacterial proteins).

Leader-Peptide Deletion

In a third approach to heterologous expression, the native leader peptide of a protein of the invention is deleted. In addition, it is preferred that no fusion partner is used.

Thus the invention provides a method for the heterologous expression of a protein of the invention, in which (a) the protein's leader peptide is deleted and, optionally, (b) no fusion partner is used.

The method will typically involve the steps of: obtaining nucleic acid encoding a protein of the invention; manipulating said nucleic acid to remove nucleotides that encode the protein's leader peptide. The resulting nucleic acid may be inserted in an expression vector, or may already be part of an expression vector. The first amino acid of the expressed protein will be that of the mature native protein.

This method can increase the levels of expression. For protein 919, for example, expression levels in *E. coli* are much higher when the leader peptide is deleted. Increased expression may be due to altered localisation in the absence of the leader peptide.

The method is preferably used for the expression of 919, ORF46, 961, 050-1, 760 and 287.

Domain-Based Expression

In a fourth approach to heterologous expression, the protein is expressed as domains. This may be used in association with fusion systems (e.g. GST or His-tag fusions).

Thus the invention provides a method for the heterologous expression of a protein of the invention, in which (a) at least one domain in the protein is deleted and, optionally, (b) no fusion partner is used.

The method will typically involve the steps of: obtaining nucleic acid encoding a protein of the invention; manipulating said nucleic acid to remove at least one domain from within the protein. The resulting nucleic acid may be inserted into an expression vector, or may already be part of an expression vector. Where no fusion partners are used, the first amino acid of the expressed protein will be that of a domain of the protein.

A protein is typically divided into notional domains by aligning it with known sequences in databases and then determining regions of the protein which show different alignment patterns from each other.

The method is preferably used for the expression of protein 287. This protein can be notionally split into three domains, referred to as A B & C (see FIG. 5). Domain B aligns strongly with IgA proteases, domain C aligns strongly with transferrin-binding proteins, and domain A shows no strong alignment with database sequences. An alignment of polymorphic forms of 287 is disclosed in WO00/66741.

Once a protein has been divided into domains, these can be (a) expressed singly (b) deleted from with the protein e.g. protein ABCD→ABD, ACD, BCD etc. or (c) rearranged e.g. protein ABC→ACB, CAB etc. These three strategies can be combined with fusion partners is desired.

ORF46 has also been notionally split into two domains—a first domain (amino acids 1-433) which is well-conserved between species and serogroups, and a second domain (amino acids 433-608) which is not well-conserved. The second domain is preferably deleted. An alignment of polymorphic forms of ORF46 is disclosed in WO00/66741.

Protein 564 has also been split into domains (FIG. 8), as have protein 961 (FIG. 12) and protein 502 (amino acids 28-167 of the MC58 protein).

Hybrid Proteins

In a fifth approach to heterologous expression, two or more (e.g. 3, 4, 5, 6 or more) proteins of the invention are expressed as a single hybrid protein. It is preferred that no non-Neisserial fusion partner (e.g. GST or poly-His) is used.

This offers two advantages. Firstly, a protein that may be unstable or poorly expressed on its own can be assisted by adding a suitable hybrid partner that overcomes the problem. Secondly, commercial manufacture is simplified—only one expression and purification need be employed in order to produce two separately-useful proteins.

Thus the invention provides a method for the simultaneous heterologous expression of two or more proteins of the invention, in which said two or more proteins of the invention are fused (i.e. they are translated as a single polypeptide chain).

The method will typically involve the steps of: obtaining a first nucleic acid encoding a first protein of the invention; obtaining a second nucleic acid encoding a second protein of the invention; ligating the first and second nucleic acids. The resulting nucleic acid may be inserted into an expression vector, or may already be part of an expression vector.

Preferably, the constituent proteins in a hybrid protein according to the invention will be from the same strain.

The fused proteins in the hybrid may be joined directly, or may be joined via a linker peptide e.g. via a poly-glycine linker (i.e. $G_n$ where n=3, 4, 5, 6, 7, 8, 9, 10 or more) or via a short peptide sequence which facilitates cloning. It is evidently preferred not to join a ΔG protein to the C-terminus of a poly-glycine linker.

The fused proteins may lack native leader peptides or may include the leader peptide sequence of the N-terminal fusion partner.

The method is well suited to the expression of proteins orf1, orf4, orf25, orf40, Orf46/46.1, orf83, 233, 287, 292L, 564, 687, 741, 907, 919, 953, 961 and 983.

The 42 hybrids indicated by 'X' in the following table of form NH$_2$-A-B—COOH are preferred:

| A | B | | | | | | |
|---|---|---|---|---|---|---|---|
|   | ORF46.1 | 287 | 741 | 919 | 953 | 961 | 983 |
| ORF46.1 |   | X | X | X | X | X | X |
| 287 | X |   | X | X | X | X | X |
| 741 | X | X |   | X | X | X | X |
| 919 | X | X | X |   | X | X | X |
| 953 | X | X | X | X |   | X | X |
| 961 | X | X | X | X | X |   | X |
| 983 | X | X | X | X | X | X |   |

Preferred proteins to be expressed as hybrids are thus ORF46.1, 287, 741, 919, 953, 961 and 983. These may be used in their essentially full-length form, or poly-glycine deletions (ΔG) forms may be used (e.g. ΔG-287, ΔGTbp2, ΔG741, ΔG983 etc.), or truncated forms may be used (e.g. Δ1-287, Δ2-287 etc.), or domain-deleted versions may be used (e.g. 287B, 287C, 287BC, ORF46$_{1-433}$, ORF46$_{433-608}$, ORF46, 961c etc.).

Particularly preferred are: (a) a hybrid protein comprising 919 and 287; (b) a hybrid protein comprising 953 and 287; (c) a hybrid protein comprising 287 and ORF46.1; (d) a hybrid protein comprising ORF1 and ORF46.1; (e) a hybrid protein comprising 919 and ORF46.1; (f) a hybrid protein comprising ORF46.1 and 919; (g) a hybrid protein comprising ORF46.1, 287 and 919; (h) a hybrid protein comprising 919 and 519; and (i) a hybrid protein comprising ORF97 and 225. Further embodiments are shown in FIG. 14.

Where 287 is used, it is preferably at the C-terminal end of a hybrid; if it is to be used at the N-terminus, if is preferred to use a ΔG form of 287 is used (e.g. as the N-terminus of a hybrid with ORF46.1, 919, 953 or 961).

Where 287 is used, this is preferably from strain 2996 or from strain 394/98.

Where 961 is used, this is preferably at the N-terminus. Domain forms of 961 may be used.

Alignments of polymorphic forms of ORF46, 287, 919 and 953 are disclosed in WO00/66741. Any of these polymorphs can be used according to the present invention.

Temperature

In a sixth approach to heterologous expression, proteins of the invention are expressed at a low temperature.

Expressed Neisserial proteins (e.g. 919) may be toxic to *E. coli*, which can be avoided by expressing the toxic protein at a temperature at which its toxic activity is not manifested.

Thus the present invention provides a method for the heterologous expression of a protein of the invention, in which expression of a protein of the invention is carried out at a temperature at which a toxic activity of the protein is not manifested.

A preferred temperature is around 30° C. This is particularly suited to the expression of 919.

Mutations

As discussed above, expressed Neisserial proteins may be toxic to *E. coli*. This toxicity can be avoided by mutating the protein to reduce or eliminate the toxic activity. In particular, mutations to reduce or eliminate toxic enzymatic activity can be used, preferably using site-directed mutagenesis.

In a seventh approach to heterologous expression, therefore, an expressed protein is mutated to reduce or eliminate toxic activity.

Thus the invention provides a method for the heterologous expression of a protein of the invention, in which protein is mutated to reduce or eliminate toxic activity.

The method is preferably used for the expression of protein 907, 919 or 922. A preferred mutation in 907 is at Glu-117 (e.g. Glu→÷Gly); preferred mutations in 919 are at Glu-255 (e.g. Glu→Gly) and/or Glu-323 (e.g. Glu→Gly); preferred mutations in 922 are at Glu-164 (e.g. Glu→Gly), Ser-213 (e.g. Ser→Gly) and/or Asn-348 (e.g. Asn→Gly).

Alternative Vectors

In a eighth approach to heterologous expression, an alternative vector used to express the protein. This may be to improve expression yields, for instance, or to utilise plasmids that are already approved for GMP use.

Thus the invention provides a method for the heterologous expression of a protein of the invention, in which an alternative vector is used. The alternative vector is preferably pSM214, with no fusion partners. Leader peptides may or may not be included.

This approach is particularly useful for protein 953. Expression and localisation of 953 with its native leader peptide expressed from pSM214 is much better than from the pET vector.

pSM214 may also be used with: ΔG287, Δ2-287, Δ3-287, Δ4-287, Orf46.1, 961L, 961, 961(MC58), 961c, 961c-L, 919, 953 and ΔG287-Orf46.1.

Another suitable vector is pET-24b (Novagen; uses kanamycin resistance), again using no fusion partners. pET-24b is preferred for use with: ΔG287K, Δ2-287K, Δ3-287K, M-287K, Orf46.1-K, Orf46A-K, 961-K (MC58), 961a-K, 961b-K, 961c-K, 961c-L-K, 961d-K, ΔG287-919-K, ΔG287-Orf46.1-K and ΔG287-961-K.

Multimeric Form

In a ninth approach to heterologous expression, a protein is expressed or purified such that it adopts a particular multimeric form.

This approach is particularly suited to protein 953. Purification of one particular multimeric form of 953 (the monomeric form) gives a protein with greater bactericidal activity than other forms (the dimeric form).

Proteins 287 and 919 may be purified in dimeric forms.

Protein 961 may be purified in a 180 kDa oligomeric form (e.g. a tetramer).

Lipidation

In a tenth approach to heterologous expression, a protein is expressed as a lipidated protein.

Thus the invention provides a method for the heterologous expression of a protein of the invention, in which the protein is expressed as a lipidated protein.

This is particularly useful for the expression of 919, 287, ORF4, 406, 576-1, and ORF25. Polymorphic forms of 919, 287 and ORF4 are disclosed in WO00/66741.

The method will typically involve the use of an appropriate leader peptide without using an N-terminal fusion partner.

C-Terminal Deletions

In an eleventh approach to heterologous expression, the C-terminus of a protein of the invention is mutated. In addition, it is preferred that no fusion partner is used.

Thus the invention provides a method for the heterologous expression of a protein of the invention, in which (a) the protein's C-terminus region is mutated and, optionally, (b) no fusion partner is used.

The method will typically involve the steps of: obtaining nucleic acid encoding a protein of the invention; manipulating said nucleic acid to mutate nucleotides that encode the protein's C-terminus portion. The resulting nucleic acid may be inserted into an expression vector, or may already be part of an expression vector. The first amino acid of the expressed protein will be that of the mature native protein.

The mutation may be a substitution, insertion or, preferably, a deletion.

This method can increase the levels of expression, particularly for proteins 730, ORF29 and ORF46. For protein 730, a C-terminus region of around 65 to around 214 amino acids may be deleted; for ORF46, the C-terminus region of around 175 amino acids may be deleted; for ORF29, the C-terminus may be deleted to leave around 230-370 N-terminal amino acids.

Leader Peptide Mutation

In a twelfth approach to heterologous expression, the leader peptide of the protein is mutated. This is particularly useful for the expression of protein 919.

Thus the invention provides a method for the heterologous expression of a protein of the invention, in which the protein's leader peptide is mutated.

The method will typically involve the steps of: obtaining nucleic acid encoding a protein of the invention; and manipulating said nucleic acid to mutate nucleotides within the leader peptide. The resulting nucleic acid may be inserted into an expression vector, or may already be part of an expression vector.

Poly-Glycine Deletion

In a thirteenth approach to heterologous expression, polyglycine stretches in wild-type sequences are mutated. This enhances protein expression.

The poly-glycine stretch has the sequence $(Gly)_n$, where $n \geq 4$ (e.g. 5, 6, 7, 8, 9 or more). This stretch is mutated to disrupt or remove the $(Gly)_n$. This may be by deletion (e.g. CGGGGS (SEQ ID NO:622)→CGGGS (SEQ ID NO:623), CGGS (SEQ ID NO:624), CGS or CS), by substitution (e.g. CGGGGS (SEQ ID NO:622)→CGXGGS (SEQ ID NO:625), CGXXGS (SEQ ID NO:626), CGXGXS (SEQ ID NO:627) etc.), and/or by insertion (e.g. CGGGGS (SEQ ID NO:622)→CGGXGGS (SEQ ID NO:628), CGXGGGS (SEQ ID NO:629), etc.).

This approach is not restricted to Neisserial proteins—it may be used for any protein (particularly bacterial proteins) to enhance heterologous expression. For Neisserial proteins, however, it is particularly suitable for expressing 287, 741, 983 and Tbp2. An alignment of polymorphic forms of 287 is disclosed in WO00/66741.

Thus the invention provides a method for the heterologous expression of a protein of the invention, in which (a) a polyglycine stretch within the protein is mutated.

The method will typically involve the steps of: obtaining nucleic acid encoding a protein of the invention; and manipulating said nucleic acid to mutate nucleotides that encode a poly-glycine stretch within the protein sequence. The resulting nucleic acid may be inserted into an expression vector, or may already be part of an expression vector.

Conversely, the opposite approach (i.e. introduction of poly-glycine stretches) can be used to suppress or diminish expression of a given heterologous protein.

Heterologous Host

Whilst expression of the proteins of the invention may take place in the native host (i.e. the organism in which the protein is expressed in nature), the present invention utilises a heterologous host. The heterologous host may be prokaryotic or eukaryotic. It is preferably *E. coli*, but other suitable hosts include *Bacillus subtilis, Vibrio cholerae, Salmonella typhi, Salmonenna typhimurium, Neisseria meningitidis, Neisseria gonorrhoeae, Neisseria lactamica, Neisseria cinerea, Mycobateria* (e.g. *M. tuberculosis*), yeast etc.

Vectors Etc.

As well as the methods described above, the invention provides (a) nucleic acid and vectors useful in these methods (b) host cells containing said vectors (c) proteins expressed or expressable by the methods (d) compositions comprising these proteins, which may be suitable as vaccines, for instance, or as diagnostic reagents, or as immunogenic compositions (e) these compositions for use as medicaments (e.g. as vaccines) or as diagnostic reagents (f) the use of these compositions in the manufacture of (1) a medicament for treating or preventing infection due to Neisserial bacteria (2) a diagnostic reagent for detecting the presence of Neisserial bacteria or of antibodies raised against Neisserial bacteria, and/or (3) a reagent which can raise antibodies against Neisserial bacteria and (g) a method of treating a patient, comprising administering to the patient a therapeutically effective amount of these compositions.

Sequences

The invention also provides a protein or a nucleic acid having any of the sequences set out in the following examples. It also provides proteins and nucleic acid having sequence identity to these. As described above, the degree of 'sequence identity' is preferably greater than 50% (eg. 60%, 70%, 80%, 90%, 95%, 99% or more).

Furthermore, the invention provides nucleic acid which can hybridise to the nucleic acid disclosed in the examples, preferably under "high stringency" conditions (eg. 65° C. in a 0.1×SSC, 0.5% SDS solution).

The invention also provides nucleic acid encoding proteins according to the invention.

It should also be appreciated that the invention provides nucleic acid comprising sequences complementary to those described above (eg. for antisense or probing purposes).

Nucleic acid according to the invention can, of course, be prepared in many ways (eg. by chemical synthesis, from genomic or cDNA libraries, from the organism itself etc.) and can take various forms (eg. single stranded, double stranded, vectors, probes etc.).

In addition, the term "nucleic acid" includes DNA and RNA, and also their analogues, such as those containing modified backbones, and also peptide nucleic acids (PNA) etc.

BRIEF DESCRIPTION OF DRAWINGS

FIG. 3 shows expression data for ORF1, and

FIG. 4 shows similar data for protein 961.

FIGS. 6 & 7 (SEQ ID NO:619 and 620) show deletions within domain A.

FIG. 11 shows insertion mutants of protein 730 (A: 730-C1; B: 730-C2).

FIG. 12 shows domains of protein 961.

FIG. 13 shows SDS-PAGE of ΔG proteins. Dots show the main recombinant product.

FIG. 14 shows 26 hybrid proteins according to the invention.

MODES FOR CARRYING OUT THE INVENTION

Example 1

919 and its Leader Peptide

Figure 1:
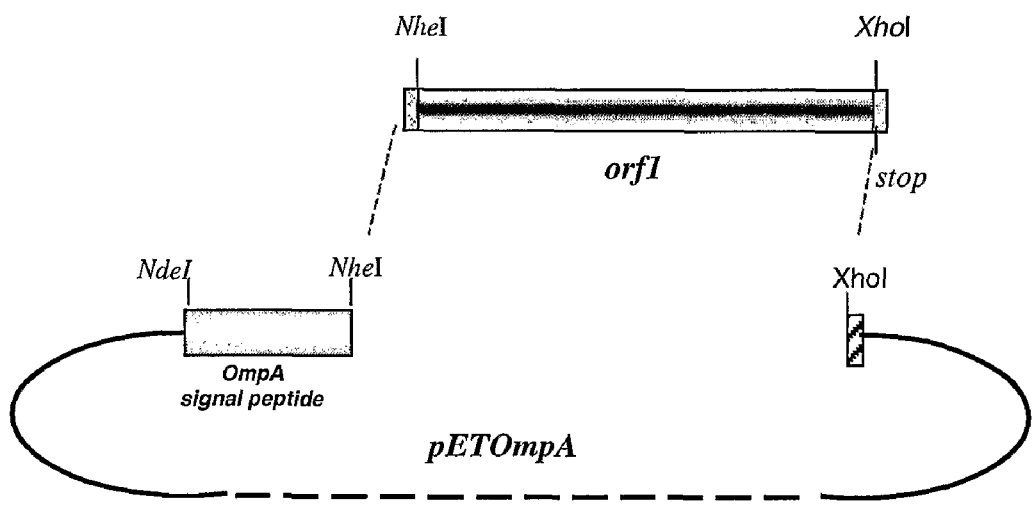
FIGS. 1 and 2 show constructs used to express proteins using heterologous leader peptides.

Protein 919 from *N. meningitidis* (serogroup B, strain 2996) has the following sequence (SEQ ID NO:1):

```
  1 MKKYLFRAAL YGIAAAILAA CQSKSIQTFP QPDTSVINGP DRPVGIPDPA

51 GTTVGGGGAV YTVVPHLSLP HWAAQDFAKS LQSFRLGCAN LKNRQGWQDV

101 CAQAFQTPVH SFQAKQFFER YFTPWQVAGN GSLAGTVTGY YEPVLKGDDR

151 RTAQARFPIY GIPDDFISVP LPAGLRSGKA LVRIRQTGKN SGTIDNTGGT

201 HTADLSRFPI TARTTAIKGR FEGSRFLPYH TRNQINGGAL DGKAPILGYA

251 EDPVELFFMH IQGSGRLKTP SGKYIRIGYA DKNEHPYVSI GRYMADKGYL

301 KLGQTSMQGI KAYMRQNPQR LAEVLGQNPS YIFFRELAGS SNDGPVGALG

351 TPLMGEYAGA VDRHYITLGA PLFVATAHPV TRKALNRLIM AQDTGSAIKG

401 AVRVDYFWGY GDEAGELAGK QKTTGYVWQL LPNGMKPEYR P*
```

The leader peptide is underlined.

The sequences of 919 from other strains can be found in FIGS. 7 and 18 of WO00/66741.

Example 2 of WO99/57280 discloses the expression of protein 919 as a His-fusion in *E. coli*. The protein is a good surface-exposed immunogen.

Three alternative expression strategies were used for 919:

1) 919 without its leader peptide (and without the mature N-terminal cysteine) and without any fusion partner ('919$^{untagged}$') (SEQ ID NO:2):

```
  1 QSKSIQTFP QPDTSVINGP DRPVGIPDPA GTTVGGGGAV YTVVPHLSLP

50 HWAAQDFAKS LQSFRLGCAN LKNRQGWQDV CAQAFQTPVH SFQAKQFFER

100 YFTPWQVAGN GSLAGTVTGY YEPVLKGDDR RTAQARFPIY GIPDDFISVP

150 LPAGLRSGKA LVRIRQTGKN SGTIDNTGGT HTADLSRFPI TARTTAIKGR

200 FEGSRFLPYH TRNQINGGAL DGKAPILGYA EDPVELFFMH IQGSGRLKTP

250 SGKYIRIGYA DKNEHPYVSI GRYMADKGYL KLGQTSMQGI KAYMRQNPQR

300 LAEVLGQNPS YIFFRELAGS SNDGPVGALG TPLMGEYAGA VDRHYITLGA

350 PLFVATAHPV TRKALNRLIM AQDTGSAIKG AVRVDYFWGY GDEAGELAGK

400 QKTTGYVWQL LPNGMKPEYR P*
```

The leader peptide and cysteine were omitted by designing the 5'-end amplification primer downstream from the predicted leader sequence.

2) 919 with its own leader peptide but without any fusion partner ('919L'); and
3) 919 with the leader peptide (MKTFFKTLSAAALALILAA (SEQ ID NO:630)) from ORF4 ('919LOrf4') (SEQ ID NO:3).

```
  1 MKTFFKTLS AAALALILAA CQSKSIQTFP QPDTSVINGP DRPVGIPDPA

50 GTTVGGGGAV YTVVPHLSLP HWAAQDFAKS LQSFRLGCAN LKNRQGWQDV

100 CAQAFQTPVH SFQAKQFFER YFTPWQVAGN GSLAGTVTGY YEPVLKGDDR

150 RTAQARFPIY GIPDDFISVP LPAGLRSGKA LVRIRQTGKN SGTIDNTGGT
```

```
200 HTADLSRFPI TARTTAIKGR FEGSRFLPYH TRNQINGGAL DGKAPILGYA

250 EDPVELFFMH IQGSGRLKTP SGKYIRIGYA DKNEHPYVSI GRYMADKGYL

300 KLGQTSMQGI KSYMRQNPQR LAEVLGQNPS YIFFRELAGS SNDGPVGALG

350 TPLMGEYAGA VDRHYITLGA PLFVATAHPV TRKALNRLIM AQDTGSAIKG

400 AVRVDYFWGY GDEAGELAGK QKTTGYVWQL LPNGMKPEYR P*
```

To make this construct, the entire sequence encoding the ORF4 leader peptide was included in the 5'-primer as a tail (primer 919Lorf4 For). A NheI restriction site was generated by a double nucleotide change in the sequence coding for the ORF4 leader (no amino acid changes), to allow different genes to be fused to the ORF4 leader peptide sequence. A stop codon was included in all the 3'-end primer sequences.

All three forms of the protein were expressed and could be purified.

The '919L' and '919LOrf4' expression products were both lipidated, as shown by the incorporation of [$^3$H]-palmitate label. 919$^{untagged}$ did not incorporate the $^3$H label and was located intracellularly.

919LOrf4 could be purified more easily than 919L. It was purified and used to immunise mice. The resulting sera gave excellent results in FACS and ELISA tests, and also in the bactericidal assay. The lipoprotein was shown to be localised in the outer membrane.

919$^{untagged}$ gave excellent ELISA titres and high serum bactericidal activity. FACS confirmed its cell surface location.

Example 2

919 and Expression Temperature

Growth of *E. coli* expressing the 919LOrf4 protein at 37° C. resulted in lysis of the bacteria. In order to overcome this problem, the recombinant bacteria were grown at 30° C. Lysis was prevented without preventing expression.

Example 3

Mutation of 907, 919 and 922

It was hypothesised that proteins 907, 919 and 922 are murein hydrolases, and more particularly lytic transglycosylases. Murein hydrolases are located on the outer membrane and participate in the degradation of peptidoglycan.

The purified proteins 919$^{untagged}$, 919Lorf4, 919-His (i.e. with a C-terminus His-tag) and 922-His were thus tested for murein hydrolase activity [Ursinus & Holtje (1994) *J. Bact.* 176:338-343]. Two different assays were used, one determining the degradation of insoluble murein sacculus into soluble muropeptides and the other measuring breakdown of poly (MurNAc-GlcNAc)$_{n>30}$ glycan strands.

The first assay uses murein sacculi radiolabelled with meso-2,6-diamino-3,4,5-[$^3$H]pimelic acid as substrate. Enzyme (3-10 μg total) was incubated for 45 minutes at 37° C. in a total volume of 100 μl comprising 10 mM Tris-maleate (pH 5.5), 10 mM MgCl$_2$, 0.2% v/v Triton X-100 and [$^3$H]A$_2$ pm labelled murein sacculi (about 10000 cpm). The assay mixture was placed on ice for 15 minutes with 100 μl of 1% w/v N-acetyl-N,N,N-trimethylammonium for 15 minutes and precipitated material pelleted by centrifugation at 10000 g for 15 minutes. The radioactivity in the supernatant was measured by liquid scintillation counting. *E. coli* soluble lytic transglycosylase Slt70 was used as a positive control for the assay; the negative control comprised the above assay solution without enzyme.

All proteins except 919-His gave positive results in the first assay.

The second assay monitors the hydrolysis of poly(Mur-NAc-GlcNAc)glycan strands. Purified strands, poly(Mur-NAc-GlcNAc)$_{n>30}$ labelled with N-acetyl-D-1-[$^3$]glucosamine were incubated with 3 μg of 919L in 10 mM Tris-maleate (pH 5.5), 10 mM MgCl$_2$ and 0.2% v/v Triton X-100 for 30 min at 37° C. The reaction was stopped by boiling for 5 minutes and the pH of the sample adjusted to about 3.5 by addition of 10 μl of 20% v/v phosphoric acid. Substrate and product were separated by reversed phase HPLC on a NUCLEOSIL® 300 C$_{18}$ column (an octadecyl modified silica phase for HPLC) as described by Harz et. al. [*Anal. Biochem.* (1990) 190:120-128]. The *E. coli* lytic transglycosylase Mlt A was used as a positive control in the assay. The negative control was performed in the absence of enzyme.

By this assay, the ability of 919LOrf4 to hydrolyse isolated glycan strands was demonstrated when anhydrodisaccharide subunits were separated from the oligosaccharide by HPLC.

Protein 919Lorf4 was chosen for kinetic analyses. The activity of 919Lorf4 was enhanced 3.7-fold by the addition of 0.2% v/v Triton X-100 in the assay buffer. The presence of Triton X-100 had no effect on the activity of 919$^{untagged}$. The effect of pH on enzyme activity was determined in Tris-Maleate buffer over a range of 5.0 to 8.0. The optimal pH for the reaction was determined to be 5.5. Over the temperature range 18° C. to 42° C., maximum activity was observed at 37° C. The effect of various ions on murein hydrolase activity was determined by performing the reaction in the presence of a variety of ions at a final concentration of 10 mM. Maximum activity was found with Mg$^{2+}$, which stimulated activity 2.1-fold. Mn$^{2+}$ and Ca$^{2+}$ also stimulated enzyme activity to a similar extent while the addition Ni$^{2+}$ and EDTA had no significant effect. In contrast, both Fe$^{2+}$ and Zn$^{2+}$ significantly inhibited enzyme activity.

The structures of the reaction products resulting from the digestion of unlabelled *E. coli* murein sacculus were analysed by reversed-phase HPLC as described by Glauner [*Anal. Biochem.* (1988) 172:451-464]. Murein sacculi digested with the muramidase Cellosyl were used to calibrate and standardise the Hypersil ODS column. The major reaction products were 1,6 anhydrodisaccharide tetra and tri peptides, demonstrating the formation of 1,6 anhydromuraminic acid intramolecular bond.

These results demonstrate experimentally that 919 is a murein hydrolase and in particular a member of the lytic transglycosylase family of enzymes. Furthermore the ability of 922-His to hydrolyse murein sacculi suggests this protein is also a lytic transglycosylase.

This activity may help to explain the toxic effects of 919 when expressed in *E. coli*.

In order to eliminate the enzymatic activity, rational mutagenesis was used. 907, 919 and 922 show fairly low homology to three membrane-bound lipidated murein lytic transglycosylases from *E. coli*:

- 919 (441aa) is 27.3% identical over 440aa overlap to *E. coli* MLTA (P46885);
- 922 (369aa) is 38.7% identical over 310aa overlap to *E. coli* MLTB (P41052); and
- 907-2 (207aa) is 26.8% identical over 149aa overlap to *E. coli* MLTC (P52066).

907-2 also shares homology with *E. coli* MLTD (P23931) and Slt70 (P03810), a soluble lytic transglycosylase that is located in the periplasmic space. No significant sequence homology can be detected among 919, 922 and 907-2, and the same is true among the corresponding MLTA, MLTB and MLTC proteins.

Crystal structures are available for Slt70 [1QTEA; 1QTEB; Thunnissen et al. (1995) *Biochemistry* 34:12729-12737] and for Slt35 [1LTM; 1QUS; 1QUT; van Asselt et al. (1999) *Structure Fold Des* 7:1167-80] which is a soluble form of the 40 kDa MLTB.

The catalytic residue (a glutamic acid) has been identified for both Slt70 and MLTB.

In the case of Slt70, mutagenesis studies have demonstrated that even a conservative substitution of the catalytic Glu505 with a glutamine (Gln) causes the complete loss of enzymatic activity. Although Slt35 has no obvious sequence similarity to Slt70, their catalytic domains shows a surprising similarity. The corresponding catalytic residue in MLTB is Glu162.

Another residue which is believed to play an important role in the correct folding of the enzymatic cleft is a well-conserved glycine (Gly) downstream of the glutamic acid. Recently, Terrak et al. [*Mol. Microbiol.* (1999) 34:350-64] have suggested the presence of another important residue which is an aromatic amino acid located around 70-75 residues downstream of the catalytic glutamic acid.

Sequence alignment of Slt70 (SEQ ID NO:5) with 907-2 (SEQ ID NO:4) and of MLTB (SEQ ID NO:7) with 922 (SEQ ID NO:6) were performed in order to identify the corresponding catalytic residues in the MenB antigens.

The two alignments in the region of the catalytic domain are reported below:

```
907-2/Slt70:

90        100       110      ▼120       130       140
        907-2.pep    ERRRLLVNIQYESSRAG--LDTQIVLGLIEVESAFRQYAISGVGARGLMQVMPFWKNYIG
                     ||    |   ||   ::   :|   :   : :::: : |||:     :| ||| |||:||   ::
        slty_ecoli   ERFPLAYNDLFKRYTSGKEIPQSYAMAIARQESAWNPKVKSPVGASGLMQIMPGTATHTV
                        480       490       500    ▲ 510       520       530
                                                    GLU505

922/MLTB 150       160    ▼ 170       180       190       200
        922.pep      VAQKYGVPAELIVAVIGIETNYGKNTGSFRVADALATLGFDYPRRAGFFQKELVELLKLA
                     :  |    ||||   |:||::||:||   :|:     |:    |:  ||||||:::|||||     :|:    ||    :| :|
        mltb_ecoli   AWQVYGVPPEIIVGIIGVETRWGRVMGKTRILDALATLSFNYPRRAEYFSGELETFLLMA
                        150       160 ▲ 170       180       190       200
                                         GLU162

210       220       230       240       250       260
        922.pep      KEEGGDVFAFKGSYAGAMGMPQFMPSSYRKWAVDYDGDGHRDIWGNVGDVAASVANYMKQ
                     ::|    |  :  :|||:|||||   |||||||:::|||::||||    ::|    |  |:   :|||||:|
        mltb_ecoli   RDEQDDPLNLKGSFAGAMGYGQFMPSSYKQYAVDFSGDGHINLWDPV-DAIGSVANYFKA
                        210       220       230       240       250       260
```

From these alignments, it results that the corresponding catalytic glutamate in 907-2 is Glu117, whereas in 922 is Glu164. Both antigens also share downstream glycines that could have a structural role in the folding of the enzymatic cleft (in bold), and 922 has a conserved aromatic residue around 70aa downstream (in bold).

In the case of protein 919, no 3D structure is available for its *E. coli* homologue MLTA, and nothing is known about a possible catalytic residue. Nevertheless, three amino acids in 919 (SEQ ID NO:8) are predicted as catalytic residues by alignment with MLTA (SEQ ID NO:9):

```
919/MLTA 240       250    ▼ 260       270       280       290
        919.pep      ALDGKAPILGYAEDPVELFFMHIQGSGRLKTPSGKYIRI-GYADKNEHPYVSIGRYMADK
                     ||:|    ||:|:::  ::    |:|    :|||||       :|:  :  :||  ||   |   |||:    :|:
        mlta_ecoli.p ALSDKY-ILAYSNSLMDNFIMDVQGSGYIDFGDGSPLNFFSYAGKNGHAYRSIGKVLIDR
                        170       180       190       200       210

300       310       320     ▼ 330       340      ◊350     ◊
        919.pep      GYLKLGQTSMQGIKSYMRQNPQ-RLAEVLGQNPSYIFFRELAGSSNDGPV-GALGTPLMG
                     |:|   :   |||:|:   :   :    :  ::    |:|   ||||:||:     :     ||   ||   ::||:|
        mlta_ecoli.p GEVKKEDMSMQAIRHWGETHSEAEVRELLEQNPSFVFFKPQSFA----PVKGASAVPLVG
                        220       230       240       250       260       270
```

-continued

```
              360 ▼          o                   390        400    ◊◊410
919.pep       EYAGAVDRHYITLGAPLFVATAHPVTRKALN-----RLIMAQDTGSAIKGAVRVDYFWGY
              : :  ||   |   |:  |:: :     :      : |    ||::| |:|:|||   : | : |
mlta_ecoli.p  RASVASDRSIIPPGTTLLAEVPLLDNNGKFNGQYELRLMVALDVGGAIKGQ-HFDIYQGI
                 280       290       300       310       320       330

420       o
919.pep       GDEAGELAGKQKTTGYVWQLLP
              | |||:  ||    |  ||| |
mlta_ecoli.p  GPEAGHRAGWYNHYGRVWVLKT
                 340       350
```

The three possible catalytic residues are shown by the symbol ▼:
1) Glu255 (Asp in MLTA), followed by three conserved glycines (Gly263, Gly265 and Gly272) and three conserved aromatic residues located approximately 75-77 residues downstream. These downstream residues are shown by □.
2) Glu323 (conserved in MLTA), followed by 2 conserved glycines (Gly347 and Gly355) and two conserved aromatic residues located 84-85 residues downstream (Tyr406 or Phe407). These downstream residues are shown by ◊.
3) Asp362 (instead of the expected Glu), followed by one glycine (Gly 369) and a conserved aromatic residue (Trp428). These downstream residues are shown by o.

Alignments of polymorphic forms of 919 are disclosed in WO00/66741.

Based on the prediction of catalytic residues, three mutants of the 919 and one mutant of 907, containing each a single amino acid substitution, have been generated. The glutamic acids in position 255 and 323 and the aspartic acids in position 362 of the 919 protein and the glutamic acid in position 117 of the 907 protein, were replaced with glycine residues using PCR-based SDM. To do this, internal primers containing a codon change from Glu or Asp to Gly were designed:

| Primers | SEQ ID NO | Sequences | Codon change |
|---|---|---|---|
| 919-E255 for | 10 | CGAAGACCCCGTCGgtCT GAA TTTTTTTATG | → Ggt |
| 919-E255 rev | 11 | GTGCATAAAAAAAAGacC GACGGGGTCT | |
| 919-E323 for | 12 | AACGCCTCGCCGgtGTTT GAA TGGGTCA | → Ggt |
| 919-E323 rev | 13 | TTTGACCCAAAACacCGG CGAGGCG | |
| 919-D362 for | 14 | TGCCGGCGCAGTCGgtCG GAC GCACTACA | → Ggt |
| 919-D362 rev | 15 | TAATGTAGTGCCGacCGA CTGCGCCG | |
| 907-E117 for | 16 | TGATTGAGGTGGgtAGCG GAA CGTTCCG | → Ggt |
| 907-E117 rev | 17 | GGCGGAACGCGCTacCCA CCTCAAT | |

Underlined nucleotides code for glycine; the mutated nucleotides are in lower case.

To generate the 919-E255, 919-E323 and 919-E362 mutants, PCR was performed using 20 ng of the pET 919-LOrf4 DNA as template, and the following primer pairs:
1) Orf4L for/919-E255 rev
2) 919-E255 for/919L rev
3) Orf4L for/919-E323 rev
4) 919-E323 for/919L rev
5) Orf4L for/919-D362 rev
6) 919-D362 for/919L rev The second round of PCR was performed using the product of PCR 1-2, 3-4 or 5-6 as template, and as forward and reverse primers the "Orf4L for" and "919L rev" respectively.

For the mutant 907-E117, PCR have been performed using 200 ng of chromosomal DNA of the 2996 strain as template and the following primer pairs:
7) 907L for/907-E117 rev
8) 907-E117 for/907L rev The second round of PCR was performed using the products of PCR 7 and 8 as templates and the oligos "907L for" and "907L rev" as primers.

The PCR fragments containing each mutation were processed following the standard procedure, digested with NdeI and XhoI restriction enzymes and cloned into pET-21b+ vector. The presence of each mutation was confirmed by sequence analysis.

Mutation of Glu117 to Gly in 907 is carried out similarly, as is mutation of residues Glu164, Ser213 and Asn348 in 922.

The E255G mutant of 919 shows a 50% reduction in activity; the E323G mutant shows a 70% reduction in activity; the E362G mutant shows no reduction in activity.

Example 4

Multimeric Form

287-GST, 919$^{untagged}$ and 953-His were subjected to gel filtration for analysis of quaternary structure or preparative purposes. The molecular weight of the native proteins was estimated using either FPLC Superose 12 (H/R 10/30) or SUPERDEX™ 75 gel filtration columns (prepacked columns, Pharmacia). The buffers used for chromatography for 287, 919 and 953 were 50 mM Tris-HCl (pH 8.0), 20 mM Bicine (pH 8.5) and 50 mM Bicine (pH 8.0), respectively. Additionally each buffer contained 150-200 mM NaCl and 10% v/v glycerol. Proteins were dialysed against the appropriate buffer and applied in a volume of 200 μl. Gel filtration was performed with a flow rate of 0.5-2.0 ml/min and the eluate monitored at 280 nm. Fractions were collected and analysed by SDS-PAGE. Blue dextran 2000 and the molecular weight standards ribonuclease A, chymotrypsin A ovalbumin, albumin (Pharmacia) were used to calibrate the column. The molecular weight of the sample was estimated from a calibration curve of $K_{av}$ vs. log $M_r$ of the standards. Before gel filtration, 287-GST was digested with thrombin to cleave the GST moiety.

The estimated molecular weights for 287, 919 and 953-His were 73 kDa, 47 kDa and 43 kDa respectively. These results suggest 919 is monomeric while both 287 and 953 are principally dimeric in their nature. In the case of 953-His, two peaks were observed during gel filtration. The major peak (80%) represented a dimeric conformation of 953 while the minor peak (20%) had the expected size of a monomer. The monomeric form of 953 was found to have greater bactericidal activity than the dimer.

Example 5 pSM214 and pET-24b Vectors 953 protein with its native leader peptide and no fusion partners was expressed from the pET vector and also from pSM214 [Velati Bellini et al. (1991) *J. Biotechnol.* 18, 177-192].

The 953 sequence was cloned as a full-length gene into pSM214 using the *E. coli* MM294-1 strain as a host. To do this, the entire DNA sequence of the 953 gene (from ATG to the STOP codon) was amplified by PCR using the following primers:

```
                                          (SEQ ID NO: 18)
953L for/2 CCGGAATTCTTATGAAAAAAATCATCTTCG  Eco RI
CCGC (SEQ ID NO: 19)
953L rev/2 GCCCAAGCTTTTATTGTTTGGCTGCCTCG   Hind III
ATT
``` which contain EcoRI and HindIII restriction sites, respectively. The amplified fragment was digested with EcoRI and HindIII and ligated with the pSM214 vector digested with the same two enzymes. The ligated plasmid was transformed into *E. coli* MM294-1 cells (by incubation in ice for 65 minutes at 37° C.) and bacterial cells plated on LB agar containing 20 µg/ml of chloramphenicol.

Recombinant colonies were grown over-night at 37° C. in 4 ml of LB broth containing 20 µg/ml of chloramphenicol; bacterial cells were centrifuged and plasmid DNA extracted as and analysed by restriction with EcoRI and HindIII. To analyse the ability of the recombinant colonies to express the protein, they were inoculated in LB broth containing 20 µg/ml of chloramphenicol and let to grown for 16 hours at 37° C. Bacterial cells were centrifuged and resuspended in PBS. Expression of the protein was analysed by SDS-PAGE and Coomassie Blue staining.

Expression levels were unexpectedly high from the pSM214 plasmid.

Oligos used to clone sequences into pSM-214 vectors were as follows:

```
                                                              (SEQ ID NO: 20)
ΔG287           Fwd CCGGAATTCTTATG-TCGCCCGATGTTAAATCGGCGGA     EcoRI (SEQ ID NO: 21)
(pSM-214)       Rev GCCCAAGCTT-TCAATCCTGCTCTTTTTTGCCG          HindIII (SEQ ID NO: 22)
Δ2 287          Fwd CCGGAATTCTTATG-AGCCAAGATATGGCGGCAGT        EcoRI (SEQ ID NO: 23)
(pSM-214)       Rev GCCCAAGCTT-TCAATCCTGCTCTTTTTTGCCG          HindIII (SEQ ID NO: 24)
Δ3 287          Fwd CCGGAATTCTTATG-TCCGCCGAATCCGCAAATCA        EcoRI (SEQ ID NO: 25)
(pSM-214)       Rev GCCCAAGCTT-TCAATCCTGCTCTTTTTTGCCG          HindIII (SEQ ID NO: 26)
Δ4 287          Fwd CCGGAATTCTTATG-GGAAGGGTTGATTTGGCTAATG      EcoRI (SEQ ID NO: 27)
(pSM-214)       Rev GCCCAAGCTT-TCAATCCTGCTCTTTTTTGCCG          HindIII (SEQ ID NO: 28)
Orf46.1         Fwd CCGGAATTCTTATG-TCAGATTTGGCAAACGATTCTT      EcoRI (SEQ ID NO: 29)
(pSM-214)       Rev GCCCAAGCTT-TTACGTATCATATTTCACGTGCTTC       HindIII (SEQ ID NO: 30)
ΔG287-Orf46.1 Fwd CCGGAATTCTTATG-TCGCCCGATGTTAAATCGGCGGA EcoRI (SEQ ID NO: 31)
(pSM-214)       Rev GCCCAAGCTT-TTACGTATCATATTTCACGTGCTTC       HindIII (SEQ ID NO: 32)
919             Fwd CCGGAATTCTTATG-CAAAGCAAGAGCATCCAAACCT      EcoRI (SEQ ID NO: 33)
(pSM-214)       Rev GCCCAAGCTT-TTACGGGCGGTATTCGGGCT            HindIII (SEQ ID NO: 34)
961L            Fwd CCGGAATTCATATG-AAACACTTTCCATCC             EcoRI (SEQ ID NO: 35)
(pSM-214)       Rev GCCCAAGCTT-TTACCACTCGTAATTGAC              HindIII (SEQ ID NO: 36)
961             Fwd CCGGAATTCATATG-GCCACAAGCGACGAC             EcoRI (SEQ ID NO: 37)
(pSM-214)       Rev GCCCAAGCTT-TTACCACTCGTAATTGAC              HindIII
```

```
961c L          Fwd CCGGAATTCTTATG-AAACACTTTCCATCC            (SEQ ID NO: 38)
                                                              EcoRI pSM-214         Rev GCCCAAGCTT-TCAACCCACGTTGTAAGGTTG           (SEQ ID NO: 39)
                                                              HindIII 961c            Fwd CCGGAATTCTTATG-GCCACAAACGACGACG            (SEQ ID NO: 40)
                                                              EcoRI pSM-214         Rev GCCCAAGCTT-TCAACCCACGTTGTAAGGTTG           (SEQ ID NO: 41)
                                                              HindIII 953             Fwd CCGGAATTCTTATG-GCCACCTACAAAGTGGACGA        (SEQ ID NO: 42)
                                                              EcoRI (pSM-214)       Rev GCCCAAGCTT-TTATTGTTTGGCTGCCTCGATT          (SEQ ID NO: 43)
                                                              HindIII
```

These sequences were manipulated, cloned and expressed as described for 953L.

For the pET-24 vector, sequences were cloned and the proteins expressed in pET-24 as described below for pET21. pET2 has the same sequence as pET-21, but with the kanamycin resistance cassette instead of ampicillin cassette.

Oligonucleotides used to clone sequences into pET-24b vector were:

```
ΔG 287 K        Fwd CGCGGATCCGCTAGC-CCCGATGTTAAATCGGC§         (SEQ ID NO: 44)
                                                              NheI

Rev CCCGCTCGAG-TCAATCCTGCTCTTTTTTGCC*          (SEQ ID NO: 45)
                                                              XhoI

Δ2 287 K        Fwd CGCGGATCCGCTAGC-CAAGATATGGCGGCAGT§         (SEQ ID NO: 46)
                                                              NheI

Δ3 287 K        Fwd CGCGGATCCGCTAGC-GCCGAATCCGCAAATCA§         (SEQ ID NO: 47)
                                                              NheI

Δ4 287 K        Fwd CGCGCTAGC-GGAAGGGTTGATTTGGCTAATGG§         (SEQ ID NO: 48)
                                                              NheI

Orf46.1 K       Fwd GGGAATTCCATATG-GGCATTTCCCGCAAAATATC        (SEQ ID NO: 49)
                                                              NdeI

Rev CCCGCTCGAG-TTACGTATCATATTTCACGTGC          (SEQ ID NO: 50)
                                                              XhoI

Orf46A K        Fwd GGGAATTCCATATG-GGCATTTCCCGCAAAATATC        (SEQ ID NO: 51)
                                                              NdeI

Rev CCCGCTCGAG-TTATTCTATGCCTTGTGCGGCAT         (SEQ ID NO: 52)
                                                              XhoI

961 K           Fwd CGCGGATCCCATATG-GCCACAAGCGACGACGA          (SEQ ID NO: 53)
                                                              NdeI (MC58)          Rev CCCGCTCGAG-TTACCACTCGTAATTGAC              (SEQ ID NO: 54)
                                                              XhoI

961a K          Fwd CGCGGATCCCATATG-GCCACAAACGACG              (SEQ ID NO: 55)
                                                              NdeI

Rev CCCGCTCGAG-TCATTTAGCAATATTATCTTTGTTC       (SEQ ID NO: 56)
                                                              XhoI

961b K          Fwd CGCGGATCCCATATG-AAAGCAAACAGTGCCGAC         (SEQ ID NO: 57)
                                                              NdeI

Rev CCCGCTCGAG-TTACCACTCGTAATTGAC              (SEQ ID NO: 58)
                                                              XhoI

961c K          Fwd CGCGGATCCCATATG-GCCACAAACGACG              (SEQ ID NO: 59)
                                                              NdeI

Rev CCCGCTCGAG-TTAACCCACGTTGTAAGGT             (SEQ ID NO: 60)
                                                              XhoI
```

-continued

```
                                                       (SEQ ID NO: 61)
961cL K           Fwd CGCGGATCCCATATG-ATGAAACACTTTCCATCC    NdeI (SEQ ID NO: 62)
                  Rev CCCGCTCGAG-TTAACCCACGTTGTAAGGT         XhoI (SEQ ID NO: 63)
961d K            Fwd CGCGGATCCCATATG-GCCACAAACGACG          NdeI (SEQ ID NO: 64)
                  Rev CCCGCTCGAG-TCAGTCTGACACTGTTTTATCC      XhoI (SEQ ID NO: 65)
ΔG 287-919 K      Fwd CGCGGATCCGCTAGC-CCCGATGTTAAATCGGC      NheI (SEQ ID NO: 66)
                  Rev CCCGCTCGAG-TTACGGGCGGTATTCGG           XhoI (SEQ ID NO: 67)
ΔG 287-Orf46.1 K  Fwd CGCGGATCCGCTAGC-CCCGATGTTAAATCGGC      NheI (SEQ ID NO: 68)
                  Rev CCCGCTCGAG-TTACGTATCATATTTCACGTGC      XhoI (SEQ ID NO: 69)
ΔG 287-961 K      Fwd CGCGGATCCGCTAGC-CCCGATGTTAAATCGGC      NheI (SEQ ID NO: 70)
                  Rev CCCGCTCGAG-TTACCACTCGTAATTGAC          XhoI
```

*This primer was used as a Reverse primer for all the 287 forms.
§Forward primers used in combination with the ΔG278 K reverse primer.

Example 6

ORF1 and its Leader Peptide

ORF1 from *N. meningitidis* (serogroup B, strain MC58) is predicted to be an outer membrane or secreted protein. It has the following sequence (SEQ ID NO:71):

```
  1 MKTTDKRTTE THRKAPKTGR IRFSPAYLAI CLSFGILPQA WAGHTYFGIN

51 YQYYRDFAEN KGKFAVGAKD IEVYNKKGEL VGKSMTKAPM IDFSVVSRNG

101 VAALVGDQYI VSVAHNGGYN NVDFGAEGRN PDQHRFTYKI VKRNNYKAGT

151 KGHPYGGDYH MPRLHKFVTD AEPVEMTSYM DGRKYIDQNN YPDRVRIGAG

201 RQYWRSDEDE PNNRESSYHI ASAYSWLVGG NTFAQNGSGG GTVNLGSEKI

251 KHSPYGFLPT GGSFGDSGSP MFIYDAQKQK WLINGVLQTG NPYIGKSNGF

301 QLVRKDWFYD EIFAGDTHSV FYEPRQNGKY SFNDDNNGTG KINAKHEHNS

351 LPNRLKTRTV QLFNVSLSET AREPVYHAAG GVNSYRPRLN NGENISFIDE

401 GKGELILTSN INQGAGGLYF QGDFTVSPEN NETWQGAVH  ISEDSTVTWK

451 VNGVANDRLS KIGKGTLHVQ AKGENQGSIS VGDGTVILDQ QADDKGKKQA

501 FSEIGLVSGR GTVQLNADNQ FNPDKLYFGF RGGRLDLNGH SLSFHRIQNT

551 DEGAMIVNHN QDKESTVTIT GNKDIATTGN NNSLDSKKEI AYNGWFGEKD

601 TTKTNGRLNL VYQPAAEDRT LLLSGGTNLN GNITQTNGKL FFSGRPTPHA

651 YNHLNDHWSQ KEGIPRGEIV WDNDWINRTF KAENFQIKGG QAVVSRNVAK

701 VKGDWHLSNH AQAVFGVAPH QSHTICTRSD WTGLTNCVEK TITDDKVIAS

751 LTKTDISGNV DLADHAHLNL TGLATLNGNL SANGDTRYTV SHNATQNGNL

801 SLVGNAQATF NQATLNGNTS ASGNASFNLS DHAVQNGSLT LSGNAKANVS

851 HSALNGNVSL ADKAVFHFES SRFTGQISGG KDTALHLKDS EWTLPSGTEL
```

```
 901  GNLNLDNATI  TLNSAYRHDA  AGAQTGSATD  APRRRSRRSR  RSLLSVTPPT
 951  SVESRFNTLT  VNGKLNGQGT  FRFMSELFGY  RSDKLKLAES  SEGTYTLAVN
1001  NTGNEPASLE  QLTVVEGKDN  KPLSENLNFT  LQNEHVDAGA  WRYQLIRKDG
1051  EFRLHNPVKE  QELSDKLGKA  EAKKQAEKDN  AQSLDALIAA  GRDAVEKTES
1101  VAEPARQAGG  ENVGIMQAEE  EKKRVQADKD  TALAKQREAE  TRPATTAFPR
1151  ARRARRDLPQ  LQPQPQPQPQ  RDLISRYANS  GLSEFSATLN  SVFAVQDELD
1201  RVFAEDRRNA  VWTSGIRDTK  HYRSQDFRAY  RQQTDLRQIG  MQKNLGSGRV
1251  GILFSHNRTE  NTFDDGIGNS  ARLAHGAVFG  QYGIDRFYIG  ISAGAGFSSG
1301  SLSDGIGGKI  RRRVLHYGIQ  ARYRAGFGGF  GIEPHIGATR  YFVQKADYRY
1351  ENVNIATPGL  AFNRYRAGIK  ADYSFKPAQH  ISITPYLSLS  YTDAASGKVR
1401  TRVNTAVLAQ  DFGKTRSAEW  GVNAEIKGFT  LSLHAAAAKG  PQLEAQHSAG
1451  IKLGYRW*
```

The leader peptide is underlined.

A polymorphic form of ORF1 is disclosed in WO99/55873.

Three expression strategies have been used for ORF1:
1) ORF1 using a His tag, following WO99/24578 (ORF1-His);
2) ORF1 with its own leader peptide but without any fusion partner ('ORF1L'); and
3) ORF1 with the leader peptide (MKKTAIAIAVALAGFATVAQA (SEQ ID NO:72)) from *E. coli* OmpA ('Orf1LOmpA') (SEQ ID NO:73):

To make this construct, the clone pET911LOmpA (see below) was digested with the NheI and XhoI restriction enzymes and the fragment corresponding to the vector carrying the OmpA leader sequence was purified (pETLOmpA). The ORF1 gene coding for the mature protein was amplified using the oligonucleotides ORF1-For and ORF1-Rev (including the NheI and XhoI restriction sites, respectively), digested with NheI and XhoI and ligated to the purified pETOmpA fragment (see FIG. 1). An additional AS dipeptide was introduced by the NheI site.

MKKTAIAIAVALAGFATVAQAASAGHTYFGINYQYYRDFAENKGKFAVGAKDIEVYNKKGELVGKSMTKAPMIDFSV

VSRNGVAALVGDQYIVSVAHNGGYNNVDFGAEGRNPDQHRFTYKIVKRNNYKAGTKGHPYGGDYHMPRLHKFVTDAE

PVEMTSYMDGRKYIDQNNYPDRVRIGAGRQYWRSDEDEPNNRESSYHIASAYSWLVGGNTFAQNGSGGGTVNLGSEK

IKHSPYGFLPTGGSFGDSGSPMFIYDAQKQKWLINGVLQTGNPYIGKSNGFQLVRKDWFYDEIFAGDTHSVFYEPRQ

NGKYSFNDDNNGTGKINAKHEHNSLPNRLKTRTVQLFNVSLSETAREPVYHAAGGVNSYRPRLNNGENISFIDEGKG

ELILTSNINQGAGGLYFQGDFTVSPENNETWQGAGVHISEDSTVTWKVNGVANDRLSKIGKGTLHVQAKGENQGSIS

VGDGTVILDQQADDKGKKQAFSEIGLVSGRGTVQLNADNQFNPDKLYFGFRGGRLDLNGHSLSFHRIQNTDEGAMIV

NHNQDKESTVTITGNKDIATTGNNNSLDSKKEIAYNGWFGEKDTTKTNGRLNLVYQPAAEDRTLLLSGGTNLNGNIT

QTNGKLFFSGRPTPHAYNHLNDHWSQKEGIPRGEIVWDNDWINRTFKAENFQIKGGQAVVSRNVAKVKGDWHLSNHA

QAVFGVAPHQSHTICTRSDWTGLTNCVEKTITDDKVIASLTKTDISGNVDLADHAHLNLTGLATLNGNLSANGDTRY

TVSHNATQNGNLSLVGNAQATFNQATLNGNTSASGNASFNLSDHAVQNGSLTLSGNAKANVSHSALNGNVSLADKAV

FHFESSRFTGQISGGKDTALHLKDSEWTLPSGTELGNLNLDNATITLNSAYRHDAAGAQTGSATDAPRRRSRRSRS

LLSVTPPTSVESRFNTLTVNGKLNGQGTFRFMSELFGYRSDKLKLAESSEGTYTLAVNNTGNEPASLEQLTVVEGKD

NKPLSENLNFTLQNEHVDAGAWRYQLIRKDGEFRLHNPVKEQELSDKLGKAEAKKQAEKDNAQSLDALIAAGRDAVE

KTESVAEPARQAGGENVGIMQAEEEKKRVQADKDTALAKQREAETRPATTAFPRARRARRDLPQLQPQPQPQPQRDL

ISRYANSGLSEFSATLNSVFAVQDELDRVFAEDRRNAVWTSGIRDTKHYRSQDFRAYRQQTDLRQIGMQKNLGSGRV

GILFSHNRTENTFDDGIGNSARLAHGAVFGQYGIDRFYIGISAGAGFSSGSLSDGIGGKIRRRVLHYGIQARYRAGF

GGFGIEPHIGATRYFVQKADYRYENVNIATPGLAFNRYRAGIKADYSFKPAQHISITPYLSLSYTDAASGKVRTRVN

TAVLAQDFGKTRSAEWGVNAEIKGFTLSLHAAAAKGPQLEAQHSAGIKLGYRW*

All three forms of the protein were expressed. The His-tagged protein could be purified and was confirmed as surface exposed, and possibly secreted (see FIG. 3). The protein was used to immunise mice, and the resulting sera gave excellent results in the bactericidal assay.

ORF1LOmpA was purified as total membranes, and was localised in both the inner and outer membranes. Unexpectedly, sera raised against ORF1LOmpA show even better ELISA and anti-bactericidal properties than those raised against the His-tagged protein.

ORF1L was purified as outer membranes, where it is localised.

Example 7

Protein 911 and its Leader Peptide

Protein 911 from *N. meningitidis* (serogroup B, strain MC58) has the following sequence (SEQ ID NO:74):

```
  1 MKKNILEFWV GLFVLIGAAA VAFLAFRVAG GAAFGGSDKT YAVYADFGDI

51 GGLKVNAPVK SAGVLVGRVG AIGLDPKSYQ ARVRLDLDGK YQFSSDVSAQ

101 ILTSGLLGEQ YIGLQQGGDT ENLAAGDTIS VTSSAMVLEN LIGKFMTSFA

151 EKNADGGNAE KAAE*
```

The leader peptide is underlined.
Three expression strategies have been used for 911:
1) 911 with its own leader peptide but without any fusion partner ('911L');
2) 911 with the leader peptide from *E. coli* OmpA ('911LOmpA').
   To make this construct, the entire sequence encoding the OmpA leader peptide was included in the 5'-primer as a tail (primer 911LOmpA Forward). A NheI restriction site was inserted between the sequence coding for the OmpA leader peptide and the 911 gene encoding the predicted mature protein (insertion of one amino acid, a serine), to allow the use of this construct to clone different genes downstream the OmpA leader peptide sequence.
3) 911 with the leader peptide (MKYLLPTAAAGLL-LAAQPAMA (SEQ ID NO:75)) from *Erwinia carotovora* PelB ('911LpelB').
   To make this construct, the 5'-end PCR primer was designed downstream from the leader sequence and included the NcoI restriction site in order to have the 911 fused directly to the PelB leader sequence; the 3'-end primer included the STOP codon. The expression vector used was pET22b+ (Novagen), which carries the coding sequence for the PelB leader peptide. The NcoI site introduces an additional methionine after the PelB sequence.

All three forms of the protein were expressed. ELISA titres were highest using 911L, with 919LOmpA also giving good results.

Example 8

ORF46

The complete ORF46 protein from *N. meningitidis* (serogroup B, strain 2996) has the following sequence (SEQ ID NO:76):

```
  1 LGISRKISLI LSILAVCLPM HAHASDLAND SFIRQVLDRQ HFEPDGKYHL

51 FGSRGELAER SGHIGLGKIQ SHQLGNLMIQ QAAIKGNIGY IVRFSDHGHE

101 VHSPFDNHAS HSDSDEAGSP VDGFSLYRIH WDGYEHHPAD GYDGPQGGGY

151 PAPKGARDIY SYDIKGVAQN IRLNLTDNRS TGQRLADRFH NAGSMLTQGV

201 GDGFKRATRY SPELDRSGNA AEAFNGTADI VKNIIGAAGE IVGAGDAVQG
```

-continued

```
251  ISEGSNIAVM HGLGLLSTEN KMARINDLAD MAQLKDYAAA AIRDWAVQNP

301  NAAQGIEAVS NIFMAAIPIK GIGAVRGKYG LGGITAHPIK RSQMGAIALP

351  KGKSAVSDNF ADAAYAKYPS PYHSRNIRSN LEQRYGKENI TSSTVPPSNG

401  KNVKLADQRH PKTGVPFDGK GFPNFEKHVK YDTKLDIQEL SGGGIPKAKP

451  VSDAKPRWEV DRKLNKLTTR EQVEKNVQEI RNGNKNSNFS QHAQLEREIN

501  KLKSADEINF ADGMGKFTDS MNDKAFSRLV KSVKENGFTN PVVEYVEING

551  KAYIVRGNNR VFAAEYLGRI HELKFKKVDF PVPNTSWKNP TDVLNESGNV

601  KRPRYRSK*
```

The leader peptide is underlined.
The sequences of ORF46 from other strains can be found in WO00/66741.

Three expression strategies have been used for ORF46:
1) ORF46 with its own leader peptide but without any fusion partner ('ORF46-2L');

ORF46 without its leader peptide and without any fusion partner ('ORF46-2'), with the leader peptide omitted by designing the 5'-end amplification primer downstream from the predicted leader sequence (SEQ ID NO:77):

```
  1  SDLANDSFIR QVLDRQHFEP DGKYHLFGSR GELAERSGHI GLGKIQSHQL

51  GNLMIQQAAI KGNIGYIVRF SDHGHEVHSP FDNHASHSDS DEAGSPVDGF

101  SLYRIHWDGY EHHPADGYDG PQGGGYPAPK GARDIYSYDI KGVAQNIRLN

151  LTDNRSTGQR LADRFHNAGS MLTQGVGDGF KRATRYSPEL DRSGNAAEAF

201  NGTADIVKNI IGAAGEIVGA GDAVQGISEG SNIAVMHGLG LLSTENKMAR

251  INDLADMAQL KDYAAAAIRD WAVQNPNAAQ GIEAVSNIFM AAIPIKGIGA

301  VRGKYGLGGI TAHPIKRSQM GAIALPKGKS AVSDNFADAA YAKYPSPYHS

351  RNIRSNLEQR YGKENITSST VPPSNGKNVK LADQRHPKTG VPFDGKGFPN

401  FEKHVKYDTK LDIQELSGGG IPKAKPVSDA KPRWEVDRKL NKLTTREQVE

451  KNVQEIRNGN KNSNFSQHAQ LEREINKLKS ADEINFADGM GKFTDSMNDK

501  AFSRLVKSVK ENGFTNPVVE YVEINGKAYI VRGNNRVFAA EYLGRIHELK

551  FKKVDFPVPN TSWKNPTDVL NESGNVKRPR YRSK*
```

3) ORF46 as a truncated protein, consisting of the first 433 amino acids ('ORF46.1L'), constructed by designing PCR primers to amplify a partial sequence corresponding to aa 1-433.

A STOP codon was included in the 3'-end primer sequences.

ORF46-2L is expressed at a very low level to *E. coli*. Removal of its leader peptide (ORF46-2) does not solve this problem. The truncated ORF46.1L form (first 433 amino acids, which are well conserved between serogroups and species), however, is well-expressed and gives excellent results in ELISA test and in the bactericidal assay.

ORF46.1 has also been used as the basis of hybrid proteins. It has been fused with 287, 919, and ORF1. The hybrid proteins were generally insoluble, but gave some good ELISA and bactericidal results (against the homologous 2996 strain):

| Protein | ELISA | Bactericidal Ab |
|---|---|---|
| Orf1-Orf46.1-His | 850 | 256 |
| 919-Orf46.1-His | 12900 | 512 |
| 919-287-Orf46-His | n.d. | n.d. |
| Orf46.1-287His | 150 | 8192 |
| Orf46.1-919His | 2800 | 2048 |
| Orf46.1-287-919His | 3200 | 16384 |

For comparison, 'triple' hybrids of ORF46.1, 287 (either as a GST fusion, or in ΔG287 form) and 919 were constructed and tested against various strains (including the homologous 2996 strain) versus a simple mixture of the three antigens. FCA was used as adjuvant:

| | 2996 | BZ232 | MC58 | NGH38 | F6124 | BZ133 |
|---|---|---|---|---|---|---|
| Mixture | 8192 | 256 | 512 | 1024 | >2048 | >2048 |
| ORF46.1-287-919his | 16384 | 256 | 4096 | 8192 | 8192 | 8192 |
| ΔG287-919-ORF46.1his | 8192 | 64 | 4096 | 8192 | 8192 | 16384 |
| ΔG287-ORF46.1-919his | 4096 | 128 | 256 | 8192 | 512 | 1024 |

Again, the hybrids show equivalent or superior immunological activity.

Hybrids of two proteins (strain 2996) were compared to the individual proteins against various heterologous strains:

|  | 1000 | MC58 | F6124 (MenA) |
|---|---|---|---|
| ORF46.1-His | <4 | 4096 | <4 |
| ORF1-His | 8 | 256 | 128 |
| ORF1-ORF46.1-His | 1024 | 512 | 1024 |

Again, the hybrid shows equivalent or superior immunological activity.

Example 9

Protein 961

The complete 961 protein from *N. meningitidis* (serogroup B, strain MC58) has the following sequence (SEQ ID NO:78):

```
  1 MSMKHFPAKV LTTAILATFC SGALAATSDD DVKKAATVAI VAAYNNGQEI
 51 NGFKAGETIY DIGEDGTITQ KDATAADVEA DDFKGLGLKK VVTNLTKTVN
101 ENKQNVDAKV KAAESEIEKL TTKLADTDAA LADTDAALDE TTNALNKLGE
151 NITTFAEETK TNIVKIDEKL EAVADTVDKH AEAFNDIADS LDETNTKADE
201 AVKTANEAKQ TAEETKQNVD AKVEAAETAA GKAEAAAGTA NTAADKAEAV
251 AAKVTDIKAD IATNKADIAK NSARIDSLDK NVANLRKETR QGLAEQAALS
301 GLFQPYNVGR FNVTAAVGGY KSESAVAIGT GFRFTENFAA KAGVAVGTSS
351 GSSAAYHVGV NYEW*
```

The leader peptide is underlined.
Three approaches to 961 expression were used:
1) 961 using a GST fusion, following WO99/57280 ('GST961');
2) 961 with its own leader peptide but without any fusion partner ('961L'); and
3) 961 without its leader peptide and without any fusion partner ('961$^{untagged}$') with the leader peptide omitted by designing the 5'-end PCR primer downstream from the predicted leader sequence.

All three forms of the protein were expressed. The GST-fusion protein could be purified and antibodies against it confirmed that 961 is surface exposed (FIG. 4). The protein was used to immunise mice, and the resulting sera gave excellent results in the bactericidal assay. 961L could also be purified and gave very high ELISA titres.

Protein 961 appears to be phase variable. Furthermore, it is not found in all strains of *N. meningitidis*.

Example 10

Protein 287

Protein 287 from *N. meningitidis* (serogroup B, strain 2996) has the following sequence (SEQ ID NO:79):

```
  1 MFERSVIAMA CIFALSACGG GGGGSPDVKS ADTLSKPAAP VVAEKETEVK
 51 EDAPQAGSQG QGAPSTQGSQ DMAAVSAENT GNGGAATTDK PKNEDEGPQN
101 DMPQNSAESA NQTGNNQPAD SSDSAPASNP APANGGSNFG RVDLANGVLI
151 DGPSQNITLT HCKGDSCNGD NLLDEEAPSK SEFENLNESE RIEKYKKDGK
201 SDKFTNLVAT AVQANGTNKY VIIYKDKSAS SSSARFRRSA RSRRSLPAEM
251 PLIPVNQADT LIVDGEAVSL TGHSGNIFAP EGNYRYLTYG AEKLPGGSYA
301 LRVQGEPAKG EMLAGTAVYN GEVLHFHTEN GRPYPTRGRF AAKVDFGSKS
```

```
351  VDGIIDSGDD LHMGTQKFKA AIDGNGFKGT WTENGGGDVS GRFYGPAGEE

401  VAGKYSYRPT DAEKGGFGVF AGKKEQD*
```

The leader peptide is shown underlined.

Figure 5:
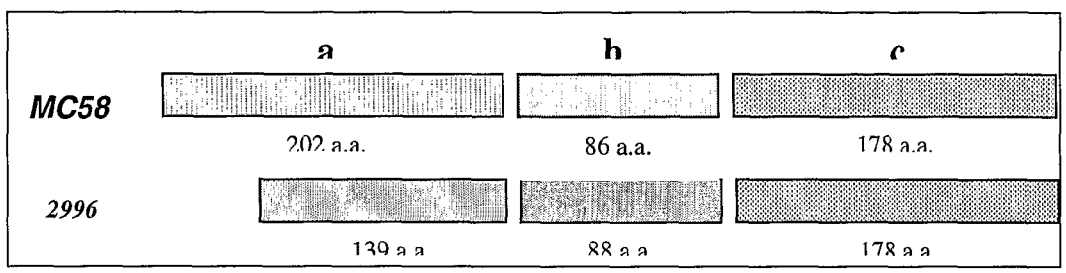
FIG. 5 shows domains of protein 287.

The sequences of 287 from other strains can be found in FIGS. 5 and 15 of WO00/66741.

Example 9 of WO99/57280 discloses the expression of 287 as a GST-fusion in *E. coli*.

A number of further approaches to expressing 287 in *E. coli* have been used, including:
1) 287 as a His-tagged fusion ('287-His');
2) 287 with its own leader peptide but without any fusion partner ('287L');
3) 287 with the ORF4 leader peptide and without any fusion partner ('287LOrf4'); and
4) 287 without its leader peptide and without any fusion partner ('287$^{untagged}$') (SEQ ID NO:80):

```
  1  CGGGGGGSPD VKSADTLSKP AAPVVAEKET EVKEDAPQAG SQGQGAPSTQ

51  GSQDMAAVSA ENTGNGGAAT TDKPKNEDEG PQNDMPQNSA ESANQTGNNQ

101  PADSSDSAPA SNPAPANGGS NFGRVDLANG VLIDGPSQNI TLTHCKGDSC

151  NGDNLLDEEA PSKSEFENLN ESERIEKYKK DGKSDKFTNL VATAVQANGT

201  NKYVIIYKDK SASSSSARFR RSARSRRSLP AEMPLIPVNQ ADTLIVDGEA

251  VSLTGHSGNI FAPEGNYRYL TYGAEKLPGG SYALRVQGEP AKGEMLAGTA

301  VYNGEVLHFH TENGRPYPTR GRFAAKVDFG SKSVDGIIDS GDDLHMGTQK

351  FKAAIDGNGF KGTWTENGGG DVSGRFYGPA GEEVAGKYSY RPTDAEKGGF

401  GVFAGKKEQD *
```

All these proteins could be expressed and purified.

'287L' and '287LOrf4' were confirmed as lipoproteins.

Figure 2:
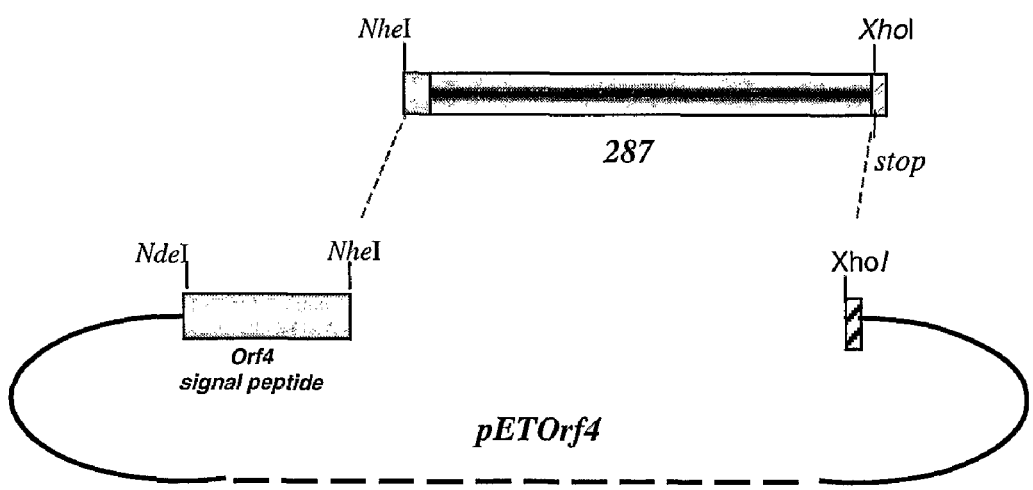

As shown in FIG. 2, '287LOrf4' was constructed by digesting 919LOrf4 with NheI and XhoI. The entire ORF4 leader peptide was restored by the addition of a DNA sequence coding for the missing amino acids, as a tail, in the 5'-end primer (287LOrf4 for), fused to 287 coding sequence. The 287 gene coding for the mature protein was amplified using the oligonucleotides 287LOrf4 For and Rev (including the NheI and XhoI sites, respectively), digested with NheI and XhoI and ligated to the purified pETOrf4 fragment.

Example 11

Further Non-Fusion Proteins with/without Native Leader Peptides

A similar approach was adopted for *E. coli* expression of further proteins from WO99/24578, WO99/36544 and WO99/57280.

The following were expressed without a fusion partner: 008, 105, 117-1, 121-1, 122-1, 128-1, 148, 216, 243, 308, 593, 652, 726, 982, and Orf143-1. Protein 117-1 was confirmed as surface-exposed by FACS and gave high ELISA titres.

The following were expressed with the native leader peptide but without a fusion partner: 111, 149, 206, 225-1, 235, 247-1, 274, 283, 286, 292, 401, 406, 502-1, 503, 519-1, 525-1, 552, 556, 557, 570, 576-1, 580, 583, 664, 759, 907, 913, 920-1, 926, 936-1, 953, 961, 983, 989, Orf4, Orf7-1, Orf9-1, Orf23, Orf25, Orf37, Orf38, Orf40, Orf40.1, Orf40.2, Orf72-1, Orf76-1, Orf85-2, Orf91, Orf97-1, Orf119, Orf143.1. These proteins are given the suffix 'L'.

His-tagged protein 760 was expressed with and without its leader peptide. The deletion of the signal peptide greatly increased expression levels. The protein could be purified most easily using 2M urea for solubilisation.

His-tagged protein 264 was well-expressed using its own signal peptide, and the 30 kDa protein gave positive Western blot results.

All proteins were successfully expressed.

The localisation of 593, 121-1, 128-1, 593, 726, and 982 in the cytoplasm was confirmed.

The localisation of 920-1L, 953L, ORF9-1L, ORF85-2L, ORF97-1L, 570L, 580L and 664L in the periplasm was confirmed.

The localisation of ORF40L in the outer membrane, and 008 and 519-1L in the inner membrane was confirmed. ORF25L, ORF4L, 406L, 576-1L were all confirmed as being localised in the membrane.

Protein 206 was found not to be a lipoprotein.

ORF25 and ORF40 expressed with their native leader peptides but without fusion partners, and protein 593 expressed without its native leader peptide and without a fusion partner, raised good anti-bactericidal sera. Surprisingly, the forms of ORF25 and ORF40 expressed without fusion partners and using their own leader peptides (i.e. 'ORF25L' and 'ORF40L') give better results in the bactericidal assay than the fusion proteins.

Proteins 920L and 953L were subjected to N-terminal sequencing, giving HRVWVETAH (SEQ ID NO:81) and ATYKVDEYHANARFAF (SEQ ID NO:82), respectively. This sequencing confirms that the predicted leader peptides were cleaved and, when combined with the periplasmic location, confirms that the proteins are correctly processed and localised by *E. coli* when expressed from their native leader peptides.

The N-terminal sequence of protein 519.1L localised in the inner membrane was MEFFIILLA (SEQ ID NO:83), indicating that the leader sequence is not cleaved. It may therefore function as both an uncleaved leader sequence and a transmembrane anchor in a manner similar to the leader peptide of PBP1 from *N. gonorrhoeae* [Ropp & Nicholas (1997) *J. Bact.* 179:2783-2787.]. Indeed the N-terminal region exhibits strong hydrophobic character and is predicted by the Tmpred. program to be transmembrane.

Example 12

Lipoproteins

The incorporation of palmitate in recombinant lipoproteins was demonstrated by the method of Kraft et. al. [*J. Bact.* (1998) 180:3441-3447.]. Single colonies harbouring the plasmid of interest were grown overnight at 37° C. in 20 ml of LB/Amp (100 μg/ml) liquid culture. The culture was diluted to an $OD_{550}$ of 0.1 in 5.0 ml of fresh medium LB/Amp medium containing 5 μC/ml [$^3$H] palmitate (Amersham). When the $OD_{550}$ of the culture reached 0.4-0.8, recombinant lipoprotein was induced for 1 hour with IPTG (final concentration 1.0 mM). Bacteria were harvested by centrifugation in a bench top centrifuge at 2700 g for 15 min and washed twice with 1.0 ml cold PBS. Cells were resuspended in 120 μl of 20 mM Tris-HCl (pH 8.0), 1 mM EDTA, 1.0% w/v SDS and lysed by boiling for 10 min. After centrifugation at 13000 g for 10 min the supernatant was collected and proteins precipitated by the addition of 1.2 ml cold acetone and left for 1 hour at −20° C. Protein was pelleted by centrifugation at 13000 g for 10 min and resuspended in 20-50 μl (calculated to standardise loading with respect to the final O.D of the culture) of 1.0% w/v SDS. An aliquot of 15 μl was boiled with 5 μl of SDS-PAGE sample buffer and analysed by SDS-PAGE. After electrophoresis gels were fixed for 1 hour in 10% v/v acetic acid and soaked for 30 minutes in Amplify solution (Amersham). The gel was vacuum-dried under heat and exposed to Hyperfilm (Kodak) overnight −80° C.

Incorporation of the [$^3$H] palmitate label, confirming lipidation, was found for the following proteins: Orf4L, Orf25L, 287L, 287LOrf4, 406.L, 576L, 926L, 919L and 919LOrf4.

Example 13

Domains in 287

Based on homology of different regions of 287 to proteins that belong to different functional classes, it was split into three 'domains', as shown in FIG. 5. The second domain shows homology to IgA proteases, and the third domain shows homology to transferrin-binding proteins.

Each of the three 'domains' shows a different degree of sequence conservation between *N. meningitidis* strains—domain C is 98% identical, domain A is 83% identical, whilst domain B is only 71% identical. Note that protein 287 in strain MC58 is 61 amino acids longer than that of strain 2996. An alignment of the two sequences is shown in FIG. 7, and alignments for various strains are disclosed in WO00/66741 (see FIGS. 5 and 15 therein).

The three domains were expressed individually as C-terminal His-tagged proteins. This was done for the MC58 and 2996 strains, using the following constructs:

287a-MC58 (aa 1-202), 287b-MC58 (aa 203-288), 287c-MC58 (aa 311-488).

287a-2996 (aa 1-139), 287b-2996 (aa 140-225), 287c-2996 (aa 250-427).

To make these constructs, the stop codon sequence was omitted in the 3'-end primer sequence. The 5' primers included the NheI restriction site, and the 3' primers included a XhoI as a tail, in order to direct the cloning of each amplified fragment into the expression vector pET21b+ using NdeI-XhoI, NheI-XhoI or NdeI-HindIII restriction sites.

All six constructs could be expressed, but 287b-MC8 required denaturation and refolding for solubilisation.

Deletion of domain A is described below ('Δ4 287-His').

Immunological data (serum bactericidal assay) were also obtained using the various domains from strain 2996, against the homologous and heterologous MenB strains, as well as MenA (F6124 strain) and MenC (BZ133 strain):

|             | 2996  | BZ232 | MC58 | NGH38 | 394/98 | MenA  | MenC  |
|-------------|-------|-------|------|-------|--------|-------|-------|
| 287-His     | 32000 | 16    | 4096 | 4096  | 512    | 8000  | 16000 |
| 287(B)-His  | 256   | —     | —    | —     | —      | 16    | —     |
| 287(C)-His  | 256   | —     | 32   | 512   | 32     | 2048  | >2048 |
| 287(B-C)-His| 64000 | 128   | 4096 | 64000 | 1024   | 64000 | 32000 |

Using the domains of strain MC58, the following results were obtained:

|             | MC58  | 2996  | BZ232 | NGH38 | 394/98 | MenA  | MenC  |
|-------------|-------|-------|-------|-------|--------|-------|-------|
| 287-His     | 4096  | 32000 | 16    | 4096  | 512    | 8000  | 16000 |
| 287(B)-His  | 128   | 128   | —     | —     | —      | —     | 128   |
| 287(C)-His  | —     | 16    | —     | 1024  | —      | 512   | —     |
| 287(B-C)-His| 16000 | 64000 | 128   | 64000 | 512    | 64000 | >8000 |

Example 14
Deletions in 287

Figure 6:
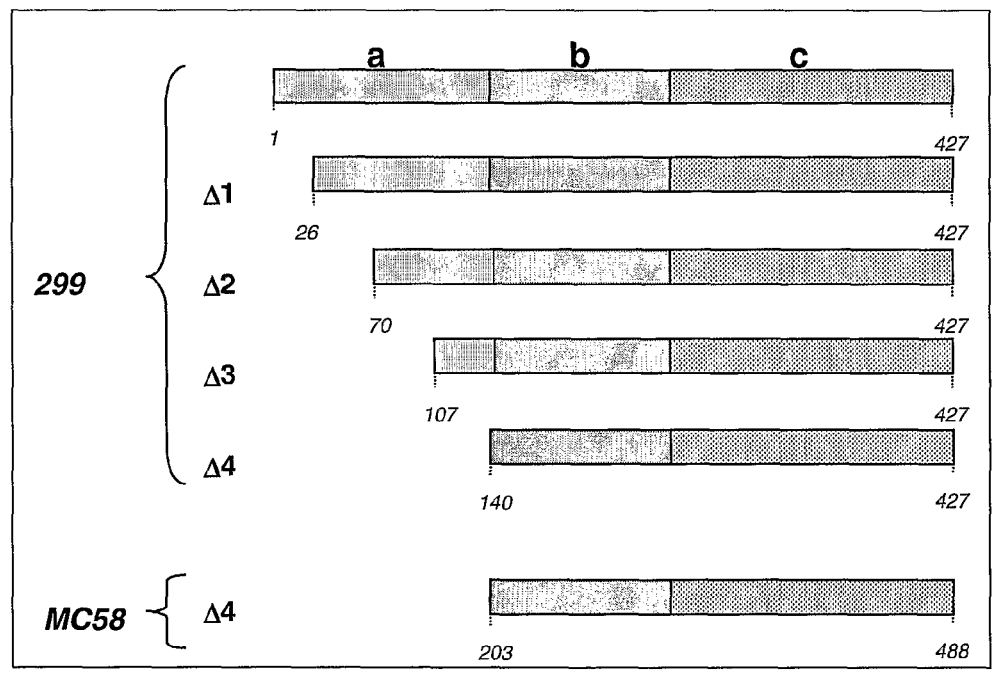

As well as expressing individual domains, 287 was also expressed (as a C-terminal His-tagged protein) by making progressive deletions within the first domain. These Four deletion mutants of protein 287 from strain 2996 were used (FIG. 6):

1) '287-His', consisting of amino acids 18-427 (i.e. leader peptide deleted);
2) 'Δ1 287-His', consisting of amino acids 26-427;
3) 'Δ2 287-His', consisting of amino acids 70-427;
4) 'Δ3 287-His', consisting of amino acids 107-427; and
5) 'Δ4 287-His', consisting of amino acids 140-427 (=287-bc).

The 'Δ4' protein was also made for strain MC58 ('Δ4 287MC58-His'; aa 203-488).

The constructs were made in the same way as 287a/b/c, as described above.

All six constructs could be expressed and protein could be purified. Expression of 287-His was, however, quite poor.

Expression was also high when the C-terminal His-tags were omitted.

Immunological data (serum bactericidal assay) were also obtained using the deletion mutants, against the homologous (2996) and heterologous MenB strains, as well as MenA (F6124 strain) and MenC (BZ133 strain):

|        | 2996  | BZ232 | MC58 | NGH38 | 394/98 | MenA  | MenC   |
|--------|-------|-------|------|-------|--------|-------|--------|
| 287-his | 32000 | 16    | 4096 | 4096  | 512    | 8000  | 16000  |
| Δ1 287-His | 16000 | 128 | 4096 | 4096 | 1024   | 8000  | 16000  |
| Δ2 287-His | 16000 | 128 | 4096 | >2048 | 512   | 16000 | >8000  |
| Δ3 287-His | 16000 | 128 | 4096 | >2048 | 512   | 16000 | >8000  |
| Δ4 287-His | 64000 | 128 | 4096 | 64000 | 1024  | 64000 | 32000  |

The same high activity for the Δ4 deletion was seen using the sequence from strain MC58.

As well as showing superior expression characteristics, therefore, the mutants are immunologically equivalent or superior.

Example 15

Poly-Glycine Deletions

The 'Δ1 287-His' construct of the previous example differs from 287-His and from '287$^{untagged}$' only by a short N-terminal deletion (GGGGGGS) (SEQ ID NO:631). Using an expression vector which replaces the deleted serine with a codon present in the Nhe cloning site, however, this amounts to a deletion only of $(Gly)_6$ (SEQ ID NO:632). Thus, the deletion of this $(Gly)_6$ sequence (SEQ ID NO:632) has been shown to have a dramatic effect on protein expression.

The protein lacking the N-terminal amino acids up to GGGGGG (SEQ ID NO:632) is called 'ΔG 287'. In strain MC58, its sequence (leader peptide underlined) is (SEQ ID NO:84):

→ ΔG287

```
  1 MFKRSVIAMA CIFALSACGG GGGGSPDVKS ADTLSKPAAP VVSEKETEAK
 51 EDAPQAGSQG QGAPSAQGSQ DMAAVSEENT GNGGAVTADN PKNEDEVAQN
101 DMPQNAAGTD SSTPNHTPDP NMLAGNMENQ ATDAGESSQP ANQPDMANAA
151 DGMQGDDPSA GGQNAGNTAA QGANQAGNNQ AAGSSDPIPA SNPAPANGGS
201 NFGRVDLANG VLIDGPSQNI TLTHCKGDSC SGNNFLDEEV QLKSEFEKLS
251 DADKISNYKK DGKNDKFVGL VADSVQMKGI NQYIIFYKPK PTSFARFRRS
301 ARSRRSLPAE MPLIPVNQAD TLIVDGEAVS LTGHSGNIFA PEGNYRYLTY
351 GAEKLPGGSY ALRVQGEPAK GEMLAGAAVY NGEVLHFHTE NGRPYPTRGR
401 FAAKVDFGSK SVDGIIDSGD DLHMGTQKFK AAIDGNGFKG TWTENGSGDV
451 SGKFYGPAGE EVAGKYSYRP TDAEKGGFGV FAGKKEQD*
```

ΔG287, with or without His-tag ('ΔG287-His' and 'ΔG287K', respectively), are expressed at very good levels in comparison with the '287-His' or '287$^{untagged}$'.

On the basis of gene variability data, variants of ΔG287-His were expressed in *E. coli* from a number of MenB strains, in particular from strains 2996, MC58, 1000, and BZ232. The results were also good.

It was hypothesised that poly-Gly deletion might be a general strategy to improve expression. Other MenB lipoproteins containing similar $(Gly)_n$ motifs (near the N-terminus, downstream of a cysteine) were therefore identified, namely Tbp2 (NMB0460) (SEQ ID NO:85), 741 (NMB 1870) (SEQ ID NO:86) and 983 (NMB 1969) (SEQ ID NO:87):

TBP2 → ΔGTbp2

```
  1 MNNPLVNQAA MVLPVFLLSA CLGGGGSFDL DSVDTEAPRP APKYQDVFSE
 51 KPQAQKDQGG YGFAMRLKRR NWYPQAKEDE VKLDESDWEA TGLPDEPKEL
101 PKRQKSVIEK VETDSDNNIY SSPYLKPSNH QNGNTGNGIN QPKNQAKDYE
151 NFKYVYSGWF YKHAKREFNL KVEPKSAKNG DDGYIFYHGK EPSRQLPASG
201 KITYKGVWHF ATDTKKGQKF REIIQPSKSQ GDRYSGFSGD DGEEYSNKNK
251 STLTDGQEGY GFTSNLEVDF HNKKLTGKLI RNNANTDNNQ ATTTQYYSLE
301 AQVTGNRFNG KATATDKPQQ NSETKEHPFV SDSSSLSGGF FGPQGEELGF
```

```
351  RFLSDDQKVA VVGSAKTKDK PANGNTAAAS GGTDAAASNG AAGTSSENGK

401  LTTVLDAVEL KLGDKEVQKL DNFSNAAQLV VDGIMIPLLP EASESGNNQA

451  NQGTNGGTAF TRKFDHTPES DKKDAQAGTQ TNGAQTASNT AGDTNGKTKT

501  YEVEVCCSNL NYLKYGMLTR KNSKSAMQAG ESSSQADAKT EQVEQSMFLQ

551  GERTDEKEIP SEQNIVYRGS WYGYIANDKS TSWSGNASNA TSGNRAEFTV

601  NFADKKITGT LTADNRQEAT FTIDGNIKDN GFEGTAKTAE SGFDLDQSNT

651  TRTPKAYITD AKVQGGFYGP KAEELGGWFA YPGDKQTKNA TNASGNSSAT

701  VVFGAKRQQP VR*

741 ↱ ΔG741
  1  VNRTAFCCLS LTTALILTAC SSGGGGVAAD IGAGLADALT APLDHKDKGL

51  QSLTLDQSVR KNEKLKLAAQ GAEKTYGNGD SLNTGKLKND KVSRFDFIRQ

101  IEVDGQLITL ESGEFQVYKQ SHSALTAFQT EQIQDSEHSG KMVAKRQFRI

151  GDIAGEHTSF DKLPEGGRAT YRGTAFGSDD AGGKLTYTID FAAKQGNGKI

201  EHLKSPELNV DLAAADIKPD GKRHAVISGS VLYNQAEKGS YSLGIFGGKA

251  QEVAGSAEVK TVNGIRHIGL AAKQ*

983 ↱ ΔG983
  1  MRTTPTFPTK TFKPTAMALA VATTLSACLG GGGGGTSAPD FNAGGTGIGS

51  NSRATTAKSA AVSYAGIKNE MCKDRSMLCA GRDDVAVTDR DAKINAPPPN

101  LHTGDFPNPN DAYKNLINLK PAIEAGYTGR GVEVGIVDTG ESVGSISFPE

151  LYGRKEHGYN ENYKNYTAYM RKEAPEDGGG KDIEASFDDE AVIETEAKPT

201  DIRHVKEIGH IDLVSHIIGG RSVDGRPAGG IAPDATLHIM NTNDETKNEM

251  MVAAIRNAWV KLGERGVRIV NNSFGTTSRA GTADLFQIAN SEEQYRQALL

301  DYSGGDKTDE GIRLMQQSDY GNLSYHIRNK NMLFIFSTGN DAQAQPNTYA

351  LLPFYEKDAQ KGIITVAGVD RSGEKFKREM YGEPGTEPLE YGSNHCGITA

401  MWCLSAPYEA SVRFTRTNPI QIAGTSFSAP IVTGTAALLL QKYPWMSNDN

451  LRTTLLTTAQ DIGAVGVDSK FGWGLLDAGK AMNGPASFPF GDFTADTKGT

501  SDIAYSFRND ISGTGGLIKK GGSQLQLHGN NTYTGKTIIE GGSLVLYGNN

551  KSDMRVETKG ALIYNGAASG GSLNSDGIVY LADTDQSGAN ETVHIKGSLQ

601  LDGKGTLYTR LGKLLKVDGT AIIGGKLYMS ARGKGAGYLN STGRRVPFLS

651  AAKIGQDYSF FTNIETDGGL LASLDSVEKT AGSEGDTLSY YVRRGNAART

701  ASAAAHSAPA GLKHAVEQGG SNLENLMVEL DASESSATPE TVETAAADRT

751  DMPGIRPYGA TFRAAAAVQH ANAADGVRIF NSLAATVYAD STAAHADMQG

801  RRLKAVSDGL DHNGTGLRVI AQTQQDGGTW EQGGVEGKMR GSTQTVGIAA

851  KTGENTTAAA TLGMGRSTWS ENSANAKTDS ISLFAGIRHD AGDIGYLKGL

901  FSYGRYKNSI SRSTGADEHA EGSVNGTLMQ LGALGGVNVP FAATGDLTVE

951  GGLRYDLLKQ DAFAEKGSAL GWSGNSLTEG TLVGLAGLKL SQPLSDKAVL

1001 FATAGVERDL NGRDYTVTGG FTGATAATGK TGARNMPHTR LVAGLGADVE

1051 FGNGWNGLAR YSYAGSKQYG NHSGRVGVGY RF*
```

Tbp2 and 741 genes were from strain MC58; 983 and 287 genes were from strain 2996. These were cloned in pET vector and expressed in *E. coli* without the sequence coding for their leader peptides or as "ΔG forms", both fused to a C-terminal His-tag. In each case, the same effect was seen—expression was good in the clones carrying the deletion of the poly-glycine stretch, and poor or absent if the glycines were present in the expressed protein:

| ORF | Express. | Purification | Bact. Activity |
| --- | --- | --- | --- |
| 287-His(2996) | +/− | + | + |
| '287^untagged'(2996) | +/− | nd | nd |
| ΔG287-His(2996) | + | + | + |
| ΔG287K(2996) | + | + | + |
| ΔG287-His(MC58) | + | + | + |
| ΔG287-His(1000) | + | + | + |
| ΔG287-His(BZ232) | + | + | + |
| Tbp2-His(MC58) | +/− | nd | nd |
| ΔGTbp2-His(MC58) | + | + | |
| 741-His(MC58) | +/− | nd | nd |
| ΔG741-His(MC58) | + | + | |
| 983-His (2996) | + | + | |
| ΔG983-His (2996) | + | + | |

SDS-PAGE of the proteins is shown in FIG. 13.

ΔG287 and Hybrids

ΔG287 proteins were made and purified for strains MC58, 1000 and BZ232. Each of these gave high ELISA titres and also serum bactericidal titres of >8192. ΔG287K, expressed from pET-24b, gave excellent titres in ELISA and the serum bactericidal assay. ΔG287-ORF46.1K may also be expressed in pET-24b.

ΔG287 was also fused directly in-frame upstream of 919 (SEQ ID NOS:88 and 89), 953 (SEQ ID NOS:90 and 91), 961 (SEQ ID NOS:92 and 93) (sequences shown below) and ORF46.1:

```
ΔG287-919
   1 ATGGCTAGCC CCGATGTTAA ATCGGCGGAC ACGCTGTCAA AACCGGCCGC
  51 TCCTGTTGTT GCTGAAAAAG AGACAGAGGT AAAAGAAGAT GCGCCACAGG
 101 CAGGTTCTCA AGGACAGGGC GCGCCATCCA CACAAGGCAG CCAAGATATG
 151 GCGGCAGTTT CGGCAGAAAA TACAGGCAAT GGCGGTGCGG CAACAACGGA
 201 CAAACCCAAA AATGAAGACG AGGGACCGCA AAATGATATG CCGCAAAATT
 251 CCGCCGAATC CGCAAATCAA ACAGGGAACA ACCAACCCGC CGATTCTTCA
 301 GATTCCGCCC CCGCGTCAAA CCCTGCACCT GCGAATGGCG GTAGCAATTT
 351 TGGAAGGGGT GATTTGGCTA ATGGCGTTTT GATTGATGGG CCGTCGCAAA
 401 ATATAACGTT GACCCACTGT AAAGGCGATT CTTGTAATGG TGATAATTTA
 451 TTGGATGAAG AAGCACCGTC AAAATCAGAA TTTGAAAATT TAAATGAGTC
 501 TGAACGAATT GAGAAATATA AGAAAGATGG GAAAAGCGAT AAATTTACTA
 551 ATTTGGTTGC GACAGCAGTT CAAGCTAATG GAACTAACAA ATATGTCATC
 601 ATTTATAAAG ACAAGTCCGC TTCATCTTCA TCTGCGCGAT TCAGGCGTTC
 651 TGCACGGTCG AGGAGGTCGC TTCCTGCCGA GATGCCGCTA ATCCCCGTCA
 701 ATCAGGCGGA TACGCTGATT GTCGATGGGG AAGCGGTCAG CCTGACGGGG
 751 CATTCCGGCA ATATCTTCGC GCCCGAAGGG AATTACCGGT ATCTGACTTA
 801 CGGGGCGGAA AAATTGCCCG GCGGATCGTA TGCCCTCCGT GTGCAAGGCG
 851 AACCGGCAAA AGGCGAAATG CTTGCTGGCA CGGCCGTGTA CAACGGCGAA
 901 GTGCTGCATT TTCATACGGA AAACGGCCGT CCGTACCCGA CTAGAGGCAG
 951 GTTTGCCGCA AAAGTCGATT TCGGCAGCAA ATCTGTGGAC GGCATTATCG
1001 ACAGCGGCGA TGATTTGCAT ATGGGTACGC AAAAATTCAA AGCCGCCATC
1051 GATGGAAACG GCTTTAAGGG GACTTGGACG GAAAATGGCG GCGGGGATGT
1101 TTCCGGAAGG TTTTACGGCC CGGCCGGCGA GGAAGTGGCG GGAAAATACA
1151 GCTATCGCCC GACAGATGCG GAAAAGGGCG GATTCGGCGT GTTTGCCGGC
1201 AAAAAGAGC AGGATGGATC CGGAGGAGGA GGATGCCAAA GCAAGAGCAT
1251 CCAAACCTTT CCGCAACCCG ACACATCCGT CATCAACGGC CCGGACCGGC
1301 CGGTCGGCAT CCCCGACCCC GCCGGAACGA CGGTCGGCGG CGGCGGGGCC
```

-continued

```
1351 GTCTATACCG TTGTACCGCA CCTGTCCCTG CCCCACTGGG CGGCGCAGGA

1401 TTTCGCCAAA AGCCTGCAAT CCTTCCGCCT CGGCTGCGCC AATTTGAAAA

1451 ACCGCCAAGG CTGGCAGGAT GTGTGCGCCC AAGCCTTTCA AACCCCCGTC

1501 CATTCCTTTC AGGCAAAACA GTTTTTTGAA CGCTATTTCA CGCCGTGGCA

1551 GGTTGCAGGC AACGGAAGCC TTGCCGGTAC GGTTACCGGC TATTACGAGC

1601 CGGTGCTGAA GGGCGACGAC AGGCGGACGG CACAAGCCCG CTTCCCGATT

1651 TACGGTATTC CCGACGATTT TATCTCCGTC CCCCTGCCTG CCGGTTTGCG

1701 GAGCGGAAAA GCCCTTGTCC GCATCAGGCA GACGGGAAAA ACAGCGGCA

1751 CAATCGACAA TACCGGCGGC ACACATACCG CCGACCTCTC CCGATTCCCC

1801 ATCACCGCGC GCACAACGGA ATCAAAGGC AGGTTTGAAG GAAGCCGCTT

1851 CCTCCCCTAC CACACGCGCA ACCAAATCAA CGGCGGCGCG CTTGACGGCA

1901 AAGCCCCGAT ACTCGGTTAC GCCGAAGACC CCGTCGAACT TTTTTTTATG

1951 CACATCCAAG GCTCGGGCCG TCTGAAAACC CCGTCCGGCA AATACATCCG

2001 CATCGGCTAT GCCGACAAAA ACGAACATCC CTACGTTTCC ATCGGACGCT

2051 ATATGGCGGA CAAAGGCTAC CTCAAGCTCG GGCAGACCTC GATGCAGGGC

2101 ATCAAAGCCT ATATGCGGCA AAATCCGCAA CGCCTCGCCG AAGTTTTGGG

2151 TCAAAACCCC AGCTATATCT TTTTCCGCGA GCTTGCCGGA AGCAGCAATG

2201 ACGGTCCCGT CGGCGCACTG GGCACGCCGT TGATGGGGGA ATATGCCGGC

2251 GCAGTCGACC GGCACTACAT TACCTTGGGC GCGCCCTTAT TTGTCGCCAC

2301 CGCCCATCCG GTTACCCGCA AAGCCCTCAA CCGCCTGATT ATGGCGCAGG

2351 ATACCGGCAG CGCGATTAAA GGCGCGGTGC GCGTGGATTA TTTTTGGGGA

2401 TACGGCGACG AAGCCGGCGA ACTTGCCGGC AAACAGAAAA CCACGGGTTA

2451 CGTCTGGCAG CTCCTACCCA ACGGTATGAA GCCCGAATAC CGCCCGTAAC

2501 TCGAG

1 MASPDVKSAD TLSKPAAPVV AEKETEVKED APQAGSQGQG APSTQGSQDM

51 AAVSAENTGN GGAATTDKPK NEDEGPQNDM PQNSAESANQ TGNNQPADSS

101 DSAPASNPAP ANGGSNFGRV DLANGVLIDG PSQNITLTHC KGDSCNGDNL

151 LDEEAPSKSE FENLNESERI EKYKKDGKSD KFTNLVATAV QANGTNKYVI

201 IYKDKSASSS SARFRRSARS RRSLPAEMPL IPVNQADTLI VDGEAVSLTG

251 HSGNIFAPEG NYRYLTYGAE KLPGGSYALR VQGEPAKGEM LAGTAVYNGE

301 VLHFHTENGR PYPTRGRFAA KVDFGSKSVD GIIDSGDDLH MGTQKFKAAI

351 DGNGFKGTWT ENGGGDVSGR FYGPAGEEVA GKYSYRPTDA EKGGFGVFAG

401 KKEQDGSGGG GCQSKSIQTF PQPDTSVING PDRPVGIPDP AGTTVGGGGA

451 VYTVVPHLSL PHWAAQDFAK SLQSFRLGCA NLKNRQGWQD VCAQAFQTPV

501 HSFQAKQFFE RYFTPWQVAG NGSLAGTVTG YYEPVLKGDD RRTAQARFPI

551 YGIPDDFISV PLPAGLRSGK ALVRIRQTGK NSGTIDNTGG THTADLSRFP

601 ITARTTAIKG RFEGSRFLPY HTRNQINGGA LDGKAPILGY AEDPVELFFM

651 HIQGSGRLKT PSGKYIRIGY ADKNEHPYVS IGRYMADKGY LKLGQTSMQG

701 IKAYMRQNPQ RLAEVLGQNP SYIFFRELAG SSNDGPVGAL GTPLMGEYAG

751 AVDRHYITLG APLFVATAHP VTRKALNRLI MAQDTGSAIK GAVRVDYFWG
```

```
801 YGDEAGELAG KQKTTGYVWQ LLPNGMKPEY RP*
```

ΔG287-953

```
   1 ATGGCTAGCC CCGATGTTAA ATCGGCGGAC ACGCTGTCAA AACCGGCCGC
  51 TCCTGTTGTT GCTGAAAAAG AGACAGAGGT AAAAGAAGAT GCGCCACAGG
 101 CAGGTTCTCA AGGACAGGGC GCGCCATCCA CACAAGGCAG CCAAGATATG
 151 GCGGCAGTTT CGGCAGAAAA TACAGGCAAT GGCGGTGCGG CAACAACGGA
 201 CAAACCCAAA AATGAAGACG AGGGACCGCA AAATGATATG CCGCAAAATT
 251 CCGCCGAATC CGCAAATCAA ACAGGGAACA ACCAACCCGC CGATTCTTCA
 301 GATTCCGCCC CCGCGTCAAA CCCTGCACCT GCGAATGGCG GTAGCAATTT
 351 TGGAAGGGTT GATTTGGCTA ATGGCGTTTT GATTGATGGG CCGTCGCAAA
 401 ATATAACGTT GACCCACTGT AAAGGCGATT CTTGTAATGG TGATAATTTA
 451 TTGGATGAAG AAGCACCGTC AAAATCAGAA TTTGAAAATT TAAATGAGTC
 501 TGAACGAATT GAGAAATATA AGAAGATGG GAAAAGCGAT AAATTTACTA
 551 ATTTGGTTGC GACAGCAGTT CAAGCTAATG GAACTAACAA ATATGTCATC
 601 ATTTATAAAG ACAAGTCCGC TTCATCTTCA TCTGCGCGAT TCAGGCGTTC
 651 TGCACGGTCG AGGAGGTCGC TTCCTGCCGA GATGCCGCTA ATCCCCGTCA
 701 ATCAGGCGGA TACGCTGATT GTCGATGGGG AAGCGGTCAG CCTGACGGGG
 751 CATTCCGGCA ATATCTTCGC GCCCGAAGGG AATTACCGGT ATCTGACTTA
 801 CGGGGCGGAA AAATTGCCCG GCGGATCGTA TGCCCTCCGT GTGCAAGGCG
 851 AACCGGCAAA AGGCGAAATG CTTGCTGGCA CGGCCGTGTA CAACGGCGAA
 901 GTGCTGCATT TCATACGGA AAACGGCCGT CCGTACCCGA CTAGAGGCAG
 951 GTTTGCCGCA AAAGTCGATT TCGGCAGCAA ATCTGTGGAC GGCATTATCG
1001 ACAGCGGCGA TGATTTGCAT ATGGGTACGC AAAAATTCAA AGCCGCCATC
1051 GATGGAAACG GCTTTAAGGG GACTTGGACG AAAATGGCG GCGGGGATGT
1101 TTCCGGAAGG TTTTACGGCC CGGCCGGCGA GGAAGTGGCG GAAAATACA
1151 GCTATCGCCC GACAGATGCG GAAAAGGGCG GATTCGGCGT GTTTGCCGGC
1201 AAAAAGAGC AGGATGGATC CGGAGGAGGA GGAGCCACCT ACAAAGTGGA
1251 CGAATATCAC GCCAACGCCC GTTTCGCCAT CGACCATTTC AACACCAGCA
1301 CCAACGTCGG CGGTTTTTAC GGTCTGACCG GTTCCGTCGA GTTCGACCAA
1351 GCAAAACGCG ACGGTAAAAT CGACATCACC ATCCCCGTTG CCAACCTGCA
1401 AAGCGGTTCG CAACACTTTA CCGACCACCT GAAATCAGCC GACATCTTCG
1451 ATGCCGCCCA ATATCCGGAC ATCCGCTTTG TTTCCACCAA ATTCAACTTC
1501 AACGGCAAAA AACTGGTTTC CGTTGACGGC AACCTGACCA TGCACGGCAA
1551 AACCGCCCCC GTCAAACTCA AGCCGAAAA ATTCAACTGC TACCAAAGCC
1601 CGATGGCGAA AACCGAAGTT TGCGGCGGCG ACTTCAGCAC CACCATCGAC
1651 CGCACCAAAT GGGGCGTGGA CTACCTCGTT AACGTTGGTA TGACCAAAAG
1701 CGTCCGCATC GACATCCAAA TCGAGGCAGC CAAACAATAA CTCGAG
```

```
   1 MASPDVKSAD TLSKPAAPVV AEKETEVKED APQAGSQGQG APSTQGSQDM
  51 AAVSAENTGN GGAATTDKPK NEDEGPQNDM PQNSAESANQ TGNNQPADSS
```

-continued

```
101 DSAPASNPAP ANGGSNFGRV DLANGVLIDG PSQNITLTHC KGDSCNGDNL

151 LDEEAPSKSE FENLNESERI EKYKKDGKSD KFTNLVATAV QANGTNKYVI

201 IYKDKSASSS SARFRRSARS RRSLPAEMPL IPVNQADTLI VDGEAVSLTG

251 HSGNIFAPEG NYRYLTYGAE KLPGGSYALR VQGEPAKGEM LAGTAVYNGE

301 VLHFHTENGR PYPTRGRFAA KVDFGSKSVD GIIDSGDDLH MGTQKFKAAI

351 DGNGFKGTWT ENGGGDVSGR FYGPAGEEVA GKYSYRPTDA EKGGFGVFAG

401 KKEQDGSGGG GATYKVDEYH ANARFAIDHF NTSTNVGGFY GLTGSVEFDQ

451 AKRDGKIDIT IPVANLQSGS QHFTDHLKSA DIFDAAQYPD IRFVSTKFNF

501 NGKKLVSVDG NLTMHGKTAP VKLKAEKFNC YQSPMAKTEV CGGDFSTTID

551 RTKWGVDYLV NVGMTKSVRI DIQIEAAKQ*
```

ΔG287-961

```
   1 ATGGCTAGCC CCGATGTTAA ATCGGCGGAC ACGCTGTCAA AACCGGCCGC

51 TCCTGTTGTT GCTGAAAAAG AGACAGAGGT AAAAGAAGAT GCGCCACAGG

101 CAGGTTCTCA AGGACAGGGC GCGCCATCCA CACAAGGCAG CCAAGATATG

151 GCGGCAGTTT CGGCAGAAAA TACAGGCAAT GGCGGTGCGG CAACAACGGA

201 CAAACCCAAA AATGAAGACG AGGGACCGCA AAATGATATG CCGCAAAATT

251 CCGCCGAATC CGCAAATCAA ACAGGGAACA ACCAACCCGC CGATTCTTCA

301 GATTCCGCCC CCGCGTCAAA CCCTGCACCT GCGAATGGCG GTAGCAATTT

351 TGGAAGGGTT GATTTGGCTA ATGGCGTTTT GATTGATGGG CCGTCGCAAA

401 ATATAACGTT GACCCACTGT AAAGGCGATT CTTGTAATGG TGATAATTTA

451 TTGGATGAAG AAGCACCGTC AAAATCAGAA TTTGAAAATT TAAATGAGTC

501 TGAACGAATT GAGAAATATA AGAAAGATGG GAAAAGCGAT AAATTTACTA

551 ATTTGGTTGC GACAGCAGTT CAAGCTAATG GAACTAACAA ATATGTCATC

601 ATTTATAAAG ACAAGTCCGC TTCATCTTCA TCTGCGCGAT TCAGGCGTTC

651 TGCACGGTCG AGGAGGTCGC TTCCTGCCGA GATGCCGCTA ATCCCCGTCA

701 ATCAGGCGGA TACGCTGATT GTCGATGGGG AAGCGGTCAG CCTGACGGGG

751 CATTCCGGCA ATATCTTCGC GCCCGAAGGG AATTACCGGT ATCTGACTTA

801 CGGGGCGGAA AAATTGCCCG GCGGATCGTA TGCCCTCCGT GTGCAAGGCG

851 AACCGGCAAA AGGCGAAATG CTTGCTGGCA CGGCCGTGTA CAACGGCGAA

901 GTGCTGCATT TTCATACGGA AAACGGCCGT CCGTACCCGA CTAGAGGCAG

951 GTTTGCCGCA AAAGTCGATT TCGGCAGCAA ATCTGTGGAC GGCATTATCG

1001 ACAGCGGCGA TGATTTGCAT ATGGGTACGC AAAAATTCAA AGCCGCCATC

1051 GATGGAAACG GCTTTAAGGG GACTTGGACG GAAAATGGCG GCGGGGATGT

1101 TTCCGGAAGG TTTTACGGCC CGGCCGGCGA GGAAGTGGCG GGAAAATACA

1151 GCTATCGCCC GACAGATGCG GAAAAGGGCG GATTCGGCGT GTTTGCCGGC

1201 AAAAAAGAGC AGGATGGATC CGGAGGAGGA GGAGCCACAA ACGACGACGA

1251 TGTTAAAAAA GCTGCCACTG TGGCCATTGC TGCTGCCTAC AACAATGGCC

1301 AAGAAATCAA CGGTTTCAAA GCTGGAGAGA CCATCTACGA CATTGATGAA

1351 GACGGCACAA TTACCAAAAA AGACGCAACT GCAGCCGATG TTGAAGCCGA

1401 CGACTTTAAA GGTCTGGGTC TGAAAAAAGT CGTGACTAAC CTGACCAAAA

1451 CCGTCAATGA AAACAAACAA AACGTCGATG CCAAAGTAAA AGCTGCAGAA
```

```
-continued
1501 TCTGAAATAG AAAAGTTAAC AACCAAGTTA GCAGACACTG ATGCCGCTTT

1551 AGCAGATACT GATGCCGCTC TGGATGCAAC CACCAACGCC TTGAATAAAT

1601 TGGGAGAAAA TATAACGACA TTTGCTGAAG AGACTAAGAC AAATATCGTA

1651 AAAATTGATG AAAAATTAGA AGCCGTGGCT GATACCGTCG ACAAGCATGC

1701 CGAAGCATTC AACGATATCG CCGATTCATT GGATGAAACC AACACTAAGG

1751 CAGACGAAGC CGTCAAAACC GCCAATGAAG CCAAACAGAC GGCCGAAGAA

1801 ACCAAACAAA ACGTCGATGC CAAAGTAAAA GCTGCAGAAA CTGCAGCAGG

1851 CAAAGCCGAA GCTGCCGCTG GCACAGCTAA TACTGCAGCC GACAAGGCCG

1901 AAGCTGTCGC TGCAAAAGTT ACCGACATCA AAGCTGATAT CGCTACGAAC

1951 AAAGATAATA TTGCTAAAAA AGCAAACAGT GCCGACGTGT ACACCAGAGA

2001 AGAGTCTGAC AGCAAATTTG TCAGAATTGA TGGTCTGAAC GCTACTACCG

2051 AAAAATTGGA CACACGCTTG GCTTCTGCTG AAAAATCCAT TGCCGATCAC

2101 GATACTCGCC TGAACGGTTT GGATAAAACA GTGTCAGACC TGCGCAAAGA

2151 AACCCGCCAA GGCCTTGCAG AACAAGCCGC GCTCTCCGGT CTGTTCCAAC

2201 CTTACAACGT GGGTCGGTTC AATGTAACGG CTGCAGTCGG CGGCTACAAA

2251 TCCGAATCGG CAGTCGCCAT CGGTACCGGC TTCCGCTTTA CCGAAAACTT

2301 TGCCGCCAAA GCAGGCGTGG CAGTCGGCAC TTCGTCCGGT TCTTCCGCAG

2351 CCTACCATGT CGGCGTCAAT TACGAGTGGT AACTCGAG
```

```
  1 MASPDVKSAD TLSKPAAPVV AEKETEVKED APQAGSQGQG APSTQGSQDM
 51 AAVSAENTGN GGAATTDKPK NEDEGPQNDM PQNSAESANQ TGNNQPADSS
101 DSAPASNPAP ANGGSNFGRV DLANGVLIDG PSQNITLTHC KGDSCNGDNL
151 LDEEAPSKSE FENLNESERI EKYKKDGKSD KFTNLVATAV QANGTNKYVI
201 IYKDKSASSS SARFRRSARS RRSLPAEMPL IPVNQADTLI VDGEAVSLTG
251 HSGNIFAPEG NYRYLTYGAE KLPGGSYALR VQGEPAKGEM LAGTAVYNGE
301 VLHFHTENGR PYPTRGRFAA KVDFGSKSVD GIIDSGDDLH MGTQKFKAAI
351 DGNGFKGTWT ENGGGDVSGR FYGPAGEEVA GKYSYRPTDA EKGGFGVFAG
401 KKEQDGSGGG GATNDDDVKK AATVAIAAAY NNGQEINGFK AGETIYDIDE
451 DGTITKKDAT AADVEADDFK GLGLKKVVTN LTKTVNENKQ NVDAKVKAAE
501 SEIEKLTTKL ADTDAALADT DAALDATTNA LNKLGENITT FAEETKTNIV
551 KIDEKLEAVA DTVDKHAEAF NDIADSLDET NTKADEAVKT ANEAKQTAEE
601 TKQNVDAKVK AAETAAGKAE AAAGTANTAA DKAEAVAAKV TDIKADIATN
651 KDNIAKKANS ADVYTREESD SKFVRIDGLN ATTEKLDTRL ASAEKSIADH
701 DTRLNGLDKT VSDLRKETRQ GLAEQAALSG LFQPYNVGRF NVTAAVGGYK
751 SESAVAIGTG FRFTENPAAK AGVAVGTSSG SSAAYHVGVN YEW*
```

|  | ELISA | Bactericidal |
|---|---|---|
| ΔG287-953-His | 3834 | 65536 |
| ΔG287-961-His | 108627 | 65536 |

The bactericidal efficacy (homologous strain) of antibodies raised against the hybrid proteins was compared with antibodies raised against simple mixtures of the component antigens (using 287-GST) for 919 and ORF46.1:

|  | Mixture with 287 | Hybrid with ΔG287 |
|---|---|---|
| 919 | 32000 | 128000 |
| ORF46.1 | 128 | 16000 |

Data for bactericidal activity against heterologous MenB strains and against serotypes A and C were also obtained:

| | 919 | | ORF46.1 | |
|---|---|---|---|---|
| Strain | Mixture | Hybrid | Mixture | Hybrid |
| NGH38 | 1024 | 32000 | — | 16384 |
| MC58 | 512 | 8192 | — | 512 |
| BZ232 | 512 | 512 | — | — |
| MenA (F6124) | 512 | 32000 | — | 8192 |

-continued

| | 919 | | ORF46.1 | |
|---|---|---|---|---|
| Strain | Mixture | Hybrid | Mixture | Hybrid |
| MenC (C11) | >2048 | >2048 | — | — |
| MenC (BZ133) | >4096 | 64000 | — | 8192 |

The hybrid proteins with ΔG287 at the N-terminus are therefore immunologically superior to simple mixtures, with ΔG287-ORF46.1 being particularly effective, even against heterologous strains. ΔG287-ORF46.1K may be expressed in pET-24b.

The same hybrid proteins were made using New Zealand strain 394/98 rather than 2996:

```
ΔG287NZ-919 (SEQ ID NOS: 94 AND 95)
   1 ATGGCTAGCC CCGATGTCAA GTCGGCGGAC ACGCTGTCAA AACCTGCCGC
  51 CCCTGTTGTT TCTGAAAAAG AGACAGAGGC AAAGGAAGAT GCGCCACAGG
 101 CAGGTTCTCA AGGACAGGGC GCGCCATCCG CACAAGGCGG TCAAGATATG
 151 GCGGCGGTTT CGGAAGAAAA TACAGGCAAT GGCGGTGCGG CAGCAACGGA
 201 CAAACCCAAA AATGAAGACG AGGGGGCGCA AAATGATATG CCGCAAAATG
 251 CCGCCGATAC AGATAGTTTG ACACCGAATC ACACCCCGGC TTCGAATATG
 301 CCGGCCGGAA ATATGGAAAA CCAAGCACCG GATGCCGGGG AATCGGAGCA
 351 GCCGGCAAAC CAACCGGATA TGGCAAATAC GGCGGACGGA ATGCAGGGTG
 401 ACGATCCGTC GGCAGGCGGG GAAAATGCCG GCAATACGGC TGCCCAAGGT
 451 ACAAATCAAG CCGAAAACAA TCAAACCGCC GGTTCTCAAA ATCCTGCCTC
 501 TTCAACCAAT CCTAGCGCCA CGAATAGCGG TGGTGATTTT GGAAGGACGA
 551 ACGTGGGCAA TTCTGTTGTG ATTGACGGGC CGTCGCAAAA TATAACGTTG
 601 ACCCACTGTA AAGGCGATTC TTGTAGTGGC AATAATTTCT TGGATGAAGA
 651 AGTACAGCTA AAATCAGAAT TTGAAAAATT AAGTGATGCA GACAAAATAA
 701 GTAATTACAA GAAAGATGGG AAGAATGACG GGAAGAATGA TAAATTTGTC
 751 GGTTTGGTTG CCGATAGTGT GCAGATGAAG GGAATCAATC AATATATTAT
 801 CTTTTATAAA CCTAAACCCA CTTCATTTGC GCGATTTAGG CGTTCTGCAC
 851 GGTCGAGGCG GTCGCTTCCG GCCGAGATGC CGCTGATTCC CGTCAATCAG
 901 GCGGATACGC TGATTGTCGA TGGGGAAGCG GTCAGCCTGA CGGGGCATTC
 951 CGGCAATATC TTCGCGCCCG AAGGGAATTA CCGGTATCTG ACTTACGGGG
1001 CGGAAAAATT GCCCGGCGGA TCGTATGCCC TCCGTGTTCA AGGCGAACCT
1051 TCAAAAGGCG AAATGCTCGC GGGCACGGCA GTGTACAACG GCGAAGTGCT
1101 GCATTTTCAT ACGGAAAACG GCCGTCCGTC CCCGTCCAGA GGCAGGTTTG
1151 CCGCAAAAGT CGATTTCGGC AGCAAATCTG TGGACGGCAT TATCGACAGC
1201 GGCGATGGTT TGCATATGGG TACGCAAAAA TTCAAAGCCG CCATCGATGG
1251 AAACGGCTTT AAGGGGACTT GGACGGAAAA TGGCGGCGGG GATGTTTCCG
1301 GAAAGTTTTA CGGCCCGGCC GGCGAGGAAG TGGCGGGAAA ATACAGCTAT
1351 CGCCCAACAG ATGCGGAAAA GGGCGGATTC GGCGTGTTTG CCGGCAAAAA
1401 AGAGCAGGAT GGATCCGGAG GAGGAGGATG CCAAAGCAAG AGCATCCAAA
1451 CCTTTCCGCA ACCCGACACA TCCGTCATCA ACGGCCCGGA CCGGCCGGTC
1501 GGCATCCCCG ACCCCGCCGG AACGACGGTC GGCGGCGGCG GGGCCGTCTA
```

-continued

```
1551 TACCGTTGTA CCGCACCTGT CCCTGCCCCA CTGGGCGGCG CAGGATTTCG
1601 CCAAAAGCCT GCAATCCTTC CGCCTCGGCT GCGCCAATTT GAAAAACCGC
1651 CAAGGCTGGC AGGATGTGTG CGCCCAAGCC TTTCAAACCC CCGTCCATTC
1701 CTTTCAGGCA AAACAGTTTT TTGAACGCTA TTTCACGCCG TGGCAGGTTG
1751 CAGGCAACGG AAGCCTTGCC GGTACGGTTA CCGGCTATTA CGAGCCGGTG
1801 CTGAAGGGCG ACGACAGGCG GACGGCACAA GCCCGCTTCC CGATTTACGG
1851 TATTCCCGAC GATTTTATCT CCGTCCCCCT GCCTGCCGGT TGCGGAGCG
1901 GAAAAGCCCT TGTCCGCATC AGGCAGACGG GAAAAAACAG CGGCACAATC
1951 GACAATACCG GCGGCACACA TACCGCCGAC CTCTCCCGAT TCCCCATCAC
2001 CGCGCGCACA ACGGCAATCA AAGGCAGGTT TGAAGGAAGC CGCTTCCTCC
2051 CCTACCACAC GCGCAACCAA ATCAACGGCG GCGCGCTTGA CGGCAAAGCC
2101 CCGATACTCG GTTACGCCGA AGACCCCGTC GAACTTTTTT TTATGCACAT
2151 CCAAGGCTCG GGCCGTCTGA AAACCCCGTC CGGCAAATAC ATCCGCATCG
2201 GCTATGCCGA CAAAAACGAA CATCCCTACG TTTCCATCGG ACGCTATATG
2251 GCGGACAAAG GCTACCTCAA GCTCGGGCAG ACCTCGATGC AGGGCATCAA
2301 AGCCTATATG CGGCAAAATC CGCAACGCCT CGCCGAAGTT TTGGGTCAAA
2351 ACCCCAGCTA TATCTTTTTC CGCGAGCTTG CCGGAAGCAG CAATGACGGT
2401 CCCGTCGGCG CACTGGGCAC GCCGTTGATG GGGGAATATG CCGGCGCAGT
2451 CGACCGGCAC TACATTACCT TGGGCGCGCC CTTATTTGTC GCCACCGCCC
2501 ATCCGGTTAC CCGCAAAGCC CTCAACCGCC TGATTATGGC GCAGGATACC
2551 GGCAGCGCGA TTAAAGGCGC GGTGCGCGTG GATTATTTTT GGGGATACGG
2601 CGACGAAGCC GGCGAACTTG CCGGCAAACA GAAAACCACG GGTTACGTCT
2651 GGCAGCTCCT ACCCAACGGT ATGAAGCCCG AATACCGCCC GTAAAAGCTT
   1 MASPDVKSAD TLSKPAAPVV SEKETEAKED APQAGSQGQG APSAQGGQDM
  51 AAVSEENTGN GGAAATDKPK NEDEGAQNDM PQNAADTDSL TPNHTPASNM
 101 PAGNMENQAP DAGESEQPAN QPDMANTADG MQGDDPSAGG ENAGNTAAQG
 151 TNQAENNQTA GSQNPASSTN PSATNSGGDF GRTNVGNSVV IDGPSQNITL
 201 THCKGDSCSG NNFLDEEVQL KSEFEKLSDA DKISNYKKDG KNDGKNDKFV
 251 GLVADSVQMK GINQYIIFYK PKPTSFARFR RSARSRRSLP AEMPLIPVNQ
 301 ADTLIVDGEA VSLTGHSGNI FAPEGNYRYL TYGAEKLPGG SYALRVQGEP
 351 SKGEMLAGTA VYNGEVLHFH TENGRPSPSR GRFAAKVDFG SKSVDGIIDS
 401 GDGLHMGTQK FKAAIDGNGF KGTWTENGGG DVSGKFYGPA GEEVAGKYSY
 451 RPTDAEKGGF GVPAGKKEQD GSGGGGCQSK SIQTFPQPDT SVINGPDRPV
 501 GIPDPAGTTV GGGGAVYTVV PHLSLPHWAA QDFAKSLQSF RLGCANLKNR
 551 QGWQDVCAQA FQTPVHSFQA KQFFERYFTP WQVAGNGSLA GTVTGYYEPV
 601 LKGDDRRTAQ ARFPIYGIPD DFISVPLPAG LRSGKALVRI RQTGKNSGTI
 651 DNTGGTHTAD LSRFPITART TAIKGRFEGS RFLPYHTRNQ INGGALDGKA
 701 PILGYAEDPV ELFFMHIQGS GRLKTPSGKY IRIGYADKNE HPYVSIGRYM
 751 ADKGYLKLGQ TSMQGIKAYM RQNPQRLAEV LGQNPSYIFF RELAGSSNDG
 801 PVGALGTPLM GEYAGAVDRH YITLGAPLFV ATAHPVTRKA LNRLIMAQDT
```

-continued

851 GSAIKGAVRV DYFWGYGDEA GELAGKQKTT GYVWQLLPNG MKPEYRP*

ΔG287NZ-953 (SEQ ID NOS: 96 AND 97)
```
   1 ATGGCTAGCC CCGATGTCAA GTCGGCGGAC ACGCTGTCAA AACCTGCCGC
  51 CCCTGTTGTT TCTGAAAAAG AGACAGAGGC AAAGGAAGAT GCGCCACAGG
 101 CAGGTTCTCA AGGACAGGGC GCGCCATCCG CACAAGGCGG TCAAGATATG
 151 GCGGCGGTTT CGGAAGAAAA TACAGGCAAT GGCGGTGCGG CAGCAACGGA
 201 CAAACCCAAA ATGAAGACGA GGGGGCGCA AAATGATATG CCGCAAAATG
 251 CCGCCGATAC AGATAGTTTG ACACCGAATC ACACCCCGGC TTCGAATATG
 301 CCGGCCGGAA ATATGGAAAA CCAAGCACCG GATGCCGGGG AATCGGAGCA
 351 GCCGGCAAAC CAACCGGATA TGGCAAATAC GGCGGACGGA ATGCAGGGTG
 401 ACGATCCGTC GGCAGGCGGG GAAATGCCG GCAATACGGC TGCCCAAGGT
 451 ACAAATCAAG CCGAAAACAA TCAAACCGCC GGTTCTCAAA ATCCTGCCTC
 501 TTCAACCAAT CCTAGCGCCA CGAATAGCGG TGGTGATTTT GGAAGGACGA
 551 ACGTGGGCAA TTCTGTTGTG ATTGACGGGC CGTCGCAAAA TATAACGTTG
 601 ACCCACTGTA AAGGCGATTC TTGTAGTGGC AATAATTTCT TGGATGAAGA
 651 AGTACAGCTA AAATCAGAAT TTGAAAAATT AAGTGATGCA GACAAAATAA
 701 GTAATTACAA GAAAGATGGG AAGAATGACG GGAAGAATGA TAAATTTGTC
 751 GGTTTGGTTG CCGATAGTGT GCAGATGAAG GGAATCAATC AATATATTAT
 801 CTTTTATAAA CCTAAACCCA CTTCATTTGC GCGATTTAGG CGTTCTGCAC
 851 GGTCGAGGCG GTCGCTTCCG GCCGAGATGC CGCTGATTCC CGTCAATCAG
 901 GCGGATACGC TGATTGTCGA TGGGGAAGCG GTCAGCCTGA CGGGGCATTC
 951 CGGCAATATC TTCGCGCCCG AAGGGAATTA CCGGTATCTG ACTTACGGGG
1001 CGGAAAAATT GCCCGGCGGA TCGTATGCCC TCCGTGTTCA AGGCGAACCT
1051 TCAAAGGCG AAATGCTCGC GGGCACGGCA GTGTACAACG GCGAAGTGCT
1101 GCATTTTCAT ACGGAAAACG GCCGTCCGTC CCCGTCCAGA GGCAGGTTTG
1151 CCGCAAAAGT CGATTTCGGC AGCAAATCTG TGGACGGCAT TATCGACAGC
1201 GGCGATGGTT GCATATGGG TACGCAAAAA TTCAAAGCCG CCATCGATGG
1251 AAACGGCTTT AAGGGGACTT GGACGGAAAA TGGCGGCGGG GATGTTTCCG
1301 GAAAGTTTTA CGGCCCGGCC GGCGAGGAAG TGGCGGGAAA ATACAGCTAT
1351 CGCCCAACAG ATGCGGAAAA GGGCGGATTC GGCGTGTTTG CCGGCAAAAA
1401 AGAGCAGGAT GGATCCGGAG GAGGAGGAGC CACCTACAAA GTGGACGAAT
1451 ATCACGCCAA CGCCCGTTTC GCCATCGACC ATTTCAACAC CAGCACCAAC
1501 GTCGGCGGTT TTTACGGTCT GACCGGTTCC GTCGAGTTCG ACCAAGCAAA
1551 ACGCGACGGT AAAATCGACA TCACCATCCC CGTTGCCAAC CTGCAAAGCG
1601 GTTCGCAACA CTTTACCGAC CACCTGAAAT CAGCCGACAT CTTCGATGCC
1651 GCCCAATATC CGGACATCCG CTTTGTTTCC ACCAAATTCA ACTTCAACGG
1701 CAAAAAACTG GTTTCCGTTG ACGGCAACCT GACCATGCAC GGCAAAACCG
1751 CCCCCGTCAA ACTCAAAGCC GAAAAATTCA ACTGCTACCA AAGCCCGATG
1801 GCGAAAACCG AAGTTTGCGG CGGCGACTTC AGCACCACCA TCGACCGCAC
1851 CAAATGGGGC GTGGACTACC TCGTTAACGT TGGTATGACC AAAAGCGTCC
1901 GCATCGACAT CCAAATCGAG GCAGCCAAAC AATAAAAGCT T
```

-continued

```
  1 MASPDVKSAD TLSKPAAPVV SEKETEAKED APQAGSQGQG APSAQGGQDM

51 AAVSEENTGN GGAAATDKPK NEDEGAQNDM PQNAADTDSL TPNHTPASNM

101 PAGNMENQAP DAGESEQPAN QPDMANTADG MQGDDPSAGG ENAGNTAAQG

151 TNQAENNQTA GSQNPASSTN PSATNSGGDF GRTNVGNSVV IDGPSQNITL

201 THCKGDSCSG NNFLDEEVQL KSEFEKLSDA DKISNYKKDG KNDGKNDKFV

251 GLVADSVQMK GINQYIIFYK PKPTSFARFR RSARSRRSLP AEMPLIPVNQ

301 ADTLIVDGEA VSLTGHSGNI FAPEGNYRYL TYGAEKLPGG SYALRVQGEP

351 SKGEMLAGTA VYNGEVLHFH TENGRPSPSR GRFAAKVDFG SKSVDGIIDS

401 GDGLHMGTQK FKAAIDNGNF KGTWTENGGG DVSGKFYGPA GEEVAGKYSY

451 RPTDAEKGGF GVFAGKKEQD GSGGGGATYK VDEYHANARF AIDHFNTSTN

501 VGGFYGLTGS VEFDQAKRDG KIDITIPVAN LQSGSQHFTD HLKSADIFDA

551 AQYPDIRFVS TKFNFNGKKL VSVDGNLTMH GKTAPVKLKA EKFNCYQSPM

601 AKTEVCGGDF STTIDRTKWG VDYLVNVGMT KSVRIDIQIE AAKQ*
```

ΔG287NZ-961 (SEQ ID NOS: 98 AND 99)

```
   1 ATGGCTAGCC CCGATGTCAA GTCGGCGGAC ACGCTGTCAA AACCTGCCGC

51 CCCTGTTGTT TCTGAAAAAG AGACAGAGGC AAAGGAAGAT GCGCCACAGG

101 CAGGTTCTCA AGGACAGGGC GCGCCATCCG CACAAGGCGG TCAAGATATG

151 GCGGCGGTTT CGGAAGAAAA TACAGGCAAT GGCGGTGCGG CAGCAACGGA

201 CAAACCCAAA ATGAAGACG AGGGGCGCA AAATGATATG CCGCAAAATG

251 CCGCCGATAC AGATAGTTTG ACACCGAATC ACACCCCGGC TTCGAATATG

301 CCGGCCGGAA ATATGGAAAA CCAAGCACCG GATGCCGGGG AATCGGAGCA

351 GCCGGCAAAC CAACCGGATA TGGCAAATAC GGCGGACGGA ATGCAGGGTG

401 ACGATCCGTC GGCAGGCGGG GAAAATGCCG GCAATACGGC TGCCCAAGGT

451 ACAAATCAAG CCGAAAACAA TCAAACCGCC GGTTCTCAAA ATCCTGCCTC

501 TTCAACCAAT CCTAGCGCCA CGAATAGCGG TGGTGATTTT GGAAGGACGA

551 ACGTGGGCAA TTCTGTTGTG ATTGACGGGC CGTCGCAAAA TATAACGTTG

601 ACCCACTGTA AAGGCGATTC TTGTAGTGGC AATAATTTCT TGGATGAAGA

651 AGTACAGCTA AAATCAGAAT TTGAAAAATT AAGTGATGCA GACAAAATAA

701 GTAATTACAA GAAAGATGGG AAGAATGACG GAAGAATGA TAAATTTGTC

751 GGTTTGGTTG CCGATAGTGT GCAGATGAAG GGAATCAATC AATATATTAT

801 CTTTTATAAA CCTAAACCCA CTTCATTTGC GCGATTTAGG CGTTCTGCAC

851 GGTCGAGGCG GTCGCTTCCG GCCGAGATGC CGCTGATTCC CGTCAATCAG

901 GCGGATACGC TGATTGTCGA TGGGGAAGCG GTCAGCCTGA CGGGGCATTC

951 CGGCAATATC TTCGCGCCCG AAGGGAATTA CCGGTATCTG ACTTACGGGG

1001 CGGAAAAATT GCCCGGCGGA TCGTATGCCC TCCGTGTTCA AGGCGAACCT

1051 TCAAAAGGCG AAATGCTCGC GGGCACGGCA GTGTACAACG GCGAAGTGCT

1101 GCATTTTCAT ACGGAAAACG GCCGTCCGTC CCCGTCCAGA GGCAGGTTTG

1151 CCGCAAAAGT CGATTTCGGC AGCAAATCTG TGGACGGCAT TATCGACAGC

1201 GGCGATGGTT TGCATATGGG TACGCAAAAA TTCAAAGCCG CCATCGATGG

1251 AAACGGCTTT AAGGGGACTT GGACGGAAAA TGGCGGCGGG GATGTTTCCG

1301 GAAAGTTTTA CGGCCCGGCC GGCGAGGAAG TGGCGGGAAA ATACAGCTAT
```

```
1351 CGCCCAACAG ATGCGGAAAA GGGCGGATTC GGCGTGTTTG CCGGCAAAAA

1401 AGAGCAGGAT GGATCCGGAG GAGGAGGAGC ACAAACGAC GACGATGTTA

1451 AAAAAGCTGC CACTGTGGCC ATTGCTGCTG CCTACAACAA TGGCCAAGAA

1501 ATCAACGGTT TCAAAGCTGG AGAGACCATC TACGACATTG ATGAAGACGG

1551 CACAATTACC AAAAAAGACG CAACTGCAGC CGATGTTGAA GCCGACGACT

1601 TTAAAGGTCT GGGTCTGAAA AAAGTCGTGA CTAACCTGAC CAAAACCGTC

1651 AATGAAAACA AACAAAACGT CGATGCCAAA GTAAAAGCTG CAGAATCTGA

1701 AATAGAAAAG TTAACAACCA AGTTAGCAGA CACTGATGCC GCTTTAGCAG

1751 ATACTGATGC CGCTCTGGAT GCAACCACCA ACGCCTTGAA TAAATTGGGA

1801 GAAAATATAA CGACATTTGC TGAAGAGACT AAGACAAATA TCGTAAAAAT

1851 TGATGAAAAA TTAGAAGCCG TGGCTGATAC CGTCGACAAG CATGCCGAAG

1901 CATTCAACGA TATCGCCGAT TCATTGGATG AAACCAACAC TAAGGCAGAC

1951 GAAGCCGTCA AAACCGCCAA TGAAGCCAAA CAGACGGCCG AAGAAACCAA

2001 ACAAAACGTC GATGCCAAAG TAAAAGCTGC AGAAACTGCA GCAGGCAAAG

2051 CCGAAGCTGC CGCTGGCACA GCTAATACTG CAGCCGACAA GGCCGAAGCT

2101 GTCGCTGCAA AAGTTACCGA CATCAAAGCT GATATCGCTA CGAACAAAGA

2151 TAATATTGCT AAAAAAGCAA ACAGTGCCGA CGTGTACACC AGAAGAAGT

2201 CTGACAGCAA ATTTGTCAGA ATTGATGGTC TGAACGCTAC TACCGAAAAA

2251 TTGGACACAC GCTTGGCTTC TGCTGAAAAA TCCATTGCCG ATCACGATAC

2301 TCGCCTGAAC GGTTTGGATA AACAGTGTC AGACCTGCGC AAAGAAACCC

2351 GCCAAGGCCT TGCAGAACAA GCCGCGCTCT CCGGTCTGTT CCAACCTTAC

2401 AACGTGGGTC GGTTCAATGT AACGGCTGCA GTCGGCGGCT ACAAATCCGA

2451 ATCGGCAGTC GCCATCGGTA CCGGCTTCCG CTTTACCGAA AACTTTGCCG

2501 CCAAAGCAGG CGTGGCAGTC GGCACTTCGT CCGGTTCTTC CGCAGCCTAC

2551 CATGTCGGCG TCAATTACGA GTGGTAAAAG CTT

1 MASPDVKSAD TLSKPAAPVV SEKETEAKED APQAGSQGQG APSAQGGQDM

51 AAVSEENTGN GGAAATDKPK NEDEGAQNDM PQNAADTDSL TPNHTPASNM

101 PAGNMENQAP DAGESEQPAN QPDMANTADG MQGDDPSAGG ENAGNTAAQG

151 TNQAENNQTA GSQNPASSTN PSATNSGGDF GRTNVGNSVV IDGPSQNITL

201 THCKGDSCSG NNFLDEEVQL KSEFEKLSDA DKISNYKKDG KNDGKNDKFV

251 GLVADSVQMK GINQYIIFYK PKPTSFARFR RSARSRRSLP AEMPLIPVNQ

301 ADTLIVDGEA VSLTGHSGNI FAPEGNYRYL TYGAEKLPGG SYALRVQGEP

351 SKGEMLAGTA VYNGEVLHFH TENGRPSPSR GRFAAKVDFG SKSVDGIIDS

401 GDGLHMGTQK FKAAIDGNGF KGTWTENGGG DVSGKFYGPA GEEVAGKYSY

451 RPTDAEKGGF GVFAGKKEQD GSGGGGATND DDVKKAATVA IAAAYNNGQE

501 INGFKAGETI YDIDEDGTIT KKDATAADVE ADDFKGLGLK KVVTNLTKTV

551 NENKQNVDAK VKAAESEIEK LTTKLADTDA ALADTDAALD ATTNALNKLG

601 ENITTFAEET KTNIVKIDEK LEAVADTVDK HAEAFNDIAD SLDETNTKAD

651 EAVKTANEAK QTAEETKQNV DAKVKAAETA AGKAEAAAGT ANTAADKAEA
```

```
701 VAAKVTDIKA DIATNKDNIA KKANSADVYT REESDSKFVR IDGLNATTEK

751 LDTRLASAEK SIADHDTRLN GLDKTVSDLR KETRQGLAEQ AALSGLFQPY

801 NVGRFNVTAA VGGYKSESAV AIGTGFRFTE NFAAKAGVAV GTSSGSSAAY

851 HVGVNYEW*
```

ΔG983 and Hybrids

Bactericidal titres generated in response to ΔG983 (His-fusion) were measured against various strains, including the homologous 2996 strain:

|       | 2996 | NGH38 | BZ133 |
|-------|------|-------|-------|
| ΔG983 | 512  | 128   | 128   |

ΔG983 was also expressed as a hybrid, with ORF46.1 (SEQ ID NOS:100 and 101), 741 (SEQ ID NOS:102 and 103), 961 (SEQ ID NOS:104 and 105) or 961c (SEQ ID NOS:106 and 107) at its C-terminus:

```
ΔG983-ORF46.1
    1 ATGACTTCTG CGCCCGACTT CAATGCAGGC GGTACCGGTA TCGGCAGCAA

51 CAGCAGAGCA ACAACAGCGA ATCAGCAGC AGTATCTTAC GCCGGTATCA

101 AGAACGAAAT GTGCAAAGAC AGAAGCATGC TCTGTGCCGG TCGGGATGAC

151 GTTGCGGTTA CAGACAGGGA TGCCAAAATC AATGCCCCCC CCCCGAATCT

201 GCATACCGGA GACTTTCCAA ACCCAAATGA CGCATACAAG AATTTGATCA

251 ACCTCAAACC TGCAATTGAA GCAGGCTATA CAGGACGCGG GGTAGAGGTA

301 GGTATCGTCG ACACAGGCGA ATCCGTCGGC AGCATATCCT TTCCCGAACT

351 GTATGGCAGA AAAGAACACG GCTATAACGA AAATTACAAA AACTATACGG

401 CGTATATGCG GAAGGAAGCG CCTGAAGACG GAGGCGGTAA AGACATTGAA

451 GCTTCTTTCG ACGATGAGGC CGTTATAGAG ACTGAAGCAA AGCCGACGGA

501 TATCCGCCAC GTAAAAGAAA TCGGACACAT CGATTTGGTC TCCCATATTA

551 TTGGCGGGCG TTCCGTGGAC GGCAGACCTG CAGGCGGTAT TGCGCCCGAT

601 GCGACGCTAC ACATAATGAA TACGAATGAT GAAACCAAGA ACGAAATGAT

651 GGTTGCAGCC ATCCGCAATG CATGGGTCAA GCTGGGCGAA CGTGGCGTGC

701 GCATCGTCAA TAACAGTTTT GGAACAACAT CGAGGGCAGG CACTGCCGAC

751 CTTTTCCAAA TAGCCAATTC GGAGGAGCAG TACCGCCAAG CGTTGCTCGA

801 CTATTCCGGC GGTGATAAAA CAGACGAGGG TATCCGCCTG ATGCAACAGA

851 GCGATTACGG CAACCTGTCC TACCACATCC GTAATAAAAA CATGCTTTTC

901 ATCTTTTCGA CAGGCAATGA CGCACAAGCT CAGCCCAACA CATATGCCCT

951 ATTGCCATTT TATGAAAAAG ACGCTCAAAA AGGCATTATC ACAGTCGCAG

1001 GCGTAGACCG CAGTGGAGAA AAGTTCAAAC GGGAAATGTA TGGAGAACCG

1051 GGTACAGAAC CGCTTGAGTA TGGCTCCAAC CATTGCGGAA TTACTGCCAT

1101 GTGGTGCCTG TCGGCACCCT ATGAAGCAAG CGTCCGTTTC ACCCGTACAA

1151 ACCCGATTCA AATTGCCGGA ACATCCTTTT CCGCACCCAT CGTAACCGGC
```

-continued

```
1201 ACGGCGGCTC TGCTGCTGCA GAAATACCCG TGGATGAGCA ACGACAACCT
1251 GCGTACCACG TTGCTGACGA CGGCTCAGGA CATCGGTGCA GTCGGCGTGG
1301 ACAGCAAGTT CGGCTGGGGA CTGCTGGATG CGGGTAAGGC CATGAACGGA
1351 CCCGCGTCCT TTCCGTTCGG CGACTTTACC GCCGATACGA AAGGTACATC
1401 CGATATTGCC TACTCCTTCC GTAACGACAT TTCAGGCACG GGCGGCCTGA
1451 TCAAAAAAGG CGGCAGCCAA CTGCAACTGC ACGGCAACAA CACCTATACG
1501 GGCAAAACCA TTATCGAAGG CGGTTCGCTG GTGTTGTACG GCAACAACAA
1551 ATCGGATATG CGCGTCGAAA CCAAAGGTGC GCTGATTTAT AACGGGCGG
1601 CATCCGGCGG CAGCCTGAAC AGCGACGGCA TTGTCTATCT GGCAGATACC
1651 GACCAATCCG GCGCAAACGA AACCGTACAC ATCAAAGGCA GTCTGCAGCT
1701 GGACGGCAAA GGTACGCTGT ACACACGTTT GGGCAAACTG CTGAAAGTGG
1751 ACGGTACGGC GATTATCGGC GGCAAGCTGT ACATGTCGGC ACGCGGCAAG
1801 GGGGCAGGCT ATCTCAACAG TACCGGACGA CGTGTTCCCT TCCTGAGTGC
1851 CGCCAAAATC GGGCAGGATT ATTCTTTCTT CACAAACATC GAAACCGACG
1901 GCGGCCTGCT GGCTTCCCTC GACAGCGTCG AAAAAACAGC GGGCAGTGAA
1951 GGCGACACGC TGTCCTATTA TGTCCGTCGC GGCAATGCGG CACGGACTGC
2001 TTCGGCAGCG GCACATTCCG CGCCCGCCGG TCTGAAACAC GCCGTAGAAC
2051 AGGGCGGCAG CAATCTGGAA AACCTGATGG TCGAACTGGA TGCCTCCGAA
2101 TCATCCGCAA CACCCGAGAC GGTTGAAACT GCGGCAGCCG ACCGCACAGA
2151 TATGCCGGGC ATCCGCCCCT ACGGCGCAAC TTTCCGCGCA GCGGCAGCCG
2201 TACAGCATGC GAATGCCGCC GACGGTGTAC GCATCTTCAA CAGTCTCGCC
2251 GCTACCGTCT ATGCCGACAG TACCGCCGCC CATGCCGATA TGCAGGGACG
2301 CCGCCTGAAA GCCGTATCGG ACGGGTTGGA CCACAACGGC ACGGGTCTGC
2351 GCGTCATCGC GCAAACCCAA CAGGACGGTG AACGTGGGA CAGGGCGGT
2401 GTTGAAGGCA AAATGCGCGG CAGTACCCAA ACCGTCGGCA TTGCCGCGAA
2451 AACCGGCGAA ATACGACAG CAGCCGCCAC ACTGGGCATG GGACGCAGCA
2501 CATGGAGCGA AAACAGTGCA AATGCAAAAA CCGACAGCAT TAGTCTGTTT
2551 GCAGGCATAC GGCACGATGC GGGCGATATC GGCTATCTCA AAGGCCTGTT
2601 CTCCTACGGA CGCTACAAAA ACAGCATCAG CCGCAGCACC GGTGCGGACG
2651 AACATGCGGA AGGCAGCGTC AACGGCACGC TGATGCAGCT GGGCGCACTG
2701 GGCGGTGTCA ACGTTCCGTT TGCCGCAACG GGAGATTTGA CGGTCGAAGG
2751 CGGTCTGCGC TACGACCTGC TCAAACAGGA TGCATTCGCC GAAAAAGGCA
2801 GTGCTTTGGG CTGGAGCGGC AACAGCCTCA CTGAAGGCAC GCTGGTCGGA
2851 CTCGCGGGTC TGAAGCTGTC GCAACCCTTG AGCGATAAAG CCGTCCTGTT
2901 TGCAACGGCG GGCGTGGAAC GCGACCTGAA CGGACGCGAC TACACGGTAA
2951 CGGGCGGCTT TACCGGCGCG ACTGCAGCAA CCGGCAAGAC GGGGGCACGC
3001 AATATGCCGC ACACCCGTCT GGTTGCCGGC CTGGGCGCGG ATGTCGAATT
3051 CGGCAACGGC TGGAACGGCT TGGCACGTTA CAGCTACGCC GGTTCCAAAC
3101 AGTACGGCAA CCACAGCGGA CGAGTCGGCG TAGGCTACCG GTTCCTCGAC
3151 GGTGGCGGAG GCACTGGATC CTCAGATTTG GCAAACGATT CTTTTATCCG
```

```
3201 GCAGGTTCTC GACCGTCAGC ATTTCGAACC CGACGGGAAA TACCACCTAT

3251 TCGGCAGCAG GGGGGAACTT GCCGAGCGCA GCGGCCATAT CGGATTGGGA

3301 AAAATACAAA GCCATCAGTT GGGCAACCTG ATGATTCAAC AGGCGGCCAT

3351 TAAAGGAAAT ATCGGCTACA TTGTCCGCTT TTCCGATCAC GGGCACGAAG

3401 TCCATTCCCC CTTCGACAAC CATGCCTCAC ATTCCGATTC TGATGAAGCC

3451 GGTAGTCCCG TTGACGGATT TAGCCTTTAC CGCATCCATT GGGACGGATA

3501 CGAACACCAT CCCGCCGACG GCTATGACGG CCACAGGGC GGCGGCTATC

3551 CCGCTCCCAA AGGCGCGAGG GATATATACA GCTACGACAT AAAAGGCGTT

3601 GCCCAAAATA TCCGCCTCAA CCTGACCGAC AACCGCAGCA CCGGACAACG

3651 GCTTGCCGAC CGTTTCCACA ATGCCGGTAG TATGCTGACG CAAGGAGTAG

3701 GCGACGGATT CAAACGCGCC ACCCGATACA GCCCCGAGCT GGACAGATCG

3751 GGCAATGCCG CCGAAGCCTT CAACGGCACT GCAGATATCG TTAAAAACAT

3801 CATCGGCGCG GCAGGAGAAA TTGTCGGCGC AGGCGATGCC GTGCAGGGCA

3851 TAAGCGAAGG CTCAAACATT GCTGTCATGC ACGGCTTGGG TCTGCTTTCC

3901 ACCGAAAACA AGATGGCGCG CATCAACGAT TTGGCAGATA TGGCGCAACT

3951 CAAAGACTAT GCCGCAGCAG CCATCCGCGA TTGGGCAGTC AAAACCCCA

4001 ATGCCGCACA AGGCATAGAA GCCGTCAGCA ATATCTTTAT GGCAGCCATC

4051 CCCATCAAAG GGATTGGAGC TGTTCGGGGA AAATACGGCT TGGGCGGCAT

4101 CACGGCACAT CCTATCAAGC GGTCGCAGAT GGGCGCGATC GCATTGCCGA

4151 AAGGGAAATC CGCCGTCAGC GACAATTTTG CCGATGCGGC ATACGCCAAA

4201 TACCCGTCCC CTTACCATTC CCGAAATATC CGTTCAAACT TGGAGCAGCG

4251 TTACGGCAAA GAAAACATCA CCTCCTCAAC CGTGCCGCCG TCAAACGGCA

4301 AAAATGTCAA ACTGGCAGAC CAACGCCACC CGAAGACAGG CGTACCGTTT

4351 GACGGTAAAG GGTTTCCGAA TTTTGAGAAG CACGTGAAAT ATGATACGCT

4401 CGAGCACCAC CACCACCACC ACTGA

1 MTSAPDFNAG GTGIGSNSRA TTAKSAAVSY AGIKNEMCKD RSMLCAGRDD

51 VAVTDRDAKI NAPPPNLHTG DFPNPNDAYK NLINLKPAIE AGYTGRGVEV

101 GIVDTGESVG SISFPELYGR KEHGYNENYK NYTAYMRKEA PEDGGGKDIE

151 ASFDDEAVIE TEAKPTDIRH VKEIGHIDLV SHIIGGRSVD GRPAGGIAPD

201 ATLHIMNTND ETKNEMMVAA IRNAWVKLGE RGVRIVNNSF GTTSRAGTAD

251 LFQIANSEEQ YRQALLDYSG GDKTDEGIRL MQQSDYGNLS YHIRNKNMLF

301 IFSTGNDAQA QPNTYALLPF YEKDAQKGII TVAGVDRSGE KFKREMYGEP

351 GTEPLEYGSN HCGITAMWCL SAPYEASVRF TRTNPIQIAG TSFSAPIVTG

401 TAALLLQKYP WMSNDNLRTT LLTTAQDIGA VGVDSKFGWG LLDAGKAMNG

451 PASFPFGDFT ADTKGTSDIA YSFRNDISGT GGLIKKGGSQ LQLHGNNTYT

501 GKTIIEGGSL VLYGNNKSDM RVETKGALIY NGAASGGSLN SDGIVYLADT

551 DQSGANETVH IKGSLQLDGK GTLYTRLGKL LKVDGTAIIG GKLYMSARGK

601 GAGYLNSTGR RVPFLSAAKI GQDYSFFTNI ETDGGLLASL DSVEKTAGSE

651 GDTLSYYVRR GNAARTASAA AHSAPAGLKH AVEQGGSNLE NLMVELDASE

701 SSATPETVET AAADRTDMPG IRPYGATFRA AAAVHANAA DGVRIFNSLA

751 ATVYADSTAA HADMQGRRLK AVSDGLDHNG TGLRVIAQTQ QDGGTWEQGG
```

```
 801  VEGKMRGSTQ  TVGIAAKTGE  NTTAAATLGM  GRSTWSENSA  NAKTDSISLF

851  AGIRHDAGDI  GYLKGLFSYG  RYKNSISRST  GADEHAEGSV  NGTLMQLGAL

901  GGVNVPFAAT  GDLTVEGGLR  YDLLKQDAFA  EKGSALGWSG  NSLTEGTLVG

951  LAGLKLSQPL  SDKAVLFATA  GVERDLNGRD  YTVTGGFTGA  TAATGKTGAR

1001  NMPHTRLVAG  LGADVEFGNG  WNGLARYSYA  GSKQYGNHSG  RVGVGYRFLD

1051  GGGGTGSSDL  ANDSFIRQVL  DRQHFEPDGK  YHLFGSRGEL  AERSGHIGLG

1101  KIQSHQLGNL  MIQQAAIKGN  IGYIVRFSDH  GHEVHSPFDN  HASHSDSDEA

1151  GSPVDGFSLY  RIHWDGYEHH  PADGYDGPQG  GGYPAPKGAR  DIYSYDIKGV

1201  AQNIRLNLTD  NRSTGQRLAD  RFHNAGSMLT  QGVGDGFKRA  TRYSPELDRS

1251  GNAAEAFNGT  ADIVKNIIGA  AGEIVGAGDA  VQGISEGSNI  AVMHGLGLLS

1301  TENKMARIND  LADMAQLKDY  AAAAIRDWAV  QNPNAAQGIE  AVSNIFMAAI

1351  PIKGIGAVRG  KYGLGGITAH  PIKRSQMGAI  ALPKGKSAVS  DNFADAAYAK

1401  YPSPYHSRNI  RSNLEQRYGK  ENITSSTVPP  SNGKNVKLAD  QRHPKTGVPF

1451  DGKGFPNFEK  HVKYDTLEHH  HHHH*
ΔG983-741
   1  ATGACTTCTG  CGCCCGACTT  CAATGCAGGC  GGTACCGGTA  TCGGCAGCAA

51  CAGCAGAGCA  ACAACAGCGA  ATCAGCAGC  AGTATCTTAC  GCCGGTATCA

101  AGAACGAAAT  GTGCAAAGAC  AGAAGCATGC  TCTGTGCCGG  TCGGGATGAC

151  GTTGCGGTTA  CAGACAGGGA  TGCCAAAATC  AATGCCCCCC  CCCCGAATCT

201  GCATACCGGA  GACTTTCCAA  ACCCAAATGA  CGCATACAAG  AATTTGATCA

251  ACCTCAAACC  TGCAATTGAA  GCAGGCTATA  CAGGACGCGG  GGTAGAGGTA

301  GGTATCGTCG  ACACAGGCGA  ATCCGTCGGC  AGCATATCCT  TTCCCGAACT

351  GTATGGCAGA  AAAGAACACG  GCTATAACGA  AAATTACAAA  AACTATACGG

401  CGTATATGCG  GAAGGAAGCG  CCTGAAGACG  GAGGCGGTAA  AGACATTGAA

451  GCTTCTTTCG  ACGATGAGGC  CGTTATAGAG  ACTGAAGCAA  AGCCGACGGA

501  TATCCGCCAC  GTAAAAGAAA  TCGGACACAT  CGATTTGGTC  TCCCATATTA

551  TTGGCGGGCG  TTCCGTGGAC  GGCAGACCTG  CAGGCGGTAT  TGCGCCCGAT

601  GCGACGCTAC  ACATAATGAA  TACGAATGAT  GAAACCAAGA  CGAAATGAT

651  GGTTGCAGCC  ATCCGCAATG  CATGGGTCAA  GCTGGGCGAA  CGTGGCGTGC

701  GCATCGTCAA  TAACAGTTTT  GGAACAACAT  CGAGGGCAGG  CACTGCCGAC

751  CTTTTCCAAA  TAGCCAATTC  GGAGGAGCAG  TACCGCCAAG  CGTTGCTCGA

801  CTATTCCGGC  GGTGATAAAA  CAGACGAGGG  TATCCGCCTG  ATGCAACAGA

851  GCGATTACGG  CAACCTGTCC  TACCACATCC  GTAATAAAAA  CATGCTTTTC

901  ATCTTTTCGA  CAGGCAATGA  CGCACAAGCT  CAGCCCAACA  CATATGCCCT

951  ATTGCCATTT  TATGAAAAAG  ACGCTCAAAA  AGGCATTATC  ACAGTCGCAG

1001  GCGTAGACCG  CAGTGGAGAA  AAGTTCAAAC  GGGAAATGTA  TGGAGAACCG

1051  GGTACAGAAC  CGCTTGAGTA  TGGCTCCAAC  CATTGCGGAA  TTACTGCCAT

1101  GTGGTGCCTG  TCGGCACCCT  ATGAAGCAAG  CGTCCGTTTC  ACCCGTACAA

1151  ACCCGATTCA  AATTGCCGGA  ACATCCTTTT  CCGCACCCAT  CGTAACCGGC

1201  ACGGCGGCTC  TGCTGCTGCA  GAAATACCCG  TGGATGAGCA  ACGACAACCT

1251  GCGTACCACG  TTGCTGACGA  CGGCTCAGGA  CATCGGTGCA  GTCGGCGTGG
```

-continued

```
1301 ACAGCAAGTT CGGCTGGGGA CTGCTGGATG CGGGTAAGGC CATGAACGGA
1351 CCCGCGTCCT TTCCGTTCGG CGACTTTACC GCCGATACGA AAGGTACATC
1401 CGATATTGCC TACTCCTTCC GTAACGACAT TTCAGGCACG GCGGCCTGA
1451 TCAAAAAAGG CGGCAGCCAA CTGCAACTGC ACGGCAACAA CACCTATACG
1501 GGCAAAACCA TTATCGAAGG CGGTTCGCTG GTGTTGTACG GCAACAACAA
1551 ATCGGATATG CGCGTCGAAA CCAAAGGTGC GCTGATTTAT AACGGGCGG
1601 CATCCGGCGG CAGCCTGAAC AGCGACGGCA TTGTCTATCT GGCAGATACC
1651 GACCAATCCG GCGCAAACGA AACCGTACAC ATCAAAGGCA GTCTGCAGCT
1701 GGACGGCAAA GGTACGCTGT ACACACGTTT GGGCAAACTG CTGAAAGTGG
1751 ACGGTACGGC GATTATCGGC GGCAAGCTGT ACATGTCGGC ACGCGGCAAG
1801 GGGGCAGGCT ATCTCAACAG TACCGGACGA CGTGTTCCCT TCCTGAGTGC
1851 CGCCAAAATC GGGCAGGATT ATTCTTTCTT CACAAACATC GAAACCGACG
1901 GCGGCCTGCT GGCTTCCCTC GACAGCGTCG AAAAAACAGC GGGCAGTGAA
1951 GGCGACACGC TGTCCTATTA TGTCCGTCGC GGCAATGCGG CACGGACTGC
2001 TTCGGCAGCG GCACATTCCG CGCCCGCCGG TCTGAAACAC GCCGTAGAAC
2051 AGGGCGGCAG CAATCTGGAA AACCTGATGG TCGAACTGGA TGCCTCCGAA
2101 TCATCCGCAA CACCCGAGAC GGTTGAAACT GCGGCAGCCG ACCGCACAGA
2151 TATGCCGGGC ATCCGCCCCT ACGGCGCAAC TTTCCGCGCA GCGGCAGCCG
2201 TACAGCATGC GAATGCCGCC GACGGTGTAC GCATCTTCAA CAGTCTCGCC
2251 GCTACCGTCT ATGCCGACAG TACCGCCGCC CATGCCGATA TGCAGGGACG
2301 CCGCCTGAAA GCCGTATCGG ACGGGTTGGA CCACAACGGC ACGGGTCTGC
2351 GCGTCATCGC GCAAACCCAA CAGGACGGTG AACGTGGGA CAGGGCGGT
2401 GTTGAAGGCA AAATGCGCGG CAGTACCCAA ACCGTCGGCA TTGCCGCGAA
2451 AACCGGCGAA ATACGACAG CAGCCGCCAC ACTGGGCATG GACGCAGCA
2501 CATGGAGCGA AAACAGTGCA AATGCAAAAA CCGACAGCAT TAGTCTGTTT
2551 GCAGGCATAC GGCACGATGC GGGCGATATC GGCTATCTCA AAGGCCTGTT
2601 CTCCTACGGA CGCTACAAAA ACAGCATCAG CCGCAGCACC GGTGCGGACG
2651 AACATGCGGA AGGCAGCGTC AACGGCACGC TGATGCAGCT GGGCGCACTG
2701 GGCGGTGTCA ACGTTCCGTT TGCCGCAACG GGAGATTTGA CGGTCGAAGG
2751 CGGTCTGCGC TACGACCTGC TCAAACAGGA TGCATTCGCC GAAAAAGGCA
2801 GTGCTTTGGG CTGGAGCGGC AACAGCCTCA CTGAAGGCAC GCTGGTCGGA
2851 CTCGCGGGTC TGAAGCTGTC GCAACCCTTG AGCGATAAAG CCGTCCTGTT
2901 TGCAACGGCG GGCGTGGAAC GCGACCTGAA CGGACGCGAC TACACGGTAA
2951 CGGGCGGCTT TACCGGCGCG ACTGCAGCAA CCGGCAAGAC GGGGGCACGC
3001 AATATGCCGC ACACCCGTCT GGTTGCCGGC CTGGGCGCGG ATGTCGAATT
3051 CGGCAACGGC TGGAACGGCT TGGCACGTTA CAGCTACGCC GGTTCCAAAC
3101 AGTACGGCAA CCACAGCGGA CGAGTCGGCG TAGGCTACCG GTTCCTCGAG
3151 GGATCCGGAG GGGGTGGTGT CGCCGCCGAC ATCGGTGCGG GCTTGCCGA
3201 TGCACTAACC GCACCGCTCG ACCATAAAGA CAAAGGTTTG CAGTCTTTGA
3251 CGCTGGATCA GTCCGTCAGG AAAAACGAGA AACTGAAGCT GGCGGCACAA
```

```
3301 GGTGCGGAAA AAACTTATGG AAACGGTGAC AGCCTCAATA CGGGCAAATT

3351 GAAGAACGAC AAGGTCAGCC GTTTCGACTT TATCCGCCAA ATCGAAGTGG

3401 ACGGGCAGCT CATTACCTTG GAGAGTGGAG AGTTCCAAGT ATACAAACAA

3451 AGCCATTCCG CCTTAACCGC CTTTCAGACC GAGCAAATAC AAGATTCGGA

3501 GCATTCCGGG AAGATGGTTG CGAAACGCCA GTTCAGAATC GGCGACATAG

3551 CGGGCGAACA TACATCTTTT GACAAGCTTC CCGAAGGCGG CAGGGCGACA

3601 TATCGCGGGA CGGCGTTCGG TTCAGACGAT GCCGGCGGAA AACTGACCTA

3651 CACCATAGAT TTCGCCGCCA AGCAGGGAAA CGGCAAAATC GAACATTTGA

3701 AATCGCCAGA ACTCAATGTC GACCTGGCCG CCGCCGATAT CAAGCCGGAT

3751 GGAAAACGCC ATGCCGTCAT CAGCGGTTCC GTCCTTTACA ACCAAGCCGA

3801 GAAAGGCAGT TACTCCCTCG GTATCTTTGG CGGAAAAGCC CAGGAAGTTG

3851 CCGGCAGCGC GGAAGTGAAA ACCGTAAACG GCATACGCCA TATCGGCCTT

3901 GCCGCCAAGC AACTCGAGCA CCACCACCAC CACCACTGA
```
```
   1 MTSAPDFNAG GTGIGSNSRA TTAKSAAVSY AGIKNEMCKD RSMLCAGRDD

51 VAVTDRDAKI NAPPPNLHTG DFPNPNDAYK NLINLKPAIE AGYTGRGVEV

101 GIVDTGESVG SISFPELYGR KEHGYNENYK NYTAYMRKEA PEDGGGKDIE

151 ASFDDEAVIE TEAKPTDIRH VKEIGHIDLV SHIIGGRSVD GRPAGGIAPD

201 ATLHIMNTND ETKNEMMVAA IRNAWVKLGE RGVRIVNNSF GTTSRAGTAD

251 LFQIANSEEQ YRQALLDYSG GDKTDEGIRL MQQSDYGNLS YHIRNKNMLF

301 IFSTGNDAQA QPNTYALLPF YEKDAQKGII TVAGVDRSGE KFKREMYGEP

351 GTEPLEYGSN HCGITAMWCL SAPYEASVRF TRTNPIQIAG TSFSAPIVTG

401 TAALLLQKYP WMSNDNLRTT LLTTAQDIGA VGVDSKFGWG LLDAGKAMNG

451 PASFPFGDFT ADTKGTSDIA YSFRNDISGT GGLIKKGGSQ LQLHGNNTYT

501 GKTIIEGGSL VLYGNNKSDM RVETKGALIY NGAASGGSLN SDGIVYLADT

551 DQSGANETVH IKGSLQLDGK GTLYTRLGKL LKVDGTAIIG GKLYMSARGK

601 GAGYLNSTGR RVPFLSAAKI GQDYSFFTNI ETDGGLLASL DSVEKTAGSE

651 GDTLSYYVRR GNAARTASAA AHSAPAGLKH AVEQGGSNLE NLMVELDASE

701 SSATPETVET AAADRTDMPG IRPYGATFRA AAAVQHANAA DGVRIFNSLA

751 ATVYADSTAA HADMQGRRLK AVSDGLDHNG TGLRVIAQTQ QDGGTWEQGG

801 VEGKMRGSTQ TVGIAAKTGE NTTAAATLGM GRSTWSENSA NAKTDSISLF

851 AGIRHDAGDI GYLKGLFSYG RYKNSISRST GADEHAEGSV NGTLMQLGAL

901 GGVNVPFAAT GDLTVEGGLR YDLLKQDAFA EKGSALGWSG NSLTEGTLVG

951 LAGLKLSQPL SDKAVLFATA GVERDLNGRD YTVTGGFTGA TAATGKTGAR

1001 NMPHTRLVAG LGADVEFGNG WNGLARYSYA GSKQYGNHSG RVGVGYRFLE

1051 GSGGGGVAAD IGAGLADALT APLDHKDKGL QSLTLDQSVR KNEKLKLAAQ

1101 GAEKTYGNGD SLNTGKLKND KVSRFDFIRQ IEVDGQLITL ESGEFQVYKQ

1151 SHSALTAFQT EQIQDSEHSG KMVAKRQFRI GDIAGEHTSF DKLPEGGRAT

1201 YRGTAFGSDD AGGKLTYTID FAAKQGNGKI EHLKSPELNV DLAAADIKPD

1251 GKRHAVISGS VLYNQAEKGS YSLGIFGGKA QEVAGSAEVK TVNGIRHIGL

1301 AAKQLEHHHH HH*
```

-continued

```
ΔG983-961
   1 ATGACTTCTG CGCCCGACTT CAATGCAGGC GGTACCGGTA TCGGCAGCAA
  51 CAGCAGAGCA ACAACAGCGA AATCAGCAGC AGTATCTTAC GCCGGTATCA
 101 AGAACGAAAT GTGCAAAGAC AGAAGCATGC TCTGTGCCGG TCGGGATGAC
 151 GTTGCGGTTA CAGACAGGGA TGCCAAAATC AATGCCCCCC CCCCGAATCT
 201 GCATACCGGA GACTTTCCAA ACCCAAATGA CGCATACAAG AATTTGATCA
 251 ACCTCAAACC TGCAATTGAA GCAGGCTATA CAGGACGCGG GGTAGAGGTA
 301 GGTATCGTCG ACACAGGCGA ATCCGTCGGC AGCATATCCT TTCCCGAACT
 351 GTATGGCAGA AAAGAACACG GCTATAACGA AAATTACAAA ACTATACGG
 401 CGTATATGCG GAAGGAAGCG CCTGAAGACG GAGGCGGTAA AGACATTGAA
 451 GCTTCTTTCG ACGATGAGGC CGTTATAGAG ACTGAAGCAA AGCCGACGGA
 501 TATCCGCCAC GTAAAGAAA TCGGACACAT CGATTTGGTC TCCCATATTA
 551 TTGGCGGGCG TTCCGTGGAC GGCAGACCTG CAGGCGGTAT TGCGCCCGAT
 601 GCGACGCTAC ACATAATGAA TACGAATGAT GAAACCAAGA ACGAAATGAT
 651 GGTTGCAGCC ATCCGCAATG CATGGGTCAA GCTGGGCGAA CGTGGCGTGC
 701 GCATCGTCAA TAACAGTTTT GGAACAACAT CGAGGGCAGG CACTGCCGAC
 751 CTTTTCCAAA TAGCCAATTC GGAGGAGCAG TACCGCCAAG CGTTGCTCGA
 801 CTATTCCGGC GGTGATAAAA CAGACGAGGG TATCCGCCTG ATGCAACAGA
 851 GCGATTACGG CAACCTGTCC TACCACATCC GTAATAAAAA CATGCTTTTC
 901 ATCTTTTCGA CAGGCAATGA CGCACAAGCT CAGCCCAACA CATATGCCCT
 951 ATTGCCATTT TATGAAAAAG ACGCTCAAAA AGGCATTATC ACAGTCGCAG
1001 GCGTAGACCG CAGTGGAGAA AAGTTCAAAC GGGAAATGTA TGGAGAACCG
1051 GGTACAGAAC CGCTTGAGTA TGGCTCCAAC CATTGCGGAA TTACTGCCAT
1101 GTGGTGCCTG TCGGCACCCT ATGAAGCAAG CGTCCGTTTC ACCCGTACAA
1151 ACCCGATTCA AATTGCCGGA ACATCCTTTT CCGCACCCAT CGTAACCGGC
1201 ACGGCGGCTC TGCTGCTGCA GAAATACCCG TGGATGAGCA ACGACAACCT
1251 GCGTACCACG TTGCTGACGA CGGCTCAGGA CATCGGTGCA GTCGGCGTGG
1301 ACAGCAAGTT CGGCTGGGGA CTGCTGGATG CGGGTAAGGC CATGAACGGA
1351 CCCGCGTCCT TTCCGTTCGG CGACTTTACC GCCGATACGA AGGTACATC
1401 CGATATTGCC TACTCCTTCC GTAACGACAT TTCAGGCACG GCGGCCTGA
1451 TCAAAAAAGG CGGCAGCCAA CTGCAACTGC ACGGCAACAA CACCTATACG
1501 GGCAAAACCA TTATCGAAGG CGGTTCGCTG GTGTTGTACG CAACAACAA
1551 ATCGGATATG CGCGTCGAAA CCAAAGGTGC GCTGATTTAT AACGGGGCGG
1601 CATCCGGCGG CAGCCTGAAC AGCGACGGCA TTGTCTATCT GGCAGATACC
1651 GACCAATCCG GCGCAAACGA AACCGTACAC ATCAAAGGCA GTCTGCAGCT
1701 GGACGGCAAA GGTACGCTGT ACACACGTTT GGGCAAACTG CTGAAAGTGG
1751 ACGGTACGGC GATTATCGGC GGCAAGCTGT ACATGTCGGC ACGCGGCAAG
1801 GGGGCAGGCT ATCTCAACAG TACCGGACGA CGTGTTCCCT TCCTGAGTGC
1851 CGCCAAAATC GGGCAGGATT ATTCTTTCTT CACAAACATC GAAACCGACG
1901 GCGGCCTGCT GGCTTCCCTC GACAGCGTCG AAAAAACAGC GGGCAGTGAA
1951 GGCGACACGC TGTCCTATTA TGTCCGTCGC GGCAATGCGG CACGGACTGC
```

-continued

```
2001 TTCGGCAGCG GCACATTCCG CGCCCGCCGG TCTGAAACAC GCCGTAGAAC
2051 AGGGCGGCAG CAATCTGGAA AACCTGATGG TCGAACTGGA TGCCTCCGAA
2101 TCATCCGCAA CACCCGAGAC GGTTGAAACT GCGGCAGCCG ACCGCACAGA
2151 TATGCCGGGC ATCCGCCCCT ACGGCGCAAC TTTCCGCGCA GCGGCAGCCG
2201 TACAGCATGC GAATGCCGCC GACGGTGTAC GCATCTTCAA CAGTCTCGCC
2251 GCTACCGTCT ATGCCGACAG TACCGCCGCC CATGCCGATA TGCAGGGACG
2301 CCGCCTGAAA GCCGTATCGG ACGGGTTGGA CCACAACGGC ACGGGTCTGC
2351 GCGTCATCGC GCAAACCCAA CAGGACGGTG AACGTGGGA CAGGGCGGT
2401 GTTGAAGGCA AAATGCGCGG CAGTACCCAA ACCGTCGGCA TTGCCGCGAA
2451 AACCGGCGAA ATACGACAG CAGCCGCCAC ACTGGGCATG GGACGCAGCA
2501 CATGGAGCGA AAACAGTGCA AATGCAAAAA CCGACAGCAT TAGTCTGTTT
2551 GCAGGCATAC GGCACGATGC GGGCGATATC GGCTATCTCA AAGGCCTGTT
2601 CTCCTACGGA CGCTACAAAA ACAGCATCAG CCGCAGCACC GGTGCGGACG
2651 AACATGCGGA AGGCAGCGTC AACGGCACGC TGATGCAGCT GGGCGCACTG
2701 GGCGGTGTCA ACGTTCCGTT TGCCGCAACG GGAGATTTGA CGGTCGAAGG
2751 CGGTCTGCGC TACGACCTGC TCAAACAGGA TGCATTCGCC GAAAAAGGCA
2801 GTGCTTTGGG CTGGAGCGGC AACAGCCTCA CTGAAGGCAC GCTGGTCGGA
2851 CTCGCGGGTC TGAAGCTGTC GCAACCCTTG AGCGATAAAG CCGTCCTGTT
2901 TGCAACGGCG GGCGTGGAAC GCGACCTGAA CGGACGCGAC TACACGGTAA
2951 CGGGCGGCTT TACCGGCGCG ACTGCAGCAA CCGGCAAGAC GGGGGCACGC
3001 AATATGCCGC ACACCCGTCT GGTTGCCGGC CTGGGCGCGG ATGTCGAATT
3051 CGGCAACGGC TGGAACGGCT TGGCACGTTA CAGCTACGCC GGTTCCAAAC
3101 AGTACGGCAA CCACAGCGGA CGAGTCGGCG TAGGCTACCG GTTCCTCGAG
3151 GGTGGCGGAG GCACTGGATC CGCCACAAAC GACGACGATG TTAAAAAAGC
3201 TGCCACTGTG GCCATTGCTG CTGCCTACAA CAATGGCCAA GAAATCAACG
3251 GTTTCAAAGC TGGAGAGACC ATCTACGACA TTGATGAAGA CGGCACAATT
3301 ACCAAAAAAG ACGCAACTGC AGCCGATGTT GAAGCCGACG ACTTTAAAGG
3351 TCTGGGTCTG AAAAAAGTCG TGACTAACCT GACCAAAACC GTCAATGAAA
3401 ACAAACAAAA CGTCGATGCC AAAGTAAAAG CTGCAGAATC TGAAATAGAA
3451 AAGTTAACAA CCAAGTTAGC AGACACTGAT GCCGCTTTAG CAGATACTGA
3501 TGCCGCTCTG GATGCAACCA CCAACGCCTT GAATAAATTG GGAGAAAATA
3551 TAACGACATT TGCTGAAGAG ACTAAGACAA ATATCGTAAA AATTGATGAA
3601 AAATTAGAAG CCGTGGCTGA TACCGTCGAC AAGCATGCCG AAGCATTCAA
3651 CGATATCGCC GATTCATTGG ATGAAACCAA CACTAAGGCA GACGAAGCCG
3701 TCAAAACCGC CAATGAAGCC AAACAGACGG CCGAAGAAAC CAAACAAAAC
3751 GTCGATGCCA AAGTAAAAGC TGCAGAAACT GCAGCAGGCA AAGCCGAAGC
3801 TGCCGCTGGC ACAGCTAATA CTGCAGCCGA CAAGGCCGAA GCTGTCGCTG
3851 CAAAAGTTAC CGACATCAAA GCTGATATCG CTACGAACAA AGATAATATT
3901 GCTAAAAAAG CAAACAGTGC CGACGTGTAC ACCAGAGAAG AGTCTGACAG
3951 CAAATTTGTC AGAATTGATG GTCTGAACGC TACTACCGAA AAATTGGACA
4001 CACGCTTGGC TTCTGCTGAA AAATCCATTG CCGATCACGA TACTCGCCTG
```

-continued

```
4051 AACGGTTTGG ATAAAACAGT GTCAGACCTG CGCAAAGAAA CCCGCCAAGG

4101 CCTTGCAGAA CAAGCCGCGC TCTCCGGTCT GTTCCAACCT TACAACGTGG

4151 GTCGGTTCAA TGTAACGGCT GCAGTCGGCG GCTACAAATC CGAATCGGCA

4201 GTCGCCATCG GTACCGGCTT CCGCTTTACC GAAAACTTTG CCGCCAAAGC

4251 AGGCGTGGCA GTCGGCACTT CGTCCGGTTC TTCCGCAGCC TACCATGTCG

4301 GCGTCAATTA CGAGTGGCTC GAGCACCACC ACCACCACCA CTGA

1 MTSAPDFNAG GTGIGSNSRA TTAKSAAVSY AGIKNEMCKD RSMLCAGRDD

51 VAVTDRDAKI NAPPPNLHTG DFPNPNDAYK NLINLKPAIE AGYTGRGVEV

101 GIVDTGESVG SISFPELYGR KEHGYNENYK NYTAYMRKEA PEDGGGKDIE

151 ASFDDEAVIE TEAKPTDIRH VKEIGHIDLV SHIIGGRSVD GRPAGGIAPD

201 ATLHIMNTND ETKNEMMVAA IRNAWVKLGE RGVRIVNNSF GTTSRAGTAD

251 LFQIANSEEQ YRQALLDYSG GDKTDEGIRL MQQSDYGNLS YHIRNKNMLF

301 IFSTGNDAQA QPNTYALLPF YEKDAQKGII TVAGVDRSGE KFKREMYGEP

351 GTEPLEYGSN HCGITAMWCL SAPYEASVRF TRTNPIQIAG TSFSAPIVTG

401 TAALLLQKYP WMSNDNLRTT LLTTAQDIGA VGVDSKFGWG LLDAGKAMNG

451 PASFPFGDFT ADTKGTSDIA YSFRNDISGT GGLIKKGGSQ LQLHGNNTYT

501 GKTIIEGGSL VLYGNNKSDM RVETKGALIY NGAASGGSLN SDGIVYLADT

551 DQSGANETVH IKGSLQLDGK GTLYTRLGKL LKVDGTAIIG GKLYMSARGK

601 GAGYLNSTGR RVPFLSAAKI GQDYSFFTNI ETDGGLLASL DSVEKTAGSE

651 GDTLSYYVRR GNAARTASAA AHSAPAGLKH AVEQGGSNLE NLMVELDASE

701 SSATPETVET AAADRTDMPG IRPYGATFRA AAAVQHANAA DGVRIFNSLA

751 ATVYADSTAA HADMQGRRLK AVSDGLDHNG TGLRVIAQTQ QDGGTWEQGG

801 VEGKMRGSTQ TVGIAAKTGE NTTAAATLGM GRSTWSENSA NAKTDSISLF

851 AGIRHDAGDI GYLKGLFSYG RYKNSISRST GADEHAEGSV NGTLMQLGAL

901 GGVNVPFAAT GDLTVEGGLR YDLLKQDAFA EKGSALGWSG NSLTEGTLVG

951 LAGLKLSQPL SDKAVLFATA GVERDLNGRD YTVTGGFTGA TAATGKTGAR

1001 NMPHTRLVAG LGADVEFGNG WNGLARYSYA GSKQYGNHSG RVGVGYRFLE

1051 GGGGTGSATN DDDVKKAATV AIAAAYNNGQ EINGFKAGET IYDIDEDGTI

1101 TKKDATAADV EADDFKGLGL KKVVTNLTKT VNENKQNVDA KVKAAESEIE

1151 KLTTKLADTD AALADTDAAL DATTNALNKL GENITTFAEE TKTNIVKIDE

1201 KLEAVADTVD KHAEAFNDIA DSLDETNTKA DEAVKTANEA KQTAEETKQN

1251 VDAKVKAAET AAGKAEAAAG TANTAADKAE AVAAKVTDIK ADIATNKDNI

1301 AKKANSADVY TREESDSKFV RIDGLNATTE KLDTRLASAE KSIADHDTRL

1351 NGLDKTVSDL RKETRQGLAE QAALSGLFQP YNVGRFNVTA AVGGYKSESA

1401 VAIGTGFRFT ENFAAKAGVA VGTSSGSSAA YHVGVNYEWL EHHHHHH*

ΔG983-961c
   1 ATGACTTCTG CGCCCGACTT CAATGCAGGC GGTACCGGTA TCGGCAGCAA

51 CAGCAGAGCA ACAACAGCGA AATCAGCAGC AGTATCTTAC GCCGGTATCA

101 AGAACGAAAT GTGCAAAGAC AGAAGCATGC TCTGTGCCGG TCGGGATGAC

151 GTTGCGGTTA CAGACAGGGA TGCCAAAATC AATGCCCCCC CCCCGAATCT

201 GCATACCGGA GACTTTCCAA ACCCAAATGA CGCATACAAG AATTTGATCA
```

-continued

```
 251 ACCTCAAACC TGCAATTGAA GCAGGCTATA CAGGACGCGG GGTAGAGGTA
 301 GGTATCGTCG ACACAGGCGA ATCCGTCGGC AGCATATCCT TTCCCGAACT
 351 GTATGGCAGA AAAGAACACG GCTATAACGA AAATTACAAA AACTATACGG
 401 CGTATATGCG GAAGGAAGCG CCTGAAGACG GAGGCGGTAA AGACATTGAA
 451 GCTTCTTTCG ACGATGAGGC CGTTATAGAG ACTGAAGCAA AGCCGACGGA
 501 TATCCGCCAC GTAAAAGAAA TCGGACACAT CGATTTGGTC TCCCATATTA
 551 TTGGCGGGCG TTCCGTGGAC GGCAGACCTG CAGGCGGTAT TGCGCCCGAT
 601 GCGACGCTAC ACATAATGAA TACGAATGAT GAAACCAAGA ACGAAATGAT
 651 GGTTGCAGCC ATCCGCAATG CATGGGTCAA GCTGGGCGAA CGTGGCGTGC
 701 GCATCGTCAA TAACAGTTTT GGAACAACAT CGAGGGCAGG CACTGCCGAC
 751 CTTTTCCAAA TAGCCAATTC GGAGGAGCAG TACCGCCAAG CGTTGCTCGA
 801 CTATTCCGGC GGTGATAAAA CAGACGAGGG TATCCGCCTG ATGCAACAGA
 851 GCGATTACGG CAACCTGTCC TACCACATCC GTAATAAAAA CATGCTTTTC
 901 ATCTTTTCGA CAGGCAATGA CGCACAAGCT CAGCCCAACA CATATGCCCT
 951 ATTGCCATTT TATGAAAAAG ACGCTCAAAA AGGCATTATC ACAGTCGCAG
1001 GCGTAGACCG CAGTGGAGAA AAGTTCAAAC GGGAAATGTA TGGAGAACCG
1051 GGTACAGAAC CGCTTGAGTA TGGCTCCAAC CATTGCGGAA TTACTGCCAT
1101 GTGGTGCCTG TCGGCACCCT ATGAAGCAAG CGTCCGTTTC ACCCGTACAA
1151 ACCCGATTCA AATTGCCGGA ACATCCTTTT CCGCACCCAT CGTAACCGGC
1201 ACGGCGGCTC TGCTGCTGCA GAAATACCCG TGGATGAGCA ACGACAACCT
1251 GCGTACCACG TTGCTGACGA CGGCTCAGGA CATCGGTGCA GTCGGCGTGG
1301 ACAGCAAGTT CGGCTGGGGA CTGCTGGATG CGGGTAAGGC CATGAACGGA
1351 CCCGCGTCCT TTCCGTTCGG CGACTTTACC GCCGATACGA AAGGTACATC
1401 CGATATTGCC TACTCCTTCC GTAACGACAT TTCAGGCACG GGCGGCCTGA
1451 TCAAAAAAGG CGGCAGCCAA CTGCAACTGC ACGGCAACAA CACCTATACG
1501 GGCAAAACCA TTATCGAAGG CGGTTCGCTG GTGTTGTACG GCAACAACAA
1551 ATCGGATATG CGCGTCGAAA CCAAAGGTGC GCTGATTTAT AACGGGGCGG
1601 CATCCGGCGG CAGCCTGAAC AGCGACGGCA TTGTCTATCT GGCAGATACC
1651 GACCAATCCG GCGCAAACGA AACCGTACAC ATCAAAGGCA GTCTGCAGCT
1701 GGACGGCAAA GGTACGCTGT ACACACGTTT GGGCAAACTG CTGAAAGTGG
1751 ACGGTACGGC GATTATCGGC GGCAAGCTGT ACATGTCGGC ACGCGGCAAG
1801 GGGCAGGCT ATCTCAACAG TACCGGACGA CGTGTTCCCT TCCTGAGTGC
1851 CGCCAAAATC GGGCAGGATT ATTCTTTCTT CACAAACATC GAAACCGACG
1901 GCGGCCTGCT GGCTTCCCTC GACAGCGTCG AAAAAACAGC GGGCAGTGAA
1951 GGCGACACGC TGTCCTATTA TGTCCGTCGC GGCAATGCGG CACGGACTGC
2001 TTCGGCAGCG GCACATTCCG CGCCCGCCGG TCTGAAACAC GCCGTAGAAC
2051 AGGGCGGCAG CAATCTGGAA AACCTGATGG TCGAACTGGA TGCCTCCGAA
```

```
-continued
2101  TCATCCGCAA CACCCGAGAC GGTTGAAACT GCGGCAGCCG ACCGCACAGA

2151  TATGCCGGGC ATCCGCCCCT ACGGCGCAAC TTTCCGCGCA GCGGCAGCCG

2201  TACAGCATGC GAATGCCGCC GACGGTGTAC GCATCTTCAA CAGTCTCGCC

2251  GCTACCGTCT ATGCCGACAG TACCGCCGCC CATGCCGATA TGCAGGGACG

2301  CCGCCTGAAA GCCGTATCGG ACGGGTTGGA CCACAACGGC ACGGGTCTGC

2351  GCGTCATCGC GCAAACCCAA CAGGACGGTG AACGTGGGA ACAGGGCGGT

2401  GTTGAAGGCA AAATGCGCGG CAGTACCCAA ACCGTCGGCA TTGCCGCGAA

2451  AACCGGCGAA AATACGACAG CAGCCGCCAC ACTGGGCATG GGACGCAGCA

2501  CATGGAGCGA AAACAGTGCA AATGCAAAAA CCGACAGCAT TAGTCTGTTT

2551  GCAGGCATAC GGCACGATGC GGGCGATATC GGCTATCTCA AAGGCCTGTT

2601  CTCCTACGGA CGCTACAAAA ACAGCATCAG CCGCAGCACC GGTGCGGACG

2651  AACATGCGGA AGGCAGCGTC AACGGCACGC TGATGCAGCT GGGCGCACTG

2701  GGCGGTGTCA ACGTTCCGTT TGCCGCAACG GGAGATTTGA CGGTCGAAGG

2751  CGGTCTGCGC TACGACCTGC TCAAACAGGA TGCATTCGCC GAAAAAGGCA

2801  GTGCTTTGGG CTGGAGCGGC AACAGCCTCA CTGAAGGCAC GCTGGTCGGA

2851  CTCGCGGGTC TGAAGCTGTC GCAACCCTTG AGCGATAAAG CCGTCCTGTT

2901  TGCAACGGCG GGCGTGGAAC GCGACCTGAA CGGACGCGAC TACACGGTAA

2951  CGGGCGGCTT TACCGGCGCG ACTGCAGCAA CCGGCAAGAC GGGGGCACGC

3001  AATATGCCGC ACACCCGTCT GGTTGCCGGC CTGGGCGCGG ATGTCGAATT

3051  CGGCAACGGC TGGAACGGCT TGGCACGTTA CAGCTACGCC GGTTCCAAAC

3101  AGTACGGCAA CCACAGCGGA CGAGTCGGCG TAGGCTACCG GTTCCTCGAG

3151  GGTGGCGGAG GCACTGGATC CGCCACAAAC GACGACGATG TTAAAAAAGC

3201  TGCCACTGTG GCCATTGCTG CTGCCTACAA CAATGGCCAA GAAATCAACG

3251  GTTTCAAAGC TGGAGAGACC ATCTACGACA TTGATGAAGA CGGCACAATT

3301  ACCAAAAAAG ACGCAACTGC AGCCGATGTT GAAGCCGACG ACTTTAAAGG

3351  TCTGGGTCTG AAAAAAGTCG TGACTAACCT GACCAAAACC GTCAATGAAA

3401  ACAAACAAAA CGTCGATGCC AAAGTAAAAG CTGCAGAATC TGAAATAGAA

3451  AAGTTAACAA CCAAGTTAGC AGACACTGAT GCCGCTTTAG CAGATACTGA

3501  TGCCGCTCTG GATGCAACCA CCAACGCCTT GAATAAATTG GGAGAAAATA

3551  TAACGACATT TGCTGAAGAG ACTAAGACAA ATATCGTAAA AATTGATGAA

3601  AAATTAGAAG CCGTGGCTGA TACCGTCGAC AAGCATGCCG AAGCATTCAA

3651  CGATATCGCC GATTCATTGG ATGAAACCAA CACTAAGGCA GACGAAGCCG

3701  TCAAAACCGC CAATGAAGCC AAACAGACGG CCGAAGAAAC CAAACAAAAC

3751  GTCGATGCCA AAGTAAAAGC TGCAGAAACT GCAGCAGGCA AAGCCGAAGC

3801  TGCCGCTGGC ACAGCTAATA CTGCAGCCGA CAAGGCCGAA GCTGTCGCTG

3851  CAAAAGTTAC CGACATCAAA GCTGATATCG CTACGAACAA AGATAATATT

3901  GCTAAAAAAG CAAACAGTGC CGACGTGTAC ACCAGAGAAG AGTCTGACAG
```

-continued

```
3951 CAAATTTGTC AGAATTGATG GTCTGAACGC TACTACCGAA AAATTGGACA

4001 CACGCTTGGC TTCTGCTGAA AAATCCATTG CCGATCACGA TACTCGCCTG

4051 AACGGTTTGG ATAAAACAGT GTCAGACCTG CGCAAAGAAA CCCGCCAAGG

4101 CCTTGCAGAA CAAGCCGCGC TCTCCGGTCT GTTCCAACCT TACAACGTGG

4151 GTCTCGAGCA CCACCACCAC CACCACTGA

1 MTSAPDFNAG GTGIGSNSRA TTAKSAAVSY AGIKNEMCKD RSMLCAGRDD

51 VAVTDRDAKI NAPPPNLHTG DFPNPNDAYK NLINLKPAIE AGYTGRGVEV

101 GIVDTGESVG SISFPELYGR KEHGYNENYK NYTAYMRKEA PEDGGGKDIE

151 ASFDDEAVIE TEAKPTDIRH VKEIGHIDLV SHIIGGRSVD GRPAGGIAPD

201 ATLHIMNTND ETKNEMMVAA IRNAWVKLGE RGVRIVNNSF GTTSRAGTAD

251 LFQIANSEEQ YRQALLDYSG GDKTDEGIRL MQQSDYGNLS YHIRNKNMLF

301 IFSTGNDAQA QPNTYALLPF YEKDAQKGII TVAGVDRSGE KFKREMYGEP

351 GTEPLEYGSN HCGITAMWCL SAPYEASVRF TRTNPIQIAG TSFSAPIVTG

401 TAALLLQKYP WMSNDNLRTT LLTTAQDIGA VGVDSKFGWG LLDAGKAMNG

451 PASFPFGDFT ADTKGTSDIA YSFRNDISGT GGLIKKGGSQ LQLHGNNTYT

501 GKTIIEGGSL VLYGNNKSDM RVETKGALIY NGAASGGSLN SDGIVYLADT

551 DQSGANETVH IKGSLQLDGK GTLYTRLGKL LKVDGTAIIG GKLYMSARGK

601 GAGYLNSTGR RVPFLSAAKI GQDYSFFTNI ETDGGLLASL DSVEKTAGSE

651 GDTLSYYVRR GNAARTASAA AHSAPAGLKH AVEQGGSNLE NLMVELDASE

701 SSATPETVET AAADRTDMPG IRPYGATFRA AAAVQHANAA DGVRIFNSLA

751 ATVYADSTAA HADMQGRRLK AVSDGLDHNG TGLRVIAQTQ QDGGTWEQGG

801 VEGKMRGSTQ TVGIAAKTGE NTTAAATLGM GRSTWSENSA NAKTDSISLF

851 AGIRHDAGDI GYLKGLFSYG RYKNSISRST GADEHAEGSV NGTLMQLGAL

901 GGVNVPFAAT GDLTVEGGLR YDLLKQDAFA EKGSALGWSG NSLTEGTLVG

951 LAGLKLSQPL SDKAVLFATA GVERDLNGRD YTVTGGFTGA TAATGKTGAR

1001 NMPHTRLVAG LGADVEFGNG WNGLARYSYA GSKQYGNHSG RVGVGYRFLE

1051 GGGGTGSATN DDDVKKAATV AIAAAYNNGQ EINGFKAGET IYDIDEDGTI

1101 TKKDATAADV EADDFKGLGL KKVVTNLTKT VNENKQNVDA KVKAAESEIE

1151 KLTTKLADTD AALADTDAAL DATTNALNKL GENITTFAEE TKTNIVKIDE

1201 KLEAVADTVD KHAEAFNDIA DSLDETNTKA DEAVKTANEA KQTAEETKQN
```

```
                           -continued
1251 VDAKVKAAET AAGKAEAAAG TANTAADKAE AVAAKVTDIK ADIATNKDNI

1301 AKKANSADVY TREESDSKFV RIDGLNATTE KLDTRLASAE KSIADHDTRL

1351 NGLDKTVSDL RKETRQGLAE QAALSGLFQP YNVGLEHHHH HH*
```

ΔG741 and Hybrids

Bactericidal titres generated in response to ΔG741 (His-fusion) were measured against various strains, including the homologous 2996 strain:

|  | 2996 | MC58 | NGH38 | F6124 | BZ133 |
|---|---|---|---|---|---|
| ΔG741 | 512 | 131072 | >2048 | 16384 | >2048 |

As can be seen, the ΔG741-induced anti-bactericidal titre is particularly high against heterologous strain MC58.

ΔG741 was also fused directly in-frame upstream of proteins 961 (SEQ ID NOS:108 and 109), 961c (SEQ ID NOS: 110 and 111), 983 (SEQ ID NOS:112 and 113) and ORF46.1 (SEQ ID NOS:114 and 115):

```
ΔG741-961
    1 ATGGTCGCCG CCGACATCGG TGCGGGGCTT GCCGATGCAC TAACCGCACC

51 GCTCGACCAT AAAGACAAAG GTTTGCAGTC TTTGACGCTG GATCAGTCCG

101 TCAGGAAAAA CGAGAAACTG AAGCTGGCGG CACAAGGTGC GGAAAAAACT

151 TATGGAAACG GTGACAGCCT CAATACGGGC AAATTGAAGA ACGACAAGGT

201 CAGCCGTTTC GACTTTATCC GCCAAATCGA AGTGGACGGG CAGCTCATTA

251 CCTTGGAGAG TGGAGAGTTC CAAGTATACA AACAAAGCCA TTCCGCCTTA

301 ACCGCCTTTC AGACCGAGCA AATACAAGAT TCGGAGCATT CCGGGAAGAT

351 GGTTGCGAAA CGCCAGTTCA GAATCGGCGA CATAGCGGGC GAACATACAT

401 CTTTTGACAA GCTTCCCGAA GGCGGCAGGG CGACATATCG CGGGACGGCG

451 TTCGGTTCAG ACGATGCCGG CGGAAAACTG ACCTACACCA TAGATTTCGC

501 CGCCAAGCAG GGAAACGGCA AAATCGAACA TTTGAAATCG CCAGAACTCA

551 ATGTCGACCT GGCCGCCGCC GATATCAAGC CGGATGGAAA ACGCCATGCC

601 GTCATCAGCG GTTCCGTCCT TTACAACCAA GCCGAGAAAG GCAGTTACTC

651 CCTCGGTATC TTTGGCGGAA AAGCCCAGGA AGTTGCCGGC AGCGCGGAAG

701 TGAAAACCGT AAACGGCATA CGCCATATCG GCCTTGCCGC CAAGCAACTC

751 GAGGGTGGCG GAGGCACTGG ATCCGCCACA AACGACGACG ATGTTAAAAA

801 AGCTGCCACT GTGGCCATTG CTGCTGCCTA CAACAATGGC CAAGAAATCA

851 ACGGTTTCAA AGCTGGAGAG ACCATCTACG ACATTGATGA AGACGGCACA

901 ATTACCAAAA AAGACGCAAC TGCAGCCGAT GTTGAAGCCG ACGACTTTAA

951 AGGTCTGGGT CTGAAAAAAG TCGTGACTAA CCTGACCAAA ACCGTCAATG

1001 AAAACAAACA AAACGTCGAT GCCAAAGTAA AGCTGCAGA ATCTGAAATA

1051 GAAAAGTTAA CAACCAAGTT AGCAGACACT GATGCCGCTT TAGCAGATAC

1101 TGATGCCGCT CTGGATGCAA CCACCAACGC CTTGAATAAA TTGGGAGAAA

1151 ATATAACGAC ATTTGCTGAA GAGACTAAGA CAAATATCGT AAAAATTGAT

1201 GAAAAATTAG AAGCCGTGGC TGATACCGTC GACAAGCATG CCGAAGCATT

1251 CAACGATATC GCCGATTCAT TGGATGAAAC CAACACTAAG GCAGACGAAG
```

-continued

```
1301 CCGTCAAAAC CGCCAATGAA GCCAAACAGA CGGCCGAAGA AACCAAACAA
1351 AACGTCGATG CCAAAGTAAA AGCTGCAGAA ACTGCAGCAG GCAAAGCCGA
1401 AGCTGCCGCT GGCACAGCTA ATACTGCAGC CGACAAGGCC GAAGCTGTCG
1451 CTGCAAAAGT TACCGACATC AAAGCTGATA TCGCTACGAA CAAAGATAAT
1501 ATTGCTAAAA AAGCAAACAG TGCCGACGTG TACACCAGAG AAGAGTCTGA
1551 CAGCAAATTT GTCAGAATTG ATGGTCTGAA CGCTACTACC GAAAAATTGG
1601 ACACACGCTT GGCTTCTGCT GAAAAATCCA TTGCCGATCA CGATACTCGC
1651 CTGAACGGTT TGGATAAAAC AGTGTCAGAC CTGCGCAAAG AAACCCGCCA
1701 AGGCCTTGCA GAACAAGCCG CGCTCTCCGG TCTGTTCCAA CCTTACAACG
1751 TGGGTCGGTT CAATGTAACG GCTGCAGTCG GCGGCTACAA ATCCGAATCG
1801 GCAGTCGCCA TCGGTACCGG CTTCCGCTTT ACCGAAAACT TTGCCGCCAA
1851 AGCAGGCGTG GCAGTCGGCA CTTCGTCCGG TTCTTCCGCA GCCTACCATG
1901 TCGGCGTCAA TTACGAGTGG CTCGAGCACC ACCACCACCA CCACTGA

1 MVAADIGAGL ADALTAPLDH KDKGLQSLTL DQSVRKNEKL KLAAQGAEKT
  51 YGNGDSLNTG KLKNDKVSRF DFIRQIEVDG QLITLESGEF QVYKQSHSAL
 101 TAFQTEQIQD SEHSGKMVAK RQFRIGDIAG EHTSFDKLPE GGRATYRGTA
 151 FGSDDAGGKL TYTIDFAAKQ GNGKIEHLKS PELNVDLAAA DIKPDGKRHA
 201 VISGSVLYNQ AEKGSYSLGI FGGKAQEVAG SAEVKTVNGI RHIGLAAKQL
 251 EGGGGTGSAT NDDDVKKAAT VAIAAAYNNG QEINGFKAGE TIYDIDEDGT
 301 ITKKDATAAD VEADDFKGLG LKKVVTNLTK TVNENKQNVD AKVKAAESEI
 351 EKLTTKLADT DAALADTAA LDATTNALNK LGENITTFAE ETKTNIVKID
 401 EKLEAVADTV DKHAEAFNDI ADSLDETNTK ADEAVKTANE AKQTAEETKQ
 451 NVDAKVKAAE TAAGKAEAAA GTANTAADKA EAVAAKVTDI KADIATNKDN
 501 IAKKANSADV YTREESDSKF VRIDGLNATT EKLDTRLASA EKSIADHDTR
 551 LNGLDKTVSD LRKETRQGLA EQAALSGLFQ PYNVGRFNVT AAVGGYKSES
 601 AVAIGTGFRF TENFAAKAGV AVGTSSGSSA AYHVGVNYEW LEHHHHHH*
```

ΔG741-961c
```
   1 ATGGTCGCCG CCGACATCGG TGCGGGGCTT GCCGATGCAC TAACCGCACC
  51 GCTCGACCAT AAAGACAAAG GTTTGCAGTC TTTGACGCTG GATCAGTCCG
 101 TCAGGAAAAA CGAGAAACTG AAGCTGGCGG CACAAGGTGC GGAAAAAACT
 151 TATGGAAACG GTGACAGCCT CAATACGGGC AAATTGAAGA ACGACAAGGT
 201 CAGCCGTTTC GACTTTATCC GCCAAATCGA AGTGGACGGG CAGCTCATTA
 251 CCTTGGAGAG TGGAGAGTTC CAAGTATACA AACAAAGCCA TTCCGCCTTA
 301 ACCGCTTTC AGACCGAGCA AATACAAGAT TCGGAGCATT CCGGGAAGAT
 351 GGTTGCGAAA CGCCAGTTCA GAATCGGCGA CATAGCGGGC GAACATACAT
 401 CTTTTGACAA GCTTCCCGAA GGCGGCAGGG CGACATATCG CGGGACGGCG
 451 TTCGGTTCAG ACGATGCCGG CGGAAAACTG ACCTACACCA TAGATTTCGC
 501 CGCCAAGCAG GGAAACGGCA AAATCGAACA TTTGAAATCG CCAGAACTCA
 551 ATGTCGACCT GGCCGCCGCC GATATCAAGC CGGATGGAAA ACGCCATGCC
 601 GTCATCAGCG GTTCCGTCCT TTACAACCAA GCCGAGAAAG GCAGTTACTC
 651 CCTCGGTATC TTTGGCGGAA AAGCCCAGGA AGTTGCCGGC AGCGCGGAAG
```

```
 701  TGAAAACCGT AAACGGCATA CGCCATATCG GCCTTGCCGC CAAGCAACTC
 751  GAGGGTGGCG GAGGCACTGG ATCCGCCACA AACGACGACG ATGTTAAAAA
 801  AGCTGCCACT GTGGCCATTG CTGCTGCCTA CAACAATGGC CAAGAAATCA
 851  ACGGTTTCAA AGCTGGAGAG ACCATCTACG ACATTGATGA AGACGGCACA
 901  ATTACCAAAA AAGACGCAAC TGCAGCCGAT GTTGAAGCCG ACGACTTTAA
 951  AGGTCTGGGT CTGAAAAAAG TCGTGACTAA CCTGACCAAA ACCGTCAATG
1001  AAAACAAACA AAACGTCGAT GCCAAAGTAA AAGCTGCAGA ATCTGAAATA
1051  GAAAAGTTAA CAACCAAGTT AGCAGACACT GATGCCGCTT TAGCAGATAC
1101  TGATGCCGCT CTGGATGCAA CCACCAACGC CTTGAATAAA TTGGGAGAAA
1151  ATATAACGAC ATTTGCTGAA GAGACTAAGA CAAATATCGT AAAAATTGAT
1201  GAAAAATTAG AAGCCGTGGC TGATACCGTC GACAAGCATG CCGAAGCATT
1251  CAACGATATC GCCGATTCAT TGGATGAAAC CAACACTAAG GCAGACGAAG
1301  CCGTCAAAAC CGCCAATGAA GCCAAACAGA CGGCCGAAGA AACCAAACAA
1351  AACGTCGATG CCAAAGTAAA AGCTGCAGAA ACTGCAGCAG GCAAAGCCGA
1401  AGCTGCCGCT GGCACAGCTA ATACTGCAGC CGACAAGGCC GAAGCTGTCG
1451  CTGCAAAAGT TACCGACATC AAAGCTGATA TCGCTACGAA CAAAGATAAT
1501  ATTGCTAAAA AAGCAAACAG TGCCGACGTG TACACCAGAG AAGAGTCTGA
1551  CAGCAAATTT GTCAGAATTG ATGGTCTGAA CGCTACTACC GAAAAATTGG
1601  ACACACGCTT GGCTTCTGCT GAAAAATCCA TTGCCGATCA CGATACTCGC
1651  CTGAACGGTT TGGATAAAAC AGTGTCAGAC CTGCGCAAAG AAACCCGCCA
1701  AGGCCTTGCA GAACAAGCCG CGCTCTCCGG TCTGTTCCAA CCTTACAACG
1751  TGGGTCTCGA GCACCACCAC CACCACCACT GA

1  MVAADIGAGL ADALTAPLDH KDKGLQSLTL DQSVRKNEKL KLAAQGAEKT
  51  YGNGDSLNTG KLKNDKVSRF DFIRQIEVDG QLITLESGEF QVYKQSHSAL
 101  TAFQTEQIQD SEHSGKMVAK RQFRIGDIAG EHTSFDKLPE GGRATYRGTA
 151  FGSDDAGGKL TYTIDFAAKQ GNGKIEHLKS PELNVDLAAA DIKPDGKRHA
 201  VISGSVLYNQ AEKGSYSLGI FGGKAQEVAG SAEVKTVNGI RHIGLAAKQL
 251  EGGGGTGSAT NDDDVKKAAT VAIAAAYNNG QEINGFKAGE TIYDIDEDGT
 301  ITKKDATAAD VEADDFKGLG LKKVVTNLTK TVNENKQNVD AKVKAAESEI
 351  EKLTTKLADT DAALADTDAA LDATTNALNK LGENITTFAE ETKTNIVKID
 401  EKLEAVADTV DKHAEAFNDI ADSLDETNTK ADEAVKTANE AKQTAEETKQ
 451  NVDAKVKAAE TAAGKAEAAA GTANTAADKA EAVAAKVTDI KADIATNKDN
 501  IAKKANSADV YTREESDSKF VRIDGLNATT EKLDTRLASA EKSIADHDTR
 551  LNGLDKTVSD LRKETRQGLA EQAALSGLFQ PYNVGLEHHH HHH*

ΔG741-983
   1  ATGGTCGCCG CCGACATCGG TGCGGGGCTT GCCGATGCAC TAACCGCACC
  51  GCTCGACCAT AAAGACAAAG GTTTGCAGTC TTTGACGCTG GATCAGTCCG
 101  TCAGGAAAAA CGAGAAACTG AAGCTGGCGG CACAAGGTGC GGAAAAAACT
 151  TATGGAAACG GTGACAGCCT CAATACGGGC AAATTGAAGA ACGACAAGGT
 201  CAGCCGTTTC GACTTTATCC GCCAAATCGA AGTGGACGGG CAGCTCATTA
 251  CCTTGGAGAG TGGAGAGTTC CAAGTATACA AACAAAGCCA TTCCGCCTTA
```

-continued

```
 301 ACCGCCTTTC AGACCGAGCA AATACAAGAT TCGGAGCATT CCGGGAAGAT
 351 GGTTGCGAAA CGCCAGTTCA GAATCGGCGA CATAGCGGGC GAACATACAT
 401 CTTTTGACAA GCTTCCCGAA GGCGGCAGGG CGACATATCG CGGGACGGCG
 451 TTCGGTTCAG ACGATGCCGG CGGAAAACTG ACCTACACCA TAGATTTCGC
 501 CGCCAAGCAG GGAAACGGCA AAATCGAACA TTTGAAATCG CCAGAACTCA
 551 ATGTCGACCT GGCCGCCGCC GATATCAAGC CGGATGGAAA ACGCCATGCC
 601 GTCATCAGCG GTTCCGTCCT TTACAACCAA GCCGAGAAAG GCAGTTACTC
 651 CCTCGGTATC TTTGGCGGAA AAGCCCAGGA AGTTGCCGGC AGCGCGGAAG
 701 TGAAAACCGT AAACGGCATA CGCCATATCG GCCTTGCCGC CAAGCAACTC
 751 GAGGGATCCG GCGGAGGCGG CACTTCTGCG CCCGACTTCA ATGCAGGCGG
 801 TACCGGTATC GGCAGCAACA GCAGAGCAAC AACAGCGAAA TCAGCAGCAG
 851 TATCTTACGC CGGTATCAAG AACGAAATGT GCAAAGACAG AAGCATGCTC
 901 TGTGCCGGTC GGGATGACGT TGCGGTTACA GACAGGGATG CCAAAATCAA
 951 TGCCCCCCCC CCGAATCTGC ATACCGGAGA CTTTCCAAAC CCAAATGACG
1001 CATACAAGAA TTTGATCAAC CTCAAACCTG CAATTGAAGC AGGCTATACA
1051 GGACGCGGGG TAGAGGTAGG TATCGTCGAC ACAGGCGAAT CCGTCGGCAG
1101 CATATCCTTT CCCGAACTGT ATGGCAGAAA AGAACACGGC TATAACGAAA
1151 ATTACAAAAA CTATACGGCG TATATGCGGA AGGAAGCGCC TGAAGACGGA
1201 GGCGGTAAAG ACATTGAAGC TTCTTTCGAC GATGAGGCCG TTATAGAGAC
1251 TGAAGCAAAG CCGACGGATA TCCGCCACGT AAAAGAAATC GGACACATCG
1301 ATTTGGTCTC CCATATTATT GGCGGGCGTT CCGTGGACGG CAGACCTGCA
1351 GGCGGTATTG CGCCCGATGC GACGCTACAC ATAATGAATA CGAATGATGA
1401 AACCAAGAAC GAAATGATGG TTGCAGCCAT CCGCAATGCA TGGGTCAAGC
1451 TGGGCGAACG TGGCGTGCGC ATCGTCAATA ACAGTTTTGG AACAACATCG
1501 AGGGCAGGCA CTGCCGACCT TTTCCAAATA GCCAATTCGG AGGAGCAGTA
1551 CCGCCAAGCG TTGCTCGACT ATTCCGGCGG TGATAAAACA GACGAGGGTA
1601 TCCGCCTGAT GCAACAGAGC GATTACGGCA ACCTGTCCTA CCACATCCGT
1651 AATAAAAACA TGCTTTTCAT CTTTTCGACA GGCAATGACG CACAAGCTCA
1701 GCCCAACACA TATGCCCTAT TGCCATTTTA TGAAAAAGAC GCTCAAAAAG
1751 GCATTATCAC AGTCGCAGGC GTAGACCGCA GTGGAGAAAA GTTCAAACGG
1801 GAAATGTATG GAGAACCGGG TACAGAACCG CTTGAGTATG CTCCAACCA
1851 TTGCGGAATT ACTGCCATGT GGTGCCTGTC GGCACCCTAT GAAGCAAGCG
1901 TCCGTTTCAC CCGTACAAAC CCGATTCAAA TTGCCGGAAC ATCCTTTTCC
1951 GCACCCATCG TAACCGGCAC GGCGGCTCTG CTGCTGCAGA ATACCCGTG
2001 GATGAGCAAC GACAACCTGC GTACCACGTT GCTGACGACG GCTCAGGACA
2051 TCGGTGCAGT CGGCGTGGAC AGCAAGTTCG GCTGGGGACT GCTGGATGCG
2101 GGTAAGGCCA TGAACGGACC CGCGTCCTTT CCGTTCGGCG ACTTTACCGC
2151 CGATACGAAA GGTACATCCG ATATTGCCTA CTCCTTCCGT AACGACATTT
2201 CAGGCACGGG CGGCCTGATC AAAAAAGGCG GCAGCCAACT GCAACTGCAC
2251 GGCAACAACA CCTATACGGG CAAAACCATT ATCGAAGGCG GTTCGCTGGT
```

```
2301 GTTGTACGGC AACAACAAAT CGGATATGCG CGTCGAAACC AAAGGTGCGC
2351 TGATTTATAA CGGGGCGGCA TCCGGCGGCA GCCTGAACAG CGACGGCATT
2401 GTCTATCTGG CAGATACCGA CCAATCCGGC GCAAACGAAA CCGTACACAT
2451 CAAAGGCAGT CTGCAGCTGG ACGGCAAAGG TACGCTGTAC ACACGTTTGG
2501 GCAAACTGCT GAAAGTGGAC GGTACGGCGA TTATCGGCGG CAAGCTGTAC
2551 ATGTCGGCAC GCGGCAAGGG GGCAGGCTAT CTCAACAGTA CCGGACGACG
2601 TGTTCCCTTC CTGAGTGCCG CCAAAATCGG GCAGGATTAT TCTTTCTTCA
2651 CAAACATCGA ACCGACGGC GGCCTGCTGG CTTCCCTCGA CAGCGTCGAA
2701 AAAACAGCGG GCAGTGAAGG CGACACGCTG TCCTATTATG TCCGTCGCGG
2751 CAATGCGGCA CGGACTGCTT CGGCAGCGGC ACATTCCGCG CCCGCCGGTC
2801 TGAAACACGC CGTAGAACAG GGCGGCAGCA ATCTGGAAAA CCTGATGGTC
2851 GAACTGGATG CCTCCGAATC ATCCGCAACA CCCGAGACGG TTGAAACTGC
2901 GGCAGCCGAC CGCACAGATA TGCCGGGCAT CCGCCCCTAC GGCGCAACTT
2951 TCCGCGCAGC GGCAGCCGTA CAGCATGCGA ATGCCGCCGA CGGTGTACGC
3001 ATCTTCAACA GTCTCGCCGC TACCGTCTAT GCCGACAGTA CCGCCGCCCA
3051 TGCCGATATG CAGGGACGCC GCCTGAAAGC CGTATCGGAC GGGTTGGACC
3101 ACAACGGCAC GGGTCTGCGC GTCATCGCGC AAACCCAACA GGACGGTGGA
3151 ACGTGGGAAC AGGGCGGTGT TGAAGGCAAA ATGCGCGGCA GTACCCAAAC
3201 CGTCGGCATT GCCGCGAAAA CCGGCGAAAA TACGACAGCA GCCGCCACAC
3251 TGGGCATGGG ACGCAGCACA TGGAGCGAAA ACAGTGCAAA TGCAAAAACC
3301 GACAGCATTA GTCTGTTTGC AGGCATACGG CACGATGCGG GCGATATCGG
3351 CTATCTCAAA GGCCTGTTCT CCTACGGACG CTACAAAAAC AGCATCAGCC
3401 GCAGCACCGG TGCGGACGAA CATGCGGAAG CAGCGTCAA CGGCACGCTG
3451 ATGCAGCTGG GCGCACTGGG CGGTGTCAAC GTTCCGTTTG CCGCAACGGG
3501 AGATTTGACG GTCGAAGGCG GTCTGCGCTA CGACCTGCTC AAACAGGATG
3551 CATTCGCCGA AAAAGGCAGT GCTTTGGGCT GGAGCGGCAA CAGCCTCACT
3601 GAAGGCACGC TGGTCGGACT CGCGGGTCTG AAGCTGTCGC AACCCTTGAG
3651 CGATAAAGCC GTCCTGTTTG CAACGGCGGG CGTGGAACGC GACCTGAACG
3701 GACGCGACTA CACGGTAACG GGCGGCTTTA CCGGCGCGAC TGCAGCAACC
3751 GGCAAGACGG GGGCACGCAA TATGCCGCAC ACCCGTCTGG TTGCCGGCCT
3801 GGGCGCGGAT GTCGAATTCG GCAACGGCTG GAACGGCTTG CACGTTACA
3851 GCTACGCCGG TTCCAAACAG TACGGCAACC ACAGCGGACG AGTCGGCGTA
3901 GGCTACCGGT TCCTCGAGCA CCACCACCAC CACCACTGA
   1 MVAADIGAGL ADALTAPLDH KDKGLQSLTL DQSVRKNEKL KLAAQGAEKT
  51 YGNGDSLNTG KLKNDKVSRF DFIRQIEVDG QLITLESGEF QVYKQSHSAL
 101 TAFQTEQIQD SEHSGKMVAK RQFRIGDIAG EHTSFDKLPE GGRATYRGTA
 151 FGSDDAGGKL TYTIDFAAKQ GNGKIEHLKS PELNVDLAAA DIKPDGKRHA
 201 VISGSVLYNQ AEKGSYSLGI FGGKAQEVAG SAEVKTVNGI RHIGLAAKQL
 251 EGSGGGGTSA PDFNAGGTGI GSNSRATTAK SAAVSYAGIK NEMCKDRSML
 301 CAGRDDVAVT DRDAKINAPP PNLHTGDFPN PNDAYKNLIN LKPAIEAGYT
 351 GRGVEVGIVD TGESVGSISF PELYGRKEHG YNENYKNYTA YMRKEAPEDG
```

```
 401 GGKDIEASFD DEAVIETEAK PTDIRHVKEI GHIDLVSHII GGRSVDGRPA
 451 GGIAPDATLH IMNTNDETKN EMMVAAIRNA WVKLGERGVR IVNNSFGTTS
 501 RAGTADLFQI ANSEEQYRQA LLDYSGGDKT DEGIRLMQQS DYGNLSYHIR
 551 NKNMLFIFST GNDAQAQPNT YALLPFYEKD AQKGIITVAG VDRSGEKFKR
 601 EMYGEPGTEP LEYGSNHCGI TAMWCLSAPY EASVRFTRTN PIQIAGTSFS
 651 APIVTGTAAL LLQKYPWMSN DNLRTTLLTT AQDIGAVGVD SKFGWGLLDA
 701 GKAMNGPASF PFGDFTADTK GTSDIAYSFR NDISGTGGLI KKGGSQLQLH
 751 GNNTYTGKTI IEGGSLVLYG NNKSDMRVET KGALIYNGAA SGGSLNSDGI
 801 VYLADTDQSG ANETVHIKGS LQLDGKGTLY TRLGKLLKVD GTAIIGGKLY
 851 MSARGKGAGY LNSTGRRVPF LSAAKIGQDY SFFTNIETDG GLLASLDSVE
 901 KTAGSEGDTL SYYVRRGNAA RTASAAAHSA PAGLKHAVEQ GGSNLENLMV
 951 ELDASESSAT PETVETAAAD RTDMPGIRPY GATFRAAAAV QHANAADGVR
1001 IFNSLAATVY ADSTAAHADM QGRRLKAVSD GLDHNGTGLR VIAQTQQDGG
1051 TWEQGGVEGK MRGSTQTVGI AAKTGENTTA AATLGMGRST WSENSANAKT
1101 DSISLFAGIR HDAGDIGYLK GLFSYGRYKN SISRSTGADE HAEGSVNGTL
1151 MQLGALGGVN VPFAATGDLT VEGGLRYDLL KQDAFAEKGS ALGWSGNSLT
1201 EGTLVGLAGL KLSQPLSDKA VLFATAGVER DLNGRDYTVT GGFTGATAAT
1251 GKTGARNMPH TRLVAGLGAD VEFGNGWNGL ARYSYAGSKQ YGNHSGRVGV
1301 GYRFLEHHHH HH*
ΔG741-ORF46.1
   1 ATGGTCGCCG CCGACATCGG TGCGGGGCTT GCCGATGCAC TAACCGCACC
  51 GCTCGACCAT AAAGACAAAG GTTTGCAGTC TTTGACGCTG GATCAGTCCG
 101 TCAGGAAAAA CGAGAAACTG AAGCTGGCGG CACAAGGTGC GGAAAAAACT
 151 TATGGAAACG GTGACAGCCT CAATACGGGC AAATTGAAGA CGACAAGGT
 201 CAGCCGTTTC GACTTTATCC GCCAAATCGA AGTGGACGGG CAGCTCATTA
 251 CCTTGGAGAG TGGAGAGTTC CAAGTATACA ACAAAGCCA TTCCGCCTTA
 301 ACCGCCTTTC AGACCGAGCA ATACAAGAT TCGGAGCATT CCGGGAAGAT
 351 GGTTGCGAAA CGCCAGTTCA GAATCGGCGA CATAGCGGGC GAACATACAT
 401 CTTTTGACAA GCTTCCCGAA GGCGGCAGGG CGACATATCG CGGGACGGCG
 451 TTCGGTTCAG ACGATGCCGG CGGAAAACTG ACCTACACCA TAGATTTCGC
 501 CGCCAAGCAG GGAAACGGCA AAATCGAACA TTTGAAATCG CCAGAACTCA
 551 ATGTCGACCT GGCCGCCGCC GATATCAAGC CGGATGGAAA ACGCCATGCC
 601 GTCATCAGCG GTTCCGTCCT TTACAACCAA GCCGAGAAAG GCAGTTACTC
 651 CCTCGGTATC TTTGGCGGAA AAGCCCAGGA AGTTGCCGGC AGCGCGGAAG
 701 TGAAAACCGT AAACGGCATA CGCCATATCG GCCTTGCCGC CAAGCAACTC
 751 GACGGTGGCG GAGGCACTGG ATCCTCAGAT TTGGCAAACG ATTCTTTTAT
 801 CCGGCAGGTT CTCGACCGTC AGCATTTCGA ACCCGACGGG AAATACCACC
 851 TATTCGGCAG CAGGGGGGAA CTTGCCGAGC GCAGCGGCCA TATCGGATTG
 901 GGAAAAATAC AAAGCCATCA GTTGGGCAAC CTGATGATTC AACAGGCGGC
 951 CATTAAAGGA ATATCGGCT ACATTGTCCG CTTTTCCGAT CACGGGCACG
1001 AAGTCCATTC CCCCTTCGAC AACCATGCCT CACATTCCGA TTCTGATGAA
```

-continued

```
1051 GCCGGTAGTC CCGTTGACGG ATTTAGCCTT TACCGCATCC ATTGGGACGG

1101 ATACGAACAC CATCCCGCCG ACGGCTATGA CGGGCCACAG GGCGGCGGCT

1151 ATCCCGCTCC CAAAGGCGCG AGGGATATAT ACAGCTACGA CATAAAAGGC

1201 GTTGCCCAAA ATATCCGCCT CAACCTGACC GACAACCGCA GCACCGGACA

1251 ACGGCTTGCC GACCGTTTCC ACAATGCCGG TAGTATGCTG ACGCAAGGAG

1301 TAGGCGACGG ATTCAAACGC GCCACCCGAT ACAGCCCCGA GCTGGACAGA

1351 TCGGGCAATG CCGCCGAAGC CTTCAACGGC ACTGCAGATA TCGTTAAAAA

1401 CATCATCGGC GCGGCAGGAG AAATTGTCGG CGCAGGCGAT GCCGTGCAGG

1451 GCATAAGCGA AGGCTCAAAC ATTGCTGTCA TGCACGGCTT GGGTCTGCTT

1501 TCCACCGAAA ACAAGATGGC GCGCATCAAC GATTTGGCAG ATATGGCGCA

1551 ACTCAAAGAC TATGCCGCAG CAGCCATCCG CGATTGGGCA GTCCAAAACC

1601 CCAATGCCGC ACAAGGCATA GAAGCCGTCA GCAATATCTT TATGGCAGCC

1651 ATCCCCATCA AGGGATTGG AGCTGTTCGG GGAAAATACG GCTTGGGCGG

1701 CATCACGGCA CATCCTATCA AGCGGTCGCA GATGGGCGCG ATCGCATTGC

1751 CGAAAGGGAA ATCCGCCGTC AGCGACAATT TTGCCGATGC GGCATACGCC

1801 AAATACCCGT CCCCTTACCA TTCCCGAAAT ATCCGTTCAA ACTTGGAGCA

1851 GCGTTACGGC AAAGAAAACA TCACCTCCTC AACCGTGCCG CCGTCAAACG

1901 GCAAAAATGT CAAACTGGCA GACCAACGCC ACCCGAAGAC AGGCGTACCG

1951 TTTGACGGTA AAGGGTTTCC GAATTTTGAG AAGCACGTGA AATATGATAC

2001 GCTCGAGCAC CACCACCACC ACCACTGA

1 MVAADIGAGL ADALTAPLDH KDKGLQSLTL DQSVRKNEKL KLAAQGAEKT

51 YGNGDSLNTG KLKNDKVSRF DFIRQIEVDG QLITLESGEF QVYKQSHSAL

101 TAFQTEQIQD SEHSGKMVAK RQFRIGDIAG EHTSFDKLPE GGRATYRGTA

151 FGSDDAGGKL TYTIDFAAKQ GNGKIEHLKS PELNVDLAAA DIKPDGKRHA

201 VISGSVLYNQ AEKGSYSLGI FGGKAQEVAG SAEVKTVNGI RHIGLAAKQL

251 DGGGTGSSD LANDSFIRQV LDRQHFEPDG KYHLFGSRGE LAERSGHIGL

301 GKIQSHQLGN LMIQQAAIKG NIGYIVRFSD HGHEVHSPFD NHASHSDSDE

351 AGSPVDGFSL YRIHWDGYEH HPADGYDGPQ GGGYPAPKGA RDIYSYDIKG

401 VAQNIRLNLT DNRSTGQRLA DRFHNAGSML TQGVGDGFKR ATRYSPELDR

451 SGNAAEAFNG TADIVKNIIG AAGEIVGAGD AVQGISEGSN IAVMHGLGLL

501 STENKMARIN DLADMAQLKD YAAAAIRDWA VQNPNAAQGI EAVSNIFMAA

551 IPIKGIGAVR GKYGLGGITA HPIKRSQMGA IALPKGKSAV SDNFADAAYA

601 KYPSPYHSRN IRSNLEQRYG KENITSSTVP PSNGKNVKLA DQRHPKTGVP

651 FDGKGFPNFE KHVKYDTLEH HHHHH*
```

Example 16

C-Terminal Fusions ('hybrids') with 287/ΔG287

According to the invention, hybrids of two proteins A & B may be either NH₂-A-B—COOH or NH₂—B-A-COOH. The effect of this difference was investigated using protein 287 either C-terminal (in '287-His' form) or N-terminal (in ΔG287 form—sequences shown above) to 919, 953 and ORF46.1. A panel of strains was used, including homologous strain 2996. FCA was used as adjuvant:

|  | 287 & 919 | | 287 & 953 | | 287 & ORF46.1 | |
| --- | --- | --- | --- | --- | --- | --- |
| Strain | ΔG287-919 | 919-287 | ΔG287-953 | 953-287 | ΔG287-46.1 | 46.1-287 |
| 2996 | 128000 | 16000 | 65536 | 8192 | 16384 | 8192 |
| BZ232 | 256 | 128 | 128 | <4 | <4 | <4 |
| 1000 | 2048 | <4 | <4 | <4 | <4 | <4 |
| MC58 | 8192 | 1024 | 16384 | 1024 | 512 | 128 |
| NGH38 | 32000 | 2048 | >2048 | 4096 | 16384 | 4096 |
| 394/98 | 4096 | 32 | 256 | 128 | 128 | 16 |
| MenA (F6124) | 32000 | 2048 | >2048 | 32 | 8192 | 1024 |
| MenC (BZ133) | 64000 | >8192 | >8192 | <16 | 8192 | 2048 |

Better bactericidal titres are generally seen with 287 at the N-terminus (in the ΔG form)

When fused to protein 961 [NH₂-ΔG287-961-COOH—sequence shown above], the resulting protein is insoluble and must be denatured and renatured for purification. Following renaturation, around 50% of the protein was found to remain insoluble. The soluble and insoluble proteins were compared, and much better bactericidal titres were obtained with the soluble protein (FCA as adjuvant):

|  | 2996 | BZ232 | MC58 | NGH38 | F6124 | BZ133 |
| --- | --- | --- | --- | --- | --- | --- |
| Soluble | 65536 | 128 | 4096 | >2048 | >2048 | 4096 |
| Insoluble | 8192 | <4 | <4 | 16 | n.d. | n.d. |

Titres with the insoluble form were, however, improved by using alum adjuvant instead:

| Insoluble | 32768 | 128 | 4096 | >2048 | >2048 | 2048 |
| --- | --- | --- | --- | --- | --- | --- |

Example 17

N-Terminal Fusions ('Hybrids') to 287

Expression of protein 287 as full-length with a C-terminal His-tag, or without its leader peptide but with a C-terminal His-tag, gives fairly low expression levels. Better expression is achieved using a N-terminal GST-fusion.

As an alternative to using GST as an N-terminal fusion partner, 287 was placed at the C-terminus of protein 919 ('919-287'), of protein 953 ('953-287'), and of proteins ORF46.1 ('ORF46.1-287'). In both cases, the leader peptides were deleted, and the hybrids were direct in-frame fusions.

To generate the 953-287 hybrid, the leader peptides of the two proteins were omitted by designing the forward primer downstream from the leader of each sequence; the stop codon sequence was omitted in the 953 reverse primer but included in the 287 reverse primer. For the 953 gene, the 5' and the 3' primers used for amplification included a NdeI and a BamHI restriction sites respectively, whereas for the amplification of the 287 gene the 5' and the 3' primers included a BamHI and a XhoI restriction sites respectively. In this way a sequential directional cloning of the two genes in pET21b+, using NdeI-BamHI (to clone the first gene) and subsequently BamHI-XhoI (to clone the second gene) could be achieved.

The 919-287 hybrid was obtained by cloning the sequence coding for the mature portion of 287 into the XhoI site at the 3'-end of the 919-His clone in pET21b+. The primers used for amplification of the 287 gene were designed for introducing a SalI restriction site at the 5'- and a XhoI site at the 3'- of the PCR fragment. Since the cohesive ends produced by the SalI and XhoI restriction enzymes are compatible, the 287 PCR product digested with SalI-XhoI could be inserted in the pET21b-919 clone cleaved with XhoI.

The ORF46.1-287 hybrid was obtained similarly.

The bactericidal efficacy (homologous strain) of antibodies raised against the hybrid proteins was compared with antibodies raised against simple mixtures of the component antigens:

|  | Mixture with 287 | Hybrid with 287 |
| --- | --- | --- |
| 919 | 32000 | 16000 |
| 953 | 8192 | 8192 |
| ORF46.1 | 128 | 8192 |

Data for bactericidal activity against heterologous MenB strains and against serotypes A and C were also obtained for 919-287 and 953-287:

|  | 919 | | 953 | | ORF46.1 | |
| --- | --- | --- | --- | --- | --- | --- |
| Strain | Mixture | Hybrid | Mixture | Hybrid | Mixture | Hybrid |
| MC58 | 512 | 1024 | 512 | 1024 | — | 1024 |
| NGH38 | 1024 | 2048 | 2048 | 4096 | — | 4096 |
| BZ232 | 512 | 128 | 1024 | 16 | — | — |
| MenA (F6124) | 512 | 2048 | 2048 | 32 | — | 1024 |
| MenC (C11) | >2048 | n.d. | >2048 | n.d. | — | n.d. |
| MenC (BZ133) | >4096 | >8192 | >4096 | <16 | — | 2048 |

Hybrids of ORF46.1 and 919 were also constructed. Best results (four-fold higher titre) were achieved with 919 at the N-terminus.

Hybrids 919-519His, ORF97-225His and 225-ORF97His were also tested. These gave moderate ELISA fitres and bactericidal antibody responses.

Example 18

The Leader Peptide from Orf4

As shown above, the leader peptide of ORF4 can be fused to the mature sequence of other proteins (e.g. proteins 287 and 919). It is able to direct lipidation in *E. coli*.

Example 19

Domains in 564

Figure 8:
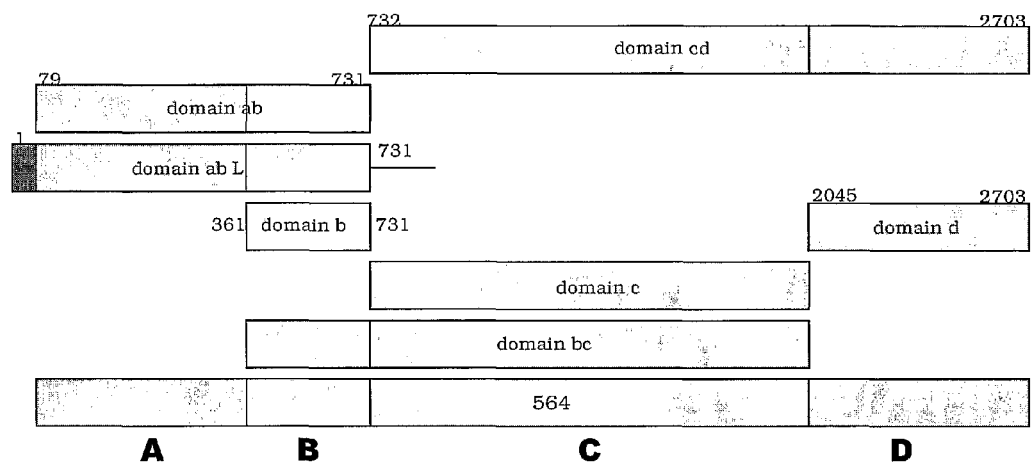
FIG. 8 shows domains of protein 564.

The protein '564' is very large (2073aa), and it is difficult to clone and express it in complete form. To facilitate expression, the protein has been divided into four domains, as shown in FIG. 8 (according to the MC58 sequence):

| Domain | A | B | C | D |
| --- | --- | --- | --- | --- |
| Amino Acids | 79-360 | 361-731 | 732-2044 | 2045-2073 |

These domains show the following homologies:
Domain A shows homology to other bacterial toxins:

| | | |
| --- | --- | --- |
| gb\|AAG03431.1\|AE004443_9 | probable hemagglutinin [*Pseudomonas aeruginosa*] | (38%) |
| gb\|AAC31981.1\|(139897) | HecA [*Pectobacterium chrysanthemi*] | (45%) |
| emb\|CAA36409.1\|(X52156) | filamentous hemagglutinin [*Bordetella pertussis*] | (31%) |
| gb\|AAC79757.1\|(AF057695) | large supernatant protein1 [*Haemophilus ducreyi*] | (26%) |
| gb\|AAA25657.1\|(M30186) | HpmA precursor [*Proteus mirabilis*] | (29%) |

Domain B shows no homology, and is specific to 564.
Domain C shows homology to:

| | | |
| --- | --- | --- |
| gb\|AAF84995.1\|AE004032 | HA-like secreted protein [*Xylella fastidiosa*] | (33%) |
| gb\|AAG05850.1\|AE004673 | hypothetical protein [*Pseudomonas aeruginosa*] | (27%) |
| gb\|AAF68414.1AF237928 | putative FHA [*Pasteurella multocisida*] | (23%) |
| gb\|AAC79757.1\|(AF057695) | large supernatant protein1 [*Haemophilus ducreyi*] | (23%) |
| pir\|\|S21010 | FHA B precursor [*Bordetella pertussis*] | (20%) |

Domain D shows homology to other bacterial toxins:
gb|AAF84995.1|AE004032__14 HA-like secreted protein [*Xylella fastidiosa*] (29%)

Using the MC58 strain sequence, good intracellular expression of 564ab was obtained in the form of GST-fusions (no purification) and his-tagged protein; this domain-pair was also expressed as a lipoprotein, which showed moderate expression in the outer membrane/supernatant fraction.

The b domain showed moderate intracellular expression when expressed as a his-tagged product (no purification), and good expression as a GST-fusion.

The c domain showed good intracellular expression as a GST-fusion, but was insoluble. The d domain showed moderate intracellular expression as a his-tagged product (no purification). The cd protein domain-pair showed moderate intracellular expression (no purification) as a GST-fusion.

Good bactericidal assay titres were observed using the c domain and the be pair.

Example 20

The 919 Leader Peptide

Figure 9:
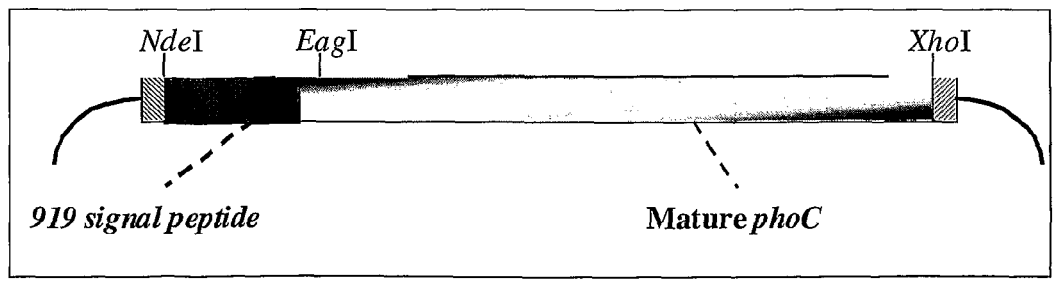
FIG. 9 shows the PhoC reporter gene driven by the 919 leader peptide.

The 20mer leader peptide (SEQ ID NO:633) from 919 is discussed in example 1 above:
MKKYLFRAAL YGIAAAILAA As shown in example 1, deletion of this leader improves heterologous expression, as does substitution with the ORF4 leader peptide. The influence of the 919 leader on expression was investigated by fusing the coding sequence to the PhoC reporter gene from *Morganella morganii* [Thaller et al. (1994) *Microbiology* 140:1341-1350]. The construct (SEQ ID NO:116) was cloned in the pET21-b plasmid between the NdeI and XhoI sites (FIG. 9):

```
  1 MKKYLFRAAL YGIAAAILAA AIPAGNDATT KPDLYYLKNE
    QAIDSLKLLP

51 PPPEVGSIQF LNDQAMYEKG RMLRNTERGK QAQADADLAA
    GGVATAFSGA

101 FGYPITEKDS PELYKLLTNM IEDAGDLATR SAKEHYMRIR
    PFAFYGTETC
```

-continued

```
151 NTKDQKKLST NGSYPSGHTS IGWATALVLA EVNPANQDAI
    LERGYQLGQS

201 RVICGYHWQS DVDAARIVGS AAVATLHSDP AFQAQLAKAK
    QEFAQKSQK*
```

The level of expression of PhoC from this plasmid is >200-fold lower than that found for the same construct but containing the native PhoC signal peptide. The same result was obtained even after substitution of the T7 promoter with the *E. coli* Plac promoter. This means that the influence of the 919 leader sequence on expression does not depend on the promoter used.

In order to investigate if the results observed were due to some peculiarity of the 919 signal peptide nucleotide sequence (secondary structure formation, sensitivity to RNAases, etc.) or to protein instability induced by the presence of this signal peptide, a number of mutants were generated. The approach used was a substitution of nucleotides of the 919 signal peptide sequence by cloning synthetic linkers containing degenerate codons. In this way, mutants were obtained with nucleotide and/or amino acid substitutions.

Two different linkers were used, designed to produce mutations in two different regions of the 919 signal peptide sequence, in the first 19 base pairs (L1) (SEQ ID NO:117) and between bases 20-36 (S1) (SEQ ID NO:118).

L1: 5' T ATG AAa/g TAc/t c/tTN TTt/c a/cGC GCC GCC CTG TAC GGC ATC GCC GCC GCC ATC CTC GCC GCC GCG ATC CC 3'

S1: 5' T ATG AAA AAA TAC CTA TTC CGa/g GCN GCN c/tTa/g TAc/t GGc/g ATC GCC GCC GCC ATC CTC GCC GCC GCG ATC CC 3'

The alignment of some of the mutants obtained is given below.

```
L1 mutants:
9L1-aATGAAGAAGTACCTTTTCAGCGCCGCC~~~~~~~~~~~~~~~~~~~~~~~~~~~~~~~~ (SEQ ID NO: 119)

9L1-eATGAAAAAATACTTTTTCCGCGCCGCC~~~~~~~~~~~~~~~~~~~~~~~~~~~~~~~~ (SEQ ID NO: 120)

9L1-dATGAAAAAATACTTTTTCCGCGCCGCC~~~~~~~~~~~~~~~~~~~~~~~~~~~~~~~~ (SEQ ID NO: 121)

9L1-fATGAAAAAATATCTCTTTAGCGCCGCCCTGTACGGCATCGCCGCCGCCATCCTCGCCGCC (SEQ ID NO:
     122)

919spATGAAAAAATACCTATTCCGCGCCGCCCTGTACGGCATCGCCGCCGCCATCCTCGCCGCC (SEQ ID NO:
     123)

9L1a  MKKYLFSAA~~~~~~~~~~~ (SEQ ID NO: 124)

9L1e  MKKYFFRAA~~~~~~~~~~~ (SEQ ID NO: 125)

9L1d  MKKYFFRAA~~~~~~~~~~~ (SEQ ID NO: 126)

9L1f  MKKYLFSAALYGIAAAILAA (SEQ ID NO: 127)

919spMKKYLFRAALYGIAAAILAA (i.e. native signal peptide) (SEQ ID NO: 128)

S1 mutants:
9S1-eATGAAAAAATACCTATTC.................ATCGCCGCCGCCATCCTCGCCGCC (SEQ ID NO:
     129)

9S1-cATGAAAAAATACCTATTCCGAGCTGCCCAATACGGCATCGCCGCCGCCATCCTCGCCGCC (SEQ ID NO:
     130)

9S1-bATGAAAAAATACCTATTCCGGGCCGCCCAATACGGCATCGCCGCCGCCATCCTCGCCGCC (SEQ ID NO:
     131)

9S1-iATGAAAAAATACCTATTCCGGGCGGCTTTGTACGGGATCGCCGCCGCCATCCTCGCCGCC (SEQ ID NO:
     132)

919spATGAAAAAATACCTATTCCGCGCCGCCCTGTACGGCATCGCCGCCGCCATCCTCGCCGCC (SEQ ID NO:
     123)

9S1e  MKKYLF......IAAAILAA (SEQ ID NO: 133)

9S1c  MKKYLFRAAQYGIAAAILAA (SEQ ID NO: 134)

9S1b  MKKYLFRAAQYGIAAAILAA (SEQ ID NO: 135)

9S1i  MKKYLFRAALYGIAAAILAA (SEQ ID NO: 136)

919spMKKYLFRAALYGIAAAILAA (SEQ ID NO: 128)
```

As shown in the sequences alignments, most of the mutants analysed contain in-frame deletions which were unexpectedly produced by the host cells.

Figure 10:
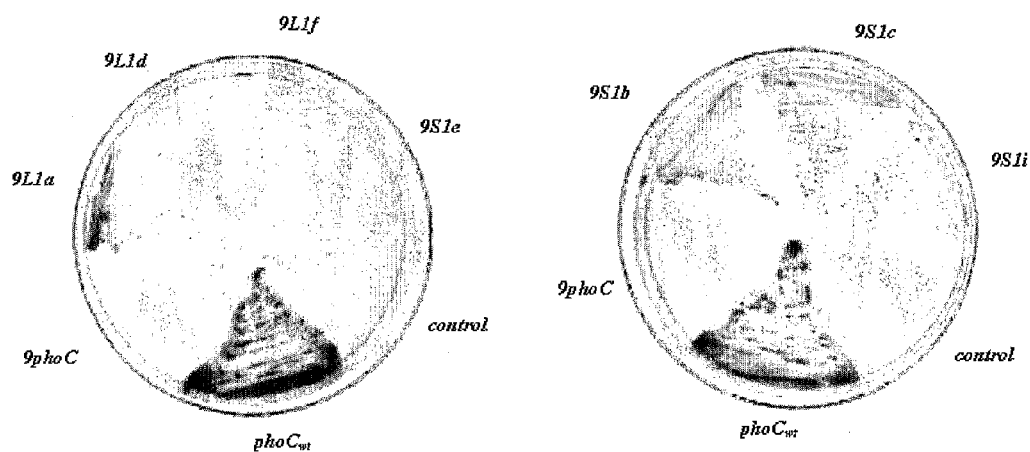
FIG. 10 shows the results obtained using mutants of the leader peptide.

Selection of the mutants was performed by transforming *E. coli* BL21(DE3) cells with DNA prepared from a mixture of L1 and S1 mutated clones. Single transformants were screened for high PhoC activity by streaking them onto LB plates containing 100 μg/ml ampicillin, 50 μg/ml methyl green, 1 mg/ml PDP (phenolphthaleindiphosphate). On this medium PhoC-producing cells become green (FIG. 10).

A quantitative analysis of PhoC produced by these mutants was carried out in liquid medium using pNPP as a substrate for PhoC activity. The specific activities measured in cell extracts and supernatants of mutants grown in liquid medium for 0, 30, 90, 180 min. were:

| | CELL EXTRACTS | | | |
|---|---|---|---|---|
| | 0 | 30 | 90 | 180 |
| control | 0.00 | 0.00 | 0.00 | 0.00 |
| 9phoC | 1.11 | 1.11 | 3.33 | 4.44 |
| 9S1e | 102.12 | 111.00 | 149.85 | 172.05 |

-continued

| | CELL EXTRACTS | | | |
|---|---|---|---|---|
| | 0 | 30 | 90 | 180 |
| 9L1a | 206.46 | 111.00 | 94.35 | 83.25 |
| 9L1d | 5.11 | 4.77 | 4.00 | 3.11 |
| 9L1f | 27.75 | 94.35 | 82.14 | 36.63 |
| 9S1b | 156.51 | 111.00 | 72.15 | 28.86 |
| 9S1c | 72.15 | 33.30 | 21.09 | 14.43 |

CELL EXTRACTS

|       | 0      | 30     | 90     | 180    |
|-------|--------|--------|--------|--------|
| 9S1i  | 156.51 | 83.25  | 55.50  | 26.64  |
| phoCwt| 194.25 | 180.93 | 149.85 | 142.08 |

SUPERNATANTS

|         | 0     | 30    | 90    | 180    |
|---------|-------|-------|-------|--------|
| control | 0.00  | 0.00  | 0.00  | 0.00   |
| 9phoC   | 0.33  | 0.00  | 0.00  | 0.00   |
| 9S1e    | 0.11  | 0.22  | 0.44  | 0.89   |
| 9L1a    | 4.88  | 5.99  | 5.99  | 7.22   |
| 9L1d    | 0.11  | 0.11  | 0.11  | 0.11   |
| 9L1f    | 0.11  | 0.22  | 0.11  | 0.11   |
| 9S1b    | 1.44  | 1.44  | 1.44  | 1.67   |
| 9S1c    | 0.44  | 0.78  | 0.56  | 0.67   |
| 9S1i    | 0.22  | 0.44  | 0.22  | 0.78   |
| phoCwt  | 34.41 | 43.29 | 87.69 | 177.60 |

Some of the mutants produce high amounts of PhoC and in particular, mutant 9L1a can secrete PhoC in the culture medium. This is noteworthy since the signal peptide sequence of this mutant is only 9 amino acids long. This is the shortest signal peptide described to date.

Example 21

C-Terminal Deletions of Maf-Related Proteins

MafB-related proteins include 730, ORF46 and ORF29. The 730 protein from MC58 has the following sequence (SEQ ID NO:137):

```
  1 VKPLRRLTNL LAACAVAAAA LIQPALAADL AQDPFITDNA QRQHYEPGGK

51 YHLFGDPRGS VSDRTGKINV IQDYTHQMGN LLIQQANING TIGYHTRFSG

101 HGHEEHAPFD NHAADSASEE KGNVDEGFTV YRLNWEGHEH HPADAYDGPK

151 GGNYPKPTGA RDEYTYHVNG TARSIKLNPT DTRSIRQRIS DNYSNLGSNF

201 SDRADEANRK MFEHNAKLDR WGNSMEFING VAAGALNPFI SAGEALGIGD

251 ILYGTRYAID KAAMRNIAPL PAEGKFAVIG GLGSVAGFEK NTREAVDRWI

301 QENPNAAETV EAVFNVAAAA KVAKLAKAAK PGKAAVSGDF ADSYKKKLAL

351 SDSARQLYQN AKYREALDIH YEDLIRRKTD GSSKFINGRE IDAVTNDALI

401 QAKRTISAID KPKNFLNQKN RKQIKATIEA ANQQGKRAEF WFKYGVHSQV

451 KSYIESKGGI VKTGLGD*
```

The leader peptide is underlined.
730 shows similar features to ORF46 (see example 8 above):
  as for Orf46, the conservation of the 730 sequence among MenB, MenA and gonococcus is high (>80%) only for the N-terminal portion. The C-terminus, from ~340, is highly divergent.
  its predicted secondary structure contains a hydrophobic segment spanning the central region of the molecule (aa. 227-247).
  expression of the full-length gene in *E. coli* gives very low yields of protein. Expression from tagged or untagged constructs where the signal peptide sequence has been omitted has a toxic effect on the host cells. In other words, the presence of the full-length mature protein in the cytoplasm is highly toxic for the host cell while its translocation to the periplasm (mediated by the signal peptide) has no detectable effect on cell viability. This "intracellular toxicity" of 730 is particularly high since clones for expression of the leaderless 730 can only be obtained at very low frequency using a recA genetic background (*E. coli* strains: HB101 for cloning; HMS174(DE3) for expression).

To overcome this toxicity, a similar approach was used for 730 as described in example 8 for ORF46. Four C-terminal truncated forms were obtained, each of which is well expressed. All were obtained from intracellular expression of His-tagged leaderless 730.

Form A consists of the N-terminal hydrophilic region of the mature protein (aa. 28-226). This was purified as a soluble His-tagged product, having a higher-than-expected MW.

Form B extends to the end of the region conserved between serogroups (aa. 28-340). This was purified as an insoluble His-tagged product.

The C-terminal truncated forms named C1 and C2 were obtained after screening for clones expressing high levels of 730-His clones in strain HMS174(DE3). Briefly, the pET21b plasmid containing the His-tagged sequence coding for the full-length mature 730 protein was used to transform the recA strain HMS174(DE3). Transformants were obtained at low frequency which showed two phenotypes: large colonies and very small colonies. Several large and small colonies were analysed for expression of the 730-His clone. Only cells from large colonies over-expressed a protein recognised by anti-730A antibodies. However the protein over-expressed in different clones showed differences in molecular mass. Sequencing of two of the clones revealed that in both cases integration of an *E. coli* IS sequence had occurred within the sequence coding for the C terminal region of 730. The two integration events have produced in-frame fusion with 1 additional codon in the case of C1, and 12 additional codons in the case of C2 (FIG. 11). The resulting "mutant" forms of 730 have the following sequences:

```
730-C1 (due to an IS1 insertion - FIG. 11A) (SEQ ID NO: 138)

1 MADLAQDPFI TDNAQRQHYE PGGKYHLFGD PRGSVSDRTG KINVIQDYTH

51 QMGNLLIQQA NINGTIGYHT RFSGHGHEEH APFDNHAADS ASEEKGNVDE

101 GFTVYRLNWE GHEHHPADAY DGPKGGNYPK PTGARDEYTY HVNGTARSIK

151 LNPTDTRSIR QRISDNYSNL GSNFSDRADE ANRKMFEHNA KLDRWGNSME

201 FINGVAAGAL NPFISAGEAL GIGDILYGTR YAIDKAAMRN IAPLPAEGKF

251 AVIGGLGSVA GFEKNTREAV DRWIQENPNA AETVEAVFNV AAAAKVAKLA

301 KAAKPGKAAV SGDFADSYKK KLALSDSARQ LYQNAKYREA LDIHYEDLIR

351 RKTDGSSKFI NGREIDAVTN DALIQAR*
```

The additional amino acid produced by the insertion is underlined.

```
730-C2 (due to an IS5 insertion - FIG. 11B) (SEQ ID NO: 139)

1 MADLAQDPFI TDNAQRQHYE PGGKYHLFGD PRGSVSDRTG KINVIQDYTH

51 QMGNLLIQQA NINGTIGYHT RFSGHGHEEH APFDNHAADS ASEEKGNVDE

101 GFTVYRLNWE GHEHHPADAY DGPKGGNYPK PTGARDEYTY HVNGTARSIK

151 LNPTDTRSIR QRISDNYSNL GSNFSDRADE ANRKMFEHNA KLDRWGNSME

201 FINGVAAGAL NPFISAGEAL GIGDILYGTR YAIDKAAMRN IAPLPAEGKF

251 AVIGGLGSVA GFEKNTREAV DRWIQENPNA AETVEAVFNV AAAAKVAKLA

301 KAAKPGKAAV SGDFADSYKK KLALSDSARQ LYQNAKYREA LGKVRISGEI

351 LLG*
```

The additional amino acids produced by the insertion are underlined.

In conclusion, intracellular expression of the 730-C1 form gives very high level of protein and has no toxic effect on the host cells, whereas the presence of the native C-terminus is toxic. These data suggest that the "intracellular toxicity" of 730 is associated with the C-terminal 65 amino acids of the protein.

Equivalent truncation of ORF29 to the first 231 or 368 amino acids has been performed, using expression with or without the leader peptide (amino acids 1-26; deletion gives cytoplasmic expression) and with or without a His-tag.

Example 22

Domains in 961

As described in example 9 above, the GST-fusion of 961 was the best-expressed in *E. coli*. To improve expression, the protein was divided into domains (FIG. 12).

The domains of 961 were designed on the basis of YadA (an adhesin produced by *Yersinia* which has been demonstrated to be an adhesin localized on the bacterial surface that forms oligomers that generate surface projection [Hoiczyk et al. (2000) *EMBO J.* 19:5989-99]) and are: leader peptide, head domain, coiled-coil region (stalk), and membrane anchor domain.

These domains were expressed with or without the leader peptide, and optionally fused either to C-terminal His-tag or to N-terminal GST. *E. coli* clones expressing different domains of 961 were analyzed by SDS-PAGE and western blot for the production and localization of the expressed protein, from over-night (o/n) culture or after 3 hours induction with IPTG. The results were:

| | Total lysate (Western Blot) | Periplasm (Western Blot) | Supernatant (Western Blot) | OMV SDS-PAGE |
|---|---|---|---|---|
| 961 (o/n) | − | − | − | |
| 961 (IPTG) | +/− | − | − | |
| 961-L (o/n) | + | − | − | + |
| 961-L (IPTG) | + | − | − | + |
| 961c-L (o/n) | − | − | − | |
| 961c-L (IPTG) | + | + | + | |
| 961Δ$_1$-L (o/n) | − | − | − | |
| 961Δ$_1$-L (IPTG) | + | − | − | + |

The results show that in *E. coli*:

961-L is highly expressed and localized on the outer membrane. By western blot analysis two specific bands have been detected: one at ~45 kDa (the predicted molecular weight) and one at ~180 kDa, indicating that 961-L can form oligomers. Additionally, these aggregates are more expressed in the over-night culture (without IPTG induction). OMV preparations of this clone were used to immunize mice and serum was obtained. Using over-night culture (predominantly by oligomeric form) the serum was bactericidal; the IPTG-induced culture (predominantly monomeric) was not bactericidal.

961Δ₁-L (with a partial deletion in the anchor region) is highly expressed and localized on the outer membrane, but does not form oligomers;

the 961c-L (without the anchor region) is produced in soluble form and exported in the supernatant.

Titres in ELISA and in the serum bactericidal assay using His-fusions were as follows:

|  | ELISA | Bactericidal |
|---|---|---|
| 961a (aa 24-268) | 24397 | 4096 |
| 961b (aa 269-405) | 7763 | 64 |
| 961c-L | 29770 | 8192 |
| 961c (2996) | 30774 | >65536 |
| 961c (MC58) | 33437 | 16384 |
| 961d | 26069 | >65536 |

*E. coli* clones expressing different forms of 961 (961, 961-L, 961Δ₁-L and 961c-L) were used to investigate if the 961 is an adhesin (c.f. YadA). An adhesion assay was performed using (a) the human epithelial cells and (b) *E. coli* clones after either over-night culture or three hours IPTG induction. 961-L grown over-night (961Δ₁-L) and IPTG-induced 961c-L (the clones expressing protein on surface) adhere to human epithelial cells.

961c was also used in hybrid proteins (see above). As 961 and its domain variants direct efficient expression, they are ideally suited as the N-terminal portion of a hybrid protein.

Example 23

Further Hybrids

Further hybrid proteins of the invention are shown below (see also FIG. 14). These are advantageous when compared to the individual proteins:

```
ORF46.1-741 (SEQ ID NOs: 140 and 141)
   1 ATGTCAGATT TGGCAAACGA TTCTTTTATC CGGCAGGTTC TCGACCGTCA
  51 GCATTTCGAA CCCGACGGGA ATACCACCT ATTCGGCAGC AGGGGGGAAC
 101 TTGCCGAGCG CAGCGGCCAT ATCGGATTGG GAAAAATACA AAGCCATCAG
 151 TTGGGCAACC TGATGATTCA ACAGGCGGCC ATTAAAGGAA ATATCGGCTA
 201 CATTGTCCGC TTTTCCGATC ACGGGCACGA AGTCCATTCC CCCTTCGACA
 251 ACCATGCCTC ACATTCCGAT TCTGATGAAG CCGGTAGTCC CGTTGACGGA
 301 TTTAGCCTTT ACCGCATCCA TTGGGACGGA TACGAACACC ATCCCGCCGA
 351 CGGCTATGAC GGGCCACAGG GCGGCGGCTA TCCCGCTCCC AAAGGCGCGA
 401 GGGATATATA CAGCTACGAC ATAAAAGGCG TTGCCCAAAA TATCCGCCTC
 451 AACCTGACCG ACAACCGCAG CACCGGACAA CGGCTTGCCG ACCGTTTCCA
 501 CAATGCCGGT AGTATGCTGA CGCAAGGAGT AGGCGACGGA TTCAAACGCG
 551 CCACCCGATA CAGCCCCGAG CTGGACAGAT CGGGCAATGC CGCCGAAGCC
 601 TTCAACGGCA CTGCAGATAT CGTTAAAAAC ATCATCGGCG CGGCAGGAGA
 651 AATTGTCGGC GCAGGCGATG CCGTGCAGGG CATAAGCGAA GGCTCAAACA
 701 TTGCTGTCAT GCACGGCTTG GGTCTGCTTT CCACCGAAAA CAAGATGGCG
 751 CGCATCAACG ATTTGGCAGA TATGGCGCAA CTCAAAGACT ATGCCGCAGC
 801 AGCCATCCGC GATTGGGCAG TCCAAAACCC CAATGCCGCA CAAGGCATAG
 851 AAGCCGTCAG CAATATCTTT ATGGCAGCCA TCCCCATCAA AGGGATTGGA
 901 GCTGTTCGGG GAAAATACGG CTTGGGCGGC ATCACGGCAC ATCCTATCAA
 951 GCGGTCGCAG ATGGGCGCGA TCGCATTGCC GAAAGGGAAA TCCGCCGTCA
1001 GCGACAATTT TGCCGATGCG GCATACGCCA AATACCCGTC CCCTTACCAT
1051 TCCCGAAATA TCCGTTCAAA CTTGGAGCAG CGTTACGGCA AAGAAAACAT
1101 CACCTCCTCA ACCGTGCCGC CGTCAAACGG CAAAAATGTC AAACTGGCAG
1151 ACCAACGCCA CCCGAAGACA GGCGTACCGT TTGACGGTAA AGGGTTTCCG
1201 AATTTTGAGA AGCACGTGAA ATATGATACG GGATCCGAG GGGGTGGTGT
1251 CGCCGCCGAC ATCGGTGCGG GGCTTGCCGA TGCACTAACC GCACCGCTCG
1301 ACCATAAAGA CAAAGGTTTG CAGTCTTTGA CGCTGGATCA GTCCGTCAGG
1351 AAAAACGAGA AACTGAAGCT GGCGGCACAA GGTGCGGAAA AAACTTATGG
```

```
-continued
1401 AAACGGTGAC AGCCTCAATA CGGGCAAATT GAAGAACGAC AAGGTCAGCC

1451 GTTTCGACTT TATCCGCCAA ATCGAAGTGG ACGGGCAGCT CATTACCTTG

1501 GAGAGTGGAG AGTTCCAAGT ATACAAACAA AGCCATTCCG CCTTAACCGC

1551 CTTTCAGACC GAGCAAATAC AAGATTCGGA GCATTCCGGG AAGATGGTTG

1601 CGAAACGCCA GTTCAGAATC GGCGACATAG CGGGCGAACA TACATCTTTT

1651 GACAAGCTTC CCGAAGGCGG CAGGGCGACA TATCGCGGGA CGGCGTTCGG

1701 TTCAGACGAT GCCGGCGGAA AACTGACCTA CACCATAGAT TTCGCCGCCA

1751 AGCAGGGAAA CGGCAAAATC GAACATTTGA AATCGCCAGA ACTCAATGTC

1801 GACCTGGCCG CCGCCGATAT CAAGCCGGAT GGAAAACGCC ATGCCGTCAT

1851 CAGCGGTTCC GTCCTTTACA ACCAAGCCGA GAAAGGCAGT TACTCCCTCG

1901 GTATCTTTGG CGGAAAAGCC CAGGAAGTTG CCGGCAGCGC GGAAGTGAAA

1951 ACCGTAAACG GCATACGCCA TATCGGCCTT GCCGCCAAGC AACTCGAGCA

2001 CCACCACCAC CACCACTGA
```

```
   1 MSDLANDSFI RQVLDRQHFE PDGKYHLFGS RGELAERSGH IGLGKIQSHQ

51 LGNLMIQQAA IKGNIGYIVR FSDHGHEVHS PFDNHASHSD SDEAGSPVDG

101 FSLYRIHWDG YEHHPADGYD GPQGGGYPAP KGARDIYSYD IKGVAQNIRL

151 NLTDNRSTGQ RLADRFHNAG SMLTQGVGDG FKRATRYSPE LDRSGNAAEA

201 FNGTADIVKN IIGAAGEIVG AGDAVQGISE GSNIAVMHGL GLLSTENKMA

251 RINDLADMAQ LKDYAAAAIR DWAVQNPNAA QGIEAVSNIF MAAIPIKGIG

301 AVRGKYGLGG ITAHPIKRSQ MGAIALPKGK SAVSDNFADA AYAKYPSPYH

351 SRNIRSNLEQ RYGKENITSS TVPPSNGKNV KLADQRHPKT GVPFDGKGFP

401 NFEKHVKYDT GSGGGGVAAD IGAGLADALT APLDHKDKGL QSLTLDQSVR

451 KNEKLKLAAQ GAEKTYGNGD SLNTGKLKND KVSRFDFIRQ IEVDGQLITL

501 ESGEFQVYKQ SHSALTAFQT EQIQDSEHSG KMVAKRQFRI GDIAGEHTSF

551 DKLPEGGRAT YRGTAFGSDD AGGKLTYTID FAAKQGNGKI EHLKSPELNV

601 DLAAADIKPD GKRHAVISGS VLYNQAEKGS YSLGIFGGKA QEVAGSAEVK

651 TVNGIRHIGL AAKQLEHHHH HH*
```

ORF46.1-961 (SEQ ID NOs: 142 and 143)
```
   1 ATGTCAGATT TGGCAAACGA TTCTTTTATC CGGCAGGTTC TCGACCGTCA

51 GCATTTCGAA CCCGACGGGA ATACCACCT ATTCGGCAGC AGGGGGGAAC

101 TTGCCGAGCG CAGCGGCCAT ATCGGATTGG GAAAATACA AAGCCATCAG

151 TTGGGCAACC TGATGATTCA ACAGGCGGCC ATTAAAGGAA ATATCGGCTA

201 CATTGTCCGC TTTTCCGATC ACGGGCACGA AGTCCATTCC CCCTTCGACA

251 ACCATGCCTC ACATTCCGAT TCTGATGAAG CCGGTAGTCC CGTTGACGGA

301 TTTAGCCTTT ACCGCATCCA TTGGGACGGA TACGAACACC ATCCCGCCGA

351 CGGCTATGAC GGGCCACAGG GCGGCGGCTA TCCCGCTCCC AAAGGCGCGA

401 GGGATATATA CAGCTACGAC ATAAAAGGCG TTGCCCAAAA TATCCGCCTC

451 AACCTGACCG ACAACCGCAG CACCGGACAA CGGCTTGCCG ACCGTTTCCA

501 CAATGCCGGT AGTATGCTGA CGCAAGGAGT AGGCGACGGA TTCAAACGCG

551 CCACCCGATA CAGCCCCGAG CTGGACAGAT CGGGCAATGC CGCCGAAGCC

601 TTCAACGGCA CTGCAGATAT CGTTAAAAAC ATCATCGGCG CGGCAGGAGA
```

```
 651 AATTGTCGGC GCAGGCGATG CCGTGCAGGG CATAAGCGAA GGCTCAAACA
 701 TTGCTGTCAT GCACGGCTTG GGTCTGCTTT CCACCGAAAA CAAGATGGCG
 751 CGCATCAACG ATTTGGCAGA TATGGCGCAA CTCAAAGACT ATGCCGCAGC
 801 AGCCATCCGC GATTGGGCAG TCCAAAACCC CAATGCCGCA CAAGGCATAG
 851 AAGCCGTCAG CAATATCTTT ATGGCAGCCA TCCCCATCAA AGGGATTGGA
 901 GCTGTTCGGG GAAAATACGG CTTGGGCGGC ATCACGGCAC ATCCTATCAA
 951 GCGGTCGCAG ATGGGCGCGA TCGCATTGCC GAAAGGGAAA TCCGCCGTCA
1001 GCGACAATTT TGCCGATGCG GCATACGCCA ATACCCGTCC CCTTACCAT
1051 TCCCGAAATA TCCGTTCAAA CTTGGAGCAG CGTTACGGCA AGAAAACAT
1101 CACCTCCTCA ACCGTGCCGC CGTCAAACGG CAAAAATGTC AAACTGGCAG
1151 ACCAACGCCA CCCGAAGACA GGCGTACCGT TTGACGGTAA AGGGTTTCCG
1201 AATTTTGAGA AGCACGTGAA ATATGATACG GGATCCGGAG GAGGAGGAGC
1251 CACAAACGAC GACGATGTTA AAAAGCTGCA CACTGTGGCC ATTGCTGCTG
1301 CCTACAACAA TGGCCAAGAA ATCAACGGTT CAAAGCTGG AGAGACCATC
1351 TACGACATTG ATGAAGACGG CACAATTACC AAAAAAGACG CAACTGCAGC
1401 CGATGTTGAA GCCGACGACT TTAAAGGTCT GGGTCTGAAA AAAGTCGTGA
1451 CTAACCTGAC CAAAACCGTC AATGAAAACA ACAAAACGT CGATGCCAAA
1501 GTAAAAGCTG CAGAATCTGA AATAGAAAG TTAACAACCA AGTTAGCAGA
1551 CACTGATGCC GCTTTAGCAG ATACTGATGC CGCTCTGGAT GCAACCACCA
1601 ACGCCTTGAA TAAATTGGGA GAAATATAA CGACATTTGC TGAAGAGACT
1651 AAGACAAATA TCGTAAAAAT TGATGAAAAA TTAGAAGCCG TGGCTGATAC
1701 CGTCGACAAG CATGCCGAAG CATTCAACGA TATCGCCGAT TCATTGGATG
1751 AAACCAACAC TAAGGCAGAC GAAGCCGTCA AAACCGCCAA TGAAGCCAAA
1801 CAGACGGCCG AAGAAACCAA ACAAAACGTC GATGCCAAAG TAAAAGCTGC
1851 AGAAACTGCA GCAGGCAAAG CCGAAGCTGC CGCTGGCACA GCTAATACTG
1901 CAGCCGACAA GGCCGAAGCT GTCGCTGCAA AAGTTACCGA CATCAAAGCT
1951 GATATCGCTA CGAACAAAGA TAATATTGCT AAAAAAGCAA ACAGTGCCGA
2001 CGTGTACACC AGAGAAGAGT CTGACAGCAA ATTTGTCAGA ATTGATGGTC
2051 TGAACGCTAC TACCGAAAAA TTGGACACAC GCTTGGCTTC TGCTGAAAAA
2101 TCCATTGCCG ATCACGATAC TCGCCTGAAC GGTTTGGATA AACAGTGTC
2151 AGACCTGCGC AAAGAAACCC GCCAAGGCCT TGCAGAACAA GCCGCGCTCT
2201 CCGGTCTGTT CCAACCTTAC AACGTGGGTC GGTTCAATGT AACGGCTGCA
2251 GTCGGCGGCT ACAAATCCGA ATCGGCAGTC GCCATCGGTA CCGGCTTCCG
2301 CTTTACCGAA AACTTTGCCG CCAAAGCAGG CGTGGCAGTC GGCACTTCGT
2351 CCGGTTCTTC CGCAGCCTAC CATGTCGGCG TCAATTACGA GTGGCTCGAG
2401 CACCACCACC ACCACCACTG A
   1 MSDLANDSFI RQVLDRQHFE PDGKYHLFGS RGELAERSGH IGLGKIQSHQ
  51 LGNLMIQQAA IKGNIGYIVR FSDHGHEVHS PFDNHASHSD SDEAGSPVDG
 101 FSLYRIHWDG YEHHPADGYD GPQGGGYPAP KGARDIYSYD IKGVAQNIRL
 151 NLTDNRSTGQ RLADRFHNAG SMLTQGVGDG FKRATRYSPE LDRSGNAAEA
 201 FNGTADIVKN IIGAAGEIVG AGDAVQGISE GSNIAVMHGL GLLSTENKMA
```

```
251 RINDLADMAQ LKDYAAAAIR DWAVQNPNAA QGIEAVSNIF MAAIPIKGIG

301 AVRGKYGLGG ITAHPIKRSQ MGAIALPKGK SAVSDNFADA AYAKYPSPYH

351 SRNIRSNLEQ RYGKENITSS TVPPSNGKNV KLADQRHPKT GVPFDGKGFP

401 NFEKHVKYDT GSGGGGATND DDVKKAATVA IAAAYNNGQE INGFKAGETI

451 YDIDEDGTIT KKDATAADVE ADDFKGLGLK KVVTNLTKTV NENKQNVDAK

501 VKAAESEIEK LTTKLADTDA ALADTDAALD ATTNALNKLG ENITTFAEET

551 KTNIVKIDEK LEAVADTVDK HAEAFNDIAD SLDETNTKAD EAVKTANEAK

601 QTAEETKQNV DAKVKAAETA AGKAEAAAGT ANTAADKAEA VAAKVTDIKA

651 DIATNKDNIA KKANSADVYT REESDSKFVR IDGLNATTEK LDTRLASAEK

701 SIADHDTRLN GLDKTVSDLR KETRQGLAEQ AALSGLFQPY NVGRFNVTAA

751 VGGYKSESAV AIGTGFRFTE NFAAKAGVAV GTSSGSSAAY HVGVNYEWLE

801 HHHHHH*
```

ORF46.1-961c (SEQ ID NOs: 144 and 145)
```
   1 ATGTCAGATT GGCAAACGA TTCTTTTATC CGGCAGGTTC TCGACCGTCA

51 GCATTTCGAA CCCGACGGGA ATACCACCT ATTCGGCAGC AGGGGGGAAC

101 TTGCCGAGCG CAGCGGCCAT ATCGGATTGG GAAAAATACA AAGCCATCAG

151 TTGGGCAACC TGATGATTCA ACAGGCGGCC ATTAAAGGAA ATATCGGCTA

201 CATTGTCCGC TTTTCCGATC ACGGGCACGA AGTCCATTCC CCCTTCGACA

251 ACCATGCCTC ACATTCCGAT TCTGATGAAG CCGGTAGTCC CGTTGACGGA

301 TTTAGCCTTT ACCGCATCCA TTGGGACGGA TACGAACACC ATCCCGCCGA

351 CGGCTATGAC GGGCCACAGG GCGGCGGCTA TCCCGCTCCC AAAGGCGCGA

401 GGGATATATA CAGCTACGAC ATAAAAGGCG TTGCCCAAAA TATCCGCCTC

451 AACCTGACCG ACAACCGCAG CACCGGACAA CGGCTTGCCG ACCGTTTCCA

501 CAATGCCGGT AGTATGCTGA CGCAAGGAGT AGGCGACGGA TTCAAACGCG

551 CCACCCGATA CAGCCCCGAG CTGGACAGAT CGGGCAATGC CGCCGAAGCC

601 TTCAACGGCA CTGCAGATAT CGTTAAAAAC ATCATCGGCG CGGCAGGAGA

651 AATTGTCGGC GCAGGCGATG CCGTGCAGGG CATAAGCGAA GGCTCAAACA

701 TTGCTGTCAT GCACGGCTTG GGTCTGCTTT CCACCGAAAA CAAGATGGCG

751 CGCATCAACG ATTTGGCAGA TATGGCGCAA CTCAAAGACT ATGCCGCAGC

801 AGCCATCCGC GATTGGGCAG TCCAAAACCC CAATGCCGCA CAAGGCATAG

851 AAGCCGTCAG CAATATCTTT ATGGCAGCCA TCCCCATCAA AGGGATTGGA

901 GCTGTTCGGG GAAAATACGG CTTGGGCGGC ATCACGGCAC ATCCTATCAA

951 GCGGTCGCAG ATGGGCGCGA TCGCATTGCC GAAAGGGAAA TCCGCCGTCA

1001 GCGACAATTT TGCCGATGCG CATACGCCA ATACCCGTC CCCTTACCAT

1051 TCCCGAAATA TCCGTTCAAA CTTGGAGCAG CGTTACGGCA AAGAAAACAT

1101 CACCTCCTCA ACCGTGCCGC CGTCAAACGG CAAAAATGTC AAACTGGCAG

1151 ACCAACGCCA CCCGAAGACA GGCGTACCGT TTGACGGTAA AGGGTTTCCG

1201 AATTTTGAGA AGCACGTGAA ATATGATACG GGATCCGGAG GAGGAGGAGC

1251 CACAAACGAC GACGATGTTA AAAAAGCTGC CACTGTGGCC ATTGCTGCTG

1301 CCTACAACAA TGGCCAAGAA ATCAACGGTT TCAAAGCTGG AGAGACCATC

1351 TACGACATTG ATGAAGACGG CACAATTACC AAAAAAGACG CAACTGCAGC
```

```
1401 CGATGTTGAA GCCGACGACT TTAAAGGTCT GGGTCTGAAA AAAGTCGTGA

1451 CTAACCTGAC CAAAACCGTC AATGAAAACA AACAAAACGT CGATGCCAAA

1501 GTAAAAGCTG CAGAATCTGA AATAGAAAAG TTAACAACCA AGTTAGCAGA

1551 CACTGATGCC GCTTTAGCAG ATACTGATGC CGCTCTGGAT GCAACCACCA

1601 ACGCCTTGAA TAAATTGGGA GAAAATATAA CGACATTTGC TGAAGAGACT

1651 AAGACAAATA TCGTAAAAAT TGATGAAAAA TTAGAAGCCG TGGCTGATAC

1701 CGTCGACAAG CATGCCGAAG CATTCAACGA TATCGCCGAT TCATTGGATG

1751 AAACCAACAC TAAGGCAGAC GAAGCCGTCA AAACCGCCAA TGAAGCCAAA

1801 CAGACGGCCG AAGAAACCAA ACAAAACGTC GATGCCAAAG TAAAAGCTGC

1851 AGAAACTGCA GCAGGCAAAG CCGAAGCTGC CGCTGGCACA GCTAATACTG

1901 CAGCCGACAA GGCCGAAGCT GTCGCTGCAA AAGTTACCGA CATCAAAGCT

1951 GATATCGCTA CGAACAAAGA TAATATTGCT AAAAAAGCAA ACAGTGCCGA

2001 CGTGTACACC AGAGAAGAGT CTGACAGCAA ATTTGTCAGA ATTGATGGTC

2051 TGAACGCTAC TACCGAAAAA TTGGACACAC GCTTGGCTTC TGCTGAAAAA

2101 TCCATTGCCG ATCACGATAC TCGCCTGAAC GGTTTGGATA AAACAGTGTC

2151 AGACCTGCGC AAAGAAACCC GCCAAGGCCT TGCAGAACAA GCCGCGCTCT

2201 CCGGTCTGTT CCAACCTTAC AACGTGGGTC TCGAGCACCA CCACCACCAC

2251 CACTGA

1 MSDLANDSFI RQVLDRQHFE PDGKYHLFGS RGELAERSGH IGLGKIQSHQ

51 LGNLMIQQAA IKGNIGYIVR FSDHGHEVHS PFDNHASHSD SDEAGSPVDG

101 FSLYRIHWDG YEHHPADGYD GPQGGGYPAP KGARDIYSYD IKGVAQNIRL

151 NLTDNRSTGQ RLADRFHNAG SMLTQGVGDG FKRATRYSPE LDRSGNAAEA

201 FNGTADIVKN IIGAAGEIVG AGDAVQGISE GSNIAVMHGL GLLSTENKMA

251 RINDLADMAQ LKDYAAAAIR DWAVQNPNAA QGIEAVSNIF MAAIPIKGIG

301 AVRGKYGLGG ITAHPIKRSQ MGAIALPKGK SAVSDNFADA AYAKYPSPYH

351 SRNIRSNLEQ RYGKENITSS TVPPSNGKNV KLADQRHPKT GVPFDGKGFP

401 NFEKHVKYDT GSGGGGATND DDVKKAATVA IAAAYNNGQE INGFKAGETI

451 YDIDEDGTIT KKDATAADVE ADDFKGLGLK KVVTNLTKTV NENKQNVDAK

501 VKAAESEIEK LTTKLADTDA ALADTDAALD ATTNALNKLG ENITTFAEET

551 KTNIVKIDEK LEAVADTVDK HAEAFNDIAD SLDETNTKAD EAVKTANEAK

601 QTAEETKQNV DAKVKAAETA AGKAEAAAGT ANTAADKAEA VAAKVTDIKA

651 DIATNKDNIA KKANSADVYT REESDSKFVR IDGLNATTEK LDTRLASAEK

701 SIADHDTRLN GLDKTVSDLR KETRQGLAEQ AALSGLFQPY NVGLEHHHHH

751 H*

961-ORF46.1 (SEQ ID NOs: 146 and 147)
   1 ATGGCCACAA ACGACGACGA TGTTAAAAAA GCTGCCACTG TGGCCATTGC

51 TGCTGCCTAC AACAATGGCC AAGAAATCAA CGGTTTCAAA GCTGGAGAGA

101 CCATCTACGA CATTGATGAA GACGGCACAA TTACCAAAAA AGACGCAACT

151 GCAGCCGATG TTGAAGCCGA CGACTTTAAA GGTCTGGGTC TGAAAAAAGT

201 CGTGACTAAC CTGACCAAAA CCGTCAATGA AAACAAACAA ACGTCGATG

251 CCAAAGTAAA AGCTGCAGAA TCTGAAATAG AAAAGTTAAC AACCAAGTTA
```

-continued

```
 301 GCAGACACTG ATGCCGCTTT AGCAGATACT GATGCCGCTC TGGATGCAAC
 351 CACCAACGCC TTGAATAAAT TGGGAGAAAA TATAACGACA TTTGCTGAAG
 401 AGACTAAGAC AAATATCGTA AAAATTGATG AAAAATTAGA AGCCGTGGCT
 451 GATACCGTCG ACAAGCATGC CGAAGCATTC AACGATATCG CCGATTCATT
 501 GGATGAAACC AACACTAAGG CAGACGAAGC CGTCAAAACC GCCAATGAAG
 551 CCAAACAGAC GGCCGAAGAA ACCAAACAAA ACGTCGATGC CAAAGTAAAA
 601 GCTGCAGAAA CTGCAGCAGG CAAAGCCGAA GCTGCCGCTG CACAGCTAA
 651 TACTGCAGCC GACAAGGCCG AAGCTGTCGC TGCAAAAGTT ACCGACATCA
 701 AAGCTGATAT CGCTACGAAC AAAGATAATA TTGCTAAAAA AGCAAACAGT
 751 GCCGACGTGT ACACCAGAGA AGAGTCTGAC AGCAAATTTG TCAGAATTGA
 801 TGGTCTGAAC GCTACTACCG AAAAATTGGA CACACGCTTG GCTTCTGCTG
 851 AAAAATCCAT TGCCGATCAC GATACTCGCC TGAACGGTTT GGATAAAACA
 901 GTGTCAGACC TGCGCAAAGA AACCCGCCAA GGCCTTGCAG AACAAGCCGC
 951 GCTCTCCGGT CTGTTCCAAC CTTACAACGT GGGTCGGTTC AATGTAACGG
1001 CTGCAGTCGG CGGCTACAAA TCCGAATCGG CAGTCGCCAT CGGTACCGGC
1051 TTCCGCTTTA CCGAAAACTT TGCCGCCAAA GCAGGCGTGG CAGTCGGCAC
1101 TTCGTCCGGT TCTTCCGCAG CCTACCATGT CGGCGTCAAT TACGAGTGGG
1151 GATCCGGAGG AGGAGGATCA GATTTGGCAA ACGATTCTTT TATCCGGCAG
1201 GTTCTCGACC GTCAGCATTT CGAACCCGAC GGGAAATACC ACCTATTCGG
1251 CAGCAGGGGG GAACTTGCCG AGCGCAGCGG CCATATCGGA TTGGGAAAAA
1301 TACAAAGCCA TCAGTTGGGC AACCTGATGA TTCAACAGGC GGCCATTAAA
1351 GGAAATATCG GCTACATTGT CCGCTTTTCC GATCACGGGC ACGAAGTCCA
1401 TTCCCCCTTC GACAACCATG CCTCACATTC CGATTCTGAT GAAGCCGGTA
1451 GTCCCGTTGA CGGATTTAGC CTTTACCGCA TCCATTGGGA CGGATACGAA
1501 CACCATCCCG CCGACGGCTA TGACGGGCCA CAGGGCGGCG GCTATCCCGC
1551 TCCCAAAGGC GCGAGGGATA TATACAGCTA CGACATAAAA GGCGTTGCCC
1601 AAAATATCCG CCTCAACCTG ACCGACAACC GCAGCACCGG ACAACGGCTT
1651 GCCGACCGTT TCCACAATGC CGGTAGTATG CTGACGCAAG GAGTAGGCGA
1701 CGGATTCAAA CGCGCCACCC GATACAGCCC CGAGCTGGAC AGATCGGGCA
1751 ATGCCGCCGA AGCCTTCAAC GGCACTGCAG ATATCGTTAA AAACATCATC
1801 GGCGCGGCAG GAGAAATTGT CGGCGCAGGC GATGCCGTGC AGGGCATAAG
1851 CGAAGGCTCA AACATTGCTG TCATGCACGG CTTGGGTCTG CTTTCCACCG
1901 AAAACAAGAT GGCGCGCATC AACGATTTGG CAGATATGGC GCAACTCAAA
1951 GACTATGCCG CAGCAGCCAT CCGCGATTGG GCAGTCCAAA ACCCCAATGC
2001 CGCACAAGGC ATAGAAGCCG TCAGCAATAT CTTTATGGCA GCCATCCCCA
2051 TCAAAGGGAT TGGAGCTGTT CGGGGAAAAT ACGGCTTGGG CGGCATCACG
2101 GCACATCCTA TCAAGCGGTC GCAGATGGGC GCGATCGCAT TGCCGAAAGG
2151 GAAATCCGCC GTCAGCGACA ATTTTGCCGA TGCGGCATAC GCCAAATACC
2201 CGTCCCCTTA CCATTCCCGA AATATCCGTT CAAACTTGGA GCAGCGTTAC
2251 GGCAAAGAAA ACATCACCTC CTCAACCGTG CCGCCGTCAA ACGGCAAAAA
```

```
-continued
2301 TGTCAAACTG GCAGACCAAC GCCACCCGAA GACAGGCGTA CCGTTTGACG

2351 GTAAAGGGTT TCCGAATTTT GAGAAGCACG TGAAATATGA TACGCTCGAG

2401 CACCACCACC ACCACCACTG A

1 MATNDDDVKK AATVAIAAAY NNGQEINGFK AGETIYDIDE DGTITKKDAT

51 AADVEADDFK GLGLKKVVTN LTKTVNENKQ NVDAKVKAAE SEIEKLTTKL

101 ADTDAALADT DAALDATTNA LNKLGENITT FAEETKTNIV KIDEKLEAVA

151 DTVDKHAEAF NDIADSLDET NTKADEAVKT ANEAKQTAEE TKQNVDAKVK

201 AAETAAGKAE AAAGTANTAA DKAEAVAAKV TDIKADIATN KDNIAKKANS

251 ADVYTREESD SKFVRIDGLN ATTEKLDTRL ASAEKSIADH DTRLNGLDKT

301 VSDLRKETRQ GLAEQAALSG LFQPYNVGRF NVTAAVGGYK SESAVAIGTG

351 FRFTENFAAK AGVAVGTSSG SSAAYHVGVN YEWGSGGGGS DLANDSFIRQ

401 VLDRQHFEPD GKYHLFGSRG ELAERSGHIG LGKIQSHQLG NLMIQQAAIK

451 GNIGYIVRFS DHGHEVHSPF DNHASHSDSD EAGSPVDGFS LYRIHWDGYE

501 HHPADGYDGP QGGGYPAPKG ARDIYSYDIK GVAQNIRLNL TDNRSTGQRL

551 ADRFHNAGSM LTQGVGDGFK RATRYSPELD RSGNAAEAFN GTADIVKNII

601 GAAGEIVGAG DAVQGISEGS NIAVMHGLGL LSTENKMARI NDLADMAQLK

651 DYAAAAIRDW AVQNPNAAQG IEAVSNIFMA AIPIKGIGAV RGKYGLGGIT

701 AHPIKRSQMG AIALPKGKSA VSDNFADAAY AKYPSPYHSR NIRSNLEQRY

751 GKENITSSTV PPSNGKNVKL ADQRHPKTGV PFDGKGFPNF EKHVKYDTLE

801 HHHHHH*

961-741 (SEQ ID NOs: 148 and 149)
   1 ATGGCCACAA ACGACGACGA TGTTAAAAAA GCTGCCACTG TGGCCATTGC

51 TGCTGCCTAC AACAATGGCC AAGAAATCAA CGGTTTCAAA GCTGGAGAGA

101 CCATCTACGA CATTGATGAA GACGGCACAA TTACCAAAAA AGACGCAACT

151 GCAGCCGATG TTGAAGCCGA CGACTTTAAA GGTCTGGGTC TGAAAAAAGT

201 CGTGACTAAC CTGACCAAAA CCGTCAATGA AAACAAACAA AACGTCGATG

251 CCAAAGTAAA AGCTGCAGAA TCTGAAATAG AAAAGTTAAC AACCAAGTTA

301 GCAGACACTG ATGCCGCTTT AGCAGATACT GATGCCGCTC TGGATGCAAC

351 CACCAACGCC TTGAATAAAT TGGGAGAAAA TATAACGACA TTTGCTGAAG

401 AGACTAAGAC AAATATCGTA AAAATTGATG AAAAATTAGA AGCCGTGGCT

451 GATACCGTCG ACAAGCATGC CGAAGCATTC AACGATATCG CCGATTCATT

501 GGATGAAACC AACACTAAGG CAGACGAAGC CGTCAAAACC GCCAATGAAG

551 CCAAACAGAC GGCCGAAGAA ACCAAACAAA ACGTCGATGC CAAAGTAAAA

601 GCTGCAGAAA CTGCAGCAGG CAAAGCCGAA GCTGCCGCTG GCACAGCTAA

651 TACTGCAGCC GACAAGGCCG AAGCTGTCGC TGCAAAAGTT ACCGACATCA

701 AAGCTGATAT CGCTACGAAC AAAGATAATA TTGCTAAAAA AGCAAACAGT

751 GCCGACGTGT ACACCAGAGA AGAGTCTGAC AGCAAATTTG TCAGAATTGA

801 TGGTCTGAAC GCTACTACCG AAAAATTGGA CACACGCTTG GCTTCTGCTG

851 AAAAATCCAT TGCCGATCAC GATACTCGCC TGAACGGTTT GGATAAAACA

901 GTGTCAGACC TGCGCAAAGA AACCCGCCAA GGCCTTGCAG AACAAGCCGC

951 GCTCTCCGGT CTGTTCCAAC CTTACAACGT GGGTCGGTTC AATGTAACGG
```

```
1001 CTGCAGTCGG CGGCTACAAA TCCGAATCGG CAGTCGCCAT CGGTACCGGC

1051 TTCCGCTTTA CCGAAAACTT TGCCGCCAAA GCAGGCGTGG CAGTCGGCAC

1101 TTCGTCCGGT TCTTCCGCAG CCTACCATGT CGGCGTCAAT TACGAGTGGG

1151 GATCCGGAGG GGGTGGTGTC GCCGCCGACA TCGGTGCGGG GCTTGCCGAT

1201 GCACTAACCG CACCGCTCGA CCATAAAGAC AAAGGTTTGC AGTCTTTGAC

1251 GCTGGATCAG TCCGTCAGGA AAAACGAGAA ACTGAAGCTG GCGGCACAAG

1301 GTGCGGAAAA AACTTATGGA AACGGTGACA GCCTCAATAC GGGCAAATTG

1351 AAGAACGACA AGGTCAGCCG TTTCGACTTT ATCCGCCAAA TCGAAGTGGA

1401 CGGGCAGCTC ATTACCTTGG AGAGTGGAGA GTTCCAAGTA TACAAACAAA

1451 GCCATTCCGC CTTAACCGCC TTTCAGACCG AGCAAATACA GATTCGGAG

1501 CATTCCGGGA AGATGGTTGC GAAACGCCAG TTCAGAATCG GCGACATAGC

1551 GGGCGAACAT ACATCTTTTG ACAAGCTTCC CGAAGGCGGC AGGGCGACAT

1601 ATCGCGGGAC GGCGTTCGGT TCAGACGATG CCGGCGGAAA ACTGACCTAC

1651 ACCATAGATT TCGCCGCCAA GCAGGGAAAC GGCAAAATCG AACATTTGAA

1701 ATCGCCAGAA CTCAATGTCG ACCTGGCCGC CGCCGATATC AAGCCGGATG

1751 GAAAACGCCA TGCCGTCATC AGCGGTTCCG TCCTTTACAA CCAAGCCGAG

1801 AAAGGCAGTT ACTCCCTCGG TATCTTTGGC GGAAAAGCCC AGGAAGTTGC

1851 CGGCAGCGCG GAAGTGAAAA CCGTAAACGG CATACGCCAT ATCGGCCTTG

1901 CCGCCAAGCA ACTCGAGCAC CACCACCAC ACCACTGA

1 MATNDDDVKK AATVAIAAAY NNGQEINGFK AGETIYDIDE DGTITKKDAT

51 AADVEADDFK GLGLKKVVTN LTKTVNENKQ NVDAKVKAAE SEIEKLTTKL

101 ADTDAALADT DAALDATTNA LNKLGENITT FAEETKTNIV KIDEKLEAVA

151 DTVDKHAEAF NDIADSLDET NTKADEAVKT ANEAKQTAEE TKQNVDAKVK

201 AAETAAGKAE AAAGTANTAA DKAEAVAAKV TDIKADIATN KDNIAKKANS

251 ADVYTREESD SKFVRIDGLN ATTEKLDTRL ASAEKSIADH DTRLNGLDKT

301 VSDLRKETRQ GLAEQAALSG LFQPYNVGRF NVTAAVGGYK SESAVAIGTG

351 FRFTENFAAK AGVAVGTSSG SSAAYHVGVN YEWGSGGGGV AADIGAGLAD

401 ALTAPLDHKD KGLQSLTLDQ SVRKNEKLKL AAQGAEKTYG NGDSLNTGKL

451 KNDKVSRFDF IRQIEVDGQL ITLESGEFQV YKQSHSALTA FQTEQIQDSE

501 HSGKMVAKRQ FRIGDIAGEH TSFDKLPEGG RATYRGTAFG SDDAGGKLTY

551 TIDFAAKQGN GKIEHLKSPE LNVDLAAADI KPDGKRHAVI SGSVLYNQAE

601 KGSYSLGIFG GKAQEVAGSA EVKTVNGIRH IGLAAKQLEH HHHHH*

961-983 (SEQ ID NOs: 150 and 151)
   1 ATGGCCACAA ACGACGACGA TGTTAAAAAA GCTGCCACTG TGGCCATTGC

51 TGCTGCCTAC AACAATGGCC AAGAAATCAA CGGTTTCAAA GCTGGAGAGA

101 CCATCTACGA CATTGATGAA GACGGCACAA TTACCAAAAA AGACGCAACT

151 GCAGCCGATG TTGAAGCCGA CGACTTTAAA GGTCTGGGTC TGAAAAAAGT

201 CGTGACTAAC CTGACCAAAA CCGTCAATGA AAACAAACAA AACGTCGATG

251 CCAAAGTAAA AGCTGCAGAA TCTGAAATAG AAAAGTTAAC AACCAAGTTA

301 GCAGACACTG ATGCCGCTTT AGCAGATACT GATGCCGCTC TGGATGCAAC

351 CACCAACGCC TTGAATAAAT TGGGAGAAAA TATAACGACA TTTGCTGAAG
```

-continued

```
 401 AGACTAAGAC AAATATCGTA AAAATTGATG AAAAATTAGA AGCCGTGGCT

451 GATACCGTCG ACAAGCATGC CGAAGCATTC AACGATATCG CCGATTCATT

501 GGATGAAACC AACACTAAGG CAGACGAAGC CGTCAAAACC GCCAATGAAG

551 CCAAACAGAC GGCCGAAGAA ACCAAACAAA ACGTCGATGC CAAAGTAAAA

601 GCTGCAGAAA CTGCAGCAGG CAAAGCCGAA GCTGCCGCTG GCACAGCTAA

651 TACTGCAGCC GACAAGGCCG AAGCTGTCGC TGCAAAAGTT ACCGACATCA

701 AAGCTGATAT CGCTACGAAC AAAGATAATA TTGCTAAAAA AGCAAACAGT

751 GCCGACGTGT ACACCAGAGA AGAGTCTGAC AGCAAATTTG TCAGAATTGA

801 TGGTCTGAAC GCTACTACCG AAAAATTGGA CACACGCTTG GCTTCTGCTG

851 AAAAATCCAT TGCCGATCAC GATACTCGCC TGAACGGTTT GGATAAAACA

901 GTGTCAGACC TGCGCAAAGA AACCCGCCAA GGCCTTGCAG AACAAGCCGC

951 GCTCTCCGGT CTGTTCCAAC CTTACAACGT GGGTCGGTTC AATGTAACGG

1001 CTGCAGTCGG CGGCTACAAA TCCGAATCGG CAGTCGCCAT CGGTACCGGC

1051 TTCCGCTTTA CCGAAAACTT TGCCGCCAAA GCAGGCGTGG CAGTCGGCAC

1101 TTCGTCCGGT TCTTCCGCAG CCTACCATGT CGGCGTCAAT TACGAGTGGG

1151 GATCCGGCGG AGGCGGCACT TCTGCGCCCG ACTTCAATGC AGGCGGTACC

1201 GGTATCGGCA GCAACAGCAG AGCAACAACA GCGAAATCAG CAGCAGTATC

1251 TTACGCCGGT ATCAAGAACG AAATGTGCAA AGACAGAAGC ATGCTCTGTG

1301 CCGGTCGGGA TGACGTTGCG GTTACAGACA GGGATGCCAA AATCAATGCC

1351 CCCCCCCCGA ATCTGCATAC CGGAGACTTT CCAAACCCAA ATGACGCATA

1401 CAAGAATTTG ATCAACCTCA AACCTGCAAT TGAAGCAGGC TATACAGGAC

1451 GCGGGGTAGA GGTAGGTATC GTCGACACAG GCGAATCCGT CGGCAGCATA

1501 TCCTTTCCCG AACTGTATGG CAGAAAAGAA CACGGCTATA ACGAAAATTA

1551 CAAAAACTAT ACGGCGTATA TGCGGAAGGA AGCGCCTGAA GACGGAGGCG

1601 GTAAAGACAT TGAAGCTTCT TTCGACGATG AGGCCGTTAT AGAGACTGAA

1651 GCAAAGCCGA CGGATATCCG CCACGTAAAA GAAATCGGAC ACATCGATTT

1701 GGTCTCCCAT ATTATTGGCG GCGTTCCGT GGACGGCAGA CCTGCAGGCG

1751 GTATTGCGCC CGATGCGACG CTACACATAA TGAATACGAA TGATGAAACC

1801 AAGAACGAAA TGATGGTTGC AGCCATCCGC AATGCATGGG TCAAGCTGGG

1851 CGAACGTGGC GTGCGCATCG TCAATAACAG TTTTGGAACA ACATCGAGGG

1901 CAGGCACTGC CGACCTTTTC CAAATAGCCA ATTCGGAGGA GCAGTACCGC

1951 CAAGCGTTGC TCGACTATTC CGGCGGTGAT AAAACAGACG AGGGTATCCG

2001 CCTGATGCAA CAGAGCGATT ACGGCAACCT GTCCTACCAC ATCCGTAATA

2051 AAAACATGCT TTTCATCTTT TCGACAGGCA ATGACGCACA AGCTCAGCCC

2101 AACACATATG CCCTATTGCC ATTTTATGAA AAAGACGCTC AAAAAGGCAT

2151 TATCACAGTC GCAGGCGTAG ACCGCAGTGG AGAAAAGTTC AAACGGGAAA

2201 TGTATGGAGA ACCGGGTACA GAACCGCTTG AGTATGGCTC CAACCATTGC

2251 GGAATTACTG CCATGTGGTG CCTGTCGGCA CCCTATGAAG CAAGCGTCCG

2301 TTTCACCCGT ACAAACCCGA TTCAAATTGC CGGAACATCC TTTTCCGCAC

2351 CCATCGTAAC CGGCACGGCG GCTCTGCTGC TGCAGAAATA CCCGTGGATG

2401 AGCAACGACA ACCTGCGTAC CACGTTGCTG ACGACGGCTC AGGACATCGG
```

-continued

```
2451 TGCAGTCGGC GTGGACAGCA AGTTCGGCTG GGGACTGCTG GATGCGGGTA
2501 AGGCCATGAA CGGACCCGCG TCCTTTCCGT TCGGCGACTT TACCGCCGAT
2551 ACGAAAGGTA CATCCGATAT TGCCTACTCC TTCCGTAACG ACATTTCAGG
2601 CACGGGCGGC CTGATCAAAA AAGGCGGCAG CCAACTGCAA CTGCACGGCA
2651 ACAACACCTA TACGGGCAAA ACCATTATCG AAGGCGGTTC GCTGGTGTTG
2701 TACGGCAACA ACAAATCGGA TATGCGCGTC GAAACCAAAG GTGCGCTGAT
2751 TTATAACGGG GCGGCATCCG GCGGCAGCCT GAACAGCGAC GGCATTGTCT
2801 ATCTGGCAGA TACCGACCAA TCCGGCGCAA ACGAAACCGT ACACATCAAA
2851 GGCAGTCTGC AGCTGGACGG CAAAGGTACG CTGTACACAC GTTTGGGCAA
2901 ACTGCTGAAA GTGGACGGTA CGGCGATTAT CGGCGGCAAG CTGTACATGT
2951 CGGCACGCGG CAAGGGGCA GGCTATCTCA ACAGTACCGG ACGACGTGTT
3001 CCCTTCCTGA GTGCCGCCAA AATCGGGCAG GATTATTCTT TCTTCACAAA
3051 CATCGAAACC GACGGCGGCC TGCTGGCTTC CCTCGACAGC GTCGAAAAAA
3101 CAGCGGGCAG TGAAGGCGAC ACGCTGTCCT ATTATGTCCG TCGCGGCAAT
3151 GCGGCACGGA CTGCTTCGGC AGCGGCACAT TCCGCGCCCG CCGGTCTGAA
3201 ACACGCCGTA GAACAGGGCG GCAGCAATCT GGAAAACCTG ATGGTCGAAC
3251 TGGATGCCTC CGAATCATCC GCAACACCCG AGACGGTTGA AACTGCGGCA
3301 GCCGACCGCA CAGATATGCC GGGCATCCGC CCCTACGGCG CAACTTTCCG
3351 CGCAGCGGCA GCCGTACAGC ATGCGAATGC CGCCGACGGT GTACGCATCT
3401 TCAACAGTCT CGCCGCTACC GTCTATGCCG ACAGTACCGC CGCCCATGCC
3451 GATATGCAGG GACGCCGCCT GAAAGCCGTA TCGGACGGGT TGGACCACAA
3501 CGGCACGGGT CTGCGCGTCA TCGCGCAAAC CCAACAGGAC GGTGGAACGT
3551 GGGAACAGGG CGGTGTTGAA GGCAAAATGC GCGGCAGTAC CCAAACCGTC
3601 GGCATTGCCG CGAAAACCGG CGAAAATACG ACAGCAGCCG CCACACTGGG
3651 CATGGGACGC AGCACATGGA GCGAAAACAG TGCAAATGCA AAAACCGACA
3701 GCATTAGTCT GTTTGCAGGC ATACGGCACG ATGCGGGCGA TATCGGCTAT
3751 CTCAAAGGCC TGTTCTCCTA CGGACGCTAC AAAAACAGCA TCAGCCGCAG
3801 CACCGGTGCG GACGAACATG CGGAAGGCAG CGTCAACGGC ACGCTGATGC
3851 AGCTGGGCGC ACTGGGCGGT GTCAACGTTC CGTTTGCCGC AACGGGAGAT
3901 TTGACGGTCG AAGGCGGTCT GCGCTACGAC CTGCTCAAAC AGGATGCATT
3951 CGCCGAAAAA GGCAGTGCTT TGGGCTGGAG CGGCAACAGC CTCACTGAAG
4001 GCACGCTGGT CGGACTCGCG GGTCTGAAGC TGTCGCAACC CTTGAGCGAT
4051 AAAGCCGTCC TGTTTGCAAC GGCGGGCGTG GAACGCGACC TGAACGGACG
4101 CGACTACACG GTAACGGGCG GCTTTACCGG CGCGACTGCA GCAACCGGCA
4151 AGACGGGGGC ACGCAATATG CCGCACACCC GTCTGGTTGC CGGCCTGGGC
4201 GCGGATGTCG AATTCGGCAA CGGCTGGAAC GGCTTGGCAC GTTACAGCTA
4251 CGCCGGTTCC AAACAGTACG GCAACCACAG CGGACGAGTC GGCGTAGGCT
4301 ACCGGTTCCT CGAGCACCAC CACCACCACC ACTGA
   1 MATNDDDVKK AATVAIAAAY NNGQEINGFK AGETIYDIDE DGTITKKDAT
  51 AADVEADDFK GLGLKKVVTN LTKTVNENKQ NVDAKVKAAE SEIEKLTTKL
```

```
101 ADTDAALADT DAALDATTNA LNKLGENITT FAEETKTNIV KIDEKLEAVA

151 DTVDKHAEAF NDIADSLDET NTKADEAVKT ANEAKQTAEE TKQNVDAKVK

201 AAETAAGKAE AAAGTANTAA DKAEAVAAKV TDIKADIATN KDNIAKKANS

251 ADVYTREESD SKFVRIDGLN ATTEKLDTRL ASAEKSIADH DTRLNGLDKT

301 VSDLRKETRQ GLAEQAALSG LFQPYNVGRF NVTAAVGGYK SESAVAIGTG

351 FRFTENFAAK AGVAVGTSSG SSAAYHVGVN YEWGSGGGGT SAPDFNAGGT

401 GIGSNSRATT AKSAAVSYAG IKNEMCKDRS MLCAGRDDVA VTDRDAKINA

451 PPPNLHTGDF PNPNDAYKNL INLKPAIEAG YTGRGVEVGI VDTGESVGSI

501 SFPELYGRKE HGYNENYKNY TAYMRKEAPE DGGGKDIEAS FDDEAVIETE

551 AKPTDIRHVK EIGHIDLVSH IIGGRSVDGR PAGGIAPDAT LHIMNTNDET

601 KNEMMVAAIR NAWVKLGERG VRIVNNSFGT TSRAGTADLF QIANSEEQYR

651 QALLDYSGGD KTDEGIRLMQ QSDYGNLSYH IRNKNMLFIF STGNDAQAQP

701 NTYALLPFYE KDAQKGIITV AGVDRSGEKF KREMYGEPGT EPLEYGSNHC

751 GITAMWCLSA PYEASVRFTR TNPIQIAGTS FSAPIVTGTA ALLLQKYPWM

801 SNDNLRTTLL TTAQDIGAVG VDSKFGWGLL DAGKAMNGPA SFPFGDFTAD

851 TKGTSDIAYS FRNDISGTGG LIKKGGSQLQ LHGNNTYTGK TIIEGGSLVL

901 YGNNKSDMRV ETKGALIYNG AASGGSLNSD GIVYLADTDQ SGANETVHIK

951 GSLQLDGKGT LYTRLGKLLK VDGTAIIGGK LYMSARGKGA GYLNSTGRRV

1001 PFLSAAKIGQ DYSFFTNIET DGGLLASLDS VEKTAGSEGD TLSYYVRRGN

1051 AARTASAAAH SAPAGLKHAV EQGGSNLENL MVELDASESS ATPETVETAA

1101 ADRTDMPGIR PYGATFRAAA AVQHANAADG VRIFNSLAAT VYADSTAAHA

1151 DMQGRRLKAV SDGLDHNGTG LRVIAQTQQD GGTWEQGGVE GKMRGSTQTV

1201 GIAAKTGENT TAAATLGMGR STWSENSANA KTDSISLFAG IRHDAGDIGY

1251 LKGLFSYGRY KNSISRSTGA DEHAEGSVNG TLMQLGALGG VNVPFAATGD

1301 LTVEGGLRYD LLKQDAFAEK GSALGWSGNS LTEGTLVGLA GLKLSQPLSD

1351 KAVLFATAGV ERDLNGRDYT VTGGFTGATA ATGKTGARNM PHTRLVAGLG

1401 ADVEFGNGWN GLARYSYAGS KQYGNHSGRV GVGYRFLEHH HHHH*
961c-ORF46.1 (SEQ ID NOs: 152 and 153)
    1 ATGGCCACAA ACGACGACGA TGTTAAAAAA GCTGCCACTG TGGCCATTGC

51 TGCTGCCTAC AACAATGGCC AAGAAATCAA CGGTTTCAAA GCTGGAGAGA

101 CCATCTACGA CATTGATGAA GACGGCACAA TTACCAAAAA AGACGCAACT

151 GCAGCCGATG TTGAAGCCGA CGACTTTAAA GGTCTGGGTC TGAAAAAAGT

201 CGTGACTAAC CTGACCAAAA CCGTCAATGA AACAAACAA AACGTCGATG

251 CCAAAGTAAA AGCTGCAGAA TCTGAAATAG AAAAGTTAAC AACCAAGTTA

301 GCAGACACTG ATGCCGCTTT AGCAGATACT GATGCCGCTC TGGATGCAAC

351 CACCAACGCC TTGAATAAAT TGGGAGAAAA TATAACGACA TTTGCTGAAG

401 AGACTAAGAC AAATATCGTA AAAATTGATG AAAAATTAGA AGCCGTGGCT

451 GATACCGTCG ACAAGCATGC CGAAGCATTC AACGATATCG CCGATTCATT

501 GGATGAAACC AACACTAAGG CAGACGAAGC CGTCAAAACC GCCAATGAAG

551 CCAAACAGAC GGCCGAAGAA ACCAAACAAA ACGTCGATGC CAAAGTAAAA

601 GCTGCAGAAA CTGCAGCAGG CAAAGCCGAA GCTGCCGCTG GCACAGCTAA
```

-continued

```
 651 TACTGCAGCC GACAAGGCCG AAGCTGTCGC TGCAAAAGTT ACCGACATCA

701 AAGCTGATAT CGCTACGAAC AAAGATAATA TTGCTAAAAA AGCAAACAGT

751 GCCGACGTGT ACACCAGAGA AGAGTCTGAC AGCAAATTTG TCAGAATTGA

801 TGGTCTGAAC GCTACTACCG AAAAATTGGA CACACGCTTG GCTTCTGCTG

851 AAAAATCCAT TGCCGATCAC GATACTCGCC TGAACGGTTT GGATAAAACA

901 GTGTCAGACC TGCGCAAAGA AACCCGCCAA GGCCTTGCAG AACAAGCCGC

951 GCTCTCCGGT CTGTTCCAAC CTTACAACGT GGGTGGATCC GGAGGAGGAG

1001 GATCAGATTT GGCAAACGAT TCTTTTATCC GGCAGGTTCT CGACCGTCAG

1051 CATTTCGAAC CCGACGGGAA ATACCACCTA TTCGGCAGCA GGGGGGAACT

1101 TGCCGAGCGC AGCGGCCATA TCGGATTGGG AAAAATACAA AGCCATCAGT

1151 TGGGCAACCT GATGATTCAA CAGGCGGCCA TTAAAGGAAA TATCGGCTAC

1201 ATTGTCCGCT TTTCCGATCA CGGGCACGAA GTCCATTCCC CCTTCGACAA

1251 CCATGCCTCA CATTCCGATT CTGATGAAGC CGGTAGTCCC GTTGACGGAT

1301 TTAGCCTTTA CCGCATCCAT TGGGACGGAT ACGAACACCA TCCCGCCGAC

1351 GGCTATGACG GGCCACAGGG CGGCGGCTAT CCCGCTCCCA AAGGCGCGAG

1401 GGATATATAC AGCTACGACA TAAAAGGCGT TGCCCAAAAT ATCCGCCTCA

1451 ACCTGACCGA CAACCGCAGC ACCGGACAAC GGCTTGCCGA CCGTTTCCAC

1501 AATGCCGGTA GTATGCTGAC GCAAGGAGTA GGCGACGGAT TCAAACGCGC

1551 CACCCGATAC AGCCCCGAGC TGGACAGATC GGGCAATGCC GCCGAAGCCT

1601 TCAACGGCAC TGCAGATATC GTTAAAAACA TCATCGGCGC GGCAGGAGAA

1651 ATTGTCGGCG CAGGCGATGC CGTGCAGGGC ATAAGCGAAG GCTCAAACAT

1701 TGCTGTCATG CACGGCTTGG GTCTGCTTTC CACCGAAAAC AAGATGGCGC

1751 GCATCAACGA TTTGGCAGAT ATGGCGCAAC TCAAAGACTA TGCCGCAGCA

1801 GCCATCCGCG ATTGGGCAGT CCAAAACCCC AATGCCGCAC AAGGCATAGA

1851 AGCCGTCAGC AATATCTTTA TGGCAGCCAT CCCCATCAAA GGGATTGGAG

1901 CTGTTCGGGG AAAATACGGC TTGGGCGGCA TCACGGCACA TCCTATCAAG

1951 CGGTCGCAGA TGGGCGCGAT CGCATTGCCG AAAGGGAAAT CCGCCGTCAG

2001 CGACAATTTT GCCGATGCGG CATACGCCAA ATACCCGTCC CCTTACCATT

2051 CCCGAAATAT CCGTTCAAAC TTGGAGCAGC GTTACGGCAA AGAAAACATC

2101 ACCTCCTCAA CCGTGCCGCC GTCAAACGGC AAAAATGTCA AACTGGCAGA

2151 CCAACGCCAC CCGAAGACAG GCGTACCGTT TGACGGTAAA GGGTTTCCGA

2201 ATTTTGAGAA GCACGTGAAA TATGATACGC TCGAGCACCA CCACCACCAC

2251 CACTGA

1 MATNDDDVKK AATVAIAAAY NNGQEINGFK AGETIYDIDE DGTITKKDAT

51 AADVEADDFK GLGLKKVVTN LTKTVNENKQ NVDAKVKAAE SEIEKLTTKL

101 ADTDAALADT DAALDATTNA LNKLGENITT FAEETKTNIV KIDEKLEAVA

151 DTVDKHAEAF NDIADSLDET NTKADEAVKT ANEAKQTAEE TKQNVDAKVK

201 AAETAAGKAE AAAGTANTAA DKAEAVAAKV TDIKADIATN KDNIAKKANS

251 ADVYTREESD SKFVRIDGLN ATTEKLDTRL ASAEKSIADH DTRLNGLDKT

301 VSDLRKETRQ GLAEQAALSG LFQPYNVGGS GGGGSDLAND SFIRQVLDRQ

351 HFEPDGKYHL FGSRGELAER SGHIGLGKIQ SHQLGNLMIQ QAAIKGNIGY
```

-continued

```
 401 IVRFSDHGHE VHSPFDNHAS HSDSDEAGSP VDGFSLYRIH WDGYEHHPAD

451 GYDGPQGGGY PAPKGARDIY SYDIKGVAQN IRLNLTDNRS TGQRLADRFH

501 NAGSMLTQGV GDGFKRATRY SPELDRSGNA AEAFNGTADI VKNIIGAAGE

551 IVGAGDAVQG ISEGSNIAVM HGLGLLSTEN KMARINDLAD MAQLKDYAAA

601 AIRDWAVQNP NAAQGIEAVS NIFMAAIPIK GIGAVRGKYG LGGITAHPIK

651 RSQMGAIALP KGKSAVSDNF ADAAYAKYPS PYHSRNIRSN LEQRYGKENI

701 TSSTVPPSNG KNVKLADQRH PKTGVPFDGK GFPNFEKHVK YDTLEHHHHH

751 H*
```

961c-741 (SEQ ID NOs: 154 and 155)
```
    1 ATGGCCACAA ACGACGACGA TGTTAAAAAA GCTGCCACTG TGGCCATTGC

51 TGCTGCCTAC AACAATGGCC AAGAAATCAA CGGTTTCAAA GCTGGAGAGA

101 CCATCTACGA CATTGATGAA GACGGCACAA TTACCAAAAA AGACGCAACT

151 GCAGCCGATG TTGAAGCCGA CGACTTTAAA GGTCTGGGTC TGAAAAAAGT

201 CGTGACTAAC CTGACCAAAA CCGTCAATGA AAACAAACAA AACGTCGATG

251 CCAAAGTAAA AGCTGCAGAA TCTGAAATAG AAAAGTTAAC AACCAAGTTA

301 GCAGACACTG ATGCCGCTTT AGCAGATACT GATGCCGCTC TGGATGCAAC

351 CACCAACGCC TTGAATAAAT TGGGAGAAAA TATAACGACA TTTGCTGAAG

401 AGACTAAGAC AAATATCGTA AAAATTGATG AAAAATTAGA AGCCGTGGCT

451 GATACCGTCG ACAAGCATGC CGAAGCATTC AACGATATCG CCGATTCATT

501 GGATGAAACC AACACTAAGG CAGACGAAGC CGTCAAAACC GCCAATGAAG

551 CCAAACAGAC GGCCGAAGAA ACCAAACAAA ACGTCGATGC CAAAGTAAAA

601 GCTGCAGAAA CTGCAGCAGG CAAAGCCGAA GCTGCCGCTG GCACAGCTAA

651 TACTGCAGCC GACAAGGCCG AAGCTGTCGC TGCAAAAGTT ACCGACATCA

701 AAGCTGATAT CGCTACGAAC AAAGATAATA TTGCTAAAAA AGCAAACAGT

751 GCCGACGTGT ACACCAGAGA AGAGTCTGAC AGCAAATTTG TCAGAATTGA

801 TGGTCTGAAC GCTACTACCG AAAAATTGGA CACACGCTTG GCTTCTGCTG

851 AAAAATCCAT TGCCGATCAC GATACTCGCC TGAACGGTTT GGATAAAACA

901 GTGTCAGACC TGCGCAAAGA AACCCGCCAA GGCCTTGCAG AACAAGCCGC

951 GCTCTCCGGT CTGTTCCAAC CTTACAACGT GGGTGGATCC GGAGGGGGTG

1001 GTGTCGCCGC CGACATCGGT GCGGGCTTG CCGATGCACT AACCGCACCG

1051 CTCGACCATA AGACAAAGG TTTGCAGTCT TTGACGCTGG ATCAGTCCGT

1101 CAGGAAAAAC GAGAAACTGA AGCTGGCGGC ACAAGGTGCG GAAAAAACTT

1151 ATGGAAACGG TGACAGCCTC AATACGGGCA AATTGAAGAA CGACAAGGTC

1201 AGCCGTTTCG ACTTTATCCG CCAAATCGAA GTGGACGGGC AGCTCATTAC

1251 CTTGGAGAGT GGAGAGTTCC AAGTATACAA ACAAAGCCAT TCCGCCTTAA

1301 CCGCCTTTCA GACCGAGCAA ATACAAGATT CGGAGCATTC CGGGAAGATG

1351 GTTGCGAAAC GCCAGTTCAG AATCGGCGAC ATAGCGGGCG AACATACATC

1401 TTTTGACAAG CTTCCCGAAG GCGGCAGGGC GACATATCGC GGGACGGCGT

1451 TCGGTTCAGA CGATGCCGGC GGAAAACTGA CCTACACCAT AGATTTCGCC

1501 GCCAAGCAGG GAAACGGCAA AATCGAACAT TTGAAATCGC CAGAACTCAA

1551 TGTCGACCTG GCCGCCGCCG ATATCAAGCC GGATGGAAAA CGCCATGCCG
```

-continued

```
1601 TCATCAGCGG TTCCGTCCTT TACAACCAAG CCGAGAAAGG CAGTTACTCC
1651 CTCGGTATCT TTGGCGGAAA AGCCCAGGAA GTTGCCGGCA GCGCGGAAGT
1701 GAAAACCGTA ACGGCATAC GCCATATCGG CCTTGCCGCC AAGCAACTCG
1751 AGCACCACCA CCACCACCAC TGA

1 MATNDDDVKK AATVAIAAAY NNGQEINGFK AGETIYDIDE DGTITKKDAT
  51 AADVEADDFK GLGLKKVVTN LTKTVNENKQ NVDAKVKAAE SEIEKLTTKL
 101 ADTDAALADT DAALDATTNA LNKLGENITT FAEETKTNIV KIDEKLEAVA
 151 DTVDKHAEAF NDIADSLDET NTKADEAVKT ANEAKQTAEE TKQNVDAKVK
 201 AAETAAGKAE AAAGTANTAA DKAEAVAAKV TDIKADIATN KDNIAKKANS
 251 ADVYTREESD SKFVRIDGLN ATTEKLDTRL ASAEKSIADH DTRLNGLDKT
 301 VSDLRKETRQ GLAEQAALSG LFQPYNVGGS GGGGVAADIG AGLADALTAP
 351 LDHKDKGLQS LTLDQSVRKN EKLKLAAQGA EKTYGNGDSL NTGKLKNDKV
 401 SRFDFIRQIE VDGQLITLES GEFQVYKQSH SALTAFQTEQ IQDSEHSGKM
 451 VAKRQFRIGD IAGEHTSFDK LPEGGRATYR GTAFGSDDAG GKLTYTIDFA
 501 AKQGNGKIEH LKSPELNVDL AAADIKPDGK RHAVISGSVL YNQAEKGSYS
 551 LGIFGGKAQE VAGSAEVKTV NGIRHIGLAA KQLEHHHHHH *
```

961c-983 (SEQ ID NOS: 156 and 157)
```
   1 ATGGCCACAA ACGACGACGA TGTTAAAAAA GCTGCCACTG TGGCCATTGC
  51 TGCTGCCTAC AACAATGGCC AAGAAATCAA CGGTTTCAAA GCTGGAGAGA
 101 CCATCTACGA CATTGATGAA GACGGCACAA TTACCAAAAA AGACGCAACT
 151 GCAGCCGATG TTGAAGCCGA CGACTTTAAA GGTCTGGGTC TGAAAAAAGT
 201 CGTGACTAAC CTGACCAAAA CCGTCAATGA AACAAACAA ACGTCGATG
 251 CCAAAGTAAA AGCTGCAGAA TCTGAAATAG AAAAGTTAAC AACCAAGTTA
 301 GCAGACACTG ATGCCGCTTT AGCAGATACT GATGCCGCTC TGGATGCAAC
 351 CACCAACGCC TTGAATAAAT TGGGAGAAAA TATAACGACA TTTGCTGAAG
 401 AGACTAAGAC AAATATCGTA AAAATTGATG AAAAATTAGA AGCCGTGGCT
 451 GATACCGTCG ACAAGCATGC CGAAGCATTC AACGATATCG CCGATTCATT
 501 GGATGAAACC AACACTAAGG CAGACGAAGC CGTCAAAACC GCCAATGAAG
 551 CCAAACAGAC GGCCGAAGAA ACCAAACAAA ACGTCGATGC CAAAGTAAAA
 601 GCTGCAGAAA CTGCAGCAGG CAAAGCCGAA GCTGCCGCTG GCACAGCTAA
 651 TACTGCAGCC GACAAGGCCG AAGCTGTCGC TGCAAAAGTT ACCGACATCA
 701 AAGCTGATAT CGCTACGAAC AAAGATAATA TTGCTAAAAA AGCAAACAGT
 751 GCCGACGTGT ACACCAGAGA AGAGTCTGAC AGCAAATTTG TCAGAATTGA
 801 TGGTCTGAAC GCTACTACCG AAAAATTGGA CACACGCTTG GCTTCTGCTG
 851 AAAAATCCAT TGCCGATCAC GATACTCGCC TGAACGGTTT GGATAAAACA
 901 GTGTCAGACC TGCGCAAAGA AACCCGCCAA GGCCTTGCAG AACAAGCCGC
 951 GCTCTCCGGT CTGTTCCAAC CTTACAACGT GGGTGGATCC GGCGGAGGCG
1001 GCACTTCTGC GCCCGACTTC AATGCAGGCG GTACCGGTAT CGGCAGCAAC
1051 AGCAGAGCAA CAACAGCGAA ATCAGCAGCA GTATCTTACG CCGGTATCAA
1101 GAACGAAATG TGCAAAGACA GAAGCATGCT CTGTGCCGGT CGGGATGACG
1151 TTGCGGTTAC AGACAGGGAT GCCAAAATCA ATGCCCCCCC CCCGAATCTG
```

-continued

```
1201 CATACCGGAG ACTTTCCAAA CCCAAATGAC GCATACAAGA ATTTGATCAA
1251 CCTCAAACCT GCAATTGAAG CAGGCTATAC AGGACGCGGG GTAGAGGTAG
1301 GTATCGTCGA CACAGGCGAA TCCGTCGGCA GCATATCCTT TCCCGAACTG
1351 TATGGCAGAA AAGAACACGG CTATAACGAA AATTACAAAA ACTATACGGC
1401 GTATATGCGG AAGGAAGCGC CTGAAGACGG AGGCGGTAAA GACATTGAAG
1451 CTTCTTTCGA CGATGAGGCC GTTATAGAGA CTGAAGCAAA GCCGACGGAT
1501 ATCCGCCACG TAAAAGAAAT CGGACACATC GATTTGGTCT CCCATATTAT
1551 TGGCGGGCGT TCCGTGGACG GCAGACCTGC AGGCGGTATT GCGCCCGATG
1601 CGACGCTACA CATAATGAAT ACGAATGATG AAACCAAGAA CGAAATGATG
1651 GTTGCAGCCA TCCGCAATGC ATGGGTCAAG CTGGGCGAAC GTGGCGTGCG
1701 CATCGTCAAT AACAGTTTTG GAACAACATC GAGGGCAGGC ACTGCCGACC
1751 TTTTCCAAAT AGCCAATTCG GAGGAGCAGT ACCGCCAAGC GTTGCTCGAC
1801 TATTCCGGCG GTGATAAAAC AGACGAGGGT ATCCGCCTGA TGCAACAGAG
1851 CGATTACGGC AACCTGTCCT ACCACATCCG TAATAAAAAC ATGCTTTTCA
1901 TCTTTTCGAC AGGCAATGAC GCACAAGCTC AGCCCAACAC ATATGCCCTA
1951 TTGCCATTTT ATGAAAAAGA CGCTCAAAAA GGCATTATCA CAGTCGCAGG
2001 CGTAGACCGC AGTGGAGAAA AGTTCAAACG GGAAATGTAT GGAGAACCGG
2051 GTACAGAACC GCTTGAGTAT GGCTCCAACC ATTGCGGAAT TACTGCCATG
2101 TGGTGCCTGT CGGCACCCTA TGAAGCAAGC GTCCGTTTCA CCCGTACAAA
2151 CCCGATTCAA ATTGCCGGAA CATCCTTTTC CGCACCCATC GTAACCGGCA
2201 CGGCGGCTCT GCTGCTGCAG AAATACCCGT GGATGAGCAA CGACAACCTG
2251 CGTACCACGT TGCTGACGAC GGCTCAGGAC ATCGGTGCAG TCGGCGTGGA
2301 CAGCAAGTTC GGCTGGGGAC TGCTGGATGC GGGTAAGGCC ATGAACGGAC
2351 CCGCGTCCTT TCCGTTCGGC GACTTTACCG CCGATACGAA AGGTACATCC
2401 GATATTGCCT ACTCCTTCCG TAACGACATT TCAGGCACGG GCGGCCTGAT
2451 CAAAAAAGGC GGCAGCCAAC TGCAACTGCA CGGCAACAAC ACCTATACGG
2501 GCAAAACCAT TATCGAAGGC GGTTCGCTGG TGTTGTACGG CAACAACAAA
2551 TCGGATATGC GCGTCGAAAC CAAAGGTGCG CTGATTTATA ACGGGGCGGC
2601 ATCCGGCGGC AGCCTGAACA GCGACGGCAT TGTCTATCTG GCAGATACCG
2651 ACCAATCCGG CGCAAACGAA ACCGTACACA TCAAAGGCAG TCTGCAGCTG
2701 GACGGCAAAG GTACGCTGTA CACACGTTTG GGCAAACTGC TGAAAGTGGA
2751 CGGTACGGCG ATTATCGGCG GCAAGCTGTA CATGTCGGCA CGCGGCAAGG
2801 GGGCAGGCTA TCTCAACAGT ACCGGACGAC GTGTTCCCTT CCTGAGTGCC
2851 GCCAAAATCG GCAGGATTA TTCTTTCTTC ACAAACATCG AAACCGACGG
2901 CGGCCTGCTG GCTTCCCTCG ACAGCGTCGA AAAAACAGCG GGCAGTGAAG
2951 GCGACACGCT GTCCTATTAT GTCCGTCGCG GCAATGCGGC ACGGACTGCT
3001 TCGGCAGCGG CACATTCCGC GCCCGCCGGT CTGAAACACG CCGTAGAACA
3051 GGGCGGCAGC AATCTGGAAA ACCTGATGGT CGAACTGGAT GCCTCCGAAT
3101 CATCCGCAAC ACCCGAGACG GTTGAAACTG CGGCAGCCGA CCGCACAGAT
3151 ATGCCGGGCA TCCGCCCCTA CGGCGCAACT TTCCGCGCAG CGGCAGCCGT
```

```
-continued
3201 ACAGCATGCG AATGCCGCCG ACGGTGTACG CATCTTCAAC AGTCTCGCCG

3251 CTACCGTCTA TGCCGACAGT ACCGCCGCCC ATGCCGATAT GCAGGGACGC

3301 CGCCTGAAAG CCGTATCGGA CGGGTTGGAC CACAACGGCA CGGGTCTGCG

3351 CGTCATCGCG CAAACCCAAC AGGACGGTGG AACGTGGGAA CAGGGCGGTG

3401 TTGAAGGCAA AATGCGCGGC AGTACCCAAA CCGTCGGCAT TGCCGCGAAA

3451 ACCGGCGAAA ATACGACAGC AGCCGCCACA CTGGGCATGG GACGCAGCAC

3501 ATGGAGCGAA AACAGTGCAA ATGCAAAAAC CGACAGCATT AGTCTGTTTG

3551 CAGGCATACG GCACGATGCG GGCGATATCG GCTATCTCAA AGGCCTGTTC

3601 TCCTACGGAC GCTACAAAAA CAGCATCAGC CGCAGCACCG GTGCGGACGA

3651 ACATGCGAAA GGCAGCGTCA ACGGCACGCT GATGCAGCTG GGCGCACTGG

3701 GCGGTGTCAA CGTTCCGTTT GCCGCAACGG GAGATTTGAC GGTCGAAGGC

3751 GGTCTGCGCT ACGACCTGCT CAAACAGGAT GCATTCGCCG AAAAAGGCAG

3801 TGCTTTGGGC TGGAGCGGCA ACAGCCTCAC TGAAGGCACG CTGGTCGGAC

3851 TCGCGGGTCT GAAGCTGTCG CAACCCTTGA GCGATAAAGC CGTCCTGTTT

3901 GCAACGGCGG GCGTGGAACG CGACCTGAAC GGACGCGACT ACACGGTAAC

3951 GGGCGGCTTT ACCGGCGCGA CTGCAGCAAC CGGCAAGACG GGGGCACGCA

4001 ATATGCCGCA CACCCGTCTG GTTGCCGGCC TGGGCGCGGA TGTCGAATTC

4051 GGCAACGGCT GGAACGGCTT GGCACGTTAC AGCTACGCCG GTTCCAAACA

4101 GTACGGCAAC CACAGCGGAC GAGTCGGCGT AGGCTACCGG TTCCTCGAGC

4151 ACCACCACCA CCACCACTGA

1 MATNDDDVKK AATVAIAAAY NNGQEINGFK AGETIYDIDE DGTITKKDAT

51 AADVEADDFK GLGLKKVVTN LTKTVNENKQ NVDAKVKAAE SEIEKLTTKL

101 ADTDAALADT DAALDATTNA LNKLGENITT FAEETKTNIV KIDEKLEAVA

151 DTVDKHAEAF NDIADSLDET NTKADEAVKT ANEAKQTAEE TKQNVDAKVK

201 AAETAAGKAE AAAGTANTAA DKAEAVAAKV TDIKADIATN KDNIAKKANS

251 ADVYTREESD SKFVRIDGLN ATTEKLDTRL ASAEKSIADH DTRLNGLDKT

301 VSDLRKETRQ GLAEQAALSG LFQPYNVGGS GGGGTSAPDF NAGGTGIGSN

351 SRATTAKSAA VSYAGIKNEM CKDRSMLCAG RDDVAVTDRD AKINAPPPNL

401 HTGDFPNPND AYKNLINLKP AIEAGYTGRG VEVGIVDTGE SVGSISFPEL

451 YGRKEHGYNE NYKNYTAYMR KEAPEDGGGK DIEASFDDEA VIETEAKPTD

501 IRHVKEIGHI DLVSHIIGGR SVDGRPAGGI APDATLHIMN TNDETKNEMM

551 VAAIRNAWVK LGERGVRIVN NSFGTTSRAG TADLFQIANS EEQYRQALLD

601 YSGGDKTDEG IRLMQQSDYG NLSYHIRNKN MLFIFSTGND AQAQPNTYAL

651 LPFYEKDAQK GIITVAGVDR SGEKFKREMY GEPGTEPLEY GSNHCGITAM

701 WCLSAPYEAS VRFTRTNPIQ IAGTSFSAPI VTGTAALLLQ KYPWMSNDNL

751 RTTLLTTAQD IGAVGVDSKF GWGLLDAGKA MNGPASFPFG DFTADTKGTS

801 DIAYSFRNDI SGTGGLIKKG GSQLQLHGNN TYTGKTIIEG GSLVLYGNNK

851 SDMRVETKGA LIYNGAASGG SLNSDGIVYL ADTDQSGANE TVHIKGSLQL

901 DGKGTLYTRL GKLLKVDGTA IIGGKLYMSA RGKGAGYLNS TGRRVPFLSA

951 AKIGQDYSFF TNIETDGGLL ASLDSVEKTA GSEGDTLSYY VRRGNAARTA

1001 SAAAHSAPAG LKHAVEQGGS NLENLMVELD ASESSATPET VETAAADRTD
```

-continued

```
1051 MPGIRPYGAT FRAAAAVQHA NAADGVRIFN SLAATVYADS TAAHADMQGR

1101 RLKAVSDGLD HNGTGLRVIA QTQQDGGTWE QGGVEGKMRG STQTVGIAAK

1151 TGENTTAAAT LGMGRSTWSE NSANAKTDSI SLFAGIRHDA GDIGYLKGLF

1201 SYGRYKNSIS RSTGADEHAE GSVNGTLMQL GALGGVNVPF AATGDLTVEG

1251 GLRYDLLKQD AFAEKGSALG WSGNSLTEGT LVGLAGLKLS QPLSDKAVLF

1301 ATAGVERDLN GRDYTVTGGF TGATAATGKT GARNMPHTRL VAGLGADVEF

1351 GNGWNGLARY SYAGSKQYGN HSGRVGVGYR FLEHHHHHH*
```

961cL-ORF46.1 (SEQ ID NOS: 158 and 159)

```
   1 ATGAAACACT TTCCATCCAA AGTACTGACC ACAGCCATCC TTGCCACTTT

51 CTGTAGCGGC GCACTGGCAG CCACAAACGA CGACGATGTT AAAAAGCTG

101 CCACTGTGGC CATTGCTGCT GCCTACAACA ATGGCCAAGA AATCAACGGT

151 TTCAAAGCTG GAGAGACCAT CTACGACATT GATGAAGACG GCACAATTAC

201 CAAAAAGAC GCAACTGCAG CCGATGTTGA AGCCGACGAC TTTAAAGGTC

251 TGGGTCTGAA AAAGTCGTG ACTAACCTGA CCAAAACCGT CAATGAAAAC

301 AAACAAAACG TCGATGCCAA AGTAAAAGCT GCAGAATCTG AAATAGAAAA

351 GTTAACAACC AAGTTAGCAG ACACTGATGC CGCTTTAGCA GATACTGATG

401 CCGCTCTGGA TGCAACCACC AACGCCTTGA ATAAATTGGG AGAAAATATA

451 ACGACATTTG CTGAAGAGAC TAAGACAAAT ATCGTAAAAA TTGATGAAAA

501 ATTAGAAGCC GTGGCTGATA CCGTCGACAA GCATGCCGAA GCATTCAACG

551 ATATCGCCGA TTCATTGGAT GAAACCAACA CTAAGGCAGA CGAAGCCGTC

601 AAAACCGCCA ATGAAGCCAA ACAGACGGCC GAAGAAACCA ACAAAAACGT

651 CGATGCCAAA GTAAAAGCTG CAGAAACTGC AGCAGGCAAA GCCGAAGCTG

701 CCGCTGGCAC AGCTAATACT GCAGCCGACA AGGCCGAAGC TGTCGCTGCA

751 AAAGTTACCG ACATCAAAGC TGATATCGCT ACGAACAAAG ATAATATTGC

801 TAAAAAAGCA AACAGTGCCG ACGTGTACAC CAGAGAAGAG TCTGACAGCA

851 AATTTGTCAG AATTGATGGT CTGAACGCTA CTACCGAAAA ATTGGACACA

901 CGCTTGGCTT CTGCTGAAAA ATCCATTGCC GATCACGATA CTCGCCTGAA

951 CGGTTTGGAT AAAACAGTGT CAGACCTGCG CAAAGAAACC CGCCAAGGCC

1001 TTGCAGAACA AGCCGCGCTC TCCGGTCTGT TCCAACCTTA CAACGTGGGT

1051 GGATCCGGAG GAGGAGGATC AGATTTGGCA AACGATTCTT TTATCCGGCA

1101 GGTTCTCGAC CGTCAGCATT TCGAACCCGA CGGGAAATAC CACCTATTCG

1151 GCAGCAGGGG GGAACTTGCC GAGCGCAGCG GCCATATCGG ATTGGGAAAA

1201 ATACAAAGCC ATCAGTTGGG CAACCTGATG ATTCAACAGG CGGCCATTAA

1251 AGGAAATATC GGCTACATTG TCCGCTTTTC CGATCACGGG CACGAAGTCC

1301 ATTCCCCCTT CGACAACCAT GCCTCACATT CCGATTCTGA TGAAGCCGGT

1351 AGTCCCGTTG ACGGATTTAG CCTTTACCGC ATCCATTGGG ACGGATACGA

1401 ACACCATCCC GCCGACGGCT ATGACGGGCC ACAGGGCGG GGCTATCCCG

1451 CTCCCAAAGG CGCGAGGGAT ATATACAGCT ACGACATAAA AGGCGTTGCC

1501 CAAAATATCC GCCTCAACCT GACCGACAAC CGCAGCACCG GACAACGGCT

1551 TGCCGACCGT TTCCACAATG CCGGTAGTAT GCTGACGCAA GGAGTAGGCG

1601 ACGGATTCAA ACGCGCCACC CGATACAGCC CCGAGCTGGA CAGATCGGGC
```

-continued

```
1651 AATGCCGCCG AAGCCTTCAA CGGCACTGCA GATATCGTTA AAAACATCAT

1701 CGGCGCGGCA GGAGAAATTG TCGGCGCAGG CGATGCCGTG CAGGGCATAA

1751 GCGAAGGCTC AAACATTGCT GTCATGCACG GCTTGGGTCT GCTTTCCACC

1801 GAAAACAAGA TGGCGCGCAT CAACGATTTG GCAGATATGG CGCAACTCAA

1851 AGACTATGCC GCAGCAGCCA TCCGCGATTG GCAGTCCAA AACCCCAATG

1901 CCGCACAAGG CATAGAAGCC GTCAGCAATA TCTTTATGGC AGCCATCCCC

1951 ATCAAAGGGA TTGGAGCTGT TCGGGGAAAA TACGGCTTGG GCGGCATCAC

2001 GGCACATCCT ATCAAGCGGT CGCAGATGGG CGCGATCGCA TTGCCGAAAG

2051 GGAAATCCGC CGTCAGCGAC AATTTTGCCG ATGCGGCATA CGCCAAATAC

2101 CCGTCCCCTT ACCATTCCCG AAATATCCGT TCAAACTTGG AGCAGCGTTA

2151 CGGCAAAGAA AACATCACCT CCTCAACCGT GCCGCCGTCA ACGGCAAAA

2201 ATGTCAAACT GGCAGACCAA CGCCACCCGA AGACAGGCGT ACCGTTTGAC

2251 GGTAAAGGGT TTCCGAATTT TGAGAAGCAC GTGAAATATG ATACGTAACT

2301 CGAG

1 MKHFPSKVLT TAILATFCSG ALAATNDDDV KKAATVAIAA AYNNGQEING

51 FKAGETIYDI DEDGTITKKD ATAADVEADD FKGLGLKKVV TNLTKTVNEN

101 KQNVDAKVKA AESEIEKLTT KLADTDAALA DTDAALDATT NALNKLGENI

151 TTFAEETKTN IVKIDEKLEA VADTVDKHAE AFNDIADSLD ETNTKADEAV

201 KTANEAKQTA EETKQNVDAK VKAAETAAGK AEAAAGTANT AADKAEAVAA

251 KVTDIKADIA TNKDNIAKKA NSADVYTREE SDSKFVRIDG LNATTEKLDT

301 RLASAEKSIA DHDTRLNGLD KTVSDLRKET RQGLAEQAAL SGLFQPYNVG

351 GSGGGGSDLA NDSFIRQVLD RQHFEPDGKY HLFGSRGELA ERSGHIGLGK

401 IQSHQLGNLM IQQAAIKGNI GYIVRFSDHG HEVHSPFDNH ASHSDSDEAG

451 SPVDGFSLYR IHWDGYEHHP ADGYDGPQGG GYPAPKGARD IYSYDIKGVA

501 QNIRLNLTDN RSTGQRLADR FHNAGSMLTQ GVGDGFKRAT RYSPELDRSG

551 NAAEAFNGTA DIVKNIIGAA GEIVGAGDAV QGISEGSNIA VMHGLGLLST

601 ENKMARINDL ADMAQLKDYA AAAIRDWAVQ NPNAAQGIEA VSNIFMAAIP

651 IKGIGAVRGK YGLGGITAHP IKRSQMGAIA LPKGKSAVSD NFADAAYAKY

701 PSPYHSRNIR SNLEQRYGKE NITSSTVPPS NGKNVKLADQ RHPKTGVPFD

751 GKGFPNFEKH VKYDT*
```

961cL-741 (SEQ ID NOS: 160 and 161)
```
   1 ATGAAACACT TTCCATCCAA AGTACTGACC ACAGCCATCC TTGCCACTTT

51 CTGTAGCGGC GCACTGGCAG CCACAAACGA CGACGATGTT AAAAAAGCTG

101 CCACTGTGGC CATTGCTGCT GCCTACAACA ATGGCCAAGA AATCAACGGT

151 TTCAAAGCTG GAGAGACCAT CTACGACATT GATGAAGACG GCACAATTAC

201 CAAAAAGAC GCAACTGCAG CCGATGTTGA AGCCGACGAC TTTAAAGGTC

251 TGGGTCTGAA AAAAGTCGTG ACTAACCTGA CCAAAACCGT CAATGAAAAC

301 AAACAAAACG TCGATGCCAA AGTAAAAGCT GCAGAATCTG AAATAGAAAA

351 GTTAACAACC AAGTTAGCAG ACACTGATGC CGCTTTAGCA GATACTGATG

401 CCGCTCTGGA TGCAACCACC AACGCCTTGA ATAAATTGGG AGAAATATA

451 ACGACATTTG CTGAAGAGAC TAAGACAAAT ATCGTAAAAA TTGATGAAAA
```

-continued

```
 501 ATTAGAAGCC GTGGCTGATA CCGTCGACAA GCATGCCGAA GCATTCAACG
 551 ATATCGCCGA TTCATTGGAT GAAACCAACA CTAAGGCAGA CGAAGCCGTC
 601 AAAACCGCCA ATGAAGCCAA ACAGACGGCC GAAGAAACCA AACAAAACGT
 651 CGATGCCAAA GTAAAAGCTG CAGAAACTGC AGCAGGCAAA GCCGAAGCTG
 701 CCGCTGGCAC AGCTAATACT GCAGCCGACA AGGCCGAAGC TGTCGCTGCA
 751 AAAGTTACCG ACATCAAAGC TGATATCGCT ACGAACAAAG ATAATATTGC
 801 TAAAAAAGCA AACAGTGCCG ACGTGTACAC CAGAGAAGAG TCTGACAGCA
 851 AATTTGTCAG AATTGATGGT CTGAACGCTA CTACCGAAAA ATTGGACACA
 901 CGCTTGGCTT CTGCTGAAAA ATCCATTGCC GATCACGATA CTCGCCTGAA
 951 CGGTTTGGAT AAAACAGTGT CAGACCTGCG CAAAGAAACC CGCCAAGGCC
1001 TTGCAGAACA AGCCGCGCTC TCCGGTCTGT TCCAACCTTA CAACGTGGGT
1051 GGATCCGGAG GGGGTGGTGT CGCCGCCGAC ATCGGTGCGG GGCTTGCCGA
1101 TGCACTAACC GCACCGCTCG ACCATAAAGA CAAAGGTTTG CAGTCTTTGA
1151 CGCTGGATCA GTCCGTCAGG AAAAACGAGA AACTGAAGCT GGCGGCACAA
1201 GGTGCGGAAA AAACTTATGG AAACGGTGAC AGCCTCAATA CGGGCAAATT
1251 GAAGAACGAC AAGGTCAGCC GTTTCGACTT TATCCGCCAA ATCGAAGTGG
1301 ACGGGCAGCT CATTACCTTG GAGAGTGGAG AGTTCCAAGT ATACAAACAA
1351 AGCCATTCCG CCTTAACCGC CTTTCAGACC GAGCAAATAC AAGATTCGGA
1401 GCATTCCGGG AAGATGGTTG CGAAACGCCA GTTCAGAATC GGCGACATAG
1451 CGGGCGAACA TACATCTTTT GACAAGCTTC CCGAAGGCGG CAGGGCGACA
1501 TATCGCGGGA CGGCGTTCGG TTCAGACGAT GCCGGCGGAA AACTGACCTA
1551 CACCATAGAT TTCGCCGCCA AGCAGGGAAA CGGCAAAATC GAACATTTGA
1601 AATCGCCAGA ACTCAATGTC GACCTGGCCG CCGCCGATAT CAAGCCGGAT
1651 GGAAAACGCC ATGCCGTCAT CAGCGGTTCC GTCCTTTACA ACCAAGCCGA
1701 GAAAGGCAGT TACTCCCTCG GTATCTTTGG CGGAAAAGCC CAGGAAGTTG
1751 CCGGCAGCGC GGAAGTGAAA ACCGTAAACG GCATACGCCA TATCGGCCTT
1801 GCCGCCAAGC AACTCGAGCA CCACCACCAC CACCACTGA
   1 MKHFPSKVLT TAILATFCSG ALAATNDDDV KKAATVAIAA AYNNGQEING
  51 FKAGETIYDI DEDGTITKKD ATAADVEADD FKGLGLKKVV TNLTKTVNEN
 101 KQNVDAKVKA AESEIEKLTT KLADTDAALA DTDAALDATT NALNKLGENI
 151 TTFAEETKTN IVKIDEKLEA VADTVDKHAE AFNDIADSLD ETNTKADEAV
 201 KTANEAKQTA EETKQNVDAK VKAAETAAGK AEAAAGTANT AADKAEAVAA
 251 KVTDIKADIA TNKDNIAKKA NSADVYTREE SDSKFVRIDG LNATTEKLDT
 301 RLASAEKSIA DHDTRLNGLD KTVSDLRKET RQGLAEQAAL SGLFQPYNVG
 351 GSGGGVAAD IGAGLADALT APLDHKDKGL QSLTLDQSVR KNEKLKLAAQ
 401 GAEKTYGNGD SLNTGKLKND KVSRFDFIRQ IEVDGQLITL ESGEFQVYKQ
 451 SHSALTAFQT EQIQDSEHSG KMVAKRQFRI GDIAGEHTSF DKLPEGGRAT
 501 YRGTAFGSDD AGGKLTYTID FAAKQGNGKI EHLKSPELNV DLAAADIKPD
 551 GKRHAVISGS VLYNQAEKGS YSLGIFGGKA QEVAGSAEVK TVNGIRHIGL
 601 AAKQLEHHHH HH*
```

-continued

961cL-983 (SEQ ID NOS: 162 and 163)

```
   1 ATGAAACACT TTCCATCCAA AGTACTGACC ACAGCCATCC TTGCCACTTT
  51 CTGTAGCGGC GCACTGGCAG CCACAAACGA CGACGATGTT AAAAAAGCTG
 101 CCACTGTGGC CATTGCTGCT GCCTACAACA ATGGCCAAGA AATCAACGGT
 151 TTCAAAGCTG GAGAGACCAT CTACGACATT GATGAAGACG GCACAATTAC
 201 CAAAAAAGAC GCAACTGCAG CCGATGTTGA AGCCGACGAC TTTAAAGGTC
 251 TGGGTCTGAA AAAGTCGTG ACTAACCTGA CCAAAACCGT CAATGAAAAC
 301 AAACAAAACG TCGATGCCAA AGTAAAAGCT GCAGAATCTG AAATAGAAAA
 351 GTTAACAACC AAGTTAGCAG ACACTGATGC CGCTTTAGCA GATACTGATG
 401 CCGCTCTGGA TGCAACCACC AACGCCTTGA ATAAATTGGG AGAAAATATA
 451 ACGACATTTG CTGAAGAGAC TAAGACAAAT ATCGTAAAAA TTGATGAAAA
 501 ATTAGAAGCC GTGGCTGATA CCGTCGACAA GCATGCCGAA GCATTCAACG
 551 ATATCGCCGA TTCATTGGAT GAAACCAACA CTAAGGCAGA CGAAGCCGTC
 601 AAACCGCCA ATGAAGCCAA ACAGACGGCC GAAGAAACCA AACAAAACGT
 651 CGATGCCAAA GTAAAAGCTG CAGAAACTGC AGCAGGCAAA GCCGAAGCTG
 701 CCGCTGGCAC AGCTAATACT GCAGCCGACA AGGCCGAAGC TGTCGCTGCA
 751 AAAGTTACCG ACATCAAAGC TGATATCGCT ACGAACAAAG ATAATATTGC
 801 TAAAAAAGCA ACAGTGCCG ACGTGTACAC CAGAGAAGAG TCTGACAGCA
 851 AATTTGTCAG AATTGATGGT CTGAACGCTA CTACCGAAAA ATTGGACACA
 901 CGCTTGGCTT CTGCTGAAAA ATCCATTGCC GATCACGATA CTCGCCTGAA
 951 CGGTTTGGAT AAAACAGTGT CAGACCTGCG CAAAGAAACC CGCCAAGGCC
1001 TTGCAGAACA AGCCGCGCTC TCCGGTCTGT TCCAACCTTA CAACGTGGGT
1051 GGATCCGGCG GAGGCGGCAC TTCTGCGCCC GACTTCAATG CAGGCGGTAC
1101 CGGTATCGGC AGCAACAGCA GAGCAACAAC AGCGAAATCA GCAGCAGTAT
1151 CTTACGCCGG TATCAAGAAC GAAATGTGCA AGACAGAAG CATGCTCTGT
1201 GCCGGTCGGG ATGACGTTGC GGTTACAGAC AGGGATGCCA AAATCAATGC
1251 CCCCCCCCG AATCTGCATA CCGGAGACTT TCCAAACCCA AATGACGCAT
1301 ACAAGAATTT GATCAACCTC AAACCTGCAA TTGAAGCAGG CTATACAGGA
1351 CGCGGGGTAG AGGTAGGTAT CGTCGACACA GGCGAATCCG TCGGCAGCAT
1401 ATCCTTTCCC GAACTGTATG CAGAAAAGA ACACGGCTAT AACGAAAATT
1451 ACAAAAACTA TACGGCGTAT ATGCGGAAGG AAGCGCCTGA AGACGGAGGC
1501 GGTAAAGACA TTGAAGCTTC TTTCGACGAT GAGGCCGTTA TAGAGACTGA
1551 AGCAAAGCCG ACGGATATCC GCCACGTAAA AGAAATCGGA CACATCGATT
1601 TGGTCTCCCA TATTATTGGC GGGCGTTCCG TGGACGGCAG ACCTGCAGGC
1651 GGTATTGCGC CCGATGCGAC GCTACACATA ATGAATACGA ATGATGAAAC
1701 CAAGAACGAA ATGATGGTTG CAGCCATCCG CAATGCATGG GTCAAGCTGG
1751 GCGAACGTGG CGTGCGCATC GTCAATAACA GTTTTGGAAC AACATCGAGG
1801 GCAGGCACTG CCGACCTTTT CCAAATAGCC AATTCGGAGG AGCAGTACCG
1851 CCAAGCGTTG CTCGACTATT CCGGCGGTGA TAAAACAGAC GAGGGTATCC
1901 GCCTGATGCA ACAGAGCGAT TACGGCAACC TGTCCTACCA CATCCGTAAT
1951 AAAAACATGC TTTTCATCTT TTCGACAGGC AATGACGCAC AAGCTCAGCC
```

-continued

```
2001 CAACACATAT GCCCTATTGC CATTTTATGA AAAAGACGCT CAAAAAGGCA

2051 TTATCACAGT CGCAGGCGTA GACCGCAGTG GAGAAAAGTT CAAACGGGAA

2101 ATGTATGGAG AACCGGGTAC AGAACCGCTT GAGTATGGCT CCAACCATTG

2151 CGGAATTACT GCCATGTGGT GCCTGTCGGC ACCCTATGAA GCAAGCGTCC

2201 GTTTCACCCG TACAAACCCG ATTCAAATTG CCGGAACATC CTTTTCCGCA

2251 CCCATCGTAA CCGGCACGGC GGCTCTGCTG CTGCAGAAAT ACCCGTGGAT

2301 GAGCAACGAC AACCTGCGTA CCACGTTGCT GACGACGGCT CAGGACATCG

2351 GTGCAGTCGG CGTGGACAGC AAGTTCGGCT GGGGACTGCT GGATGCGGGT

2401 AAGGCCATGA ACGGACCCGC GTCCTTTCCG TTCGGCGACT TTACCGCCGA

2451 TACGAAAGGT ACATCCGATA TTGCCTACTC CTTCCGTAAC GACATTTCAG

2501 GCACGGGCGG CCTGATCAAA AAAGGCGGCA GCCAACTGCA ACTGCACGGC

2551 AACAACACCT ATACGGGCAA AACCATTATC GAAGGCGGTT CGCTGGTGTT

2601 GTACGGCAAC AACAAATCGG ATATGCGCGT CGAAACCAAA GGTGCGCTGA

2651 TTTATAACGG GGCGGCATCC GGCGGCAGCC TGAACAGCGA CGGCATTGTC

2701 TATCTGGCAG ATACCGACCA ATCCGGCGCA AACGAAACCG TACACATCAA

2751 AGGCAGTCTG CAGCTGGACG GCAAAGGTAC GCTGTACACA CGTTTGGGCA

2801 AACTGCTGAA AGTGGACGGT ACGGCGATTA TCGGCGGCAA GCTGTACATG

2851 TCGGCACGCG GCAAGGGGGC AGGCTATCTC AACAGTACCG ACGACGTGT

2901 TCCCTTCCTG AGTGCCGCCA AAATCGGGCA GGATTATTCT TTCTTCACAA

2951 ACATCGAAAC CGACGGCGGC CTGCTGGCTT CCCTCGACAG CGTCGAAAAA

3001 ACAGCGGGCA GTGAAGGCGA CACGCTGTCC TATTATGTCC GTCGCGGCAA

3051 TGCGGCACGG ACTGCTTCGG CAGCGGCACA TTCCGCGCCC GCCGGTCTGA

3101 ACACGCCGT AGAACAGGGC GGCAGCAATC TGGAAAACCT GATGGTCGAA

3151 CTGGATGCCT CCGAATCATC CGCAACACCC GAGACGGTTG AAACTGCGGC

3201 AGCCGACCGC ACAGATATGC CGGGCATCCG CCCCTACGGC GCAACTTTCC

3251 GCGCAGCGGC AGCCGTACAG CATGCGAATG CCGCCGACGG TGTACGCATC

3301 TTCAACAGTC TCGCCGCTAC CGTCTATGCC GACAGTACCG CCGCCCATGC

3351 CGATATGCAG GGACGCCGCC TGAAAGCCGT ATCGGACGGG TTGGACCACA

3401 ACGGCACGGG TCTGCGCGTC ATCGCGCAAA CCCAACAGGA CGGTGGAACG

3451 TGGGAACAGG GCGGTGTTGA AGGCAAAATG CGCGGCAGTA CCCAAACCGT

3501 CGGCATTGCC GCGAAAACCG GCGAAAATAC GACAGCAGCC GCCACACTGG

3551 GCATGGGACG CAGCACATGG AGCGAAAACA GTGCAAATGC AAAAACCGAC

3601 AGCATTAGTC TGTTTGCAGG CATACGGCAC GATGCGGGCG ATATCGGCTA

3651 TCTCAAAGGC CTGTTCTCCT ACGACGCTA CAAAAACAGC ATCAGCCGCA

3701 GCACCGGTGC GGACGAACAT GCGGAAGGCA GCGTCAACGG CACGCTGATG

3751 CAGCTGGGCG CACTGGGCGG TGTCAACGTT CCGTTTGCCG CAACGGGAGA

3801 TTTGACGGTC GAAGGCGGTC TGCGCTACGA CCTGCTCAAA CAGGATGCAT

3851 TCGCCGAAAA AGGCAGTGCT TTGGGCTGGA GCGGCAACAG CCTCACTGAA
```

```
3901 GGCACGCTGG TCGGACTCGC GGGTCTGAAG CTGTCGCAAC CCTTGAGCGA

3951 TAAAGCCGTC CTGTTTGCAA CGGCGGGCGT GGAACGCGAC CTGAACGGAC

4001 GCGACTACAC GGTAACGGGC GGCTTTACCG GCGCGACTGC AGCAACCGGC

4051 AAGACGGGGG CACGCAATAT GCCGCACACC CGTCTGGTTG CCGGCCTGGG

4101 CGCGGATGTC GAATTCGGCA ACGGCTGGAA CGGCTTGGCA CGTTACAGCT

4151 ACGCCGGTTC CAAACAGTAC GGCAACCACA GCGGACGAGT CGGCGTAGGC

4201 TACCGGTTCT GACTCGAG

1 MKHFPSKVLT TAILATFCSG ALAATNDDDV KKAATVAIAA AYNNGQEING

51 FKAGETIYDI DEDGTITKKD ATAADVEADD FKGLGLKKVV TNLTKTVNEN

101 KQNVDAKVKA AESEIEKLTT KLADTDAALA DTDAALDATT NALNKLGENI

151 TTFAEETKTN IVKIDEKLEA VADTVDKHAE AFNDIADSLD ETNTKADEAV

201 KTANEAKQTA EETKQNVDAK VKAAETAAGK AEAAAGTANT AADKAEAVAA

251 KVTDIKADIA TNKDNIAKKA NSADVYTREE SDSKFVRIDG LNATTEKLDT

301 RLASAEKSIA DHDTRLNGLD KTVSDLRKET RQGLAEQAAL SGLFQPYNVG

351 GSGGGGTSAP DFNAGGTGIG SNSRATTAKS AAVSYAGIKN EMCKDRSMLC

401 AGRDDVAVTD RDAKINAPPP NLHTGDFPNP NDAYKNLINL KPAIEAGYTG

451 RGVEVGIVDT GESVGSISFP ELYGRKEHGY NENYKNYTAY MRKEAPEDGG

501 GKDIEASFDD EAVIETEAKP TDIRHVKEIG HIDLVSHIIG GRSVDGRPAG

551 GIAPDATLHI MNTNDETKNE MMVAAIRNAW VKLGERGVRI VNNSFGTTSR

601 AGTADLFQIA NSEEQYRQAL LDYSGGDKTD EGIRLMQQSD YGNLSYHIRN

651 KNMLFIFSTG NDAQAQPNTY ALLPFYEKDA QKGIITVAGV DRSGEKFKRE

701 MYGEPGTEPL EYGSNHCGIT AMWCLSAPYE ASVRFTRTNP IQIAGTSFSA

751 PIVTGTAALL LQKYPWMSND NLRTTLLTTA QDIGAVGVDS KFGWGLLDAG

801 KAMNGPASFP FGDFTADTKG TSDIAYSFRN DISGTGGLIK KGGSQLQLHG

851 NNTYTGKTII EGGSLVLYGN NKSDMRVETK GALIYNGAAS GGSLNSDGIV

901 YLADTDQSGA NETVHIKGSL QLDGKGTLYT RLGKLLKVDG TAIIGGKLYM

951 SARGKGAGYL NSTGRRVPFL SAAKIGQDYS FFTNIETDGG LLASLDSVEK

1001 TAGSEGDTLS YYVRRGNAAR TASAAAHSAP AGLKHAVEQG GSNLENLMVE

1051 LDASESSATP ETVETAAADR TDMPGIRPYG ATFRAAAAVQ HANAADGVRI

1101 FNSLAATVYA DSTAAHADMQ GRRLKAVSDG LDHNGTGLRV IAQTQQDGGT

1151 WEQGGVEGKM RGSTQTVGIA AKTGENTTAA ATLGMGRSTW SENSANAKTD

1201 SISLFAGIRH DAGDIGYLKG LFSYGRYKNS ISRSTGADEH AEGSVNGTLM

1251 QLGALGGVNV PFAATGDLTV EGGLRYDLLK QDAFAEKGSA LGWSGNSLTE

1301 GTLVGLAGLK LSQPLSDKAV LFATAGVERD LNGRDYTVTG GFTGATAATG

1351 KTGARNMPHT RLVAGLGADV EFGNGWNGLA RYSYAGSKQY GNHSGRVGVG

1401 YRF*
```

It will be understood that the invention has been described by way of example only and modifications may be made whilst remaining within the scope and spirit of the invention. For instance, the use of proteins from other strains is envisaged [e.g. see WO00/66741 for polymorphic sequences for ORF4, ORF40, ORF46, 225, 235, 287, 519, 726, 919 and 953].

Experimental Details

FPLC Protein Purification

The following table summarises the FPLC protein purification that was used:

| Protein | PI | Column | Buffer | pH | Protocol |
|---|---|---|---|---|---|
| 121.1$^{untagged}$ | 6.23 | Mono Q | Tris | 8.0 | A |
| 128.1$^{untagged}$ | 5.04 | Mono Q | Bis-Tris propane | 6.5 | A |
| 406.1L | 7.75 | Mono Q | Diethanolamine | 9.0 | B |
| 576.1L | 5.63 | Mono Q | Tris | 7.5 | B |
| 593$^{untagged}$ | 8.79 | Mono S | Hepes | 7.4 | A |
| 726$^{untagged}$ | 4.95 | Hi-trap S | Bis-Tris | 6.0 | A |
| 919$^{untagged}$ | 10.5(-leader) | Mono S | Bicine | 8.5 | C |
| 919LOrf4 | 10.4(-leader) | Mono S | Tris | 8.0 | B |
| 920L | 6.92(-leader) | Mono Q | Diethanolamine | 8.5 | A |
| 953L | 7.56(-leader) | Mono S | MES | 6.6 | D |
| 982$^{untagged}$ | 4.73 | Mono Q | Bis-Tris propane | 6.5 | A |
| 919-287 | 6.58 | Hi-trap Q | Tris | 8.0 | A |
| 953-287 | 4.92 | Mono Q | Bis-Tris propane | 6.2 | A |

Buffer solutions included 20-120 mM NaCl, 5.0 mg/ml CHAPS and 10% v/v glycerol. The dialysate was centrifuged at 13000 g for 20 min and applied to either a mono Q or mono S FPLC ion-exchange resin. Buffer and ion exchange resins were chosen according to the pI of the protein of interest and the recommendations of the FPLC protocol manual [Pharmacia: *FPLC Ion Exchange and Chromatofocussing; Principles and Methods*. Pharmacia Publication]. Proteins were eluted using a step-wise NaCl gradient. Purification was analysed by SDS-PAGE and protein concentration determined by the Bradford method.

The letter in the 'protocol' column refers to the following:

FPLC-A: Clones 121.1, 128.1, 593, 726, 982, periplasmic protein 920L and hybrid proteins 919-287, 953-287 were purified from the soluble fraction of *E. coli* obtained after disruption of the cells. Single colonies harbouring the plasmid of interest were grown overnight at 37° C. in 20 ml of LB/Amp (100 µg/ml) liquid culture. Bacteria were diluted 1:30 in 1.0 L of fresh medium and grown at either 30° C. or 37° C. until the OD$_{550}$ reached 0.6-08. Expression of recombinant protein was induced with IPTG at a final concentration of 1.0 mM. After incubation for 3 hours, bacteria were harvested by centrifugation at 8000 g for 15 minutes at 4° C. When necessary cells were stored at −20° C. All subsequent procedures were performed on ice or at 4° C. For cytosolic proteins (121.1, 128.1, 593, 726 and 982) and periplasmic protein 920L, bacteria were resuspended in 25 ml of PBS containing complete protease inhibitor (Boehringer-Mannheim). Cells were lysed by sonication using a Branson SONIFIER® 450 (ultrasonic cell disruption/homogenizer). Disrupted cells were centrifuged at 8000 g for 30 min to sediment unbroken cells and inclusion bodies and the supernatant taken to 35% v/v saturation by the addition of 3.9 M $(NH_4)_2SO_4$. The precipitate was sedimented at 8000 g for 30 minutes. The supernatant was taken to 70% v/v saturation by the addition of 3.9 M $(NH_4)_2SO_4$ and the precipitate collected as above. Pellets containing the protein of interest were identified by SDS-PAGE and dialysed against the appropriate ion-exchange buffer (see below) for 6 hours or overnight. The periplasmic fraction from *E. coli* expressing 953L was prepared according to the protocol of Evans et. al. [*Infect. Immun.* (1974) 10:1010-1017] and dialysed against the appropriate ion-exchange buffer. Buffer and ion exchange resin were chosen according to the pI of the protein of interest and the recommendations of the FPLC protocol manual (Pharmacia). Buffer solutions included 20 mM NaCl, and 10% (v/v) glycerol. The dialysate was centrifuged at 13000 g for 20 min and applied to either a mono Q or mono S FPLC ion-exchange resin. Buffer and ion exchange resin were chosen according to the pI of the protein of interest and the recommendations of the FPLC protocol manual (Pharmacia). Proteins were eluted from the ion-exchange resin using either step-wise or continuous NaCl gradients. Purification was analysed by SDS-PAGE and protein concentration determined by Bradford method. Cleavage of the leader peptide of periplasmic proteins was demonstrated by sequencing the $NH_2$-terminus (see below).

FPLC-B: These proteins were purified from the membrane fraction of *E. coli*. Single colonies harbouring the plasmid of interest were grown overnight at 37° C. in 20 ml of LB/Amp (100 µg/ml) liquid culture. Bacteria were diluted 1:30 in 1.0 L of fresh medium. Clones 406.1L and 919LOrf4 were grown at 30° C. and Orf25L and 576.1L at 37° C. until the OD$_{550}$ reached 0.6-0.8. In the case of 919LOrf4, growth at 30° C. was essential since expression of recombinant protein at 37° C. resulted in lysis of the cells. Expression of recombinant protein was induced with IPTG at a final concentration of 1.0 mM. After incubation for 3 hours, bacteria were harvested by centrifugation at 8000 g for 15 minutes at 4° C. When necessary cells were stored at −20° C. All subsequent procedures were performed at 4° C. Bacteria were resuspended in 25 ml of PBS containing complete protease inhibitor (Boehringer-Mannheim) and lysed by osmotic shock with 2-3 passages through a French Press. Unbroken cells were removed by centrifugation at 5000 g for 15 min and membranes precipitated by centrifugation at 100000 g (Beckman Ti50, 38000 rpm) for 45 minutes. A Dounce homogenizer was used to re-suspend the membrane pellet in 7.5 ml of 20 mM Tris-HCl (pH 8.0), 1.0 M NaCl and complete protease inhibitor. The suspension was mixed for 2-4 hours, centrifuged at 100000 g for 45 min and the pellet resuspended in 7.5 ml of 20 mM Tris-HCl (pH 8.0), 1.0M NaCl, 5.0 mg/ml CHAPS, 10% (v/v) glycerol and complete protease inhibitor. The solution was mixed overnight, centrifuged at 100000 g for 45 minutes and the supernatant dialysed for 6 hours against an appropriately selected buffer. In the case of Orf25.L, the pellet obtained after CHAPS extraction was found to contain the recombinant protein. This fraction, without further purification, was used to immunise mice.

FPLC-C: Identical to FPLC-A, but purification was from the soluble fraction obtained after permeabilising *E. coli* with polymyxin B, rather than after cell disruption.

FPLC-D: A single colony harbouring the plasmid of interest was grown overnight at 37° C. in 20 ml of LB/Amp (100 µg/ml) liquid culture. Bacteria were diluted 1:30 in 1.0 L of fresh medium and grown at 30° C. until the OD$_{550}$ reached 0.6-0.8. Expression of recombinant protein was induced with IPTG at a final concentration of 1.0 mM. After incubation for 3 hours, bacteria were harvested by centrifugation at 8000 g for 15 minutes at 4° C. When necessary cells were stored at −20° C. All subsequent procedures were performed on ice or at 4° C. Cells were resuspended in 20 mM Bicine (pH 8.5), 20 mM NaCl, 10% (v/v) glycerol, complete protease inhibitor (Boehringer-Mannheim) and disrupted using a Branson SONIFIER® 450 (ultrasonic cell disruption/homogenizer). The sonicate was centrifuged at 8000 g for 30 min to sediment unbroken cells and inclusion bodies. The recombinant protein was precipitated from solution between 35% v/v and 70% v/v saturation by the addition of 3.9M $(NH_4)_2SO_4$. The precipitate was sedimented at 8000 g for 30 minutes, resuspended in 20 mM Bicine (pH 8.5), 20 mM NaCl, 10% (v/v) glycerol and dialysed against this buffer for 6 hours or overnight. The dialysate was centrifuged at 13000 g for 20 min and applied to the FPLC resin. The protein was eluted from the column using a step-wise NaCl gradients. Purification was analysed by SDS-PAGE and protein concentration determined by Bradford method.

Cloning Strategy and Oligonucleotide Design

Genes coding for antigens of interest were amplified by PCR, using oligonucleotides designed on the basis of the genomic sequence of *N. meningitidis* B MC58. Genomic DNA from strain 2996 was always used as a template in PCR reactions, unless otherwise specified, and the amplified fragments were cloned in the expression vector pET21b+ (Novagen) to express the protein as C-terminal His-tagged product, or in pET-24b+ (Novagen) to express the protein in 'untagged' form (e.g. ΔG 287K).

Where a protein was expressed without a fusion partner and with its own leader peptide (if present), amplification of the open reading frame (ATG to STOP codons) was performed.

Where a protein was expressed in 'untagged' form, the leader peptide was omitted by designing the 5'-end amplification primer downstream from the predicted leader sequence.

The melting temperature of the primers used in PCR depended on the number and type of hybridising nucleotides in the whole primer, and was determined using the formulae:

$T_{m1} = 4(G+C) + 2(A+T)$ (tail excluded)

$T_{m2} = 64.9 + 0.41(\%GC) - 600/N$ (whole primer)

The melting temperatures of the selected oligonucleotides were usually 65-70° C. for the whole oligo and 50-60° C. for the hybridising region alone.

Oligonucleotides were synthesised using a Perkin Elmer 394 DNA/RNA Synthesizer, eluted from the columns in 2.0 ml $NH_4OH$, and deprotected by 5 hours incubation at 56° C. The oligos were precipitated by addition of 0.3M Na-Acetate and 2 volumes ethanol. The samples were centrifuged and the pellets resuspended in water.

| | | Sequences | SEQ ID NO | Restriction site |
|---|---|---|---|---|
| Orf1L | Fwd | CGCGGATCCGCTAGC-AAAACAACCGACAAACGG | 164 | NheI |
| | Rev | CCCGCTCGAG-TTACCAGCGGTAGCCTA | 165 | XhoI |
| Orf1 | Fwd | CTAGCTAGC-GGACACACTTATTTCGGCATC | 166 | NheI |
| | Rev | CCCGCTCGAG- TTACCAGCGGTAGCCTAATTTG | 167 | XhoI |
| Orf1LOmpA | Fwd | | | NdeI-(NheI) |
| | Rev | CCCGCTCGAG- | 168 | XhoI |
| Orf4L | Fwd | CGCGGATCCCATATG-AAAACTTCTTCAAAACC | 169 | NdeI |
| | Rev | CCCGCTCGAG-TTATTTGGCTGCGCCTTC | 170 | XhoI |
| Orf7-1L | Fwd | GCGGCATTAAT-ATGTTGAGAAAATTGTTGAAATGG | 171 | AseI |
| | Rev | GCGGCCTCGAG-TTATTTTTTCAAAATATATTTGC | 172 | XhoI |
| Orf9-1L | Fwd | GCGGCCATATG-TTACCTAACCGTTTCAAAATGT | 173 | NdeI |
| | Rev | GCGGCCTCGAG-TTATTTCCGAGGTTTTCGGG | 174 | XhoI |
| Orf23L | Fwd | CGCGGATCCCATATG-ACACGCTTCAAATATTC | 175 | NdeI |
| | Rev | CCCGCTCGAG-TTATTTAAACCGATAGGTAAA | 176 | XhoI |
| Orf25-1 His | Fwd | CGCGGATCCCATATG-GGCAGGGAAGAACCGC | 177 | NdeI |
| | Rev | GCCCAAGCTT-ATCGATGGAATAGCCGCG | 178 | HindIII |
| Orf29-1 b-His (MC58) | Fwd | CGCGGATCCGCTAGC-AACGGTTTGGATGCCCG | 179 | NheI |
| | Rev | CCCGCTCGAG-TTTGTCTAAGTTCCTGATAT | 180 | XhoI |
| | | CCCGCTCGAG-ATTCCCACCTGCCATC | 181 | |
| Orf29-1 b-L (MC58) | Fwd | CGCGGATCCGCTAGC-ATGAATTTGCCTATTCAAAAAT | 182 | NheI |
| | Rev | CCCGCTCGAG-TTAATTCCCACCTGCCATC | 183 | XhoI |
| Orf29-1 c-His (MC58) | Fwd | CGCGGATCCGCTAGC-ATGAATTTGCCTATTCAAAAAT | 184 | NheI |
| | Rev | CCCGCTCGAG-TTGGACGATGCCCGCGA | 185 | XhoI |
| Orf29-1 c-L (MC58) | Fwd | CGCGGATCCGCTAGC-ATGAATTTGCCTATTCAAAAAT | 186 | NheI |
| | Rev | CCCGCTCGAG-TTATTGGACGATGCCCGC | 187 | XhoI |
| Orf25L | Fwd | CGCGGATCCCATATG-TATCGCAAACTGATTGC | 188 | NdeI |
| | Rev | CCCGCTCGAG-CTAATCGATGGAATAGCC | 189 | XhoI |
| Orf37L | Fwd | CGCGGATCCCATATG-AAACAGACAGTCAAATG | 190 | NdeI |
| | Rev | CCCGCTCGAG-TCAATAACCCGCCTTCAG | 191 | XhoI |
| Orf38L | Fwd | CGCGGATCCCATATG-TTACGTTTGACTGCTTTAGCCGTATGCACC | 192 | NdeI |
| | Rev | CCCGCTCGAG-TTATTTTGCCGCGTTAAAAGCGTCGGCAAC | 193 | XhoI |
| Orf40L | Fwd | CGCGGATCCCATATG-AACAAAATATACCGCAT | 194 | NdeI |
| | Rev | CCCGCTCGAG-TTACCACTGATAACCGAC | 195 | XhoI |
| Orf40.2-His | Fwd | CGCGGATCCCATATG-ACCGATGACGACGATTTAT | 196 | NdeI |
| | Rev | GCCCAAGCTT-CCACTGATAACCGACAGA | 197 | HindIII |
| Orf40.2L | Fwd | CGCGGATCCCATATG-AACAAAATATACCGCAT | 198 | NdeI |
| | Rev | GCCCAAGCTT-TTACCACTGATAACCGAC | 199 | HindIII |
| Orf46-2L | Fwd | GGGAATTCCATATG-GGCATTTCCCGCAAAATATC | 200 | NdeI |
| | Rev | CCCGCTCGAG-TTATTTACTCCTATAACGAGGTCTCTTAAC | 201 | XhoI |
| Orf46-2 | Fwd | GGGAATTCCATATG-TCAGATTTGGCAAACGATTCTT | 202 | NdeI |
| | Rev | CCCGCTCGAG-TTATTTACTCCTATAACGAGGTCTCTTAAC | 203 | XhoI |

-continued

| | | Sequences | SEQ ID NO | Restriction site |
|---|---|---|---|---|
| Orf46.1L | Fwd | GGGAATTCCATATG-GGCATTTCCCGCAAAATATC | 204 | NdeI |
| | Rev | CCCGCTCGAG-TTACGTATCATATTTCACGTGC | 205 | XhoI |
| orf46. (His-GST) | Fwd | GGGAATTCCATATGCACGTGAAATATGATACGAAG | 206 | BamHI-NdeI |
| | Rev | CCCGCTCGAGTTTACTCCTATAACGAGGTCTCTTAAC | 207 | XhoI |
| orf46.1-His | Fwd | GGGAATTCCATATGTCAGATTTGGCAAACGATTCTT | 208 | NdeI |
| | Rev | CCCGCTCGAGCGTATCATATTTCACGTGC | 209 | XhoI |
| orf46.2-His | Fwd | GGGAATTCCATATGTCAGATTTGGCAAACGATTCTT | 210 | NdeI |
| | Rev | CCCGCTCGAGTTTACTCCTATAACGAGGTCTCTTAAC | 211 | XhoI |
| Orf65-1-(His/GST) (MC58) | Fwd | CGCGGATCCCATATG-CAAAATGCGTTCAAATCCC | 212 | BamHI-NdeI |
| | Rev | CGCGGATCCCATATG-AACAAAATATACCGCAT | 213 | |
| | | CCCGCTCGAG-TTTGCTTTCGATAGAACGG | 214 | |
| Orf72-1L | Fwd | GCGGCCATATG-GTCATAAAATATACAAATTTGAA | 215 | NdeI |
| | Rev | GCGGCCTCGAG-TTAGCCTGAGACCTTTGCAAATT | 216 | XhoI |
| Orf76-1L | Fwd | GCGGCCATATG-AAACAGAAAAAAACCGCTG | 217 | NdeI |
| | Rev | GCGGCCTCGAG-TTACGGTTTGACACCGTTTTC | 218 | XhoI |
| Orf83.1L | Fwd | CGCGGATCCCATATG-AAAACCCTGCTCCTC | 219 | NdeI |
| | Rev | CCCGCTCGAG-TTATCCTCCTTTGCGGC | 220 | XhoI |
| Orf85-2L | Fwd | GCGGCCATATG-GCAAAAATGATGAAATGGG | 221 | NdeI |
| | Rev | GCGGCCTCGAG-TTATCGGCGCGGCGGGCC | 222 | XhoI |
| Orf91L (MC58) | Fwd | GCGGCCATATGAAAAAATCCTCCCTCATCA | 223 | NdeI |
| | Rev | GCGGCCTCGAGTTATTTGCCGCCGTTTTTGGC | 224 | XhoI |
| Orf91-His(MC58) | Fwd | GCGGCCATATGGCCCCTGCCGACGCGGTAAG | 225 | NdeI |
| | Rev | GCGGCCTCGAGTTTGCCGCCGTTTTTGGCTTTC | 226 | XhoI |
| Orf97-1L | Fwd | GCGGCCATATG-AAACACATACTCCCCCTGA | 227 | NdeI |
| | Rev | GCGGCCTCGAG-TTATTCGCCTACGGTTTTTTG | 228 | XhoI |
| Orf119L (MC58) | Fwd | GCGGCCATATGATTTACATCGTACTGTTTC | 229 | NdeI |
| | Rev | GCGGCCTCGAGTTAGGAGAACAGGCGCAATGC | 230 | XhoI |
| Orf119-His(MC58) | Fwd | GCGGCCATATGTACAACATGTATCAGGAAAAC | 231 | NdeI |
| | Rev | GCGGCCTCGAGGGAGAACAGGCGCAATGCGG | 232 | XhoI |
| Orf137.1 (His-GST) (MC58) | Fwd | CGCGGATCCGCTAGCTGCGGCACGGCGGG | 233 | BamHI-NheI |
| | Rev | CCCGCTCGAGATAACGGTATGCCGCCAG | 234 | XhoI |
| Orf143-1L | Fwd | CGCGGATCCCATATG-GAATCAACACTTTCAC | 235 | NdeI |
| | Rev | CCCGCTCGAG-TTACACGCGGTTGCTGT | 236 | XhoI |
| 008 | Fwd | CGCGGATCCCATATG-AACAACAGACATTTTG | 237 | NdeI |
| | Rev | CCCGCTCGAG-TTACCTGTCCGGTAAAAG | 238 | XhoI |
| 050-1(48) | Fwd | CGCGGATCCGCTAGC-ACCGTCATCAAACAGGAA | 239 | NheI |
| | Rev | CCCGCTCGAG-TCAAGATTCGACGGGGA | 240 | XhoI |
| 105 | Fwd | CGCGGATCCCATATG-TCCGCAAACGAATACG | 241 | NdeI |
| | Rev | CCCGCTCGAG-TCAGTGTTCTGCCAGTTT | 242 | XhoI |
| 111L | Fwd | CGCGGATCCCATATG-CCGTCTGAAACACG | 243 | NdeI |
| | Rev | CCCGCTCGAG-TTAGCGGAGCAGTTTTTC | 244 | XhoI |
| 117-1 | Fwd | CGCGGATCCCATATG-ACCGCCATCAGCC | 245 | NdeI |
| | Rev | CCCGCTCGAG-TTAAAGCGGGTAACGC | 246 | XhoI |
| 121-1 | Fwd | GCGGCCATATG-GAAACACAGCTTTACATCGG | 247 | NdeI |
| | Rev | GCGGCCTCGAG-TCAATAATAATATCCCGCG | 248 | XhoI |
| 122-1 | Fwd | GCGGCCATATG-ATTAAAATCCGCAATATCC | 249 | NdeI |
| | Rev | GCGGCCTCGAG-TTAAATCTTGGTAGATTGGATTGG | 250 | XhoI |
| 128-1 | Fwd | GCGGCCATATG-ACTGACAACGCACTGCTCC | 251 | NdeI |
| | Rev | GCGGCCTCGAG-TCAGACCGCGTTGTCGAAAC | 252 | XhoI |
| 148 | Fwd | CGCGGATCCCATATG-GCGTTAAAAACATCAAA | 253 | NdeI |
| | Rev | CCCGCTCGAG-TCAGCCCTTCATACAGC | 254 | XhoI |
| 149.1L (MC58) | Fwd | GCGGCATTAATGGCACAAACTACACTCAAACC | 255 | AseI |
| | Rev | GCGGCCTCGAGTTAAAACTTCACGTTCACGCCG | 256 | XhoI |
| 149.1-His(MC58) | Fwd | GCGGCATTAATGCATGAAACTGAGCAATCGGTGG | 257 | AseI |
| | Rev | GCGGCCTCGAGAAACTTCACGTTCACGCCGCCGGTAAA | 258 | XhoI |
| 205 (His-GST) (MC58) | Fwd | CGCGGATCCCATATGGGCAAATCCGAAAATACG | 259 | BamHI-NdeI |
| | Rev | CCCGCTCGAGATAATGGCGGCGGCGG | 260 | XhoI |
| 206L | Fwd | CGCGGATCCCATATG-TTTCCCCCCGACAA | 261 | NdeI |
| | Rev | CCCGCTCGAG-TCATTCTGTAAAAAAAGTATG | 262 | XhoI |
| 214 (His-GST) (MC58) | Fwd | CGCGGATCCCATATGCTTCAAAGCGACAGCAG | 263 | BamHI-NdeI |
| | Rev | CCCGCTCGAGTTCGGATTTTTGCGTACTC | 264 | XhoI |
| 216 | Fwd | CGCGGATCCCATATG-GCAATGGCAGAAAACG | 265 | NdeI |
| | Rev | CCCGCTCGAG-CTATACAATCCGTGCCG | 266 | XhoI |
| 225-1L | Fwd | CGCGGATCCCATATG-GATTCTTTTTCAAACC | 267 | NdeI |
| | Rev | CCCGCTCGAG-TCAGTTCAGAAAGCGGG | 268 | XhoI |
| 235L | Fwd | CGCGGATCCCATATG-AAACCTTTGATTTTAGG | 269 | NdeI |
| | Rev | CCCGCTCGAG-TTATTTGGGCTGCTCTTC | 270 | XhoI |
| 243 | Fwd | CGCGGATCCCATATG-GTAATCGTCTGGTTG | 271 | NdeI |
| | Rev | CCCGCTCGAG-CTACGACTTGGTTACCG | 272 | XhoI |
| 247-1L | Fwd | GCGGCCATATG-AGACGTAAAATGCTAAAGCTAC | 273 | NdeI |
| | Rev | GCGGCCTCGAG-TCAAAGTGTTCTGTTTGCGC | 274 | XhoI |
| 264-His | Fwd | GCGGCCATATG-TTGACTTTACCCGAAAAA | 275 | NdeI |
| | Rev | GCGGCCTCGAG-GCCGGCGGTCAATACCGCCCGAA | 276 | XhoI |
| 270 (His-GST) (MC58) | Fwd | CGCGGATCCCATATGGCGCAATGCGATTTGAC | 277 | BamHI-NdeI |
| | Rev | CCCGCTCGAGTTCGGCGGTAAATGCCG | 278 | XhoI |

-continued

| | | Sequences | SEQ ID NO | Restriction site |
|---|---|---|---|---|
| 274L | Fwd | GCGGCCATATG-GCGGGGCCGATTTTTGT | 279 | NdeI |
| | Rev | GCGGCCTCGAG-TTATTTGCTTTCAGTATTATTG | 280 | XhoI |
| 283L | Fwd | GCGGCCATATG-AACTTTGCTTTATCCGTCA | 281 | NdeI |
| | Rev | GCGGCCTCGAG-TTAACGGCAGTATTTGTTTAC | 282 | XhoI |
| 285-His | Fwd | CGCGGATCCCATATGGGTTTGCGCTTCGGGC | 283 | BamHI |
| | Rev | GCCCAAGCTTTTTTCCTTTGCCGTTTCCG | 284 | HindIII |
| 286-His (MC58) | Fwd | CGCGGATCCCATATG-GCCGACCTTTCCGAAAA | 285 | NdeI |
| | Rev | CCCGCTCGAG-GAAGCGCGTTCCCAAGC | 286 | XhoI |
| 286L (MC58) | Fwd | CGCGGATCCCATATG-CACGACACCCGTAC | 287 | NdeI |
| | Rev | CCCGCTCGAG-TTAGAAGCGCGTTCCCAA | 288 | XhoI |
| 287L | Fwd | CTAGCTAGC-TTTAAACGCAGCGTAATCGCAATGG | 289 | NheI |
| | Rev | CCCGCTCGAG-TCAATCCTGCTCTTTTTTGCC | 290 | XhoI |
| 287 | Fwd | CTAGCTAGC-GGGGGCGGCGGTGGCG | 291 | NheI |
| | Rev | CCCGCTCGAG-TCAATCCTGCTCTTTTTTGCC | 292 | XhoI |
| 287LOrf4 | Fwd | CTAGCTAGCGCTCATCCTCGCCGCC-TGCGGGGCGGCGGT | 293 | NheI |
| | Rev | CCCGCTCGAG-TCAATCCTGCTCTTTTTTGCC | 294 | XhoI |
| 287-fu | Fwd | CGGGGATCC-GGGGGCGGCGGTGGCG | 295 | BamHI |
| | Rev | CCCGCTCGAG-TCAATCCTGCTCTTTTTTGCC | 296 | XhoI |
| 287-His | Fwd | CTAGCTAGC-GGGGGCGGCGGTGGCG | 297 | NheI |
| | Rev | CCCGCTCGAG-ATCCTGCTCTTTTTTGCC * | 298 | XhoI |
| 287-His(2996) | Fwd | CTAGCTAGC-TGCGGGGGCGGCGGTGGCG | 299 | NheI |
| | Rev | CCCGCTCGAG-ATCCTGCTCTTTTTTGCC | 300 | XhoI |
| Δ1 287-His | Fwd | CGCGGATCCGCTAGC-CCCGATGTTAAATCGGG § | 301 | NheI |
| Δ2 287-His | Fwd | CGCGGATCCGCTAGC-CAAGATATGGCGGCAGT § | 302 | NheI |
| Δ3 287-His | Fwd | CGCGGATCCGCTAGC-GCCGAATCCGCAAATCA § | 303 | NheI |
| Δ4 287-His | Fwd | CGCGCTAGC-GGAAGGGTTGATTTGGCTAATGG § | 304 | NheI |
| Δ4 287MC58-His | Fwd | CGCGCTAGC-GGAAGGGTTGATTTGGCTAATGG § | 305 | NheI |
| 287a-His | Fwd | CGCCATATG-TTTAAACGCAGCGTAATCGC | 306 | NdeI |
| | Rev | CCCGCTCGAG-AAAATTGCTACCGCCATTCGCAGG | 307 | XhoI |
| 287b-His | Fwd | CGCCATATG-GGAAGGGTTGATTTGGCTAATGG | 308 | NdeI |
| 287b-2996-His | Rev | CCCGCTCGAG-CTTGTCTTTATAAATGATGACATATTTG | 309 | XhoI |
| 287b-MC58-His | Rev | CCCGCTCGAG-TTTATAAAAGATAATATATTGATTGATTCC | 310 | XhoI |
| 287c-2996-His | Fwd | CGCGCTAGC-ATGCCGCTGATTCCCGTCAATC § | 311 | NheI |
| '287untagged' (2996) | Fwd | CTAGCTAGC-GGGGGCGGCGGTGGCG | 312 | NheI |
| | Rev | CCCGCTCGAG-TCAATCCTGCTCTTTTTTGCC | 313 | XhoI |
| ΔG287-His * | Fwd | CGCGGATCCGCTAGC-CCCGATGTTAAATCGGC | 314 | NheI |
| | Rev | CCCGCTCGAG-ATCCTGCTCTTTTTTGCC | 315 | XhoI |
| ΔG287K(2996) | Fwd | CGCGGATCCGCTAGC-CCCGATGTTAAATCGGC | 316 | NheI |
| | Rev | CCCGCTCGAG-TCAATCCTGCTCTTTTTTGCC | 317 | XhoI |
| ΔG 287-L | Fwd | CGCGGATCCGCTAGC-TTTGAACGCAGTGTGATTGCAATGGCTTGTATTTTGCC CTTTCAGCCTGT TCGCCCGATGTTAAATCGGCG | 318 | NheI |
| | Rev | CCCGCTCGAG-TCAATCCTGCTCTTTTTTGCC | 319 | XhoI |
| ΔG 287-Orf4L | Fwd | CGCGGATCCGCTAGC-AAAACCTTCTTCAAAACCCTTTCCGCCGCCGCACTCGCG CTCATCCTCGCCGCCTGC TCGCCCGATGTTAAATCG | 320 | NheI |
| | Rev | CCCGCTCGAG-TCAATCCTGCTCTTTTTTGCC | 321 | XhoI |
| 292L | Fwd | CGCGGATCCCATATG-AAAACCAAGTTAATCAAA | 322 | NdeI |
| | Rev | CCCGCTCGAG-TTATTGATTTTTGCGGATGA | 323 | XhoI |
| 308-1 | Fwd | CGCGGATCCCATATG-TTAAATCGGGTATTTTATC | 324 | NdeI |
| | Rev | CCCGCTCGAG-TTAATCCGCCATTCCCTG | 325 | XhoI |
| 401L | Fwd | CGGCCATATG-AAATTACAACAATTGGCTG | 326 | NdeI |
| | Rev | GCGGCCTCGAG-TTACCTTACGTTTTTCAAAG | 327 | XhoI |
| 406L | Fwd | CGCGGATCCCATATG-CAAGCACGGCTGCT | 328 | NdeI |
| | Rev | CCCGCTCGAG-TCAAGGTTGTCCTTGTCTA | 329 | XhoI |
| 502-1L | Fwd | CGCGGATCCCATATG-ATGAAACCGCACAAC | 330 | NdeI |
| | Rev | CCCGCTCGAG-TCAGTTGCTCAACACGTC | 331 | XhoI |
| 502-A (His-GST) | Fwd | CGCGGATCCCATATGGTAGACGCGCTTAAGCA | 332 | BamHI-NdeI |
| | Rev | CCCGCTCGAGAGCTGCATGGCGGCG | 333 | XhoI |
| 503-1L | Fwd | CGCGGATCCCATATG-GCACGGTCGTTATAC | 334 | NdeI |
| | Rev | CCCGCTCGAG-CTACCGCGCATTCCTG | 335 | XhoI |
| 519-1L | Fwd | GCGGCCATATG-GAATTTTTCATTATCTTGTT | 336 | NdeI |
| | Rev | GCGGCCTCGAG-TTATTTGGCGGTTTTGCTGC | 337 | XhoI |
| 525-1L | Fwd | GCGGCCATATG-AAGTATGTCCGGTTATTTTTC | 338 | NdeI |
| | Rev | GCGGCCTCGAG-TTATCGGCTTGTGCAACGG | 339 | XhoI |
| 529-(His/GST) (MC58) | Fwd | CGCGGATCCGCTAGC-TCCGGCAGCAAAACCGA | 340 | BamHI-NheI |
| | Rev | GCCCAAGCTT-ACGCAGTTCGGAATGGAG | 341 | HindIII |
| 552L | Fwd | GCCGCCATATGTTGAATATTAAACTGAAAACCTTG | 342 | |
| | Rev | GCGGCCTCGAGTTATTCTGATGCCTTTTCCC | 343 | XhoI |
| 556L | Fwd | GCCGCCATATGGACAATAAGACCAAACTG | 344 | NdeI |
| | Rev | GCCGCCTCGAGTTAACGGTGCGGACGTTTC | 345 | XhoI |
| 557L | Fwd | CGCGGATCCCATATG-AACAAACTGTTTCTTAC | 346 | NdeI |
| | Rev | CCCGCTCGAG-TCATTCCGCCTTCAGAAA | 347 | XhoI |

-continued

| | | Sequences | SEQ ID NO | Restriction site |
|---|---|---|---|---|
| 564ab-(His/GST) (MC58) | Fwd | CGCGGATCCCATATG-CAAGGTATCGTTGCCGACAAATCCGCACCT | 348 | BamHI-NdeI |
| | Rev | CCCGCTCGAG-AGCTAATTGTGCTTGGTTTGCAGATAGGAGTT | 349 | XhoI |
| 564abL (MC58) | Fwd | CGCGGATCCCATATG-AACCGCACCCTGTACAAAGTTGTATTTAACAAACATC | 350 | NdeI |
| | Rev | CCCGCTCGAG-TTAAGCTAATTGTGCTTGGTTTGCAGATAGGAGTT | 351 | XhoI |
| 564b-(His/GST) (MC58) | Fwd | CGCGGATCCCATATG-ACGGGAGAAAATCATGCGGTTTCACTTCATG | 352 | BamHI-NdeI |
| | Rev | CCCGCTCGAG-AGCTAATTGTGCTTGGTTTGCAGATAGGAGTT | 353 | XhoI |
| 564c-(His/GST) (MC58) | Fwd | CGCGGATCCCATATG-GTTTCAGACGGCCTATACAACCAACATGGTGAAATT | 354 | BamHI-NdeI |
| | Rev | CCCGCTCGAG-GCGGTAACTGCCGCTTGCACTGAATCCGTAA | 355 | XhoI |
| 564bc-(His/GST) (MC58) | Fwd | CGCGGATCCCATATG-ACGGGAGAAAATCATGCGGTTTCACTTCATG | 356 | BamHI-NdeI |
| | Rev | CCCGCTCGAG-GCGGTAACTGCCGCTTGCACTGAATCCGTAA | 357 | XhoI |
| 564d-(His/GST) (MC58) | Fwd | CGCGGATCCCATATG-CAAAGCAAAGTCAAAGCAGACCATGCCTCCGTAA | 358 | BamHI-NdeI |
| | Rev | CCCGCTCGAG-TCTTTTCCTTTCAATTATAACTTTAGTAGGTTCAATTTTGGTCCCC | 359 | XhoI |
| 564cd-(His/GST) (MC58) | Fwd | CGCGGATCCCATATG-GTTTCAGACGGCCTATACAACCAACATGGTGAAATT | 360 | BamHI-NdeI |
| | Rev | CCCGCTCGAG-TCTTTTCCTTTCAATTATAACTTTAGTAGGTTCAATTTTGGTCCCC | 361 | XhoI |
| 570L | Fwd | GCGGCCATATG-ACCCGTTTGACCCGCG | 362 | NdeI |
| | Rev | GCGGCCTCGAG-TCAGCGGGCGTTCATTTCTT | 363 | XhoI |
| 576-1L | Fwd | CGCGGATCCCATATG-AACACCATTTTCAAAATC | 364 | NdeI |
| | Rev | CCCGCTCGAG-TTAATTTACTTTTTTGATGTCG | 365 | XhoI |
| 580L | Fwd | GCGGCCATATG-GATTCGCCCAAGGTCGG | 366 | NdeI |
| | Rev | GCGGCCTCGAG-CTACACTTCCCCGAAGTGG | 367 | XhoI |
| 583L | Fwd | CGCGGATCCCATATG-ATAGTTGACCAAAGCC | 368 | NdeI |
| | Rev | CCCGCTCGAG-TTATTTTTCCGATTTTCGG | 369 | XhoI |
| 593 | Fwd | GCGGCCATATG-CTTGAACTGAACGGACT | 370 | NdeI |
| | Rev | GCGGCCTCGAG-TCAGCGGAAGCGGACGATT | 371 | XhoI |
| 650 (His-GST) (MC58) | Fwd | CGCGGATCCCATATGTCCAAACTCAAAACCATCG | 372 | BamHI-NdeI |
| | Rev | CCCGCTCGAGGCTTCCAATCAGTTTGACC | 373 | XhoI |
| 652 | Fwd | GCGGCCATATG-AGCGCAATCGTTGATATTTC | 374 | NdeI |
| | Rev | GCGGCCTCGAG-TTATTTGCCCAGTTGGTAGAATG | 375 | XhoI |
| 664L | Fwd | GCGGCCATATG-GTGATACATCCGCACTACTTC | 376 | NdeI |
| | Rev | GCGGCCTCGAG-TCAAAATCGAGTTTTACACCA | 377 | XhoI |
| 726 | Fwd | GCGGCCATATG-ACCATCTATTTCAAAAACGG | 378 | NdeI |
| | Rev | GCGGCCTCGAG-TCAGCCGATGTTTAGCGTCCATT | 379 | XhoI |
| 741-His(MC58) | Fwd | CGCGGATCCCATATG-AGCAGCGGAGGGGGTG | 380 | NdeI |
| | Rev | CCCGCTCGAG-TTGCTTGGCGGCAAGGC | 381 | XhoI |
| ΔG741-His(MC58) | Fwd | CGCGGATCCCATATG-GTCGCGCCGACATCG | 382 | NdeI |
| | Rev | CCCGCTCGAG-TTGCTTGGCGGCAAGGC | 383 | XhoI |
| 686-2-(His/GST) (MC58) | Fwd | CGCGGATCCCATATG-GGCGGTTCGGAAGGCG | 384 | BamHI-NdeI |
| | Rev | CCCGCTCGAG-TTGAACACTGATGTCTTTTCCGA | 385 | XhoI |
| 719-(His/GST) (MC58) | Fwd | CGCGGATCCGCTAGC-AAACTGTCGTTGGTGTTAAC | 386 | BamHI-NheI |
| | Rev | CCCGCTCGAG-TTGACCCGCTCCACGG | 387 | XhoI |
| 730-His (MC58) | Fwd | GCCGCCATATGGCGGACTTGGCGCAAGACCC | 388 | NdeI |
| | Rev | GCGGCCTCGAGATCTCCTAAACCTGTTTTAACAATGCCG | 389 | XhoI |
| 730A-His (MC58) | Fwd | GCCGCCATATGGCGGACTTGGCGCAAGACCC | 390 | NdeI |
| | Rev | GCGGCCTCGAGCTCCATGCTGTTGCCCCAGC | 391 | XhoI |
| 730B-His (MC58) | Fwd | GCCGCCATATGGCGGACTTGGCGCAAGACCC | 392 | NdeI |
| | Rev | GCGGCCTCGAGAAAATCCCCGCTAACCGCAG | 393 | XhoI |
| 741-His (MC58) | Fwd | CGCGGATCCCATATG-AGCAGCGGAGGGGGTG | 394 | NdeI |
| | Rev | CCCGCTCGAG-TTGCTTGGCGGCAAGGC | 395 | XhoI |
| ΔG741-His (MC58) | Fwd | CGCGGATCCCATATG-GTCGCGCCGACATCG | 396 | NdeI |
| | Rev | CCCGCTCGAG-TTGCTTGGCGGCAAGGC | 397 | XhoI |
| 743 (His-GST) | Fwd | CGCGGATCCCATATGGACGGTGTTGTGCCTGTT | 398 | BamHI-NdeI |
| | Rev | CCCGCTCGAGCTTACGGATCAAATTGACG | 399 | XhoI |
| 757 (His-GST) (MC58) | Fwd | CGCGGATCCCATATGGGCAGCCAATCTGAAGAA | 400 | BamHI-NdeI |
| | Rev | CCCGCTCGAGCTCAGCTTTTGCCGTCAA | 401 | XhoI |
| 759-His/GST (MC58) | Fwd | CGCGGATCCGCTAGC-TACTCATCCATTGTCCGC | 402 | BamHI-NheI |
| | Rev | CCCGCTCGAG-CCAGTTGTAGCCTATTTTG | 403 | XhoI |
| 759L (MC58) | Fwd | CGCGGATCCGCTAGC-ATGCGCTTCACACACAC | 404 | NheI |
| | Rev | CCCGCTCGAG-TTACCAGTTGTAGCCTATTT | 405 | XhoI |
| 760-His | Fwd | GCCGCCATATGGCACAAACGGAAGGTTTGGAA | 406 | NdeI |
| | Rev | GCCGCCTCGAGAAAACTGTAACGCAGGTTTGCCGTC | 407 | XhoI |

| | | Sequences | SEQ ID NO | Restriction site |
|---|---|---|---|---|
| 769-His (MC58) | Fwd | GCGGCCATATGGAAGAAACACCGCGCGAACCG | 408 | NdeI |
| | Rev | GCGGCCTCGAGGAACGTTTTATTAAACTCGAC | 409 | XhoI |
| 907L | Fwd | GCGGC<u>CATATG</u>-AGAAAACCGACCGATACCCTA | 410 | NdeI |
| | Rev | GCGGC<u>CTCGAG</u>-TCAACGCCACTGCCAGCGGTTG | 411 | XhoI |
| 911L | Fwd | CGCGGATCC<u>CATATG</u>-AAGAAGAACATATTGGAATTTTG GGTCGGACTG | 412 | NdeI |
| | Rev | CCCG<u>CTCGAG</u>-TTATTCGGCGGCTTTTTCCGCATTGCCG | 413 | XhoI |
| 911LOmpA | Fwd | GGGAATTC<u>CATATG</u>AAAAAGACAGCTATCGCGATTGCA GTGGCACTGGCTGGTTTCGCTACCGTAGCGCAGGCC<u>GC TAGC</u>-GCTTTCCGCGTGGCCGGCGGTGC | 414 | NdeI-(NheI) |
| | Rev | CCCG<u>CTCGAG</u>-TTATTCGGCGCTTTTTCCGCATTGCCG | 415 | XhoI |
| 911LPeIB | Fwd | CATG<u>CCATGG</u>-CTTTCCGCGTGGCCGGCGGTGC | 416 | NcoI |
| | Rev | CCCG<u>CTCGAG</u>-TTATTCGGCGGCTTTTTCCGCATTGCCG | 417 | XhoI |
| 913-His/GST (MC58) | Fwd | CGCG<u>GATCCCATATG</u>-TTTGCCGAAACCCGCC | 418 | BamHI-NdeI |
| | Rev | CCCG<u>CTCGAG</u>-AGGTTGTGTTCCAGGTTG | 419 | XhoI |
| 913L (MC58) | Fwd | CGCGGATCC<u>CATATG</u>-AAAAAAACCGCCTATG | 420 | NdeI |
| | Rev | CCCG<u>CTCGAG</u>-TTAAGGTTGTGTTCCAGG | 421 | XhoI |
| 919L | Fwd | CGCGGATCC<u>CATATG</u>-AAAAAATACCTATTCCGC | 422 | NdeI |
| | Rev | CCCG<u>CTCGAG</u>-TTACGGGCGGTATTCGG | 423 | XhoI |
| 919 | Fwd | CGCGGATCC<u>CATATG</u>-CAAAGCAAGAGCATCCAAA | 424 | NdeI |
| | Rev | CCCG<u>CTCGAG</u>-TTACGGGCGGTATTCGG | 425 | XhoI |
| 919L Orf4 | Fwd | GGGAATTC<u>CATATG</u>AAAACCTTCTTCAAAACCCTTTCCG CCGCCG<u>CGCTAGC</u>GCTCATCCTCGCCGCC-TGCCAAAGCAAGAGCATC | 426 | NdeI-(NheI) |
| | Rev | CCCG<u>CTCGAG</u>-TTACGGGCGGTATTCGGGCTTCATACCG | 427 | XhoI |
| (919)-287fusion | Fwd | CGCGGATCC<u>GTCGAC</u>-TGTGGGGGCGGCGGTGGC | 428 | SalI |
| | Rev | CCCG<u>CTCGAG</u>-TCAATCCTGCTCTTTTTTGCC | 429 | XhoI |
| 920-1L | Fwd | GCGGC<u>CATATG</u>-AAGAAAACATTGACACTGC | 430 | NdeI |
| | Rev | GCGGC<u>CTCGAG</u>-TTAATGGTGCGAATGACCGAT | 431 | XhoI |
| 925-His/GST (MC58)<sup>GATE</sup> | Fwd | ggggacaagtttgtacaaaaaagcaggctTGCGGCAAG GATGCCGG | 432 | attB1 |
| | Rev | ggggaccactttgtacaagaaagctgggtCTAAAGCAA CAATGCCGG | 433 | attB2 |
| 926L | Fwd | CGCGGATCC<u>CATATG</u>-AAACACACCGTATCC | 434 | NdeI |
| | Rev | CCCG<u>CTCGAG</u>-TTATCTCGTGCGCGCC | 435 | XhoI |
| 927-2-(His/GST) (MC58) | Fwd | CGCG<u>GATCCCATATG</u>-AGCCCCGCGCCGATT | 436 | BamHI-NdeI |
| | Rev | CCCG<u>CTCGAG</u>-TTTTTGTGCGGTCAGGCG | 437 | XhoI |
| 932-His/GST (MC58)<sup>GATE</sup> | Fwd | ggggacaagtttgtacaaaaaagcaggctTGTTCGTTT GGGGGATTTAAACCAAACCAAATC | 438 | attB1 |
| 935 (His-GST) (MC58) | For | CGCG<u>GATCCCATATG</u>GCGGATGCGCCCGCG | 439 | BamHI-NdeI |
| | Rev | CCCG<u>CTCGAG</u>AAACCGCCAATCCGCC | 440 | XhoI |
| 936-1L | Rev | ggggaccactttgtacaagaaagctgggtTCATTTTGT TTTTCCTTCTTCTCGAGGCCATT | 441 | attB2 |
| | Fwd | CGCGGATCC<u>CATATG</u>-AAACCCAAACCGCAC | 442 | NdeI |
| | Rev | CCCG<u>CTCGAG</u>-TCAGCGTTGGACGTAGT | 443 | XhoI |
| 953L | Fwd | GGGAATTC<u>CATATG</u>-AAAAAAATCATCTTCGCCG | 444 | NdeI |
| | Rev | CCCG<u>CTCGAG</u>-TTATTGTTTGGCTGCCTCGAT | 445 | XhoI |
| 953-fu | Fwd | GGGAATTC<u>CATATG</u>-GCCACCTACAAAGTGGACG | 446 | NdeI |
| | Rev | CGGG<u>GATCC</u>-TTGTTTGGCTGCCTCGATTTG | 447 | BamHI |
| 954 (His-GST) (MC58) | Fwd | CGCG<u>GATCCCATATG</u>CAAGAACAATCGCAGAAAG | 448 | BamHI-NdeI |
| | Rev | CCCG<u>CTCGAG</u>TTTTTTCGGCAAATTGCTT | | |
| 958-His/GST (MC58)<sup>GATE</sup> | Fwd | ggggacaagtttgtacaaaaaagcaggctGCCGATGC CGTTGCGG | 450 | attB1 |
| | Rev | ggggaccactttgtacaagaaagctgggtTCAGGGTC GTTTGTTGCG | 451 | attB2 |
| 961L | Fwd | CGCGGATCC<u>CATATG</u>-AAACACTTTCCATCC | 452 | NdeI |
| | Rev | CCCG<u>CTCGAG</u>-TTACCACTCGTAATTGAC | 453 | XhoI |
| 961 | Fwd | CGCGGATCC<u>CATATG</u>-GCCACAAGCGACGAC | 454 | NdeI |
| | Rev | CCCG<u>CTCGAG</u>-TTACCACTCGTAATTGAC | 455 | XhoI |
| 961 c (His/GST) | Fwd | CGCG<u>GATCCCATATG</u>-GCCACAAACGACG | 456 | BamHI-NdeI |
| | Rev | CCCG<u>CTCGAG</u>-ACCCACGTTGTAAGGTTG | 457 | XhoI |
| 961 c-(His/GST) (MC58) | Fwd | CGCG<u>GATCCCATATG</u>-GCCACAAGCGACGACGA | 458 | BamHI-NdeI |
| | Rev | CCCG<u>CTCGAG</u>-ACCCACGTTGTAAGGTTG | 459 | XhoI |
| 961 c-L | Fwd | CGCGGATCC<u>CATATG</u>-ATGAAACACTTTCCATCC | 460 | NdeI |
| | Rev | CCCG<u>CTCGAG</u>-TTAACCCACGTTGTAAGGT | 461 | XhoI |
| 961 c-L (MC58) | Fwd | CGCGGATCC<u>CATATG</u>-ATGAAACACTTTCCATCC | 462 | NdeI |
| | Rev | CCCG<u>CTCGAG</u>-TTACCCACGTTGTAAGGT | 463 | XhoI |
| 961 d (His/GST) | Fwd | CGCG<u>GATCCCATATG</u>-GCCACAAACGACG | 464 | BamHI-NdeI |
| | Rev | CCCG<u>CTCGAG</u>-GTCTGACACTGTTTTATCC | 465 | XhoI |
| 961 Δ1-L | Fwd | CGCGGATCC<u>CATATG</u>-ATGAAACACTTTCCATCC | 466 | NdeI |
| | Rev | CCCG<u>CTCGAG</u>-TTATGCTTTGGCGGCAAAG | 467 | XhoI |
| fu 961-... | Fwd | CGCGGATCC<u>CATATG</u>-GCCACAAACGACGAC | 468 | NdeI |
| | Rev | CGCG<u>GGATCC</u>-CCACTCGTAATTGACGCC | 469 | BamHI |
| fu 961-... (MC58) | Fwd | CGCGGATCC<u>CATATG</u>-GCCACAAGCGACGAC | 470 | NdeI |
| | Rev | CGCG<u>GGATCC</u>-CCACTCGTAATTGACGCC | 471 | BamHI |
| fu 961 c-... | Fwd | CGCGGATCC<u>CATATG</u>-GCCACAAACGACGAC | 472 | NdeI |
| | Rev | CGCG<u>GGATCC</u>-ACCCACGTTGTAAGGTTG | 473 | BamHI |

| Sequences | | | SEQ ID NO | Restriction site |
|---|---|---|---|---|
| fu 961 c-L-... | Fwd | CGCGGATCC-CATATG-ATGAAACACTTTCCATCC | 474 | NdeI |
| | Rev | CGCGGATCC-ACCCACGTTGTAAGGTTG | 475 | BamHI |
| fu (961)-741(MC58)-His | Fwd | CGCGGATCC-GGAGGGGGTGGTGTCG | 476 | BamHI |
| | Rev | CCCCGCTCGAG-TTGCTTGGCGGCAAGGC | 477 | XhoI |
| fu (961)-983-His | Fwd | CGCGGATCC-GGCGGAGGCGGCACTT | 478 | BamHI |
| | Rev | CCCCGCTCGAG-GAACCGGTAGCCTACG | 479 | XhoI |
| fu (961)-Orf46.1-His | Fwd | CGCGGATCCGGTGGTGGTGGT-TCAGATTTGGCAAACGATTC | 480 | BamHI |
| | Rev | CCCCGCTCGAG-CGTATCATATTTCACGTGC | 481 | XhoI |
| fu (961 c-L)-741(MC58) | Fwd | CGCGGATCC-GGAGGGGGTGGTGTCG | 482 | BamHI |
| | Rev | CCCCGCTCGAG-TTATTGCTTGGCGGCAAG | 483 | XhoI |
| fu (961c-L)-983 | Fwd | CGCGGATCC-GGCGGAGGCGGCACTT | 484 | BamHI |
| | Rev | CCCCGCTCGAG-TCAGAACCGGTAGCCTAC | 485 | XhoI |
| fu (961c-L)-Orf46.1 | Fwd | CGCGGATCCGGTGGTGGTGGT-TCAGATTTGGCAAACGATTC | 486 | BamHI |
| | Rev | CCCCGCTCGAG-TTACGTATCATATTTCACGTGC | 487 | XhoI |
| 961-(His/GST) (MC58) | Fwd | CGCGGATCCCATATG-GCCACAAGCGACGACG | 488 | BamHI-NdeI |
| | Rev | CCCCGCTCGAG-CCACTCGTAATTGACGCC | 489 | XhoI |
| 961 Δ1-His | Fwd | CGCGGATCCCATATG-GCCACAAACGACGAC | 490 | NdeI |
| | Rev | CCCCGCTCGAG-TGCTTTGGCGGCAAAGTT | 491 | XhoI |
| 961a-(His/GST) | Fwd | CGCGGATCCCATATG-GCCACAAACGACGAC | 492 | BamHI-NdeI |
| | Rev | CCCCGCTCGAG-TTTAGCAATATTATCTTTGTTCGTAGC | 493 | XhoI |
| 961b-(His/GST) | Fwd | CGCGGATCCCATATG-AAAGCAAACCGTGCCGA | 494 | BamHI-NdeI |
| | Rev | CCCCGCTCGAG-CCACTCGTAATTGACGCC | 495 | XhoI |
| 961-His/GST$^{GATE}$ | Fwd | ggggacaagtttgtacaaaaaagcaggctGCAGCCACAAACGACGACGATGTTAAAAAAGC | 496 | attB1 |
| | Rev | ggggaccactttgtacaagaaagctgggtTTACCACTCGTAATTGACGCCGACATGGTAGG | 497 | attB2 |
| 982 | Fwd | GCGGCCATATG-GCAGCAAAAGACGTACAGTT | 498 | NdeI |
| | Rev | GCGGCCTCGAG-TTACATCATGCCGCCCATACCA | 499 | XhoI |
| 983-His (2996) | Fwd | CGCGGATCCGCTAGC-TTAGGCGGCGGCGGAG | 500 | NheI |
| | Rev | CCCCGCTCGAG-GAACCGGTAGCCTACG | 501 | XhoI |
| ΔG983-His (2996) | Fwd | CCCCTAGCTAGC-ACTTCTGCGCCCGACTT | 502 | NheI |
| | Rev | CCCCGCTCGAG-GAACCGGTAGCCTACG | 503 | XhoI |
| 983-His | Fwd | CGCGGATCCGCTAGC-TTAGGCGGCGGCGGAG | 504 | NheI |
| | Rev | CCCCGCTCGAG-GAACCGGTAGCCTACG | 505 | XhoI |
| ΔG983-His | Fwd | CGCGGATCCGCTAGC-ACTTCTGCGCCCGACTT | 506 | NheI |
| | Rev | CCCCGCTCGAG-GAACCGGTAGCCTACG | 507 | XhoI |
| 983L | Fwd | CGCGGATCCGCTAGC-CGAACGACCCCAACCTTCCCTACAAAAACTTTCAA | 508 | NheI |
| | Rev | CCCCGCTCGAG-TCAGAACCGACGTGCCAAGCCGTTC | 509 | XhoI |
| 987-His (MC58) | Fwd | GCGCCATATGCCCCCACTGGAAGAACGGACG | 510 | NdeI |
| | Rev | GCGCCTCGAGTAATAAACCTTCTATGGGCAGCAG | 511 | XhoI |
| 989-(His/GST) (MC58) | Fwd | CGCGGATCCCATATG-TCCGTCCACGCATCCG | 512 | BamHI-NdeI |
| | Rev | CCCCGCTCGAG-TTTGAATTTGTAGGTGTATTG | 513 | XhoI |
| 989L (MC58) | Fwd | CGCGGATCCCATATG-ACCCCTTCCGCACT | 514 | NdeI |
| | Rev | CCCCGCTCGAG-TTATTTGAATTTGTAGGTGTAT | 515 | XhoI |
| CrgA-His (MC58) | Fwd | CGCGGATCCCATATG-AAAACCAATTCAGAAGAA | 513 | NdeI |
| | Rev | CCCCGCTCGAG-TCCACAGAGATTGTTCC | 517 | XhoI |
| PilC1-ES (MC58) | Fwd | GATGCCCGAAGGGCGGG | 518 | |
| | Rev | GCCCAAGCTT-TCAGAAGAAGACTTCACGC | 519 | |
| PilC1-His (MC58) | Fwd | CGCGGATCCCATATG-CAAACCCATAAATACGCTATT | 520 | NdeI |
| | Rev | GCCCAAGCTT-GAAGAAGACTTCACGCCAG | 521 | HindIII |
| Δ1PilC1-His (MC58) | Fwd | CGCGGATCCCATATG-GTCTTTTTCGACAATACCGA | 522 | NdeI |
| | Rev | GCCCAAGCTT- | 523 | HindIII |
| PilC1L (MC58) | Fwd | CGCGGATCCCATATG-AATAAACTTTAAAAAGGCGG | 524 | NdeI |
| | Rev | GCCCAAGCTT-TCAGAAGAAGACTTCACGC | 525 | HindIII |
| ΔGTbp2-His (MC58) | Fwd | CGCGAATCCCATATG-TTCGATCTTGATTCTGTCGA | 526 | NdeI |
| | Rev | CCCCGCTCGAG-TCGCACAGGCTGTTGGCG | 527 | XhoI |
| Tbp2-His (MC58) | Fwd | CGCGAATCCCATATG-TTGGCGGAGGCGGCAG | 528 | NdeI |
| | Rev | CCCCGCTCGAG-TCGCACAGGCTGTTGGCG | 529 | XhoI |
| Tbp2-His(MC58) | Fwd | CGCGAATCCCATATG-TTGGGCGGAGGCGGCAG | 530 | NdeI |
| | Rev | CCCCGCTCGAG-TCGCACAGGCTGTTGGCG | 531 | XhoI |
| NMB0109-(His/GST) (MC58) | Fwd | CGCGGATCCCATATG-GCAAATTTGGAGGTGCGC | 532 | BamHI-NdeI |
| | Rev | CCCCGCTCGAG-TTCGGAGCGGTTGAAGC | 533 | XhoI |
| NMB0109L (MC58) | Fwd | CGCGGATCCCATATG-CAACGTCGTATTATAACCC | 534 | NdeI |
| | Rev | CCCCGCTCGAG-TTATTCGGAGCGGTTGAAG | 535 | XhoI |
| NMB0207-(His/GST) (MC58) | Fwd | CGCGGATCCCATATG-GGCATCAAAGTCGCCATCAACGGCTAC | 536 | BamHI-NdeI |
| | Rev | CCCCGCTCGAG-TTTGAGCGGCGCACTTCAAGTCCG | 537 | XhoI |
| NMB0462-(His/GST) (MC58) | Fwd | CGCGGATCCCATATG-GGCGGCAGCGAAAAAAAC | 538 | BamHI-NdeI |
| | Rev | CCCCGCTCGAG-GTTGGTGCCGACTTTGAT | 539 | XhoI |
| NMB0623-(His/GST) (MC58) | Fwd | CGCGGATCCCATATG-GGCGGCGGAAGCGATA | 540 | BamHI-NdeI |
| | Rev | CCCCGCTCGAG-TTTGCCCGCTTTGAGCC | 541 | XhoI |

-continued

| | | Sequences | SEQ ID NO | Restriction site |
|---|---|---|---|---|
| NMB0625 (His-GST) (MC58) | Fwd | CGCGGATCCCATATGGGCAAATCCGAAAATACG | 542 | BamHI-NdeI |
| | Rev | CCCGCTCGAGCATCCCGTACTGTTTCG | 543 | XhoI |
| NMB0634 (His/GST) (MC58) | Fwd | ggggacaagtttgtacaaaaaagcaggctCCGACATTACCGTGTACAACGGCCAACAAGAA | 544 | attB1 |
| | Rev | ggggaccactttgtacaagaaagctgggtCTTATTTCATACCGGCTTGCTCAAGCAGCCGG | 545 | attB2 |
| NMB0776-His/GST (MC58)$^{GATE}$ | Fwd | ggggacaagtttgtacaaaaaagcaggctGATACGGTGTTTTCCTGTAAAACGGACAACAA | 546 | attB1 |
| | Rev | ggggaccactttgtacaagaaagctgggtCTAGGAAAAATCGTCATCGTTGAAATTCGCC | 547 | attB2 |
| NMB1115-His/GST (MC58)$^{GATE}$ | Fwd | ggggacaagtttgtacaaaaaagcaggctATGCACCCCATCGAAACC | 548 | attB1 |
| | Rev | ggggaccactttgtacaagaaagctgggtCTAGTCTTGCAGTGCCTC | 549 | attB2 |
| NMB1343-(His/GST) (MC58) | Fwd | CGCGGATCCCATATG-GGAAATTCTTATATAGAGGCATTAG | 550 | BamHI-NdeI |
| | Rev | CCCGCTCGAG-GTTAATTTCTATCAACTCTTTAGCAATAAT | 551 | XhoI |
| NMB1369 (His-GST (MC58) | Fwd | CGCGGATCCCATATGGCCTGCCAAGACGACA | 552 | BamHI-NdeI |
| | Rev | CCCGCTCGAGCCGCCTCCTGCCGAAA | 553 | XhoI |
| NMB1551 (His-GST) (MC58) | Fwd | CGCGGATCCCATATGGCAGAGATCTGTTTGATAA | 554 | BamHI-NdeI |
| | Rev | CCCGCTCGAGCGGTTTTCCGCCCAATG | 555 | XhoI |
| NMB1899 (His-GST) (MC58) | Fwd | CGCGGATCCCATATGCAGCCGGATACGGTC | 556 | BamHI-NdeI |
| | Rev | CCCGCTCGAGAATCACTTCCAACACAAAT | 557 | XhoI |
| NMB2050-(His/GST) (MC58) | Fwd | CGCGGATCCCATATG-TGGTTGCTGATGAAGGGC | 558 | BamHI-NdeI |
| | Rev | CCCGCTCGAG-GACTGCTTCATCTTCTGC | 559 | XhoI |
| NMB2050L (MC58) | Fwd | CGCGGATCCCATATG-GAACTGATGACTGTTTTGC | 560 | NdeI |
| | Rev | CCCGCTCGAG-TCAGACTGCTTCATCTTCT | 561 | XhoI |
| NMB2159-(His/GST) (MC58) | Fwd | CGCGGATCCCATATG-AGCATTAAAGTAGCGATTAACGGTTTCGGC | 562 | BamHI-NdeI |
| | Rev | CCCGCTCGAG-GATTTTGCCTGCGAAGTATTCCAAAGTGCG | 563 | XhoI |
| fu-ΔG287 . . . -His | Fwd | CGCGGATCCGCTAGC-CCCGATGTTAAATCGGC | 564 | NheI |
| | Rev | CGGGGATCC-ATCCTGCTCTTTTTTGCCGG | 565 | BamHI |
| fu-(ΔG287)-919-His | Fwd | CGCGGATCCGGTGGTGGTGGT-CAAAGCAAGAGCATCCAAACC | 566 | BamHI |
| | Rev | CCCAAGCTT-TTCGGGCGGTATTCGGGCTTC | 567 | HindIII |
| fu-(ΔG287)-953-His | Fwd | CGCGGATCCGGTGGTGGTGGT-GCCACCTACAAAGTGGAC | 568 | BamHI |
| | Rev | GCCCAAGCTT-TTGTTTGGCTGCCTCGAT | 569 | HindIII |
| fu-(ΔG287)-961-His | Fwd | CGCGGATCCGGTGGTGGTGGT-ACAAGCGACGACG | 570 | BamHI |
| | Rev | GCCCAAGCTT-CCACTCGTAATTGACGCC | 571 | HindIII |
| fu-(ΔG287)-Orf46.1-His | Fwd | CGCGGATCCGGTGGTGGTGGT-TCAGATTTGGCAAACGATTC | 572 | BamHI |
| | Rev | CCCAAGCTT-CGTATCATATTTCACGTGC | 573 | HindIII |
| fu-(ΔG287-919)-Orf46.1-His | Fwd | CCCAAGCTTGGTGGTGGTGGTGGT-TCAGATTTGGCAAACGATTC | 574 | HindIII |
| | Rev | CCCGCTCGAG-CGTATCATATTTCACGTGC | 575 | XhoI |
| fu-(ΔG287-Orf46.1)-919-His | Fwd | CCCAAGCTTGGTGGTGGTGGTGGT-CAAAGCAAGAGCATCCAAACC | 576 | HindIII |
| | Rev | CCCGCTCGAG-CGGGCGGTATTCGGGCTT | 577 | XhoI |
| fu ΔG287(394.98)- . . . | Fwd | CGCGGATCCGCTAGC-CCCGATGTTAAATCGGC | 578 | NheI |
| | Rev | CGGGGATCC-ATCCTGCTCTTTTTTGCCGG | 579 | BamHI |
| fu Orf1-(Orf46.1)-His | Fwd | CGCGGATCCGCTAGC-GGACACACTTATTTCGGCATC | 580 | NheI |
| | Rev | CGCGGATCC-CCAGCGGTAGCCTAATTTGAT | 581 | |
| fu (Orf1)-Orf46.1-His | Fwd | CGCGGATCCGGTGGTGGTGGT-TCAGATTTGGCAAACGATTC | 582 | BamHI |
| | Rev | CCCAAGCTT-CGTATCATATTTCACGTGC | 583 | HindIII |
| fu (919)-Orf46.1-His | Fwd1 | GCGGCGTCGACGGTGGCGGAGGCACTGGATCCTCAG | 584 | SalI |
| | Fwd2 | GGAGGCACTGGATCCTCAGATTTGGCAAACGATTC | 585 | |
| | Rev | CCCGCTCGAG-CGTATCATATTTCACGTGC | 586 | XhoI |
| Fu orf46- . . . | Fwd | GGAATTCCATATGTCAGATTTGGCAAACGATTC | 587 | NdeI |
| | Rev | CGCGGATCCCGTATCATATTTCACGTGC | 588 | BamHI |
| Fu (orf46)-287-His | Fwd | CGGGGATCCGGGGCGGCGGTGGCG | 589 | BamHI |
| | Rev | CCCAAGCTTATCCTGCTCTTTTTTGCCGGC | 590 | HindIII |
| Fu (orf46)-919-His | Fwd | CGCGGATCCGGTGGTGGTGGTCAAAGCAAGAGCATCCAAACC | 591 | BamHI |
| | Rev | CCCAAGCTTCGGGCGGTATTCGGGCTTC | 592 | HindIII |
| Fu (orf46-919)-287-His | Fwd | CCCAAGCTTGGGGCGGCGGTGGCG | 593 | HindIII |
| | Rev | CCCGCTCGAGATCCTGCTCTTTTTTGCCGGC | 594 | XhoI |
| Fu (orf46-287)-919-His | Fwd | CCCAAGCTTGGTGGTGGTGGTGGTCAAAGCAAGAGCATCCAAACC | 595 | HindIII |
| | Rev | CCCGCTCGAGCGGGCGGTATTCGGGCTT | 596 | XhoI |
| (ΔG741)-961c-His | Fwd1 | GGAGGCACTGGATCCGCAGCCACAAACGACGCGA | 597 | XhoI |
| | Fwd2 | GCGGCCTCGAG-GGTGGCGGAGGCACTGGATCCGCAG | 598 | |
| | Rev | CCCGCTCGAG-ACCCAGCTTGTAAGGTTG | 599 | XhoI |

-continued

| | | Sequences | SEQ ID NO | Restriction site |
|---|---|---|---|---|
| (ΔG741)-961-His | Fwd1 | GGAGGCACTGGATCCGCAGCCACAAACGACGACGA | 600 | XhoI |
| | Fwd2 | GCGGCCTCGAG-GGTGGCGGAGGCACTGGATCCGCAG | 601 | |
| | Rev | CCCGCTCGAG-CCACTCGTAATTGACGCC | 602 | XhoI |
| (ΔG741)-983-His | Fwd | GCGGCCTCGAG-GGATCCGGCGGAGGCGGCACTTCTGCG | 603 | XhoI |
| | Rev | CCCGCTCGAG-GAACCGGTAGCCTACG | 604 | XhoI |
| (ΔG741)-orf46.1-His | Fwd1 | GGAGGCACTGGATCCTCAGATTTGGCAAACGATTC | 605 | SalI |
| | Fwd2 | GCGGCGTCGACGGTGGCGGAGGCACTGGATCCTCAGA | 606 | |
| | Rev | CCCGCTCGAG-CGTATCATATTTCACGTGC | 607 | XhoI |
| (ΔG983)-741 (MC58)-His | Fwd | GCGGCCTCGAG-GGATCCGGAGGGGGTGGTGTCGCC | 608 | XhoI |
| | Rev | CCCGCTCGAG-TTGCTTGGCGGCAAG | 609 | XhoI |
| (ΔG983)-961c-His | Fwd1 | GGAGGCACTGGATCCGCAGCCACAAACGACGACGA | 610 | XhoI |
| | Fwd2 | GCGGCCTCGAG-GGTGGCGGAGGCACTGGATCCGCAG | 611 | |
| | Rev | CCCGCTCGAG-ACCCAGCTTGTAAGGTTG | 612 | XhoI |
| (ΔG983)-961-His | Fwd1 | GGAGGCACTGGATCCGCAGCCACAAACGACGACGA | 613 | XhoI |
| | Fwd2 | GCGGCCTCGAG-GGTGGCGGAGGCACTGGATCCGCAG | 614 | |
| | Rev | CCCGCTCGAG-CCACTCGTAATTGACGCC | 615 | XhoI |
| (ΔG983)-Orf46.1-His | Fwd1 | GGAGGCACTGGATCCTCAGATTTGGCAAACGATTC | 616 | SalI |
| | Fwd2 | GCGGCGTCGACGGTGGCGGAGGCACTGGATCCTCAGA | 617 | |
| | Rev | CCCGCTCGAG-CGTATCATATTTCACGTGC | 618 | XhoI |

In all constructs starting with an ATG not followed by a unique NheI site, the ATG codon is part of the NdeI site used for cloning. The constructs made using NheI as a cloning site at the 5' end (e.g. all those containing 287 at the N-terminus) have two additional codons (GCT AGC) fused to the coding sequence of the antigen.

Preparation of Chromosomal DNA Templates

N. meningitidis strains 2996, MC58, 394.98, 1000 and BZ232 (and others) were grown to exponential phase in 100 ml of GC medium, harvested by centrifugation, and resuspended in 5 ml buffer (20% w/v sucrose, 50 mM Tris-HCl, 50 mM EDTA, pH8). After 10 minutes incubation on ice, the bacteria were lysed by adding 10 ml of lysis solution (50 mM NaCl, 1% Na-Sarkosyl, 50 µg/ml Proteinase K), and the suspension incubated at 37° C. for 2 hours. Two phenol extractions (equilibrated to pH 8) and one CHCl$_3$/isoamylalcohol (24:1) extraction were performed. DNA was precipitated by addition of 0.3M sodium acetate and 2 volumes of ethanol, and collected by centrifugation. The pellet was washed once with 70% (v/v) ethanol and redissolved in 4.0 ml TE buffer (10 mM Tris-HCl, 1 mM EDTA, pH 8.0). The DNA concentration was measured by reading OD$_{260}$.

PCR Amplification

The standard PCR protocol was as follows: 200 ng of genomic DNA from 2996, MC581000, or BZ232 strains or 10 ng of plasmid DNA preparation of recombinant clones were used as template in the presence of 40 µM of each oligonucleotide primer, 400-800 µM dNTPs solution, 1×PCR buffer (including 1.5 mM MgCl$_2$), 2.5 units TaqI DNA polymerase (using Perkin-Elmer AMPLITAQ® DNA Polymerase kit, Boehringher Mannheim EXPAND™ Long Template kit).

After a preliminary 3 minute incubation of the whole mix at 95° C., each sample underwent a two-step amplification: the first 5 cycles were performed using the hybridisation temperature that excluded the restriction enzyme tail of the primer (T$_{m1}$). This was followed by 30 cycles according to the hybridisation temperature calculated for the whole length oligos (T$_{m2}$). Elongation times, performed at 68° C. or 72° C., varied according to the length of the Orf to be amplified. In the case of Orf1 the elongation time, starting from 3 minutes, was increased by 15 seconds each cycle. The cycles were completed with a 10 minute extension step at 72° C.

The amplified DNA was either loaded directly on a 1% agarose gel. The DNA fragment corresponding to the band of correct size was purified from the gel using the Qiagen Gel Extraction Kit, following the manufacturer's protocol.

Digestion of PCR Fragments and of the Cloning Vectors

The purified DNA corresponding to the amplified fragment was digested with the appropriate restriction enzymes for cloning into pET-21b+, pET22b+ or pET-24b+. Digested fragments were purified using the QIAquick PCR purification kit (following the manufacturer's instructions) and eluted with either H$_2$O or 10 mM Tris, pH 8.5. Plasmid vectors were digested with the appropriate restriction enzymes, loaded onto a 1.0% agarose gel and the band corresponding to the digested vector purified using the Qiagen QIAquick Gel Extraction Kit.

Cloning

The fragments corresponding to each gene, previously digested and purified, were ligated into pET21b+, pET22b+ or pET-24b+. A molar ratio of 3:1 fragment/vector was used with T4 DNA ligase in the ligation buffer supplied by the manufacturer.

Recombinant plasmid was transformed into competent E. coli DH5 or HB101 by incubating the ligase reaction solution and bacteria for 40 minutes on ice, then at 37° C. for 3 minutes.

This was followed by the addition of 800 µl LB broth and incubation at 37° C. for 20 minutes. The cells were centrifuged at maximum speed in an Eppendorf microfuge, resuspended in approximately 200 µl of the supernatant and plated onto LB ampicillin (100 mg/ml) agar.

Screening for recombinant clones was performed by growing randomly selected colonies overnight at 37° C. in 4.0 ml of LB broth+100 µg/ml ampicillin. Cells were pelleted and plasmid DNA extracted using the Qiagen QIAprep Spin Miniprep Kit, following the manufacturer's instructions. Approximately 1 µg of each individual miniprep was digested with the appropriate restriction enzymes and the digest loaded onto a 1-1.5% agarose gel (depending on the expected insert size), in parallel with the molecular weight marker (1 kb DNA Ladder, GIBCO®). Positive clones were selected on the basis of the size of insert.

Expression

After cloning each gene into the expression vector, recombinant plasmids were transformed into E. coli strains suitable for expression of the recombinant protein. 1 µl of each construct was used to transform E. coli BL21-DE3 as described above. Single recombinant colonies were inoculated into 2 ml LB+Amp (100 µg/ml), incubated at 37° C. overnight, then diluted 1:30 in 20 ml of LB+Amp (100 µg/ml) in 100 ml flasks, to give an $OD_{600}$ between 0.1 and 0.2. The flasks were incubated at 30° C. or at 37° C. in a gyratory water bath shaker until $OD_{600}$ indicated exponential growth suitable for induction of expression (0.4-0.8 OD). Protein expression was induced by addition of 1.0 mM IPTG. After 3 hours incubation at 30° C. or 37° C. the $OD_{600}$ was measured and expression examined. 1.0 ml of each sample was centrifuged in a microfuge, the pellet resuspended in PBS and analysed by SDS-PAGE and Coomassie Blue staining.

Gateway Cloning and Expression

Sequences labelled GATE were cloned and expressed using the GATEWAY Cloning Technology (GIBCO®-BRL). Recombinational cloning (RC) is based on the recombination reactions that mediate the integration and excision of phage into and from the E. coli genome, respectively. The integration involves recombination of the attP site of the phage DNA within the attB site located in the bacterial genome (BP reaction) and generates an integrated phage genome flanked by attL and attR sites. The excision recombines attL and attR sites back to attP and attB sites (LR reaction). The integration reaction requires two enzymes [the phage protein Integrase (Int) and the bacterial protein integration host factor (IHF)] (BP clonase). The excision reaction requires Int, IHF, and an additional phage enzyme, Excisionase (Xis) (LR clonase). Artificial derivatives of the 25-bp bacterial attB recombination site, referred to as B1 and B2, were added to the 5' end of the primers used in PCR reactions to amplify Neisserial ORFs. The resulting products were BP cloned into a "Donor vector" containing complementary derivatives of the phage attP recombination site (P1 and P2) using BP clonase. The resulting "Entry clones" contain ORFs flanked by derivatives of the attL site (L1 and L2) and were subcloned into expression "destination vectors" which contain derivatives of the attL-compatible attR sites (R1 and R2) using LR clonase. This resulted in "expression clones" in which ORFs are flanked by B1 and B2 and fused in frame to the GST or His N terminal tags.

The E. coli strain used for GATEWAY expression is BL21-SI. Cells of this strain are induced for expression of the T7 RNA polymerase by growth in medium containing salt (0.3 M NaCl).

Note that this system gives N-terminus His tags.

Preparation of Membrane Proteins.

Fractions composed principally of either inner, outer or total membrane were isolated in order to obtain recombinant proteins expressed with membrane-localisation leader sequences. The method for preparation of membrane fractions, enriched for recombinant proteins, was adapted from Filip et. al. [J. Bact. (1973) 115:717-722] and Davies et. al. [J. Immunol. Meth. (1990) 143:215-225]. Single colonies harbouring the plasmid of interest were grown overnight at 37° C. in 20 ml of LB/Amp (100 µg/ml) liquid culture. Bacteria were diluted 1:30 in 1.0 L of fresh medium and grown at either 30° C. or 37° C. until the $OD_{550}$ reached 0.6-0.8. Expression of recombinant protein was induced with IPTG at a final concentration of 1.0 mM. After incubation for 3 hours, bacteria were harvested by centrifugation at 8000 g for 15 minutes at 4° C. and resuspended in 20 ml of 20 mM Tris-HCl (pH 7.5) and complete protease inhibitors (Boehringer-Mannheim). All subsequent procedures were performed at 4° C. or on ice.

Cells were disrupted by sonication using a Branson SONIFIER® 450 (ultrasonic cell disruption/homogenizer) and centrifuged at 5000 g for 20 min to sediment unbroken cells and inclusion bodies. The supernatant, containing membranes and cellular debris, was centrifuged at 50000 g (Beckman Ti50, 29000 rpm) for 75 min, washed with 20 mM Bis-tris propane (pH 6.5), 1.0 M NaCl, 10% (v/v) glycerol and sedimented again at 50000 g for 75 minutes. The pellet was resuspended in 20 mM Tris-HCl (pH 7.5), 2.0% (v/v) Sarkosyl, complete protease inhibitor (1.0 mM EDTA, final concentration) and incubated for 20 minutes to dissolve inner membrane. Cellular debris was pelleted by centrifugation at 5000 g for 10 min and the supernatant centrifuged at 75000 g for 75 minutes (Beckman Ti50, 33000 rpm). Proteins 008L and 519L were found in the supernatant suggesting inner membrane localisation. For these proteins both inner and total membrane fractions (washed with NaCl as above) were used to immunise mice. Outer membrane vesicles obtained from the 75000 g pellet were washed with 20 mM Tris-HCl (pH 7.5) and centrifuged at 75000 g for 75 minutes or overnight. The OMV was finally resuspended in 500 µl of 20 mM Tris-HCl (pH 7.5), 10% v/v glycerol. Orf1L and Orf40L were both localised and enriched in the outer membrane fraction which was used to immunise mice. Protein concentration was estimated by standard Bradford Assay (Bio-Rad), while protein concentration of inner membrane fraction was determined with the DC protein assay (Bio-Rad). Various fractions from the isolation procedure were assayed by SDS-PAGE.

Purification of His-Tagged Proteins

Various forms of 287 were cloned from strains 2996 and MC58. They were constructed with a C-terminus His-tagged fusion and included a mature form (aa 18-427), constructs with deletions (Δ1, Δ2, Δ3 and Δ4) and clones composed of either B or C domains. For each clone purified as a His-fusion, a single colony was streaked and grown overnight at 37° C. on a LB/Amp (100 µg/ml) agar plate. An isolated colony from this plate was inoculated into 20 ml of LB/Amp (100 µg/ml) liquid medium and grown overnight at 37° C. with shaking. The overnight culture was diluted 1:30 into 1.0 L LB/Amp (100 µg/ml) liquid medium and allowed to grow at the optimal temperature (30 or 37° C.) until the $OD_{550}$ reached 0.6-0.8. Expression of recombinant protein was induced by addition of IPTG (final concentration 1.0 mM) and the culture incubated for a further 3 hours. Bacteria were harvested by centrifugation at 8000 g for 15 min at 4° C. The bacterial pellet was resuspended in 7.5 ml of either (i) cold buffer A (300 mM NaCl, 50 mM phosphate buffer, 10 mM imidazole, pH 8.0) for soluble proteins or (ii) buffer B (10 mM Tris-HCl, 100 mM phosphate buffer, pH 8.8 and, optionally, 8M urea) for insoluble proteins. Proteins purified in a soluble form included 287-His, Δ1, Δ2, Δ3 and Δ4287-His, Δ4287MC58-His, 287c-His and 287cMC58-His. Protein 287bMC58-His was insoluble and purified accordingly. Cells were disrupted by sonication on ice four times for 30 sec at 40 W using a Branson SONIFIER® 450 (ultrasonic cell disruption/homogenizer) and centrifuged at 13000×g for 30 min at 4° C. For insoluble proteins, pellets were resuspended in 2.0 ml buffer C (6 M guanidine hydrochloride, 100 mM phosphate buffer, 10 mM Tris-HCl, pH 7.5 and treated with 10 passes of a Dounce homogenizer. The homogenate was centrifuged at 13000 g for 30 min and the supernatant retained. Supernatants for both soluble and insoluble preparations were mixed with 150 µl $Ni^{2+}$-resin (previously equilibrated with either buffer A or buffer B, as appropriate) and incubated at room temperature with gentle agitation for 30 min. The resin was Chelating SEPHAROSE™ Fast Flow (IMAC medium, Pharmacia), prepared according to the manufacturer's protocol. The batch-wise preparation was centrifuged at 700 g for 5 min at 4° C. and the supernatant discarded. The resin was washed twice (batch-wise) with 10 ml buffer A or B for 10 min, resuspended in 1.0 ml buffer A or B and loaded onto a disposable column. The resin continued to be washed with either (i) buffer A at 4° C. or (ii) buffer B at room temperature, until the $OD_{280}$ of the flow-through reached 0.02-0.01. The resin was further washed with either (i) cold buffer C (300 mM NaCl, 50 mM phosphate buffer, 20 mM imidazole, pH 8.0) or (ii) buffer D (10 mM Tris-HCl, 100 mM phosphate buffer, pH 6.3 and, optionally, 8M urea) until $OD_{280}$ of the flow-through reached 0.02-0.01. The His-fusion protein was eluted by addition of 700 µl of either (i) cold elution buffer A (300 mM NaCl, 50 mM phosphate buffer, 250 mM imidazole, pH 8.0) or (ii) elution buffer B (10 mM Tris-HCl, 100 mM phosphate buffer, pH 4.5 and, optionally, 8M urea) and fractions collected until the $OD_{280}$ indicated all the recombinant protein was obtained. 20 µl aliquots of each elution fraction were analysed by SDS-PAGE. Protein concentrations were estimated using the Bradford assay.

Renaturation of Denatured His-Fusion Proteins.

Denaturation was required to solubilize 287bMC8, so a renaturation step was employed prior to immunisation. Glycerol was added to the denatured fractions obtained above to give a final concentration of 10% v/v. The proteins were diluted to 200 µg/ml using dialysis buffer I (10% v/v glycerol, 0.5M arginine, 50 mM phosphate buffer, 5.0 mM reduced glutathione, 0.5 mM oxidised glutathione, 2.0M urea, pH 8.8) and dialysed against the same buffer for 12-14 hours at 4° C. Further dialysis was performed with buffer II (10% v/v glycerol, 0.5M arginine, 50 mM phosphate buffer, 5.0 mM reduced glutathione, 0.5 mM oxidised glutathione, pH 8.8) for 12-14 hours at 4° C. Protein concentration was estimated using the formula:

$$\text{Protein(mg/ml)} = (1.55 \times OD_{280}) - (0.76 \times OD_{260})$$

Amino Acid Sequence Analysis.

Automated sequence analysis of the $NH_2$-terminus of proteins was performed on a Beckman sequencer (LF 3000) equipped with an on-line phenylthiohydantoin-amino acid analyser (System Gold) according to the manufacturer's recommendations.

Immunization

Balb/C mice were immunized with antigens on days 0, 21 and 35 and sera analyzed at day 49.

Sera Analysis—ELISA

The acapsulated MenB M7 and the capsulated strains were plated on chocolate agar plates and incubated overnight at 37° C. with 5% $CO_2$. Bacterial colonies were collected from the agar plates using a sterile dracon swab and inoculated into Mueller-Hinton Broth (Difco) containing 0.25% glucose. Bacterial growth was monitored every 30 minutes by following $OD_{620}$. The bacteria were let to grow until the OD reached the value of 0.4-0.5. The culture was centrifuged for 10 minutes at 4000 rpm. The supernatant was discarded and bacteria were washed twice with PBS, resuspended in PBS containing 0.025% formaldehyde, and incubated for 1 hour at 37° C. and then overnight at 4° C. with stirring. 100 µl bacterial cells were added to each well of a 96 well Greiner plate and incubated overnight at 4° C. The wells were then washed three times with PBT washing buffer (0.1% TWEEN®-20 (Polysorbate 20, Sigma Aldrich) in PBS). 200 µl of saturation buffer (2.7% polyvinylpyrrolidone 10 in water) was added to each well and the plates incubated for 2 hours at 37° C. Wells were washed three times with PBT. 200 µl of diluted sera (Dilution buffer: 1% BSA, 0.1% TWEEN®-20 (Polysorbate 20, Sigma Aldrich), 0.1% $NaN_3$ in PBS) were added to each well and the plates incubated for 2 hours at 37° C. Wells were washed three times with PBT. 100 µl of HRP-conjugated rabbit anti-mouse (Dako) serum diluted 1:2000 in dilution buffer were added to each well and the plates were incubated for 90 minutes at 37° C. Wells were washed three times with PBT buffer. 100 µl of substrate buffer for HRP (25 ml of citrate buffer pH5, 10 mg of O-phenildiamine and 10 µl of $H_2O_2$) were added to each well and the plates were left at room temperature for 20 minutes. 100 µl 12.5% $H_2SO_4$ was added to each well and $OD_{490}$ was followed. The ELISA titers were calculated abitrarely as the dilution of sera which gave an $OD_{490}$ value of 0.4 above the level of preimmune sera. The ELISA was considered positive when the dilution of sera with $OD_{490}$ of 0.4 was higher than 1:400.

Sera Analysis—FACS Scan Bacteria Binding Assay

The acapsulated MenB M7 strain was plated on chocolate agar plates and incubated overnight at 37° C. with 5% $CO_2$. Bacterial colonies were collected from the agar plates using a sterile dracon swab and inoculated into 4 tubes containing 8 ml each Mueller-Hinton Broth (Difco) containing 0.25% glucose. Bacterial growth was monitored every 30 minutes by following $OD_{620}$. The bacteria were let to grow until the OD reached the value of 0.35-0.5. The culture was centrifuged for 10 minutes at 4000 rpm. The supernatant was discarded and the pellet was resuspended in blocking buffer (1% BSA in PBS, 0.4% $NaN_3$) and centrifuged for 5 minutes at 4000 rpm. Cells were resuspended in blocking buffer to reach $OD_{620}$ of 0.05. 100 µl bacterial cells were added to each well of a COSTAR® 96 well plate. 100 µl of diluted (1:100, 1:200, 1:400) sera (in blocking buffer) were added to each well and plates incubated for 2 hours at 4° C. Cells were centrifuged for 5 minutes at 4000 rpm, the supernatant aspirated and cells washed by addition of 200 µl/well of blocking buffer in each well. 100 µl of R-Phicoerytrin conjugated $F(ab)_2$ goat anti-mouse, diluted 1:100, was added to each well and plates incubated for 1 hour at 4° C. Cells were spun down by centrifugation at 4000 rpm for 5 minutes and washed by addition of 200 µl/well of blocking buffer. The supernatant was aspirated and cells resuspended in 200 µl/well of PBS, 0.25% formaldehyde. Samples were transferred to FACScan tubes and read. The condition for FACScan (Laser Power 15 mW) setting were: FL2 on; FSC-H threshold: 92; FSC PMT Voltage: E 01; SSC PMT: 474; Amp. Gains 6.1; FL-2 PMT: 586; compensation values: 0.

Sera Analysis—Bactericidal Assay

N. meningitidis strain 2996 was grown overnight at 37° C. on chocolate agar plates (starting from a frozen stock) with 5% $CO_2$. Colonies were collected and used to inoculate 7 ml Mueller-Hinton broth, containing 0.25% glucose to reach an $OD_{620}$ of 0.05-0.08. The culture was incubated for approximately 1.5 hours at 37 degrees with shacking until the $OD_{620}$ reached the value of 0.23-0.24. Bacteria were diluted in 50 mM Phosphate buffer pH 7.2 containing 10 mM $MgCl_2$, 10 mM $CaCl_2$ and 0.5% (w/v) BSA (assay buffer) at the working dilution of $10^5$ CFU/ml. The total volume of the final reaction mixture was 50 µl with 25 µl of serial two fold dilution of test serum, 12.5 µl of bacteria at the working dilution, 12.5 µl of baby rabbit complement (final concentration 25%).

Controls included bacteria incubated with complement serum, immune sera incubated with bacteria and with complement inactivated by heating at 56° C. for 30'. Immediately after the addition of the baby rabbit complement, 10 µl of the controls were plated on Mueller-Hinton agar plates using the tilt method (time 0). The 96-wells plate was incubated for 1 hour at 37° C. with rotation. 7 µl of each sample were plated on Mueller-Hinton agar plates as spots, whereas 10 µl of the controls were plated on Mueller-Hinton agar plates using the tilt method (time 1). Agar plates were incubated for 18 hours at 37 degrees and the colonies corresponding to time 0 and time 1 were counted.

Sera Analysis—Western Blots

Purified proteins (500 ng/lane), outer membrane vesicles (5 μg) and total cell extracts (25 μg) derived from MenB strain 2996 were loaded onto a 12% SDS-polyacrylamide gel and transferred to a nitrocellulose membrane. The transfer was performed for 2 hours at 150 mA at 4° C., using transfer buffer (0.3% Tris base, 1.44% glycine, 20% (v/v) methanol). The membrane was saturated by overnight incubation at 4° C. in saturation buffer (10% skimmed milk, 0.1% Triton X100 in PBS). The membrane was washed twice with washing buffer (3% skimmed milk, 0.1% Triton X100 in PBS) and incubated for 2 hours at 37° C. with mice sera diluted 1:200 in washing buffer. The membrane was washed twice and incubated for 90 minutes with a 1:2000 dilution of horseradish peroxidase labelled anti-mouse Ig. The membrane was washed twice with 0.1% Triton X100 in PBS and developed with the Opti-4CN Substrate Kit (Bio-Rad). The reaction was stopped by adding water.

The OMVs were prepared as follows: *N. meningitidis* strain 2996 was grown overnight at 37 degrees with 5% $CO_2$ on 5 GC plates, harvested with a loop and resuspended in 10 ml of 20 mM Tris-HCl pH 7.5, 2 mM EDTA. Heat inactivation was performed at 56° C. for 45 minutes and the bacteria disrupted by sonication for 5 minutes on ice (50% duty cycle, 50% output, Branson SONIFIER® 3 mm microtip). Unbroken cells were removed by centrifugation at 5000 g for 10 minutes, the supernatant containing the total cell envelope fraction recovered and further centrifuged overnight at 50000 g at the temperature of 4° C. The pellet containing the membranes was resuspended in 2% sarkosyl, 20 mM Tris-HCl pH 7.5, 2 mM EDTA and incubated at room temperature for 20 minutes to solubilise the inner membranes. The suspension was centrifuged at 10000 g for 10 minutes to remove aggregates, the supernatant was further centrifuged at 50000 g for 3 hours. The pellet, containing the outer membranes was washed in PBS and resuspended in the same buffer. Protein concentration was measured by the D.C. Bio-Rad Protein assay (Modified Lowry method), using BSA as a standard.

Total cell extracts were prepared as follows: *N. meningitidis* strain 2996 was grown overnight on a GC plate, harvested with a loop and resuspended in 1 ml of 20 mM Tris-HCl. Heat inactivation was performed at 56° C. for 30 minutes.

961 Domain Studies

Cellular fractions preparation Total lysate, periplasm, supernatant and OMV of *E. coli* clones expressing different domains of 961 were prepared using bacteria from over-night cultures or after 3 hours induction with IPTG. Briefly, the periplasm were obtained suspending bacteria in saccarose 25% and Tris 50 mM (pH 8) with polimixine 100 μg/ml. After 1 hr at room temperature bacteria were centrifuged at 13000 rpm for 15 min and the supernatant were collected. The culture supernatant were filtered with 0.2 μm and precipitated with TCA 50% in ice for two hours. After centrifugation (30 min at 13000 rp) pellets were rinsed twice with ethanol 70% and suspended in PBS. The OMV preparation was performed as previously described. Each cellular fraction were analyzed in SDS-PAGE or in Western Blot using the polyclonal antiserum raised against GST-961.

Adhesion assay Chang epithelial cells (Wong-Kilbourne derivative, clone 1-5c-4, human conjunctiva) were maintained in DMEM (GIBCO®) supplemented with 10% heat-inactivated FCS, 15 mM L-glutamine and antibiotics.

For the adherence assay, sub-confluent culture of Chang epithelial cells were rinsed with PBS and treated with trypsin-EDTA (Gibco), to release them from the plastic support. The cells were then suspended in PBS, counted and dilute in PBS to $5 \times 10^5$ cells/ml.

Bacteria from over-night cultures or after induction with IPTG, were pelleted and washed twice with PBS by centrifuging at 13000 for 5 min. Approximately $2-3 \times 10^8$ (cfu) were incubated with 0.5 mg/ml FITC (Sigma) in 1 ml buffer containing 50 mM $NaHCO_3$ and 100 mM NaCl pH 8, for 30 min at room temperature in the dark. FITC-labeled bacteria were wash 2-3 times and suspended in PBS at $1-1.5 \times 10^9$/ml. 2000 of this suspension ($2-3 \times 10^8$) were incubated with 200 μl ($1 \times 10^5$) epithelial cells for 30 min a 37° C. Cells were than centrifuged at 2000 rpm for 5 min to remove non-adherent bacteria, suspended in 200 μl of PBS, transferred to FACScan tubes and read

---

What is claimed:

1. An immunogenic protein comprising a sequence having greater than 90% sequence identity to a sequence represented by SEQ ID NO: 84, in which at least one domain in the protein is deleted, wherein the at least one domain is selected from the group comprising amino acids 1-24 of SEQ ID NO: 84, amino acids 1-69 of SEQ ID NO: 84, amino acids 1-106 of SEQ ID NO: 84, amino acids 1-202 of SEQ ID NO: 84, amino acids 203-288 of SEQ ID NO: 84, and amino acids 289-488 of SEQ ID NO: 84, and wherein the protein has at least one domain.

2. The immunogenic protein of claim 1, in which the N-terminal domain of the protein is mutated.

3. The immunogenic protein of claim 1, wherein the protein includes a C-terminal His-tag.

4. The immunogenic protein of claim 1, wherein the protein includes an N-terminal GST.

5. The immunogenic protein of claim 1, wherein the immunogenic protein is at the N-terminus of a hybrid protein.

6. The immunogenic protein claim 1, wherein the protein comprises a sequence having greater than 95% sequence identity to a sequence represented by SEQ ID NO: 84.

7. A method for producing an immunogenic protein comprising expressing in a heterologous host a protein comprising the immunogenic protein of claim 1; and purifying the protein.

8. The method of claim 7, in which the N-terminal domain of the protein is mutated.

9. The method of claim 7, in which the heterologous host is an *E. coli* host.

10. The method of claim 7, wherein the protein includes a C-terminal His-tag.

11. The method of claim 7, wherein the protein includes an N-terminal GST.

12. The method of claim 7, wherein the immunogenic protein is at the N-terminus of a hybrid protein.

13. The method of claim 7, wherein the protein comprises a sequence having greater than 95% sequence identity to a sequence represented by SEQ ID NO: 84.

* * * * *

SEQUENCE LISTING

```
<160> NUMBER OF SEQ ID NOS: 633

<210> SEQ ID NO 1
<211> LENGTH: 441
<212> TYPE: PRT
<213> ORGANISM: Neisseria meningitidis

<400> SEQUENCE: 1

Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95
```

```
Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ala Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Ala Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
            435                 440

<210> SEQ ID NO 2
<211> LENGTH: 420
<212> TYPE: PRT
<213> ORGANISM: Neisseria meningitidis

<400> SEQUENCE: 2

Gln Ser Lys Ser Ile Gln Thr Phe Pro Gln Pro Asp Thr Ser Val Ile
1               5                   10                  15

Asn Gly Pro Asp Arg Pro Val Gly Ile Pro Asp Pro Ala Gly Thr Thr
            20                  25                  30
```

Val Gly Gly Gly Gly Ala Val Tyr Thr Val Val Pro His Leu Ser Leu
             35                  40                  45

Pro His Trp Ala Ala Gln Asp Phe Ala Lys Ser Leu Gln Ser Phe Arg
 50                  55                  60

Leu Gly Cys Ala Asn Leu Lys Asn Arg Gln Gly Trp Gln Asp Val Cys
 65                  70                  75                  80

Ala Gln Ala Phe Gln Thr Pro Val His Ser Phe Gln Ala Lys Gln Phe
                 85                  90                  95

Phe Glu Arg Tyr Phe Thr Pro Trp Gln Val Ala Gly Asn Gly Ser Leu
                100                 105                 110

Ala Gly Thr Val Thr Gly Tyr Tyr Glu Pro Val Leu Lys Gly Asp Asp
                115                 120                 125

Arg Arg Thr Ala Gln Ala Arg Phe Pro Ile Tyr Gly Ile Pro Asp Asp
                130                 135                 140

Phe Ile Ser Val Pro Leu Pro Ala Gly Leu Arg Ser Gly Lys Ala Leu
145                 150                 155                 160

Val Arg Ile Arg Gln Thr Gly Lys Asn Ser Gly Thr Ile Asp Asn Thr
                165                 170                 175

Gly Gly Thr His Thr Ala Asp Leu Ser Arg Phe Pro Ile Thr Ala Arg
                180                 185                 190

Thr Thr Ala Ile Lys Gly Arg Phe Glu Gly Ser Arg Phe Leu Pro Tyr
                195                 200                 205

His Thr Arg Asn Gln Ile Asn Gly Gly Ala Leu Asp Gly Lys Ala Pro
                210                 215                 220

Ile Leu Gly Tyr Ala Glu Asp Pro Val Glu Leu Phe Phe Met His Ile
225                 230                 235                 240

Gln Gly Ser Gly Arg Leu Lys Thr Pro Ser Gly Lys Tyr Ile Arg Ile
                245                 250                 255

Gly Tyr Ala Asp Lys Asn Glu His Pro Tyr Val Ser Ile Gly Arg Tyr
                260                 265                 270

Met Ala Asp Lys Gly Tyr Leu Lys Leu Gly Gln Thr Ser Met Gln Gly
                275                 280                 285

Ile Lys Ala Tyr Met Arg Gln Asn Pro Gln Arg Leu Ala Glu Val Leu
                290                 295                 300

Gly Gln Asn Pro Ser Tyr Ile Phe Phe Arg Glu Leu Ala Gly Ser Ser
305                 310                 315                 320

Asn Asp Gly Pro Val Gly Ala Leu Gly Thr Pro Leu Met Gly Glu Tyr
                325                 330                 335

Ala Gly Ala Val Asp Arg His Tyr Ile Thr Leu Gly Ala Pro Leu Phe
                340                 345                 350

Val Ala Thr Ala His Pro Val Thr Arg Lys Ala Leu Asn Arg Leu Ile
                355                 360                 365

Met Ala Gln Asp Thr Gly Ser Ala Ile Lys Gly Ala Val Arg Val Asp
                370                 375                 380

Tyr Phe Trp Gly Tyr Gly Asp Glu Ala Gly Glu Leu Ala Gly Lys Gln
385                 390                 395                 400

Lys Thr Thr Gly Tyr Val Trp Gln Leu Leu Pro Asn Gly Met Lys Pro
                405                 410                 415

Glu Tyr Arg Pro
            420

<210> SEQ ID NO 3
<211> LENGTH: 440
<212> TYPE: PRT

<213> ORGANISM: Artificial Sequence
<220> FEATURE:
<223> OTHER INFORMATION: 919

<400> SEQUENCE: 3

```
Met Lys Thr Phe Phe Lys Thr Leu Ser Ala Ala Leu Ala Leu Ile
1               5                   10                  15

Leu Ala Ala Cys Gln Ser Lys Ser Ile Gln Thr Phe Pro Gln Pro Asp
            20                  25                  30

Thr Ser Val Ile Asn Gly Pro Asp Arg Pro Val Gly Ile Pro Asp Pro
        35                  40                  45

Ala Gly Thr Thr Val Gly Gly Gly Ala Val Tyr Thr Val Val Pro
    50                  55                  60

His Leu Ser Leu Pro His Trp Ala Ala Gln Asp Phe Ala Lys Ser Leu
65                  70                  75                  80

Gln Ser Phe Arg Leu Gly Cys Ala Asn Leu Lys Asn Arg Gln Gly Trp
                85                  90                  95

Gln Asp Val Cys Ala Gln Ala Phe Gln Thr Pro Val His Ser Phe Gln
            100                 105                 110

Ala Lys Gln Phe Phe Glu Arg Tyr Phe Thr Pro Trp Gln Val Ala Gly
        115                 120                 125

Asn Gly Ser Leu Ala Gly Thr Val Thr Gly Tyr Tyr Glu Pro Val Leu
130                 135                 140

Lys Gly Asp Asp Arg Arg Thr Ala Gln Ala Arg Phe Pro Ile Tyr Gly
145                 150                 155                 160

Ile Pro Asp Asp Phe Ile Ser Val Pro Leu Pro Ala Gly Leu Arg Ser
                165                 170                 175

Gly Lys Ala Leu Val Arg Ile Arg Gln Thr Gly Lys Asn Ser Gly Thr
            180                 185                 190

Ile Asp Asn Thr Gly Gly Thr His Thr Ala Asp Leu Ser Arg Phe Pro
        195                 200                 205

Ile Thr Ala Arg Thr Thr Ala Ile Lys Gly Arg Phe Glu Gly Ser Arg
    210                 215                 220

Phe Leu Pro Tyr His Thr Arg Asn Gln Ile Asn Gly Gly Ala Leu Asp
225                 230                 235                 240

Gly Lys Ala Pro Ile Leu Gly Tyr Ala Glu Asp Pro Val Glu Leu Phe
                245                 250                 255

Phe Met His Ile Gln Gly Ser Gly Arg Leu Lys Thr Pro Ser Gly Lys
            260                 265                 270

Tyr Ile Arg Ile Gly Tyr Ala Asp Lys Asn Glu His Pro Tyr Val Ser
        275                 280                 285

Ile Gly Arg Tyr Met Ala Asp Lys Gly Tyr Leu Lys Leu Gly Gln Thr
    290                 295                 300

Ser Met Gln Gly Ile Lys Ser Tyr Met Arg Gln Asn Pro Gln Arg Leu
305                 310                 315                 320

Ala Glu Val Leu Gly Gln Asn Pro Ser Tyr Ile Phe Phe Arg Glu Leu
                325                 330                 335

Ala Gly Ser Ser Asn Asp Gly Pro Val Gly Ala Leu Gly Thr Pro Leu
            340                 345                 350

Met Gly Glu Tyr Ala Gly Ala Val Asp Arg His Tyr Ile Thr Leu Gly
        355                 360                 365

Ala Pro Leu Phe Val Ala Thr Ala His Pro Val Thr Arg Lys Ala Leu
    370                 375                 380

Asn Arg Leu Ile Met Ala Gln Asp Thr Gly Ser Ala Ile Lys Gly Ala
385                 390                 395                 400
```

Val Arg Val Asp Tyr Phe Trp Gly Tyr Gly Asp Glu Ala Gly Glu Leu
            405                 410                 415

Ala Gly Lys Gln Lys Thr Thr Gly Tyr Val Trp Gln Leu Leu Pro Asn
            420                 425                 430

Gly Met Lys Pro Glu Tyr Arg Pro
            435                 440

<210> SEQ ID NO 4
<211> LENGTH: 58
<212> TYPE: PRT
<213> ORGANISM: Artificial Sequence
<220> FEATURE:
<223> OTHER INFORMATION: 907-2.pep

<400> SEQUENCE: 4

Glu Arg Arg Arg Leu Leu Val Asn Ile Gln Tyr Glu Ser Ser Arg Ala
1               5                   10                  15

Gly Leu Asp Thr Gln Ile Val Leu Gly Leu Ile Glu Val Glu Ser Ala
            20                  25                  30

Phe Arg Gln Tyr Ala Ile Ser Gly Val Gly Ala Arg Gly Leu Met Gln
            35                  40                  45

Val Met Pro Phe Trp Lys Asn Tyr Ile Gly
        50                  55

<210> SEQ ID NO 5
<211> LENGTH: 60
<212> TYPE: PRT
<213> ORGANISM: Artificial Sequence
<220> FEATURE:
<223> OTHER INFORMATION: Escherichia coli

<400> SEQUENCE: 5

Glu Arg Phe Pro Leu Ala Tyr Asn Asp Leu Phe Lys Arg Tyr Thr Ser
1               5                   10                  15

Gly Lys Glu Ile Pro Gln Ser Tyr Ala Met Ala Ile Ala Arg Gln Glu
            20                  25                  30

Ser Ala Trp Asn Pro Lys Val Lys Ser Pro Val Gly Ala Ser Gly Leu
            35                  40                  45

Met Gln Ile Met Pro Gly Thr Ala Thr His Thr Val
        50                  55                  60

<210> SEQ ID NO 6
<211> LENGTH: 120
<212> TYPE: PRT
<213> ORGANISM: Artificial Sequence
<220> FEATURE:
<223> OTHER INFORMATION: 922.pep

<400> SEQUENCE: 6

Val Ala Gln Lys Tyr Gly Val Pro Ala Glu Leu Ile Val Ala Val Ile
1               5                   10                  15

Gly Ile Glu Thr Asn Tyr Gly Lys Asn Thr Gly Ser Phe Arg Val Ala
            20                  25                  30

Asp Ala Leu Ala Thr Leu Gly Phe Asp Tyr Pro Arg Arg Ala Gly Phe
            35                  40                  45

Phe Gln Lys Glu Leu Val Glu Leu Leu Lys Leu Ala Lys Glu Glu Gly
        50                  55                  60

Gly Asp Val Phe Ala Phe Lys Gly Ser Tyr Ala Gly Ala Met Gly Met
65                  70                  75                  80

Pro Gln Phe Met Pro Ser Ser Tyr Arg Lys Trp Ala Val Asp Tyr Asp

```
                     85                  90                  95

Gly Asp Gly His Arg Asp Ile Trp Gly Asn Val Gly Asp Val Ala Ala
                100                 105                 110

Ser Val Ala Asn Tyr Met Lys Gln
        115                 120

<210> SEQ ID NO 7
<211> LENGTH: 119
<212> TYPE: PRT
<213> ORGANISM: Artificial Sequence
<220> FEATURE:
<223> OTHER INFORMATION: Escherichia coli

<400> SEQUENCE: 7

Ala Trp Gln Val Tyr Gly Val Pro Pro Glu Ile Ile Val Gly Ile Ile
1               5                   10                  15

Gly Val Glu Thr Arg Trp Gly Arg Val Met Gly Lys Thr Arg Ile Leu
            20                  25                  30

Asp Ala Leu Ala Thr Leu Ser Phe Asn Tyr Pro Arg Arg Ala Glu Tyr
        35                  40                  45

Phe Ser Gly Glu Leu Glu Thr Phe Leu Leu Met Ala Arg Asp Glu Gln
 50                  55                  60

Asp Asp Pro Leu Asn Leu Lys Gly Ser Phe Ala Gly Ala Met Gly Tyr
65                  70                  75                  80

Gly Gln Phe Met Pro Ser Ser Tyr Lys Gln Tyr Ala Val Asp Phe Ser
                85                  90                  95

Gly Asp Gly His Ile Asn Leu Trp Asp Pro Val Asp Ala Ile Gly Ser
                100                 105                 110

Val Ala Asn Tyr Phe Lys Ala
        115

<210> SEQ ID NO 8
<211> LENGTH: 194
<212> TYPE: PRT
<213> ORGANISM: Artificial Sequence
<220> FEATURE:
<223> OTHER INFORMATION: 919.pep

<400> SEQUENCE: 8

Ala Leu Asp Gly Lys Ala Pro Ile Leu Gly Tyr Ala Glu Asp Pro Val
1               5                   10                  15

Glu Leu Phe Phe Met His Ile Gln Gly Ser Gly Arg Leu Lys Thr Pro
            20                  25                  30

Ser Gly Lys Tyr Ile Arg Ile Gly Tyr Ala Asp Lys Asn Glu His Pro
        35                  40                  45

Tyr Val Ser Ile Gly Arg Tyr Met Ala Asp Lys Gly Tyr Leu Lys Leu
    50                  55                  60

Gly Gln Thr Ser Met Gln Gly Ile Lys Ser Tyr Met Arg Gln Asn Pro
65                  70                  75                  80

Gln Arg Leu Ala Glu Val Leu Gly Gln Asn Pro Ser Tyr Ile Phe Phe
                85                  90                  95

Arg Glu Leu Ala Gly Ser Ser Asn Asp Gly Pro Val Gly Ala Leu Gly
                100                 105                 110

Thr Pro Leu Met Gly Glu Tyr Ala Gly Ala Val Asp Arg His Tyr Ile
                115                 120                 125

Thr Leu Gly Ala Pro Leu Phe Val Ala Thr Ala His Pro Val Thr Arg
            130                 135                 140

Lys Ala Leu Asn Arg Leu Ile Met Ala Gln Asp Thr Gly Ser Ala Ile
```

```
              145                 150                 155                 160
Lys Gly Ala Val Arg Val Asp Tyr Phe Trp Gly Tyr Gly Asp Glu Ala
                165                 170                 175
Gly Glu Leu Ala Gly Lys Gln Lys Thr Thr Gly Tyr Val Trp Gln Leu
            180                 185                 190
Leu Pro

<210> SEQ ID NO 9
<211> LENGTH: 196
<212> TYPE: PRT
<213> ORGANISM: Escherichia coli

<400> SEQUENCE: 9

Ala Leu Ser Asp Lys Tyr Ile Leu Ala Tyr Ser Asn Ser Leu Met Asp
1               5                   10                  15
Asn Phe Ile Met Asp Val Gln Gly Ser Gly Tyr Ile Asp Phe Gly Asp
                20                  25                  30
Gly Ser Pro Leu Asn Phe Phe Ser Tyr Ala Gly Lys Asn Gly His Ala
            35                  40                  45
Tyr Arg Ser Ile Gly Lys Val Leu Ile Asp Arg Gly Glu Val Lys Lys
50                  55                  60
Glu Asp Met Ser Met Gln Ala Ile Arg His Trp Gly Glu Thr His Ser
65                  70                  75                  80
Glu Ala Glu Val Arg Glu Leu Leu Glu Gln Asn Pro Ser Phe Val Phe
                85                  90                  95
Phe Lys Pro Gln Ser Phe Ala Pro Val Lys Gly Ala Ser Ala Val Pro
            100                 105                 110
Leu Val Gly Arg Ala Ser Val Ala Ser Asp Arg Ser Ile Ile Pro Pro
        115                 120                 125
Gly Thr Thr Leu Leu Ala Glu Val Pro Leu Leu Asp Asn Asn Gly Lys
130                 135                 140
Phe Asn Gly Gln Tyr Glu Leu Arg Leu Met Val Ala Leu Asp Val Gly
145                 150                 155                 160
Gly Ala Ile Lys Gly Gln His Phe Asp Ile Tyr Gln Gly Ile Gly Pro
                165                 170                 175
Glu Ala Gly His Arg Ala Gly Trp Tyr Asn His Tyr Gly Arg Val Trp
            180                 185                 190
Val Leu Lys Thr
        195

<210> SEQ ID NO 10
<211> LENGTH: 28
<212> TYPE: DNA
<213> ORGANISM: Artificial Sequence
<220> FEATURE:
<223> OTHER INFORMATION: Oligonucleotide

<400> SEQUENCE: 10
cgaagacccc gtcggtcttt tttttatg                                          28

<210> SEQ ID NO 11
<211> LENGTH: 28
<212> TYPE: DNA
<213> ORGANISM: Artificial Sequence
<220> FEATURE:
<223> OTHER INFORMATION: Oligonucleotide

<400> SEQUENCE: 11
gtgcataaaa aaaagaccga cggggtct                                          28
```

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide

<400> SEQUENCE: 12
aacgcctcgc cggtgttttg ggtca                                      25

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide

<400> SEQUENCE: 13
tttgacccaa acaccggcg aggcg                                       25

<210> SEQ ID NO 14
<211> LENGTH: 26
<212> TYPE: DNA
<213> ORGANISM: Artificial Sequence
<220> FEATURE:
<223> OTHER INFORMATION: Oligonucleotide

<400> SEQUENCE: 14
tgccggcgca gtcggtcggc actaca                                     26

<210> SEQ ID NO 15
<211> LENGTH: 26
<212> TYPE: DNA
<213> ORGANISM: Artificial Sequence
<220> FEATURE:
<223> OTHER INFORMATION: Oligonucleotide

<400> SEQUENCE: 15
taatgtagtg ccgaccgact gcgccg                                     26

<210> SEQ ID NO 16
<211> LENGTH: 25
<212> TYPE: DNA
<213> ORGANISM: Artificial Sequence
<220> FEATURE:
<223> OTHER INFORMATION: Oligonucleotide

<400> SEQUENCE: 16
tgattgaggt gggtagcgcg ttccg                                      25

<210> SEQ ID NO 17
<211> LENGTH: 25
<212> TYPE: DNA
<213> ORGANISM: Artificial Sequence
<220> FEATURE:
<223> OTHER INFORMATION: Oligonucleotide

<400> SEQUENCE: 17
ggcggaacgc gctacccacc tcaat                                      25

<210> SEQ ID NO 18
<211> LENGTH: 34
<212> TYPE: DNA
<213> ORGANISM: Artificial Sequence
<220> FEATURE:
<223> OTHER INFORMATION: Oligonucleotide

<400> SEQUENCE: 18
ccggaattct tatgaaaaaa atcatcttcg ccgc                                34

<210> SEQ ID NO 19
<211> LENGTH: 32
<212> TYPE: DNA
<213> ORGANISM: Artificial Sequence
<220> FEATURE:
<223> OTHER INFORMATION: Oligonucleotide

<400> SEQUENCE: 19
gcccaagctt ttattgtttg gctgcctcga tt                                  32

<210> SEQ ID NO 20
<211> LENGTH: 37
<212> TYPE: DNA
<213> ORGANISM: Artificial Sequence
<220> FEATURE:
<223> OTHER INFORMATION: Oligonucleotide

<400> SEQUENCE: 20
ccggaattct tatgtcgccc gatgttaaat cggcgga                             37

<210> SEQ ID NO 21
<211> LENGTH: 32
<212> TYPE: DNA
<213> ORGANISM: Artificial Sequence
<220> FEATURE:
<223> OTHER INFORMATION: Oligonucleotide

<400> SEQUENCE: 21
gcccaagctt tcaatcctgc tcttttttgc cg                                  32

<210> SEQ ID NO 22
<211> LENGTH: 34
<212> TYPE: DNA
<213> ORGANISM: Artificial Sequence
<220> FEATURE:
<223> OTHER INFORMATION: Oligonucleotide

<400> SEQUENCE: 22
ccggaattct tatgagccaa gatatggcgg cagt                                34

<210> SEQ ID NO 23
<211> LENGTH: 32
<212> TYPE: DNA
<213> ORGANISM: Artificial Sequence
<220> FEATURE:
<223> OTHER INFORMATION: Oligonucleotide

<400> SEQUENCE: 23
gcccaagctt tcaatcctgc tcttttttgc cg                                  32

<210> SEQ ID NO 24
<211> LENGTH: 34
<212> TYPE: DNA
<213> ORGANISM: Artificial Sequence
<220> FEATURE:
<223> OTHER INFORMATION: Oligonucleotide

<400> SEQUENCE: 24
ccggaattct tatgtccgcc gaatccgcaa atca                                34

<210> SEQ ID NO 25
<211> LENGTH: 32

```
<212> TYPE: DNA
<213> ORGANISM: Artificial Sequence
<220> FEATURE:
<223> OTHER INFORMATION: Oligonucleotide

<400> SEQUENCE: 25
gcccaagctt tcaatcctgc tcttttttgc cg                              32

<210> SEQ ID NO 26
<211> LENGTH: 36
<212> TYPE: DNA
<213> ORGANISM: Artificial Sequence
<220> FEATURE:
<223> OTHER INFORMATION: Oligonucleotide

<400> SEQUENCE: 26
ccggaattct tatgggaagg gttgatttgg ctaatg                          36

<210> SEQ ID NO 27
<211> LENGTH: 32
<212> TYPE: DNA
<213> ORGANISM: Artificial Sequence
<220> FEATURE:
<223> OTHER INFORMATION: Oligonucleotide

<400> SEQUENCE: 27
gcccaagctt tcaatcctgc tcttttttgc cg                              32

<210> SEQ ID NO 28
<211> LENGTH: 36
<212> TYPE: DNA
<213> ORGANISM: Artificial Sequence
<220> FEATURE:
<223> OTHER INFORMATION: Oligonucleotide

<400> SEQUENCE: 28
ccggaattct tatgtcagat ttggcaaacg attctt                          36

<210> SEQ ID NO 29
<211> LENGTH: 35
<212> TYPE: DNA
<213> ORGANISM: Artificial Sequence
<220> FEATURE:
<223> OTHER INFORMATION: Oligonucleotide

<400> SEQUENCE: 29
gcccaagctt ttacgtatca tatttcacgt gcttc                           35

<210> SEQ ID NO 30
<211> LENGTH: 37
<212> TYPE: DNA
<213> ORGANISM: Artificial Sequence
<220> FEATURE:
<223> OTHER INFORMATION: Oligonucleotide

<400> SEQUENCE: 30
ccggaattct tatgtcgccc gatgttaaat cggcgga                         37

<210> SEQ ID NO 31
<211> LENGTH: 35
<212> TYPE: DNA
<213> ORGANISM: Artificial Sequence
<220> FEATURE:
<223> OTHER INFORMATION: Oligonucleotide

<400> SEQUENCE: 31
gcccaagctt ttacgtatca tatttcacgt gcttc                           35
```

<210> SEQ ID NO 32
<211> LENGTH: 36
<212> TYPE: DNA
<213> ORGANISM: Artificial Sequence
<220> FEATURE:
<223> OTHER INFORMATION: Oligonucleotide

<400> SEQUENCE: 32
ccggaattct tatgcaaagc aagagcatcc aaacct                         36

<210> SEQ ID NO 33
<211> LENGTH: 30
<212> TYPE: DNA
<213> ORGANISM: Artificial Sequence
<220> FEATURE:
<223> OTHER INFORMATION: Oligonucleotide

<400> SEQUENCE: 33
gcccaagctt ttacgggcgg tattcgggct                                30

<210> SEQ ID NO 34
<211> LENGTH: 29
<212> TYPE: DNA
<213> ORGANISM: Artificial Sequence
<220> FEATURE:
<223> OTHER INFORMATION: Oligonucleotide

<400> SEQUENCE: 34
ccggaattca tatgaaacac tttccatcc                                 29

<210> SEQ ID NO 35
<211> LENGTH: 28
<212> TYPE: DNA
<213> ORGANISM: Artificial Sequence
<220> FEATURE:
<223> OTHER INFORMATION: Oligonucleotide

<400> SEQUENCE: 35
gcccaagctt ttaccactcg taattgac                                  28

<210> SEQ ID NO 36
<211> LENGTH: 29
<212> TYPE: DNA
<213> ORGANISM: Artificial Sequence
<220> FEATURE:
<223> OTHER INFORMATION: Oligonucleotide

<400> SEQUENCE: 36
ccggaattca tatggccaca agcgacgac                                 29

<210> SEQ ID NO 37
<211> LENGTH: 28
<212> TYPE: DNA
<213> ORGANISM: Artificial Sequence
<220> FEATURE:
<223> OTHER INFORMATION: Oligonucleotide

<400> SEQUENCE: 37
gcccaagctt ttaccactcg taattgac                                  28

<210> SEQ ID NO 38
<211> LENGTH: 29
<212> TYPE: DNA
<213> ORGANISM: Artificial Sequence
<220> FEATURE:
<223> OTHER INFORMATION: Oligonucleotide

```
<400> SEQUENCE: 38
ccggaattct tatgaaacac tttccatcc                                      29

<210> SEQ ID NO 39
<211> LENGTH: 31
<212> TYPE: DNA
<213> ORGANISM: Artificial Sequence
<220> FEATURE:
<223> OTHER INFORMATION: Oligonucleotide

<400> SEQUENCE: 39
gcccaagctt tcaacccacg ttgtaaggtt g                                   31

<210> SEQ ID NO 40
<211> LENGTH: 30
<212> TYPE: DNA
<213> ORGANISM: Artificial Sequence
<220> FEATURE:
<223> OTHER INFORMATION: Oligonucleotide

<400> SEQUENCE: 40
ccggaattct tatggccaca aacgacgacg                                     30

<210> SEQ ID NO 41
<211> LENGTH: 31
<212> TYPE: DNA
<213> ORGANISM: Artificial Sequence
<220> FEATURE:
<223> OTHER INFORMATION: Oligonucleotide

<400> SEQUENCE: 41
gcccaagctt tcaacccacg ttgtaaggtt g                                   31

<210> SEQ ID NO 42
<211> LENGTH: 34
<212> TYPE: DNA
<213> ORGANISM: Artificial Sequence
<220> FEATURE:
<223> OTHER INFORMATION: Oligonucleotide

<400> SEQUENCE: 42
ccggaattct tatggccacc tacaaagtgg acga                                34

<210> SEQ ID NO 43
<211> LENGTH: 32
<212> TYPE: DNA
<213> ORGANISM: Artificial Sequence
<220> FEATURE:
<223> OTHER INFORMATION: Oligonucleotide

<400> SEQUENCE: 43
gcccaagctt ttattgtttg gctgcctcga tt                                  32

<210> SEQ ID NO 44
<211> LENGTH: 32
<212> TYPE: DNA
<213> ORGANISM: Artificial Sequence
<220> FEATURE:
<223> OTHER INFORMATION: Oligonucleotide

<400> SEQUENCE: 44
cgcggatccg ctagccccga tgttaaatcg gc                                  32

<210> SEQ ID NO 45
<211> LENGTH: 31
```

```
<212> TYPE: DNA
<213> ORGANISM: Artificial Sequence
<220> FEATURE:
<223> OTHER INFORMATION: Oligonucleotide

<400> SEQUENCE: 45
cccgctcgag tcaatcctgc tctttttgc c                              31

<210> SEQ ID NO 46
<211> LENGTH: 32
<212> TYPE: DNA
<213> ORGANISM: Artificial Sequence
<220> FEATURE:
<223> OTHER INFORMATION: Oligonucleotide

<400> SEQUENCE: 46
cgcggatccg ctagccaaga tatggcggca gt                            32

<210> SEQ ID NO 47
<211> LENGTH: 32
<212> TYPE: DNA
<213> ORGANISM: Artificial Sequence
<220> FEATURE:
<223> OTHER INFORMATION: Oligonucleotide

<400> SEQUENCE: 47
cgcggatccg ctagcgccga atccgcaaat ca                            32

<210> SEQ ID NO 48
<211> LENGTH: 32
<212> TYPE: DNA
<213> ORGANISM: Artificial Sequence
<220> FEATURE:
<223> OTHER INFORMATION: Oligonucleotide

<400> SEQUENCE: 48
cgcgctagcg aagggttga tttggctaat gg                             32

<210> SEQ ID NO 49
<211> LENGTH: 34
<212> TYPE: DNA
<213> ORGANISM: Artificial Sequence
<220> FEATURE:
<223> OTHER INFORMATION: Oligonucleotide

<400> SEQUENCE: 49
gggaattcca tatgggcatt tcccgcaaaa tatc                          34

<210> SEQ ID NO 50
<211> LENGTH: 32
<212> TYPE: DNA
<213> ORGANISM: Artificial Sequence
<220> FEATURE:
<223> OTHER INFORMATION: Oligonucleotide

<400> SEQUENCE: 50
cccgctcgag ttacgtatca tatttcacgt gc                            32

<210> SEQ ID NO 51
<211> LENGTH: 34
<212> TYPE: DNA
<213> ORGANISM: Artificial Sequence
<220> FEATURE:
<223> OTHER INFORMATION: Oligonucleotide

<400> SEQUENCE: 51
gggaattcca tatgggcatt tcccgcaaaa tatc                          34
```

<210> SEQ ID NO 52
<211> LENGTH: 33
<212> TYPE: DNA
<213> ORGANISM: Artificial Sequence
<220> FEATURE:
<223> OTHER INFORMATION: Oligonucleotide

<400> SEQUENCE: 52
cccgctcgag ttattctatg ccttgtgcgg cat                          33

<210> SEQ ID NO 53
<211> LENGTH: 32
<212> TYPE: DNA
<213> ORGANISM: Artificial Sequence
<220> FEATURE:
<223> OTHER INFORMATION: Oligonucleotide

<400> SEQUENCE: 53
cgcggatccc atatggccac aagcgacgac ga                           32

<210> SEQ ID NO 54
<211> LENGTH: 28
<212> TYPE: DNA
<213> ORGANISM: Artificial Sequence
<220> FEATURE:
<223> OTHER INFORMATION: Oligonucleotide

<400> SEQUENCE: 54
cccgctcgag ttaccactcg taattgac                                28

<210> SEQ ID NO 55
<211> LENGTH: 28
<212> TYPE: DNA
<213> ORGANISM: Artificial Sequence
<220> FEATURE:
<223> OTHER INFORMATION: Oligonucleotide

<400> SEQUENCE: 55
cgcggatccc atatggccac aaacgacg                                28

<210> SEQ ID NO 56
<211> LENGTH: 35
<212> TYPE: DNA
<213> ORGANISM: Artificial Sequence
<220> FEATURE:
<223> OTHER INFORMATION: Oligonucleotide

<400> SEQUENCE: 56
cccgctcgag tcatttagca atattatctt tgttc                        35

<210> SEQ ID NO 57
<211> LENGTH: 33
<212> TYPE: DNA
<213> ORGANISM: Artificial Sequence
<220> FEATURE:
<223> OTHER INFORMATION: Oligonucleotide

<400> SEQUENCE: 57
cgcggatccc atatgaaagc aaacagtgcc gac                          33

<210> SEQ ID NO 58
<211> LENGTH: 28
<212> TYPE: DNA
<213> ORGANISM: Artificial Sequence
<220> FEATURE:
<223> OTHER INFORMATION: Oligonucleotide

```
<400> SEQUENCE: 58
cccgctcgag ttaccactcg taattgac                                              28

<210> SEQ ID NO 59
<211> LENGTH: 28
<212> TYPE: DNA
<213> ORGANISM: Artificial Sequence
<220> FEATURE:
<223> OTHER INFORMATION: Oligonucleotide

<400> SEQUENCE: 59
cgcggatccc atatggccac aaacgacg                                              28

<210> SEQ ID NO 60
<211> LENGTH: 29
<212> TYPE: DNA
<213> ORGANISM: Artificial Sequence
<220> FEATURE:
<223> OTHER INFORMATION: Oligonucleotide

<400> SEQUENCE: 60
cccgctcgag ttaacccacg ttgtaaggt                                             29

<210> SEQ ID NO 61
<211> LENGTH: 33
<212> TYPE: DNA
<213> ORGANISM: Artificial Sequence
<220> FEATURE:
<223> OTHER INFORMATION: Oligonucleotide

<400> SEQUENCE: 61
cgcggatccc atatgatgaa acactttcca tcc                                        33

<210> SEQ ID NO 62
<211> LENGTH: 29
<212> TYPE: DNA
<213> ORGANISM: Artificial Sequence
<220> FEATURE:
<223> OTHER INFORMATION: Oligonucleotide

<400> SEQUENCE: 62
cccgctcgag ttaacccacg ttgtaaggt                                             29

<210> SEQ ID NO 63
<211> LENGTH: 28
<212> TYPE: DNA
<213> ORGANISM: Artificial Sequence
<220> FEATURE:
<223> OTHER INFORMATION: Oligonucleotide

<400> SEQUENCE: 63
cgcggatccc atatggccac aaacgacg                                              28

<210> SEQ ID NO 64
<211> LENGTH: 32
<212> TYPE: DNA
<213> ORGANISM: Artificial Sequence
<220> FEATURE:
<223> OTHER INFORMATION: Oligonucleotide

<400> SEQUENCE: 64
cccgctcgag tcagtctgac actgttttat cc                                         32

<210> SEQ ID NO 65
<211> LENGTH: 32
```

-continued

<212> TYPE: DNA
<213> ORGANISM: Artificial Sequence
<220> FEATURE:
<223> OTHER INFORMATION: Oligonucleotide

<400> SEQUENCE: 65
cgcggatccg ctagccccga tgttaaatcg gc 32

<210> SEQ ID NO 66
<211> LENGTH: 27
<212> TYPE: DNA
<213> ORGANISM: Artificial Sequence
<220> FEATURE:
<223> OTHER INFORMATION: Oligonucleotide

<400> SEQUENCE: 66
cccgctcgag ttacgggcgg tattcgg 27

<210> SEQ ID NO 67
<211> LENGTH: 32
<212> TYPE: DNA
<213> ORGANISM: Artificial Sequence
<220> FEATURE:
<223> OTHER INFORMATION: Oligonucleotide

<400> SEQUENCE: 67
cgcggatccg ctagccccga tgttaaatcg gc 32

<210> SEQ ID NO 68
<211> LENGTH: 32
<212> TYPE: DNA
<213> ORGANISM: Artificial Sequence
<220> FEATURE:
<223> OTHER INFORMATION: Oligonucleotide

<400> SEQUENCE: 68
cccgctcgag ttacgtatca tatttcacgt gc 32

<210> SEQ ID NO 69
<211> LENGTH: 32
<212> TYPE: DNA
<213> ORGANISM: Artificial Sequence
<220> FEATURE:
<223> OTHER INFORMATION: Oligonucleotide

<400> SEQUENCE: 69
cgcggatccg ctagccccga tgttaaatcg gc 32

<210> SEQ ID NO 70
<211> LENGTH: 28
<212> TYPE: DNA
<213> ORGANISM: Artificial Sequence
<220> FEATURE:
<223> OTHER INFORMATION: Oligonucleotide

<400> SEQUENCE: 70
cccgctcgag ttaccactcg taattgac 28

<210> SEQ ID NO 71
<211> LENGTH: 1457
<212> TYPE: PRT
<213> ORGANISM: Neisseria meningitidis

<400> SEQUENCE: 71

Met Lys Thr Thr Asp Lys Arg Thr Thr Glu Thr His Arg Lys Ala Pro
1 5 10 15

-continued

```
Lys Thr Gly Arg Ile Arg Phe Ser Pro Ala Tyr Leu Ala Ile Cys Leu
            20                  25                  30
Ser Phe Gly Ile Leu Pro Gln Ala Trp Ala Gly His Thr Tyr Phe Gly
        35                  40                  45
Ile Asn Tyr Gln Tyr Tyr Arg Asp Phe Ala Glu Asn Lys Gly Lys Phe
    50                  55                  60
Ala Val Gly Ala Lys Asp Ile Glu Val Tyr Asn Lys Lys Gly Glu Leu
65                  70                  75                  80
Val Gly Lys Ser Met Thr Lys Ala Pro Met Ile Asp Phe Ser Val Val
                85                  90                  95
Ser Arg Asn Gly Val Ala Ala Leu Val Gly Asp Gln Tyr Ile Val Ser
            100                 105                 110
Val Ala His Asn Gly Gly Tyr Asn Asn Val Asp Phe Gly Ala Glu Gly
        115                 120                 125
Arg Asn Pro Asp Gln His Arg Phe Thr Tyr Lys Ile Val Lys Arg Asn
    130                 135                 140
Asn Tyr Lys Ala Gly Thr Lys Gly His Pro Tyr Gly Gly Asp Tyr His
145                 150                 155                 160
Met Pro Arg Leu His Lys Phe Val Thr Asp Ala Glu Pro Val Glu Met
                165                 170                 175
Thr Ser Tyr Met Asp Gly Arg Lys Tyr Ile Asp Gln Asn Asn Tyr Pro
            180                 185                 190
Asp Arg Val Arg Ile Gly Ala Gly Arg Gln Tyr Trp Arg Ser Asp Glu
        195                 200                 205
Asp Glu Pro Asn Asn Arg Glu Ser Ser Tyr His Ile Ala Ser Ala Tyr
    210                 215                 220
Ser Trp Leu Val Gly Gly Asn Thr Phe Ala Gln Asn Gly Ser Gly Gly
225                 230                 235                 240
Gly Thr Val Asn Leu Gly Ser Glu Lys Ile Lys His Ser Pro Tyr Gly
                245                 250                 255
Phe Leu Pro Thr Gly Gly Ser Phe Gly Asp Ser Gly Ser Pro Met Phe
            260                 265                 270
Ile Tyr Asp Ala Gln Lys Gln Lys Trp Leu Ile Asn Gly Val Leu Gln
        275                 280                 285
Thr Gly Asn Pro Tyr Ile Gly Lys Ser Asn Gly Phe Gln Leu Val Arg
    290                 295                 300
Lys Asp Trp Phe Tyr Asp Glu Ile Phe Ala Gly Asp Thr His Ser Val
305                 310                 315                 320
Phe Tyr Glu Pro Arg Gln Asn Gly Lys Tyr Ser Phe Asn Asp Asp Asn
                325                 330                 335
Asn Gly Thr Gly Lys Ile Asn Ala Lys His Glu His Asn Ser Leu Pro
            340                 345                 350
Asn Arg Leu Lys Thr Arg Thr Val Gln Leu Phe Asn Val Ser Leu Ser
        355                 360                 365
Glu Thr Ala Arg Glu Pro Val Tyr His Ala Ala Gly Val Asn Ser
    370                 375                 380
Tyr Arg Pro Arg Leu Asn Asn Gly Glu Asn Ile Ser Phe Ile Asp Glu
385                 390                 395                 400
Gly Lys Gly Glu Leu Ile Leu Thr Ser Asn Ile Asn Gln Gly Ala Gly
                405                 410                 415
Gly Leu Tyr Phe Gln Gly Asp Phe Thr Val Ser Pro Glu Asn Asn Glu
            420                 425                 430
Thr Trp Gln Gly Ala Gly Val His Ile Ser Glu Asp Ser Thr Val Thr
        435                 440                 445
```

```
Trp Lys Val Asn Gly Val Ala Asn Asp Arg Leu Ser Lys Ile Gly Lys
    450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Asp Lys Gly
                485                 490                 495

Lys Lys Gln Ala Phe Ser Glu Ile Gly Leu Val Ser Gly Arg Gly Thr
                500                 505                 510

Val Gln Leu Asn Ala Asp Asn Gln Phe Asn Pro Asp Lys Leu Tyr Phe
                515                 520                 525

Gly Phe Arg Gly Gly Arg Leu Asp Leu Asn Gly His Ser Leu Ser Phe
530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Asn Ser Leu Asp Ser Lys Lys Glu Ile Ala Tyr
                580                 585                 590

Asn Gly Trp Phe Gly Glu Lys Asp Thr Thr Lys Thr Asn Gly Arg Leu
                595                 600                 605

Asn Leu Val Tyr Gln Pro Ala Ala Glu Asp Arg Thr Leu Leu Leu Ser
            610                 615                 620

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Asn Asp
                    645                 650                 655

His Trp Ser Gln Lys Glu Gly Ile Pro Arg Gly Glu Ile Val Trp Asp
                660                 665                 670

Asn Asp Trp Ile Asn Arg Thr Phe Lys Ala Glu Asn Phe Gln Ile Lys
                675                 680                 685

Gly Gly Gln Ala Val Val Ser Arg Asn Val Ala Lys Val Lys Gly Asp
690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
                725                 730                 735

Cys Val Glu Lys Thr Ile Thr Asp Asp Lys Val Ile Ala Ser Leu Thr
                740                 745                 750

Lys Thr Asp Ile Ser Gly Asn Val Asp Leu Ala Asp His Ala His Leu
            755                 760                 765

Asn Leu Thr Gly Leu Ala Thr Leu Asn Gly Asn Leu Ser Ala Asn Gly
        770                 775                 780

Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asp His
                820                 825                 830

Ala Val Gln Asn Gly Ser Leu Thr Leu Ser Gly Asn Ala Lys Ala Asn
            835                 840                 845

Val Ser His Ser Ala Leu Asn Gly Asn Val Ser Leu Ala Asp Lys Ala
        850                 855                 860

Val Phe His Phe Glu Ser Ser Arg Phe Thr Gly Gln Ile Ser Gly Gly
```

```
                865                 870                 875                 880
Lys Asp Thr Ala Leu His Leu Lys Asp Ser Glu Trp Thr Leu Pro Ser
                    885                 890                 895
Gly Thr Glu Leu Gly Asn Leu Asn Leu Asp Asn Ala Thr Ile Thr Leu
                    900                 905                 910
Asn Ser Ala Tyr Arg His Asp Ala Ala Gly Ala Gln Thr Gly Ser Ala
                    915                 920                 925
Thr Asp Ala Pro Arg Arg Ser Arg Arg Ser Arg Arg Ser Leu Leu
                    930                 935                 940
Ser Val Thr Pro Pro Thr Ser Val Glu Ser Arg Phe Asn Thr Leu Thr
945                 950                 955                 960
Val Asn Gly Lys Leu Asn Gly Gln Gly Thr Phe Arg Phe Met Ser Glu
                    965                 970                 975
Leu Phe Gly Tyr Arg Ser Asp Lys Leu Lys Leu Ala Glu Ser Ser Glu
                    980                 985                 990
Gly Thr Tyr Thr Leu Ala Val Asn Asn Thr Gly Asn Glu Pro Ala Ser
                    995                 1000                1005
Leu Glu Gln Leu Thr Val Val Glu Gly Lys Asp Asn Lys Pro Leu Ser
                    1010                1015                1020
Glu Asn Leu Asn Phe Thr Leu Gln Asn Glu His Val Asp Ala Gly Ala
1025                1030                1035                1040
Trp Arg Tyr Gln Leu Ile Arg Lys Asp Gly Glu Phe Arg Leu His Asn
                    1045                1050                1055
Pro Val Lys Glu Gln Glu Leu Ser Asp Lys Leu Gly Lys Ala Glu Ala
                    1060                1065                1070
Lys Lys Gln Ala Glu Lys Asp Asn Ala Gln Ser Leu Asp Ala Leu Ile
                    1075                1080                1085
Ala Ala Gly Arg Asp Ala Val Glu Lys Thr Glu Ser Val Ala Glu Pro
                    1090                1095                1100
Ala Arg Gln Ala Gly Gly Glu Asn Val Gly Ile Met Gln Ala Glu Glu
1105                1110                1115                1120
Glu Lys Lys Arg Val Gln Ala Asp Lys Asp Thr Ala Leu Ala Lys Gln
                    1125                1130                1135
Arg Glu Ala Glu Thr Arg Pro Ala Thr Thr Ala Phe Pro Arg Ala Arg
                    1140                1145                1150
Arg Ala Arg Arg Asp Leu Pro Gln Leu Gln Pro Gln Pro Gln Pro Gln
                    1155                1160                1165
Pro Gln Arg Asp Leu Ile Ser Arg Tyr Ala Asn Ser Gly Leu Ser Glu
                    1170                1175                1180
Phe Ser Ala Thr Leu Asn Ser Val Phe Ala Val Gln Asp Glu Leu Asp
1185                1190                1195                1200
Arg Val Phe Ala Glu Asp Arg Arg Asn Ala Val Trp Thr Ser Gly Ile
                    1205                1210                1215
Arg Asp Thr Lys His Tyr Arg Ser Gln Asp Phe Arg Ala Tyr Arg Gln
                    1220                1225                1230
Gln Thr Asp Leu Arg Gln Ile Gly Met Gln Lys Asn Leu Gly Ser Gly
                    1235                1240                1245
Arg Val Gly Ile Leu Phe Ser His Asn Arg Thr Glu Asn Thr Phe Asp
                    1250                1255                1260
Asp Gly Ile Gly Asn Ser Ala Arg Leu Ala His Gly Ala Val Phe Gly
1265                1270                1275                1280
Gln Tyr Gly Ile Asp Arg Phe Tyr Ile Gly Ile Ser Ala Gly Ala Gly
                    1285                1290                1295
```

```
Phe Ser Ser Gly Ser Leu Ser Asp Gly Ile Gly Gly Lys Ile Arg Arg
            1300                1305                1310

Arg Val Leu His Tyr Gly Ile Gln Ala Arg Tyr Arg Ala Gly Phe Gly
        1315                1320                1325

Gly Phe Gly Ile Glu Pro His Ile Gly Ala Thr Arg Tyr Phe Val Gln
    1330                1335                1340

Lys Ala Asp Tyr Arg Tyr Glu Asn Val Asn Ile Ala Thr Pro Gly Leu
1345                1350                1355                1360

Ala Phe Asn Arg Tyr Arg Ala Gly Ile Lys Ala Asp Tyr Ser Phe Lys
            1365                1370                1375

Pro Ala Gln His Ile Ser Ile Thr Pro Tyr Leu Ser Leu Ser Tyr Thr
        1380                1385                1390

Asp Ala Ala Ser Gly Lys Val Arg Thr Arg Val Asn Thr Ala Val Leu
    1395                1400                1405

Ala Gln Asp Phe Gly Lys Thr Arg Ser Ala Glu Trp Gly Val Asn Ala
1410                1415                1420

Glu Ile Lys Gly Phe Thr Leu Ser Leu His Ala Ala Ala Lys Gly
1425                1430                1435                1440

Pro Gln Leu Glu Ala Gln His Ser Ala Gly Ile Lys Leu Gly Tyr Arg
            1445                1450                1455

Trp
```

```
<210> SEQ ID NO 72
<211> LENGTH: 21
<212> TYPE: PRT
<213> ORGANISM: Escherichia coli

<400> SEQUENCE: 72

Met Lys Lys Thr Ala Ile Ala Ile Ala Val Ala Leu Ala Gly Phe Ala
1               5                   10                  15

Thr Val Ala Gln Ala
            20
```

```
<210> SEQ ID NO 73
<211> LENGTH: 1439
<212> TYPE: PRT
<213> ORGANISM: Neisseria meningitidis

<400> SEQUENCE: 73

Met Lys Lys Thr Ala Ile Ala Ile Ala Val Ala Leu Ala Gly Phe Ala
1               5                   10                  15

Thr Val Ala Gln Ala Ala Ser Ala Gly His Thr Tyr Phe Gly Ile Asn
            20                  25                  30

Tyr Gln Tyr Tyr Arg Asp Phe Ala Glu Asn Lys Gly Lys Phe Ala Val
        35                  40                  45

Gly Ala Lys Asp Ile Glu Val Tyr Asn Lys Lys Gly Glu Leu Val Gly
    50                  55                  60

Lys Ser Met Thr Lys Ala Pro Met Ile Asp Phe Ser Val Val Ser Arg
65                  70                  75                  80

Asn Gly Val Ala Ala Leu Val Gly Asp Gln Tyr Ile Val Ser Val Ala
                85                  90                  95

His Asn Gly Gly Tyr Asn Asn Val Asp Phe Gly Ala Glu Gly Arg Asn
            100                 105                 110

Pro Asp Gln His Arg Phe Thr Tyr Lys Ile Val Lys Arg Asn Asn Tyr
        115                 120                 125

Lys Ala Gly Thr Lys Gly His Pro Tyr Gly Gly Asp Tyr His Met Pro
    130                 135                 140
```

-continued

```
Arg Leu His Lys Phe Val Thr Asp Ala Glu Pro Val Glu Met Thr Ser
145                 150                 155                 160

Tyr Met Asp Gly Arg Lys Tyr Ile Asp Gln Asn Asn Tyr Pro Asp Arg
            165                 170                 175

Val Arg Ile Gly Ala Gly Arg Gln Tyr Trp Arg Ser Asp Glu Asp Glu
        180                 185                 190

Pro Asn Asn Arg Glu Ser Ser Tyr His Ile Ala Ser Ala Tyr Ser Trp
            195                 200                 205

Leu Val Gly Gly Asn Thr Phe Ala Gln Asn Gly Ser Gly Gly Gly Thr
210                 215                 220

Val Asn Leu Gly Ser Glu Lys Ile Lys His Ser Pro Tyr Gly Phe Leu
225                 230                 235                 240

Pro Thr Gly Gly Ser Phe Gly Asp Ser Gly Ser Pro Met Phe Ile Tyr
                245                 250                 255

Asp Ala Gln Lys Gln Lys Trp Leu Ile Asn Gly Val Leu Gln Thr Gly
            260                 265                 270

Asn Pro Tyr Ile Gly Lys Ser Asn Gly Phe Gln Leu Val Arg Lys Asp
        275                 280                 285

Trp Phe Tyr Asp Glu Ile Phe Ala Gly Asp Thr His Ser Val Phe Tyr
        290                 295                 300

Glu Pro Arg Gln Asn Gly Lys Tyr Ser Phe Asn Asp Asp Asn Asn Gly
305                 310                 315                 320

Thr Gly Lys Ile Asn Ala Lys His Glu His Asn Ser Leu Pro Asn Arg
                325                 330                 335

Leu Lys Thr Arg Thr Val Gln Leu Phe Asn Val Ser Leu Ser Glu Thr
            340                 345                 350

Ala Arg Glu Pro Val Tyr His Ala Ala Gly Val Asn Ser Tyr Arg
        355                 360                 365

Pro Arg Leu Asn Asn Gly Glu Asn Ile Ser Phe Ile Asp Glu Gly Lys
370                 375                 380

Gly Glu Leu Ile Leu Thr Ser Asn Ile Asn Gln Gly Ala Gly Gly Leu
385                 390                 395                 400

Tyr Phe Gln Gly Asp Phe Thr Val Ser Pro Glu Asn Asn Glu Thr Trp
                405                 410                 415

Gln Gly Ala Gly Val His Ile Ser Glu Asp Ser Thr Val Thr Trp Lys
            420                 425                 430

Val Asn Gly Val Ala Asn Asp Arg Leu Ser Lys Ile Gly Lys Gly Thr
        435                 440                 445

Leu His Val Gln Ala Lys Gly Glu Asn Gln Gly Ser Ile Ser Val Gly
450                 455                 460

Asp Gly Thr Val Ile Leu Asp Gln Gln Ala Asp Asp Lys Gly Lys Lys
465                 470                 475                 480

Gln Ala Phe Ser Glu Ile Gly Leu Val Ser Gly Arg Gly Thr Val Gln
                485                 490                 495

Leu Asn Ala Asp Asn Gln Phe Asn Pro Asp Lys Leu Tyr Phe Gly Phe
            500                 505                 510

Arg Gly Gly Arg Leu Asp Leu Asn Gly His Ser Leu Ser Phe His Arg
        515                 520                 525

Ile Gln Asn Thr Asp Glu Gly Ala Met Ile Val Asn His Asn Gln Asp
        530                 535                 540

Lys Glu Ser Thr Val Thr Ile Thr Gly Asn Lys Asp Ile Ala Thr Thr
545                 550                 555                 560

Gly Asn Asn Asn Ser Leu Asp Ser Lys Lys Glu Ile Ala Tyr Asn Gly
```

```
                    565                 570                 575
Trp Phe Gly Glu Lys Asp Thr Thr Lys Thr Asn Gly Arg Leu Asn Leu
                580                 585                 590

Val Tyr Gln Pro Ala Ala Glu Asp Arg Thr Leu Leu Leu Ser Gly Gly
                595                 600             605

Thr Asn Leu Asn Gly Asn Ile Thr Gln Thr Asn Gly Lys Leu Phe Phe
            610                 615             620

Ser Gly Arg Pro Thr Pro His Ala Tyr Asn His Leu Asn Asp His Trp
625                 630                 635                 640

Ser Gln Lys Glu Gly Ile Pro Arg Gly Glu Ile Val Trp Asp Asn Asp
                645                 650                 655

Trp Ile Asn Arg Thr Phe Lys Ala Glu Asn Phe Gln Ile Lys Gly Gly
                660                 665             670

Gln Ala Val Val Ser Arg Asn Val Ala Lys Val Lys Gly Asp Trp His
            675                 680             685

Leu Ser Asn His Ala Gln Ala Val Phe Gly Val Ala Pro His Gln Ser
            690                 695                 700

His Thr Ile Cys Thr Arg Ser Asp Trp Thr Gly Leu Thr Asn Cys Val
705                 710                 715                 720

Glu Lys Thr Ile Thr Asp Asp Lys Val Ile Ala Ser Leu Thr Lys Thr
                        725                 730             735

Asp Ile Ser Gly Asn Val Asp Leu Ala Asp His Ala His Leu Asn Leu
                740                 745                 750

Thr Gly Leu Ala Thr Leu Asn Gly Asn Leu Ser Ala Asn Gly Asp Thr
            755                 760             765

Arg Tyr Thr Val Ser His Asn Ala Thr Gln Asn Gly Asn Leu Ser Leu
    770                 775                 780

Val Gly Asn Ala Gln Ala Thr Phe Asn Gln Ala Thr Leu Asn Gly Asn
785                 790                 795                 800

Thr Ser Ala Ser Gly Asn Ala Ser Phe Asn Leu Ser Asp His Ala Val
                805                 810                 815

Gln Asn Gly Ser Leu Thr Leu Ser Gly Asn Ala Lys Ala Asn Val Ser
                820                 825             830

His Ser Ala Leu Asn Gly Asn Val Ser Leu Ala Asp Lys Ala Val Phe
835                 840                 845

His Phe Glu Ser Ser Arg Phe Thr Gly Gln Ile Ser Gly Gly Lys Asp
                850                 855                 860

Thr Ala Leu His Leu Lys Asp Ser Glu Trp Thr Leu Pro Ser Gly Thr
865                 870                 875                 880

Glu Leu Gly Asn Leu Asn Leu Asp Asn Ala Thr Ile Thr Leu Asn Ser
                        885                 890                 895

Ala Tyr Arg His Asp Ala Ala Gly Ala Gln Thr Gly Ser Ala Thr Asp
                900                 905             910

Ala Pro Arg Arg Arg Ser Arg Ser Arg Ser Leu Leu Ser Val
            915                 920             925

Thr Pro Pro Thr Ser Val Glu Ser Arg Phe Asn Thr Leu Thr Val Asn
    930                 935                 940

Gly Lys Leu Asn Gly Gln Gly Thr Phe Arg Phe Met Ser Glu Leu Phe
945                 950                 955                 960

Gly Tyr Arg Ser Asp Lys Leu Lys Leu Ala Glu Ser Ser Glu Gly Thr
                965                 970                 975

Tyr Thr Leu Ala Val Asn Asn Thr Gly Asn Glu Pro Ala Ser Leu Glu
            980                 985                 990
```

-continued

Gln Leu Thr Val Val Glu Gly Lys Asp Asn Lys Pro Leu Ser Glu Asn
    995                 1000                1005

Leu Asn Phe Thr Leu Gln Asn Glu His Val Asp Ala Gly Ala Trp Arg
    1010                1015                1020

Tyr Gln Leu Ile Arg Lys Asp Gly Glu Phe Arg Leu His Asn Pro Val
1025                1030                1035                1040

Lys Glu Gln Glu Leu Ser Asp Lys Leu Gly Lys Ala Glu Ala Lys Lys
                1045                1050                1055

Gln Ala Glu Lys Asp Asn Ala Gln Ser Leu Asp Ala Leu Ile Ala Ala
                1060                1065                1070

Gly Arg Asp Ala Val Glu Lys Thr Glu Ser Val Ala Glu Pro Ala Arg
                1075                1080                1085

Gln Ala Gly Gly Glu Asn Val Gly Ile Met Gln Ala Glu Glu Glu Lys
                1090                1095                1100

Lys Arg Val Gln Ala Asp Lys Asp Thr Ala Leu Ala Lys Gln Arg Glu
1105                1110                1115                1120

Ala Glu Thr Arg Pro Ala Thr Thr Ala Phe Pro Arg Ala Arg Arg Ala
                1125                1130                1135

Arg Arg Asp Leu Pro Gln Leu Gln Pro Gln Pro Gln Pro Gln Pro Gln
                1140                1145                1150

Arg Asp Leu Ile Ser Arg Tyr Ala Asn Ser Gly Leu Ser Glu Phe Ser
                1155                1160                1165

Ala Thr Leu Asn Ser Val Phe Ala Val Gln Asp Glu Leu Asp Arg Val
                1170                1175                1180

Phe Ala Glu Asp Arg Arg Asn Ala Val Trp Thr Ser Gly Ile Arg Asp
1185                1190                1195                1200

Thr Lys His Tyr Arg Ser Gln Asp Phe Arg Ala Tyr Arg Gln Gln Thr
                1205                1210                1215

Asp Leu Arg Gln Ile Gly Met Gln Lys Asn Leu Gly Ser Gly Arg Val
                1220                1225                1230

Gly Ile Leu Phe Ser His Asn Arg Thr Glu Asn Thr Phe Asp Asp Gly
                1235                1240                1245

Ile Gly Asn Ser Ala Arg Leu Ala His Gly Ala Val Phe Gly Gln Tyr
                1250                1255                1260

Gly Ile Asp Arg Phe Tyr Ile Gly Ile Ser Ala Gly Ala Gly Phe Ser
1265                1270                1275                1280

Ser Gly Ser Leu Ser Asp Gly Ile Gly Gly Lys Ile Arg Arg Arg Val
                1285                1290                1295

Leu His Tyr Gly Ile Gln Ala Arg Tyr Arg Ala Gly Phe Gly Gly Phe
                1300                1305                1310

Gly Ile Glu Pro His Ile Gly Ala Thr Arg Tyr Phe Val Gln Lys Ala
                1315                1320                1325

Asp Tyr Arg Tyr Glu Asn Val Asn Ile Ala Thr Pro Gly Leu Ala Phe
                1330                1335                1340

Asn Arg Tyr Arg Ala Gly Ile Lys Ala Asp Tyr Ser Phe Lys Pro Ala
1345                1350                1355                1360

Gln His Ile Ser Ile Thr Pro Tyr Leu Ser Leu Ser Tyr Thr Asp Ala
                1365                1370                1375

Ala Ser Gly Lys Val Arg Thr Arg Val Asn Thr Ala Val Leu Ala Gln
                1380                1385                1390

Asp Phe Gly Lys Thr Arg Ser Ala Glu Trp Gly Val Asn Ala Glu Ile
                1395                1400                1405

Lys Gly Phe Thr Leu Ser Leu His Ala Ala Ala Ala Lys Gly Pro Gln
                1410                1415                1420

Leu Glu Ala Gln His Ser Ala Gly Ile Lys Leu Gly Tyr Arg Trp
1425                1430                1435

<210> SEQ ID NO 74
<211> LENGTH: 164
<212> TYPE: PRT
<213> ORGANISM: Neisseria meningitidis

<400> SEQUENCE: 74

Met Lys Lys Asn Ile Leu Glu Phe Trp Val Gly Leu Phe Val Leu Ile
1               5                   10                  15

Gly Ala Ala Val Ala Phe Leu Ala Phe Arg Val Ala Gly Gly Ala
            20                  25                  30

Ala Phe Gly Gly Ser Asp Lys Thr Tyr Ala Val Tyr Ala Asp Phe Gly
        35                  40                  45

Asp Ile Gly Gly Leu Lys Val Asn Ala Pro Val Lys Ser Ala Gly Val
    50                  55                  60

Leu Val Gly Arg Val Gly Ala Ile Gly Leu Asp Pro Lys Ser Tyr Gln
65                  70                  75                  80

Ala Arg Val Arg Leu Asp Leu Asp Gly Lys Tyr Gln Phe Ser Ser Asp
                85                  90                  95

Val Ser Ala Gln Ile Leu Thr Ser Gly Leu Leu Gly Glu Gln Tyr Ile
            100                 105                 110

Gly Leu Gln Gln Gly Gly Asp Thr Glu Asn Leu Ala Ala Gly Asp Thr
        115                 120                 125

Ile Ser Val Thr Ser Ser Ala Met Val Leu Glu Asn Leu Ile Gly Lys
    130                 135                 140

Phe Met Thr Ser Phe Ala Glu Lys Asn Ala Asp Gly Gly Asn Ala Glu
145                 150                 155                 160

Lys Ala Ala Glu

<210> SEQ ID NO 75
<211> LENGTH: 21
<212> TYPE: PRT
<213> ORGANISM: Erwinia carotovora

<400> SEQUENCE: 75

Met Lys Tyr Leu Leu Pro Thr Ala Ala Ala Gly Leu Leu Leu Ala Ala
1               5                   10                  15

Gln Pro Ala Met Ala
            20

<210> SEQ ID NO 76
<211> LENGTH: 608
<212> TYPE: PRT
<213> ORGANISM: Neisseria meningitidis ORF46

<400> SEQUENCE: 76

Leu Gly Ile Ser Arg Lys Ile Ser Leu Ile Leu Ser Ile Leu Ala Val
1               5                   10                  15

Cys Leu Pro Met His Ala His Ala Ser Asp Leu Ala Asn Asp Ser Phe
            20                  25                  30

Ile Arg Gln Val Leu Asp Arg Gln His Phe Glu Pro Asp Gly Lys Tyr
        35                  40                  45

His Leu Phe Gly Ser Arg Gly Glu Leu Ala Glu Arg Ser His Ile
    50                  55                  60

Gly Leu Gly Lys Ile Gln Ser His Gln Leu Gly Asn Leu Met Ile Gln
65                  70                  75                  80

```
Gln Ala Ala Ile Lys Gly Asn Ile Gly Tyr Ile Val Arg Phe Ser Asp
                85                  90                  95
His Gly His Glu Val His Ser Pro Phe Asp Asn His Ala Ser His Ser
            100                 105                 110
Asp Ser Asp Glu Ala Gly Ser Pro Val Asp Gly Phe Ser Leu Tyr Arg
            115                 120                 125
Ile His Trp Asp Gly Tyr Glu His His Pro Ala Asp Gly Tyr Asp Gly
        130                 135                 140
Pro Gln Gly Gly Gly Tyr Pro Ala Pro Lys Gly Ala Arg Asp Ile Tyr
145                 150                 155                 160
Ser Tyr Asp Ile Lys Gly Val Ala Gln Asn Ile Arg Leu Asn Leu Thr
                165                 170                 175
Asp Asn Arg Ser Thr Gly Gln Arg Leu Ala Asp Arg Phe His Asn Ala
            180                 185                 190
Gly Ser Met Leu Thr Gln Gly Val Gly Asp Gly Phe Lys Arg Ala Thr
            195                 200                 205
Arg Tyr Ser Pro Glu Leu Asp Arg Ser Gly Asn Ala Ala Glu Ala Phe
        210                 215                 220
Asn Gly Thr Ala Asp Ile Val Lys Asn Ile Ile Gly Ala Ala Gly Glu
225                 230                 235                 240
Ile Val Gly Ala Gly Asp Ala Val Gln Gly Ile Ser Glu Gly Ser Asn
                245                 250                 255
Ile Ala Val Met His Gly Leu Gly Leu Leu Ser Thr Glu Asn Lys Met
            260                 265                 270
Ala Arg Ile Asn Asp Leu Ala Asp Met Ala Gln Leu Lys Asp Tyr Ala
            275                 280                 285
Ala Ala Ala Ile Arg Asp Trp Ala Val Gln Asn Pro Asn Ala Ala Gln
        290                 295                 300
Gly Ile Glu Ala Val Ser Asn Ile Phe Met Ala Ala Ile Pro Ile Lys
305                 310                 315                 320
Gly Ile Gly Ala Val Arg Gly Lys Tyr Gly Leu Gly Gly Ile Thr Ala
                325                 330                 335
His Pro Ile Lys Arg Ser Gln Met Gly Ala Ile Ala Leu Pro Lys Gly
            340                 345                 350
Lys Ser Ala Val Ser Asp Asn Phe Ala Asp Ala Ala Tyr Ala Lys Tyr
            355                 360                 365
Pro Ser Pro Tyr His Ser Arg Asn Ile Arg Ser Asn Leu Glu Gln Arg
        370                 375                 380
Tyr Gly Lys Glu Asn Ile Thr Ser Ser Thr Val Pro Pro Ser Asn Gly
385                 390                 395                 400
Lys Asn Val Lys Leu Ala Asp Gln Arg His Pro Lys Thr Gly Val Pro
                405                 410                 415
Phe Asp Gly Lys Gly Phe Pro Asn Phe Glu Lys His Val Lys Tyr Asp
            420                 425                 430
Thr Lys Leu Asp Ile Gln Glu Leu Ser Gly Gly Ile Pro Lys Ala
            435                 440                 445
Lys Pro Val Ser Asp Ala Lys Pro Arg Trp Glu Val Asp Arg Lys Leu
        450                 455                 460
Asn Lys Leu Thr Thr Arg Glu Gln Val Glu Lys Asn Val Gln Glu Ile
465                 470                 475                 480
Arg Asn Gly Asn Lys Asn Ser Asn Phe Ser Gln His Ala Gln Leu Glu
                485                 490                 495
Arg Glu Ile Asn Lys Leu Lys Ser Ala Asp Glu Ile Asn Phe Ala Asp
```

```
                   500              505                510
Gly Met Gly Lys Phe Thr Asp Ser Met Asn Asp Lys Ala Phe Ser Arg
                515                  520                 525

Leu Val Lys Ser Val Lys Glu Asn Gly Phe Thr Asn Pro Val Val Glu
            530                 535                 540

Tyr Val Glu Ile Asn Gly Lys Ala Tyr Ile Val Arg Gly Asn Asn Arg
545                 550                 555                 560

Val Phe Ala Ala Glu Tyr Leu Gly Arg Ile His Glu Leu Lys Phe Lys
                565                 570                 575

Lys Val Asp Phe Pro Val Pro Asn Thr Ser Trp Lys Asn Pro Thr Asp
                580                 585                 590

Val Leu Asn Glu Ser Gly Asn Val Lys Arg Pro Arg Tyr Arg Ser Lys
                595                 600                 605

<210> SEQ ID NO 77
<211> LENGTH: 584
<212> TYPE: PRT
<213> ORGANISM: Artificial Sequence
<220> FEATURE:
<223> OTHER INFORMATION: ORF46-2

<400> SEQUENCE: 77

Ser Asp Leu Ala Asn Asp Ser Phe Ile Arg Gln Val Leu Asp Arg Gln
1               5                   10                  15

His Phe Glu Pro Asp Gly Lys Tyr His Leu Phe Gly Ser Arg Gly Glu
                20                  25                  30

Leu Ala Glu Arg Ser Gly His Ile Gly Leu Gly Lys Ile Gln Ser His
            35                  40                  45

Gln Leu Gly Asn Leu Met Ile Gln Gln Ala Ala Ile Lys Gly Asn Ile
        50                  55                  60

Gly Tyr Ile Val Arg Phe Ser Asp His Gly His Glu Val His Ser Pro
65                  70                  75                  80

Phe Asp Asn His Ala Ser His Ser Asp Ser Asp Glu Ala Gly Ser Pro
                85                  90                  95

Val Asp Gly Phe Ser Leu Tyr Arg Ile His Trp Asp Gly Tyr Glu His
            100                 105                 110

His Pro Ala Asp Gly Tyr Asp Gly Pro Gln Gly Gly Tyr Pro Ala
        115                 120                 125

Pro Lys Gly Ala Arg Asp Ile Tyr Ser Tyr Asp Ile Lys Gly Val Ala
130                 135                 140

Gln Asn Ile Arg Leu Asn Leu Thr Asp Asn Ser Thr Gly Gln Arg
145                 150                 155                 160

Leu Ala Asp Arg Phe His Asn Ala Gly Ser Met Leu Thr Gln Gly Val
                165                 170                 175

Gly Asp Gly Phe Lys Arg Ala Thr Arg Tyr Ser Pro Glu Leu Asp Arg
            180                 185                 190

Ser Gly Asn Ala Ala Glu Ala Phe Asn Gly Thr Ala Asp Ile Val Lys
        195                 200                 205

Asn Ile Ile Gly Ala Ala Gly Glu Ile Val Gly Ala Gly Asp Ala Val
    210                 215                 220

Gln Gly Ile Ser Glu Gly Ser Asn Ile Ala Val Met His Gly Leu Gly
225                 230                 235                 240

Leu Leu Ser Thr Glu Asn Lys Met Ala Arg Ile Asn Asp Leu Ala Asp
                245                 250                 255

Met Ala Gln Leu Lys Asp Tyr Ala Ala Ala Ile Arg Asp Trp Ala
            260                 265                 270
```

Val Gln Asn Pro Asn Ala Ala Gln Gly Ile Glu Ala Val Ser Asn Ile
        275                 280                 285

Phe Met Ala Ala Ile Pro Ile Lys Gly Ile Gly Ala Val Arg Gly Lys
        290                 295                 300

Tyr Gly Leu Gly Gly Ile Thr Ala His Pro Ile Lys Arg Ser Gln Met
305                 310                 315                 320

Gly Ala Ile Ala Leu Pro Lys Gly Lys Ser Ala Val Ser Asp Asn Phe
                325                 330                 335

Ala Asp Ala Ala Tyr Ala Lys Tyr Pro Ser Pro Tyr His Ser Arg Asn
                340                 345                 350

Ile Arg Ser Asn Leu Glu Gln Arg Tyr Gly Lys Glu Asn Ile Thr Ser
                355                 360                 365

Ser Thr Val Pro Pro Ser Asn Gly Lys Asn Val Lys Leu Ala Asp Gln
        370                 375                 380

Arg His Pro Lys Thr Gly Val Pro Phe Asp Gly Lys Gly Phe Pro Asn
385                 390                 395                 400

Phe Glu Lys His Val Lys Tyr Asp Thr Lys Leu Asp Ile Gln Glu Leu
                405                 410                 415

Ser Gly Gly Gly Ile Pro Lys Ala Lys Pro Val Ser Asp Ala Lys Pro
        420                 425                 430

Arg Trp Glu Val Asp Arg Lys Leu Asn Lys Leu Thr Thr Arg Glu Gln
435                 440                 445

Val Glu Lys Asn Val Gln Glu Ile Arg Asn Gly Asn Lys Asn Ser Asn
        450                 455                 460

Phe Ser Gln His Ala Gln Leu Glu Arg Glu Ile Asn Lys Leu Lys Ser
465                 470                 475                 480

Ala Asp Glu Ile Asn Phe Ala Asp Gly Met Gly Lys Phe Thr Asp Ser
                485                 490                 495

Met Asn Asp Lys Ala Phe Ser Arg Leu Val Lys Ser Val Lys Glu Asn
        500                 505                 510

Gly Phe Thr Asn Pro Val Val Glu Tyr Val Glu Ile Asn Gly Lys Ala
        515                 520                 525

Tyr Ile Val Arg Gly Asn Asn Arg Val Phe Ala Ala Glu Tyr Leu Gly
        530                 535                 540

Arg Ile His Glu Leu Lys Phe Lys Lys Val Asp Phe Pro Val Pro Asn
545                 550                 555                 560

Thr Ser Trp Lys Asn Pro Thr Asp Val Leu Asn Glu Ser Gly Asn Val
                565                 570                 575

Lys Arg Pro Arg Tyr Arg Ser Lys
                580

<210> SEQ ID NO 78
<211> LENGTH: 364
<212> TYPE: PRT
<213> ORGANISM: Neisseria meningitidis

<400> SEQUENCE: 78

Met Ser Met Lys His Phe Pro Ala Lys Val Leu Thr Thr Ala Ile Leu
1               5                   10                  15

Ala Thr Phe Cys Ser Gly Ala Leu Ala Ala Thr Ser Asp Asp Asp Val
                20                  25                  30

Lys Lys Ala Ala Thr Val Ala Ile Val Ala Ala Tyr Asn Asn Gly Gln
            35                  40                  45

Glu Ile Asn Gly Phe Lys Ala Gly Glu Thr Ile Tyr Asp Ile Gly Glu
        50                  55                  60

Asp Gly Thr Ile Thr Gln Lys Asp Ala Thr Ala Ala Asp Val Glu Ala
65                  70                  75                  80

Asp Asp Phe Lys Gly Leu Gly Leu Lys Lys Val Val Thr Asn Leu Thr
            85                  90                  95

Lys Thr Val Asn Glu Asn Lys Gln Asn Val Asp Ala Lys Val Lys Ala
        100                 105                 110

Ala Glu Ser Glu Ile Glu Lys Leu Thr Thr Lys Leu Ala Asp Thr Asp
            115                 120                 125

Ala Ala Leu Ala Asp Thr Asp Ala Ala Leu Asp Glu Thr Thr Asn Ala
        130                 135                 140

Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
                165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
        195                 200                 205

Lys Gln Thr Ala Glu Glu Thr Lys Gln Asn Val Asp Ala Lys Val Lys
    210                 215                 220

Ala Ala Glu Thr Ala Ala Gly Lys Ala Glu Ala Ala Gly Thr Ala
225                 230                 235                 240

Asn Thr Ala Ala Asp Lys Ala Glu Ala Val Ala Lys Val Thr Asp
                245                 250                 255

Ile Lys Ala Asp Ile Ala Thr Asn Lys Ala Asp Ile Ala Lys Asn Ser
                260                 265                 270

Ala Arg Ile Asp Ser Leu Asp Lys Asn Val Ala Asn Leu Arg Lys Glu
            275                 280                 285

Thr Arg Gln Gly Leu Ala Glu Gln Ala Ala Leu Ser Gly Leu Phe Gln
        290                 295                 300

Pro Tyr Asn Val Gly Arg Phe Asn Val Thr Ala Ala Val Gly Gly Tyr
305                 310                 315                 320

Lys Ser Glu Ser Ala Val Ala Ile Gly Thr Gly Phe Arg Phe Thr Glu
            325                 330                 335

Asn Phe Ala Ala Lys Ala Gly Val Ala Val Gly Thr Ser Ser Gly Ser
            340                 345                 350

Ser Ala Ala Tyr His Val Gly Val Asn Tyr Glu Trp
        355                 360

<210> SEQ ID NO 79
<211> LENGTH: 427
<212> TYPE: PRT
<213> ORGANISM: Neisseria meningitidis

<400> SEQUENCE: 79

Met Phe Glu Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ala Glu Lys Glu Thr Glu
        35                  40                  45

Val Lys Glu Asp Ala Pro Gln Ala Gly Ser Gln Gly Gln Gly Ala Pro
    50                  55                  60

Ser Thr Gln Gly Ser Gln Asp Met Ala Ala Val Ser Ala Glu Asn Thr
65                  70                  75                  80

Gly Asn Gly Gly Ala Ala Thr Thr Asp Lys Pro Lys Asn Glu Asp Glu
                85                  90                  95

Gly Pro Gln Asn Asp Met Pro Gln Asn Ser Ala Glu Ser Ala Asn Gln
            100                 105                 110

Thr Gly Asn Asn Gln Pro Ala Asp Ser Ser Asp Ser Ala Pro Ala Ser
            115                 120                 125

Asn Pro Ala Pro Ala Asn Gly Gly Ser Asn Phe Gly Arg Val Asp Leu
            130                 135                 140

Ala Asn Gly Val Leu Ile Asp Gly Pro Ser Gln Asn Ile Thr Leu Thr
145                 150                 155                 160

His Cys Lys Gly Asp Ser Cys Asn Gly Asp Asn Leu Leu Asp Glu Glu
                165                 170                 175

Ala Pro Ser Lys Ser Glu Phe Glu Asn Leu Asn Glu Ser Glu Arg Ile
            180                 185                 190

Glu Lys Tyr Lys Lys Asp Gly Lys Ser Asp Lys Phe Thr Asn Leu Val
            195                 200                 205

Ala Thr Ala Val Gln Ala Asn Gly Thr Asn Lys Tyr Val Ile Ile Tyr
210                 215                 220

Lys Asp Lys Ser Ala Ser Ser Ser Ala Arg Phe Arg Arg Ser Ala
225                 230                 235                 240

Arg Ser Arg Arg Ser Leu Pro Ala Glu Met Pro Leu Ile Pro Val Asn
                245                 250                 255

Gln Ala Asp Thr Leu Ile Val Asp Gly Glu Ala Val Ser Leu Thr Gly
            260                 265                 270

His Ser Gly Asn Ile Phe Ala Pro Glu Gly Asn Tyr Arg Tyr Leu Thr
            275                 280                 285

Tyr Gly Ala Glu Lys Leu Pro Gly Gly Ser Tyr Ala Leu Arg Val Gln
            290                 295                 300

Gly Glu Pro Ala Lys Gly Glu Met Leu Ala Gly Thr Ala Val Tyr Asn
305                 310                 315                 320

Gly Glu Val Leu His Phe His Thr Gly Asn Gly Arg Pro Tyr Pro Thr
                325                 330                 335

Arg Gly Arg Phe Ala Ala Lys Val Asp Phe Gly Ser Lys Ser Val Asp
            340                 345                 350

Gly Ile Ile Asp Ser Gly Asp Asp Leu His Met Gly Thr Gln Lys Phe
            355                 360                 365

Lys Ala Ala Ile Asp Gly Asn Gly Phe Lys Gly Thr Trp Thr Glu Asn
            370                 375                 380

Gly Gly Gly Asp Val Ser Gly Arg Phe Tyr Gly Pro Ala Gly Glu Glu
385                 390                 395                 400

Val Ala Gly Lys Tyr Ser Tyr Arg Pro Thr Ala Glu Lys Gly Gly
                405                 410                 415

Phe Gly Val Phe Ala Gly Lys Lys Glu Gln Asp
            420                 425

<210> SEQ ID NO 80
<211> LENGTH: 410
<212> TYPE: PRT
<213> ORGANISM: Artificial Sequence
<220> FEATURE:
<223> OTHER INFORMATION: 287untagged

<400> SEQUENCE: 80

Cys Gly Gly Gly Gly Gly Ser Pro Asp Val Lys Ser Ala Asp Thr
1               5                   10                  15

Leu Ser Lys Pro Ala Ala Pro Val Val Ala Glu Lys Glu Thr Glu Val
            20                  25                  30

Lys Glu Asp Ala Pro Gln Ala Gly Ser Gln Gly Gln Gly Ala Pro Ser
        35                  40                  45

Thr Gln Gly Ser Gln Asp Met Ala Ala Val Ser Ala Glu Asn Thr Gly
50                  55                  60

Asn Gly Gly Ala Ala Thr Thr Asp Lys Pro Lys Asn Glu Asp Glu Gly
65                  70                  75                  80

Pro Gln Asn Asp Met Pro Gln Asn Ser Ala Glu Ser Ala Asn Gln Thr
                85                  90                  95

Gly Asn Asn Gln Pro Ala Asp Ser Ser Asp Ser Ala Pro Ala Ser Asn
            100                 105                 110

Pro Ala Pro Ala Asn Gly Gly Ser Asn Phe Gly Arg Val Asp Leu Ala
        115                 120                 125

Asn Gly Val Leu Ile Asp Gly Pro Ser Gln Asn Ile Thr Leu Thr His
130                 135                 140

Cys Lys Gly Asp Ser Cys Asn Gly Asp Asn Leu Leu Asp Glu Glu Ala
145                 150                 155                 160

Pro Ser Lys Ser Glu Phe Glu Asn Leu Asn Glu Ser Glu Arg Ile Glu
                165                 170                 175

Lys Tyr Lys Lys Asp Gly Lys Ser Asp Lys Phe Thr Asn Leu Val Ala
            180                 185                 190

Thr Ala Val Gln Ala Asn Gly Thr Asn Lys Tyr Val Ile Ile Tyr Lys
        195                 200                 205

Asp Lys Ser Ala Ser Ser Ser Ala Arg Phe Arg Arg Ser Ala Arg
210                 215                 220

Ser Arg Arg Ser Leu Pro Ala Glu Met Pro Leu Ile Pro Val Asn Gln
225                 230                 235                 240

Ala Asp Thr Leu Ile Val Asp Gly Glu Ala Val Ser Leu Thr Gly His
                245                 250                 255

Ser Gly Asn Ile Phe Ala Pro Glu Gly Asn Tyr Arg Tyr Leu Thr Tyr
            260                 265                 270

Gly Ala Glu Lys Leu Pro Gly Gly Ser Tyr Ala Leu Arg Val Gln Gly
        275                 280                 285

Glu Pro Ala Lys Gly Glu Met Leu Ala Gly Thr Ala Val Tyr Asn Gly
290                 295                 300

Glu Val Leu His Phe His Thr Glu Asn Gly Arg Pro Tyr Pro Thr Arg
305                 310                 315                 320

Gly Arg Phe Ala Ala Lys Val Asp Phe Gly Ser Lys Ser Val Asp Gly
                325                 330                 335

Ile Ile Asp Ser Gly Asp Asp Leu His Met Gly Thr Gln Lys Phe Lys
            340                 345                 350

Ala Ala Ile Asp Gly Asn Gly Phe Lys Gly Thr Trp Thr Glu Asn Gly
        355                 360                 365

Gly Gly Asp Val Ser Gly Arg Phe Tyr Gly Pro Ala Gly Glu Glu Val
370                 375                 380

Ala Gly Lys Tyr Ser Tyr Arg Pro Thr Asp Ala Glu Lys Gly Gly Phe
385                 390                 395                 400

Gly Val Phe Ala Gly Lys Lys Glu Gln Asp
                405                 410

<210> SEQ ID NO 81
<211> LENGTH: 9
<212> TYPE: PRT
<213> ORGANISM: Artificial Sequence

```
<220> FEATURE:
<223> OTHER INFORMATION: 920L N-terminal

<400> SEQUENCE: 81

His Arg Val Trp Val Glu Thr Ala His
1               5

<210> SEQ ID NO 82
<211> LENGTH: 16
<212> TYPE: PRT
<213> ORGANISM: Artificial Sequence
<220> FEATURE:
<223> OTHER INFORMATION: 953L N-terminal

<400> SEQUENCE: 82

Ala Thr Tyr Lys Val Asp Glu Tyr His Ala Asn Ala Arg Phe Ala Phe
1               5                   10                  15

<210> SEQ ID NO 83
<211> LENGTH: 9
<212> TYPE: PRT
<213> ORGANISM: Artificial Sequence
<220> FEATURE:
<223> OTHER INFORMATION: 519.1L N-terminal

<400> SEQUENCE: 83

Met Glu Phe Phe Ile Ile Leu Leu Ala
1               5

<210> SEQ ID NO 84
<211> LENGTH: 488
<212> TYPE: PRT
<213> ORGANISM: Artificial Sequence
<220> FEATURE:
<223> OTHER INFORMATION: deltaG287

<400> SEQUENCE: 84

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
                20                  25                  30

Thr Leu Ser Lys Pro Ala Ala Pro Val Val Ser Glu Lys Glu Thr Glu
            35                  40                  45

Ala Lys Glu Asp Ala Pro Gln Ala Gly Ser Gln Gln Gly Ala Pro
        50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
                100                 105                 110

Thr Pro Asn His Thr Pro Asp Pro Asn Met Leu Ala Gly Asn Met Glu
            115                 120                 125

Asn Gln Ala Thr Asp Ala Gly Glu Ser Ser Gln Pro Ala Asn Gln Pro
        130                 135                 140

Asp Met Ala Asn Ala Ala Asp Gly Met Gln Gly Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190
```

```
Pro Ala Pro Ala Asn Gly Gly Ser Asn Phe Gly Arg Val Asp Leu Ala
        195                 200                 205
Asn Gly Val Leu Ile Asp Gly Pro Ser Gln Asn Ile Thr Leu Thr His
210                 215                 220
Cys Lys Gly Asp Ser Cys Ser Gly Asn Asn Phe Leu Asp Glu Glu Val
225                 230                 235                 240
Gln Leu Lys Ser Glu Phe Glu Lys Leu Ser Asp Ala Asp Lys Ile Ser
            245                 250                 255
Asn Tyr Lys Lys Asp Gly Lys Asn Asp Lys Phe Val Gly Leu Val Ala
            260                 265                 270
Asp Ser Val Gln Met Lys Gly Ile Asn Gln Tyr Ile Ile Phe Tyr Lys
        275                 280                 285
Pro Lys Pro Thr Ser Phe Ala Arg Phe Arg Arg Ser Ala Arg Ser Arg
290                 295                 300
Arg Ser Leu Pro Ala Glu Met Pro Leu Ile Pro Val Asn Gln Ala Asp
305                 310                 315                 320
Thr Leu Ile Val Asp Gly Glu Ala Val Ser Leu Thr Gly His Ser Gly
            325                 330                 335
Asn Ile Phe Ala Pro Glu Gly Asn Tyr Arg Tyr Leu Thr Tyr Gly Ala
            340                 345                 350
Glu Lys Leu Pro Gly Gly Ser Tyr Ala Leu Arg Val Gln Gly Glu Pro
        355                 360                 365
Ala Lys Gly Glu Met Leu Ala Gly Ala Ala Val Tyr Asn Gly Glu Val
370                 375                 380
Leu His Phe His Thr Glu Asn Gly Arg Pro Tyr Pro Thr Arg Gly Arg
385                 390                 395                 400
Phe Ala Ala Lys Val Asp Phe Gly Ser Lys Ser Val Asp Gly Ile Ile
            405                 410                 415
Asp Ser Gly Asp Asp Leu His Met Gly Thr Gln Lys Phe Lys Ala Ala
            420                 425                 430
Ile Asp Gly Asn Gly Phe Lys Gly Thr Trp Thr Glu Asn Gly Ser Gly
        435                 440                 445
Asp Val Ser Gly Lys Phe Tyr Gly Pro Ala Gly Glu Glu Val Ala Gly
450                 455                 460
Lys Tyr Ser Tyr Arg Pro Thr Asp Ala Glu Lys Gly Gly Phe Gly Val
465                 470                 475                 480
Phe Ala Gly Lys Lys Glu Gln Asp
            485

<210> SEQ ID NO 85
<211> LENGTH: 712
<212> TYPE: PRT
<213> ORGANISM: Artificial Sequence
<220> FEATURE:
<223> OTHER INFORMATION: TBP2

<400> SEQUENCE: 85

Met Asn Asn Pro Leu Val Asn Gln Ala Ala Met Val Leu Pro Val Phe
1               5                   10                  15
Leu Leu Ser Ala Cys Leu Gly Gly Gly Ser Phe Asp Leu Asp Ser
            20                  25                  30
Val Asp Thr Glu Ala Pro Arg Pro Ala Pro Lys Tyr Gln Asp Val Phe
        35                  40                  45
Ser Glu Lys Pro Gln Ala Gln Lys Asp Gln Gly Gly Tyr Gly Phe Ala
    50                  55                  60
Met Arg Leu Lys Arg Arg Asn Trp Tyr Pro Gln Ala Lys Glu Asp Glu
```

-continued

```
                65                  70                  75                  80
            Val Lys Leu Asp Glu Ser Asp Trp Glu Ala Thr Gly Leu Pro Asp Glu
                            85                  90                  95
            Pro Lys Glu Leu Pro Lys Arg Gln Lys Ser Val Ile Glu Lys Val Glu
                            100                 105                 110
            Thr Asp Ser Asp Asn Asn Ile Tyr Ser Ser Pro Tyr Leu Lys Pro Ser
                            115                 120                 125
            Asn His Gln Asn Gly Asn Thr Gly Asn Gly Ile Asn Gln Pro Lys Asn
                130                 135                 140
            Gln Ala Lys Asp Tyr Glu Asn Phe Lys Tyr Val Tyr Ser Gly Trp Phe
            145                 150                 155                 160
            Tyr Lys His Ala Lys Arg Glu Phe Asn Leu Lys Val Glu Pro Lys Ser
                            165                 170                 175
            Ala Lys Asn Gly Asp Asp Gly Tyr Ile Phe Tyr His Gly Lys Glu Pro
                            180                 185                 190
            Ser Arg Gln Leu Pro Ala Ser Gly Lys Ile Thr Tyr Lys Gly Val Trp
                            195                 200                 205
            His Phe Ala Thr Asp Thr Lys Lys Gly Gln Lys Phe Arg Glu Ile Ile
                210                 215                 220
            Gln Pro Ser Lys Ser Gln Gly Asp Arg Tyr Ser Gly Phe Ser Gly Asp
            225                 230                 235                 240
            Asp Gly Glu Glu Tyr Ser Asn Lys Asn Lys Ser Thr Leu Thr Asp Gly
                            245                 250                 255
            Gln Glu Gly Tyr Gly Phe Thr Ser Asn Leu Glu Val Asp Phe His Asn
                            260                 265                 270
            Lys Lys Leu Thr Gly Lys Leu Ile Arg Asn Asn Ala Asn Thr Asp Asn
                            275                 280                 285
            Asn Gln Ala Thr Thr Thr Gln Tyr Tyr Ser Leu Glu Ala Gln Val Thr
                290                 295                 300
            Gly Asn Arg Phe Asn Gly Lys Ala Thr Ala Thr Asp Lys Pro Gln Gln
            305                 310                 315                 320
            Asn Ser Glu Thr Lys Glu His Pro Phe Val Ser Asp Ser Ser Ser Leu
                            325                 330                 335
            Ser Gly Gly Phe Phe Gly Pro Gln Gly Glu Glu Leu Gly Phe Arg Phe
                            340                 345                 350
            Leu Ser Asp Asp Gln Lys Val Ala Val Val Gly Ser Ala Lys Thr Lys
                            355                 360                 365
            Asp Lys Pro Ala Asn Gly Asn Thr Ala Ala Ser Gly Gly Thr Asp
                370                 375                 380
            Ala Ala Ala Ser Asn Gly Ala Ala Gly Thr Ser Ser Glu Asn Gly Lys
            385                 390                 395                 400
            Leu Thr Thr Val Leu Asp Ala Val Glu Leu Lys Leu Gly Asp Lys Glu
                            405                 410                 415
            Val Gln Lys Leu Asp Asn Phe Ser Asn Ala Ala Gln Leu Val Val Asp
                            420                 425                 430
            Gly Ile Met Ile Pro Leu Leu Pro Glu Ala Ser Glu Ser Gly Asn Asn
                            435                 440                 445
            Gln Ala Asn Gln Gly Thr Asn Gly Gly Thr Ala Phe Thr Arg Lys Phe
                            450                 455                 460
            Asp His Thr Pro Glu Ser Asp Lys Lys Asp Ala Gln Ala Gly Thr Gln
            465                 470                 475                 480
            Thr Asn Gly Ala Gln Thr Ala Ser Asn Thr Ala Gly Asp Thr Asn Gly
                            485                 490                 495
```

```
Lys Thr Lys Thr Tyr Glu Val Glu Val Cys Cys Ser Asn Leu Asn Tyr
            500                 505                 510

Leu Lys Tyr Gly Met Leu Thr Arg Lys Asn Ser Lys Ser Ala Met Gln
            515                 520                 525

Ala Gly Glu Ser Ser Ser Gln Ala Asp Ala Lys Thr Glu Gln Val Glu
530                 535                 540

Gln Ser Met Phe Leu Gln Gly Glu Arg Thr Asp Glu Lys Glu Ile Pro
545                 550                 555                 560

Ser Glu Gln Asn Ile Val Tyr Arg Gly Ser Trp Tyr Gly Tyr Ile Ala
                565                 570                 575

Asn Asp Lys Ser Thr Ser Trp Ser Gly Asn Ala Ser Asn Ala Thr Ser
            580                 585                 590

Gly Asn Arg Ala Glu Phe Thr Val Asn Phe Ala Asp Lys Lys Ile Thr
        595                 600                 605

Gly Thr Leu Thr Ala Asp Asn Arg Gln Glu Ala Thr Phe Thr Ile Asp
    610                 615                 620

Gly Asn Ile Lys Asp Asn Gly Phe Glu Gly Thr Ala Lys Thr Ala Glu
625                 630                 635                 640

Ser Gly Phe Asp Leu Asp Gln Ser Asn Thr Thr Arg Thr Pro Lys Ala
                645                 650                 655

Tyr Ile Thr Asp Ala Lys Val Gln Gly Gly Phe Tyr Gly Pro Lys Ala
            660                 665                 670

Glu Glu Leu Gly Gly Trp Phe Ala Tyr Pro Gly Asp Lys Gln Thr Lys
        675                 680                 685

Asn Ala Thr Asn Ala Ser Gly Asn Ser Ser Ala Thr Val Val Phe Gly
    690                 695                 700

Ala Lys Arg Gln Gln Pro Val Arg
705                 710

<210> SEQ ID NO 86
<211> LENGTH: 274
<212> TYPE: PRT
<213> ORGANISM: Artificial Sequence
<220> FEATURE:
<223> OTHER INFORMATION: 741

<400> SEQUENCE: 86

Val Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
        115                 120                 125

Gln Thr Glu Gln Ile Gln Asp Ser Glu His Ser Gly Lys Met Val Ala
    130                 135                 140

Lys Arg Gln Phe Arg Ile Gly Asp Ile Ala Gly Glu His Thr Ser Phe
```

-continued

```
                145                 150                 155                 160
Asp Lys Leu Pro Glu Gly Gly Arg Ala Thr Tyr Arg Gly Thr Ala Phe
                    165                 170                 175

Gly Ser Asp Asp Ala Gly Gly Lys Leu Thr Tyr Thr Ile Asp Phe Ala
                180                 185                 190

Ala Lys Gln Gly Asn Gly Lys Ile Glu His Leu Lys Ser Pro Glu Leu
            195                 200                 205

Asn Val Asp Leu Ala Ala Ala Asp Ile Lys Pro Asp Gly Lys Arg His
        210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
                260                 265                 270

Lys Gln

<210> SEQ ID NO 87
<211> LENGTH: 1082
<212> TYPE: PRT
<213> ORGANISM: Artificial Sequence
<220> FEATURE:
<223> OTHER INFORMATION: 983

<400> SEQUENCE: 87

Met Arg Thr Thr Pro Thr Phe Pro Thr Lys Thr Phe Lys Pro Thr Ala
1               5                   10                  15

Met Ala Leu Ala Val Ala Thr Thr Leu Ser Ala Cys Leu Gly Gly Gly
                20                  25                  30

Gly Gly Gly Thr Ser Ala Pro Asp Phe Asn Ala Gly Gly Thr Gly Ile
            35                  40                  45

Gly Ser Asn Ser Arg Ala Thr Thr Ala Lys Ser Ala Val Ser Tyr
        50                  55                  60

Ala Gly Ile Lys Asn Glu Met Cys Lys Asp Arg Ser Met Leu Cys Ala
65                  70                  75                  80

Gly Arg Asp Asp Val Ala Val Thr Asp Arg Asp Ala Lys Ile Asn Ala
                85                  90                  95

Pro Pro Pro Asn Leu His Thr Gly Asp Phe Pro Asn Pro Asn Asp Ala
            100                 105                 110

Tyr Lys Asn Leu Ile Asn Leu Lys Pro Ala Ile Glu Ala Gly Tyr Thr
        115                 120                 125

Gly Arg Gly Val Glu Val Gly Ile Val Asp Thr Gly Glu Ser Val Gly
    130                 135                 140

Ser Ile Ser Phe Pro Glu Leu Tyr Gly Arg Lys Glu His Gly Tyr Asn
145                 150                 155                 160

Glu Asn Tyr Lys Asn Tyr Thr Ala Tyr Met Arg Lys Glu Ala Pro Glu
                165                 170                 175

Asp Gly Gly Lys Asp Ile Glu Ala Ser Phe Asp Asp Glu Ala Val
            180                 185                 190

Ile Glu Thr Glu Ala Lys Pro Thr Asp Ile Arg His Val Lys Glu Ile
        195                 200                 205

Gly His Ile Asp Leu Val Ser His Ile Ile Gly Gly Arg Ser Val Asp
    210                 215                 220

Gly Arg Pro Ala Gly Gly Ile Ala Pro Asp Ala Thr Leu His Ile Met
225                 230                 235                 240
```

-continued

```
Asn Thr Asn Asp Glu Thr Lys Asn Glu Met Met Val Ala Ala Ile Arg
                245                 250                 255

Asn Ala Trp Val Lys Leu Gly Glu Arg Gly Val Arg Ile Val Asn Asn
            260                 265                 270

Ser Phe Gly Thr Thr Ser Arg Ala Gly Thr Ala Asp Leu Phe Gln Ile
        275                 280                 285

Ala Asn Ser Glu Glu Gln Tyr Arg Gln Ala Leu Leu Asp Tyr Ser Gly
    290                 295                 300

Gly Asp Lys Thr Asp Glu Gly Ile Arg Leu Met Gln Gln Ser Asp Tyr
305                 310                 315                 320

Gly Asn Leu Ser Tyr His Ile Arg Asn Lys Asn Met Leu Phe Ile Phe
                325                 330                 335

Ser Thr Gly Asn Asp Ala Gln Ala Gln Pro Asn Thr Tyr Ala Leu Leu
            340                 345                 350

Pro Phe Tyr Glu Lys Asp Ala Gln Lys Gly Ile Ile Thr Val Ala Gly
        355                 360                 365

Val Asp Arg Ser Gly Glu Lys Phe Lys Arg Glu Met Tyr Gly Glu Pro
    370                 375                 380

Gly Thr Glu Pro Leu Glu Tyr Gly Ser Asn His Cys Gly Ile Thr Ala
385                 390                 395                 400

Met Trp Cys Leu Ser Ala Pro Tyr Glu Ala Ser Val Arg Phe Thr Arg
                405                 410                 415

Thr Asn Pro Ile Gln Ile Ala Gly Thr Ser Phe Ser Ala Pro Ile Val
            420                 425                 430

Thr Gly Thr Ala Ala Leu Leu Leu Gln Lys Tyr Pro Trp Met Ser Asn
        435                 440                 445

Asp Asn Leu Arg Thr Thr Leu Leu Thr Thr Ala Gln Asp Ile Gly Ala
    450                 455                 460

Val Gly Val Asp Ser Lys Phe Gly Trp Gly Leu Leu Asp Ala Gly Lys
465                 470                 475                 480

Ala Met Asn Gly Pro Ala Ser Phe Pro Phe Gly Asp Phe Thr Ala Asp
                485                 490                 495

Thr Lys Gly Thr Ser Asp Ile Ala Tyr Ser Phe Arg Asn Asp Ile Ser
            500                 505                 510

Gly Thr Gly Gly Leu Ile Lys Lys Gly Gly Ser Gln Leu Gln Leu His
        515                 520                 525

Gly Asn Asn Thr Tyr Thr Gly Lys Thr Ile Ile Glu Gly Gly Ser Leu
    530                 535                 540

Val Leu Tyr Gly Asn Asn Lys Ser Asp Met Arg Val Glu Thr Lys Gly
545                 550                 555                 560

Ala Leu Ile Tyr Asn Gly Ala Ala Ser Gly Gly Ser Leu Asn Ser Asp
                565                 570                 575

Gly Ile Val Tyr Leu Ala Asp Thr Asp Gln Ser Gly Ala Asn Glu Thr
            580                 585                 590

Val His Ile Lys Gly Ser Leu Gln Leu Asp Gly Lys Gly Thr Leu Tyr
        595                 600                 605

Thr Arg Leu Gly Lys Leu Leu Lys Val Asp Gly Thr Ala Ile Ile Gly
    610                 615                 620

Gly Lys Leu Tyr Met Ser Ala Arg Gly Lys Gly Ala Gly Tyr Leu Asn
625                 630                 635                 640

Ser Thr Gly Arg Arg Val Pro Phe Leu Ser Ala Ala Lys Ile Gly Gln
                645                 650                 655

Asp Tyr Ser Phe Phe Thr Asn Ile Glu Thr Asp Gly Gly Leu Leu Ala
            660                 665                 670
```

```
Ser Leu Asp Ser Val Glu Lys Thr Ala Gly Ser Glu Gly Asp Thr Leu
            675                 680                 685
Ser Tyr Tyr Val Arg Arg Gly Asn Ala Ala Arg Thr Ala Ser Ala Ala
        690                 695                 700
Ala His Ser Ala Pro Ala Gly Leu Lys His Val Glu Gln Gly Gly
705                 710                 715                 720
Ser Asn Leu Glu Asn Leu Met Val Glu Leu Asp Ala Ser Glu Ser Ser
                725                 730                 735
Ala Thr Pro Glu Thr Val Glu Thr Ala Ala Asp Arg Thr Asp Met
            740                 745                 750
Pro Gly Ile Arg Pro Tyr Gly Ala Thr Phe Arg Ala Ala Ala Ala Val
        755                 760                 765
Gln His Ala Asn Ala Ala Asp Gly Val Arg Ile Phe Asn Ser Leu Ala
770                 775                 780
Ala Thr Val Tyr Ala Asp Ser Thr Ala Ala His Ala Asp Met Gln Gly
785                 790                 795                 800
Arg Arg Leu Lys Ala Val Ser Asp Gly Leu Asp His Asn Gly Thr Gly
                805                 810                 815
Leu Arg Val Ile Ala Gln Thr Gln Gln Asp Gly Gly Thr Trp Glu Gln
                820                 825                 830
Gly Gly Val Glu Gly Lys Met Arg Gly Ser Thr Gln Thr Val Gly Ile
            835                 840                 845
Ala Ala Lys Thr Gly Glu Asn Thr Thr Ala Ala Thr Leu Gly Met
850                 855                 860
Gly Arg Ser Thr Trp Ser Glu Asn Ser Ala Asn Ala Lys Thr Asp Ser
865                 870                 875                 880
Ile Ser Leu Phe Ala Gly Ile Arg His Asp Ala Gly Asp Ile Gly Tyr
                885                 890                 895
Leu Lys Gly Leu Phe Ser Tyr Gly Arg Tyr Lys Asn Ser Ile Ser Arg
                900                 905                 910
Ser Thr Gly Ala Asp Glu His Ala Glu Gly Ser Val Asn Gly Thr Leu
                915                 920                 925
Met Gln Leu Gly Ala Leu Gly Gly Val Asn Val Pro Phe Ala Ala Thr
            930                 935                 940
Gly Asp Leu Thr Val Glu Gly Gly Leu Arg Tyr Asp Leu Leu Lys Gln
945                 950                 955                 960
Asp Ala Phe Ala Glu Lys Gly Ser Ala Leu Gly Trp Ser Gly Asn Ser
                965                 970                 975
Leu Thr Glu Gly Thr Leu Val Gly Leu Ala Gly Leu Lys Leu Ser Gln
                980                 985                 990
Pro Leu Ser Asp Lys Ala Val Leu Phe Ala Thr Ala Gly Val Glu Arg
            995                 1000                1005
Asp Leu Asn Gly Arg Asp Tyr Thr Val Thr Gly Gly Phe Thr Gly Ala
    1010                1015                1020
Thr Ala Ala Thr Gly Lys Thr Gly Ala Arg Asn Met Pro His Thr Arg
1025                1030                1035                1040
Leu Val Ala Gly Leu Gly Ala Asp Val Glu Phe Gly Asn Gly Trp Asn
                1045                1050                1055
Gly Leu Ala Arg Tyr Ser Tyr Ala Gly Ser Lys Gln Tyr Gly Asn His
            1060                1065                1070
Ser Gly Arg Val Gly Val Gly Tyr Arg Phe
        1075                1080
```

```
<210> SEQ ID NO 88
<211> LENGTH: 2505
<212> TYPE: DNA
<213> ORGANISM: Artificial Sequence
<220> FEATURE:
<223> OTHER INFORMATION: deltaG287-919

<400> SEQUENCE: 88
atggctagcc ccgatgttaa atcggcggac acgctgtcaa aaccggccgc tcctgttgtt     60
gctgaaaaag agacagaggt aaaagaagat gcgccacagg caggttctca aggacagggc    120
gcgccatcca cacaaggcag ccaagatatg gcggcagttt cggcagaaaa tacaggcaat    180
ggcggtgcgg caacaacgga caaacccaaa aatgaagacg agggaccgca aaatgatatg    240
ccgcaaaatt ccgccgaatc cgcaaatcaa cagggaaca accaacccgc cgattcttca    300
gattccgccc ccgcgtcaaa ccctgcacct gcgaatggcg gtagcaattt tggaagggtt    360
gatttggcta atggcgtttt gattgatggg ccgtcgcaaa atataacgtt gacccactgt    420
aaaggcgatt cttgtaatgg tgataattta ttggatgaag aagcaccgtc aaaatcagaa    480
tttgaaaatt taaatgagtc tgaacgaatt gagaaatata agaaagatgg gaaaagcgat    540
aaatttacta atttggttgc gacagcagtt caagctaatg gaactaacaa atatgtcatc    600
atttataaag acaagtccgc ttcatcttca tctgcgcgat tcaggcgttc tgcacggtcg    660
aggaggtcgc ttcctgccga gatgccgcta atccccgtca atcaggcgga tacgctgatt    720
gtcgatgggg aagcggtcag cctgacgggg cattccggca atatcttcgc gcccgaaggg    780
aattaccggt atctgactta cggggcgaa aaattgcccg gcggatcgta tgccctccgt    840
gtgcaaggcg aaccggcaaa aggcgaaatg cttgctggca cggccgtgta acggcgaa    900 gtgctgcatt tcatacggaa aaacggccgt ccgtacccga ctagaggcag gttttgccgca    960 aaagtcgatt tcggcagcaa atctgtggac ggcattatcg acagcggcga tgatttgcat   1020
atgggtacgc aaaaattcaa agccgccatc gatggaaacg gctttaaggg gacttggacg   1080
gaaaatggcg gcgggatgt ttccggaagg ttttacggcc cggccggcga ggaagtggcg   1140
ggaaaataca gctatcgccc gacagatgcg gaaaagggcg gattcggcgt gtttgccggc   1200
aaaaaagagc aggatggatc cggaggagga ggatgccaaa gcaagagcat ccaaaccttt   1260
ccgcaacccg acacatccgt catcaacggc ccggaccggc cggtcggcat ccccgacccc   1320
gccggaacga cggtcggcgg cggcggggcc gtctataccg ttgtaccgca cctgtccctg   1380
ccccactggg cggcgcagga tttcgccaaa agcctgcaat ccttccgcct cggctgcgcc   1440 aatttgaaa accgccaagg ctggcaggat gtgtgcgccc aagcctttca acccccgtc    1500 cattcctttc aggcaaaaca gtttttgaa cgctatttca cgccgtggca ggttgcaggc   1560
aacggaagcc ttgccggtac ggttaccggc tattacgagc cggtgctgaa gggcgacgac   1620
aggcggacgg cacaagcccg cttcccgatt tacggtattc ccgacgattt tatctccgtc   1680
cccctgcctg ccggtttgcg gagcggaaaa gcccttgtcc gcatcaggca gacgggaaaa   1740
aacagcggca aatcgacaa taccggcggc acacataccg ccgacctctc ccgattcccc   1800
atcaccgcgc gcacaacggc aatcaaaggc aggtttgaag aagccgcctt cctcccctac   1860
cacacgcgca accaaatcaa cggcggcgcg cttgacggca agccccgat actcggttac   1920 gccgaagacc ccgtcgaact ttttttatg cacatccaag gctcgggccg tctgaaaacc   1980
ccgtccggca aatacatccg catcggctat gccgacaaaa acgaacatcc ctacgtttcc   2040
atcggacgct atatgcggga caaaggctac ctcaagctcg gcagacctc gatgcagggc   2100 atcaaagcct atatgcggca aaatccgcaa cgcctcgccg aagttttggg tcaaaacccc   2160
```

-continued

```
agctatatct ttttccgcga gcttgccgga agcagcaatg acggtcccgt cggcgcactg    2220
ggcacgccgt tgatggggga atatgccggc gcagtcgacc ggcactacat taccttgggc    2280
gcgcccttat ttgtcgccac cgcccatccg gttacccgca aagccctcaa ccgcctgatt    2340
atggcgcagg ataccggcag cgcgattaaa ggcgcggtgc gcgtggatta ttttggggga    2400
tacggcgacg aagccggcga acttgccggc aaacagaaaa ccacgggtta cgtctggcag    2460
ctcctaccca acggtatgaa gcccgaatac cgcccgtaac tcgag                    2505
```

<210> SEQ ID NO 89
<211> LENGTH: 832
<212> TYPE: PRT
<213> ORGANISM: Artificial Sequence
<220> FEATURE:
<223> OTHER INFORMATION: deltaG287-919

<400> SEQUENCE: 89

```
Met Ala Ser Pro Asp Val Lys Ser Ala Asp Thr Leu Ser Lys Pro Ala
  1               5                  10                  15

Ala Pro Val Val Ala Glu Lys Glu Thr Glu Val Lys Glu Asp Ala Pro
             20                  25                  30

Gln Ala Gly Ser Gln Gly Gln Gly Ala Pro Ser Thr Gln Gly Ser Gln
         35                  40                  45

Asp Met Ala Ala Val Ser Ala Glu Asn Thr Gly Asn Gly Gly Ala Ala
     50                  55                  60

Thr Thr Asp Lys Pro Lys Asn Glu Asp Glu Gly Pro Gln Asn Asp Met
 65                  70                  75                  80

Pro Gln Asn Ser Ala Glu Ser Ala Asn Gln Thr Gly Asn Asn Gln Pro
                 85                  90                  95

Ala Asp Ser Ser Asp Ser Ala Pro Ala Ser Asn Pro Ala Pro Ala Asn
            100                 105                 110

Gly Gly Ser Asn Phe Gly Arg Val Asp Leu Ala Asn Gly Val Leu Ile
        115                 120                 125

Asp Gly Pro Ser Gln Asn Ile Thr Leu Thr His Cys Lys Gly Asp Ser
    130                 135                 140

Cys Asn Gly Asp Asn Leu Leu Asp Glu Glu Ala Pro Ser Lys Ser Glu
145                 150                 155                 160

Phe Glu Asn Leu Asn Glu Ser Glu Arg Ile Glu Lys Tyr Lys Lys Asp
                165                 170                 175

Gly Lys Ser Asp Lys Phe Thr Asn Leu Val Ala Thr Ala Val Gln Ala
            180                 185                 190

Asn Gly Thr Asn Lys Tyr Val Ile Ile Tyr Lys Asp Lys Ser Ala Ser
        195                 200                 205

Ser Ser Ser Ala Arg Phe Arg Arg Ser Ala Arg Ser Arg Arg Ser Leu
    210                 215                 220

Pro Ala Glu Met Pro Leu Ile Pro Val Asn Gln Ala Asp Thr Leu Ile
225                 230                 235                 240

Val Asp Gly Glu Ala Val Ser Leu Thr Gly His Ser Gly Asn Ile Phe
                245                 250                 255

Ala Pro Glu Gly Asn Tyr Arg Tyr Leu Thr Tyr Gly Ala Glu Lys Leu
            260                 265                 270

Pro Gly Gly Ser Tyr Ala Leu Arg Val Gln Gly Glu Pro Ala Lys Gly
        275                 280                 285

Glu Met Leu Ala Gly Thr Ala Val Tyr Asn Gly Glu Val Leu His Phe
    290                 295                 300
```

```
His Thr Glu Asn Gly Arg Pro Tyr Pro Thr Arg Gly Arg Phe Ala Ala
305                 310                 315                 320

Lys Val Asp Phe Gly Ser Lys Ser Val Asp Gly Ile Ile Asp Ser Gly
                325                 330                 335

Asp Asp Leu His Met Gly Thr Gln Lys Phe Lys Ala Ala Ile Asp Gly
            340                 345                 350

Asn Gly Phe Lys Gly Thr Trp Thr Glu Asn Gly Gly Gly Asp Val Ser
        355                 360                 365

Gly Arg Phe Tyr Gly Pro Ala Gly Glu Glu Val Ala Gly Lys Tyr Ser
    370                 375                 380

Tyr Arg Pro Thr Asp Ala Glu Lys Gly Gly Phe Gly Val Phe Ala Gly
385                 390                 395                 400

Lys Lys Glu Gln Asp Gly Ser Gly Gly Gly Cys Gln Ser Lys Ser
                405                 410                 415

Ile Gln Thr Phe Pro Gln Pro Asp Thr Ser Val Ile Asn Gly Pro Asp
            420                 425                 430

Arg Pro Val Gly Ile Pro Asp Pro Ala Gly Thr Thr Val Gly Gly Gly
        435                 440                 445

Gly Ala Val Tyr Thr Val Val Pro His Leu Ser Leu Pro His Trp Ala
450                 455                 460

Ala Gln Asp Phe Ala Lys Ser Leu Gln Ser Phe Arg Leu Gly Cys Ala
465                 470                 475                 480

Asn Leu Lys Asn Arg Gln Gly Trp Gln Asp Val Cys Ala Gln Ala Phe
                485                 490                 495

Gln Thr Pro Val His Ser Phe Gln Ala Lys Gln Phe Phe Glu Arg Tyr
            500                 505                 510

Phe Thr Pro Trp Gln Val Ala Gly Asn Gly Ser Leu Ala Gly Thr Val
        515                 520                 525

Thr Gly Tyr Tyr Glu Pro Val Leu Lys Gly Asp Asp Arg Thr Ala
    530                 535                 540

Gln Ala Arg Phe Pro Ile Tyr Gly Ile Pro Asp Asp Phe Ile Ser Val
545                 550                 555                 560

Pro Leu Pro Ala Gly Leu Arg Ser Gly Lys Ala Leu Val Arg Ile Arg
                565                 570                 575

Gln Thr Gly Lys Asn Ser Gly Thr Ile Asp Asn Thr Gly Gly Thr His
            580                 585                 590

Thr Ala Asp Leu Ser Arg Phe Pro Ile Thr Ala Arg Thr Thr Ala Ile
        595                 600                 605

Lys Gly Arg Phe Glu Gly Ser Arg Phe Leu Pro Tyr His Thr Arg Asn
610                 615                 620

Gln Ile Asn Gly Gly Ala Leu Asp Gly Lys Ala Pro Ile Leu Gly Tyr
625                 630                 635                 640

Ala Glu Asp Pro Val Glu Leu Phe Phe Met His Ile Gln Gly Ser Gly
                645                 650                 655

Arg Leu Lys Thr Pro Ser Gly Lys Tyr Ile Arg Ile Gly Tyr Ala Asp
            660                 665                 670

Lys Asn Glu His Pro Tyr Val Ser Ile Gly Arg Tyr Met Ala Asp Lys
        675                 680                 685

Gly Tyr Leu Lys Leu Gly Gln Thr Ser Met Gln Gly Ile Lys Ala Tyr
    690                 695                 700

Met Arg Gln Asn Pro Gln Arg Leu Ala Glu Val Leu Gly Gln Asn Pro
705                 710                 715                 720

Ser Tyr Ile Phe Phe Arg Glu Leu Ala Gly Ser Ser Asn Asp Gly Pro
                725                 730                 735
```

```
Val Gly Ala Leu Gly Thr Pro Leu Met Gly Glu Tyr Ala Gly Ala Val
            740                 745                 750

Asp Arg His Tyr Ile Thr Leu Gly Ala Pro Leu Phe Val Ala Thr Ala
        755                 760                 765

His Pro Val Thr Arg Lys Ala Leu Asn Arg Leu Ile Met Ala Gln Asp
    770                 775                 780

Thr Gly Ser Ala Ile Lys Gly Ala Val Arg Val Asp Tyr Phe Trp Gly
785                 790                 795                 800

Tyr Gly Asp Glu Ala Gly Glu Leu Ala Gly Lys Gln Lys Thr Thr Gly
            805                 810                 815

Tyr Val Trp Gln Leu Leu Pro Asn Gly Met Lys Pro Glu Tyr Arg Pro
        820                 825                 830

<210> SEQ ID NO 90
<211> LENGTH: 1746
<212> TYPE: DNA
<213> ORGANISM: Artificial Sequence
<220> FEATURE:
<223> OTHER INFORMATION: deltaG287-953

<400> SEQUENCE: 90
atggctagcc ccgatgttaa atcggcggac acgctgtcaa aaccggccgc tcctgttgtt      60
gctgaaaaag agacagaggt aaaagaagat gcgccacagg caggttctca aggacagggc     120
gcgccatcca cacaaggcag ccaagatatg gcggcagttt cggcagaaaa tacaggcaat     180
ggcggtgcgg caacaacgga caaacccaaa aatgaagacg agggaccgca aaatgatatg     240
ccgcaaaatt ccgccgaatc cgcaaatcaa acagggaaca accaacccgc cgattcttca     300
gattccgccc ccgcgtcaaa ccctgcacct gcgaatggcg gtagcaattt tggaagggtt     360
gatttggcta atggcgtttt gattgatggg ccgtcgcaaa atataacgtt gacccactgt     420
aaaggcgatt cttgtaatgg tgataattta ttggatgaag aagcaccgtc aaaatcagaa     480
tttgaaaatt taaatgagtc tgaacgaatt gagaaatata agaaagatgg gaaaagcgat     540
aaatttacta atttggttgc gacagcagtt caagctaatg gaactaacaa atatgtcatc     600
atttataaag acaagtccgc ttcatcttca tctgcgcgat tcaggcgttc tgcacggtcg     660
aggaggtcgc ttcctgccga gatgccgcta atccccgtca atcaggcgga tacgctgatt     720
gtcgatgggg aagcggtcag cctgacgggg cattccggca atatcttcgc gcccgaaggg     780
aattaccggt atctgactta cggggcggaa aaattgcccg gcggatcgta tgccctccgt     840
gtgcaaggcg aaccggcaaa aggcgaaatg cttgctggca cggccgtgta acaacggcgaa    900
gtgctgcatt tcatacggaa aaacggccgt ccgtacccga ctagaggcag gtttgccgca     960
aaagtcgatt tcggcagcaa atctgtggac ggcattatcg acagcggcga tgatttgcat    1020
atgggtacgc aaaaattcaa agccgccatc gatggaaacg gctttaaggg gacttggacg    1080
gaaaatggcg gcggggatgt ttccggaagg ttttacggcc cggccggcga ggaagtggcg    1140
ggaaaataca gctatcgccc gacagatgcg gaaaagggcg gattcggcgt gtttgccggc    1200
aaaaagagc aggatggatc cggaggagga ggagccacct acaaagtgga cgaatatcac    1260
gccaacgccc gtttcgccat cgaccatttc aacaccagca ccaacgtcgg cggtttttac    1320
ggtctgaccg gttccgtcga gttcgaccaa gcaaacgcg acggtaaaat cgacatcacc    1380
atccccgttg ccaacctgca aagcggttcg caacacttta ccgaccacct gaaatcagcc    1440
gacatcttcg atgccgccca atatccggac atccgctttg tttccaccaa attcaacttc    1500
aacggcaaaa aactggtttc cgttgacggc aacctgacca tgcacggcaa aaccgccccc    1560
```

```
gtcaaactca aagccgaaaa attcaactgc taccaaagcc cgatggcgaa aaccgaagtt   1620
tgcggcggcg acttcagcac caccatcgac cgcaccaaat ggggcgtgga ctacctcgtt   1680
aacgttggta tgaccaaaag cgtccgcatc gacatccaaa tcgaggcagc caaacaataa   1740
ctcgag                                                               1746
```

<210> SEQ ID NO 91
<211> LENGTH: 579
<212> TYPE: PRT
<213> ORGANISM: Artificial Sequence
<220> FEATURE:
<223> OTHER INFORMATION: deltaG287-953

<400> SEQUENCE: 91

```
Met Ala Ser Pro Asp Val Lys Ser Ala Asp Thr Leu Ser Lys Pro Ala
1               5                   10                  15

Ala Pro Val Val Ala Glu Lys Glu Thr Glu Val Lys Glu Asp Ala Pro
            20                  25                  30

Gln Ala Gly Ser Gln Gly Gln Gly Ala Pro Ser Thr Gln Gly Ser Gln
        35                  40                  45

Asp Met Ala Ala Val Ser Ala Glu Asn Thr Gly Asn Gly Gly Ala Ala
    50                  55                  60

Thr Thr Asp Lys Pro Lys Asn Glu Asp Glu Gly Pro Gln Asn Asp Met
65                  70                  75                  80

Pro Gln Asn Ser Ala Glu Ser Ala Asn Gln Thr Gly Asn Asn Gln Pro
                85                  90                  95

Ala Asp Ser Ser Asp Ser Ala Pro Ala Ser Asn Pro Ala Pro Ala Asn
            100                 105                 110

Gly Gly Ser Asn Phe Gly Arg Val Asp Leu Ala Asn Gly Val Leu Ile
        115                 120                 125

Asp Gly Pro Ser Gln Asn Ile Thr Leu Thr His Cys Lys Gly Asp Ser
    130                 135                 140

Cys Asn Gly Asp Asn Leu Leu Asp Glu Glu Ala Pro Ser Lys Ser Glu
145                 150                 155                 160

Phe Glu Asn Leu Asn Glu Ser Glu Arg Ile Glu Lys Tyr Lys Lys Asp
                165                 170                 175

Gly Lys Ser Asp Lys Phe Thr Asn Leu Val Ala Thr Ala Val Gln Ala
            180                 185                 190

Asn Gly Thr Asn Lys Tyr Val Ile Ile Tyr Lys Asp Lys Ser Ala Ser
        195                 200                 205

Ser Ser Ser Ala Arg Phe Arg Arg Ser Ala Arg Ser Arg Arg Ser Leu
    210                 215                 220

Pro Ala Glu Met Pro Leu Ile Pro Val Asn Gln Ala Asp Thr Leu Ile
225                 230                 235                 240

Val Asp Gly Glu Ala Val Ser Leu Thr Gly His Ser Gly Asn Ile Phe
                245                 250                 255

Ala Pro Glu Gly Asn Tyr Arg Tyr Leu Thr Tyr Gly Ala Glu Lys Leu
            260                 265                 270

Pro Gly Gly Ser Tyr Ala Leu Arg Val Gln Gly Glu Pro Ala Lys Gly
        275                 280                 285

Glu Met Leu Ala Gly Thr Ala Val Tyr Asn Gly Glu Val Leu His Phe
    290                 295                 300

His Thr Glu Asn Gly Arg Pro Tyr Pro Thr Arg Gly Arg Phe Ala Ala
305                 310                 315                 320

Lys Val Asp Phe Gly Ser Lys Ser Val Asp Gly Ile Ile Asp Ser Gly
```

```
                    325                 330                 335
Asp Asp Leu His Met Gly Thr Gln Lys Phe Lys Ala Ala Ile Asp Gly
                340                 345                 350

Asn Gly Phe Lys Gly Thr Trp Thr Glu Asn Gly Gly Asp Val Ser
            355                 360                 365

Gly Arg Phe Tyr Gly Pro Ala Gly Glu Glu Val Ala Gly Lys Tyr Ser
        370                 375                 380

Tyr Arg Pro Thr Asp Ala Glu Lys Gly Gly Phe Gly Val Phe Ala Gly
385                 390                 395                 400

Lys Lys Glu Gln Asp Gly Ser Gly Gly Gly Ala Thr Tyr Lys Val
                405                 410                 415

Asp Glu Tyr His Ala Asn Ala Arg Phe Ala Ile Asp His Phe Asn Thr
                420                 425                 430

Ser Thr Asn Val Gly Gly Phe Tyr Gly Leu Thr Gly Ser Val Glu Phe
            435                 440                 445

Asp Gln Ala Lys Arg Asp Gly Lys Ile Asp Ile Thr Ile Pro Val Ala
        450                 455                 460

Asn Leu Gln Ser Gly Ser Gln His Phe Thr Asp His Leu Lys Ser Ala
465                 470                 475                 480

Asp Ile Phe Asp Ala Ala Gln Tyr Pro Asp Ile Arg Phe Val Ser Thr
                485                 490                 495

Lys Phe Asn Phe Asn Gly Lys Lys Leu Val Ser Val Asp Gly Asn Leu
                500                 505                 510

Thr Met His Gly Lys Thr Ala Pro Val Lys Leu Lys Ala Glu Lys Phe
            515                 520                 525

Asn Cys Tyr Gln Ser Pro Met Ala Lys Thr Glu Val Cys Gly Gly Asp
        530                 535                 540

Phe Ser Thr Thr Ile Asp Arg Thr Lys Trp Gly Val Asp Tyr Leu Val
545                 550                 555                 560

Asn Val Gly Met Thr Lys Ser Val Arg Ile Asp Ile Gln Ile Glu Ala
                565                 570                 575

Ala Lys Gln

<210> SEQ ID NO 92
<211> LENGTH: 2388
<212> TYPE: DNA
<213> ORGANISM: Artificial Sequence
<220> FEATURE:
<223> OTHER INFORMATION: deltaG287-961

<400> SEQUENCE: 92
atggctagcc cgatgttaa atcggcggac acgctgtcaa aaccggccgc tcctgttgtt      60
gctgaaaaag agacagaggt aaaagaagat gcgccacagg caggttctca aggacagggc     120
gcgccatcca cacaaggcag ccaagatatg cggcagtttt cggcagaaaa tacaggcaat     180
ggcggtgcgg caacaacgga caaacccaaa aatgaagacg agggaccgca aaatgatatg     240
ccgcaaaatt ccgccgaatc cgcaaatcaa cagggaaca accaacccgc cgattcttca     300
gattccgccc ccgcgtcaaa ccctgcacct gcgaatggcg gtagcaattt tggaagggtt     360
gatttggcta atggcgtttt gattgatggg ccgtcgcaaa atataacgtt gacccactgt     420
aaaggcgatt cttgtaatgg tgataattta ttggatgaag aagcaccgtc aaaatcagaa     480
tttgaaaatt taaatgagtc tgaacgaatt gagaaatata agaaagatgg gaaaagcgat     540
aaatttacta atttggttgc gacagcagtt caagctaatg gaactaacaa atatgtcatc     600
atttataaag acaagtccgc ttcatcttca tctgcgcgat tcaggcgttc tgcacggtcg     660
```

```
aggaggtcgc ttcctgccga gatgccgcta atccccgtca atcaggcgga tacgctgatt      720
gtcgatgggg aagcggtcag cctgacgggg cattccggca atatcttcgc gcccgaaggg      780
aattaccggt atctgactta cggggcggaa aaattgcccg gcggatcgta tgccctccgt      840
gtgcaaggcg aaccggcaaa aggcgaaatg cttgctggca cggccgtgta caacggcgaa      900
gtgctgcatt ttcatacgga aaacggccgt ccgtacccga ctagaggcag gtttgccgca      960
aaagtcgatt tcggcagcaa atctgtggac ggcattatcg acagcggcga tgatttgcat     1020
atgggtacgc aaaaattcaa agccgccatc gatggaaacg ctttaaggg acttggacg       1080 gaaaatggcg gcggggatgt tccggaaggt ttttacggcc cggccggcga ggaagtggcg     1140
ggaaaataca gctatcgccc gacagatgcg gaaaagggcg gattcggcgt gtttgccggc     1200
aaaaaagagc aggatggatc cggaggagga ggagccacaa acgacgacga tgttaaaaaa     1260
gctgccactg tggccattgc tgctgcctac aacaatggcc aagaaatcaa cggtttcaaa     1320
gctggagaga ccatctacga cattgatgaa acggcacaa ttaccaaaaa agacgcaact     1380
gcagccgatg ttgaagccga cgactttaaa ggtctgggtc tgaaaaaagt cgtgactaac     1440
ctgaccaaaa ccgtcaatga aaacaaacaa acgtcgatg ccaaagtaaa agctgcagaa     1500
tctgaaatag aaaagttaac aaccaagtta gcagacactg atgccgcttt agcagatact     1560
gatgccgctc tggatgcaac caccaacgcc ttgaataaat tggagaaaaa tataacgaca     1620
tttgctgaag agactaagac aaatatcgta aaaattgatg aaaaattaga gccgtggct      1680 gataccgtcg acaagcatgc cgaagcattc aacgatatcg ccgattcatt ggatgaaacc     1740
aacactaagg cagacgaagc cgtcaaaacc gccaatgaag ccaaacagac ggccgaagaa     1800
accaaacaaa acgtcgatgc caaagtaaaa gctgcagaaa ctgcagcagg caaagccgaa     1860
gctgccgctg gcacagctaa tactgcagcc gacaaggccg aagctgtcgc tgcaaaagtt     1920
accgacatca agctgatat cgctacgaac aaagataata ttgctaaaaa agcaaacagt     1980
gccgacgtgt acaccagaga agagtctgac agcaaatttg tcagaattga tggtctgaac     2040
gctactaccg aaaaattgga cacacgcttg gcttctgctg aaaaatccat tgccgatcac     2100
gatactcgcc tgaacggttt ggataaaaca gtgtcagacc tgcgcaaaga aacccgccaa     2160
ggccttgcag aacaagccgc gctctccggt ctgttccaac cttacaacgt gggtcggttc     2220
aatgtaacgg ctgcagtcgg cggctacaaa tccgaatcgg cagtcgccat cggtaccggc     2280
ttccgcttta ccgaaaaactt tgccgccaaa gcaggcgtgg cagtcggcac ttcgtccggt     2340
tcttccgcag cctaccatgt cggcgtcaat tacgagtggt aactcgag                  2388
```

<210> SEQ ID NO 93
<211> LENGTH: 793
<212> TYPE: PRT
<213> ORGANISM: Artificial Sequence
<220> FEATURE:
<223> OTHER INFORMATION: deltaG287-961

<400> SEQUENCE: 93

```
Met Ala Ser Pro Asp Val Lys Ser Ala Asp Thr Leu Ser Lys Pro Ala
1               5                   10                  15

Ala Pro Val Val Ala Glu Lys Glu Thr Glu Val Lys Glu Asp Ala Pro
            20                  25                  30

Gln Ala Gly Ser Gln Gly Gln Gly Ala Pro Ser Thr Gln Gly Ser Gln
        35                  40                  45

Asp Met Ala Ala Val Ser Ala Glu Asn Thr Gly Asn Gly Gly Ala Ala
    50                  55                  60
```

```
Thr Thr Asp Lys Pro Lys Asn Glu Asp Glu Gly Pro Gln Asn Asp Met
 65                  70                  75                  80

Pro Gln Asn Ser Ala Glu Ser Ala Asn Gln Thr Gly Asn Asn Gln Pro
                 85                  90                  95

Ala Asp Ser Ser Asp Ser Ala Pro Ala Ser Asn Pro Ala Pro Ala Asn
            100                 105                 110

Gly Gly Ser Asn Phe Gly Arg Val Asp Leu Ala Asn Gly Val Leu Ile
            115                 120                 125

Asp Gly Pro Ser Gln Asn Ile Thr Leu Thr His Cys Lys Gly Asp Ser
        130                 135                 140

Cys Asn Gly Asp Asn Leu Leu Asp Glu Glu Ala Pro Ser Lys Ser Glu
145                 150                 155                 160

Phe Glu Asn Leu Asn Glu Ser Glu Arg Ile Glu Lys Tyr Lys Lys Asp
                165                 170                 175

Gly Lys Ser Asp Lys Phe Thr Asn Leu Val Ala Thr Ala Val Gln Ala
            180                 185                 190

Asn Gly Thr Asn Lys Tyr Val Ile Ile Tyr Lys Asp Lys Ser Ala Ser
        195                 200                 205

Ser Ser Ser Ala Arg Phe Arg Arg Ser Ala Arg Ser Arg Arg Ser Leu
210                 215                 220

Pro Ala Glu Met Pro Leu Ile Pro Val Asn Gln Ala Asp Thr Leu Ile
225                 230                 235                 240

Val Asp Gly Glu Ala Val Ser Leu Thr Gly His Ser Gly Asn Ile Phe
                245                 250                 255

Ala Pro Glu Gly Asn Tyr Arg Tyr Leu Thr Tyr Gly Ala Glu Lys Leu
            260                 265                 270

Pro Gly Gly Ser Tyr Ala Leu Arg Val Gln Gly Glu Pro Ala Lys Gly
        275                 280                 285

Glu Met Leu Ala Gly Thr Ala Val Tyr Asn Gly Glu Val Leu His Phe
            290                 295                 300

His Thr Glu Asn Gly Arg Pro Tyr Pro Thr Arg Gly Arg Phe Ala Ala
305                 310                 315                 320

Lys Val Asp Phe Gly Ser Lys Ser Val Asp Gly Ile Ile Asp Ser Gly
                325                 330                 335

Asp Asp Leu His Met Gly Thr Gln Lys Phe Lys Ala Ala Ile Asp Gly
            340                 345                 350

Asn Gly Phe Lys Gly Thr Trp Thr Glu Asn Gly Gly Asp Val Ser
        355                 360                 365

Gly Arg Phe Tyr Gly Pro Ala Gly Glu Glu Val Ala Gly Lys Tyr Ser
370                 375                 380

Tyr Arg Pro Thr Asp Ala Glu Lys Gly Phe Gly Val Phe Ala Gly
385                 390                 395                 400

Lys Lys Glu Gln Asp Gly Ser Gly Gly Gly Ala Thr Asn Asp Asp
                405                 410                 415

Asp Val Lys Lys Ala Ala Thr Val Ala Ile Ala Ala Tyr Asn Asn
            420                 425                 430

Gly Gln Glu Ile Asn Gly Phe Lys Ala Gly Glu Thr Ile Tyr Asp Ile
        435                 440                 445

Asp Glu Asp Gly Thr Ile Thr Lys Lys Asp Ala Thr Ala Ala Asp Val
    450                 455                 460

Glu Ala Asp Asp Phe Lys Gly Leu Gly Leu Lys Lys Val Val Thr Asn
465                 470                 475                 480

Leu Thr Lys Thr Val Asn Glu Asn Lys Gln Asn Val Asp Ala Lys Val
```

|     |     |     |     | 485 |     |     |     | 490 |     |     |     | 495 |     |
| --- | --- | --- | --- | --- | --- | --- | --- | --- | --- | --- | --- | --- | --- |
| Lys | Ala | Ala | Glu | Ser | Glu | Ile | Glu | Lys | Leu | Thr | Thr | Lys | Leu | Ala | Asp |
|     |     |     |     | 500 |     |     |     |     | 505 |     |     |     |     | 510 |     |
| Thr | Asp | Ala | Ala | Leu | Ala | Asp | Thr | Asp | Ala | Ala | Leu | Asp | Ala | Thr | Thr |
|     |     |     | 515 |     |     |     |     | 520 |     |     |     |     | 525 |     |     |

Lys Ala Ala Glu Ser Glu Ile Glu Lys Leu Thr Thr Lys Leu Ala Asp
                  500                     505                     510
Thr Asp Ala Ala Leu Ala Asp Thr Asp Ala Ala Leu Asp Ala Thr Thr
              515                     520                     525
Asn Ala Leu Asn Lys Leu Gly Glu Asn Ile Thr Thr Phe Ala Glu Glu
              530                     535                     540
Thr Lys Thr Asn Ile Val Lys Ile Asp Glu Lys Leu Glu Ala Val Ala
545                     550                     555                     560
Asp Thr Val Asp Lys His Ala Glu Ala Phe Asn Asp Ile Ala Asp Ser
                  565                     570                     575
Leu Asp Glu Thr Asn Thr Lys Ala Asp Glu Ala Val Lys Thr Ala Asn
              580                     585                     590
Glu Ala Lys Gln Thr Ala Glu Glu Thr Lys Gln Asn Val Asp Ala Lys
              595                     600                     605
Val Lys Ala Ala Glu Thr Ala Ala Gly Lys Ala Glu Ala Ala Ala Gly
    610                     615                     620
Thr Ala Asn Thr Ala Ala Asp Lys Ala Glu Ala Val Ala Ala Lys Val
625                     630                     635                     640
Thr Asp Ile Lys Ala Asp Ile Ala Thr Asn Lys Asp Asn Ile Ala Lys
                  645                     650                     655
Lys Ala Asn Ser Ala Asp Val Tyr Thr Arg Glu Glu Ser Asp Ser Lys
              660                     665                     670
Phe Val Arg Ile Asp Gly Leu Asn Ala Thr Thr Glu Lys Leu Asp Thr
    675                     680                     685
Arg Leu Ala Ser Ala Glu Lys Ser Ile Ala Asp His Asp Thr Arg Leu
    690                     695                     700
Asn Gly Leu Asp Lys Thr Val Ser Asp Leu Arg Lys Glu Thr Arg Gln
705                     710                     715                     720
Gly Leu Ala Glu Gln Ala Ala Leu Ser Gly Leu Phe Gln Pro Tyr Asn
                  725                     730                     735
Val Gly Arg Phe Asn Val Thr Ala Ala Val Gly Gly Tyr Lys Ser Glu
              740                     745                     750
Ser Ala Val Ala Ile Gly Thr Gly Phe Arg Phe Thr Glu Asn Phe Ala
              755                     760                     765
Ala Lys Ala Gly Val Ala Val Gly Thr Ser Ser Gly Ser Ser Ala Ala
              770                     775                     780
Tyr His Val Gly Val Asn Tyr Glu Trp
785                     790

<210> SEQ ID NO 94
<211> LENGTH: 2700
<212> TYPE: DNA
<213> ORGANISM: Artificial Sequence
<220> FEATURE:
<223> OTHER INFORMATION: deltaG287NZ-919

<400> SEQUENCE: 94
atggctagcc ccgatgtcaa gtcggcggac acgctgtcaa aacctgccgc ccctgttgtt     60
tctgaaaaag agacagaggc aaaggaagat gcgccacagg caggttctca aggacagggc    120
gcgccatccg cacaaggcgg tcaagatatg gcggcggttt cggaagaaaa tacaggcaat    180
ggcggtgcgg cagcaacgga caaacccaaa aatgaagacg aggggcgca aaatgatatg    240 ccgcaaaatg ccgccgatac agatagtttg acaccgaatc acaccccggc ttcgaatatg    300
ccggccggaa atatggaaaa ccaagcaccg gatgccgggg aatcggagca gccggcaaac    360

```
caaccggata tggcaaatac ggcggacgga atgcagggtg acgatccgtc ggcaggcggg    420
gaaaatgccg gcaatacggc tgcccaaggt acaaatcaag ccgaaaacaa tcaaaccgcc    480
ggttctcaaa atcctgcctc ttcaaccaat cctagcgcca cgaatagcgg tggtgatttt    540
ggaaggacga acgtgggcaa ttctgttgtg attgacgggc cgtcgcaaaa tataacgttg    600
acccactgta aaggcgattc ttgtagtggc aataatttct tggatgaaga agtacagcta    660
aaatcagaat ttgaaaaatt aagtgatgca gacaaaataa gtaattacaa gaaagatggg    720
aagaatgacg ggaagaatga taaatttgtc ggtttggttg ccgatagtgt gcagatgaag    780
ggaatcaatc aatatattat cttttataaa cctaaaccca cttcatttgc gcgatttagg    840
cgttctgcac ggtcgaggcg gtcgcttccg gccgagatgc cgctgattcc cgtcaatcag    900
gcggatacgc tgattgtcga tggggaagcg gtcagcctga cggggcattc cggcaatatc    960
ttcgcgcccg aagggaatta ccggtatctg acttacgggg cggaaaaatt gcccggcgga   1020
tcgtatgccc tccgtgttca aggcgaacct tcaaaaggcg aaatgctcgc gggcacggca   1080
gtgtacaacg gcgaagtgct gcattttcat acggaaaacg ccgtccgtc cccgtccaga   1140 ggcaggtttg ccgcaaaagt cgatttcggc agcaaatctg tggacggcat tatcgacagc   1200
ggcgatggtt tgcatatggg tacgcaaaaa ttcaaagccg ccatcgatgg aaacggcttt   1260
aaggggactt ggacggaaaa tggcggcggg gatgtttccg gaaagtttta cggcccggcc   1320
ggcgaggaag tggcgggaaa atacagctat cgcccaacag atgcggaaaa gggcggattc   1380
ggcgtgtttg ccggcaaaaa agagcaggat ggatccggag gaggaggatg ccaaagcaag   1440
agcatccaaa cctttccgca acccgacaca tccgtcatca acggcccgga ccggccggtc   1500
ggcatccccg accccgccgg aacgacggtc ggcggcggcg gggccgtcta taccgttgta   1560
ccgcacctgt ccctgcccca ctgggcggcg caggatttcg ccaaaagcct gcaatccttc   1620
cgcctcggct gcgccaattt gaaaaaccgc caaggctggc aggatgtgtg cgcccaagcc   1680
tttcaaaccc ccgtccattc cttcaggca aaacagtttt tgaacgcta tttcacgccg   1740 tggcaggttg caggcaacgg aagccttgcc ggtacggtta ccggctatta cgagccggtg   1800
ctgaagggcg acgacaggcg gacggcacaa gcccgcttcc cgatttacgg tattcccgac   1860
gattttatct ccgtcccct gcctgccggt ttgcggagcg gaaaagccct tgtccgcatc   1920
aggcagacgg gaaaaaacag cggcacaatc gacaataccg gcggcacaca taccgccgac   1980
ctctcccgat tccccatcac cgcgcgcaca acggcaatca aaggcaggtt tgaaggaagc   2040
cgcttcctcc cctaccacac gcgcaaccaa atcaacggcg gcgcgcttga cggcaaagcc   2100
ccgatactcg gttacgccga agaccccgtc gaactttttt ttatgcacat ccaaggctcg   2160
ggccgtctga aaccccgtc cggcaaatac atccgcatcg gctatgccga caaaaacgaa   2220
catccctacg tttccatcgg acgctatatg gcggacaaag gctacctcaa gctcgggcag   2280
acctcgatgc agggcatcaa agcctatatg cggcaaaatc cgcaacgcct cgccgaagtt   2340
ttgggtcaaa accccagcta tatctttttc cgcgagcttg ccggaagcag caatgacggt   2400
cccgtcggcg cactgggcac gccgttgatg ggggaatatg ccggcgcagt cgaccggcac   2460
tacattacct tgggcgcgcc cttatttgtc gccaccgccc atccggttac ccgcaaagcc   2520
ctcaaccgcc tgattatggc gcaggatacc ggcagcgcga ttaaaggcgc ggtgcgcgtg   2580
gattattttt ggggatacgg cgacgaagcc ggcgaacttg ccggcaaaca gaaaaccacg   2640
ggttacgtct ggcagctcct acccaacggt atgaagcccg aataccgccc gtaaaagctt   2700
```

<210> SEQ ID NO 95
<211> LENGTH: 897
<212> TYPE: PRT
<213> ORGANISM: Artificial Sequence
<220> FEATURE:
<223> OTHER INFORMATION: deltaG287NZ-919

<400> SEQUENCE: 95

```
Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
        35                  40                  45

Asp Met Ala Ala Val Ser Glu Glu Asn Thr Gly Asn Gly Gly Ala Ala
50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Asp Pro Ser Ala Gly Gly Glu Asn Ala Gly
130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Glu Val Leu His
        355                 360                 365

Phe His Thr Glu Asn Gly Arg Pro Ser Pro Ser Arg Gly Arg Phe Ala
370                 375                 380
```

```
Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                    405                 410                 415

Gly Asn Gly Phe Lys Gly Thr Trp Thr Glu Asn Gly Gly Gly Asp Val
                420                 425                 430

Ser Gly Lys Phe Tyr Gly Pro Ala Gly Glu Glu Val Ala Gly Lys Tyr
                435                 440                 445

Ser Tyr Arg Pro Thr Asp Ala Glu Lys Gly Gly Phe Gly Val Phe Ala
            450                 455                 460

Gly Lys Lys Glu Gln Asp Gly Ser Gly Gly Gly Cys Gln Ser Lys
465                 470                 475                 480

Ser Ile Gln Thr Phe Pro Gln Pro Asp Thr Ser Val Ile Asn Gly Pro
                    485                 490                 495

Asp Arg Pro Val Gly Ile Pro Asp Pro Ala Gly Thr Thr Val Gly Gly
                500                 505                 510

Gly Gly Ala Val Tyr Thr Val Val Pro His Leu Ser Leu Pro His Trp
                515                 520                 525

Ala Ala Gln Asp Phe Ala Lys Ser Leu Gln Ser Phe Arg Leu Gly Cys
            530                 535                 540

Ala Asn Leu Lys Asn Arg Gln Gly Trp Gln Asp Val Cys Ala Gln Ala
545                 550                 555                 560

Phe Gln Thr Pro Val His Ser Phe Gln Ala Lys Gln Phe Phe Glu Arg
                565                 570                 575

Tyr Phe Thr Pro Trp Gln Val Ala Gly Asn Gly Ser Leu Ala Gly Thr
                580                 585                 590

Val Thr Gly Tyr Tyr Glu Pro Val Leu Lys Gly Asp Asp Arg Arg Thr
            595                 600                 605

Ala Gln Ala Arg Phe Pro Ile Tyr Gly Ile Pro Asp Asp Phe Ile Ser
            610                 615                 620

Val Pro Leu Pro Ala Gly Leu Arg Ser Gly Lys Ala Leu Val Arg Ile
625                 630                 635                 640

Arg Gln Thr Gly Lys Asn Ser Gly Thr Ile Asp Asn Thr Gly Gly Thr
                645                 650                 655

His Thr Ala Asp Leu Ser Arg Phe Pro Ile Thr Ala Arg Thr Thr Ala
                660                 665                 670

Ile Lys Gly Arg Phe Glu Gly Ser Arg Phe Leu Pro Tyr His Thr Arg
                675                 680                 685

Asn Gln Ile Asn Gly Gly Ala Leu Asp Gly Lys Ala Pro Ile Leu Gly
                690                 695                 700

Tyr Ala Glu Asp Pro Val Glu Leu Phe Phe Met His Ile Gln Gly Ser
705                 710                 715                 720

Gly Arg Leu Lys Thr Pro Ser Gly Lys Tyr Ile Arg Ile Gly Tyr Ala
                725                 730                 735

Asp Lys Asn Glu His Pro Tyr Val Ser Ile Gly Arg Tyr Met Ala Asp
                740                 745                 750

Lys Gly Tyr Leu Lys Leu Gly Gln Thr Ser Met Gln Gly Ile Lys Ala
            755                 760                 765

Tyr Met Arg Gln Asn Pro Gln Arg Leu Ala Glu Val Leu Gly Gln Asn
            770                 775                 780

Pro Ser Tyr Ile Phe Phe Arg Glu Leu Ala Gly Ser Ser Asn Asp Gly
785                 790                 795                 800

Pro Val Gly Ala Leu Gly Thr Pro Leu Met Gly Glu Tyr Ala Gly Ala
```

```
                805                 810                 815
Val Asp Arg His Tyr Ile Thr Leu Gly Ala Pro Leu Phe Val Ala Thr
            820                 825                 830

Ala His Pro Val Thr Arg Lys Ala Leu Asn Arg Leu Ile Met Ala Gln
        835                 840                 845

Asp Thr Gly Ser Ala Ile Lys Gly Ala Val Arg Val Asp Tyr Phe Trp
    850                 855                 860

Gly Tyr Gly Asp Glu Ala Gly Glu Leu Ala Gly Lys Gln Lys Thr Thr
865                 870                 875                 880

Gly Tyr Val Trp Gln Leu Leu Pro Asn Gly Met Lys Pro Glu Tyr Arg
                885                 890                 895

Pro

<210> SEQ ID NO 96
<211> LENGTH: 1941
<212> TYPE: DNA
<213> ORGANISM: Artificial Sequence
<220> FEATURE:
<223> OTHER INFORMATION: deltaG287NZ-953

<400> SEQUENCE: 96
atggctagcc ccgatgtcaa gtcggcggac acgctgtcaa aacctgccgc ccctgttgtt      60
tctgaaaaag agacagaggc aaaggaagat gcgccacagg caggttctca aggacagggc     120
gcgccatccg cacaaggcgg tcaagatatg gcggcggttt cggaagaaaa tacaggcaat     180
ggcggtgcgg cagcaacgga caaacccaaa aatgaagacg agggggcgca aaatgatatg     240
ccgcaaaatg ccgccgatac agatagtttg acaccgaatc acaccccggc ttcgaatatg     300
ccggccggaa atatggaaaa ccaagcaccg gatgccgggg aatcgagcaa gccggcaaac     360
caaccggata tggcaaatac ggcggacgga atgcagggtg acgatccgtc ggcaggcggg     420
gaaaatgccg gcaatacggc tgcccaaggt acaaatcaag ccgaaaacaa tcaaaccgcc     480
ggttctcaaa atcctgcctc ttcaaccaat cctagcgcca cgaatagcgg tggtgatttt     540
ggaaggacga acgtgggcaa ttctgttgtg attgacgggc gtcgcaaaaa tataacgttg     600
acccactgta aaggcgattc ttgtagtggc aataatttct tggatgaaga agtacagcta     660
aaatcagaat ttgaaaaatt aagtgatgca gacaaaataa gtaattacaa gaaagatggg     720
aagaatgacg ggaagaatga taaatttgtc ggtttggttg ccgatagtgt gcagatgaag     780
ggaatcaatc aatatattat cttttataaa cctaaaccca cttcatttgc gcgatttagg     840
cgttctgcac ggtcgaggcg gtcgcttccg gccgagatgc cgctgattcc cgtcaatcag     900
gcggatacgc tgattgtcga tggggaagcg gtcagcctga cggggcattc cggcaatatc     960
ttcgcgcccg aagggaatta ccggtatctg acttacgggg cggaaaaatt gcccggcgga    1020
tcgtatgccc tccgtgttca aggcgaacct tcaaaaggcg aaatgctcgc gggcacggca    1080
gtgtacaacg gcgaagtgct gcattttcat acggaaaacg gccgtccgtc cccgtccaga    1140
ggcaggtttg ccgcaaaagt cgatttcggc agcaaatctg tggacggcat tatcgacagc    1200
ggcgatggtt tgcatatggg tacgcaaaaa ttcaagccgg ccatcgatgg aaacggcttt    1260
aaggggactt ggacggaaaa tggcggcggg gatgtttccg aaagttttac cggccggcc     1320
ggcgaggaag tggcggaaaa atacagctat cgcccaacag atgcgaaaaa gggcggattc    1380
ggcgtgtttg ccggcaaaaa agagcaggat ggatccggag gaggaggagc cacctacaaa    1440
gtggacgaat atcacgccaa cgccgtttc gccatcgacc atttcaacac cagcaccaac    1500
gtcggcggtt tttacggtct gaccggttcc gtcgagttcg accagcaaa acgcgacggt    1560
```

```
aaaatcgaca tcaccatccc cgttgccaac ctgcaaagcg gttcgcaaca ctttaccgac    1620
cacctgaaat cagccgacat cttcgatgcc gcccaatatc cggacatccg ctttgtttcc    1680
accaaattca acttcaacgg caaaaaactg gtttccgttg acggcaacct gaccatgcac    1740
ggcaaaaccg cccccgtcaa actcaaagcc gaaaaattca actgctacca aagcccgatg    1800
gcgaaaaccg aagtttgcgg cggcgacttc agcaccacca tcgaccgcac caaatggggc    1860
gtggactacc tcgttaacgt tggtatgacc aaaagcgtcc gcatcgacat ccaaatcgag    1920
gcagccaaac aataaaagct t                                              1941
```

<210> SEQ ID NO 97
<211> LENGTH: 644
<212> TYPE: PRT
<213> ORGANISM: Artificial Sequence
<220> FEATURE:
<223> OTHER INFORMATION: deltaG287NZ-953

<400> SEQUENCE: 97

```
Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
                20                  25                  30

Gln Ala Gly Ser Gln Gly Gln Gly Ala Pro Ser Ala Gln Gly Gly Gln
            35                  40                  45

Asp Met Ala Ala Val Ser Glu Glu Asn Thr Gly Asn Gly Gly Ala Ala
        50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
                100                 105                 110

Gly Glu Ser Glu Gln Pro Ala Asn Gln Pro Asp Met Ala Asn Thr Ala
            115                 120                 125

Asp Gly Met Gln Gly Asp Asp Pro Ser Ala Gly Gly Glu Asn Ala Gly
        130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
                180                 185                 190

Gly Pro Ser Gln Asn Ile Thr Leu Thr His Cys Lys Gly Asp Ser Cys
            195                 200                 205

Ser Gly Asn Asn Phe Leu Asp Glu Glu Val Gln Leu Lys Ser Glu Phe
        210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
                260                 265                 270

Pro Thr Ser Phe Ala Arg Phe Arg Arg Ser Ala Arg Ser Arg Arg Ser
            275                 280                 285

Leu Pro Ala Glu Met Pro Leu Ile Pro Val Asn Gln Ala Asp Thr Leu
```

```
            290              295              300
Ile Val Asp Gly Glu Ala Val Ser Leu Thr Gly His Ser Gly Asn Ile
305              310              315              320

Phe Ala Pro Glu Gly Asn Tyr Arg Tyr Leu Thr Tyr Gly Ala Glu Lys
            325              330              335

Leu Pro Gly Gly Ser Tyr Ala Leu Arg Val Gln Gly Glu Pro Ser Lys
            340              345              350

Gly Glu Met Leu Ala Gly Thr Ala Val Tyr Asn Gly Val Leu His
            355              360              365

Phe His Thr Glu Asn Gly Arg Pro Ser Pro Ser Arg Gly Arg Phe Ala
370              375              380

Ala Lys Val Asp Phe Gly Ser Lys Ser Val Asp Gly Ile Ile Asp Ser
385              390              395              400

Gly Asp Gly Leu His Met Gly Thr Gln Lys Phe Lys Ala Ala Ile Asp
            405              410              415

Gly Asn Gly Phe Lys Gly Thr Trp Thr Glu Asn Gly Gly Gly Asp Val
            420              425              430

Ser Gly Lys Phe Tyr Gly Pro Ala Gly Glu Glu Val Ala Gly Lys Tyr
            435              440              445

Ser Tyr Arg Pro Thr Asp Ala Glu Lys Gly Gly Phe Gly Val Phe Ala
            450              455              460

Gly Lys Lys Glu Gln Asp Gly Ser Gly Gly Gly Ala Thr Tyr Lys
465              470              475              480

Val Asp Glu Tyr His Ala Asn Ala Arg Phe Ala Ile Asp His Phe Asn
            485              490              495

Thr Ser Thr Asn Val Gly Gly Phe Tyr Gly Leu Thr Gly Ser Val Glu
            500              505              510

Phe Asp Gln Ala Lys Arg Asp Gly Lys Ile Asp Ile Thr Ile Pro Val
            515              520              525

Ala Asn Leu Gln Ser Gly Ser Gln His Phe Thr Asp His Leu Lys Ser
            530              535              540

Ala Asp Ile Phe Asp Ala Ala Gln Tyr Pro Asp Ile Arg Phe Val Ser
545              550              555              560

Thr Lys Phe Asn Phe Asn Gly Lys Lys Leu Val Ser Val Asp Gly Asn
            565              570              575

Leu Thr Met His Gly Lys Thr Ala Pro Val Lys Leu Lys Ala Glu Lys
            580              585              590

Phe Asn Cys Tyr Gln Ser Pro Met Ala Lys Thr Glu Val Cys Gly Gly
            595              600              605

Asp Phe Ser Thr Thr Ile Asp Arg Thr Lys Trp Gly Val Asp Tyr Leu
            610              615              620

Val Asn Val Gly Met Thr Lys Ser Val Arg Ile Asp Ile Gln Ile Glu
625              630              635              640

Ala Ala Lys Gln

<210> SEQ ID NO 98
<211> LENGTH: 2583
<212> TYPE: DNA
<213> ORGANISM: Artificial Sequence
<220> FEATURE:
<223> OTHER INFORMATION: deltaG287NZ-961

<400> SEQUENCE: 98
atggctagcc ccgatgtcaa gtcggcggac acgctgtcaa aacctgccgc ccctgttgtt      60
tctgaaaaag agacagaggc aaaggaagat gcgccacagg caggttctca aggacagggc     120
```

```
gcgccatccg cacaaggcgg tcaagatatg gcggcggttt cggaagaaaa tacaggcaat      180
ggcggtgcgg cagcaacgga caaacccaaa aatgaagacg aggggggcgca aaatgatatg    240 ccgcaaaatg ccgccgatac agatagtttg acaccgaatc acaccccggc ttcgaatatg     300
ccggccggaa atatggaaaa ccaagcaccg gatgccgggg aatcggagca gccggcaaac    360
caaccggata tggcaaatac ggcggacgga atgcagggtg acgatccgtc ggcaggcggg    420
gaaaatgccg gcaatacggc tgcccaaggt acaaatcaag ccgaaaacaa tcaaaccgcc    480
ggttctcaaa atcctgcctc ttcaaccaat cctagcgcca cgaatagcgg tggtgatttt     540
ggaaggacga acgtgggcaa ttctgttgtg attgacgggc cgtcgcaaaa tataacgttg    600
acccactgta aaggcgattc ttgtagtggc aataatttct tggatgaaga agtacagcta   660
aaatcagaat ttgaaaaatt aagtgatgca gacaaaataa gtaattacaa gaaagatggg   720
aagaatgacg ggaagaatga taaatttgtc ggtttggttg ccgatagtgt gcagatgaag    780
ggaatcaatc aatatattat cttttataaa cctaaaccca cttcatttgc gcgatttagg   840
cgttctgcac ggtcgaggcg gtcgcttccg gccgagatgc cgctgattcc cgtcaatcag    900
gcggatacgc tgattgtcga tggggaagcg gtcagcctga cggggcattc cggcaatatc   960
ttcgcgcccg aagggaatta ccggtatctg acttacgggg cggaaaaatt gcccggcgga  1020
tcgtatgccc tccgtgttca aggcgaacct tcaaaaggcg aaatgctcgc gggcacggca  1080
gtgtacaacg gcgaagtgct gcattttcat acggaaaacg gccgtccgtc cccgtccaga   1140
ggcaggtttg ccgcaaaagt cgatttcggc agcaaatctg tggacggcat tatcgacagc   1200
ggcgatggtt tgcatatggg tacgcaaaaa ttcaaagccg ccatcgatgg aaacggcttt   1260
aaggggactt ggacggaaaa tggcggcggg gatgtttccg gaaagtttta cggcccggcc   1320
ggcgaggaag tggcgggaaa atacagctat cgcccaacag atgcggaaaa gggcggattc   1380
ggcgtgtttg ccggcaaaaa agagcaggat ggatccggag gaggaggagc cacaaacgac  1440
gacgatgtta aaaaagctgc cactgtggcc attgctgctg cctacaacaa tggccaagaa   1500
atcaacggtt tcaaagctgg agagaccatc tacgacattg atgaagacgg cacaattacc   1560
aaaaaagacg caactgcagc cgatgttgaa gccgacgact ttaaaggtct gggtctgaaa  1620
aaagtcgtga ctaacctgac caaaaccgtc aatgaaaaca acaaaaacgt cgatgccaaa  1680
gtaaaagctg cagaatctga aatagaaaag ttaacaacca agttagcaga cactgatgcc   1740
gctttagcag atactgatgc cgctctggat gcaaccacca acgccttgaa taaattggga  1800
gaaaatataa cgacatttgc tgaagagact aagacaaata tcgtaaaaat tgatgaaaaa   1860
ttagaagccg tggctgatac cgtcgacaag catgccgaag cattcaacga tatcgccgat   1920
tcattggatg aaaccaacac taaggcagac gaagccgtca aaaccgccaa tgaagccaaa   1980
cagacggccg aagaaccaa acaaaacgtc gatgccaaag taaaagctgc agaaactgca   2040
gcaggcaaag ccgaagctgc cgctggcaca gctaatactg cagccgacaa ggccgaagct   2100
gtcgctgcaa aagttaccga catcaaagct gatatcgcta cgaacaaaga taatattgct   2160
aaaaaagcaa acagtgccga cgtgtacacc agagaagagt ctgacagcaa atttgtcaga   2220
attgatggtc tgaacgctac taccgaaaaa ttggacacac gcttggcttc tgctgaaaaa   2280
tccattgccg atcacgatac tcgcctgaac ggtttggata aaacagtgtc agacctgcgc   2340
aaagaaaccc gccaaggcct tgcagaacaa gccgcgctct ccggtctgtt ccaaccttac   2400
aacgtgggtc ggttcaatgt aacggctgca gtcggcggct acaaatccga atcggcagtc   2460
gccatcggta ccggcttccg ctttaccgaa aactttgccg ccaaagcagg cgtggcagtc   2520
```

```
ggcacttcgt ccggttcttc cgcagcctac catgtcggcg tcaattacga gtggtaaaag    2580
ctt                                                                  2583
```

<210> SEQ ID NO 99
<211> LENGTH: 858
<212> TYPE: PRT
<213> ORGANISM: Artificial Sequence
<220> FEATURE:
<223> OTHER INFORMATION: deltaG287NZ-961

<400> SEQUENCE: 99

| | | | | | | | | | | | | | | | |
|---|---|---|---|---|---|---|---|---|---|---|---|---|---|---|---|
| Met | Ala | Ser | Pro | Asp | Val | Lys | Ser | Ala | Asp | Thr | Leu | Ser | Lys | Pro | Ala |
| 1 | | | | 5 | | | | | 10 | | | | | 15 | |
| Ala | Pro | Val | Val | Ser | Glu | Lys | Glu | Thr | Glu | Ala | Lys | Glu | Asp | Ala | Pro |
| | | | 20 | | | | | 25 | | | | | 30 | | |
| Gln | Ala | Gly | Ser | Gln | Gly | Gln | Gly | Ala | Pro | Ser | Ala | Gln | Gly | Gly | Gln |
| | | | | 35 | | | | | 40 | | | | | 45 | |
| Asp | Met | Ala | Ala | Val | Ser | Glu | Glu | Asn | Thr | Gly | Asn | Gly | Gly | Ala | Ala |
| | 50 | | | | | 55 | | | | | 60 | | | | |
| Ala | Thr | Asp | Lys | Pro | Lys | Asn | Glu | Asp | Glu | Gly | Ala | Gln | Asn | Asp | Met |
| 65 | | | | | 70 | | | | | 75 | | | | | 80 |
| Pro | Gln | Asn | Ala | Ala | Asp | Thr | Asp | Ser | Leu | Thr | Pro | Asn | His | Thr | Pro |
| | | | | 85 | | | | | 90 | | | | | 95 | |
| Ala | Ser | Asn | Met | Pro | Ala | Gly | Asn | Met | Glu | Asn | Gln | Ala | Pro | Asp | Ala |
| | | | 100 | | | | | 105 | | | | | 110 | | |
| Gly | Glu | Ser | Glu | Gln | Pro | Ala | Asn | Gln | Pro | Asp | Met | Ala | Asn | Thr | Ala |
| | | | | 115 | | | | | 120 | | | | | 125 | |
| Asp | Gly | Met | Gln | Gly | Asp | Asp | Pro | Ser | Ala | Gly | Gly | Glu | Asn | Ala | Gly |
| | 130 | | | | | 135 | | | | | 140 | | | | |
| Asn | Thr | Ala | Ala | Gln | Gly | Thr | Asn | Gln | Ala | Glu | Asn | Asn | Gln | Thr | Ala |
| 145 | | | | | 150 | | | | | 155 | | | | | 160 |
| Gly | Ser | Gln | Asn | Pro | Ala | Ser | Ser | Thr | Asn | Pro | Ser | Ala | Thr | Asn | Ser |
| | | | | 165 | | | | | 170 | | | | | 175 | |
| Gly | Gly | Asp | Phe | Gly | Arg | Thr | Asn | Val | Gly | Asn | Ser | Val | Val | Ile | Asp |
| | | | 180 | | | | | 185 | | | | | 190 | | |
| Gly | Pro | Ser | Gln | Asn | Ile | Thr | Leu | Thr | His | Cys | Lys | Gly | Asp | Ser | Cys |
| | | | | 195 | | | | | 200 | | | | | 205 | |
| Ser | Gly | Asn | Asn | Phe | Leu | Asp | Glu | Glu | Val | Gln | Leu | Lys | Ser | Glu | Phe |
| | 210 | | | | | 215 | | | | | 220 | | | | |
| Glu | Lys | Leu | Ser | Asp | Ala | Asp | Lys | Ile | Ser | Asn | Tyr | Lys | Lys | Asp | Gly |
| 225 | | | | | 230 | | | | | 235 | | | | | 240 |
| Lys | Asn | Asp | Gly | Lys | Asn | Asp | Lys | Phe | Val | Gly | Leu | Val | Ala | Asp | Ser |
| | | | | 245 | | | | | 250 | | | | | 255 | |
| Val | Gln | Met | Lys | Gly | Ile | Asn | Gln | Tyr | Ile | Ile | Phe | Tyr | Lys | Pro | Lys |
| | | | 260 | | | | | 265 | | | | | 270 | | |
| Pro | Thr | Ser | Phe | Ala | Arg | Phe | Arg | Arg | Ser | Ala | Arg | Ser | Arg | Arg | Ser |
| | | | | 275 | | | | | 280 | | | | | 285 | |
| Leu | Pro | Ala | Glu | Met | Pro | Leu | Ile | Pro | Val | Asn | Gln | Ala | Asp | Thr | Leu |
| | 290 | | | | | 295 | | | | | 300 | | | | |
| Ile | Val | Asp | Gly | Glu | Ala | Val | Ser | Leu | Thr | Gly | His | Ser | Gly | Asn | Ile |
| 305 | | | | | 310 | | | | | 315 | | | | | 320 |
| Phe | Ala | Pro | Glu | Gly | Asn | Tyr | Arg | Tyr | Leu | Thr | Tyr | Gly | Ala | Glu | Lys |
| | | | | 325 | | | | | 330 | | | | | 335 | |
| Leu | Pro | Gly | Gly | Ser | Tyr | Ala | Leu | Arg | Val | Gln | Gly | Glu | Pro | Ser | Lys |
| | | | 340 | | | | | 345 | | | | | 350 | | |

```
Gly Glu Met Leu Ala Gly Thr Ala Val Tyr Asn Gly Glu Val Leu His
            355                 360                 365
Phe His Thr Glu Asn Gly Arg Pro Ser Pro Ser Arg Gly Arg Phe Ala
    370                 375                 380
Ala Lys Val Asp Phe Gly Ser Lys Ser Val Asp Gly Ile Ile Asp Ser
385                 390                 395                 400
Gly Asp Gly Leu His Met Gly Thr Gln Lys Phe Lys Ala Ala Ile Asp
                405                 410                 415
Gly Asn Gly Phe Lys Gly Thr Trp Thr Glu Asn Gly Gly Asp Val
            420                 425                 430
Ser Gly Lys Phe Tyr Gly Pro Ala Gly Glu Val Ala Gly Lys Tyr
            435                 440                 445
Ser Tyr Arg Pro Thr Asp Ala Glu Lys Gly Gly Phe Gly Val Phe Ala
    450                 455                 460
Gly Lys Lys Glu Gln Asp Gly Ser Gly Gly Gly Ala Thr Asn Asp
465                 470                 475                 480
Asp Asp Val Lys Lys Ala Ala Thr Val Ala Ile Ala Ala Tyr Asn
                485                 490                 495
Asn Gly Gln Glu Ile Asn Gly Phe Lys Ala Gly Glu Thr Ile Tyr Asp
            500                 505                 510
Ile Asp Glu Asp Gly Thr Ile Thr Lys Asp Ala Thr Ala Ala Asp
            515                 520                 525
Val Glu Ala Asp Asp Phe Lys Gly Leu Gly Leu Lys Lys Val Val Thr
    530                 535                 540
Asn Leu Thr Lys Thr Val Asn Glu Asn Lys Gln Asn Val Asp Ala Lys
545                 550                 555                 560
Val Lys Ala Ala Glu Ser Glu Ile Glu Lys Leu Thr Thr Lys Leu Ala
                565                 570                 575
Asp Thr Asp Ala Ala Leu Ala Asp Thr Asp Ala Ala Leu Asp Ala Thr
            580                 585                 590
Thr Asn Ala Leu Asn Lys Leu Gly Glu Asn Ile Thr Thr Phe Ala Glu
            595                 600                 605
Glu Thr Lys Thr Asn Ile Val Lys Ile Asp Glu Lys Leu Glu Ala Val
    610                 615                 620
Ala Asp Thr Val Asp Lys His Ala Glu Ala Phe Asn Asp Ile Ala Asp
625                 630                 635                 640
Ser Leu Asp Glu Thr Asn Thr Lys Ala Asp Glu Ala Val Lys Thr Ala
                645                 650                 655
Asn Glu Ala Lys Gln Thr Ala Glu Glu Thr Lys Gln Asn Val Asp Ala
            660                 665                 670
Lys Val Lys Ala Ala Glu Thr Ala Ala Gly Lys Ala Glu Ala Ala Ala
            675                 680                 685
Gly Thr Ala Asn Thr Ala Ala Asp Lys Ala Glu Ala Val Ala Ala Lys
    690                 695                 700
Val Thr Asp Ile Lys Ala Asp Ile Ala Thr Asn Lys Asp Asn Ile Ala
705                 710                 715                 720
Lys Lys Ala Asn Ser Ala Asp Val Tyr Thr Arg Glu Glu Ser Asp Ser
                725                 730                 735
Lys Phe Val Arg Ile Asp Gly Leu Asn Ala Thr Thr Glu Lys Leu Asp
            740                 745                 750
Thr Arg Leu Ala Ser Ala Glu Lys Ser Ile Ala Asp His Asp Thr Arg
        755                 760                 765
Leu Asn Gly Leu Asp Lys Thr Val Ser Asp Leu Arg Lys Glu Thr Arg
```

|  |  |  |  |  |  |  |  |  |  |  |  |
|--|--|--|--|--|--|--|--|--|--|--|--|
|  | 770 |  |  | 775 |  |  | 780 |  |  |  |  |
| Gln | Gly | Leu | Ala | Glu | Gln | Ala | Ala | Leu | Ser | Gly |  |
| 785 |  |  |  | 790 |  |  |  | 795 |  |  |  |
| Leu | Phe | Gln | Pro | Tyr |  |  |  |  |  |  |  |
|  |  |  |  | 800 |  |  |  |  |  |  |  |

Asn Val Gly Arg Phe Asn Val Thr Ala Ala Val Gly Gly Tyr Lys Ser
            805                 810                 815

Glu Ser Ala Val Ala Ile Gly Thr Gly Phe Arg Phe Thr Glu Asn Phe
            820                 825                 830

Ala Ala Lys Ala Gly Val Ala Val Gly Thr Ser Ser Gly Ser Ser Ala
            835                 840                 845

Ala Tyr His Val Gly Val Asn Tyr Glu Trp
            850                 855

<210> SEQ ID NO 100
<211> LENGTH: 4425
<212> TYPE: DNA
<213> ORGANISM: Artificial Sequence
<220> FEATURE:
<223> OTHER INFORMATION: deltaG983-ORF46.1

<400> SEQUENCE: 100

| atgacttctg | cgcccgactt | caatgcaggc | ggtaccggta | tcggcagcaa | cagcagagca | 60 |
| acaacagcga | aatcagcagc | agtatcttac | gccggtatca | agaacgaaat | gtgcaaagac | 120 |
| agaagcatgc | tctgtgccgg | tcgggatgac | gttgcggtta | cagacaggga | tgccaaaatc | 180 |
| aatgccccc | ccccgaatct | gcataccgga | gactttccaa | acccaaatga | cgcatacaag | 240 |
| aatttgatca | acctcaaacc | tgcaattgaa | gcaggctata | caggacgcgg | ggtagaggta | 300 |
| ggtatcgtcg | acacaggcga | atccgtcggc | agcatatcct | ttcccgaact | gtatggcaga | 360 |
| aaagaacacg | gctataacga | aaattacaaa | aactatacgg | cgtatatgcg | gaaggaagcg | 420 |
| cctgaagacg | gaggcggtaa | agacattgaa | gcttctttcg | acgatgaggc | cgttatagag | 480 |
| actgaagcaa | agccgacgga | tatccgccac | gtaaaagaaa | tcggacacat | cgatttggtc | 540 |
| tcccatatta | ttggcgggcg | ttccgtggac | ggcagacctg | caggcggtat | tgcgcccgat | 600 |
| gcgacgctac | acataatgaa | tacgaatgat | gaaaccaaga | cgaaatgat | ggttgcagcc | 660 |
| atccgcaatg | catgggtcaa | gctgggcgaa | cgtggcgtgc | gcatcgtcaa | taacagtttt | 720 |
| ggaacaacat | cgagggcagg | cactgccgac | cttttccaaa | tagccaattc | ggaggagcag | 780 |
| taccgccaag | cgttgctcga | ctattccggc | ggtgataaaa | cagacgaggg | tatccgcctg | 840 |
| atgcaacaga | gcgattacgg | caacctgtcc | taccacatcc | gtaataaaaa | catgcttttc | 900 |
| atctttttcga | caggcaatga | cgcacaagct | cagcccaaca | catatgccct | attgccattt | 960 |
| tatgaaaaag | acgctcaaaa | aggcattatc | acagtcgcag | gcgtagaccg | cagtggagaa | 1020 |
| aagttcaaac | gggaaatgta | tggagaaccg | ggtacagaac | cgcttgagta | tggctccaac | 1080 |
| cattgcggaa | ttactgccat | gtggtgcctg | tcggcaccct | atgaagcaag | cgtccgtttc | 1140 |
| acccgtacaa | acccgattca | aattgccgga | acatcctttt | ccgcacccat | cgtaaccggc | 1200 |
| acggcggctc | tgctgctgca | gaaatacccg | tggatgagca | cgacaacct | gcgtaccacg | 1260 |
| ttgctgacga | cggctcagga | catcggtgca | gtcggcgtgg | acagcaagtt | cggctgggga | 1320 |
| ctgctggatg | cgggtaaggc | catgaacgga | cccgcgtcct | ttccgttcgg | cgactttacc | 1380 |
| gccgatacga | aaggtacatc | cgatattgcc | tactccttcc | gtaacgacat | ttcaggcacg | 1440 |
| ggcggcctga | tcaaaaaagg | cggcagccaa | ctgcaactgc | acggcaacaa | cacctatacg | 1500 |
| ggcaaaacca | ttatcgaagg | cggttcgctg | gtgttgtacg | gcaacaacaa | atcggatatg | 1560 |
| cgcgtcgaaa | ccaaaggtgc | gctgatttat | aacggggcgg | catccggcgg | cagcctgaac | 1620 |

```
agcgacggca ttgtctatct ggcagatacc gaccaatccg gcgcaaacga aaccgtacac   1680
atcaaaggca gtctgcagct ggacggcaaa ggtacgctgt acacacgttt gggcaaactg   1740
ctgaaagtgg acggtacggc gattatcggc ggcaagctgt acatgtcggc acgcggcaag   1800
ggggcaggct atctcaacag taccggacga cgtgttccct tcctgagtgc cgccaaaatc   1860
gggcaggatt attctttctt cacaaacatc gaaaccgacg gcggcctgct ggcttccctc   1920
gacagcgtcg aaaaaacagc gggcagtgaa ggcgacacgc tgtcctatta tgtccgtcgc   1980
ggcaatgcgg cacggactgc ttcggcagcg gcacattccg cgcccgccgg tctgaaacac   2040
gccgtagaac agggcggcag caatctggaa aacctgatgg tcgaactgga tgcctccgaa   2100
tcatccgcaa cacccgagac ggttgaaact gcggcagccg accgcacaga tatgccgggc   2160
atccgcccct acggcgcaac tttccgcgca gcggcagccg tacagcatgc gaatgccgcc   2220
gacggtgtac gcatcttcaa cagtctcgcc gctaccgtct atgccgacag taccgccgcc   2280
catgccgata tgcagggacg ccgcctgaaa gccgtatcgg acgggttgga ccacaacggc   2340
acgggtctgc gcgtcatcgc gcaaacccaa caggacggtg gaacgtggga cagggcggt   2400 gttgaaggca aaatgcgcgg cagtacccaa accgtcggca ttgccgcgaa aaccggcgaa   2460
aatacgacag cagccgccac actgggcatg ggacgcagca catggagcga aaacagtgca   2520
aatgcaaaaa ccgacagcat tagtctgttt gcaggcatac ggcacgatgc gggcgatatc   2580
ggctatctca aaggcctgtt ctcctacgga cgctacaaaa acagcatcag ccgcagcacc   2640
ggtgcggacg aacatgcgga aggcagcgtc aacggcacgc tgatgcagct gggcgcactg   2700
ggcggtgtca acgttccgtt tgccgcaacg ggagatttga cggtcgaagg cggtctgcgc   2760
tacgacctgc tcaaacagga tgcattcgcc gaaaaaggca gtgctttggg ctggagcggc   2820
aacagcctca ctgaaggcac gctggtcgga ctcgcgggtc tgaagctgtc gcaaccctgg   2880
agcgataaag ccgtcctgtt tgcaacgcg ggcgtggaac gcgacctgaa cggacgcgac   2940
tacacggtaa cgggcggctt taccggcgcg actgcagcaa ccggcaagac gggggcacgc   3000
aatatgccgc acacccgtct ggttgccggc ctgggcgcgg atgtcgaatt cggcaacggc   3060
tggaacggct tggcacgtta cagctacgcc ggttccaaac agtacggcaa ccacagcgga   3120
cgagtcggcg taggctaccg gttcctcgac ggtggcggag gcactggatc ctcagatttg   3180
gcaaacgatt cttttatccg gcaggttctc gaccgtcagc atttcgaacc cgacgggaaa   3240
taccacctat tcggcagcag gggggaactt gccgagcgca gcggccatat cggattggga   3300
aaaatacaaa gccatcagtt gggcaacctg atgattcaac aggcggccat taaaggaaat   3360
atcggctaca ttgtccgctt ttccgatcac gggcacgaag tccattcccc cttcgacaac   3420
catgcctcac attccgattc tgatgaagcc ggtagtcccg ttgacggatt tagcctttac   3480
cgcatccatt gggacggata cgaacaccat cccgccgacg gctatgacgg gccacagggc   3540
ggcggctatc ccgctcccaa aggcgcgagg gatatataca gctacgacat aaaaggcgtt   3600
gcccaaaata tccgcctcaa cctgaccgac aaccgcagca ccggacaacg gcttgccgac   3660
cgtttccaca atgccggtag tatgctgacg caaggagtag gcgacggatt caaacgcgcc   3720
acccgataca gccccgagct ggacagatcg ggcaatgccg ccgaagcctt caacggcact   3780
gcagatatcg ttaaaaacat catcggcgcg gcaggagaaa ttgtcggcgc aggcgatgcc   3840
gtgcagggca taagcgaagg ctcaaacatt gctgtcatgc acggcttggg tctgcttttcc   3900 accgaaaaca agatggcgcg catcaacgat ttggcagata tggcgcaact caaagactat   3960
gccgcagcag ccatccgcga ttgggcagtc caaaaccccca atgccgcaca aggcatagaa   4020
```

```
gccgtcagca atatctttat ggcagccatc cccatcaaag ggattggagc tgttcgggga      4080
aaatacggct tgggcggcat cacggcacat cctatcaagc ggtcgcagat gggcgcgatc      4140
gcattgccga aagggaaatc cgccgtcagc gacaattttg ccgatgcggc atacgccaaa      4200
tacccgtccc cttaccattc ccgaaatatc cgttcaaact tggagcagcg ttacggcaaa      4260
gaaaacatca cctcctcaac cgtgccgccg tcaaacggca aaaatgtcaa actggcagac      4320
caacgccacc cgaagacagg cgtaccgttt gacggtaaag ggtttccgaa ttttgagaag      4380
cacgtgaaat atgatacgct cgagcaccac caccaccacc actga                     4425
```

<210> SEQ ID NO 101
<211> LENGTH: 1474
<212> TYPE: PRT
<213> ORGANISM: Artificial Sequence
<220> FEATURE:
<223> OTHER INFORMATION: deltaG983-ORF46.1

<400> SEQUENCE: 101

```
Met Thr Ser Ala Pro Asp Phe Asn Ala Gly Gly Thr Gly Ile Gly Ser
1               5                   10                  15

Asn Ser Arg Ala Thr Thr Ala Lys Ser Ala Ala Val Ser Tyr Ala Gly
            20                  25                  30

Ile Lys Asn Glu Met Cys Lys Asp Arg Ser Met Leu Cys Ala Gly Arg
        35                  40                  45

Asp Asp Val Ala Val Thr Asp Arg Asp Ala Lys Ile Asn Ala Pro Pro
    50                  55                  60

Pro Asn Leu His Thr Gly Asp Phe Pro Asn Pro Asn Asp Ala Tyr Lys
65                  70                  75                  80

Asn Leu Ile Asn Leu Lys Pro Ala Ile Glu Ala Gly Tyr Thr Gly Arg
                85                  90                  95

Gly Val Glu Val Gly Ile Val Asp Thr Gly Glu Ser Val Gly Ser Ile
            100                 105                 110

Ser Phe Pro Glu Leu Tyr Gly Arg Lys Glu His Gly Tyr Asn Glu Asn
        115                 120                 125

Tyr Lys Asn Tyr Thr Ala Tyr Met Arg Lys Glu Ala Pro Glu Asp Gly
    130                 135                 140

Gly Gly Lys Asp Ile Glu Ala Ser Phe Asp Asp Glu Ala Val Ile Glu
145                 150                 155                 160

Thr Glu Ala Lys Pro Thr Asp Ile Arg His Val Lys Glu Ile Gly His
                165                 170                 175

Ile Asp Leu Val Ser His Ile Ile Gly Gly Arg Ser Val Asp Gly Arg
            180                 185                 190

Pro Ala Gly Gly Ile Ala Pro Asp Ala Thr Leu His Ile Met Asn Thr
        195                 200                 205

Asn Asp Glu Thr Lys Asn Glu Met Met Val Ala Ala Ile Arg Asn Ala
    210                 215                 220

Trp Val Lys Leu Gly Glu Arg Gly Val Arg Ile Val Asn Asn Ser Phe
225                 230                 235                 240

Gly Thr Thr Ser Arg Ala Gly Thr Ala Asp Leu Phe Gln Ile Ala Asn
                245                 250                 255

Ser Glu Glu Gln Tyr Arg Gln Ala Leu Leu Asp Tyr Ser Gly Gly Asp
            260                 265                 270

Lys Thr Asp Glu Gly Ile Arg Leu Met Gln Gln Ser Asp Tyr Gly Asn
        275                 280                 285

Leu Ser Tyr His Ile Arg Asn Lys Asn Met Leu Phe Ile Phe Ser Thr
```

```
                290                 295                 300
Gly Asn Asp Ala Gln Ala Gln Pro Asn Thr Tyr Ala Leu Leu Pro Phe
305                 310                 315                 320

Tyr Glu Lys Asp Ala Gln Lys Gly Ile Ile Thr Val Ala Gly Val Asp
                325                 330                 335

Arg Ser Gly Glu Lys Phe Lys Arg Glu Met Tyr Gly Glu Pro Gly Thr
                340                 345                 350

Glu Pro Leu Glu Tyr Gly Ser Asn His Cys Gly Ile Thr Ala Met Trp
                355                 360                 365

Cys Leu Ser Ala Pro Tyr Glu Ala Ser Val Arg Phe Thr Arg Thr Asn
                370                 375                 380

Pro Ile Gln Ile Ala Gly Thr Ser Phe Ser Ala Pro Ile Val Thr Gly
385                 390                 395                 400

Thr Ala Ala Leu Leu Leu Gln Lys Tyr Pro Trp Met Ser Asn Asp Asn
                405                 410                 415

Leu Arg Thr Thr Leu Leu Thr Thr Ala Gln Asp Ile Gly Ala Val Gly
                420                 425                 430

Val Asp Ser Lys Phe Gly Trp Gly Leu Leu Asp Ala Gly Lys Ala Met
                435                 440                 445

Asn Gly Pro Ala Ser Phe Pro Phe Gly Asp Phe Thr Ala Asp Thr Lys
                450                 455                 460

Gly Thr Ser Asp Ile Ala Tyr Ser Phe Arg Asn Asp Ile Ser Gly Thr
465                 470                 475                 480

Gly Gly Leu Ile Lys Lys Gly Ser Gln Leu Gln Leu His Gly Asn
                485                 490                 495

Asn Thr Tyr Thr Gly Lys Thr Ile Ile Glu Gly Gly Ser Leu Val Leu
                500                 505                 510

Tyr Gly Asn Asn Lys Ser Asp Met Arg Val Glu Thr Lys Gly Ala Leu
                515                 520                 525

Ile Tyr Asn Gly Ala Ala Ser Gly Gly Ser Leu Asn Ser Asp Gly Ile
                530                 535                 540

Val Tyr Leu Ala Asp Thr Asp Gln Ser Gly Ala Asn Glu Thr Val His
545                 550                 555                 560

Ile Lys Gly Ser Leu Gln Leu Asp Gly Lys Gly Thr Leu Tyr Thr Arg
                565                 570                 575

Leu Gly Lys Leu Leu Lys Val Asp Gly Thr Ala Ile Ile Gly Gly Lys
                580                 585                 590

Leu Tyr Met Ser Ala Arg Gly Lys Gly Ala Gly Tyr Leu Asn Ser Thr
                595                 600                 605

Gly Arg Arg Val Pro Phe Leu Ser Ala Lys Ile Gly Gln Asp Tyr
                610                 615                 620

Ser Phe Phe Thr Asn Ile Glu Thr Asp Gly Gly Leu Leu Ala Ser Leu
625                 630                 635                 640

Asp Ser Val Glu Lys Thr Ala Gly Ser Glu Gly Asp Thr Leu Ser Tyr
                645                 650                 655

Tyr Val Arg Arg Gly Asn Ala Ala Arg Thr Ala Ser Ala Ala Ala His
                660                 665                 670

Ser Ala Pro Ala Gly Leu Lys His Ala Val Glu Gln Gly Gly Ser Asn
                675                 680                 685

Leu Glu Asn Leu Met Val Glu Leu Asp Ala Ser Glu Ser Ser Ala Thr
                690                 695                 700

Pro Glu Thr Val Glu Thr Ala Ala Ala Asp Arg Thr Asp Met Pro Gly
705                 710                 715                 720
```

-continued

```
Ile Arg Pro Tyr Gly Ala Thr Phe Arg Ala Ala Ala Val Gln His
            725                 730                 735

Ala Asn Ala Ala Asp Gly Val Arg Ile Phe Asn Ser Leu Ala Ala Thr
            740                 745                 750

Val Tyr Ala Asp Ser Thr Ala Ala His Ala Asp Met Gln Gly Arg Arg
            755                 760                 765

Leu Lys Ala Val Ser Asp Gly Leu Asp His Asn Gly Thr Gly Leu Arg
            770                 775                 780

Val Ile Ala Gln Thr Gln Gln Asp Gly Gly Thr Trp Glu Gln Gly Gly
785                 790                 795                 800

Val Glu Gly Lys Met Arg Gly Ser Thr Gln Thr Val Gly Ile Ala Ala
            805                 810                 815

Lys Thr Gly Glu Asn Thr Thr Ala Ala Ala Thr Leu Gly Met Gly Arg
            820                 825                 830

Ser Thr Trp Ser Glu Asn Ser Ala Asn Ala Lys Thr Asp Ser Ile Ser
            835                 840                 845

Leu Phe Ala Gly Ile Arg His Asp Ala Gly Asp Ile Gly Tyr Leu Lys
            850                 855                 860

Gly Leu Phe Ser Tyr Gly Arg Tyr Lys Asn Ser Ile Ser Arg Ser Thr
865                 870                 875                 880

Gly Ala Asp Glu His Ala Glu Gly Ser Val Asn Gly Thr Leu Met Gln
            885                 890                 895

Leu Gly Ala Leu Gly Gly Val Asn Val Pro Phe Ala Ala Thr Gly Asp
            900                 905                 910

Leu Thr Val Glu Gly Gly Leu Arg Tyr Asp Leu Leu Lys Gln Asp Ala
            915                 920                 925

Phe Ala Glu Lys Gly Ser Ala Leu Gly Trp Ser Gly Asn Ser Leu Thr
            930                 935                 940

Glu Gly Thr Leu Val Gly Leu Ala Gly Leu Lys Leu Ser Gln Pro Leu
945                 950                 955                 960

Ser Asp Lys Ala Val Leu Phe Ala Thr Ala Gly Val Glu Arg Asp Leu
            965                 970                 975

Asn Gly Arg Asp Tyr Thr Val Thr Gly Gly Phe Thr Gly Ala Thr Ala
            980                 985                 990

Ala Thr Gly Lys Thr Gly Ala Arg Asn Met Pro His Thr Arg Leu Val
            995                 1000                1005

Ala Gly Leu Gly Ala Asp Val Glu Phe Gly Asn Gly Trp Asn Gly Leu
            1010                1015                1020

Ala Arg Tyr Ser Tyr Ala Gly Ser Lys Gln Tyr Gly Asn His Ser Gly
1025                1030                1035                1040

Arg Val Gly Val Gly Tyr Arg Phe Leu Asp Gly Gly Gly Thr Gly
            1045                1050                1055

Ser Ser Asp Leu Ala Asn Asp Ser Phe Ile Arg Gln Val Leu Asp Arg
            1060                1065                1070

Gln His Phe Glu Pro Asp Gly Lys Tyr His Leu Phe Gly Ser Arg Gly
            1075                1080                1085

Glu Leu Ala Glu Arg Ser Gly His Ile Gly Leu Gly Lys Ile Gln Ser
            1090                1095                1100

His Gln Leu Gly Asn Leu Met Ile Gln Gln Ala Ala Ile Lys Gly Asn
1105                1110                1115                1120

Ile Gly Tyr Ile Val Arg Phe Ser Asp His Gly His Glu Val His Ser
            1125                1130                1135

Pro Phe Asp Asn His Ala Ser His Ser Asp Ser Asp Glu Ala Gly Ser
            1140                1145                1150
```

Pro Val Asp Gly Phe Ser Leu Tyr Arg Ile His Trp Asp Gly Tyr Glu
        1155                1160                1165

His His Pro Ala Asp Gly Tyr Asp Gly Pro Gln Gly Gly Tyr Pro
    1170                1175                1180

Ala Pro Lys Gly Ala Arg Asp Ile Tyr Ser Tyr Asp Ile Lys Gly Val
1185                1190                1195                1200

Ala Gln Asn Ile Arg Leu Asn Leu Thr Asp Asn Arg Ser Thr Gly Gln
        1205                1210                1215

Arg Leu Ala Asp Arg Phe His Asn Ala Gly Ser Met Leu Thr Gln Gly
        1220                1225                1230

Val Gly Asp Gly Phe Lys Arg Ala Thr Arg Tyr Ser Pro Glu Leu Asp
        1235                1240                1245

Arg Ser Gly Asn Ala Ala Glu Ala Phe Asn Gly Thr Ala Asp Ile Val
        1250                1255                1260

Lys Asn Ile Ile Gly Ala Ala Gly Glu Ile Val Gly Ala Gly Asp Ala
1265                1270                1275                1280

Val Gln Gly Ile Ser Glu Gly Ser Asn Ile Ala Val Met His Gly Leu
        1285                1290                1295

Gly Leu Leu Ser Thr Glu Asn Lys Met Ala Arg Ile Asn Asp Leu Ala
        1300                1305                1310

Asp Met Ala Gln Leu Lys Asp Tyr Ala Ala Ala Ile Arg Asp Trp
        1315                1320                1325

Ala Val Gln Asn Pro Asn Ala Ala Gln Gly Ile Glu Ala Val Ser Asn
        1330                1335                1340

Ile Phe Met Ala Ala Ile Pro Ile Lys Gly Ile Gly Ala Val Arg Gly
1345                1350                1355                1360

Lys Tyr Gly Leu Gly Gly Ile Thr Ala His Pro Ile Leu Arg Ser Gln
        1365                1370                1375

Met Gly Ala Ile Ala Leu Pro Lys Gly Lys Ser Ala Val Ser Asp Asn
        1380                1385                1390

Phe Ala Asp Ala Ala Tyr Ala Lys Tyr Pro Ser Pro Tyr His Ser Arg
        1395                1400                1405

Asn Ile Arg Ser Asn Leu Glu Gln Arg Tyr Gly Lys Glu Asn Ile Thr
        1410                1415                1420

Ser Ser Thr Val Pro Pro Ser Asn Gly Lys Asn Val Lys Leu Ala Asp
1425                1430                1435                1440

Gln Arg His Pro Lys Thr Gly Val Pro Phe Asp Gly Lys Gly Phe Pro
        1445                1450                1455

Asn Phe Glu Lys His Val Lys Tyr Asp Thr Leu Glu His His His
        1460                1465                1470

His His

<210> SEQ ID NO 102
<211> LENGTH: 3939
<212> TYPE: DNA
<213> ORGANISM: Artificial Sequence
<220> FEATURE:
<223> OTHER INFORMATION: deltaG983-741

<400> SEQUENCE: 102
atgacttctg cgcccgactt caatgcaggc ggtaccggta tcggcagcaa cagcagagca      60
acaacagcga aatcagcagc agtatcttac gccggtatca agaacgaaat gtgcaaagac     120
agaagcatgc tctgtgccgg tcgggatgac gttgcggtta cagacaggga tgccaaaatc     180
aatgcccccc ccccgaatct gcataccgga gactttccaa acccaaatga cgcatacaag     240

```
aatttgatca acctcaaacc tgcaattgaa gcaggctata caggacgcgg ggtagaggta    300
ggtatcgtcg acacaggcga atccgtcggc agcatatcct ttcccgaact gtatggcaga    360
aaagaacacg gctataacga aaattacaaa aactatacgg cgtatatgcg gaaggaagcg    420
cctgaagacg gaggcggtaa agacattgaa gcttctttcg acgatgaggc cgttatagag    480
actgaagcaa agccgacgga tatccgccac gtaaaagaaa tcggacacat cgatttggtc    540
tcccatatta ttggcgggcg ttccgtggac ggcagacctg caggcggtat tgcgcccgat    600
gcgacgctac acataatgaa tacgaatgat gaaaccaaga acgaaatgat ggttgcagcc    660
atccgcaatg catgggtcaa gctgggcgaa cgtggcgtgc gcatcgtcaa taacagtttt    720
ggaacaacat cgagggcagg cactgccgac cttttccaaa tagccaattc ggaggagcag    780
taccgccaag cgttgctcga ctattccggc ggtgataaaa cagacgaggg tatccgcctg    840
atgcaacaga gcgattacgg caacctgtcc taccacatcc gtaataaaaa catgcttttc    900
atcttttcga caggcaatga cgcacaagct cagcccaaca catatgccct attgccattt    960
tatgaaaaag acgctcaaaa aggcattatc acagtcgcag gcgtagaccg cagtggagaa   1020
aagttcaaac gggaaatgta tggagaaccg ggtacagaac cgcttgagta tggctccaac   1080
cattgcggaa ttactgccat gtggtgcctg tcggcaccct atgaagcaag cgtccgtttc   1140
acccgtacaa acccgattca aattgccgga acatcctttt ccgcacccat cgtaaccggc   1200
acggcggctc tgctgctgca gaaatacccg tggatgagca cgacaacct gcgtaccacg    1260
ttgctgacga cggctcagga catcggtgca gtcggcgtgg acagcaagtt cggctgggga   1320
ctgctggatg cgggtaaggc catgaacgga cccgcgtcct ttccgttcgg cgactttacc   1380
gccgatacga aggtacatc cgatattgcc tactccttcc gtaacgacat ttcaggcacg    1440
ggcggcctga tcaaaaaagg cggcagccaa ctgcaactgc acggcaacaa cacctatacg   1500
ggcaaaacca ttatcgaagg cggttcgctg gtgttgtacg gcaacaacaa atcggatatg   1560
cgcgtcgaaa ccaaaggtgc gctgatttat aacggggcgg catccggcgg cagcctgaac   1620
agcgacggca ttgtctatct ggcagatacc gaccaatccg gcgcaaacga aaccgtacac   1680
atcaaaggca gtctgcagct ggacggcaaa ggtacgctgt acacacgttt gggcaaactg   1740
ctgaaagtgg acggtacggc gattatcggc ggcaagctgt acatgtcggc acgcggcaag   1800
ggggcaggct atctcaacag taccggacga cgtgttccct tcctgagtgc cgccaaaatc   1860
gggcaggatt attctttctt cacaaacatc gaaaccgacg gcggcctgct ggcttccctc   1920
gacagcgtcg aaaaaacagc gggcagtgaa ggcgacacgc tgtcctatta tgtccgtcgc   1980
ggcaatgcgg cacggactgc ttcggcagcg gcacattccg cgcccgccgg tctgaaacac   2040
gccgtagaac agggcggcag caatctggaa aacctgatgg tcgaactgga tgcctccgaa   2100
tcatccgcaa cacccgagac ggttgaaact gcggcagccg accgcacaga tatgccgggc   2160
atccgcccct acgcgcaac tttccgcgca gcggcagccg tacagcatgc gaatgccgcc   2220
gacggtgtac gcatcttcaa cagtctcgcc gctaccgtct atgccgacag taccgccgcc   2280
catgccgata tgcagggacg ccgcctgaaa gccgtatcgg acgggttgga ccacaacggc   2340
acgggtctgc cgtcatcgc gcaaacccaa caggacggtg gaacgtggga cagggcggt    2400
gttgaaggca aaatgcgcgg cagtacccaa accgtcggca ttgccgcgaa aaccggcgaa   2460
aatacgacag cagccgccac actgggcatg ggacgcagca catggagcga aaacagtgca   2520
aatgcaaaaa ccgacagcat tagtctgttt gcaggcatac ggcacgatgc gggcgatatc   2580
ggctatctca aaggcctgtt ctcctacgga cgctacaaaa acagcatcag ccgcagcacc   2640
```

```
ggtgcggacg aacatgcgga aggcagcgtc aacggcacgc tgatgcagct gggcgcactg    2700
ggcggtgtca acgttccgtt tgccgcaacg ggagatttga cggtcgaagg cggtctgcgc    2760
tacgacctgc tcaaacagga tgcattcgcc gaaaaaggca gtgctttggg ctggagcggc    2820
aacagcctca ctgaaggcac gctggtcgga ctcgcgggtc tgaagctgtc gcaaccctttg   2880 agcgataaag ccgtcctgtt tgcaacggcg ggcgtggaac gcgacctgaa cggacgcgac    2940
tacacggtaa cgggcggctt taccggcgcg actgcagcaa ccggcaagac gggggcacgc    3000
aatatgccgc acaccgtct ggttgccggc ctgggcgcgg atgtcgaatt cggcaacggc     3060
tggaacggct tggcacgtta cagctacgcc ggttccaaac agtacggcaa ccacagcgga    3120
cgagtcggcg taggctaccg gttcctcgag ggatccggag ggggtggtgt cgccgccgac    3180
atcggtgcgg ggcttgccga tgcactaacc gcaccgctcg accataaaga caaaggttg     3240 cagtctttga cgctggatca gtccgtcagg aaaaacgaga aactgaagct ggcggcacaa    3300
ggtgcggaaa aaacttatgg aaacggtgac agcctcaata cggcaaatt gaagaacgac     3360 aaggtcagcc gtttcgactt tatccgccaa atcgaagtgg acgggcagct cattaccttg    3420
gagagtggag agttccaagt atacaaacaa gccattccg ccttaaccgc ctttcagacc      3480
gagcaaatac aagattcgga gcattccggg aagatggttg cgaaacgcca gttcagaatc    3540
ggcgacatag cgggcgaaca tacatctttt gacaagcttc ccgaaggcgg cagggcgaca    3600
tatcgcggga cggcgttcgg ttcagacgat gccggcggaa aactgaccta caccatagat    3660
ttcgccgcca gcagggaaa cggcaaaatc gaacatttga atcgccaga actcaatgtc      3720 gacctggccg ccgccgatat caagccggat ggaaaacgcc atgccgtcat cagcggttcc    3780
gtcctttaca accaagccga aaaggcagt tactcccctcg gtatctttgg cggaaaagcc    3840
caggaagttg ccggcagcgc ggaagtgaaa accgtaaacg gcatacgcca tatcggcctt    3900
gccgccaagc aactcgagca ccaccaccac caccactga                            3939
```

<210> SEQ ID NO 103
<211> LENGTH: 1312
<212> TYPE: PRT
<213> ORGANISM: Artificial Sequence
<220> FEATURE:
<223> OTHER INFORMATION: deltaG983-741

<400> SEQUENCE: 103

```
Met Thr Ser Ala Pro Asp Phe Asn Ala Gly Gly Thr Gly Ile Gly Ser
 1               5                  10                  15

Asn Ser Arg Ala Thr Thr Ala Lys Ser Ala Ala Val Ser Tyr Ala Gly
             20                  25                  30

Ile Lys Asn Glu Met Cys Lys Asp Arg Ser Met Leu Cys Ala Gly Arg
         35                  40                  45

Asp Asp Val Ala Val Thr Asp Arg Asp Ala Lys Ile Asn Ala Pro Pro
     50                  55                  60

Pro Asn Leu His Thr Gly Asp Phe Pro Asn Pro Asn Asp Ala Tyr Lys
 65                  70                  75                  80

Asn Leu Ile Asn Leu Lys Pro Ala Ile Glu Ala Gly Tyr Thr Gly Arg
                 85                  90                  95

Gly Val Glu Val Gly Ile Val Asp Thr Gly Glu Ser Val Gly Ser Ile
            100                 105                 110

Ser Phe Pro Glu Leu Tyr Gly Arg Lys Glu His Gly Tyr Asn Glu Asn
        115                 120                 125

Tyr Lys Asn Tyr Thr Ala Tyr Met Arg Lys Glu Ala Pro Glu Asp Gly
```

```
             130                 135                 140
Gly Gly Lys Asp Ile Glu Ala Ser Phe Asp Asp Glu Ala Val Ile Glu
145                 150                 155                 160

Thr Glu Ala Lys Pro Thr Asp Ile Arg His Val Lys Glu Ile Gly His
                165                 170                 175

Ile Asp Leu Val Ser His Ile Ile Gly Gly Arg Ser Val Asp Gly Arg
            180                 185                 190

Pro Ala Gly Gly Ile Ala Pro Asp Ala Thr Leu His Ile Met Asn Thr
        195                 200                 205

Asn Asp Glu Thr Lys Asn Glu Met Met Val Ala Ala Ile Arg Asn Ala
    210                 215                 220

Trp Val Lys Leu Gly Glu Arg Gly Val Arg Ile Val Asn Asn Ser Phe
225                 230                 235                 240

Gly Thr Thr Ser Arg Ala Gly Thr Ala Asp Leu Phe Gln Ile Ala Asn
                245                 250                 255

Ser Glu Glu Gln Tyr Arg Gln Ala Leu Leu Asp Tyr Ser Gly Gly Asp
            260                 265                 270

Lys Thr Asp Glu Gly Ile Arg Leu Met Gln Gln Ser Asp Tyr Gly Asn
        275                 280                 285

Leu Ser Tyr His Ile Arg Asn Lys Asn Met Leu Phe Ile Phe Ser Thr
    290                 295                 300

Gly Asn Asp Ala Gln Ala Gln Pro Asn Thr Tyr Ala Leu Leu Pro Phe
305                 310                 315                 320

Tyr Glu Lys Asp Ala Gln Lys Gly Ile Ile Thr Val Ala Gly Val Asp
                325                 330                 335

Arg Ser Gly Glu Lys Phe Lys Arg Glu Met Tyr Gly Glu Pro Gly Thr
            340                 345                 350

Glu Pro Leu Glu Tyr Gly Ser Asn His Cys Gly Ile Thr Ala Met Trp
        355                 360                 365

Cys Leu Ser Ala Pro Tyr Glu Ala Ser Val Arg Phe Thr Arg Thr Asn
    370                 375                 380

Pro Ile Gln Ile Ala Gly Thr Ser Phe Ser Ala Pro Ile Val Thr Gly
385                 390                 395                 400

Thr Ala Ala Leu Leu Leu Gln Lys Tyr Pro Trp Met Ser Asn Asp Asn
                405                 410                 415

Leu Arg Thr Thr Leu Leu Thr Thr Ala Gln Asp Ile Gly Ala Val Gly
            420                 425                 430

Val Asp Ser Lys Phe Gly Trp Gly Leu Leu Asp Ala Gly Lys Ala Met
        435                 440                 445

Asn Gly Pro Ala Ser Phe Pro Phe Gly Asp Phe Thr Ala Asp Thr Lys
    450                 455                 460

Gly Thr Ser Asp Ile Ala Tyr Ser Phe Arg Asn Asp Ile Ser Gly Thr
465                 470                 475                 480

Gly Gly Leu Ile Lys Lys Gly Ser Gln Leu Gln Leu His Gly Asn
                485                 490                 495

Asn Thr Tyr Thr Gly Lys Thr Ile Ile Glu Gly Gly Ser Leu Val Leu
            500                 505                 510

Tyr Gly Asn Asn Lys Ser Asp Met Arg Val Glu Thr Lys Gly Ala Leu
        515                 520                 525

Ile Tyr Asn Gly Ala Ala Ser Gly Gly Ser Leu Asn Ser Asp Gly Ile
    530                 535                 540

Val Tyr Leu Ala Asp Thr Asp Gln Ser Gly Ala Asn Glu Thr Val His
545                 550                 555                 560
```

-continued

```
Ile Lys Gly Ser Leu Gln Leu Asp Gly Lys Gly Thr Leu Tyr Thr Arg
            565                 570                 575
Leu Gly Lys Leu Leu Lys Val Asp Gly Thr Ala Ile Ile Gly Gly Lys
        580                 585                 590
Leu Tyr Met Ser Ala Arg Gly Lys Gly Ala Gly Tyr Leu Asn Ser Thr
    595                 600                 605
Gly Arg Arg Val Pro Phe Leu Ser Ala Ala Lys Ile Gly Gln Asp Tyr
610                 615                 620
Ser Phe Phe Thr Asn Ile Glu Thr Asp Gly Gly Leu Leu Ala Ser Leu
625                 630                 635                 640
Asp Ser Val Glu Lys Thr Ala Gly Ser Glu Gly Asp Thr Leu Ser Tyr
                645                 650                 655
Tyr Val Arg Arg Gly Asn Ala Ala Arg Thr Ala Ser Ala Ala Ala His
            660                 665                 670
Ser Ala Pro Ala Gly Leu Lys His Ala Val Glu Gln Gly Gly Ser Asn
        675                 680                 685
Leu Glu Asn Leu Met Val Glu Leu Asp Ala Ser Glu Ser Ser Ala Thr
    690                 695                 700
Pro Glu Thr Val Glu Thr Ala Ala Ala Asp Arg Thr Asp Met Pro Gly
705                 710                 715                 720
Ile Arg Pro Tyr Gly Ala Thr Phe Arg Ala Ala Ala Val Gln His
                725                 730                 735
Ala Asn Ala Ala Asp Gly Val Arg Ile Phe Asn Ser Leu Ala Ala Thr
            740                 745                 750
Val Tyr Ala Asp Ser Thr Ala Ala His Ala Asp Met Gln Gly Arg Arg
        755                 760                 765
Leu Lys Ala Val Ser Asp Gly Leu Asp His Asn Gly Thr Gly Leu Arg
    770                 775                 780
Val Ile Ala Gln Thr Gln Gln Asp Gly Gly Thr Trp Glu Gln Gly Gly
785                 790                 795                 800
Val Glu Gly Lys Met Arg Gly Ser Thr Gln Thr Val Gly Ile Ala Ala
                805                 810                 815
Lys Thr Gly Glu Asn Thr Thr Ala Ala Ala Thr Leu Gly Met Gly Arg
            820                 825                 830
Ser Thr Trp Ser Glu Asn Ser Ala Asn Ala Lys Thr Asp Ser Ile Ser
        835                 840                 845
Leu Phe Ala Gly Ile Arg His Asp Ala Gly Asp Ile Gly Tyr Leu Lys
    850                 855                 860
Gly Leu Phe Ser Tyr Gly Arg Tyr Lys Asn Ser Ile Ser Arg Ser Thr
865                 870                 875                 880
Gly Ala Asp Glu His Ala Glu Gly Ser Val Asn Gly Thr Leu Met Gln
                885                 890                 895
Leu Gly Ala Leu Gly Gly Val Asn Val Pro Phe Ala Ala Thr Gly Asp
            900                 905                 910
Leu Thr Val Glu Gly Gly Leu Arg Tyr Asp Leu Leu Lys Gln Asp Ala
        915                 920                 925
Phe Ala Glu Lys Gly Ser Ala Leu Gly Trp Ser Gly Asn Ser Leu Thr
    930                 935                 940
Glu Gly Thr Leu Val Gly Leu Ala Gly Leu Lys Leu Ser Gln Pro Leu
945                 950                 955                 960
Ser Asp Lys Ala Val Leu Phe Ala Thr Ala Gly Val Glu Arg Asp Leu
                965                 970                 975
Asn Gly Arg Asp Tyr Thr Val Thr Gly Gly Phe Thr Gly Ala Thr Ala
            980                 985                 990
```

Ala Thr Gly Lys Thr Gly Ala Arg Asn Met Pro His Thr Arg Leu Val
         995                 1000                1005

Ala Gly Leu Gly Ala Asp Val Glu Phe Gly Asn Gly Trp Asn Gly Leu
    1010                1015                1020

Ala Arg Tyr Ser Tyr Ala Gly Ser Lys Gln Tyr Gly Asn His Ser Gly
1025                1030                1035                1040

Arg Val Gly Val Gly Tyr Arg Phe Leu Glu Gly Ser Gly Gly Gly Gly
        1045                1050                1055

Val Ala Ala Asp Ile Gly Ala Gly Leu Ala Asp Ala Leu Thr Ala Pro
        1060                1065                1070

Leu Asp His Lys Asp Lys Gly Leu Gln Ser Leu Thr Leu Asp Gln Ser
        1075                1080                1085

Val Arg Lys Asn Glu Lys Leu Lys Leu Ala Ala Gln Gly Ala Glu Lys
        1090                1095                1100

Thr Tyr Gly Asn Gly Asp Ser Leu Asn Thr Gly Lys Leu Lys Asn Asp
1105                1110                1115                1120

Lys Val Ser Arg Phe Asp Phe Ile Arg Gln Ile Glu Val Asp Gly Gln
        1125                1130                1135

Leu Ile Thr Leu Glu Ser Gly Glu Phe Gln Val Tyr Lys Gln Ser His
        1140                1145                1150

Ser Ala Leu Thr Ala Phe Gln Thr Glu Gln Ile Gln Asp Ser Glu His
        1155                1160                1165

Ser Gly Lys Met Val Ala Lys Arg Gln Phe Arg Ile Gly Asp Ile Ala
    1170                1175                1180

Gly Glu His Thr Ser Phe Asp Lys Leu Pro Glu Gly Gly Arg Ala Thr
1185                1190                1195                1200

Tyr Arg Gly Thr Ala Phe Gly Ser Asp Asp Ala Gly Lys Leu Thr
        1205                1210                1215

Tyr Thr Ile Asp Phe Ala Ala Lys Gln Gly Asn Gly Lys Ile Glu His
        1220                1225                1230

Leu Lys Ser Pro Glu Leu Asn Val Asp Leu Ala Ala Ala Asp Ile Lys
        1235                1240                1245

Pro Asp Gly Lys Arg His Ala Val Ile Ser Gly Ser Val Leu Tyr Asn
        1250                1255                1260

Gln Ala Glu Lys Gly Ser Tyr Ser Leu Gly Ile Phe Gly Gly Lys Ala
1265                1270                1275                1280

Gln Glu Val Ala Gly Ser Ala Glu Val Lys Thr Val Asn Gly Ile Arg
        1285                1290                1295

His Ile Gly Leu Ala Ala Lys Gln Leu Glu His His His His His His
        1300                1305                1310

<210> SEQ ID NO 104
<211> LENGTH: 4344
<212> TYPE: DNA
<213> ORGANISM: Artificial Sequence
<220> FEATURE:
<223> OTHER INFORMATION: deltaG983-961

<400> SEQUENCE: 104
atgacttctg cgcccgactt caatgcaggc ggtaccggta tcggcagcaa cagcagagca    60
acaacagcga atcagcagc agtatcttac gccggtatca gaacgaaat gtgcaaagac    120 agaagcatgc tctgtgccgg tcgggatgac gttgcggtta cagacaggga tgccaaaatc    180 aatgccccc cccgaatct gcataccgga gactttccaa acccaaatga cgcatacaag    240
aatttgatca acctcaaacc tgcaattgaa gcaggctata caggacgcgg ggtagaggta    300

```
ggtatcgtcg acacaggcga atccgtcggc agcatatcct ttcccgaact gtatggcaga      360
aaagaacacg gctataacga aaattacaaa aactatacgg cgtatatgcg gaaggaagcg      420
cctgaagacg gaggcggtaa agacattgaa gcttctttcg acgatgaggc cgttatagag      480
actgaagcaa agccgacgga tatccgccac gtaaaagaaa tcggacacat cgatttggtc      540
tcccatatta ttggcgggcg ttccgtggac ggcagacctg caggcggtat tgcgcccgat      600
gcgacgctac acataatgaa tacgaatgat gaaaccaaga acgaaatgat ggttgcagcc      660
atccgcaatg catgggtcaa gctgggcgaa cgtggcgtgc gcatcgtcaa taacagtttt      720
ggaacaacat cgagggcagg cactgccgac cttttccaaa tagccaattc ggaggagcag      780
taccgccaag cgttgctcga ctattccggc ggtgataaaa cagacgaggg tatccgcctg      840
atgcaacaga gcgattacgg caacctgtcc taccacatcc gtaataaaaa catgcttttc      900
atcttttcga caggcaatga cgcacaagct cagcccaaca catatgccct attgccattt      960
tatgaaaaag acgctcaaaa aggcattatc acagtcgcag gcgtagaccg cagtggagaa     1020
aagttcaaac gggaaatgta tggagaaccg ggtacagaac cgcttgagta tggctccaac     1080
cattgcggaa ttactgccat gtggtgcctg tcggcaccct atgaagcaag cgtccgtttc     1140
acccgtacaa acccgattca aattgccgga acatcctttt ccgcacccat cgtaaccggc     1200
acggcggctc tgctgctgca gaaatacccg tggatgagca acgacaacct gcgtaccacg     1260
ttgctgacga cggctcagga catcggtgca gtcggcgtgg acagcaagtt cggctgggga     1320
ctgctggatg cgggtaaggc catgaacgga cccgcgtcct ttccgttcgg cgactttacc     1380
gccgatacga aggtacatc cgatattgcc tactccttcc gtaacgacat ttcaggcacg     1440
ggcggcctga tcaaaaaagg cggcagccaa ctgcaactgc acggcaacaa cacctatacg     1500
ggcaaaacca ttatcgaagg cggttcgctg gtgttgtacg gcaacaacaa atcggatatg     1560
cgcgtcgaaa ccaaaggtgc gctgatttat aacggggcgg catccggcgg cagcctgaac     1620
agcgacggca ttgtctatct ggcagatacc gaccaatccg gcgcaaacga aaccgtacac     1680
atcaaaggca gtctgcagct ggacggcaaa ggtacgctgt acacacgttt gggcaaactg     1740
ctgaaagtgg acggtacggc gattatcggc ggcaagctgt acatgtcggc acgcggcaag     1800
ggggcaggct atctcaacag taccggacga cgtgttccct tcctgagtgc cgccaaaatc     1860
gggcaggatt attctttctt cacaaacatc gaaaccgacg gcggcctgct ggcttccctc     1920
gacagcgtcg aaaaaacagc gggcagtgaa ggcgacacgc tgtcctatta tgtccgtcgc     1980
ggcaatgcgg cacggactgc ttcggcagcg gcacattccg cgcccgccgg tctgaaacac     2040
gccgtagaac agggcggcag caatctggaa aacctgatgg tcgaactgga tgcctccgaa     2100
tcatccgcaa cacccgagac ggttgaaact gcggcagccg accgcacaga tatgccgggc     2160
atccgcccct acggcgcaac tttccgcgca gcggcagccg tacagcatgc gaatgccgcc     2220
gacggtgtac gcatcttcaa cagtctcgcc gctaccgtct atgccgacag taccgccgcc     2280
catgccgata tgcagggacg ccgcctgaaa gccgtatcgg acgggttgga ccacaacggc     2340
acgggtctgc gcgtcatcgc gcaaacccaa caggacggtg aacgtgggga acagggcggt     2400
gttgaaggca aaatgcgcgg cagtacccaa accgtcggca ttgccgcgaa aaccggcgaa     2460
aatacgacag cagccgccac actgggcatg ggacgcagca catggagcga aaacagtgca     2520
aatgcaaaaa ccgacagcat tagtctgttt gcaggcatac ggcacgatgc gggcgatatc     2580
ggctatctca aaggcctgtt ctcctacgga cgctacaaaa acagcatcag ccgcagcacc     2640
ggtgcggacg aacatgcgga aggcagcgtc aacggcacgc tgatgcagct gggcgcactg     2700
```

```
ggcggtgtca acgttccgtt tgccgcaacg ggagatttga cggtcgaagg cggtctgcgc    2760
tacgacctgc tcaaacagga tgcattcgcc gaaaaaggca gtgctttggg ctggagcggc    2820
aacagcctca ctgaaggcac gctggtcgga ctcgcgggtc tgaagctgtc gcaacccttg    2880
agcgataaag ccgtcctgtt tgcaacggcg ggcgtggaac gcgacctgaa cggacgcgac    2940
tacacggtaa cgggcggctt taccggcgcg actgcagcaa ccggcaagac gggggcacgc    3000
aatatgccgc acacccgtct ggttgccggc ctgggcgcgg atgtcgaatt cggcaacggc    3060
tggaacggct tggcacgtta cagctacgcc ggttccaaac agtacggcaa ccacagcgga    3120
cgagtcggcg taggctaccg gttcctcgag ggtggcggag cactggatc cgccacaaac    3180 gacgacgatg ttaaaaaagc tgccactgtg gccattgctg ctgcctacaa caatggccaa    3240
gaaatcaacg gtttcaaagc tggagagacc atctacgaca ttgatgaaga cggcacaatt    3300
accaaaaaag acgcaactgc agccgatgtt gaagccgacg actttaaagg tctgggtctg    3360
aaaaaagtcg tgactaacct gaccaaaacc gtcaatgaaa acaaacaaaa cgtcgatgcc    3420
aaagtaaaag ctgcagaatc tgaaatagaa aagttaacaa ccaagttagc agacactgat    3480
gccgctttag cagatactga tgccgctctg atgcaacca ccaacgcctt gaataaattg     3540
ggagaaaata taacgacatt tgctgaagag actaagacaa atatcgtaaa aattgatgaa    3600
aaattagaag ccgtggctga taccgtcgac aagcatgccg aagcattcaa cgatatcgcc    3660
gattcattgg atgaaaccaa cactaaggca gacgaagccg tcaaaaccgc caatgaagcc    3720
aaacagacgg ccgaagaaac caaacaaaac gtcgatgcca aagtaaaagc tgcagaaact    3780
gcagcaggca agccgaagc tgccgctggc acagctaata ctgcagccga caaggccgaa     3840
gctgtcgctg caaagttac cgacatcaaa gctgatatcg ctacgaacaa agataatatt     3900
gctaaaaaag caaacagtgc cgacgtgtac accagagaag agtctgacag caaatttgtc    3960
agaattgatg tcctgaacgc tactaccgaa aaattggaca cacgcttggc ttctgctgaa    4020
aaatccattg ccgatcacga tactcgcctg aacggtttgg ataaaacagt gtcagacctg    4080
cgcaaagaaa cccgccaagg ccttgcagaa caagccgcgc tctccggtct gttccaacct    4140
tacaacgtgg gtcggttcaa tgtaacggct gcagtcggcg gctacaaatc cgaatcggca    4200
gtcgccatcg gtaccggctt ccgctttacc gaaaactttg ccgccaaagc aggcgtggca    4260
gtcggcactt cgtccggttc ttccgcagcc taccatgtcg gcgtcaatta cgagtggctc    4320
gagcaccacc accaccacca ctga                                          4344
```

<210> SEQ ID NO 105
<211> LENGTH: 1447
<212> TYPE: PRT
<213> ORGANISM: Artificial Sequence
<220> FEATURE:
<223> OTHER INFORMATION: deltaG983-961

<400> SEQUENCE: 105

```
Met Thr Ser Ala Pro Asp Phe Asn Ala Gly Gly Thr Gly Ile Gly Ser
1               5                   10                  15

Asn Ser Arg Ala Thr Thr Ala Lys Ser Ala Ala Val Ser Tyr Ala Gly
            20                  25                  30

Ile Lys Asn Glu Met Cys Lys Asp Arg Ser Met Leu Cys Ala Gly Arg
        35                  40                  45

Asp Asp Val Ala Val Thr Asp Arg Asp Ala Lys Ile Asn Ala Pro Pro
    50                  55                  60

Pro Asn Leu His Thr Gly Asp Phe Pro Asn Pro Asn Asp Ala Tyr Lys
```

```
                65                  70                  75                  80
Asn Leu Ile Asn Leu Lys Pro Ala Ile Glu Ala Gly Tyr Thr Gly Arg
                    85                  90                  95
Gly Val Glu Val Gly Ile Val Asp Thr Gly Glu Ser Val Gly Ser Ile
                    100                 105                 110
Ser Phe Pro Glu Leu Tyr Gly Arg Lys Glu His Gly Tyr Asn Glu Asn
                    115                 120                 125
Tyr Lys Asn Tyr Thr Ala Tyr Met Arg Lys Glu Ala Pro Glu Asp Gly
                    130                 135                 140
Gly Gly Lys Asp Ile Glu Ala Ser Phe Asp Asp Glu Ala Val Ile Glu
145                 150                 155                 160
Thr Glu Ala Lys Pro Thr Asp Ile Arg His Val Lys Glu Ile Gly His
                    165                 170                 175
Ile Asp Leu Val Ser His Ile Ile Gly Gly Arg Ser Val Asp Gly Arg
                    180                 185                 190
Pro Ala Gly Gly Ile Ala Pro Asp Ala Thr Leu His Ile Met Asn Thr
                    195                 200                 205
Asn Asp Glu Thr Lys Asn Glu Met Met Val Ala Ala Ile Arg Asn Ala
210                 215                 220
Trp Val Lys Leu Gly Glu Arg Gly Val Arg Ile Val Asn Asn Ser Phe
225                 230                 235                 240
Gly Thr Thr Ser Arg Ala Gly Thr Ala Asp Leu Phe Gln Ile Ala Asn
                    245                 250                 255
Ser Glu Glu Gln Tyr Arg Gln Ala Leu Leu Asp Tyr Ser Gly Gly Asp
                    260                 265                 270
Lys Thr Asp Glu Gly Ile Arg Leu Met Gln Gln Ser Asp Tyr Gly Asn
                    275                 280                 285
Leu Ser Tyr His Ile Arg Asn Lys Asn Met Leu Phe Ile Phe Ser Thr
                    290                 295                 300
Gly Asn Asp Ala Gln Ala Gln Pro Asn Thr Tyr Ala Leu Leu Pro Phe
305                 310                 315                 320
Tyr Glu Lys Asp Ala Gln Lys Gly Ile Ile Thr Val Ala Gly Val Asp
                    325                 330                 335
Arg Ser Gly Glu Lys Phe Lys Arg Glu Met Tyr Gly Glu Pro Gly Thr
                    340                 345                 350
Glu Pro Leu Glu Tyr Gly Ser Asn His Cys Gly Ile Thr Ala Met Trp
                    355                 360                 365
Cys Leu Ser Ala Pro Tyr Glu Ala Ser Val Arg Phe Thr Arg Thr Asn
                    370                 375                 380
Pro Ile Gln Ile Ala Gly Thr Ser Phe Ser Ala Pro Ile Val Thr Gly
385                 390                 395                 400
Thr Ala Ala Leu Leu Leu Gln Lys Tyr Pro Trp Met Ser Asn Asp Asn
                    405                 410                 415
Leu Arg Thr Thr Leu Leu Thr Thr Ala Gln Asp Ile Gly Ala Val Gly
                    420                 425                 430
Val Asp Ser Lys Phe Gly Trp Gly Leu Leu Asp Ala Gly Lys Ala Met
                    435                 440                 445
Asn Gly Pro Ala Ser Phe Pro Phe Gly Asp Phe Thr Ala Asp Thr Lys
                    450                 455                 460
Gly Thr Ser Asp Ile Ala Tyr Ser Phe Arg Asn Asp Ile Ser Gly Thr
465                 470                 475                 480
Gly Gly Leu Ile Lys Lys Gly Gly Ser Gln Leu Gln Leu His Gly Asn
                    485                 490                 495
```

-continued

```
Asn Thr Tyr Thr Gly Lys Thr Ile Ile Glu Gly Gly Ser Leu Val Leu
            500                 505                 510

Tyr Gly Asn Asn Lys Ser Asp Met Arg Val Glu Thr Lys Gly Ala Leu
        515                 520                 525

Ile Tyr Asn Gly Ala Ala Ser Gly Gly Ser Leu Asn Ser Asp Gly Ile
    530                 535                 540

Val Tyr Leu Ala Asp Thr Asp Gln Ser Gly Ala Asn Glu Thr Val His
545                 550                 555                 560

Ile Lys Gly Ser Leu Gln Leu Asp Gly Lys Gly Thr Leu Tyr Thr Arg
                565                 570                 575

Leu Gly Lys Leu Leu Lys Val Asp Gly Thr Ala Ile Ile Gly Gly Lys
            580                 585                 590

Leu Tyr Met Ser Ala Arg Gly Lys Gly Ala Gly Tyr Leu Asn Ser Thr
        595                 600                 605

Gly Arg Arg Val Pro Phe Leu Ser Ala Ala Lys Ile Gly Gln Asp Tyr
    610                 615                 620

Ser Phe Phe Thr Asn Ile Glu Thr Asp Gly Gly Leu Leu Ala Ser Leu
625                 630                 635                 640

Asp Ser Val Glu Lys Thr Ala Gly Ser Glu Gly Asp Thr Leu Ser Tyr
                645                 650                 655

Tyr Val Arg Arg Gly Asn Ala Ala Arg Thr Ala Ser Ala Ala Ala His
            660                 665                 670

Ser Ala Pro Ala Gly Leu Lys His Ala Val Glu Gln Gly Gly Ser Asn
        675                 680                 685

Leu Glu Asn Leu Met Val Glu Leu Asp Ala Ser Glu Ser Ser Ala Thr
    690                 695                 700

Pro Glu Thr Val Glu Thr Ala Ala Ala Asp Arg Thr Asp Met Pro Gly
705                 710                 715                 720

Ile Arg Pro Tyr Gly Ala Thr Phe Arg Ala Ala Ala Val Gln His
                725                 730                 735

Ala Asn Ala Ala Asp Gly Val Arg Ile Phe Asn Ser Leu Ala Ala Thr
            740                 745                 750

Val Tyr Ala Asp Ser Thr Ala Ala His Ala Asp Met Gln Gly Arg Arg
        755                 760                 765

Leu Lys Ala Val Ser Asp Gly Leu Asp His Asn Gly Thr Gly Leu Arg
    770                 775                 780

Val Ile Ala Gln Thr Gln Gln Asp Gly Gly Thr Trp Glu Gln Gly Gly
785                 790                 795                 800

Val Glu Gly Lys Met Arg Gly Ser Thr Gln Thr Val Gly Ile Ala Ala
                805                 810                 815

Lys Thr Gly Glu Asn Thr Thr Ala Ala Ala Thr Leu Gly Met Gly Arg
            820                 825                 830

Ser Thr Trp Ser Glu Asn Ser Ala Asn Ala Lys Thr Asp Ser Ile Ser
        835                 840                 845

Leu Phe Ala Gly Ile Arg His Asp Ala Gly Asp Ile Gly Tyr Leu Lys
    850                 855                 860

Gly Leu Phe Ser Tyr Gly Arg Tyr Lys Asn Ser Ile Ser Arg Ser Thr
865                 870                 875                 880

Gly Ala Asp Glu His Ala Glu Gly Ser Val Asn Gly Thr Leu Met Gln
                885                 890                 895

Leu Gly Ala Leu Gly Gly Val Asn Val Pro Phe Ala Ala Thr Gly Asp
            900                 905                 910

Leu Thr Val Glu Gly Gly Leu Arg Tyr Asp Leu Leu Lys Gln Asp Ala
        915                 920                 925
```

```
Phe Ala Glu Lys Gly Ser Ala Leu Gly Trp Ser Gly Asn Ser Leu Thr
        930                 935                 940

Glu Gly Thr Leu Val Gly Leu Ala Gly Leu Lys Leu Ser Gln Pro Leu
945                 950                 955                 960

Ser Asp Lys Ala Val Leu Phe Ala Thr Ala Gly Val Glu Arg Asp Leu
                965                 970                 975

Asn Gly Arg Asp Tyr Thr Val Thr Gly Gly Phe Thr Gly Ala Thr Ala
            980                 985                 990

Ala Thr Gly Lys Thr Gly Ala Arg Asn Met Pro His Thr Arg Leu Val
        995                 1000                1005

Ala Gly Leu Gly Ala Asp Val Glu Phe Gly Asn Gly Trp Asn Gly Leu
    1010                1015                1020

Ala Arg Tyr Ser Tyr Ala Gly Ser Lys Gln Tyr Gly Asn His Ser Gly
1025                1030                1035                1040

Arg Val Gly Val Gly Tyr Arg Phe Leu Glu Gly Gly Gly Thr Gly
                1045                1050                1055

Ser Ala Thr Asn Asp Asp Asp Val Lys Lys Ala Ala Thr Val Ala Ile
            1060                1065                1070

Ala Ala Ala Tyr Asn Asn Gly Gln Glu Ile Asn Gly Phe Lys Ala Gly
        1075                1080                1085

Glu Thr Ile Tyr Asp Ile Asp Glu Asp Gly Thr Ile Thr Lys Lys Asp
    1090                1095                1100

Ala Thr Ala Ala Asp Val Glu Ala Asp Phe Lys Gly Leu Gly Leu
1105                1110                1115                1120

Lys Lys Val Val Thr Asn Leu Thr Lys Thr Val Asn Glu Asn Lys Gln
            1125                1130                1135

Asn Val Asp Ala Lys Val Lys Ala Glu Ser Glu Ile Glu Lys Leu
        1140                1145                1150

Thr Thr Lys Leu Ala Asp Thr Asp Ala Ala Leu Ala Asp Thr Asp Ala
    1155                1160                1165

Ala Leu Asp Ala Thr Thr Asn Ala Leu Asn Lys Leu Gly Glu Asn Ile
1170                1175                1180

Thr Thr Phe Ala Glu Glu Thr Lys Thr Asn Ile Val Lys Ile Asp Glu
1185                1190                1195                1200

Lys Leu Glu Ala Val Ala Asp Thr Val Asp Lys His Ala Glu Ala Phe
            1205                1210                1215

Asn Asp Ile Ala Asp Ser Leu Asp Glu Thr Asn Thr Lys Ala Asp Glu
        1220                1225                1230

Ala Val Lys Thr Ala Asn Glu Ala Lys Gln Thr Ala Glu Glu Thr Lys
    1235                1240                1245

Gln Asn Val Asp Ala Lys Val Lys Ala Ala Glu Thr Ala Ala Gly Lys
1250                1255                1260

Ala Glu Ala Ala Ala Gly Thr Ala Asn Thr Ala Ala Asp Lys Ala Glu
1265                1270                1275                1280

Ala Val Ala Ala Lys Val Thr Asp Ile Lys Ala Asp Ile Ala Thr Asn
            1285                1290                1295

Lys Asp Asn Ile Ala Lys Lys Ala Asn Ser Ala Asp Val Tyr Thr Arg
        1300                1305                1310

Glu Glu Ser Asp Ser Lys Phe Val Arg Ile Asp Gly Leu Asn Ala Thr
    1315                1320                1325

Thr Glu Lys Leu Asp Thr Arg Leu Ala Ser Ala Glu Lys Ser Ile Ala
1330                1335                1340

Asp His Asp Thr Arg Leu Asn Gly Leu Asp Lys Thr Val Ser Asp Leu
```

```
                1345             1350                1355             1360
Arg Lys Glu Thr Arg Gln Gly Leu Ala Glu Gln Ala Ala Leu Ser Gly
                1365                  1370                  1375
Leu Phe Gln Pro Tyr Asn Val Gly Arg Phe Asn Val Thr Ala Ala Val
                1380                  1385                  1390
Gly Gly Tyr Lys Ser Glu Ser Ala Val Ala Ile Gly Thr Gly Phe Arg
                1395                  1400                  1405
Phe Thr Glu Asn Phe Ala Ala Lys Ala Gly Val Ala Val Gly Thr Ser
        1410                  1415                  1420
Ser Gly Ser Ser Ala Ala Tyr His Val Gly Val Asn Tyr Glu Trp Leu
1425                  1430                  1435                  1440
Glu His His His His His His
            1445

<210> SEQ ID NO 106
<211> LENGTH: 4179
<212> TYPE: DNA
<213> ORGANISM: Artificial Sequence
<220> FEATURE:
<223> OTHER INFORMATION: deltaG983-961c

<400> SEQUENCE: 106
atgacttctg cgcccgactt caatgcaggc ggtaccggta tcggcagcaa cagcagagca      60
acaacagcga aatcagcagc agtatcttac gccggtatca gaacgaaat gtgcaaagac      120 agaagcatgc tctgtgccgg tcgggatgac gttgcggtta cagacaggga tgccaaaatc      180 aatgccccc cccgaatct gcataccgga gactttccaa acccaaatga cgcatacaag      240
aatttgatca acctcaaacc tgcaattgaa gcaggctata caggacgcgg ggtagaggta      300
ggtatcgtcg acacaggcga atccgtcggc agcatatcct tcccgaact gtatggcaga      360 aaagaacacg gctataacga aaattacaaa actatacgg cgtatatgcg gaaggaagcg      420
cctgaagacg gaggcggtaa agacattgaa gcttcttcg acgatgaggc cgttatagag      480
actgaagcaa agccgacgga tatccgccca gtaaaagaaa tcggacacat cgatttggtc      540
tcccatatta ttggcgggcg ttccgtggac ggcagacctg caggcggtat tgcgcccgat      600
gcgacgctac acataatgaa tacgaatgat gaaaccaaga acgaaatgat ggttgcagcc      660
atccgcaatg catgggtcaa gctgggcgaa cgtggcgtgc gcatcgtcaa taacagtttt      720
ggaacaacat cgagggcagg cactgccgac cttttccaaa tagccaattc ggaggagcag      780
taccgccaag cgttgctcga ctattccggc ggtgataaaa cagacgaggg tatccgcctg      840
atgcaacaga gcgattacgg caacctgtcc taccacatcc gtaataaaaa catgcttttc      900
atcttttcga caggcaatga cgcacaagct cagcccaaca catatgccct attgccattt      960
tatgaaaaag acgctcaaaa aggcattatc acagtcgcag gcgtagaccg cagtggagaa     1020
aagttcaaac gggaaatgta tggagaaccg gtacagaac cgcttgagta tggctccaac     1080
cattgcggaa ttactgccat gtggtgcctg tcggcaccct atgaagcaag cgtccgtttc     1140
acccgtacaa acccgattca aattgccgga acatcctttt ccgcacccat cgtaaccggc     1200
acggcggctc tgctgctgca gaaataccg tggatgagca cgacaacct gcgtaccacg     1260 ttgctgacga cggctcagga catcggtgca gtcggcgtgg acagcaagtt cggctgggga     1320
ctgctggatg cgggtaaggc catgaacgga cccgcgtcct ttccgttcgg cgactttacc     1380
gccgatacga aagtacatc cgatattgcc tactcctcc gtaacgacat ttcaggcacg     1440
ggcggcctga tcaaaaaagg cggcagccaa ctgcaactgc acggcaacaa cacctatacg     1500
```

```
ggcaaaacca ttatcgaagg cggttcgctg gtgttgtacg gcaacaacaa atcggatatg    1560
cgcgtcgaaa ccaaaggtgc gctgatttat aacggggcgg catccggcgg cagcctgaac    1620
agcgacggca ttgtctatct ggcagatacc gaccaatccg gcgcaaacga aaccgtacac    1680
atcaaaggca gtctgcagct ggacggcaaa ggtacgctgt acacacgttt gggcaaactg    1740
ctgaaagtgg acggtacggc gattatcggc ggcaagctgt acatgtcggc acgcggcaag    1800
ggggcaggct atctcaacag taccggacga cgtgttccct tcctgagtgc cgccaaaatc    1860
gggcaggatt attctttctt cacaaacatc gaaaccgacg gcggcctgct ggcttccctc    1920
gacagcgtcg aaaaaacagc gggcagtgaa ggcgacacgc tgtcctatta tgtccgtcgc    1980
ggcaatgcgg cacggactgc ttcggcagcg gcacattccg cgcccgccgg tctgaaacac    2040
gccgtagaac agggcggcag caatctggaa aacctgatgg tcgaactgga tgcctccgaa    2100
tcatccgcaa cacccgagac ggttgaaact gcggcagccg accgcacaga tatgccgggc    2160
atccgcccct acgcgcaac tttccgcgca cggcagccg tacagcatgc gaatgccgcc    2220
gacggtgtac gcatcttcaa cagtctcgcc gctaccgtct atgccgacag taccgccgcc    2280
catgccgata tgcagggacg ccgcctgaaa gccgtatcgg acgggttgga ccacaacggc    2340
acgggtctgc gcgtcatcgc gcaaacccaa caggacggtg aacgtgggga acagggcggt    2400
gttgaaggca aaatgcgcgg cagtacccaa accgtcggca ttgccgcgaa accggcgaa    2460 aatacgacag cagccgccac actgggcatg ggacgcagca catggagcga aaacagtgca    2520
aatgcaaaaa ccgacagcat tagtctgttt gcaggcatac ggcacgatgc gggcgatatc    2580
ggctatctca aaggcctgtt ctcctacgga cgctacaaaa acagcatcag ccgcagcacc    2640
ggtgcggacg aacatgcgga aggcagcgtc aacggcacgc tgatgcagct gggcgcactg    2700
ggcggtgtca acgttccgtt tgccgcaacg ggagatttga cggtcgaagg cggtctgcgc    2760
tacgacctgc tcaaacagga tgcattcgcc gaaaaaggca gtgctttggg ctggagcggc    2820
aacagcctca ctgaaggcac gctggtcgga ctcgcgggtc tgaagctgtc gcaacccttg    2880
agcgataaag ccgtcctgtt tgcaacggcg ggcgtggaac gcgacctgaa cggacgcgac    2940
tacacggtaa cgggcggctt taccggcgcg actgcagcaa ccggcaagac gggggcacgc    3000
aatatgccgc acacccgtct ggttgccggc ctgggcgcgg atgtcgaatt cggcaacggc    3060
tggaacggct tggcacgtta cagctacgcc ggttccaaac agtacggcaa ccacagcgga    3120
cgagtcggcg taggctaccg gttcctcgag ggtggcggag gcactggatc cgccacaaac    3180
gacgacgatg ttaaaaaagc tgccactgtg gccattgctg ctgcctacaa caatggccaa    3240
gaaatcaacg gtttcaaagc tggagagacc atctacgaca ttgatgaaga cggcacaatt    3300
accaaaaaag acgcaactgc agccgatgtt gaagccgacg actttaaagg tctgggtctg    3360
aaaaaagtcg tgactaacct gaccaaaacc gtcaatgaaa acaaacaaaa cgtcgatgcc    3420
aaagtaaaag ctgcagaatc tgaaatagaa aagttaacaa ccaagttagc agacactgat    3480
gccgctttag cagatactga tgccgctctg gatgcaacca ccaacgcctt gaataaattg    3540
ggagaaaata taacgacatt tgctgaagag actaagacaa atatcgtaaa aattgatgaa    3600
aaattagaag ccgtggctga taccgtcgac aagcatgccg aagcattcaa cgatatcgcc    3660
gattcattgg atgaaaccaa cactaaggca gacgaagccg tcaaaccgc caatgaagcc    3720 aaacagacgg ccgaagaaac caaacaaaac gtcgatgcca agtaaaaagc tgcagaaact    3780
gcagcaggca aagccgaagc tgccgctggc acagctaata ctgcagccga caggccgaa    3840 gctgtcgctg caaaagttac cgacatcaaa gctgatatcg ctacgaacaa agataatatt    3900
```

-continued

```
gctaaaaaag caaacagtgc cgacgtgtac accagagaag agtctgacag caaatttgtc   3960
agaattgatg gtctgaacgc tactaccgaa aaattggaca cacgcttggc ttctgctgaa   4020
aaatccattg ccgatcacga tactcgcctg aacggtttgg ataaaacagt gtcagacctg   4080
cgcaaagaaa cccgccaagg ccttgcagaa caagccgcgc tctccggtct gttccaacct   4140
tacaacgtgg gtctcgagca ccaccaccac caccactga                          4179
```

<210> SEQ ID NO 107
<211> LENGTH: 1392
<212> TYPE: PRT
<213> ORGANISM: Artificial Sequence
<220> FEATURE:
<223> OTHER INFORMATION: deltaG983-961c

<400> SEQUENCE: 107

```
Met Thr Ser Ala Pro Asp Phe Asn Ala Gly Gly Thr Gly Ile Gly Ser
1               5                   10                  15

Asn Ser Arg Ala Thr Thr Ala Lys Ser Ala Ala Val Ser Tyr Ala Gly
            20                  25                  30

Ile Lys Asn Glu Met Cys Lys Asp Arg Ser Met Leu Cys Ala Gly Arg
        35                  40                  45

Asp Asp Val Ala Val Thr Asp Arg Asp Ala Lys Ile Asn Ala Pro Pro
    50                  55                  60

Pro Asn Leu His Thr Gly Asp Phe Pro Asn Asn Asp Ala Tyr Lys
65                  70                  75                  80

Asn Leu Ile Asn Leu Lys Pro Ala Ile Glu Ala Gly Tyr Thr Gly Arg
                85                  90                  95

Gly Val Glu Val Gly Ile Val Asp Thr Gly Glu Ser Val Gly Ser Ile
            100                 105                 110

Ser Phe Pro Glu Leu Tyr Gly Arg Lys Glu His Gly Tyr Asn Glu Asn
        115                 120                 125

Tyr Lys Asn Tyr Thr Ala Tyr Met Arg Lys Glu Ala Pro Glu Asp Gly
    130                 135                 140

Gly Gly Lys Asp Ile Glu Ala Ser Phe Asp Asp Glu Ala Val Ile Glu
145                 150                 155                 160

Thr Glu Ala Lys Pro Thr Asp Ile Arg His Val Lys Glu Ile Gly His
                165                 170                 175

Ile Asp Leu Val Ser His Ile Ile Gly Gly Arg Ser Val Asp Gly Arg
            180                 185                 190

Pro Ala Gly Gly Ile Ala Pro Asp Ala Thr Leu His Ile Met Asn Thr
        195                 200                 205

Asn Asp Glu Thr Lys Asn Glu Met Met Val Ala Ala Ile Arg Asn Ala
    210                 215                 220

Trp Val Lys Leu Gly Glu Arg Gly Val Arg Ile Val Asn Asn Ser Phe
225                 230                 235                 240

Gly Thr Thr Ser Arg Ala Gly Thr Ala Asp Leu Phe Gln Ile Ala Asn
                245                 250                 255

Ser Glu Glu Gln Tyr Arg Gln Ala Leu Leu Asp Tyr Ser Gly Gly Asp
            260                 265                 270

Lys Thr Asp Glu Gly Ile Arg Leu Met Gln Gln Ser Asp Tyr Gly Asn
        275                 280                 285

Leu Ser Tyr His Ile Arg Asn Lys Asn Met Leu Phe Ile Phe Ser Thr
    290                 295                 300

Gly Asn Asp Ala Gln Ala Gln Pro Asn Thr Tyr Ala Leu Leu Pro Phe
305                 310                 315                 320
```

```
Tyr Glu Lys Asp Ala Gln Lys Gly Ile Ile Thr Val Ala Gly Val Asp
                325                 330                 335

Arg Ser Gly Glu Lys Phe Lys Arg Glu Met Tyr Gly Glu Pro Gly Thr
            340                 345                 350

Glu Pro Leu Glu Tyr Gly Ser Asn His Cys Gly Ile Thr Ala Met Trp
        355                 360                 365

Cys Leu Ser Ala Pro Tyr Glu Ala Ser Val Arg Phe Thr Arg Thr Asn
    370                 375                 380

Pro Ile Gln Ile Ala Gly Thr Ser Phe Ser Ala Pro Ile Val Thr Gly
385                 390                 395                 400

Thr Ala Ala Leu Leu Leu Gln Lys Tyr Pro Trp Met Ser Asn Asp Asn
                405                 410                 415

Leu Arg Thr Thr Leu Leu Thr Thr Ala Gln Asp Ile Gly Ala Val Gly
            420                 425                 430

Val Asp Ser Lys Phe Gly Trp Gly Leu Leu Asp Ala Gly Lys Ala Met
        435                 440                 445

Asn Gly Pro Ala Ser Phe Pro Phe Gly Asp Phe Thr Ala Asp Thr Lys
    450                 455                 460

Gly Thr Ser Asp Ile Ala Tyr Ser Phe Arg Asn Asp Ile Ser Gly Thr
465                 470                 475                 480

Gly Gly Leu Ile Lys Lys Gly Gly Ser Gln Leu Gln Leu His Gly Asn
                485                 490                 495

Asn Thr Tyr Thr Gly Lys Thr Ile Ile Glu Gly Gly Ser Leu Val Leu
            500                 505                 510

Tyr Gly Asn Asn Lys Ser Asp Met Arg Val Glu Thr Lys Gly Ala Leu
        515                 520                 525

Ile Tyr Asn Gly Ala Ala Ser Gly Gly Ser Leu Asn Ser Asp Gly Ile
    530                 535                 540

Val Tyr Leu Ala Asp Thr Asp Gln Ser Gly Ala Asn Glu Thr Val His
545                 550                 555                 560

Ile Lys Gly Ser Leu Gln Leu Asp Gly Lys Gly Thr Leu Tyr Thr Arg
                565                 570                 575

Leu Gly Lys Leu Leu Lys Val Asp Gly Thr Ala Ile Ile Gly Gly Lys
            580                 585                 590

Leu Tyr Met Ser Ala Arg Gly Lys Gly Ala Gly Tyr Leu Asn Ser Thr
        595                 600                 605

Gly Arg Arg Val Pro Phe Leu Ser Ala Ala Lys Ile Gly Gln Asp Tyr
    610                 615                 620

Ser Phe Phe Thr Asn Ile Glu Thr Asp Gly Gly Leu Leu Ala Ser Leu
625                 630                 635                 640

Asp Ser Val Glu Lys Thr Ala Gly Ser Glu Gly Asp Thr Leu Ser Tyr
                645                 650                 655

Tyr Val Arg Arg Gly Asn Ala Ala Arg Thr Ala Ser Ala Ala Ala His
            660                 665                 670

Ser Ala Pro Ala Gly Leu Lys His Ala Val Glu Gln Gly Gly Ser Asn
        675                 680                 685

Leu Glu Asn Leu Met Val Glu Leu Asp Ala Ser Glu Ser Ser Ala Thr
    690                 695                 700

Pro Glu Thr Val Glu Thr Ala Ala Ala Asp Arg Thr Asp Met Pro Gly
705                 710                 715                 720

Ile Arg Pro Tyr Gly Ala Thr Phe Arg Ala Ala Ala Val Gln His
                725                 730                 735

Ala Asn Ala Ala Asp Gly Val Arg Ile Phe Asn Ser Leu Ala Ala Thr
            740                 745                 750
```

```
Val Tyr Ala Asp Ser Thr Ala Ala His Ala Asp Met Gln Gly Arg Arg
            755                 760                 765

Leu Lys Ala Val Ser Asp Gly Leu Asp His Asn Gly Thr Gly Leu Arg
            770                 775                 780

Val Ile Ala Gln Thr Gln Asp Gly Gly Thr Trp Glu Gln Gly Gly
785                 790                 795                 800

Val Glu Gly Lys Met Arg Gly Ser Thr Gln Thr Val Gly Ile Ala Ala
                    805                 810                 815

Lys Thr Gly Glu Asn Thr Thr Ala Ala Ala Thr Leu Gly Met Gly Arg
                    820                 825                 830

Ser Thr Trp Ser Glu Asn Ser Ala Asn Ala Lys Thr Asp Ser Ile Ser
            835                 840                 845

Leu Phe Ala Gly Ile Arg His Asp Ala Gly Asp Ile Gly Tyr Leu Lys
            850                 855                 860

Gly Leu Phe Ser Tyr Gly Arg Tyr Lys Asn Ser Ile Ser Arg Ser Thr
865                 870                 875                 880

Gly Ala Asp Glu His Ala Glu Gly Ser Val Asn Gly Thr Leu Met Gln
                    885                 890                 895

Leu Gly Ala Leu Gly Gly Val Asn Val Pro Phe Ala Ala Thr Gly Asp
            900                 905                 910

Leu Thr Val Glu Gly Gly Leu Arg Tyr Asp Leu Leu Lys Gln Asp Ala
            915                 920                 925

Phe Ala Glu Lys Gly Ser Ala Leu Gly Trp Ser Gly Asn Ser Leu Thr
            930                 935                 940

Glu Gly Thr Leu Val Gly Leu Ala Gly Leu Lys Leu Ser Gln Pro Leu
945                 950                 955                 960

Ser Asp Lys Ala Val Leu Phe Ala Thr Ala Gly Val Glu Arg Asp Leu
                    965                 970                 975

Asn Gly Arg Asp Tyr Thr Val Thr Gly Gly Phe Thr Gly Ala Thr Ala
                    980                 985                 990

Ala Thr Gly Lys Thr Gly Ala Arg Asn Met Pro His Thr Arg Leu Val
            995                 1000                1005

Ala Gly Leu Gly Ala Asp Val Glu Phe Gly Asn Gly Trp Asn Gly Leu
            1010                1015                1020

Ala Arg Tyr Ser Tyr Ala Gly Ser Lys Gln Tyr Gly Asn His Ser Gly
1025                1030                1035                1040

Arg Val Gly Val Gly Tyr Arg Phe Leu Glu Gly Gly Gly Thr Gly
                    1045                1050                1055

Ser Ala Thr Asn Asp Asp Val Lys Lys Ala Ala Thr Val Ala Ile
            1060                1065                1070

Ala Ala Ala Tyr Asn Asn Gly Gln Glu Ile Asn Gly Phe Lys Ala Gly
            1075                1080                1085

Glu Thr Ile Tyr Asp Ile Asp Glu Asp Gly Thr Ile Thr Lys Lys Asp
            1090                1095                1100

Ala Thr Ala Ala Asp Val Glu Ala Asp Phe Lys Gly Leu Gly Leu
1105                1110                1115                1120

Lys Lys Val Val Thr Asn Leu Thr Lys Thr Val Asn Glu Asn Lys Gln
                    1125                1130                1135

Asn Val Asp Ala Lys Val Lys Ala Ala Glu Ser Glu Ile Glu Lys Leu
                    1140                1145                1150

Thr Thr Lys Leu Ala Asp Thr Asp Ala Ala Leu Ala Asp Thr Asp Ala
            1155                1160                1165

Ala Leu Asp Ala Thr Thr Asn Ala Leu Asn Lys Leu Gly Glu Asn Ile
```

Thr Thr Phe Ala Glu Glu Thr Lys Thr Asn Ile Val Lys Ile Asp Glu
1185              1190              1195              1200

Lys Leu Glu Ala Val Ala Asp Thr Val Asp Lys His Ala Glu Ala Phe
         1205              1210              1215

Asn Asp Ile Ala Asp Ser Leu Asp Glu Thr Asn Thr Lys Ala Asp Glu
    1220              1225              1230

Ala Val Lys Thr Ala Asn Glu Ala Lys Gln Thr Ala Glu Glu Thr Lys
         1235              1240              1245

Gln Asn Val Asp Ala Lys Val Lys Ala Ala Glu Thr Ala Ala Gly Lys
    1250              1255              1260

Ala Glu Ala Ala Ala Gly Thr Ala Asn Thr Ala Ala Asp Lys Ala Glu
1265              1270              1275              1280

Ala Val Ala Ala Lys Val Thr Asp Ile Lys Ala Asp Ile Ala Thr Asn
         1285              1290              1295

Lys Asp Asn Ile Ala Lys Lys Ala Asn Ser Ala Asp Val Tyr Thr Arg
    1300              1305              1310

Glu Glu Ser Asp Ser Lys Phe Val Arg Ile Asp Gly Leu Asn Ala Thr
         1315              1320              1325

Thr Glu Lys Leu Asp Thr Arg Leu Ala Ser Ala Glu Lys Ser Ile Ala
         1330              1335              1340

Asp His Asp Thr Arg Leu Asn Gly Leu Asp Lys Thr Val Ser Asp Leu
1345              1350              1355              1360

Arg Lys Glu Thr Arg Gln Gly Leu Ala Glu Gln Ala Ala Leu Ser Gly
         1365              1370              1375

Leu Phe Gln Pro Tyr Asn Val Gly Leu Glu His His His His His His
         1380              1385              1390

<210> SEQ ID NO 108
<211> LENGTH: 1947
<212> TYPE: DNA
<213> ORGANISM: Artificial Sequence
<220> FEATURE:
<223> OTHER INFORMATION: deltaG741-961

<400> SEQUENCE: 108
atggtcgccg ccgacatcgg tgcggggctt gccgatgcac taaccgcacc gctcgaccat    60
aaagacaaag gtttgcagtc tttgacgctg gatcagtccg tcaggaaaaa cgagaaactg   120
aagctggcgg cacaaggtgc ggaaaaaact tatggaaacg gtgacagcct caatacgggc   180
aaattgaaga cgacaaggt cagccgtttc gactttatcc gccaaatcga agtggacggg   240
cagctcatta ccttggagag tggagagttc aagtataca aacaaagcca ttccgcctta   300
accgcctttc agaccgagca aatacaagat tcggagcatt ccggaagat ggttgcgaaa   360 cgccagttca gaatcggcga catagcgggc gaacatacat cttttgacaa gcttcccgaa   420
ggcggcaggg cgacatatcg cgggacggcg ttcggttcag acgatgccgg cggaaaactg   480
acctacacca tagatttcgc cgccaagcag ggaaacggca aaatcgaaca tttgaaatcg   540
ccagaactca atgtcgacct ggccgccgcc gatatcaagc cggatggaaa acgccatgcc   600
gtcatcagcg gttccgtcct ttacaaccaa gccgagaaag gcagttactc cctcggtatc   660
tttggcggaa aagcccagga agttgccggc agcgcggaag tgaaaccgt aaacggcata   720 cgccatatcg gccttgccgc caagcaactc gagggtggcg aggcactgg atccgccaca   780 aacgacgacg atgttaaaaa agctgccact gtggccattg ctgctgccta acaatggc   840 caagaaatca acggtttcaa agctggagag accatctacg acattgatga agacggcaca   900

-continued

```
attaccaaaa aagacgcaac tgcagccgat gttgaagccg acgactttaa aggtctgggt      960
ctgaaaaaag tcgtgactaa cctgaccaaa accgtcaatg aaaacaaaca aaacgtcgat     1020
gccaaagtaa aagctgcaga atctgaaata gaaaagttaa caaccaagtt agcagacact     1080
gatgccgctt tagcagatac tgatgccgct ctggatgcaa ccaccaacgc cttgaataaa     1140
ttgggagaaa atataacgac atttgctgaa gagactaaga caaatatcgt aaaaattgat     1200
gaaaaattag aagccgtggc tgataccgtc gacaagcatg ccgaagcatt caacgatatc     1260
gccgattcat tggatgaaac caacactaag gcagacgaag ccgtcaaaac cgccaatgaa     1320
gccaaacaga cggccgaaga accaaacaa acgtcgatg ccaaagtaaa agctgcagaa      1380
actgcagcag gcaaagccga agctgccgct ggcacagcta atactgcagc cgacaaggcc     1440
gaagctgtcg ctgcaaaagt taccgacatc aaagctgata tcgctacgaa caaagataat     1500
attgctaaaa aagcaaacag tgccgacgtg tacaccagag aagagtctga cagcaaattt     1560
gtcagaattg atggtctgaa cgctactacc gaaaaattgg acacacgctt ggcttctgct     1620
gaaaaatcca ttgccgatca cgatactcgc ctgaacggtt tggataaaac agtgtcagac     1680
ctgcgcaaag aaacccgcca aggccttgca gaacaagccg cgctctccgg tctgttccaa     1740
ccttacaacg tgggtcggtt caatgtaacg gctgcagtcg gcggctacaa atccgaatcg     1800
gcagtcgcca tcgtaccgg cttccgcttt accgaaaact ttgccgccaa agcaggcgtg      1860
gcagtcggca cttcgtccgg ttcttccgca gcctaccatg tcggcgtcaa ttacgagtgg     1920
ctcgagcacc accaccacca ccactga                                        1947
```

<210> SEQ ID NO 109
<211> LENGTH: 648
<212> TYPE: PRT
<213> ORGANISM: Artificial Sequence
<220> FEATURE:
<223> OTHER INFORMATION: deltaG741-961

<400> SEQUENCE: 109

```
Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
            20                  25                  30

Ser Val Arg Lys Asn Glu Lys Leu Leu Ala Ala Gln Gly Ala Glu
        35                  40                  45

Lys Thr Tyr Gly Asn Gly Asp Ser Leu Asn Thr Gly Lys Leu Lys Asn
50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

Ala Gly Glu His Thr Ser Phe Asp Lys Leu Pro Glu Gly Gly Arg Ala
    130                 135                 140

Thr Tyr Arg Gly Thr Ala Phe Gly Ser Asp Asp Ala Gly Lys Leu
145                 150                 155                 160

Thr Tyr Thr Ile Asp Phe Ala Ala Lys Gln Gly Asn Gly Lys Ile Glu
                165                 170                 175
```

-continued

His Leu Lys Ser Pro Glu Leu Asn Val Asp Leu Ala Ala Asp Ile
                180                 185                 190

Lys Pro Asp Gly Lys Arg His Ala Val Ile Ser Gly Ser Val Leu Tyr
            195                 200                 205

Asn Gln Ala Glu Lys Gly Ser Tyr Ser Leu Gly Ile Phe Gly Gly Lys
        210                 215                 220

Ala Gln Glu Val Ala Gly Ser Ala Glu Val Lys Thr Val Asn Gly Ile
225                 230                 235                 240

Arg His Ile Gly Leu Ala Ala Lys Gln Leu Glu Gly Gly Gly Thr
                245                 250                 255

Gly Ser Ala Thr Asn Asp Asp Val Lys Lys Ala Ala Thr Val Ala
                260                 265                 270

Ile Ala Ala Ala Tyr Asn Asn Gly Gln Glu Ile Asn Gly Phe Lys Ala
        275                 280                 285

Gly Glu Thr Ile Tyr Asp Ile Asp Glu Asp Gly Thr Ile Thr Lys Lys
    290                 295                 300

Asp Ala Thr Ala Ala Asp Val Glu Ala Asp Phe Lys Gly Leu Gly
305                 310                 315                 320

Leu Lys Lys Val Val Thr Asn Leu Thr Lys Thr Val Asn Glu Asn Lys
                325                 330                 335

Gln Asn Val Asp Ala Lys Val Lys Ala Ala Glu Ser Glu Ile Glu Lys
            340                 345                 350

Leu Thr Thr Lys Leu Ala Asp Thr Asp Ala Ala Leu Ala Asp Thr Asp
        355                 360                 365

Ala Ala Leu Asp Ala Thr Thr Asn Ala Leu Asn Lys Leu Gly Glu Asn
370                 375                 380

Ile Thr Thr Phe Ala Glu Glu Thr Lys Thr Asn Ile Val Lys Ile Asp
385                 390                 395                 400

Glu Lys Leu Glu Ala Val Ala Asp Thr Val Asp Lys His Ala Glu Ala
                405                 410                 415

Phe Asn Asp Ile Ala Asp Ser Leu Asp Glu Thr Asn Thr Lys Ala Asp
            420                 425                 430

Glu Ala Val Lys Thr Ala Asn Glu Ala Lys Gln Thr Ala Glu Glu Thr
        435                 440                 445

Lys Gln Asn Val Asp Ala Lys Val Lys Ala Ala Glu Thr Ala Ala Gly
    450                 455                 460

Lys Ala Glu Ala Ala Ala Gly Thr Ala Asn Thr Ala Ala Asp Lys Ala
465                 470                 475                 480

Glu Ala Val Ala Ala Lys Val Thr Asp Ile Lys Ala Asp Ile Ala Thr
                485                 490                 495

Asn Lys Asp Asn Ile Ala Lys Lys Ala Asn Ser Ala Asp Val Tyr Thr
            500                 505                 510

Arg Glu Glu Ser Asp Ser Lys Phe Val Arg Ile Asp Gly Leu Asn Ala
        515                 520                 525

Thr Thr Glu Lys Leu Asp Thr Arg Leu Ala Ser Ala Glu Lys Ser Ile
    530                 535                 540

Ala Asp His Asp Thr Arg Leu Asn Gly Leu Asp Lys Thr Val Ser Asp
545                 550                 555                 560

Leu Arg Lys Glu Thr Arg Gln Gly Leu Ala Glu Gln Ala Ala Leu Ser
                565                 570                 575

Gly Leu Phe Gln Pro Tyr Asn Val Gly Arg Phe Asn Val Thr Ala Ala
            580                 585                 590

Val Gly Gly Tyr Lys Ser Glu Ser Ala Val Ala Ile Gly Thr Gly Phe
        595                 600                 605

```
Arg Phe Thr Glu Asn Phe Ala Ala Lys Ala Gly Val Ala Val Gly Thr
    610                 615                 620

Ser Ser Gly Ser Ser Ala Ala Tyr His Val Gly Val Asn Tyr Glu Trp
625             630                 635                 640

Leu Glu His His His His His His
                645

<210> SEQ ID NO 110
<211> LENGTH: 1782
<212> TYPE: DNA
<213> ORGANISM: Artificial Sequence
<220> FEATURE:
<223> OTHER INFORMATION: deltaG741-961c

<400> SEQUENCE: 110
```

| | | | | |
|---|---|---|---|---|
| atggtcgccg | ccgacatcgg | tgcggggctt | gccgatgcac | taaccgcacc | gctcgaccat | 60 |
| aaagacaaag | gtttgcagtc | tttgacgctg | gatcagtccg | tcaggaaaaa | cgagaaactg | 120 |
| aagctggcgg | cacaaggtgc | ggaaaaaact | tatggaaacg | gtgacagcct | caatacgggc | 180 |
| aaattgaaga | cgacaaggt | cagccgtttc | gactttatcc | gccaaatcga | agtggacggg | 240 |
| cagctcatta | ccttggagag | tggagagttc | caagtataca | aacaaagcca | ttccgcctta | 300 |
| accgcctttc | agaccgagca | aatacaagat | tcggagcatt | ccgggaagat | ggttgcgaaa | 360 |
| cgccagttca | gaatcggcga | catagcgggc | gaacatacat | cttttgacaa | gcttcccgaa | 420 |
| ggcggcaggg | cgacatatcg | cgggacggcg | ttcggttcag | acgatgccgg | cggaaaactg | 480 |
| acctacacca | tagatttcgc | cgccaagcag | ggaaacggca | aaatcgaaca | tttgaaatcg | 540 |
| ccagaactca | atgtcgacct | ggccgccgcc | gatatcaagc | cggatggaaa | acgccatgcc | 600 |
| gtcatcagcg | gttccgtcct | ttacaaccaa | gccgagaaag | gcagttactc | cctcggtatc | 660 |
| tttggcggaa | aagcccagga | agttgccggc | agcgcggaag | tgaaaaccgt | aaacggcata | 720 |
| cgccatatcg | gccttgccgc | caagcaactc | gagggtggcg | gaggcactgg | atccgccaca | 780 |
| aacgacgacg | atgttaaaaa | agctgccact | gtggccattg | ctgctgccta | caacaatggc | 840 |
| caagaaatca | acggtttcaa | agctggagag | accatctacg | acattgatga | agacggcaca | 900 |
| attaccaaaa | aagacgcaac | tgcagccgat | gttgaagccg | acgactttaa | aggtctgggt | 960 |
| ctgaaaaaag | tcgtgactaa | cctgaccaaa | accgtcaatg | aaaacaaaca | aaacgtcgat | 1020 |
| gccaaagtaa | aagctgcaga | atctgaaata | gaaaagttaa | caaccaagtt | agcagacact | 1080 |
| gatgccgctt | tagcagatac | tgatgccgct | ctggatgcaa | ccaccaacgc | cttgaataaa | 1140 |
| ttgggagaaa | atataacgac | atttgctgaa | gagactaaga | caaatatcgt | aaaaattgat | 1200 |
| gaaaaattag | aagccgtggc | tgataccgtc | gacaagcatg | ccgaagcatt | caacgatatc | 1260 |
| gccgattcat | ggatgaaac | caacactaag | gcagacgaag | ccgtcaaaac | cgccaatgaa | 1320 |
| gccaaacaga | cggccgaaga | aaccaaacaa | aacgtcgatg | ccaaagtaaa | agctgcagaa | 1380 |
| actgcagcag | gcaaagccga | agctgccgct | ggcacagcta | atactgcagc | cgacaaggcc | 1440 |
| gaagctgtcg | ctgcaaaagt | taccgacatc | aaagctgata | tcgctacgaa | caaagataat | 1500 |
| attgctaaaa | aagcaaacag | tgccgacgtg | tacaccagag | aagagtctga | cagcaaattt | 1560 |
| gtcagaattg | atggtctgaa | cgctactacc | gaaaaattgg | acacacgctt | ggcttctgct | 1620 |
| gaaaaatcca | ttgccgatca | cgatactcgc | ctgaacggtt | tggataaaac | agtgtcagac | 1680 |
| ctgcgcaaag | aaacccgcca | aggccttgca | gaacaagccg | cgctctccgg | tctgttccaa | 1740 |
| ccttacaacg | tgggtctcga | gcaccaccac | caccaccact | ga         |            | 1782 |

-continued

```
<210> SEQ ID NO 111
<211> LENGTH: 593
<212> TYPE: PRT
<213> ORGANISM: Artificial Sequence
<220> FEATURE:
<223> OTHER INFORMATION: deltaG741-961c

<400> SEQUENCE: 111
```

| | | | | | | | | | | | | | | | |
|---|---|---|---|---|---|---|---|---|---|---|---|---|---|---|---|
| Met | Val | Ala | Ala | Asp | Ile | Gly | Ala | Gly | Leu | Ala | Asp | Ala | Leu | Thr | Ala |
| 1 | | | | 5 | | | | | 10 | | | | | 15 | |
| Pro | Leu | Asp | His | Lys | Asp | Lys | Gly | Leu | Gln | Ser | Leu | Thr | Leu | Asp | Gln |
| | | | 20 | | | | | 25 | | | | | 30 | | |
| Ser | Val | Arg | Lys | Asn | Glu | Lys | Leu | Lys | Leu | Ala | Ala | Gln | Gly | Ala | Glu |
| | | 35 | | | | | 40 | | | | | 45 | | | |
| Lys | Thr | Tyr | Gly | Asn | Gly | Asp | Ser | Leu | Asn | Thr | Gly | Lys | Leu | Lys | Asn |
| | 50 | | | | | 55 | | | | | 60 | | | | |
| Asp | Lys | Val | Ser | Arg | Phe | Asp | Phe | Ile | Arg | Gln | Ile | Glu | Val | Asp | Gly |
| 65 | | | | | 70 | | | | | 75 | | | | | 80 |
| Gln | Leu | Ile | Thr | Leu | Glu | Ser | Gly | Glu | Phe | Gln | Val | Tyr | Lys | Gln | Ser |
| | | | | 85 | | | | | 90 | | | | | 95 | |
| His | Ser | Ala | Leu | Thr | Ala | Phe | Gln | Thr | Glu | Gln | Ile | Gln | Asp | Ser | Glu |
| | | | 100 | | | | | 105 | | | | | 110 | | |
| His | Ser | Gly | Lys | Met | Val | Ala | Lys | Arg | Gln | Phe | Arg | Ile | Gly | Asp | Ile |
| | | 115 | | | | | 120 | | | | | 125 | | | |
| Ala | Gly | Glu | His | Thr | Ser | Phe | Asp | Lys | Leu | Pro | Glu | Gly | Gly | Arg | Ala |
| | 130 | | | | | 135 | | | | | 140 | | | | |
| Thr | Tyr | Arg | Gly | Thr | Ala | Phe | Gly | Ser | Asp | Asp | Ala | Gly | Gly | Lys | Leu |
| 145 | | | | | 150 | | | | | 155 | | | | | 160 |
| Thr | Tyr | Thr | Ile | Asp | Phe | Ala | Ala | Lys | Gln | Gly | Asn | Gly | Lys | Ile | Glu |
| | | | | 165 | | | | | 170 | | | | | 175 | |
| His | Leu | Lys | Ser | Pro | Glu | Leu | Asn | Val | Asp | Leu | Ala | Ala | Ala | Asp | Ile |
| | | | 180 | | | | | 185 | | | | | 190 | | |
| Lys | Pro | Asp | Gly | Lys | Arg | His | Ala | Val | Ile | Ser | Gly | Ser | Val | Leu | Tyr |
| | | 195 | | | | | 200 | | | | | 205 | | | |
| Asn | Gln | Ala | Glu | Lys | Gly | Ser | Tyr | Ser | Leu | Gly | Ile | Phe | Gly | Gly | Lys |
| | 210 | | | | | 215 | | | | | 220 | | | | |
| Ala | Gln | Glu | Val | Ala | Gly | Ser | Ala | Glu | Val | Lys | Thr | Val | Asn | Gly | Ile |
| 225 | | | | | 230 | | | | | 235 | | | | | 240 |
| Arg | His | Ile | Gly | Leu | Ala | Ala | Lys | Gln | Leu | Glu | Gly | Gly | Gly | Gly | Thr |
| | | | | 245 | | | | | 250 | | | | | 255 | |
| Gly | Ser | Ala | Thr | Asn | Asp | Asp | Val | Lys | Lys | Ala | Ala | Thr | Val | Ala |
| | | | 260 | | | | | 265 | | | | | 270 | | |
| Ile | Ala | Ala | Ala | Tyr | Asn | Asn | Gly | Gln | Glu | Ile | Asn | Gly | Phe | Lys | Ala |
| | | 275 | | | | | 280 | | | | | 285 | | | |
| Gly | Glu | Thr | Ile | Tyr | Asp | Ile | Asp | Glu | Asp | Gly | Thr | Ile | Thr | Lys | Lys |
| | 290 | | | | | 295 | | | | | 300 | | | | |
| Asp | Ala | Thr | Ala | Ala | Asp | Val | Glu | Ala | Asp | Asp | Phe | Lys | Gly | Leu | Gly |
| 305 | | | | | 310 | | | | | 315 | | | | | 320 |
| Leu | Lys | Lys | Val | Val | Thr | Asn | Leu | Thr | Lys | Thr | Val | Asn | Glu | Asn | Lys |
| | | | | 325 | | | | | 330 | | | | | 335 | |
| Gln | Asn | Val | Asp | Ala | Lys | Val | Lys | Ala | Ala | Glu | Ser | Glu | Ile | Glu | Lys |
| | | | 340 | | | | | 345 | | | | | 350 | | |
| Leu | Thr | Thr | Lys | Leu | Ala | Asp | Thr | Asp | Ala | Ala | Leu | Ala | Asp | Thr | Asp |
| | | 355 | | | | | 360 | | | | | 365 | | | |
| Ala | Ala | Leu | Asp | Ala | Thr | Thr | Asn | Ala | Leu | Asn | Lys | Leu | Gly | Glu | Asn |

```
                370             375             380
Ile Thr Thr Phe Ala Glu Glu Thr Lys Thr Asn Ile Val Lys Ile Asp
385             390             395             400

Glu Lys Leu Glu Ala Val Ala Asp Thr Val Asp Lys His Ala Glu Ala
            405             410             415

Phe Asn Asp Ile Ala Asp Ser Leu Asp Glu Thr Asn Thr Lys Ala Asp
            420             425             430

Glu Ala Val Lys Thr Ala Asn Glu Ala Lys Gln Thr Ala Glu Glu Thr
            435             440             445

Lys Gln Asn Val Asp Ala Lys Val Lys Ala Ala Glu Thr Ala Ala Gly
450             455             460

Lys Ala Glu Ala Ala Ala Gly Thr Ala Asn Thr Ala Ala Asp Lys Ala
465             470             475             480

Glu Ala Val Ala Ala Lys Val Thr Asp Ile Lys Ala Asp Ile Ala Thr
            485             490             495

Asn Lys Asp Asn Ile Ala Lys Lys Ala Asn Ser Ala Asp Val Tyr Thr
            500             505             510

Arg Glu Glu Ser Asp Ser Lys Phe Val Arg Ile Asp Gly Leu Asn Ala
            515             520             525

Thr Thr Glu Lys Leu Asp Thr Arg Leu Ala Ser Ala Glu Lys Ser Ile
530             535             540

Ala Asp His Asp Thr Arg Leu Asn Gly Leu Asp Lys Thr Val Ser Asp
545             550             555             560

Leu Arg Lys Glu Thr Arg Gln Gly Leu Ala Glu Gln Ala Ala Leu Ser
            565             570             575

Gly Leu Phe Gln Pro Tyr Asn Val Gly Leu Glu His His His His His
            580             585             590

His

<210> SEQ ID NO 112
<211> LENGTH: 3939
<212> TYPE: DNA
<213> ORGANISM: Artificial Sequence
<220> FEATURE:
<223> OTHER INFORMATION: deltaG741-983

<400> SEQUENCE: 112
atggtcgccg ccgacatcgg tgcggggctt gccgatgcac taaccgcacc gctcgaccat    60
aaagacaaag gtttgcagtc tttgacgctg gatcagtccg tcaggaaaaa cgagaaactg   120
aagctggcgg cacaaggtgc ggaaaaaact tatggaaacg gtgacagcct caatacgggc   180
aaattgaaga cgacaaggt cagccgtttc gactttatcc gccaaatcga agtggacggg    240
cagctcatta ccttggagag tggagagttc aagtataca aacaaagcca ttccgcctta    300
accgcctttc agaccgagca aatacaagat tcggagcatt ccggaagat ggttgcgaaa    360 cgccagttca gaatcggcga catagcgggc gaacatacat cttttgacaa gcttcccgaa    420
ggcggcaggg cgacatatcg cgggacggcg ttcggttcag acgatgccgg cggaaaactg    480
acctacacca tagatttcgc cgccaagcag ggaaacggca aaatcgaaca tttgaaatcg    540
ccagaactca atgtcgacct ggccgccgcc gatatcaagc cggatggaaa acgccatgcc    600
gtcatcagcg gttccgtcct ttacaaccaa gccgagaaag gcagttactc cctcggtatc    660
tttggcggaa aagcccagga agttgccggc agcgcggaag tgaaaaccgt aaacggcata    720
cgccatatcg gccttgccgc caagcaactc gagggatccg gcgaggcgg cacttctgcg    780 cccgacttca atgcaggcgg taccggtatc ggcagcaaca gcagagcaac aacagcgaaa    840
```

```
tcagcagcag tatcttacgc cggtatcaag aacgaaatgt gcaaagacag aagcatgctc    900
tgtgccggtc gggatgacgt tgcggttaca gacagggatg ccaaaatcaa tgccccccccc   960
ccgaatctgc ataccggaga ctttccaaac ccaaatgacg catacaagaa tttgatcaac   1020
ctcaaacctg caattgaagc aggctataca ggacgcgggg tagaggtagg tatcgtcgac   1080
acaggcgaat ccgtcggcag catatccttt cccgaactgt atggcagaaa agaaacgcc    1140
tataacgaaa attacaaaaa ctatacgcg tatatgcgga aggaagcgcc tgaagacgga    1200
ggcggtaaag acattgaagc ttctttcgac gatgaggccg ttatagagac tgaagcaaag   1260
ccgacggata tccgccacgt aaaagaaatc ggacacatcg atttggtctc ccatattatt   1320
ggcgggcgtt ccgtggacgg cagacctgca ggcggtattg cgcccgatgc gacgctacac   1380
ataatgaata cgaatgatga aaccaagaac gaaatgatgg ttgcagccat ccgcaatgca   1440
tgggtcaagc tgggcgaacg tggcgtgcgc atcgtcaata acagttttgg aacaacatcg   1500
agggcaggca ctgccgacct tttccaaata gccaattcgg aggagcagta ccgccaagcg   1560
ttgctcgact attccggcgg tgataaaaca gacgagggta ccgcctgat gcaacagagc    1620
gattacggca acctgtccta ccacatccgt aataaaaaca tgcttttcat cttttcgaca   1680
ggcaatgacg cacaagctca gcccaacaca tatgccctat tgccatttta tgaaaaagac   1740
gctcaaaaag gcattatcac agtcgcaggc gtagaccgca gtggagaaaa gttcaaacgg   1800
gaaatgtatg gagaaccggg tacagaaccg cttgagtatg gctccaacca ttgcggaatt   1860
actgccatgt ggtgcctgtc ggcaccctat gaagcaagcg tccgtttcac ccgtacaaac   1920
ccgattcaaa ttgccggaac atccttttcc gcacccatcg taaccggcac ggcggctctg   1980
ctgctgcaga ataccccgtg gatgagcaac gacaacctgc gtaccacgtt gctgacgacg   2040
gctcaggaca tcggtgcagt cggcgtggac agcaagttcg gctgggact gctggatgcg    2100
ggtaaggcca tgaacggacc cgcgtccttt ccgttcggcg actttaccgc cgatacgaaa   2160
ggtacatccg atattgccta ctccttccgt aacgacattt caggcacggg cggcctgatc   2220
aaaaaaggcg gcagccaact gcaactgcac ggcaacaaca cctatacggg caaaaccatt   2280
atcgaaggcg gttcgctggt gttgtacggc aacaacaaat cggatatgcg cgtcgaaacc   2340
aaaggtgcgc tgatttataa cggggcggca tccggcggca gcctgaacag cgacggcatt   2400
gtctatctgg cagataccga ccaatccggc gcaaacgaaa ccgtacacat caaaggcagt   2460
ctgcagctgg acggcaaagg tacgctgtac acacgtttgg gcaaactgct gaaagtggac   2520
ggtacggcga ttatcggcgg caagctgtac atgtcggcac gcggcaaggg ggcaggctat   2580
ctcaacagta ccggacgacg tgttcccttc ctgagtgccg ccaaaatcgg gcaggattat   2640
tctttcttca caaacatcga aaccgacggc ggcctgctgg cttccctcga cagcgtcgaa   2700
aaaacagcgg gcagtgaagg cgacacgctg tcctattatg tccgtcgcgg caatgcggca   2760
cggactgctt cggcagcggc acattccgcg cccgccggtc tgaaacacgc cgtagaacag   2820
ggcggcagca atctgaaaaa cctgatggtc gaactggatg cctccgaatc atccgcaaca   2880
cccgagacgg ttgaaactgc ggcagccgac cgcacagata tgccgggcat ccgcccctac   2940
ggcgcaactt tccgcgcagc ggcagccgta cagcatgcga atgccgccga cggtgtacgc   3000
atcttcaaca gtctcgccgc taccgtctat gccgacagta ccgccgccca tgccgatatg   3060
cagggacgcc gcctgaaagc cgtatcggac gggttggacc acaacggcac gggtctgcgc   3120
gtcatcgcgc aaacccaaca ggacggtgga acgtgggaac agggcggtgt tgaaggcaaa   3180
atgcgcggca gtacccaaac cgtcggcatt gccgcgaaaa ccggcgaaaa tacgacagca   3240
```

```
gccgccacac tgggcatggg acgcagcaca tggagcgaaa acagtgcaaa tgcaaaaacc    3300
gacagcatta gtctgtttgc aggcatacgg cacgatgcgg gcgatatcgg ctatctcaaa    3360
ggcctgttct cctacggacg ctacaaaaac agcatcagcc gcagcaccgg tgcggacgaa    3420
catgcggaag gcagcgtcaa cggcacgctg atgcagctgg gcgcactggg cggtgtcaac    3480
gttccgtttg ccgcaacggg agatttgacg gtcgaaggcg gtctgcgcta cgacctgctc    3540
aaacaggatg cattcgccga aaaaggcagt gctttgggct ggagcggcaa cagcctcact    3600
gaaggcacgc tggtcggact cgcgggtctg aagctgtcgc aacccttgag cgataaagcc    3660
gtcctgtttg caacggcggg cgtggaacgc gacctgaacg gacgcgacta cacggtaacg    3720
ggcggcttta ccggcgcgac tgcagcaacc ggcaagacgg gggcacgcaa tatgccgcac    3780
acccgtctgg ttgccggcct gggcgcggat gtcgaattcg gcaacggctg gaacggcttg    3840
gcacgttaca gctacgccgg ttccaaacag tacggcaacc acagcggacg agtcggcgta    3900
ggctaccggt tcctcgagca ccaccaccac caccactga                          3939
```

<210> SEQ ID NO 113
<211> LENGTH: 1312
<212> TYPE: PRT
<213> ORGANISM: Artificial Sequence
<220> FEATURE:
<223> OTHER INFORMATION: deltaG741-983

<400> SEQUENCE: 113

```
Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
                20                  25                  30

Ser Val Arg Lys Asn Glu Lys Leu Lys Leu Ala Ala Gln Gly Ala Glu
            35                  40                  45

Lys Thr Tyr Gly Asn Gly Asp Ser Leu Asn Thr Gly Lys Leu Lys Asn
        50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

Ala Gly Glu His Thr Ser Phe Asp Lys Leu Pro Glu Gly Gly Arg Ala
    130                 135                 140

Thr Tyr Arg Gly Thr Ala Phe Gly Ser Asp Asp Ala Gly Gly Lys Leu
145                 150                 155                 160

Thr Tyr Thr Ile Asp Phe Ala Ala Lys Gln Gly Asn Gly Lys Ile Glu
                165                 170                 175

His Leu Lys Ser Pro Glu Leu Asn Val Asp Leu Ala Ala Ala Asp Ile
            180                 185                 190

Lys Pro Asp Gly Lys Arg His Ala Val Ile Ser Gly Ser Val Leu Tyr
        195                 200                 205

Asn Gln Ala Glu Lys Gly Ser Tyr Ser Leu Gly Ile Phe Gly Gly Lys
    210                 215                 220

Ala Gln Glu Val Ala Gly Ser Ala Glu Val Lys Thr Val Asn Gly Ile
225                 230                 235                 240
```

```
Arg His Ile Gly Leu Ala Ala Lys Gln Leu Glu Gly Ser Gly Gly Gly
            245                 250                 255
Gly Thr Ser Ala Pro Asp Phe Asn Ala Gly Thr Gly Ile Gly Ser
        260                 265                 270
Asn Ser Arg Ala Thr Thr Ala Lys Ser Ala Ala Val Ser Tyr Ala Gly
            275                 280                 285
Ile Lys Asn Glu Met Cys Lys Asp Arg Ser Met Leu Cys Ala Gly Arg
            290                 295                 300
Asp Asp Val Ala Val Thr Asp Arg Asp Ala Lys Ile Asn Ala Pro Pro
305                 310                 315                 320
Pro Asn Leu His Thr Gly Asp Phe Pro Asn Pro Asn Asp Ala Tyr Lys
                325                 330                 335
Asn Leu Ile Asn Leu Lys Pro Ala Ile Glu Ala Gly Tyr Thr Gly Arg
            340                 345                 350
Gly Val Glu Val Gly Ile Val Asp Thr Gly Glu Ser Val Gly Ser Ile
            355                 360                 365
Ser Phe Pro Glu Leu Tyr Gly Arg Lys Glu His Gly Tyr Asn Glu Asn
    370                 375                 380
Tyr Lys Asn Tyr Thr Ala Tyr Met Arg Lys Glu Ala Pro Glu Asp Gly
385                 390                 395                 400
Gly Gly Lys Asp Ile Glu Ala Ser Phe Asp Asp Glu Ala Val Ile Glu
                405                 410                 415
Thr Glu Ala Lys Pro Thr Asp Ile Arg His Val Lys Glu Ile Gly His
            420                 425                 430
Ile Asp Leu Val Ser His Ile Ile Gly Gly Arg Ser Val Asp Gly Arg
            435                 440                 445
Pro Ala Gly Gly Ile Ala Pro Asp Ala Thr Leu His Ile Met Asn Thr
450                 455                 460
Asn Asp Glu Thr Lys Asn Glu Met Met Val Ala Ala Ile Arg Asn Ala
465                 470                 475                 480
Trp Val Lys Leu Gly Glu Arg Gly Val Arg Ile Val Asn Asn Ser Phe
                485                 490                 495
Gly Thr Thr Ser Arg Ala Gly Thr Ala Asp Leu Phe Gln Ile Ala Asn
            500                 505                 510
Ser Glu Glu Gln Tyr Arg Gln Ala Leu Leu Asp Tyr Ser Gly Gly Asp
            515                 520                 525
Lys Thr Asp Glu Gly Ile Arg Leu Met Gln Gln Ser Asp Tyr Gly Asn
530                 535                 540
Leu Ser Tyr His Ile Arg Asn Lys Asn Met Leu Phe Ile Phe Ser Thr
545                 550                 555                 560
Gly Asn Asp Ala Gln Ala Gln Pro Asn Thr Tyr Ala Leu Leu Pro Phe
                565                 570                 575
Tyr Glu Lys Asp Ala Gln Lys Gly Ile Ile Thr Val Ala Gly Val Asp
            580                 585                 590
Arg Ser Gly Glu Lys Phe Lys Arg Glu Met Tyr Gly Glu Pro Gly Thr
            595                 600                 605
Glu Pro Leu Glu Tyr Gly Ser Asn His Cys Gly Ile Thr Ala Met Trp
    610                 615                 620
Cys Leu Ser Ala Pro Tyr Glu Ala Ser Val Arg Phe Thr Arg Thr Asn
625                 630                 635                 640
Pro Ile Gln Ile Ala Gly Thr Ser Phe Ser Ala Pro Ile Val Thr Gly
                645                 650                 655
Thr Ala Ala Leu Leu Leu Gln Lys Tyr Pro Trp Met Ser Asn Asp Asn
            660                 665                 670
```

-continued

```
Leu Arg Thr Thr Leu Leu Thr Thr Ala Gln Asp Ile Gly Ala Val Gly
            675                 680                 685
Val Asp Ser Lys Phe Gly Trp Gly Leu Leu Asp Ala Gly Lys Ala Met
        690                 695                 700
Asn Gly Pro Ala Ser Phe Pro Phe Gly Asp Phe Thr Ala Asp Thr Lys
705                 710                 715                 720
Gly Thr Ser Asp Ile Ala Tyr Ser Phe Arg Asn Asp Ile Ser Gly Thr
                725                 730                 735
Gly Gly Leu Ile Lys Lys Gly Ser Gln Leu Gln Leu His Gly Asn
            740                 745                 750
Asn Thr Tyr Thr Gly Lys Thr Ile Glu Gly Gly Ser Leu Val Leu
        755                 760                 765
Tyr Gly Asn Asn Lys Ser Asp Met Arg Val Glu Thr Lys Gly Ala Leu
    770                 775                 780
Ile Tyr Asn Gly Ala Ala Ser Gly Gly Ser Leu Asn Ser Asp Gly Ile
785                 790                 795                 800
Val Tyr Leu Ala Asp Thr Asp Gln Ser Gly Ala Asn Glu Thr Val His
                805                 810                 815
Ile Lys Gly Ser Leu Gln Leu Asp Gly Lys Gly Thr Leu Tyr Thr Arg
            820                 825                 830
Leu Gly Lys Leu Leu Lys Val Asp Gly Thr Ala Ile Ile Gly Gly Lys
        835                 840                 845
Leu Tyr Met Ser Ala Arg Gly Lys Ala Gly Tyr Leu Asn Ser Thr
    850                 855                 860
Gly Arg Arg Val Pro Phe Leu Ser Ala Ala Lys Ile Gly Gln Asp Tyr
865                 870                 875                 880
Ser Phe Phe Thr Asn Ile Glu Thr Asp Gly Gly Leu Leu Ala Ser Leu
                885                 890                 895
Asp Ser Val Glu Lys Thr Ala Gly Ser Glu Gly Asp Thr Leu Ser Tyr
            900                 905                 910
Tyr Val Arg Arg Gly Asn Ala Ala Arg Thr Ala Ser Ala Ala His
        915                 920                 925
Ser Ala Pro Ala Gly Leu Lys His Ala Val Glu Gln Gly Gly Ser Asn
    930                 935                 940
Leu Glu Asn Leu Met Val Glu Leu Asp Ala Ser Glu Ser Ser Ala Thr
945                 950                 955                 960
Pro Glu Thr Val Glu Thr Ala Ala Ala Asp Arg Thr Asp Met Pro Gly
                965                 970                 975
Ile Arg Pro Tyr Gly Ala Thr Phe Arg Ala Ala Ala Val Gln His
            980                 985                 990
Ala Asn Ala Ala Asp Gly Val Arg Ile Phe Asn Ser Leu Ala Ala Thr
        995                 1000                1005
Val Tyr Ala Asp Ser Thr Ala Ala His Ala Asp Met Gln Gly Arg Arg
    1010                1015                1020
Leu Lys Ala Val Ser Asp Gly Leu Asp His Asn Gly Thr Gly Leu Arg
1025                1030                1035                1040
Val Ile Ala Gln Thr Gln Gln Asp Gly Gly Thr Trp Glu Gln Gly Gly
                1045                1050                1055
Val Glu Gly Lys Met Arg Gly Ser Thr Gln Thr Val Gly Ile Ala Ala
            1060                1065                1070
Lys Thr Gly Glu Asn Thr Thr Ala Ala Ala Thr Leu Gly Met Gly Arg
        1075                1080                1085
Ser Thr Trp Ser Glu Asn Ser Ala Asn Ala Lys Thr Asp Ser Ile Ser
```

```
                      1090              1095             1100
Leu Phe Ala Gly Ile Arg His Asp Ala Gly Asp Ile Gly Tyr Leu Lys
1105                1110             1115             1120

Gly Leu Phe Ser Tyr Gly Arg Tyr Lys Asn Ser Ile Ser Arg Ser Thr
            1125             1130             1135

Gly Ala Asp Glu His Ala Glu Gly Ser Val Asn Gly Thr Leu Met Gln
        1140             1145             1150

Leu Gly Ala Leu Gly Gly Val Asn Val Pro Phe Ala Ala Thr Gly Asp
    1155             1160             1165

Leu Thr Val Glu Gly Gly Leu Arg Tyr Asp Leu Leu Lys Gln Asp Ala
    1170             1175             1180

Phe Ala Glu Lys Gly Ser Ala Leu Gly Trp Ser Gly Asn Ser Leu Thr
1185                1190             1195             1200

Glu Gly Thr Leu Val Gly Leu Ala Gly Leu Lys Leu Ser Gln Pro Leu
                1205             1210             1215

Ser Asp Lys Ala Val Leu Phe Ala Thr Ala Gly Val Glu Arg Asp Leu
            1220             1225             1230

Asn Gly Arg Asp Tyr Thr Val Thr Gly Gly Phe Thr Gly Ala Thr Ala
            1235             1240             1245

Ala Thr Gly Lys Thr Gly Ala Arg Asn Met Pro His Thr Arg Leu Val
        1250             1255             1260

Ala Gly Leu Gly Ala Asp Val Glu Phe Gly Asn Gly Trp Asn Gly Leu
1265                1270             1275             1280

Ala Arg Tyr Ser Tyr Ala Gly Ser Lys Gln Tyr Gly Asn His Ser Gly
                1285             1290             1295

Arg Val Gly Val Gly Tyr Arg Phe Leu Glu His His His His His His
            1300             1305             1310

<210> SEQ ID NO 114
<211> LENGTH: 2028
<212> TYPE: DNA
<213> ORGANISM: Artificial Sequence
<220> FEATURE:
<223> OTHER INFORMATION: deltaG741-ORF46.1

<400> SEQUENCE: 114
atggtcgccg ccgacatcgg tgcggggctt gccgatgcac taaccgcacc gctcgaccat     60
aaagacaaag gtttgcagtc tttgacgctg gatcagtccg tcaggaaaaa cgagaaactg    120
aagctggcgg cacaaggtgc ggaaaaaact tatggaaacg gtgacagcct caatacgggc    180
aaattgaaga acgacaaggt cagccgtttc gactttatcc gccaaatcga agtggacggg    240
cagctcatta ccttggagag tggagagttc aagtataca aacaaagcca ttccgcctta    300
accgcctttc agaccgagca aatacaagat tcggagcatt ccggaagat ggttgcgaaa    360 cgccagttca gaatcggcga catagcgggc gaacatacat cttttgacaa gcttcccgaa    420
ggcggcaggg cgacatatcg cgggacggcg ttcggttcag acgatgccgg cggaaaactg    480
acctacacca tagatttcgc cgccaagcag ggaaacggca aaatcgaaca tttgaaatcg    540
ccagaactca atgtcgacct ggccgccgcc gatatcaagc cggatggaaa acgccatgcc    600
gtcatcagcg gttccgtcct ttacaaccaa gccgagaaag gcagttactc cctcggtatc    660
tttggcggaa aagcccagga agttgccggc agcgcggaag tgaaaaccgt aaacggcata    720
cgccatatcg gccttgccgc caagcaactc gacggtggcg gaggcactgg atcctcagat    780
ttggcaaacg attcttttat ccggcaggtt ctcgaccgtc agcatttcga acccgacggg    840
aaataccacc tattcggcag caggggggaa cttgccgagc gcagcggcca tatcggattg    900
```

```
ggaaaaatac aaagccatca gttgggcaac ctgatgattc aacaggcggc cattaaagga      960
aatatcggct acattgtccg cttttccgat cacgggcacg aagtccattc ccccttcgac     1020
aaccatgcct cacattccga ttctgatgaa gccggtagtc ccgttgacgg atttagcctt     1080
taccgcatcc attgggacgg atacgaacac catcccgccg acggctatga cgggccacag     1140
ggcggcggct atcccgctcc caaaggcgcg agggatatat acagctacga cataaaaggc     1200
gttgcccaaa atatccgcct caacctgacc gacaaccgca gcaccggaca acggcttgcc     1260 gaccgttttcc acaatgccgg tagtatgctg acgcaaggag taggcgacgg attcaaacgc     1320
gccacccgat acagccccga gctggacaga tcgggcaatg ccgccgaagc cttcaacggc     1380
actgcagata tcgttaaaaa catcatcggc gcggcaggag aaattgtcgg cgcaggcgat     1440
gccgtgcagg cataagcga aggctcaaac attgctgtca tgcacggctt gggtctgctt     1500
tccaccgaaa acaagatggc gcgcatcaac gatttggcag atatggcgca actcaaagac     1560
tatgccgcag cagccatccg cgattgggca gtccaaaacc ccaatgccgc acaaggcata     1620
gaagccgtca gcaatatctt tatggcagcc atccccatca aagggattgg agctgttcgg     1680
ggaaaatacg gcttgggcgg catcacggca catcctatca gcggtcgca gatgggcgcg      1740 atcgcattgc cgaaagggaa atccgccgtc agcgacaatt ttgccgatgc ggcatacgcc     1800 aaataccccgt cccccttacca ttcccgaaat atccgttcaa acttggagca gcgttacggc     1860
aaagaaaaca tcacctcctc aaccgtgccg ccgtcaaacg gcaaaaatgt caaactggca     1920
gaccaacgcc acccgaagac aggcgtaccg tttgacggta aagggtttcc gaattttgag     1980
aagcacgtga aatatgatac gctcgagcac caccaccacc accactga                  2028
```

<210> SEQ ID NO 115
<211> LENGTH: 675
<212> TYPE: PRT
<213> ORGANISM: Artificial Sequence
<220> FEATURE:
<223> OTHER INFORMATION: deltaG741-ORF46.1

<400> SEQUENCE: 115

```
Met Val Ala Ala Asp Ile Gly Ala Gly Leu Ala Asp Ala Leu Thr Ala
1               5                  10                  15

Pro Leu Asp His Lys Asp Lys Gly Leu Gln Ser Leu Thr Leu Asp Gln
            20                  25                  30

Ser Val Arg Lys Asn Glu Lys Leu Lys Leu Ala Ala Gln Gly Ala Glu
        35                  40                  45

Lys Thr Tyr Gly Asn Gly Asp Ser Leu Asn Thr Gly Lys Leu Lys Asn
    50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

Ala Gly Glu His Thr Ser Phe Asp Lys Leu Pro Glu Gly Gly Arg Ala
    130                 135                 140

Thr Tyr Arg Gly Thr Ala Phe Gly Ser Asp Asp Ala Gly Gly Lys Leu
145                 150                 155                 160

Thr Tyr Thr Ile Asp Phe Ala Ala Lys Gln Gly Asn Gly Lys Ile Glu
```

```
                    165                 170                 175
His Leu Lys Ser Pro Glu Leu Asn Val Asp Leu Ala Ala Asp Ile
                180                 185                 190

Lys Pro Asp Gly Lys Arg His Ala Val Ile Ser Gly Val Leu Tyr
            195                 200                 205

Asn Gln Ala Glu Lys Gly Ser Tyr Ser Leu Gly Ile Phe Gly Gly Lys
        210                 215                 220

Ala Gln Glu Val Ala Gly Ser Ala Glu Val Lys Thr Val Asn Gly Ile
225                 230                 235                 240

Arg His Ile Gly Leu Ala Ala Lys Gln Leu Asp Gly Gly Gly Thr
                245                 250                 255

Gly Ser Ser Asp Leu Ala Asn Asp Ser Phe Ile Arg Gln Val Leu Asp
                260                 265                 270

Arg Gln His Phe Glu Pro Asp Gly Lys Tyr His Leu Phe Gly Ser Arg
            275                 280                 285

Gly Glu Leu Ala Glu Arg Ser Gly His Ile Gly Leu Gly Lys Ile Gln
        290                 295                 300

Ser His Gln Leu Gly Asn Leu Met Ile Gln Gln Ala Ile Lys Gly
305                 310                 315                 320

Asn Ile Gly Tyr Ile Val Arg Phe Ser Asp His Gly His Glu Val His
                325                 330                 335

Ser Pro Phe Asp Asn His Ala Ser His Ser Asp Ser Asp Glu Ala Gly
                340                 345                 350

Ser Pro Val Asp Gly Phe Ser Leu Tyr Arg Ile His Trp Asp Gly Tyr
            355                 360                 365

Glu His His Pro Ala Asp Gly Tyr Asp Gly Pro Gln Gly Gly Gly Tyr
        370                 375                 380

Pro Ala Pro Lys Gly Ala Arg Asp Ile Tyr Ser Tyr Asp Ile Lys Gly
385                 390                 395                 400

Val Ala Gln Asn Ile Arg Leu Asn Leu Thr Asp Asn Arg Ser Thr Gly
                405                 410                 415

Gln Arg Leu Ala Asp Arg Phe His Asn Ala Gly Ser Met Leu Thr Gln
                420                 425                 430

Gly Val Gly Asp Gly Phe Lys Arg Ala Thr Arg Tyr Ser Pro Glu Leu
            435                 440                 445

Asp Arg Ser Gly Asn Ala Ala Glu Ala Phe Asn Gly Thr Ala Asp Ile
        450                 455                 460

Val Lys Asn Ile Ile Gly Ala Ala Gly Glu Ile Val Gly Ala Gly Asp
465                 470                 475                 480

Ala Val Gln Gly Ile Ser Glu Gly Ser Asn Ile Ala Val Met His Gly
                485                 490                 495

Leu Gly Leu Leu Ser Thr Glu Asn Lys Met Ala Arg Ile Asn Asp Leu
                500                 505                 510

Ala Asp Met Ala Gln Leu Lys Asp Tyr Ala Ala Ala Ile Arg Asp
            515                 520                 525

Trp Ala Val Gln Asn Pro Asn Ala Ala Gln Gly Ile Glu Ala Val Ser
        530                 535                 540

Asn Ile Phe Met Ala Ala Ile Pro Ile Lys Gly Ile Gly Ala Val Arg
545                 550                 555                 560

Gly Lys Tyr Gly Leu Gly Gly Ile Thr Ala His Pro Ile Lys Arg Ser
                565                 570                 575

Gln Met Gly Ala Ile Ala Leu Pro Lys Gly Lys Ser Ala Val Ser Asp
            580                 585                 590
```

```
Asn Phe Ala Asp Ala Ala Tyr Ala Lys Tyr Pro Ser Pro Tyr His Ser
        595                 600                 605

Arg Asn Ile Arg Ser Asn Leu Glu Gln Arg Tyr Gly Lys Glu Asn Ile
        610                 615                 620

Thr Ser Ser Thr Val Pro Pro Ser Asn Gly Lys Asn Val Lys Leu Ala
625                 630                 635                 640

Asp Gln Arg His Pro Lys Thr Gly Val Pro Phe Asp Gly Lys Gly Phe
                645                 650                 655

Pro Asn Phe Glu Lys His Val Lys Tyr Asp Thr Leu Glu His His His
                660                 665                 670

His His His
        675

<210> SEQ ID NO 116
<211> LENGTH: 249
<212> TYPE: PRT
<213> ORGANISM: Artificial Sequence
<220> FEATURE:
<223> OTHER INFORMATION: Novel protein

<400> SEQUENCE: 116

Met Lys Lys Tyr Leu Phe Arg Ala Ala Leu Tyr Gly Ile Ala Ala Ala
1               5                   10                  15

Ile Leu Ala Ala Ala Ile Pro Ala Gly Asn Asp Ala Thr Thr Lys Pro
            20                  25                  30

Asp Leu Tyr Tyr Leu Lys Asn Glu Gln Ala Ile Asp Ser Leu Lys Leu
        35                  40                  45

Leu Pro Pro Pro Glu Val Gly Ser Ile Gln Phe Leu Asn Asp Gln
    50                  55                  60

Ala Met Tyr Glu Lys Gly Arg Met Leu Arg Asn Thr Glu Arg Gly Lys
65                  70                  75                  80

Gln Ala Gln Ala Asp Ala Asp Leu Ala Ala Gly Gly Val Ala Thr Ala
                85                  90                  95

Phe Ser Gly Ala Phe Gly Tyr Pro Ile Thr Glu Lys Asp Ser Pro Glu
            100                 105                 110

Leu Tyr Lys Leu Leu Thr Asn Met Ile Glu Asp Ala Gly Asp Leu Ala
        115                 120                 125

Thr Arg Ser Ala Lys Glu His Tyr Met Arg Ile Arg Pro Phe Ala Phe
    130                 135                 140

Tyr Gly Thr Glu Thr Cys Asn Thr Lys Asp Gln Lys Lys Leu Ser Thr
145                 150                 155                 160

Asn Gly Ser Tyr Pro Ser Gly His Thr Ser Ile Gly Trp Ala Thr Ala
                165                 170                 175

Leu Val Leu Ala Glu Val Asn Pro Ala Asn Gln Asp Ala Ile Leu Glu
            180                 185                 190

Arg Gly Tyr Gln Leu Gly Gln Ser Arg Val Ile Cys Gly Tyr His Trp
        195                 200                 205

Gln Ser Asp Val Asp Ala Ala Arg Ile Val Gly Ser Ala Ala Val Ala
    210                 215                 220

Thr Leu His Ser Asp Pro Ala Phe Gln Ala Gln Leu Ala Lys Ala Lys
225                 230                 235                 240

Gln Glu Phe Ala Gln Lys Ser Gln Lys
                245

<210> SEQ ID NO 117
<211> LENGTH: 66
<212> TYPE: DNA
```

```
<213> ORGANISM: Artificial Sequence
<220> FEATURE:
<223> OTHER INFORMATION: L1 linker
<220> FEATURE:
<221> NAME/KEY: misc_feature
<222> LOCATION: (1)...(66)
<223> OTHER INFORMATION: n = A, T/U, G or C

<400> SEQUENCE: 117
tatgaartay ytnttymgcg ccgccctgta cggcatcgcc gccgccatcc tcgccgccgc      60
gatccc                                                                 66

<210> SEQ ID NO 118
<211> LENGTH: 69
<212> TYPE: DNA
<213> ORGANISM: Artificial Sequence
<220> FEATURE:
<223> OTHER INFORMATION: S1 linker
<220> FEATURE:
<221> NAME/KEY: misc_feature
<222> LOCATION: (1)...(69)
<223> OTHER INFORMATION: n = A, T/U, G or C

<400> SEQUENCE: 118
tatgaaaaaa tacctattcc grgcngcnyt rtayggsatc gccgccgcca tcctcgccgc      60
cgcgatccc                                                              69

<210> SEQ ID NO 119
<211> LENGTH: 27
<212> TYPE: DNA
<213> ORGANISM: Artificial Sequence
<220> FEATURE:
<223> OTHER INFORMATION: 9L1-a

<400> SEQUENCE: 119
atgaagaagt accttttcag cgccgcc                                          27

<210> SEQ ID NO 120
<211> LENGTH: 27
<212> TYPE: DNA
<213> ORGANISM: Artificial Sequence
<220> FEATURE:
<223> OTHER INFORMATION: 9L1-e

<400> SEQUENCE: 120
atgaaaaaat acttttccg cgccgcc                                           27

<210> SEQ ID NO 121
<211> LENGTH: 27
<212> TYPE: DNA
<213> ORGANISM: Artificial Sequence
<220> FEATURE:
<223> OTHER INFORMATION: 9L1-d

<400> SEQUENCE: 121
atgaaaaaat acttttccg cgccgcc                                           27

<210> SEQ ID NO 122
<211> LENGTH: 60
<212> TYPE: DNA
<213> ORGANISM: Artificial Sequence
<220> FEATURE:
<223> OTHER INFORMATION: 9L1-f

<400> SEQUENCE: 122
atgaaaaaat atctctttag cgccgccctg tacggcatcg ccgccgccat cctcgccgcc      60
```

```
<210> SEQ ID NO 123
<211> LENGTH: 60
<212> TYPE: DNA
<213> ORGANISM: Artificial Sequence
<220> FEATURE:
<223> OTHER INFORMATION: 919sp

<400> SEQUENCE: 123
atgaaaaaat acctattccg cgccgccctg tacggcatcg ccgccgccat cctcgccgcc    60

<210> SEQ ID NO 124
<211> LENGTH: 9
<212> TYPE: PRT
<213> ORGANISM: Artificial Sequence
<220> FEATURE:
<223> OTHER INFORMATION: 9L1a

<400> SEQUENCE: 124

Met Lys Lys Tyr Leu Phe Ser Ala Ala
1               5

<210> SEQ ID NO 125
<211> LENGTH: 9
<212> TYPE: PRT
<213> ORGANISM: Artificial Sequence
<220> FEATURE:
<223> OTHER INFORMATION: 9L1e

<400> SEQUENCE: 125

Met Lys Lys Tyr Phe Phe Arg Ala Ala
1               5

<210> SEQ ID NO 126
<211> LENGTH: 9
<212> TYPE: PRT
<213> ORGANISM: Artificial Sequence
<220> FEATURE:
<223> OTHER INFORMATION: 9L1d

<400> SEQUENCE: 126

Met Lys Lys Tyr Phe Phe Arg Ala Ala
1               5

<210> SEQ ID NO 127
<211> LENGTH: 20
<212> TYPE: PRT
<213> ORGANISM: Artificial Sequence
<220> FEATURE:
<223> OTHER INFORMATION: 9L1f

<400> SEQUENCE: 127

Met Lys Lys Tyr Leu Phe Ser Ala Ala Leu Tyr Gly Ile Ala Ala Ala
1               5                   10                  15

Ile Leu Ala Ala
            20

<210> SEQ ID NO 128
<211> LENGTH: 20
<212> TYPE: PRT
<213> ORGANISM: Artificial Sequence
<220> FEATURE:
<223> OTHER INFORMATION: 9L1sp

<400> SEQUENCE: 128

Met Lys Lys Tyr Leu Phe Arg Ala Ala Leu Tyr Gly Ile Ala Ala Ala
1               5                   10                  15
```

Ile Leu Ala Ala
        20

<210> SEQ ID NO 129
<211> LENGTH: 42
<212> TYPE: DNA
<213> ORGANISM: Artificial Sequence
<220> FEATURE:
<223> OTHER INFORMATION: 9S1-e

<400> SEQUENCE: 129
atgaaaaaat acctattcat cgccgccgcc atcctcgccg cc                42

<210> SEQ ID NO 130
<211> LENGTH: 60
<212> TYPE: DNA
<213> ORGANISM: Artificial Sequence
<220> FEATURE:
<223> OTHER INFORMATION: 9S1-c

<400> SEQUENCE: 130
atgaaaaaat acctattccg agctgcccaa tacggcatcg ccgccgccat cctcgccgcc    60

<210> SEQ ID NO 131
<211> LENGTH: 60
<212> TYPE: DNA
<213> ORGANISM: Artificial Sequence
<220> FEATURE:
<223> OTHER INFORMATION: 9S1-b

<400> SEQUENCE: 131
atgaaaaaat acctattccg ggccgcccaa tacggcatcg ccgccgccat cctcgccgcc    60

<210> SEQ ID NO 132
<211> LENGTH: 60
<212> TYPE: DNA
<213> ORGANISM: Artificial Sequence
<220> FEATURE:
<223> OTHER INFORMATION: 9S1-i

<400> SEQUENCE: 132
atgaaaaaat acctattccg ggcggctttg tacgggatcg ccgccgccat cctcgccgcc    60

<210> SEQ ID NO 133
<211> LENGTH: 14
<212> TYPE: PRT
<213> ORGANISM: Artificial Sequence
<220> FEATURE:
<223> OTHER INFORMATION: 9S1e

<400> SEQUENCE: 133

Met Lys Lys Tyr Leu Phe Ile Ala Ala Ala Ile Leu Ala Ala
1               5                   10

<210> SEQ ID NO 134
<211> LENGTH: 20
<212> TYPE: PRT
<213> ORGANISM: Artificial Sequence
<220> FEATURE:
<223> OTHER INFORMATION: 9S1c

<400> SEQUENCE: 134

Met Lys Lys Tyr Leu Phe Arg Ala Ala Gln Tyr Gly Ile Ala Ala Ala
1               5                   10                  15

Ile Leu Ala Ala
        20

<210> SEQ ID NO 135
<211> LENGTH: 20
<212> TYPE: PRT
<213> ORGANISM: Artificial Sequence
<220> FEATURE:
<223> OTHER INFORMATION: 9S1b

<400> SEQUENCE: 135

Met Lys Lys Tyr Leu Phe Arg Ala Ala Gln Tyr Gly Ile Ala Ala Ala
1               5                   10                  15

Ile Leu Ala Ala
            20

<210> SEQ ID NO 136
<211> LENGTH: 20
<212> TYPE: PRT
<213> ORGANISM: Artificial Sequence
<220> FEATURE:
<223> OTHER INFORMATION: 9S1i

<400> SEQUENCE: 136

Met Lys Lys Tyr Leu Phe Arg Ala Ala Leu Tyr Gly Ile Ala Ala Ala
1               5                   10                  15

Ile Leu Ala Ala
            20

<210> SEQ ID NO 137
<211> LENGTH: 467
<212> TYPE: PRT
<213> ORGANISM: Artificial Sequence
<220> FEATURE:
<223> OTHER INFORMATION: 730

<400> SEQUENCE: 137

Val Lys Pro Leu Arg Arg Leu Thr Asn Leu Ala Ala Cys Ala Val
1               5                   10                  15

Ala Ala Ala Ala Leu Ile Gln Pro Ala Leu Ala Asp Leu Ala Gln
                20                  25                  30

Asp Pro Phe Ile Thr Asp Asn Ala Gln Arg Gln His Tyr Glu Pro Gly
            35                  40                  45

Gly Lys Tyr His Leu Phe Gly Asp Pro Arg Gly Ser Val Ser Asp Arg
    50                  55                  60

Thr Gly Lys Ile Asn Val Ile Gln Asp Tyr Thr His Gln Met Gly Asn
65                  70                  75                  80

Leu Leu Ile Gln Gln Ala Asn Ile Asn Gly Thr Ile Gly Tyr His Thr
                85                  90                  95

Arg Phe Ser Gly His Gly His Glu Glu His Ala Pro Phe Asp Asn His
            100                 105                 110

Ala Ala Asp Ser Ala Ser Glu Glu Lys Gly Asn Val Asp Glu Gly Phe
        115                 120                 125

Thr Val Tyr Arg Leu Asn Trp Glu Gly His Glu His Pro Ala Asp
    130                 135                 140

Ala Tyr Asp Gly Pro Lys Gly Asn Tyr Pro Lys Pro Thr Gly Ala
145                 150                 155                 160

Arg Asp Glu Tyr Thr Tyr His Val Asn Gly Thr Ala Arg Ser Ile Lys
                165                 170                 175

Leu Asn Pro Thr Asp Thr Arg Ser Ile Arg Gln Arg Ile Ser Asp Asn
            180                 185                 190

Tyr Ser Asn Leu Gly Ser Asn Phe Ser Asp Arg Ala Asp Glu Ala Asn
        195                 200                 205

Arg Lys Met Phe Glu His Asn Ala Lys Leu Asp Arg Trp Gly Asn Ser
    210                 215                 220

Met Glu Phe Ile Asn Gly Val Ala Ala Gly Ala Leu Asn Pro Phe Ile
225                 230                 235                 240

Ser Ala Gly Glu Ala Leu Gly Ile Gly Asp Ile Leu Tyr Gly Thr Arg
            245                 250                 255

Tyr Ala Ile Asp Lys Ala Ala Met Arg Asn Ile Ala Pro Leu Pro Ala
        260                 265                 270

Glu Gly Lys Phe Ala Val Ile Gly Gly Leu Gly Ser Val Ala Gly Phe
    275                 280                 285

Glu Lys Asn Thr Arg Glu Ala Val Asp Arg Trp Ile Gln Glu Asn Pro
290                 295                 300

Asn Ala Ala Glu Thr Val Glu Ala Val Phe Asn Val Ala Ala Ala Ala
305                 310                 315                 320

Lys Val Ala Lys Leu Ala Lys Ala Ala Lys Pro Gly Lys Ala Ala Val
            325                 330                 335

Ser Gly Asp Phe Ala Asp Ser Tyr Lys Lys Leu Ala Leu Ser Asp
        340                 345                 350

Ser Ala Arg Gln Leu Tyr Gln Asn Ala Lys Tyr Arg Glu Ala Leu Asp
    355                 360                 365

Ile His Tyr Glu Asp Leu Ile Arg Arg Lys Thr Asp Gly Ser Ser Lys
370                 375                 380

Phe Ile Asn Gly Arg Glu Ile Asp Ala Val Thr Asn Asp Ala Leu Ile
385                 390                 395                 400

Gln Ala Lys Arg Thr Ile Ser Ala Ile Asp Lys Pro Lys Asn Phe Leu
            405                 410                 415

Asn Gln Lys Asn Arg Lys Gln Ile Lys Ala Thr Ile Glu Ala Ala Asn
        420                 425                 430

Gln Gln Gly Lys Arg Ala Glu Phe Trp Phe Lys Tyr Gly Val His Ser
    435                 440                 445

Gln Val Lys Ser Tyr Ile Glu Ser Lys Gly Gly Ile Val Lys Thr Gly
450                 455                 460

Leu Gly Asp
465

<210> SEQ ID NO 138
<211> LENGTH: 377
<212> TYPE: PRT
<213> ORGANISM: Artificial Sequence
<220> FEATURE:
<223> OTHER INFORMATION: 730-C1

<400> SEQUENCE: 138

Met Ala Asp Leu Ala Gln Asp Pro Phe Ile Thr Asp Asn Ala Gln Arg
1               5                   10                  15

Gln His Tyr Glu Pro Gly Gly Lys Tyr His Leu Phe Gly Asp Pro Arg
            20                  25                  30

Gly Ser Val Ser Asp Arg Thr Gly Lys Ile Asn Val Ile Gln Asp Tyr
        35                  40                  45

Thr His Gln Met Gly Asn Leu Leu Ile Gln Gln Ala Asn Ile Asn Gly
    50                  55                  60

Thr Ile Gly Tyr His Thr Arg Phe Ser Gly His Gly His Glu Glu His
65                  70                  75                  80

Ala Pro Phe Asp Asn His Ala Ala Asp Ser Ala Ser Glu Glu Lys Gly
                85                  90                  95

```
Asn Val Asp Glu Gly Phe Thr Val Tyr Arg Leu Asn Trp Glu Gly His
                100                 105                 110

Glu His His Pro Ala Asp Ala Tyr Asp Gly Pro Lys Gly Gly Asn Tyr
            115                 120                 125

Pro Lys Pro Thr Gly Ala Arg Asp Glu Tyr Thr Tyr His Val Asn Gly
130                 135                 140

Thr Ala Arg Ser Ile Lys Leu Asn Pro Thr Asp Thr Arg Ser Ile Arg
145                 150                 155                 160

Gln Arg Ile Ser Asp Asn Tyr Ser Asn Leu Gly Ser Asn Phe Ser Asp
                165                 170                 175

Arg Ala Asp Glu Ala Asn Arg Lys Met Phe Glu His Asn Ala Lys Leu
            180                 185                 190

Asp Arg Trp Gly Asn Ser Met Glu Phe Ile Asn Gly Val Ala Ala Gly
        195                 200                 205

Ala Leu Asn Pro Phe Ile Ser Ala Gly Glu Ala Leu Gly Ile Gly Asp
    210                 215                 220

Ile Leu Tyr Gly Thr Arg Tyr Ala Ile Asp Lys Ala Ala Met Arg Asn
225                 230                 235                 240

Ile Ala Pro Leu Pro Ala Glu Gly Lys Phe Ala Val Ile Gly Gly Leu
                245                 250                 255

Gly Ser Val Ala Gly Phe Glu Lys Asn Thr Arg Glu Ala Val Asp Arg
            260                 265                 270

Trp Ile Gln Glu Asn Pro Asn Ala Ala Glu Thr Val Glu Ala Val Phe
        275                 280                 285

Asn Val Ala Ala Ala Lys Val Ala Lys Leu Ala Lys Ala Ala Lys
    290                 295                 300

Pro Gly Lys Ala Ala Val Ser Gly Asp Phe Ala Asp Ser Tyr Lys Lys
305                 310                 315                 320

Lys Leu Ala Leu Ser Asp Ser Ala Arg Gln Leu Tyr Gln Asn Ala Lys
                325                 330                 335

Tyr Arg Glu Ala Leu Asp Ile His Tyr Glu Asp Leu Ile Arg Arg Lys
            340                 345                 350

Thr Asp Gly Ser Ser Lys Phe Ile Asn Gly Arg Glu Ile Asp Ala Val
        355                 360                 365

Thr Asn Asp Ala Leu Ile Gln Ala Arg
    370                 375

<210> SEQ ID NO 139
<211> LENGTH: 353
<212> TYPE: PRT
<213> ORGANISM: Artificial Sequence
<220> FEATURE:
<223> OTHER INFORMATION: 730-C2

<400> SEQUENCE: 139

Met Ala Asp Leu Ala Gln Asp Pro Phe Ile Thr Asp Asn Ala Gln Arg
1               5                   10                  15

Gln His Tyr Glu Pro Gly Gly Lys Tyr His Leu Phe Gly Asp Pro Arg
                20                  25                  30

Gly Ser Val Ser Asp Arg Thr Gly Lys Ile Asn Val Ile Gln Asp Tyr
            35                  40                  45

Thr His Gln Met Gly Asn Leu Leu Ile Gln Gln Ala Asn Ile Asn Gly
        50                  55                  60

Thr Ile Gly Tyr His Thr Arg Phe Ser Gly His Gly His Glu His
65                  70                  75                  80

Ala Pro Phe Asp Asn His Ala Ala Asp Ser Ala Ser Glu Glu Lys Gly
```

|            |            |            |            |            |            |
|------------|------------|------------|------------|------------|------------|
|            | 85         |            | 90         |            | 95         |

Asn Val Asp Glu Gly Phe Thr Val Tyr Arg Leu Asn Trp Glu Gly His
            100                  105                 110

Glu His His Pro Ala Asp Ala Tyr Asp Gly Pro Lys Gly Gly Asn Tyr
     115                120                125

Pro Lys Pro Thr Gly Ala Arg Asp Glu Tyr Thr Tyr His Val Asn Gly
130               135                140

Thr Ala Arg Ser Ile Lys Leu Asn Pro Thr Asp Thr Arg Ser Ile Arg
145               150               155               160

Gln Arg Ile Ser Asp Asn Tyr Ser Asn Leu Gly Ser Asn Phe Ser Asp
     165                170                175

Arg Ala Asp Glu Ala Asn Arg Lys Met Phe Glu His Asn Ala Lys Leu
            180                185               190

Asp Arg Trp Gly Asn Ser Met Glu Phe Ile Asn Gly Val Ala Ala Gly
     195                200                205

Ala Leu Asn Pro Phe Ile Ser Ala Gly Glu Ala Leu Gly Ile Gly Asp
         210                215               220

Ile Leu Tyr Gly Thr Arg Tyr Ala Ile Asp Lys Ala Ala Met Arg Asn
225               230               235              240

Ile Ala Pro Leu Pro Ala Glu Gly Lys Phe Ala Val Ile Gly Gly Leu
         245                250               255

Gly Ser Val Ala Gly Phe Glu Lys Asn Thr Arg Glu Ala Val Asp Arg
        260                265                270

Trp Ile Gln Glu Asn Pro Asn Ala Ala Glu Thr Val Glu Ala Val Phe
     275                280                285

Asn Val Ala Ala Ala Lys Val Ala Lys Leu Ala Lys Ala Lys
         290                295               300

Pro Gly Lys Ala Ala Val Ser Gly Asp Phe Ala Asp Ser Tyr Lys Lys
305               310               315              320

Lys Leu Ala Leu Ser Asp Ser Ala Arg Gln Leu Tyr Gln Asn Ala Lys
            325                330               335

Tyr Arg Glu Ala Leu Gly Lys Val Arg Ile Ser Gly Glu Ile Leu Leu
         340                345                350

Gly

<210> SEQ ID NO 140
<211> LENGTH: 2019
<212> TYPE: DNA
<213> ORGANISM: Artificial Sequence
<220> FEATURE:
<223> OTHER INFORMATION: ORF46.1-741

<400> SEQUENCE: 140

```
atgtcagatt tggcaaacga ttcttttatc cggcaggttc tcgaccgtca gcatttcgaa      60
cccgacggga ataccacct  attcggcagc agggggaac  ttgccgagcg cagcggccat    120
atcggattgg gaaaaataca agccatcag  ttggcaacc  tgatgattca acaggcggcc    180
attaaaggaa atatcggcta cattgtccgc ttttccgatc acgggcacga agtccattcc    240
cccttcgaca ccatgccctc acattccgat tctgatgaag ccggtagtcc cgttgacgga    300
tttagccttt accgcatcca ttgggacgga tacgaacacc atcccgccga cggctatgac    360
gggccacagg gcggcggcta tcccgctccc aaaggcgcga gggatatata cagctacgac    420
ataaaaggcg ttgcccaaaa tatccgcctc aacctgaccg acaaccgcag caccggacaa    480
cggcttgccg accgtttcca caatgccggt agtatgctga cgcaaggagt aggcgacgga    540
```

-continued

```
ttcaaacgcg ccacccgata cagccccgag ctggacagat cgggcaatgc cgccgaagcc      600
ttcaacggca ctgcagatat cgttaaaaac atcatcggcg cggcaggaga aattgtcggc      660
gcaggcgatg ccgtgcaggg cataagcgaa ggctcaaaca ttgctgtcat gcacggcttg      720
ggtctgcttt ccaccgaaaa caagatggcg cgcatcaacg atttggcaga tatggcgcaa      780
ctcaaagact atgccgcagc agccatccgc gattgggcag tccaaaaccc caatgccgca      840
caaggcatag aagccgtcag caatatcttt atggcagcca tccccatcaa agggattgga      900
gctgttcggg gaaaatacgg cttgggcggc atcacggcac atcctatcaa gcggtcgcag      960
atgggcgcga tcgcattgcc gaaagggaaa tccgccgtca gcgacaattt tgccgatgcg     1020
gcatacgcca ataccccgtc cccttaccat tcccgaaata tccgttcaaa cttggagcag     1080
cgttacggca agaaaaacat cacctcctca accgtgccgc cgtcaaacgg caaaaatgtc     1140
aaactggcag accaacgcca cccgaagaca ggcgtaccgt ttgacggtaa agggtttccg     1200
aattttgaga agcacgtgaa atatgatacg ggatccggag gggtggtgt cgccgccgac     1260
atcggtgcgg ggcttgccga tgcactaacc gcaccgctcg accataaaga caaaggtttg     1320
cagtctttga cgctggatca gtccgtcagg aaaaacgaga aactgaagct ggcggcacaa     1380
ggtgcggaaa aaacttatgg aaacggtgac agcctcaata cgggcaaatt gaagaacgac     1440
aaggtcagcc gtttcgactt tatccgccaa atcgaagtgg acgggcagct cattaccttg     1500
gagagtggag agttccaagt atacaaacaa agccattccg ccttaaccgc ctttcagacc     1560
gagcaaatac aagattcgga gcattccggg aagatggttg cgaaacgcca gttcagaatc     1620
ggcgacatag cgggcgaaca tacatctttt gacaagcttc ccgaaggcgg cagggcgaca     1680
tatcgcggga cggcgttcgg ttcagacgat gccggcggaa aactgaccta caccatagat     1740
ttcgccgcca gcagggaaa cggcaaaatc gaacatttga atcgccaga actcaatgtc      1800
gacctggccg ccgccgatat caagccggat ggaaaacgcc atgccgtcat cagcggttcc     1860
gtcctttaca ccaagccga gaaaggcagt tactccctcg gtatctttgg cggaaaagcc      1920
caggaagttg ccggcagcgc ggaagtgaaa accgtaaacg gcatacgcca tatcggcctt     1980
gccgccaagc aactcgagca ccaccaccac caccactga                             2019
```

<210> SEQ ID NO 141
<211> LENGTH: 672
<212> TYPE: PRT
<213> ORGANISM: Artificial Sequence
<220> FEATURE:
<223> OTHER INFORMATION: ORF46.1-741

<400> SEQUENCE: 141

```
Met Ser Asp Leu Ala Asn Asp Ser Phe Ile Arg Gln Val Leu Asp Arg
1               5                   10                  15

Gln His Phe Glu Pro Asp Gly Lys Tyr His Leu Phe Gly Ser Arg Gly
            20                  25                  30

Glu Leu Ala Glu Arg Ser Gly His Ile Gly Leu Gly Lys Ile Gln Ser
        35                  40                  45

His Gln Leu Gly Asn Leu Met Ile Gln Gln Ala Ala Ile Lys Gly Asn
    50                  55                  60

Ile Gly Tyr Ile Val Arg Phe Ser Asp His Gly His Glu Val His Ser
65                  70                  75                  80

Pro Phe Asp Asn His Ala Ser His Ser Asp Ser Asp Glu Ala Gly Ser
                85                  90                  95

Pro Val Asp Gly Phe Ser Leu Tyr Arg Ile His Trp Asp Gly Tyr Glu
            100                 105                 110
```

```
His His Pro Ala Asp Gly Tyr Asp Gly Pro Gln Gly Gly Tyr Pro
        115                 120                 125
Ala Pro Lys Gly Ala Arg Asp Ile Tyr Ser Tyr Asp Ile Lys Gly Val
130                 135                 140
Ala Gln Asn Ile Arg Leu Asn Leu Thr Asp Asn Arg Ser Thr Gly Gln
145                 150                 155                 160
Arg Leu Ala Asp Arg Phe His Asn Ala Gly Ser Met Leu Thr Gln Gly
                165                 170                 175
Val Gly Asp Gly Phe Lys Arg Ala Thr Arg Tyr Ser Pro Glu Leu Asp
            180                 185                 190
Arg Ser Gly Asn Ala Ala Glu Ala Phe Asn Gly Thr Ala Asp Ile Val
        195                 200                 205
Lys Asn Ile Ile Gly Ala Ala Gly Glu Ile Val Gly Ala Gly Asp Ala
    210                 215                 220
Val Gln Gly Ile Ser Glu Gly Ser Asn Ile Ala Val Met His Gly Leu
225                 230                 235                 240
Gly Leu Leu Ser Thr Glu Asn Lys Met Ala Arg Ile Asn Asp Leu Ala
                245                 250                 255
Asp Met Ala Gln Leu Lys Asp Tyr Ala Ala Ala Ile Arg Asp Trp
            260                 265                 270
Ala Val Gln Asn Pro Asn Ala Ala Gln Gly Ile Glu Ala Val Ser Asn
        275                 280                 285
Ile Phe Met Ala Ala Ile Pro Ile Lys Gly Ile Gly Ala Val Arg Gly
    290                 295                 300
Lys Tyr Gly Leu Gly Gly Ile Thr Ala His Pro Ile Lys Arg Ser Gln
305                 310                 315                 320
Met Gly Ala Ile Ala Leu Pro Lys Gly Lys Ser Ala Val Ser Asp Asn
                325                 330                 335
Phe Ala Asp Ala Ala Tyr Ala Lys Tyr Pro Ser Pro Tyr His Ser Arg
            340                 345                 350
Asn Ile Arg Ser Asn Leu Glu Gln Arg Tyr Gly Lys Glu Asn Ile Thr
        355                 360                 365
Ser Ser Thr Val Pro Pro Ser Asn Gly Lys Asn Val Lys Leu Ala Asp
    370                 375                 380
Gln Arg His Pro Lys Thr Gly Val Pro Phe Asp Gly Lys Gly Phe Pro
385                 390                 395                 400
Asn Phe Glu Lys His Val Lys Tyr Asp Thr Gly Ser Gly Gly Gly
                405                 410                 415
Val Ala Ala Asp Ile Gly Ala Gly Leu Ala Asp Ala Leu Thr Ala Pro
            420                 425                 430
Leu Asp His Lys Asp Lys Gly Leu Gln Ser Leu Thr Leu Asp Gln Ser
        435                 440                 445
Val Arg Lys Asn Glu Lys Leu Lys Leu Ala Ala Gln Gly Ala Glu Lys
    450                 455                 460
Thr Tyr Gly Asn Gly Asp Ser Leu Asn Thr Gly Lys Leu Lys Asn Asp
465                 470                 475                 480
Lys Val Ser Arg Phe Asp Phe Ile Arg Gln Ile Glu Val Asp Gly Gln
                485                 490                 495
Leu Ile Thr Leu Glu Ser Gly Glu Phe Gln Val Tyr Lys Gln Ser His
            500                 505                 510
Ser Ala Leu Thr Ala Phe Gln Thr Glu Gln Ile Gln Asp Ser Glu His
        515                 520                 525
Ser Gly Lys Met Val Ala Lys Arg Gln Phe Arg Ile Gly Asp Ile Ala
```

```
            530                 535                 540
Gly Glu His Thr Ser Phe Asp Lys Leu Pro Glu Gly Gly Arg Ala Thr
545                 550                 555                 560

Tyr Arg Gly Thr Ala Phe Gly Ser Asp Asp Ala Gly Gly Lys Leu Thr
                565                 570                 575

Tyr Thr Ile Asp Phe Ala Ala Lys Gln Gly Asn Gly Lys Ile Glu His
                580                 585                 590

Leu Lys Ser Pro Glu Leu Asn Val Asp Leu Ala Ala Asp Ile Lys
                595                 600                 605

Pro Asp Gly Lys Arg His Ala Val Ile Ser Gly Ser Val Leu Tyr Asn
                610                 615                 620

Gln Ala Glu Lys Gly Ser Tyr Ser Leu Gly Ile Phe Gly Gly Lys Ala
625                 630                 635                 640

Gln Glu Val Ala Gly Ser Ala Glu Val Lys Thr Val Asn Gly Ile Arg
                645                 650                 655

His Ile Gly Leu Ala Ala Lys Gln Leu Glu His His His His His
                660                 665                 670

<210> SEQ ID NO 142
<211> LENGTH: 2421
<212> TYPE: DNA
<213> ORGANISM: Artificial Sequence
<220> FEATURE:
<223> OTHER INFORMATION: ORF46.1-961

<400> SEQUENCE: 142
atgtcagatt tggcaaacga ttcttttatc cggcaggttc tcgaccgtca gcatttcgaa      60
cccgacggga ataccacct attcggcagc agggggaaac ttgccgagcg cagcggccat     120
atcggattgg gaaaaataca agccatcag ttggcaacc tgatgattca acaggcggcc     180
attaaaggaa atatcggcta cattgtccgc ttttccgatc acgggcacga agtccattcc     240
cccttcgaca accatgcctc acattccgat tctgatgaag ccggtagtcc cgttgacgga     300
tttagccttt accgcatcca ttgggacgga tacgaacacc atcccgccga cggctatgac     360
gggccacagg gcggcggcta tcccgctccc aaaggcgcga gggatatata cagctacgac     420
ataaaaggcg ttgcccaaaa tatccgcctc aacctgaccg acaaccgcag caccggacaa     480
cggcttgccg accgttttca caatgccggt agtatgctga cgcaaggagt aggcgacgga     540
ttcaaacgcg ccacccgata cagccccgag ctggacagat cgggcaatgc cgccgaagcc     600
ttcaacgcca ctgcagatat cgttaaaaac atcatcggcg cggcaggaga aattgtcggc     660
gcaggcgatg ccgtgcaggg cataagcgaa ggctcaaaca ttgctgtcat gcacggcttg     720
ggtctgcttt ccaccgaaaa caagatggcg cgcatcaacg attggcagatat gcgcaa     780 ctcaaagact atgccgcagc agccatccgc gattgggcag tccaaaaccc caatgccgca     840
caaggcatag aagccgtcag caatatcttt atggcagcca tccccatcaa agggattgga     900
gctgttcggg gaaaatacgg cttgggcggc atcacggcac atcctatcaa gcggtcgcag     960
atgggcgcga tcgcattgcc gaaagggaaa tccgccgtca gcgacaattt tgccgatgcg    1020
gcatacgcca atacccgtc cccttaccat tcccgaaata tccgttcaaa cttggagcag    1080
cgttacggca agaaaacat cacctcctca accgtgccgc cgtcaaacgg caaaaatgtc    1140
aaactggcag accaacgcca cccgaagaca ggcgtaccgt ttgacggtaa agggtttccg    1200
aattttgaga agcacgtgaa atatgatacg ggatccggag gaggagggagc cacaaacgac    1260 gacgatgtta aaaagctgc cactgtggcc attgctgctg cctacaacaa tggccaagaa    1320
```

-continued

```
atcaacggtt tcaaagctgg agagaccatc tacgacattg atgaagacgg cacaattacc      1380
aaaaaagacg caactgcagc cgatgttgaa gccgacgact ttaaaggtct gggtctgaaa      1440
aaagtcgtga ctaacctgac caaaaccgtc aatgaaaaca acaaaacgt cgatgccaaa      1500 gtaaaagctg cagaatctga aatagaaaag ttaacaacca agttagcaga cactgatgcc      1560
gctttagcag atactgatgc cgctctggat gcaaccacca acgccttgaa taaattggga      1620
gaaaatataa cgacatttgc tgaagagact aagacaaata tcgtaaaaat tgatgaaaaa      1680
ttagaagccg tggctgatac cgtcgacaag catgccgaag cattcaacga tatcgccgat      1740
tcattggatg aaaccaacac taaggcagac gaagccgtca aaccgccaa tgaagccaaa       1800 cagacggccg aagaaaccaa acaaaacgtc gatgccaaag taaaagctgc agaaactgca      1860
gcaggcaaag ccgaagctgc cgctggcaca gctaatactg cagccgacaa ggccgaagct      1920
gtcgctgcaa aagttaccga catcaaagct gatatcgcta cgaacaaaga taatattgct      1980
aaaaaagcaa acagtgccga cgtgtacacc agagaagagt ctgacagcaa atttgtcaga      2040
attgatggtc tgaacgctac taccgaaaaa ttggacacac gcttggcttc tgctgaaaaa      2100
tccattgccg atcacgatac tcgcctgaac ggtttggata aacagtgtc agacctgcgc       2160 aaagaaaccc gccaaggcct tgcagaacaa gccgcgctct ccggtctgtt ccaaccttac      2220
aacgtgggtc ggttcaatgt aacggctgca gtcggcggct acaaatccga atcggcagtc      2280
gccatcggta ccggcttccg ctttaccgaa actttgccg ccaaagcagg cgtggcagtc       2340
ggcacttcgt ccggttcttc cgcagcctac catgtcggcg tcaattacga gtggctcgag      2400
caccaccacc accaccactg a                                               2421
```

<210> SEQ ID NO 143
<211> LENGTH: 806
<212> TYPE: PRT
<213> ORGANISM: Artificial Sequence
<220> FEATURE:
<223> OTHER INFORMATION: ORF46.1-961

<400> SEQUENCE: 143

```
Met Ser Asp Leu Ala Asn Asp Ser Phe Ile Arg Gln Val Leu Asp Arg
1               5                   10                  15

Gln His Phe Glu Pro Asp Gly Lys Tyr His Leu Phe Gly Ser Arg Gly
            20                  25                  30

Glu Leu Ala Glu Arg Ser Gly His Ile Gly Leu Gly Lys Ile Gln Ser
        35                  40                  45

His Gln Leu Gly Asn Leu Met Ile Gln Gln Ala Ile Lys Gly Asn
    50                  55                  60

Ile Gly Tyr Ile Val Arg Phe Ser Asp His Gly His Glu Val His Ser
65                  70                  75                  80

Pro Phe Asp Asn His Ala Ser His Ser Asp Ser Asp Glu Ala Gly Ser
                85                  90                  95

Pro Val Asp Gly Phe Ser Leu Tyr Arg Ile His Trp Asp Gly Tyr Glu
            100                 105                 110

His His Pro Ala Asp Gly Tyr Asp Gly Pro Gln Gly Gly Tyr Pro
        115                 120                 125

Ala Pro Lys Gly Ala Arg Asp Ile Tyr Ser Tyr Asp Ile Lys Gly Val
    130                 135                 140

Ala Gln Asn Ile Arg Leu Asn Leu Thr Asp Asn Arg Ser Thr Gly Gln
145                 150                 155                 160

Arg Leu Ala Asp Arg Phe His Asn Ala Gly Ser Met Leu Thr Gln Gly
                165                 170                 175
```

-continued

Val Gly Asp Gly Phe Lys Arg Ala Thr Arg Tyr Ser Pro Glu Leu Asp
            180                 185                 190

Arg Ser Gly Asn Ala Ala Glu Ala Phe Asn Gly Thr Ala Asp Ile Val
        195                 200                 205

Lys Asn Ile Ile Gly Ala Ala Gly Glu Ile Val Gly Ala Gly Asp Ala
210                 215                 220

Val Gln Gly Ile Ser Glu Gly Ser Asn Ile Ala Val Met His Gly Leu
225                 230                 235                 240

Gly Leu Leu Ser Thr Glu Asn Lys Met Ala Arg Ile Asn Asp Leu Ala
                245                 250                 255

Asp Met Ala Gln Leu Lys Asp Tyr Ala Ala Ala Ile Arg Asp Trp
            260                 265                 270

Ala Val Gln Asn Pro Asn Ala Ala Gln Gly Ile Glu Ala Val Ser Asn
            275                 280                 285

Ile Phe Met Ala Ala Ile Pro Ile Lys Gly Ile Gly Ala Val Arg Gly
        290                 295                 300

Lys Tyr Gly Leu Gly Gly Ile Thr Ala His Pro Ile Lys Arg Ser Gln
305                 310                 315                 320

Met Gly Ala Ile Ala Leu Pro Lys Gly Lys Ser Ala Val Ser Asp Asn
                325                 330                 335

Phe Ala Asp Ala Ala Tyr Ala Lys Tyr Pro Ser Pro Tyr His Ser Arg
            340                 345                 350

Asn Ile Arg Ser Asn Leu Glu Gln Arg Tyr Gly Lys Glu Asn Ile Thr
        355                 360                 365

Ser Ser Thr Val Pro Pro Ser Asn Gly Lys Asn Val Lys Leu Ala Asp
370                 375                 380

Gln Arg His Pro Lys Thr Gly Val Pro Phe Asp Gly Lys Gly Phe Pro
385                 390                 395                 400

Asn Phe Glu Lys His Val Lys Tyr Asp Thr Gly Ser Gly Gly Gly
                405                 410                 415

Ala Thr Asn Asp Asp Asp Val Lys Lys Ala Ala Thr Val Ala Ile Ala
            420                 425                 430

Ala Ala Tyr Asn Asn Gly Gln Glu Ile Asn Gly Phe Lys Ala Gly Glu
        435                 440                 445

Thr Ile Tyr Asp Ile Asp Glu Asp Gly Thr Ile Thr Lys Lys Asp Ala
450                 455                 460

Thr Ala Ala Asp Val Glu Ala Asp Asp Phe Lys Gly Leu Gly Leu Lys
465                 470                 475                 480

Lys Val Val Thr Asn Leu Thr Lys Thr Val Asn Glu Asn Lys Gln Asn
                485                 490                 495

Val Asp Ala Lys Val Lys Ala Ala Glu Ser Ile Glu Lys Leu Thr
            500                 505                 510

Thr Lys Leu Ala Asp Thr Asp Ala Ala Leu Ala Asp Thr Asp Ala Ala
        515                 520                 525

Leu Asp Ala Thr Thr Asn Ala Leu Asn Lys Leu Gly Glu Asn Ile Thr
530                 535                 540

Thr Phe Ala Glu Glu Thr Lys Thr Asn Ile Val Lys Ile Asp Glu Lys
545                 550                 555                 560

Leu Glu Ala Val Ala Asp Thr Val Asp Lys His Ala Glu Ala Phe Asn
                565                 570                 575

Asp Ile Ala Asp Ser Leu Asp Glu Thr Asn Thr Lys Ala Asp Glu Ala
            580                 585                 590

Val Lys Thr Ala Asn Glu Ala Lys Gln Thr Ala Glu Glu Thr Lys Gln

```
                    595              600                 605
Asn Val Asp Ala Lys Val Lys Ala Ala Glu Thr Ala Ala Gly Lys Ala
            610             615                 620
Glu Ala Ala Ala Gly Thr Ala Asn Thr Ala Ala Asp Lys Ala Glu Ala
625                 630             635                 640
Val Ala Ala Lys Val Thr Asp Ile Lys Ala Asp Ile Ala Thr Asn Lys
                645             650                 655
Asp Asn Ile Ala Lys Lys Ala Asn Ser Ala Asp Val Tyr Thr Arg Glu
            660             665                 670
Glu Ser Asp Ser Lys Phe Val Arg Ile Asp Gly Leu Asn Ala Thr Thr
        675                 680             685
Glu Lys Leu Asp Thr Arg Leu Ala Ser Ala Glu Lys Ser Ile Ala Asp
        690                 695             700
His Asp Thr Arg Leu Asn Gly Leu Asp Lys Thr Val Ser Asp Leu Arg
705             710                 715                 720
Lys Glu Thr Arg Gln Gly Leu Ala Glu Gln Ala Ala Leu Ser Gly Leu
                725                 730             735
Phe Gln Pro Tyr Asn Val Gly Arg Phe Asn Val Thr Ala Ala Val Gly
            740                 745             750
Gly Tyr Lys Ser Glu Ser Ala Val Ala Ile Gly Thr Gly Phe Arg Phe
        755             760                 765
Thr Glu Asn Phe Ala Ala Lys Ala Gly Val Ala Val Gly Thr Ser Ser
770             775                 780
Gly Ser Ser Ala Ala Tyr His Val Gly Val Asn Tyr Glu Trp Leu Glu
785             790                 795                 800
His His His His His His
            805
```

```
<210> SEQ ID NO 144
<211> LENGTH: 2256
<212> TYPE: DNA
<213> ORGANISM: Artificial Sequence
<220> FEATURE:
<223> OTHER INFORMATION: ORF46.1-961c

<400> SEQUENCE: 144
atgtcagatt tggcaaacga ttctttatc cggcaggttc tcgaccgtca gcatttcgaa      60
cccgacggga ataccacct attcggcagc agggggggaac ttgccgagcg cagcggccat    120
atcggattgg gaaaaataca agccatcag ttgggcaacc tgatgattca acaggcggcc    180 attaaggaa atatcggcta cattgtccgc ttttccgatc acgggcacga agtccattcc    240
cccttcgaca accatgcctc acattccgat tctgatgaag ccggtagtcc cgttgacgga    300
tttagccttt accgcatcca tgggacgga tacgaacacc atcccgccga cggctatgac    360
gggccacagg gcggcggcta tcccgctccc aaaggcgcga gggatatata cagctacgac    420
ataaaaggcg ttgcccaaaa tatccgcctc aacctgaccg acaaccgcag caccggacaa    480
cggcttgccg accgtttcca caatgccggt agtatgctga cgcaaggagt aggcgacgga    540
ttcaaacgcg ccaccgata cagccccgag ctggacagat cgggcaatgc cgccgaagcc    600
ttcaacggca ctgcagatat cgttaaaaac atcatcggcg cggcaggaga aattgtcggc    660
gcaggcgatg ccgtgcaggg cataagcgaa ggctcaaaca ttgctgtcat gcacggcttg    720
ggtctgcttt ccaccgaaaa caagatggcg cgcatcaacg atttggcaga tatggcgcaa    780
ctcaaagact atgccgcagc agccatccgc gattgggcag tccaaaaccc caatgccgca    840
caaggcatag aagccgtcag caatatcttt atggcagcca tccccatcaa agggattgga    900
```

```
gctgttcggg gaaaatacgg cttgggcggc atcacggcac atcctatcaa gcggtcgcag    960
atgggcgcga tcgcattgcc gaaagggaaa tccgccgtca gcgacaattt tgccgatgcg   1020
gcatacgcca ataccccgtc ccttaccat tcccgaaata tccgttcaaa cttggagcag   1080
cgttacggca agaaaacat cacctcctca accgtgccgc cgtcaaacgg caaaaatgtc   1140
aaactggcag accaacgcca cccgaagaca ggcgtaccgt ttgacggtaa agggtttccg   1200
aattttgaga agcacgtgaa atatgatacg ggatccggag gaggaggagc cacaaacgac   1260
gacgatgtta aaaaagctgc cactgtggcc attgctgctg cctacaacaa tggccaagaa   1320
atcaacggtt tcaaagctgg agagaccatc tacgacattg atgaagacgg cacaattacc   1380
aaaaaagacg caactgcagc cgatgttgaa gccgacgact ttaaaggtct gggtctgaaa   1440
aaagtcgtga ctaacctgac caaaaccgtc aatgaaaaca acaaaacgt cgatgccaaa   1500
gtaaaagctg cagaatctga aatagaaaag ttaacaacca agttagcaga cactgatgcc   1560
gctttagcag atactgatgc cgctctggat gcaaccacca acgccttgaa taaattggga   1620
gaaaatataa cgacatttgc tgaagagact aagacaaata tcgtaaaaat tgatgaaaaa   1680
ttagaagccg tggctgatac cgtcgacaag catgccgaag cattcaacga tatcgccgat   1740
tcattggatg aaaccaacac taaggcagac gaagccgtca aaaccgccaa tgaagccaaa   1800
cagacggccg aagaaaccaa acaaaacgtc gatgccaaag taaaagctgc agaaactgca   1860
gcaggcaaag ccgaagctgc cgctggcaca gctaatactg cagccgacaa ggccgaagct   1920
gtcgctgcaa aagttaccga catcaaagct gatatcgcta cgaacaaaga taatattgct   1980
aaaaaagcaa acagtgccga cgtgtacacc agagaagagt ctgacagcaa atttgtcaga   2040
attgatggtc tgaacgctac taccgaaaaa ttggacacac gcttggcttc tgctgaaaaa   2100
tccattgccg atcacgatac tcgcctgaac ggtttggata aacagtgtc agacctgcgc   2160
aaagaaaccc gccaaggcct tgcagaacaa gccgcgctct ccggtctgtt ccaaccttac   2220
aacgtgggtc tcgagcacca ccaccaccac cactga                            2256
```

<210> SEQ ID NO 145
<211> LENGTH: 751
<212> TYPE: PRT
<213> ORGANISM: Artificial Sequence
<220> FEATURE:
<223> OTHER INFORMATION: ORF46.1-961c

<400> SEQUENCE: 145

```
Met Ser Asp Leu Ala Asn Asp Ser Phe Ile Arg Gln Val Leu Asp Arg
1               5                   10                  15

Gln His Phe Glu Pro Asp Gly Lys Tyr His Leu Phe Gly Ser Arg Gly
            20                  25                  30

Glu Leu Ala Glu Arg Ser Gly His Ile Gly Leu Gly Lys Ile Gln Ser
        35                  40                  45

His Gln Leu Gly Asn Leu Met Ile Gln Gln Ala Ala Ile Lys Gly Asn
    50                  55                  60

Ile Gly Tyr Ile Val Arg Phe Ser Asp His Gly His Glu Val His Ser
65                  70                  75                  80

Pro Phe Asp Asn His Ala Ser His Ser Asp Ser Asp Glu Ala Gly Ser
                85                  90                  95

Pro Val Asp Gly Phe Ser Leu Tyr Arg Ile His Trp Asp Gly Tyr Glu
            100                 105                 110

His His Pro Ala Asp Gly Tyr Asp Gly Pro Gln Gly Gly Gly Tyr Pro
        115                 120                 125
```

```
Ala Pro Lys Gly Ala Arg Asp Ile Tyr Ser Tyr Asp Ile Lys Gly Val
    130                 135                 140

Ala Gln Asn Ile Arg Leu Asn Leu Thr Asp Asn Arg Ser Thr Gly Gln
145                 150                 155                 160

Arg Leu Ala Asp Arg Phe His Asn Ala Gly Ser Met Leu Thr Gln Gly
                165                 170                 175

Val Gly Asp Gly Phe Lys Arg Ala Thr Arg Tyr Ser Pro Glu Leu Asp
            180                 185                 190

Arg Ser Gly Asn Ala Ala Glu Ala Phe Asn Gly Thr Ala Asp Ile Val
        195                 200                 205

Lys Asn Ile Ile Gly Ala Ala Gly Glu Ile Val Gly Ala Gly Asp Ala
    210                 215                 220

Val Gln Gly Ile Ser Glu Gly Ser Asn Ile Ala Val Met His Gly Leu
225                 230                 235                 240

Gly Leu Leu Ser Thr Glu Asn Lys Met Ala Arg Ile Asn Asp Leu Ala
                245                 250                 255

Asp Met Ala Gln Leu Lys Asp Tyr Ala Ala Ala Ile Arg Asp Trp
            260                 265                 270

Ala Val Gln Asn Pro Asn Ala Ala Gln Gly Ile Glu Ala Val Ser Asn
        275                 280                 285

Ile Phe Met Ala Ala Ile Pro Ile Lys Gly Ile Gly Ala Val Arg Gly
    290                 295                 300

Lys Tyr Gly Leu Gly Gly Ile Thr Ala His Pro Ile Lys Arg Ser Gln
305                 310                 315                 320

Met Gly Ala Ile Ala Leu Pro Lys Gly Lys Ser Ala Val Ser Asp Asn
                325                 330                 335

Phe Ala Asp Ala Ala Tyr Ala Lys Tyr Pro Ser Pro Tyr His Ser Arg
            340                 345                 350

Asn Ile Arg Ser Asn Leu Glu Gln Arg Tyr Gly Lys Glu Asn Ile Thr
        355                 360                 365

Ser Ser Thr Val Pro Pro Ser Asn Gly Lys Asn Val Lys Leu Ala Asp
    370                 375                 380

Gln Arg His Pro Lys Thr Gly Val Pro Phe Asp Gly Lys Gly Phe Pro
385                 390                 395                 400

Asn Phe Glu Lys His Val Lys Tyr Asp Thr Gly Ser Gly Gly Gly Gly
                405                 410                 415

Ala Thr Asn Asp Asp Asp Val Lys Lys Ala Ala Thr Val Ala Ile Ala
            420                 425                 430

Ala Ala Tyr Asn Asn Gly Gln Glu Ile Asn Gly Phe Lys Ala Gly Glu
        435                 440                 445

Thr Ile Tyr Asp Ile Asp Glu Asp Gly Thr Ile Thr Lys Lys Asp Ala
    450                 455                 460

Thr Ala Ala Asp Val Glu Ala Asp Asp Phe Lys Gly Leu Gly Leu Lys
465                 470                 475                 480

Lys Val Val Thr Asn Leu Thr Lys Thr Val Asn Glu Asn Lys Gln Asn
                485                 490                 495

Val Asp Ala Lys Val Lys Ala Ala Glu Ser Glu Ile Glu Lys Leu Thr
            500                 505                 510

Thr Lys Leu Ala Asp Thr Asp Ala Ala Leu Ala Asp Thr Asp Ala Ala
        515                 520                 525

Leu Asp Ala Thr Thr Asn Ala Leu Asn Lys Leu Gly Glu Asn Ile Thr
    530                 535                 540

Thr Phe Ala Glu Glu Thr Lys Thr Asn Ile Val Lys Ile Asp Glu Lys
```

```
                   545                 550                 555                 560
Leu Glu Ala Val Ala Asp Thr Val Asp Lys His Ala Glu Ala Phe Asn
                    565                 570                 575
Asp Ile Ala Asp Ser Leu Asp Glu Thr Asn Thr Lys Ala Asp Glu Ala
                580                 585                 590
Val Lys Thr Ala Asn Glu Ala Lys Gln Thr Ala Glu Glu Thr Lys Gln
            595                 600                 605
Asn Val Asp Ala Lys Val Lys Ala Ala Glu Thr Ala Ala Gly Lys Ala
        610                 615                 620
Glu Ala Ala Ala Gly Thr Ala Asn Thr Ala Ala Asp Lys Ala Glu Ala
625                 630                 635                 640
Val Ala Ala Lys Val Thr Asp Ile Lys Ala Asp Ile Ala Thr Asn Lys
                645                 650                 655
Asp Asn Ile Ala Lys Lys Ala Asn Ser Ala Asp Val Tyr Thr Arg Glu
            660                 665                 670
Glu Ser Asp Ser Lys Phe Val Arg Ile Asp Gly Leu Asn Ala Thr Thr
        675                 680                 685
Glu Lys Leu Asp Thr Arg Leu Ala Ser Ala Glu Lys Ser Ile Ala Asp
    690                 695                 700
His Asp Thr Arg Leu Asn Gly Leu Asp Lys Thr Val Ser Asp Leu Arg
705                 710                 715                 720
Lys Glu Thr Arg Gln Gly Leu Ala Glu Gln Ala Ala Leu Ser Gly Leu
                725                 730                 735
Phe Gln Pro Tyr Asn Val Gly Leu Glu His His His His His His
            740                 745                 750

<210> SEQ ID NO 146
<211> LENGTH: 2421
<212> TYPE: DNA
<213> ORGANISM: Artificial Sequence
<220> FEATURE:
<223> OTHER INFORMATION: 961-ORF46.1

<400> SEQUENCE: 146
atggccacaa cgacgacga tgttaaaaaa gctgccactg tggccattgc tgctgcctac      60
aacaatggcc aagaaatcaa cggtttcaaa gctggagaga ccatctacga cattgatgaa     120
gacggcacaa ttaccaaaaa agacgcaact gcagccgatt tgaagccga cgactttaaa     180 ggtctgggtc tgaaaaaagt cgtgactaac ctgaccaaaa ccgtcaatga aacaaacaa     240 aacgtcgatg ccaaagtaaa agctgcagaa tctgaaatag aaagttaac aaccaagtta     300 gcagacactg atgccgcttt agcagatact gatgccgctc tggatgcaac caccaacgcc    360
ttgaataaat tgggagaaaa tataacgaca tttgctgaag agactaagac aaatatcgta    420
aaaattgatg aaaaattaga agccgtggct gataccgtcg acaagcatgc cgaagcattc    480
aacgatatcg ccgattcatt ggatgaaacc aacactaagg cagacgaagc cgtcaaaacc    540
gccaatgaag ccaaacagac ggccgaagaa accaaacaaa acgtcgatgc caaagtaaaa    600
gctgcagaaa ctgcagcagg caaagccgaa gctgccgctg gcacagctaa tactgcagcc    660
gacaaggccg aagctgtcgc tgcaaaagtt accgacatca agctgatat cgctacgaac    720 aaagataata ttgctaaaaa agcaaacagt gccgacgtgt acaccagaga gagtctgac     780 agcaaatttg tcagaattga tggtctgaac gctactaccg aaaaattgga cacacgcttg    840
gcttctgctg aaaaatccat tgccgatcac gatactcgcc tgaacggttt ggataaaaca    900
gtgtcagacc tgcgcaaaga aacccgccaa ggccttgcag aacaagccgc gctctccggt    960
```

-continued

```
ctgttccaac cttacaacgt gggtcggttc aatgtaacgg ctgcagtcgg cggctacaaa      1020
tccgaatcgg cagtcgccat cggtaccggc ttccgcttta ccgaaaactt tgccgccaaa      1080
gcaggcgtgg cagtcggcac ttcgtccggt tcttccgcag cctaccatgt cggcgtcaat      1140
tacgagtggg gatccggagg aggaggatca gatttggcaa acgattcttt tatccggcag      1200
gttctcgacc gtcagcattt cgaacccgac gggaaatacc acctattcgg cagcaggggg      1260
gaacttgccg agcgcagcgg ccatatcgga ttgggaaaaa tacaaagcca tcagttgggc      1320
aacctgatga ttcaacaggc ggccattaaa ggaaatatcg gctacattgt ccgcttttcc      1380
gatcacgggc acgaagtcca ttcccccttc gacaaccatg cctcacattc cgattctgat      1440
gaagccggta gtcccgttga cggatttagc ctttaccgca tccattggga cggatacgaa      1500
caccatcccg ccgacggcta tgacgggcca caggcggcg gctatcccgc tcccaaaggc      1560
gcgagggata tatacagcta cgacataaaa ggcgttgccc aaaatatccg cctcaacctg      1620
accgacaacc gcagcaccgg acaacggctt gccgaccgtt tccacaatgc cggtagtatg      1680
ctgacgcaag gagtaggcga cggattcaaa cgcgccaccc gatacagccc cgagctggac      1740
agatcgggca atgccgccga agccttcaac ggcactgcag atatcgttaa aaacatcatc      1800
ggcgcggcag gagaaattgt cggcgcaggc gatgccgtgc agggcataag cgaaggctca      1860
aacattgctg tcatgcacgg cttgggtctg ctttccaccg aaaacaagat ggcgcgcatc      1920
aacgatttgg cagatatggc gcaactcaaa gactatgccg cagcagccat ccgcgattgg      1980
gcagtccaaa accccaatgc cgcacaaggc atagaagccg tcagcaatat ctttatggca      2040
gccatcccca tcaaagggat tggagctgtt cggggaaaat acggcttggg cggcatcacg      2100
gcacatccta tcaagcggtc gcagatgggc gcgatcgcat tgccgaaagg gaaatccgcc      2160
gtcagcgaca attttgccga tgcggcatac gccaaatacc cgtcccctta ccattcccga      2220
aatatccgtt caaacttgga gcagcgttac ggcaaagaaa acatcacctc ctcaaccgtg      2280
ccgccgtcaa acggcaaaaa tgtcaaactg gcagaccaac gccacccgaa gacaggcgta      2340
ccgtttgacg gtaaagggtt tccgaatttt gagaagcacg tgaaatatga tacgctcgag      2400
caccaccacc accaccactg a                                                2421
```

<210> SEQ ID NO 147
<211> LENGTH: 806
<212> TYPE: PRT
<213> ORGANISM: Artificial Sequence
<220> FEATURE:
<223> OTHER INFORMATION: 961-ORF46.1

<400> SEQUENCE: 147

```
Met Ala Thr Asn Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
                20                  25                  30

Glu Thr Ile Tyr Asp Ile Asp Glu Asp Gly Thr Ile Thr Lys Lys Asp
            35                  40                  45

Ala Thr Ala Ala Asp Val Glu Ala Asp Phe Lys Gly Leu Gly Leu
        50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110
```

-continued

```
Ala Leu Asp Ala Thr Thr Asn Ala Leu Asn Lys Leu Gly Glu Asn Ile
            115                 120                 125

Thr Thr Phe Ala Glu Glu Thr Lys Thr Asn Ile Val Lys Ile Asp Glu
        130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Ala Glu Thr Ala Ala Gly Lys
        195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
        275                 280                 285

Asp His Asp Thr Arg Leu Asn Gly Leu Asp Lys Thr Val Ser Asp Leu
    290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Arg Phe Asn Val Thr Ala Ala Val
                325                 330                 335

Gly Gly Tyr Lys Ser Glu Ser Ala Val Ala Ile Gly Thr Gly Phe Arg
            340                 345                 350

Phe Thr Glu Asn Phe Ala Ala Lys Ala Gly Val Ala Val Gly Thr Ser
        355                 360                 365

Ser Gly Ser Ser Ala Ala Tyr His Val Gly Val Asn Tyr Glu Trp Gly
    370                 375                 380

Ser Gly Gly Gly Ser Asp Leu Ala Asn Asp Ser Phe Ile Arg Gln
385                 390                 395                 400

Val Leu Asp Arg Gln His Phe Glu Pro Asp Gly Lys Tyr His Leu Phe
                405                 410                 415

Gly Ser Arg Gly Glu Leu Ala Glu Arg Ser Gly His Ile Gly Leu Gly
            420                 425                 430

Lys Ile Gln Ser His Gln Leu Gly Asn Leu Met Ile Gln Gln Ala Ala
        435                 440                 445

Ile Lys Gly Asn Ile Gly Tyr Ile Val Arg Phe Ser Asp His Gly His
    450                 455                 460

Glu Val His Ser Pro Phe Asp Asn His Ala Ser His Ser Asp Ser Asp
465                 470                 475                 480

Glu Ala Gly Ser Pro Val Asp Gly Phe Ser Leu Tyr Arg Ile His Trp
                485                 490                 495

Asp Gly Tyr Glu His His Pro Ala Asp Gly Tyr Asp Gly Pro Gln Gly
            500                 505                 510

Gly Gly Tyr Pro Ala Pro Lys Gly Ala Arg Asp Ile Tyr Ser Tyr Asp
        515                 520                 525

Ile Lys Gly Val Ala Gln Asn Ile Arg Leu Asn Leu Thr Asp Asn Arg
```

```
                530             535             540
Ser Thr Gly Gln Arg Leu Ala Asp Arg Phe His Asn Ala Gly Ser Met
545                 550                 555                 560

Leu Thr Gln Gly Val Gly Asp Gly Phe Lys Arg Ala Thr Arg Tyr Ser
                565                 570                 575

Pro Glu Leu Asp Arg Ser Gly Asn Ala Ala Glu Ala Phe Asn Gly Thr
            580                 585                 590

Ala Asp Ile Val Lys Asn Ile Ile Gly Ala Ala Gly Glu Ile Val Gly
        595                 600                 605

Ala Gly Asp Ala Val Gln Gly Ile Ser Glu Gly Ser Asn Ile Ala Val
    610                 615                 620

Met His Gly Leu Gly Leu Leu Ser Thr Glu Asn Lys Met Ala Arg Ile
625                 630                 635                 640

Asn Asp Leu Ala Asp Met Ala Gln Leu Lys Asp Tyr Ala Ala Ala Ala
                645                 650                 655

Ile Arg Asp Trp Ala Val Gln Asn Pro Asn Ala Gln Gly Ile Glu
            660                 665                 670

Ala Val Ser Asn Ile Phe Met Ala Ile Pro Ile Lys Gly Ile Gly
        675                 680                 685

Ala Val Arg Gly Lys Tyr Gly Leu Gly Gly Ile Thr Ala His Pro Ile
    690                 695                 700

Lys Arg Ser Gln Met Gly Ile Ala Leu Pro Lys Gly Lys Ser Ala
705                 710                 715                 720

Val Ser Asp Asn Phe Ala Asp Ala Ala Tyr Ala Lys Tyr Pro Ser Pro
                725                 730                 735

Tyr His Ser Arg Asn Ile Arg Ser Asn Leu Glu Gln Arg Tyr Gly Lys
            740                 745                 750

Glu Asn Ile Thr Ser Ser Thr Val Pro Pro Ser Asn Gly Lys Asn Val
        755                 760                 765

Lys Leu Ala Asp Gln Arg His Pro Lys Thr Gly Val Pro Phe Asp Gly
    770                 775                 780

Lys Gly Phe Pro Asn Phe Glu Lys His Val Lys Tyr Asp Thr Leu Glu
785                 790                 795                 800

His His His His His His
            805

<210> SEQ ID NO 148
<211> LENGTH: 1938
<212> TYPE: DNA
<213> ORGANISM: Artificial Sequence
<220> FEATURE:
<223> OTHER INFORMATION: 961-741

<400> SEQUENCE: 148
atggccacaa acgacgacga tgttaaaaaa gctgccactg tggccattgc tgctgcctac     60
aacaatggcc aagaaatcaa cggtttcaaa gctggagaga ccatctacga cattgatgaa    120
gacggcacaa ttaccaaaaa agacgcaact gcagccgatg ttgaagccga cgactttaaa    180
ggtctgggtc tgaaaaaagt cgtgactaac ctgaccaaaa ccgtcaatga aacaaacaa     240 aacgtcgatg ccaaagtaaa agctgcagaa tctgaaatag aaaagttaac aaccaagtta    300
gcagacactg atgccgcttt agcagatact gatgccgctc tggatgcaac caccaacgcc    360
ttgaataaat gggagaaaa tataacgaca tttgctgaag agactaagac aaatatcgta    420
aaaattgatg aaaaattaga agccgtggct gataccgtcg acaagcatgc cgaagcattc    480
aacgatatcg ccgattcatt ggatgaaacc aacactaagg cagacgaagc cgtcaaaacc    540
```

```
gccaatgaag ccaaacagac ggccgaagaa accaaacaaa acgtcgatgc caaagtaaaa      600
gctgcagaaa ctgcagcagg caaagccgaa gctgccgctg cacagctaaa tactgcagcc      660
gacaaggccg aagctgtcgc tgcaaaagtt accgacatca agctgatatc gctacgaac       720
aaagataata ttgctaaaaa agcaaacagt gccgacgtgt acaccagaga agagtctgac      780
agcaaatttg tcagaattga tggtctgaac gctactaccg aaaaattgga cacacgcttg      840
gcttctgctg aaaaatccat tgccgatcac gatactcgcc tgaacggttt ggataaaaca      900
gtgtcagacc tgcgcaaaga aacccgccaa ggccttgcag aacaagccgc gctctccggt      960
ctgttccaac cttacaacgt gggtcggttc aatgtaacgg ctgcagtcgg cggctacaaa     1020
tccgaatcgg cagtcgccat cggtaccggc ttccgcttta ccgaaaactt tgccgccaaa     1080
gcaggcgtgg cagtcggcac ttcgtccggt tcttccgcag cctaccatgt cggcgtcaat     1140
tacgagtggg gatccggagg gggtggtgtc gccgccgaca tcggtgcggg gcttgccgat     1200
gcactaaccg caccgctcga ccataaagac aaaggtttgc agtctttgac gctggatcag     1260
tccgtcagga aaacgagaa actgaagctg gcggcacaag gtgcggaaaa aacttatgga     1320
aacggtgaca gcctcaatac gggcaaattg aagaacgaca aggtcagccg tttcgacttt     1380
atccgccaaa tcgaagtgga cgggcagctc attaccttgg agagtggaga gttccaagta     1440
tacaaacaaa gccattccgc cttaaccgcc tttcagaccg agcaaataca agattcggag     1500
cattccggga agatggttgc gaaacgccag ttcagaatcg gcgacatagc gggcgaacat     1560
acatcttttg acaagcttcc cgaaggcggc agggcgacat atcgcgggac ggcgttcggt     1620
tcagacgatg ccggcggaaa actgacctac accatagatt tcgccgccaa gcagggaaac     1680
ggcaaaatcg aacatttgaa atcgccagaa ctcaatgtcg acctggccgc cgccgatatc     1740
aagccggatg gaaaacgcca tgccgtcatc agcggttccg tcctttacaa ccaagccgag     1800
aaaggcagtt actccctcgg tatctttggc ggaaaagccc aggaagttgc cggcagcgcg     1860
gaagtgaaaa ccgtaaacgg catacgccat atcggccttg ccgccaagca actcgagcac     1920
caccaccacc accactga                                                    1938
```

<210> SEQ ID NO 149
<211> LENGTH: 645
<212> TYPE: PRT
<213> ORGANISM: Artificial Sequence
<220> FEATURE:
<223> OTHER INFORMATION: 961-741

<400> SEQUENCE: 149

```
Met Ala Thr Asn Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
                20                  25                  30

Glu Thr Ile Tyr Asp Ile Asp Glu Asp Gly Thr Ile Thr Lys Lys Asp
            35                  40                  45

Ala Thr Ala Ala Asp Val Glu Ala Asp Phe Lys Gly Leu Gly Leu
        50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110
```

```
Ala Leu Asp Ala Thr Thr Asn Ala Leu Asn Lys Leu Gly Glu Asn Ile
            115                 120                 125

Thr Thr Phe Ala Glu Glu Thr Lys Thr Asn Ile Val Lys Ile Asp Glu
130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
            165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Glu Thr Ala Ala Gly Lys
            195                 200                 205

Ala Glu Ala Ala Ala Gly Thr Ala Asn Thr Ala Ala Asp Lys Ala Glu
210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
            245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
            275                 280                 285

Asp His Asp Thr Arg Leu Asn Gly Leu Asp Lys Thr Val Ser Asp Leu
            290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Arg Phe Asn Val Thr Ala Ala Val
            325                 330                 335

Gly Gly Tyr Lys Ser Glu Ser Ala Val Ala Ile Gly Thr Gly Phe Arg
            340                 345                 350

Phe Thr Glu Asn Phe Ala Ala Lys Ala Gly Val Ala Val Gly Thr Ser
            355                 360                 365

Ser Gly Ser Ser Ala Ala Tyr His Val Gly Val Asn Tyr Glu Trp Gly
            370                 375                 380

Ser Gly Gly Gly Val Ala Ala Asp Ile Gly Ala Gly Leu Ala Asp
385                 390                 395                 400

Ala Leu Thr Ala Pro Leu Asp His Lys Asp Lys Gly Leu Gln Ser Leu
            405                 410                 415

Thr Leu Asp Gln Ser Val Arg Lys Asn Glu Lys Leu Lys Leu Ala Ala
            420                 425                 430

Gln Gly Ala Glu Lys Thr Tyr Gly Asn Gly Asp Ser Leu Asn Thr Gly
            435                 440                 445

Lys Leu Lys Asn Asp Lys Val Ser Arg Phe Asp Phe Ile Arg Gln Ile
450                 455                 460

Glu Val Asp Gly Gln Leu Ile Thr Leu Glu Ser Gly Glu Phe Gln Val
465                 470                 475                 480

Tyr Lys Gln Ser His Ser Ala Leu Thr Ala Phe Gln Thr Glu Gln Ile
            485                 490                 495

Gln Asp Ser Glu His Ser Gly Lys Met Val Ala Lys Arg Gln Phe Arg
            500                 505                 510

Ile Gly Asp Ile Ala Gly Glu His Thr Ser Phe Asp Lys Leu Pro Glu
            515                 520                 525

Gly Gly Arg Ala Thr Tyr Arg Gly Thr Ala Phe Gly Ser Asp Asp Ala
530                 535                 540
```

```
Gly Gly Lys Leu Thr Tyr Thr Ile Asp Phe Ala Ala Lys Gln Gly Asn
545                 550                 555                 560

Gly Lys Ile Glu His Leu Lys Ser Pro Glu Leu Asn Val Asp Leu Ala
                565                 570                 575

Ala Ala Asp Ile Lys Pro Asp Gly Lys Arg His Ala Val Ile Ser Gly
            580                 585                 590

Ser Val Leu Tyr Asn Gln Ala Glu Lys Gly Ser Tyr Ser Leu Gly Ile
        595                 600                 605

Phe Gly Gly Lys Ala Gln Glu Val Ala Gly Ser Ala Glu Val Lys Thr
    610                 615                 620

Val Asn Gly Ile Arg His Ile Gly Leu Ala Ala Lys Gln Leu Glu His
625                 630                 635                 640

His His His His His
                645

<210> SEQ ID NO 150
<211> LENGTH: 4335
<212> TYPE: DNA
<213> ORGANISM: Artificial Sequence
<220> FEATURE:
<223> OTHER INFORMATION: 961-983

<400> SEQUENCE: 150
atggccacaa acgacgacga tgttaaaaaa gctgccactg tggccattgc tgctgcctac      60
aacaatggcc aagaaatcaa cggtttcaaa gctggagaga ccatctacga cattgatgaa     120
gacggcacaa ttaccaaaaa agacgcaact gcagccgatg ttgaagccga cgactttaaa     180
ggtctgggtc tgaaaaaagt cgtgactaac ctgaccaaaa ccgtcaatga aacaaacaa      240 aacgtcgatg ccaaagtaaa agctgcagaa tctgaaatag aaaagttaac aaccaagtta     300
gcagacactg atgccgcttt agcagatact gatgccgctc tggatgcaac caccaacgcc     360
ttgaataaat gggagaaaaa tataacgaca tttgctgaag agactaagac aaaatatcgta    420 aaaattgatg aaaaattaga gccgtggct gataccgtcg acaagcatgc cgaagcattc      480
aacgatatcg ccgattcatt ggatgaaacc aacactaagg cagacgaagc cgtcaaaacc     540
gccaatgaag ccaaacagac ggccgaagaa accaaacaaa acgtcgatgc caaagtaaaa     600
gctgcagaaa ctgcagcagg caaagccgaa gctgccgctg cacagctaa tactgcagcc      660 gacaaggccg aagctgtcgc tgcaaaagtt accgacatca agctgatatc gctacgaac      720 aaagataata ttgctaaaaa agcaaacagt gccgacgtgt acaccagaga gagtctgac      780 agcaaatttg tcagaattga tggtctgaac gctactaccg aaaaattgga cacacgcttg     840
gcttctgctg aaaaatccat tgccgatcac gatactcgcc tgaacggttt ggataaaaca     900
gtgtcagacc tgcgcaaaga aacccgccaa ggccttgcag acaagccgc gctctccggt      960 ctgttccaac cttacaacgt gggtcggttc aatgtaacgg ctgcagtcgg cggctacaaa    1020
tccgaatcgg cagtcgccat cggtaccggc ttccgcttta ccgaaaactt tgccgccaaa    1080
gcaggcgtgg cagtcggcac ttcgtccggt tcttccgcag cctaccatgt cggcgtcaat    1140
tacgagtggg gatccggcgg aggcggcact tctgcgcccg acttcaatgc aggcggtacc    1200
ggtatcggca gcaacagcag agcaacaaca gcgaaatcag cagcagtatc ttacgccggt    1260
atcaagaacg aaatgtgcaa agacagaagc atgctctgtg ccggtcggga tgacgttgcg    1320
gttacagaca gggatgccaa atcaatgcc ccccccccga atctgcatac cggagacttt     1380
ccaaacccaa atgacgcata caagaatttg atcaacctca aacctgcaat tgaagcaggc    1440
```

```
tatacaggac gcggggtaga ggtaggtatc gtcgacacag gcgaatccgt cggcagcata    1500
tcctttcccg aactgtatgg cagaaaagaa cacggctata acgaaaatta caaaaactat    1560
acggcgtata tgcggaagga agcgcctgaa gacggaggcg gtaaagacat tgaagcttct    1620
ttcgacgatg aggccgttat agagactgaa gcaaagccga cggatatccg ccacgtaaaa    1680
gaaatcggac acatcgattt ggtctcccat attattggcg ggcgttccgt ggacggcaga    1740
cctgcaggcg gtattgcgcc cgatgcgacg ctacacataa tgaatacgaa tgatgaaacc    1800
aagaacgaaa tgatggttgc agccatccgc aatgcatggg tcaagctggg cgaacgtggc    1860
gtgcgcatcg tcaataacag ttttggaaca acatcgaggg caggcactgc cgacccttttc    1920 caaatagcca attcggagga gcagtaccgc caagcgttgc tcgactattc cggcggtgat    1980
aaaacagacg agggtatccg cctgatgcaa cagagcgatt acggcaacct gtcctaccac    2040
atccgtaata aaaacatgct tttcatcttt tcgacaggca atgacgcaca agctcagccc    2100
aacacatatg ccctattgcc atttatgaa aagacgctc aaaaaggcat tatcacagtc       2160
gcaggcgtag accgcagtgg agaaaagttc aaacgggaaa tgtatggaga accgggtaca    2220
gaaccgcttg agtatggctc caaccattgc ggaattactg ccatgtggtg cctgtcggca    2280
ccctatgaag caagcgtccg tttcaccccgt acaaacccga ttcaaattgc cggaacatcc    2340 tttccgcac ccatcgtaac cggcacggcg gctctgctgc tgcagaaata cccgtggatg      2400
agcaacgaca acctgcgtac cacgttgctg acgacggctc aggacatcgg tgcagtcggc    2460
gtggacagca agttcggctg gggactgctg gatgcgggta aggccatgaa cggacccgcg    2520
tcctttccgt tcggcgactt taccgccgat acgaaaggta catccgatat tgcctactcc    2580
ttccgtaacg acatttcagg cacgggcggc ctgatcaaaa aaggcggcag ccaactgcaa    2640
ctgcacggca acaaccctag tacgggcaaa accattatcg aaggcggttc gctggtgttg    2700
tacggcaaca caaatcgga tatgcgcgtc gaaaccaaag gtgcgctgat ttataacggg     2760
gcggcatccg gcggcagcct gaacagcgac ggcattgtct atctggcaga taccgaccaa    2820
tccggcgcaa acgaaaccgt acacatcaaa ggcagtctgc agctggacgg caaaggtacg    2880
ctgtacacac gtttgggcaa actgctgaaa gtggacggta cggcgattat cggcggcaag    2940
ctgtacatgt cggcacgcgg caaggggggca ggctatctca acagtaccgg acgacgtgtt    3000
cccttcctga gtgccgccaa aatcgggcag gattattctt tcttcacaaa catcgaaacc    3060
gacggcggcc tgctggcttc cctcgacagc gtcgaaaaaa cagcgggcag tgaaggcgac    3120
acgctgtcct attatgtccg tcgcggcaat gcggcacgga ctgcttcggc agcggcacat    3180
tccgcgcccg ccggtctgaa acacgccgta gaacagggcg gcagcaatct ggaaaacctg    3240
atggtcgaac tggatgcctc cgaatcatcc gcaacacccg agacggttga aactgcggca    3300
gccgaccgca cagatatgcc gggcatccgc ccctacggcg caactttccg cgcagcggca    3360
gccgtacagc atgcgaatgc cgccgacggt gtacgcatct tcaacagtct cgccgctacc    3420
gtctatgccg acagtaccgc cgcccatgcc gatatgcagg gacgccgcct gaaagccgta    3480
tcggacgggt tggaccacaa cggcacgggt ctgcgcgtca tcgcgcaaac ccaacaggac    3540
ggtggaacgt gggaacaggg cggtgttgaa ggcaaaatgc gcggcagtac ccaaaccgtc    3600
ggcattgccg cgaaaaccgg cgaaaatacg acagcagccg ccacactggg catgggacgc    3660
agcacatgga gcgaaaacag tgcaaatgca aaaaccgaca gcattagtct gtttgcaggc    3720
atacggcacg atgcgggcga tatcggctat ctcaaaggcc tgttctccta cggacgctac    3780
aaaaacagca tcagccgcag caccggtgcg gacgaacatg cggaaggcag cgtcaacggc    3840
```

-continued

```
acgctgatgc agctgggcgc actgggcggt gtcaacgttc cgtttgccgc aacgggagat    3900
ttgacggtcg aaggcggtct gcgctacgac ctgctcaaac aggatgcatt cgccgaaaaa    3960
ggcagtgctt tgggctggag cggcaacagc ctcactgaag gcacgctggt cggactcgcg    4020
ggtctgaagc tgtcgcaacc cttgagcgat aaagccgtcc tgtttgcaac ggcgggcgtg    4080
gaacgcgacc tgaacggacg cgactacacg gtaacgggcg gctttaccgg cgcgactgca    4140
gcaaccggca agacggggc acgcaatatg ccgcacaccc gtctggttgc cggcctgggc    4200
gcggatgtcg aattcggcaa cggctggaac ggcttggcac gttacagcta cgccggttcc    4260
aaacagtacg gcaaccacag cggacgagtc ggcgtaggct accggttcct cgagcaccac    4320
caccaccacc actga                                                   4335
```

<210> SEQ ID NO 151
<211> LENGTH: 1444
<212> TYPE: PRT
<213> ORGANISM: Artificial Sequence
<220> FEATURE:
<223> OTHER INFORMATION: 961-983

<400> SEQUENCE: 151

```
Met Ala Thr Asn Asp Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
            20                  25                  30

Glu Thr Ile Tyr Asp Ile Asp Glu Asp Gly Thr Ile Thr Lys Lys Asp
        35                  40                  45

Ala Thr Ala Ala Asp Val Glu Ala Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Ala Glu Thr Ala Ala Gly Lys
        195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
```

```
                    275                 280                 285
Asp His Asp Thr Arg Leu Asn Gly Leu Asp Lys Thr Val Ser Asp Leu
            290                 295                 300
Arg Lys Glu Thr Arg Gln Gly Leu Ala Glu Gln Ala Ala Leu Ser Gly
305                 310                 315                 320
Leu Phe Gln Pro Tyr Asn Val Gly Arg Phe Asn Val Thr Ala Ala Val
                325                 330                 335
Gly Gly Tyr Lys Ser Glu Ser Ala Val Ala Ile Gly Thr Gly Phe Arg
            340                 345                 350
Phe Thr Glu Asn Phe Ala Ala Lys Ala Gly Val Ala Val Gly Thr Ser
            355                 360                 365
Ser Gly Ser Ser Ala Ala Tyr His Val Gly Val Asn Tyr Glu Trp Gly
        370                 375                 380
Ser Gly Gly Gly Gly Thr Ser Ala Pro Asp Phe Asn Ala Gly Gly Thr
385                 390                 395                 400
Gly Ile Gly Ser Asn Ser Arg Ala Thr Thr Ala Lys Ser Ala Ala Val
                405                 410                 415
Ser Tyr Ala Gly Ile Lys Asn Glu Met Cys Lys Asp Arg Ser Met Leu
            420                 425                 430
Cys Ala Gly Arg Asp Asp Val Ala Val Thr Asp Arg Asp Ala Lys Ile
            435                 440                 445
Asn Ala Pro Pro Pro Asn Leu His Thr Gly Asp Phe Pro Asn Pro Asn
        450                 455                 460
Asp Ala Tyr Lys Asn Leu Ile Asn Leu Lys Pro Ala Ile Glu Ala Gly
465                 470                 475                 480
Tyr Thr Gly Arg Gly Val Glu Val Gly Ile Val Asp Thr Gly Glu Ser
                485                 490                 495
Val Gly Ser Ile Ser Phe Pro Glu Leu Tyr Gly Arg Lys Glu His Gly
            500                 505                 510
Tyr Asn Glu Asn Tyr Lys Asn Tyr Thr Ala Tyr Met Arg Lys Glu Ala
            515                 520                 525
Pro Glu Asp Gly Gly Gly Lys Asp Ile Glu Ala Ser Phe Asp Asp Glu
        530                 535                 540
Ala Val Ile Glu Thr Glu Ala Lys Pro Thr Asp Ile Arg His Val Lys
545                 550                 555                 560
Glu Ile Gly His Ile Asp Leu Val Ser His Ile Ile Gly Gly Arg Ser
                565                 570                 575
Val Asp Gly Arg Pro Ala Gly Gly Ile Ala Pro Asp Ala Thr Leu His
            580                 585                 590
Ile Met Asn Thr Asn Asp Glu Thr Lys Asn Glu Met Met Val Ala Ala
            595                 600                 605
Ile Arg Asn Ala Trp Val Lys Leu Gly Glu Arg Gly Val Arg Ile Val
        610                 615                 620
Asn Asn Ser Phe Gly Thr Thr Ser Arg Ala Gly Thr Ala Asp Leu Phe
625                 630                 635                 640
Gln Ile Ala Asn Ser Glu Glu Gln Tyr Arg Gln Ala Leu Leu Asp Tyr
                645                 650                 655
Ser Gly Gly Asp Lys Thr Asp Glu Gly Ile Arg Leu Met Gln Gln Ser
            660                 665                 670
Asp Tyr Gly Asn Leu Ser Tyr His Ile Arg Asn Lys Asn Met Leu Phe
            675                 680                 685
Ile Phe Ser Thr Gly Asn Asp Ala Gln Ala Gln Pro Asn Thr Tyr Ala
        690                 695                 700
```

```
Leu Leu Pro Phe Tyr Glu Lys Asp Ala Gln Lys Gly Ile Ile Thr Val
705                 710                 715                 720

Ala Gly Val Asp Arg Ser Gly Glu Lys Phe Arg Glu Met Tyr Gly
            725                 730                 735

Glu Pro Gly Thr Glu Pro Leu Gly Tyr Gly Ser Asn His Cys Gly Ile
                740                 745                 750

Thr Ala Met Trp Cys Leu Ser Ala Pro Tyr Glu Ala Ser Val Arg Phe
        755                 760                 765

Thr Arg Thr Asn Pro Ile Gln Ile Ala Gly Thr Ser Phe Ser Ala Pro
    770                 775                 780

Ile Val Thr Gly Thr Ala Ala Leu Leu Leu Gln Lys Tyr Pro Trp Met
785                 790                 795                 800

Ser Asn Asp Asn Leu Arg Thr Thr Leu Leu Thr Thr Ala Gln Asp Ile
                805                 810                 815

Gly Ala Val Gly Val Asp Ser Lys Phe Gly Trp Gly Leu Leu Asp Ala
                820                 825                 830

Gly Lys Ala Met Asn Gly Pro Ala Ser Phe Pro Phe Gly Asp Phe Thr
        835                 840                 845

Ala Asp Thr Lys Gly Thr Ser Asp Ile Ala Tyr Ser Phe Arg Asn Asp
850                 855                 860

Ile Ser Gly Thr Gly Gly Leu Ile Lys Lys Gly Gly Ser Gln Leu Gln
865                 870                 875                 880

Leu His Gly Asn Asn Thr Tyr Thr Gly Lys Thr Ile Ile Glu Gly Gly
                885                 890                 895

Ser Leu Val Leu Tyr Gly Asn Asn Lys Ser Asp Met Arg Val Glu Thr
                900                 905                 910

Lys Gly Ala Leu Ile Tyr Asn Gly Ala Ala Ser Gly Gly Ser Leu Asn
            915                 920                 925

Ser Asp Gly Ile Val Tyr Leu Ala Asp Thr Asp Gln Ser Gly Ala Asn
    930                 935                 940

Glu Thr Val His Ile Lys Gly Ser Leu Gln Leu Asp Gly Lys Gly Thr
945                 950                 955                 960

Leu Tyr Thr Arg Leu Gly Lys Leu Leu Lys Val Asp Gly Thr Ala Ile
                965                 970                 975

Ile Gly Gly Lys Leu Tyr Met Ser Ala Arg Gly Lys Gly Ala Gly Tyr
            980                 985                 990

Leu Asn Ser Thr Gly Arg Arg Val Pro Phe Leu Ser Ala Ala Lys Ile
        995                 1000                1005

Gly Gln Asp Tyr Ser Phe Phe Thr Asn Ile Glu Thr Asp Gly Gly Leu
    1010                1015                1020

Leu Ala Ser Leu Asp Ser Val Glu Lys Thr Ala Gly Ser Glu Gly Asp
1025                1030                1035                1040

Thr Leu Ser Tyr Tyr Val Arg Arg Gly Asn Ala Ala Arg Thr Ala Ser
                1045                1050                1055

Ala Ala Ala His Ser Ala Pro Ala Gly Leu Lys His Ala Val Glu Gln
            1060                1065                1070

Gly Gly Ser Asn Leu Glu Asn Leu Met Val Glu Leu Asp Ala Ser Glu
        1075                1080                1085

Ser Ser Ala Thr Pro Glu Thr Val Glu Thr Ala Ala Asp Arg Thr
    1090                1095                1100

Asp Met Pro Gly Ile Arg Pro Tyr Gly Ala Thr Phe Arg Ala Ala
1105                1110                1115                1120

Ala Val Gln His Ala Asn Ala Ala Asp Gly Val Arg Ile Phe Asn Ser
                1125                1130                1135
```

```
Leu Ala Ala Thr Val Tyr Ala Asp Ser Thr Ala Ala His Ala Asp Met
        1140                1145                1150

Gln Gly Arg Arg Leu Lys Ala Val Ser Asp Gly Leu Asp His Asn Gly
    1155                1160                1165

Thr Gly Leu Arg Val Ile Ala Gln Thr Gln Gln Asp Gly Gly Thr Trp
    1170                1175                1180

Glu Gln Gly Gly Val Glu Gly Lys Met Arg Gly Ser Thr Gln Thr Val
1185                1190                1195                1200

Gly Ile Ala Ala Lys Thr Gly Glu Asn Thr Thr Ala Ala Thr Leu
            1205                1210                1215

Gly Met Gly Arg Ser Thr Trp Ser Glu Asn Ser Ala Asn Ala Lys Thr
        1220                1225                1230

Asp Ser Ile Ser Leu Phe Ala Gly Ile Arg His Asp Ala Gly Asp Ile
        1235                1240                1245

Gly Tyr Leu Lys Gly Leu Phe Ser Tyr Gly Arg Tyr Lys Asn Ser Ile
    1250                1255                1260

Ser Arg Ser Thr Gly Ala Asp Glu His Ala Glu Gly Ser Val Asn Gly
1265                1270                1275                1280

Thr Leu Met Gln Leu Gly Ala Leu Gly Gly Val Asn Val Pro Phe Ala
            1285                1290                1295

Ala Thr Gly Asp Leu Thr Val Glu Gly Gly Leu Arg Tyr Asp Leu Leu
        1300                1305                1310

Lys Gln Asp Ala Phe Ala Glu Lys Gly Ser Ala Leu Gly Trp Ser Gly
            1315                1320                1325

Asn Ser Leu Thr Glu Gly Thr Leu Val Gly Leu Ala Gly Leu Lys Leu
        1330                1335                1340

Ser Gln Pro Leu Ser Asp Lys Ala Val Leu Phe Ala Thr Ala Gly Val
1345                1350                1355                1360

Glu Arg Asp Leu Asn Gly Arg Asp Tyr Thr Val Thr Gly Gly Phe Thr
            1365                1370                1375

Gly Ala Thr Ala Ala Thr Gly Lys Thr Gly Ala Arg Asn Met Pro His
        1380                1385                1390

Thr Arg Leu Val Ala Gly Leu Gly Ala Asp Val Glu Phe Gly Asn Gly
        1395                1400                1405

Trp Asn Gly Leu Ala Arg Tyr Ser Tyr Ala Gly Ser Lys Gln Tyr Gly
    1410                1415                1420

Asn His Ser Gly Arg Val Gly Val Gly Tyr Arg Phe Leu Glu His His
1425                1430                1435                1440

His His His His

<210> SEQ ID NO 152
<211> LENGTH: 2256
<212> TYPE: DNA
<213> ORGANISM: Artificial Sequence
<220> FEATURE:
<223> OTHER INFORMATION: 961c-ORF46.1

<400> SEQUENCE: 152
atggccacaa acgacgacga tgttaaaaaa gctgccactg tggccattgc tgctgcctac      60
aacaatggcc aagaaatcaa cggtttcaaa gctggagaga ccatctcacga cattgatgaa     120 gacggcacaa ttaccaaaaa agacgcaact gcagccgatg ttgaagccga cgactttaaa     180
ggtctgggtc tgaaaaaagt cgtgactaac ctgaccaaaa ccgtcaatga aaacaaacaa     240
aacgtcgatg ccaaagtaaa agctgcagaa tctgaaatag aaaagttaac aaccaagtta     300
```

```
gcagacactg atgccgcttt agcagatact gatgccgctc tggatgcaac caccaacgcc   360
ttgaataaat tgggagaaaa tataacgaca tttgctgaag agactaagac aaatatcgta   420
aaaattgatg aaaaattaga agccgtggct gataccgtcg acaagcatgc gaagcattc    480
aacgatatcg ccgattcatt ggatgaaacc aacactaagg cagacgaagc cgtcaaaacc   540
gccaatgaag ccaaacagac ggccgaagaa accaaacaaa acgtcgatgc aaagtaaaa    600
gctgcagaaa ctgcagcagg caaagccgaa gctgccgctg gcacagctaa tactgcagcc   660
gacaaggccg aagctgtcgc tgcaaaagtt accgacatca agctgatat cgctacgaac    720
aaagataata ttgctaaaaa agcaaacagt gccgacgtgt acaccagaga gagtctgac    780
agcaaatttg tcagaattga tggtctgaac gctactaccg aaaaattgga cacacgcttg   840
gcttctgctg aaaaatccat tgccgatcac gatactcgcc tgaacggttt ggataaaaca   900
gtgtcagacc tgcgcaaaga aacccgccaa ggccttgcag aacaagccgc gctctccggt   960
ctgttccaac cttacaacgt gggtggatcc ggaggaggag gatcagattt ggcaaacgat  1020
tctttttatcc ggcaggttct cgaccgtcag catttcgaac ccgacgggaa ataccaccta  1080
ttcggcagca gggggaact tgccgagcgc agcggccata tcggattggg aaaaatacaa   1140
agccatcagt tgggcaacct gatgattcaa caggcggcca ttaaaggaaa tatcggctac  1200
attgtccgct tttccgatca cgggcacgaa gtccattccc ccttcgacaa ccatgcctca  1260
cattccgatt ctgatgaagc cggtagtccc gttgacggat ttagccttta ccgcatccat  1320
tgggacggat acgaacacca tcccgccgac ggctatgacg gccacaggg cggcggctat  1380
cccgctccca aggcgcgag ggatatatac agctacgaca taaaaggcgt tgcccaaaat   1440
atccgcctca acctgaccga caaccgcagc accggacaac ggcttgccga ccgtttccac  1500
aatgccggta gtatgctgac gcaaggagta ggcgacggat tcaaacgcgc cacccgatac  1560
agccccgagc tggacagatc gggcaatgcc gccgaagcct tcaacggcac tgcagatatc  1620
gttaaaaaca tcatcggcgc ggcaggagaa attgtcggcg caggcgatgc cgtgcagggc  1680
ataagcgaag gctcaaacat tgctgtcatg cacggcttgg gtctgctttc caccgaaaac  1740
aagatggcgc gcatcaacga tttggcagat atggcgcaac tcaaagacta tgccgcagca  1800
gccatccgcg attgggcagt ccaaaacccc aatgccgcac aaggcataga agccgtcagc  1860
aatatcttta tggcagccat ccccatcaaa gggattggga ctgttcgggg aaaatacggc  1920
ttgggcggca tcacggcaca tcctatcaag cggtcgcaga tgggcgcgat cgcattgccg  1980
aaagggaaat ccgccgtcag cgacaatttt gccgatgcgg catacgccaa atacccgtcc  2040
ccttaccatt cccgaaatat ccgttcaaac ttggagcagc gttacggcaa agaaacatc   2100
acctcctcaa ccgtgccgcc gtcaaacggc aaaaatgtca aactggcaga ccaacgccac  2160
ccgaagacag gcgtaccgtt tgacggtaaa gggtttccga attttgagaa gcacgtgaaa  2220
tatgatacgc tcgagcacca ccaccaccac cactga                            2256
```

<210> SEQ ID NO 153
<211> LENGTH: 751
<212> TYPE: PRT
<213> ORGANISM: Artificial Sequence
<220> FEATURE:
<223> OTHER INFORMATION: 961c-ORF46.1

<400> SEQUENCE: 153

```
Met Ala Thr Asn Asp Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
```

-continued

```
                    20                  25                  30
Glu Thr Ile Tyr Asp Ile Asp Glu Asp Gly Thr Ile Thr Lys Lys Asp
                35                  40                  45
Ala Thr Ala Ala Asp Val Glu Ala Asp Phe Lys Gly Leu Gly Leu
     50                  55                  60
Lys Lys Val Val Thr Asn Leu Thr Lys Thr Val Asn Glu Asn Lys Gln
 65                  70                  75                  80
Asn Val Asp Ala Lys Val Lys Ala Glu Ser Glu Ile Glu Lys Leu
                 85                  90                  95
Thr Thr Lys Leu Ala Asp Thr Asp Ala Ala Leu Ala Asp Thr Asp Ala
                100                 105                 110
Ala Leu Asp Ala Thr Thr Asn Ala Leu Asn Lys Leu Gly Glu Asn Ile
             115                 120                 125
Thr Thr Phe Ala Glu Glu Thr Lys Thr Asn Ile Val Lys Ile Asp Glu
         130                 135                 140
Lys Leu Glu Ala Val Ala Asp Thr Val Asp Lys His Ala Glu Ala Phe
145                 150                 155                 160
Asn Asp Ile Ala Asp Ser Leu Asp Glu Thr Asn Thr Lys Ala Asp Glu
                165                 170                 175
Ala Val Lys Thr Ala Asn Glu Ala Lys Gln Thr Ala Glu Glu Thr Lys
             180                 185                 190
Gln Asn Val Asp Ala Lys Val Lys Ala Glu Thr Ala Ala Gly Lys
         195                 200                 205
Ala Glu Ala Ala Ala Gly Thr Ala Asn Thr Ala Ala Asp Lys Ala Glu
     210                 215                 220
Ala Val Ala Ala Lys Val Thr Asp Ile Lys Ala Asp Ile Ala Thr Asn
225                 230                 235                 240
Lys Asp Asn Ile Ala Lys Lys Ala Asn Ser Ala Asp Val Tyr Thr Arg
                245                 250                 255
Glu Glu Ser Asp Ser Lys Phe Val Arg Ile Asp Gly Leu Asn Ala Thr
                260                 265                 270
Thr Glu Lys Leu Asp Thr Arg Leu Ala Ser Ala Glu Lys Ser Ile Ala
         275                 280                 285
Asp His Asp Thr Arg Leu Asn Gly Leu Asp Lys Thr Val Ser Asp Leu
     290                 295                 300
Arg Lys Glu Thr Arg Gln Gly Leu Ala Glu Gln Ala Ala Leu Ser Gly
305                 310                 315                 320
Leu Phe Gln Pro Tyr Asn Val Gly Gly Ser Gly Gly Gly Ser Asp
                325                 330                 335
Leu Ala Asn Asp Ser Phe Ile Arg Gln Val Leu Asp Arg Gln His Phe
             340                 345                 350
Glu Pro Asp Gly Lys Tyr His Leu Phe Gly Ser Arg Gly Glu Leu Ala
         355                 360                 365
Glu Arg Ser Gly His Ile Gly Leu Gly Lys Ile Gln Ser His Gln Leu
     370                 375                 380
Gly Asn Leu Met Ile Gln Gln Ala Ala Ile Lys Gly Asn Ile Gly Tyr
385                 390                 395                 400
Ile Val Arg Phe Ser Asp His Gly His Glu Val His Ser Pro Phe Asp
                405                 410                 415
Asn His Ala Ser His Ser Asp Ser Asp Glu Ala Gly Ser Pro Val Asp
                420                 425                 430
Gly Phe Ser Leu Tyr Arg Ile His Trp Asp Gly Tyr Glu His His Pro
             435                 440                 445
```

Ala Asp Gly Tyr Asp Gly Pro Gln Gly Gly Gly Tyr Pro Ala Pro Lys
450                 455                 460

Gly Ala Arg Asp Ile Tyr Ser Tyr Asp Ile Lys Gly Val Ala Gln Asn
465                 470                 475                 480

Ile Arg Leu Asn Leu Thr Asp Asn Arg Ser Thr Gly Gln Arg Leu Ala
                485                 490                 495

Asp Arg Phe His Asn Ala Gly Ser Met Leu Thr Gln Gly Val Gly Asp
            500                 505                 510

Gly Phe Lys Arg Ala Thr Arg Tyr Ser Pro Glu Leu Asp Arg Ser Gly
            515                 520                 525

Asn Ala Ala Glu Ala Phe Asn Gly Thr Ala Asp Ile Val Lys Asn Ile
530                 535                 540

Ile Gly Ala Ala Gly Glu Ile Val Gly Ala Gly Asp Ala Val Gln Gly
545                 550                 555                 560

Ile Ser Glu Gly Ser Asn Ile Ala Val Met His Gly Leu Gly Leu Leu
                565                 570                 575

Ser Thr Glu Asn Lys Met Ala Arg Ile Asn Asp Leu Ala Asp Met Ala
            580                 585                 590

Gln Leu Lys Asp Tyr Ala Ala Ala Ile Arg Asp Trp Ala Val Gln
            595                 600                 605

Asn Pro Asn Ala Ala Gln Gly Ile Glu Ala Val Ser Asn Ile Phe Met
610                 615                 620

Ala Ala Ile Pro Ile Lys Gly Ile Gly Ala Val Arg Gly Lys Tyr Gly
625                 630                 635                 640

Leu Gly Gly Ile Thr Ala His Pro Ile Lys Arg Ser Gln Met Gly Ala
                645                 650                 655

Ile Ala Leu Pro Lys Gly Lys Ser Ala Val Ser Asp Asn Phe Ala Asp
            660                 665                 670

Ala Ala Tyr Ala Lys Tyr Pro Ser Pro Tyr His Ser Arg Asn Ile Arg
            675                 680                 685

Ser Asn Leu Glu Gln Arg Tyr Gly Lys Glu Asn Ile Thr Ser Ser Thr
690                 695                 700

Val Pro Pro Ser Asn Gly Lys Asn Val Lys Leu Ala Asp Gln Arg His
705                 710                 715                 720

Pro Lys Thr Gly Val Pro Phe Asp Gly Lys Gly Phe Pro Asn Phe Glu
                725                 730                 735

Lys His Val Lys Tyr Asp Thr Leu Glu His His His His His His
            740                 745                 750

<210> SEQ ID NO 154
<211> LENGTH: 1773
<212> TYPE: DNA
<213> ORGANISM: Artificial Sequence
<220> FEATURE:
<223> OTHER INFORMATION: 961c-741

<400> SEQUENCE: 154
atggccacaa acgacgacga tgttaaaaaa gctgccactg tggccattgc tgctgcctac     60
aacaatggcc aagaaatcaa cggtttcaaa gctggagaga ccatctacga cattgatgaa    120
gacggcacaa ttaccaaaaa agacgcaact gcagccgatg ttgaagccga cgactttaaa    180
ggtctgggtc tgaaaaaagt cgtgactaac ctgaccaaaa ccgtcaatga aacaaacaa     240 aacgtcgatg ccaaagtaaa agctgcagaa tctgaaatag aaaagttaac aaccaagtta    300
gcagacactg atgccgcttt agcagatact gatgccgctc tggatgcaac caccaacgcc    360
ttgaataaat tgggagaaaa tataacgaca tttgctgaag agactaagac aaatatcgta    420

```
aaaattgatg aaaaattaga agccgtggct gataccgtcg acaagcatgc cgaagcattc    480
aacgatatcg ccgattcatt ggatgaaacc aacactaagg cagacgaagc cgtcaaaacc    540
gccaatgaag ccaaacagac ggccgaagaa accaaacaaa acgtcgatgc caaagtaaaa    600
gctgcagaaa ctgcagcagg caaagccgaa gctgccgctg cacagctaa tactgcagcc     660 gacaaggccg aagctgtcgc tgcaaaagtt accgacatca agctgatat cgctacgaac     720 aaagataata ttgctaaaaa agcaaacagt gccgacgtgt acaccagaga agagtctgac    780
agcaaatttg tcagaattga tggtctgaac gctactaccg aaaaattgga cacacgcttg    840
gcttctgctg aaaaatccat tgccgatcac gatactcgcc tgaacggttt ggataaaaca    900
gtgtcagacc tgcgcaaaga aacccgccaa ggccttgcag aacaagccgc gctctccggt    960
ctgttccaac cttacaacgt gggtggatcc ggagggggtg gtgtcgccgc cgacatcggt    1020
gcggggcttg ccgatgcact aaccgcaccg ctcgaccata agacaaagg tttgcagtct    1080 ttgacgctgg atcagtccgt caggaaaaac gagaaactga agctggcggc acaaggtgcg    1140
gaaaaaactt atggaaacgg tgacagcctc aatacgggca aattgaagaa cgacaaggtc    1200
agccgtttcg actttatccg ccaaatcgaa gtggacgggc agctcattac cttggagagt    1260
ggagagttcc aagtatacaa acaaagccat tccgccttaa ccgcctttca gaccgagcaa    1320
atacaagatt cggagcattc cgggaagatg gttgcgaaac gccagttcag aatcggcgac    1380
atagcgggcg aacatacatc ttttgacaag cttcccgaag gcggcagggc gacatatcgc    1440
gggacggcgt tcggttcaga cgatgccggc ggaaaactga cctacaccat agatttcgcc    1500
gccaagcagg gaaacggcaa aatcgaacat ttgaaatcgc cagaactcaa tgtcgacctg    1560
gccgccgccg atatcaagcc ggatggaaaa cgccatgccg tcatcagcgg ttccgtcctt    1620
tacaaccaag ccgagaaagg cagttactcc ctcggtatct ttggcggaaa agcccaggaa    1680
gttgccggca gcgcggaagt gaaaaccgta acggcatac gccatatcgg ccttgccgcc    1740
aagcaactcg agcaccacca ccaccaccac tga                                1773
```

<210> SEQ ID NO 155
<211> LENGTH: 590
<212> TYPE: PRT
<213> ORGANISM: Artificial Sequence
<220> FEATURE:
<223> OTHER INFORMATION: 961c-741

<400> SEQUENCE: 155

```
Met Ala Thr Asn Asp Asp Asp Val Lys Lys Ala Thr Val Ala Ile
1               5                  10                  15

Ala Ala Ala Tyr Asn Asn Gly Gln Glu Ile Asn Gly Phe Lys Ala Gly
            20                  25                  30

Glu Thr Ile Tyr Asp Ile Asp Glu Asp Gly Thr Ile Thr Lys Lys Asp
        35                  40                  45

Ala Thr Ala Ala Asp Val Glu Ala Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125
```

```
Thr Thr Phe Ala Glu Glu Thr Lys Thr Asn Ile Val Lys Ile Asp Glu
        130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
                180                 185                 190

Gln Asn Val Asp Ala Lys Val Lys Ala Ala Glu Thr Ala Ala Gly Lys
                195                 200                 205

Ala Glu Ala Ala Ala Gly Thr Ala Asn Thr Ala Ala Asp Lys Ala Glu
210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
                260                 265                 270

Thr Glu Lys Leu Asp Thr Arg Leu Ala Ser Ala Glu Lys Ser Ile Ala
        275                 280                 285

Asp His Asp Thr Arg Leu Asn Gly Leu Asp Lys Thr Val Ser Asp Leu
        290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Gly Ser Gly Gly Gly Val Ala
                325                 330                 335

Ala Asp Ile Gly Ala Gly Leu Ala Asp Ala Leu Thr Ala Pro Leu Asp
                340                 345                 350

His Lys Asp Lys Gly Leu Gln Ser Leu Thr Leu Asp Gln Ser Val Arg
                355                 360                 365

Lys Asn Glu Lys Leu Lys Leu Ala Ala Gln Gly Ala Glu Lys Thr Tyr
        370                 375                 380

Gly Asn Gly Asp Ser Leu Asn Thr Gly Lys Leu Lys Asn Asp Lys Val
385                 390                 395                 400

Ser Arg Phe Asp Phe Ile Arg Gln Ile Glu Val Asp Gly Gln Leu Ile
                405                 410                 415

Thr Leu Glu Ser Gly Glu Phe Gln Val Tyr Lys Gln Ser His Ser Ala
        420                 425                 430

Leu Thr Ala Phe Gln Thr Glu Gln Ile Gln Asp Ser Glu His Ser Gly
        435                 440                 445

Lys Met Val Ala Lys Arg Gln Phe Arg Ile Gly Asp Ile Ala Gly Glu
        450                 455                 460

His Thr Ser Phe Asp Lys Leu Pro Glu Gly Gly Arg Ala Thr Tyr Arg
465                 470                 475                 480

Gly Thr Ala Phe Gly Ser Asp Asp Ala Gly Gly Lys Leu Thr Tyr Thr
                485                 490                 495

Ile Asp Phe Ala Ala Lys Gln Gly Asn Gly Lys Ile Glu His Leu Lys
                500                 505                 510

Ser Pro Glu Leu Asn Val Asp Leu Ala Ala Ala Asp Ile Lys Pro Asp
        515                 520                 525

Gly Lys Arg His Ala Val Ile Ser Gly Ser Val Leu Tyr Asn Gln Ala
        530                 535                 540

Glu Lys Gly Ser Tyr Ser Leu Gly Ile Phe Gly Gly Lys Ala Gln Glu
```

| | | | | |
|---|---|---|---|---|
| | 545 | 550 | 555 | 560 |

Val Ala Gly Ser Ala Glu Val Lys Thr Val Asn Gly Ile Arg His Ile
                   565                    570                  575

Gly Leu Ala Ala Lys Gln Leu Glu His His His His His His
                 580                  585              590

<210> SEQ ID NO 156
<211> LENGTH: 4170
<212> TYPE: DNA
<213> ORGANISM: Artificial Sequence
<220> FEATURE:
<223> OTHER INFORMATION: 961c-983

<400> SEQUENCE: 156

| | |
|---|---|
| atggccacaa acgacgacga tgttaaaaaa gctgccactg tggccattgc tgctgcctac | 60 |
| aacaatggcc aagaaatcaa cggtttcaaa gctggagaga ccatctacga cattgatgaa | 120 |
| gacggcacaa ttaccaaaaa agacgcaact gcagccgatg ttgaagccga cgactttaaa | 180 |
| ggtctgggtc tgaaaaaagt cgtgactaac ctgaccaaaa ccgtcaatga aacaaacaa | 240 |
| aacgtcgatg ccaaagtaaa agctgcagaa tctgaaatag aaaagttaac aaccaagtta | 300 |
| gcagacactg atgccgcttt agcagatact gatgccgctc tggatgcaac caccaacgcc | 360 |
| ttgaataaat ggagaaaa taacgaca tttgctgaag agactaagac aaatatcgta | 420 |
| aaaattgatg aaaaattaga agccgtggct gataccgtcg acaagcatgc cgaagcattc | 480 |
| aacgatatcg ccgattcatt ggatgaaacc aacactaagg cagacgaagc cgtcaaaacc | 540 |
| gccaatgaag ccaaacagac ggccgaagaa accaaacaaa acgtcgatgc caaagtaaaa | 600 |
| gctgcagaaa ctgcagcagg caaagccgaa gctgccgctg gcacagctaa tactgcagcc | 660 |
| gacaaggccg aagctgtcgc tgcaaaagtt accgacatca aagctgatat cgctacgaac | 720 |
| aaagataata ttgctaaaaa agcaaacagt gccgacgtgt acaccagaga agagtctgac | 780 |
| agcaaatttg tcagaattga tggtctgaac gctactaccg aaaaattgga cacacgcttg | 840 |
| gcttctgctg aaaaatccat tgccgatcac gatactcgcc tgaacggttt ggataaaaca | 900 |
| gtgtcagacc tgcgcaaaga aacccgccaa ggccttgcag acaagccgc gctctccggt | 960 |
| ctgttccaac cttacaacgt gggtggatcc ggcggaggcg gcacttctgc gcccgacttc | 1020 |
| aatgcaggcg gtaccggtat cggcagcaac agcagagcaa caacagcgaa atcagcagca | 1080 |
| gtatcttacg ccggtatcaa gaacgaaatg tgcaaagaca gaagcatgct ctgtgccggt | 1140 |
| cgggatgacg ttgcggttac agacagggat gccaaaatca atgcccccc cccgaatctg | 1200 |
| cataccggag actttccaaa cccaaatgac gcatacaaga atttgatcaa cctcaaacct | 1260 |
| gcaattgaag caggctatac aggacgcggg gtagaggtag gtatcgtcga cacaggcgaa | 1320 |
| tccgtcggca gcatatcctt tcccgaactg tatggcagaa aagaacacgg ctataacgaa | 1380 |
| aattacaaaa actatacggc gtatatgcgg aaggaagcgc tgaagacgg aggcggtaaa | 1440 |
| gacattgaag cttctttcga cgatgaggcc gttatagaga ctgaagcaaa gccgacggat | 1500 |
| atccgccacg taaagaaat cggacacatc gatttggtct cccatattat tggcgggcgt | 1560 |
| tccgtggacg gcagacctgc aggcggtatt gcgcccgatg cgacgctaca cataatgaat | 1620 |
| acgaatgatg aaaccaagaa cgaaatgatg gttcagcca tccgcaatgc atgggtcaag | 1680 |
| ctgggcgaac gtggcgtgcg catcgtcaat aacagttttg gaacaacatc gagggcaggc | 1740 |
| actgccgacc ttttccaaat agccaattcg gaggagcagt accgccaagc gttgctcgac | 1800 |
| tattccggcg tgataaaaac agacgagggt atccgcctga tgcaacagag cgattacggc | 1860 |

```
aacctgtcct accacatccg taataaaaac atgcttttca tcttttcgac aggcaatgac    1920
gcacaagctc agcccaacac atatgccta ttgccatttt atgaaaaga cgctcaaaaa     1980 ggcattatca cagtcgcagg cgtagaccgc agtggagaaa agttcaaacg gaaatgtat    2040 ggagaaccgg gtacagaacc gcttgagtat ggctccaacc attgcggaat tactgccatg   2100
tggtgcctgt cggcacccta tgaagcaagc gtccgtttca cccgtacaaa cccgattcaa   2160
attgccggaa catcctttc cgcacccatc gtaaccggca cggcggctct gctgctgcag    2220
aaatacccgt ggatgagcaa cgacaacctg cgtaccacgt tgctgacgac ggctcaggac   2280
atcggtgcag tcggcgtgga cagcaagttc ggctggggac tgctggatgc gggtaaggcc   2340
atgaacggac ccgcgtcctt tccgttcggc gactttaccg ccgatacgaa aggtacatcc   2400
gatattgcct actccttccg taacgacatt tcaggcacgg gcggcctgat caaaaaaggc   2460
ggcagccaac tgcaactgca cggcaacaac acctatacgg gcaaaaccat tatcgaaggc   2520
ggttcgctgg tgttgtacgg caacaacaaa tcggatatgc gcgtcgaaac caaaggtgcg   2580
ctgatttata cggggcggc atccggcggc agcctgaaca gcgacggcat tgtctatctg    2640
gcagataccg accaatccgg cgcaaacgaa accgtacaca tcaaaggcag tctgcagctg   2700
gacggcaaag gtacgctgta cacacgtttg ggcaaactgc tgaaagtgga cggtacggcg   2760
attatcggcg gcaagctgta catgtcggca cgcggcaagg gggcaggcta tctcaacagt   2820
accggacgac gtgttcccctt cctgagtgcc gccaaaatcg gcaggatta ttctttcttc   2880 acaaacatcg aaaccgacgg cggcctgctg gcttccctcg acagcgtcga aaaacagcg   2940 ggcagtgaag gcgacacgct gtcctattat gtccgtcgcg gcaatgcggc acggactgct   3000
tcggcagcgg cacattccgc gcccgccggt ctgaaaacacg ccgtagaaca gggcggcagc   3060
aatctggaaa acctgatggt cgaactggat gcctccgaat catccgcaac acccgagacg   3120
gttgaaactg cggcagccga ccgcacagat atgcccggca tccgccccta cggcgcaact   3180
ttccgcgcag cggcagccgt acagcatgcg aatgccgccg acggtgtacg catcttcaac   3240
agtctcgccg ctaccgtcta tgccgacagt accgccgccc atgccgatat gcagggacgc   3300
cgcctgaaag ccgtatcgga cgggttggac cacaacggca cgggtctgcg cgtcatcgcg   3360
caaacccaac aggacggtgg aacgtgggaa cagggcggtg ttgaaggcaa aatgcgcggc   3420
agtacccaaa ccgtcggcat tgccgcgaaa accggcgaaa atacgacagc agccgccaca   3480
ctgggcatgg gacgcagcac atggagcgaa aacagtgcaa atgcaaaaac cgacagcatt   3540
agtctgtttg caggcatacg gcacgatgcg ggcgatatcg gctatctcaa aggcctgttc   3600
tcctacggac gctacaaaaa cagcatcagc cgcagcaccg gtgcggacga acatgcggaa   3660
ggcagcgtca acggcacgct gatgcagctg ggcgcactgg gcggtgtcaa cgttccgttt   3720
gccgcaacgg gagatttgac ggtcgaaggc ggtctgcgct acgacctgct caaacaggat   3780
gcattcgccg aaaaaggcag tgctttgggc tggagcggca acagcctcac tgaaggcacg   3840
ctggtcggac tcgcgggtct gaagctgtcg caaccctttga gcgataaagc cgtcctgttt   3900
gcaacggcgg gcgtggaacg cgacctgaac ggacgcgact acacggtaac gggcggcttt   3960
accggcgcga ctgcagcaac cggcaagacg ggggcacgca atatgccgca cacccgtctg   4020
gttgccggcc tggcgcgga tgtcgaattc ggcaacggct ggaacggctt ggcacgttac    4080
agctacgccg gttccaaaca gtacggcaac cacagcggac gagtcggcgt aggctaccgg   4140
ttcctcgagc accaccacca ccaccactga                                    4170

<210> SEQ ID NO 157
```

<211> LENGTH: 1389
<212> TYPE: PRT
<213> ORGANISM: Artificial Sequence
<220> FEATURE:
<223> OTHER INFORMATION: 961c-983

<400> SEQUENCE: 157

```
Met Ala Thr Asn Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
            20                  25                  30

Glu Thr Ile Tyr Asp Ile Asp Glu Asp Gly Thr Ile Thr Lys Lys Asp
        35                  40                  45

Ala Thr Ala Ala Asp Val Glu Ala Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Ala Glu Thr Ala Ala Gly Lys
        195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
        275                 280                 285

Asp His Asp Thr Arg Leu Asn Gly Leu Asp Lys Thr Val Ser Asp Leu
    290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Gly Ser Gly Gly Gly Thr Ser
                325                 330                 335

Ala Pro Asp Phe Asn Ala Gly Gly Thr Gly Ile Gly Ser Asn Ser Arg
            340                 345                 350

Ala Thr Thr Ala Lys Ser Ala Ala Val Ser Tyr Ala Gly Ile Lys Asn
        355                 360                 365

Glu Met Cys Lys Asp Arg Ser Met Leu Cys Ala Gly Arg Asp Asp Val
    370                 375                 380
```

```
Ala Val Thr Asp Arg Asp Ala Lys Ile Asn Ala Pro Pro Asn Leu
385                 390                 395                 400

His Thr Gly Asp Phe Pro Asn Pro Asn Asp Ala Tyr Lys Asn Leu Ile
                405                 410                 415

Asn Leu Lys Pro Ala Ile Glu Ala Gly Tyr Thr Gly Arg Gly Val Glu
            420                 425                 430

Val Gly Ile Val Asp Thr Gly Glu Ser Val Gly Ser Ile Ser Phe Pro
        435                 440                 445

Glu Leu Tyr Gly Arg Lys Glu His Gly Tyr Asn Glu Asn Tyr Lys Asn
    450                 455                 460

Tyr Thr Ala Tyr Met Arg Lys Glu Ala Pro Glu Asp Gly Gly Lys
465                 470                 475                 480

Asp Ile Glu Ala Ser Phe Asp Asp Glu Ala Val Ile Glu Thr Glu Ala
                485                 490                 495

Lys Pro Thr Asp Ile Arg His Val Lys Glu Ile Gly His Ile Asp Leu
            500                 505                 510

Val Ser His Ile Ile Gly Gly Arg Ser Val Asp Gly Arg Pro Ala Gly
        515                 520                 525

Gly Ile Ala Pro Asp Ala Thr Leu His Ile Met Asn Thr Asn Asp Glu
530                 535                 540

Thr Lys Asn Glu Met Met Val Ala Ala Ile Arg Asn Ala Trp Val Lys
545                 550                 555                 560

Leu Gly Glu Arg Gly Val Arg Ile Val Asn Asn Ser Phe Gly Thr Thr
                565                 570                 575

Ser Arg Ala Gly Thr Ala Asp Leu Phe Gln Ile Ala Asn Ser Glu Glu
            580                 585                 590

Gln Tyr Arg Gln Ala Leu Leu Asp Tyr Ser Gly Gly Asp Lys Thr Asp
        595                 600                 605

Glu Gly Ile Arg Leu Met Gln Gln Ser Asp Tyr Gly Asn Leu Ser Tyr
    610                 615                 620

His Ile Arg Asn Lys Asn Met Leu Phe Ile Phe Ser Thr Gly Asn Asp
625                 630                 635                 640

Ala Gln Ala Gln Pro Asn Thr Tyr Ala Leu Leu Pro Phe Tyr Glu Lys
                645                 650                 655

Asp Ala Gln Lys Gly Ile Ile Thr Val Ala Gly Val Asp Arg Ser Gly
            660                 665                 670

Glu Lys Phe Lys Arg Glu Met Tyr Gly Glu Pro Gly Thr Glu Pro Leu
        675                 680                 685

Glu Tyr Gly Ser Asn His Cys Gly Ile Thr Ala Met Trp Cys Leu Ser
    690                 695                 700

Ala Pro Tyr Glu Ala Ser Val Arg Phe Thr Arg Thr Asn Pro Ile Gln
705                 710                 715                 720

Ile Ala Gly Thr Ser Phe Ser Ala Pro Ile Val Thr Gly Thr Ala Ala
                725                 730                 735

Leu Leu Leu Gln Lys Tyr Pro Trp Met Ser Asn Asp Asn Leu Arg Thr
            740                 745                 750

Thr Leu Leu Thr Thr Ala Gln Asp Ile Gly Ala Val Gly Val Asp Ser
        755                 760                 765

Lys Phe Gly Trp Gly Leu Leu Asp Ala Gly Lys Ala Met Asn Gly Pro
    770                 775                 780

Ala Ser Phe Pro Phe Gly Asp Phe Thr Ala Asp Thr Lys Gly Thr Ser
785                 790                 795                 800

Asp Ile Ala Tyr Ser Phe Arg Asn Asp Ile Ser Gly Thr Gly Gly Leu
                805                 810                 815
```

-continued

Ile Lys Lys Gly Gly Ser Gln Leu Gln Leu His Gly Asn Asn Thr Tyr
                820                 825                 830

Thr Gly Lys Thr Ile Ile Glu Gly Gly Ser Leu Val Leu Tyr Gly Asn
            835                 840                 845

Asn Lys Ser Asp Met Arg Val Glu Thr Lys Gly Ala Leu Ile Tyr Asn
850                 855                 860

Gly Ala Ala Ser Gly Gly Ser Leu Asn Ser Asp Gly Ile Val Tyr Leu
865                 870                 875                 880

Ala Asp Thr Asp Gln Ser Gly Ala Asn Glu Thr Val His Ile Lys Gly
                885                 890                 895

Ser Leu Gln Leu Asp Gly Lys Gly Thr Leu Tyr Thr Arg Leu Gly Lys
                900                 905                 910

Leu Leu Lys Val Asp Gly Thr Ala Ile Ile Gly Gly Lys Leu Tyr Met
                915                 920                 925

Ser Ala Arg Gly Lys Gly Ala Gly Tyr Leu Asn Ser Thr Gly Arg Arg
            930                 935                 940

Val Pro Phe Leu Ser Ala Ala Lys Ile Gly Gln Asp Tyr Ser Phe Phe
945                 950                 955                 960

Thr Asn Ile Glu Thr Asp Gly Gly Leu Leu Ala Ser Leu Asp Ser Val
                965                 970                 975

Glu Lys Thr Ala Gly Ser Glu Gly Asp Thr Leu Ser Tyr Tyr Val Arg
            980                 985                 990

Arg Gly Asn Ala Ala Arg Thr Ala Ser Ala Ala Ala His Ser Ala Pro
        995                 1000                1005

Ala Gly Leu Lys His Ala Val Glu Gln Gly Gly Ser Asn Leu Glu Asn
    1010                1015                1020

Leu Met Val Glu Leu Asp Ala Ser Glu Ser Ser Ala Thr Pro Glu Thr
1025                1030                1035                1040

Val Glu Thr Ala Ala Ala Asp Arg Thr Asp Met Pro Gly Ile Arg Pro
                1045                1050                1055

Tyr Gly Ala Thr Phe Arg Ala Ala Ala Val Gln His Ala Asn Ala
                1060                1065                1070

Ala Asp Gly Val Arg Ile Phe Asn Ser Leu Ala Ala Thr Val Tyr Ala
                1075                1080                1085

Asp Ser Thr Ala Ala His Ala Asp Met Gln Gly Arg Arg Leu Lys Ala
    1090                1095                1100

Val Ser Asp Gly Leu Asp His Asn Gly Thr Gly Leu Arg Val Ile Ala
1105                1110                1115                1120

Gln Thr Gln Gln Asp Gly Gly Thr Trp Glu Gln Gly Val Glu Gly
                1125                1130                1135

Lys Met Arg Gly Ser Thr Gln Thr Val Gly Ile Ala Ala Lys Thr Gly
                1140                1145                1150

Glu Asn Thr Thr Ala Ala Ala Thr Leu Gly Met Gly Arg Ser Thr Trp
    1155                1160                1165

Ser Glu Asn Ser Ala Asn Ala Lys Thr Asp Ser Ile Ser Leu Phe Ala
    1170                1175                1180

Gly Ile Arg His Asp Ala Gly Asp Ile Gly Tyr Leu Lys Gly Leu Phe
1185                1190                1195                1200

Ser Tyr Gly Arg Tyr Lys Asn Ser Ile Ser Arg Ser Thr Gly Ala Asp
                1205                1210                1215

Glu His Ala Glu Gly Ser Val Asn Gly Thr Leu Met Gln Leu Gly Ala
            1220                1225                1230

Leu Gly Gly Val Asn Val Pro Phe Ala Ala Thr Gly Asp Leu Thr Val

Glu Gly Gly Leu Arg Tyr Asp Leu Leu Lys Gln Asp Ala Phe Ala Glu
            1250            1255            1260
Lys Gly Ser Ala Leu Gly Trp Ser Gly Asn Ser Leu Thr Glu Gly Thr
1265            1270            1275            1280
Leu Val Gly Leu Ala Gly Leu Lys Leu Ser Gln Pro Leu Ser Asp Lys
                1285            1290            1295
Ala Val Leu Phe Ala Thr Ala Gly Val Glu Arg Asp Leu Asn Gly Arg
            1300            1305            1310
Asp Tyr Thr Val Thr Gly Gly Phe Thr Gly Ala Thr Ala Thr Gly
        1315            1320            1325
Lys Thr Gly Ala Arg Asn Met Pro His Thr Arg Leu Val Ala Gly Leu
    1330            1335            1340
Gly Ala Asp Val Glu Phe Gly Asn Gly Trp Asn Gly Leu Ala Arg Tyr
1345            1350            1355            1360
Ser Tyr Ala Gly Ser Lys Gln Tyr Gly Asn His Ser Gly Arg Val Gly
                1365            1370            1375
Val Gly Tyr Arg Phe Leu Glu His His His His His His
        1380            1385

<210> SEQ ID NO 158
<211> LENGTH: 2304
<212> TYPE: DNA
<213> ORGANISM: Artificial Sequence
<220> FEATURE:
<223> OTHER INFORMATION: 961cL-ORF46.1

<400> SEQUENCE: 158
atgaaacact tccatccaa agtactgacc acagccatcc ttgccacttt ctgtagcggc      60
gcactggcag ccacaaacga cgacgatgtt aaaaaagctg ccactgtggc cattgctgct    120
gcctacaaca atggccaaga atcaacggt ttcaaagctg agagaccat ctacgacatt     180 gatgaagacg gcacaattac caaaaaagac gcaactgcag ccgatgttga agccgacgac    240
tttaaaggtc tgggtctgaa aaagtcgtg actaacctga ccaaaaccgt caatgaaaac    300
aaacaaaacg tcgatgccaa agtaaaagct gcagaatctg aaatagaaaa gttaacaacc    360
aagttagcag acactgatgc cgctttagca gatactgatg ccgctctgga tgcaaccacc    420
aacgccttga ataaattggg agaaaatata acgacatttg ctgaagagac taagacaaat    480
atcgtaaaaa ttgatgaaaa attagaagcc gtggctgata ccgtcgacaa gcatgccgaa    540
gcattcaacg atatcgccga ttcattggat gaaaccaaca ctaaggcaga cgaagccgtc    600
aaaccgccca tgaagccaa acagacggcc gaagaaacca aacaaaacgt cgatgccaaa    660
gtaaaagctg cagaaactgc agcaggcaaa gccgaagctg ccgctggcac agctaatact    720
gcagccgaca aggccgaagc tgtcgctgca aaagttaccg acatcaaagc tgatatcgct    780
acgaacaaag ataatattgc taaaaaagca acagtgccg acgtgtacac cagagaagag    840
tctgacagca aatttgtcag aattgatggt ctgaacgcta ctaccgaaaa attggacaca    900
cgcttggctt ctgctgaaaa atccattgcc gatcacgata ctcgcctgaa cggtttggat    960
aaaacagtgt cagacctgcg caaagaaacc cgccaaggcc ttgcagaaca agccgcgctc   1020
tccggtctgt tccaacctta acgtgggt ggatccggag gaggaggatc agatttggca     1080
aacgattctt ttatccggca ggttctcgac cgtcagcatt tcgaaccccga cgggaaatac    1140 cacctattcg gcagcagggg ggaacttgcc gagcgcagcg ccatatcgg attgggaaaa    1200 atacaaagcc atcagttggg caacctgatg attcaacagg cggccattaa aggaaatatc    1260

```
ggctacattg tccgctttc cgatcacggg cacgaagtcc attcccctt cgacaaccat    1320 gcctcacatt ccgattctga tgaagccggt agtcccgttg acggatttag cctttaccgc    1380
atccattggg acggatacga acaccatccc gccgacggct atgacgggcc acagggcggc    1440
ggctatcccg ctcccaaagg cgcgagggat atatacagct acgacataaa aggcgttgcc    1500
caaaatatcc gcctcaacct gaccgacaac cgcagcaccg acaacggct tgccgaccgt    1560 ttccacaatg ccggtagtat gctgacgcaa ggagtaggcg acggattcaa acgcgccacc    1620
cgatacagcc ccgagctgga cagatcgggc aatgccgccg aagccttcaa cggcactgca    1680
gatatcgtta aaaacatcat cggcgcggca ggagaaattg tcggcgcagg cgatgccgtg    1740
cagggcataa gcgaaggctc aaacattgct gtcatgcacg gcttgggtct gctttccacc    1800
gaaaacaaga tggcgcgcat caacgatttg gcagatatgg cgcaactcaa agactatgcc    1860
gcagcagcca tccgcgattg ggcagtccaa accccaatg ccgcacaagg catgaagcc    1920 gtcagcaata tctttatggc agccatcccc atcaaaggga ttggagctgt tcggggaaaa    1980
tacggcttgg gcggcatcac ggcacatcct atcaagcggt cgcagatggg cgcgatcgca    2040
ttgccgaaag ggaaatccgc cgtcagcgac aattttgccg atgcggcata cgccaaatac    2100 ccgtccccttt accattcccg aaatatccgt tcaaacttgg agcagcgtta cggcaaagaa    2160
aacatcacct cctcaaccgt gccgccgtca acggcaaaaa atgtcaaact ggcagaccaa    2220
cgccacccga agacaggcgt accgtttgac ggtaaagggt ttccgaattt tgagaagcac    2280
gtgaaatatg atacgtaact cgag                                          2304
```

<210> SEQ ID NO 159
<211> LENGTH: 765
<212> TYPE: PRT
<213> ORGANISM: Artificial Sequence
<220> FEATURE:
<223> OTHER INFORMATION: 961cL-ORF46.1

<400> SEQUENCE: 159

```
Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
                20                  25                  30

Ala Ala Thr Val Ala Ile Ala Ala Ala Tyr Asn Asn Gly Gln Glu Ile
            35                  40                  45

Asn Gly Phe Lys Ala Gly Glu Thr Ile Tyr Asp Ile Asp Glu Asp Gly
        50                  55                  60

Thr Ile Thr Lys Lys Asp Ala Thr Ala Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
        115                 120                 125

Leu Ala Asp Thr Asp Ala Ala Leu Asp Ala Thr Asn Ala Leu Asn
    130                 135                 140

Lys Leu Gly Glu Asn Ile Thr Thr Phe Ala Glu Gly Thr Lys Thr Asn
145                 150                 155                 160

Ile Val Lys Ile Asp Glu Lys Leu Glu Ala Val Ala Asp Thr Val Asp
                165                 170                 175
```

-continued

```
Lys His Ala Glu Ala Phe Asn Asp Ile Ala Asp Ser Leu Asp Glu Thr
            180                 185                 190

Asn Thr Lys Ala Asp Glu Ala Val Lys Thr Ala Asn Glu Ala Lys Gln
        195                 200                 205

Thr Ala Glu Glu Thr Lys Gln Asn Val Asp Ala Lys Val Lys Ala Ala
210                 215                 220

Glu Thr Ala Ala Gly Lys Ala Glu Ala Ala Gly Thr Ala Asn Thr
225                 230                 235                 240

Ala Ala Asp Lys Ala Glu Ala Val Ala Lys Val Thr Asp Ile Lys
                245                 250                 255

Ala Asp Ile Ala Thr Asn Lys Asp Asn Ile Ala Lys Lys Ala Asn Ser
            260                 265                 270

Ala Asp Val Tyr Thr Arg Glu Glu Ser Asp Ser Lys Phe Val Arg Ile
        275                 280                 285

Asp Gly Leu Asn Ala Thr Thr Glu Lys Leu Asp Thr Arg Leu Ala Ser
        290                 295                 300

Ala Glu Lys Ser Ile Ala Asp His Asp Thr Arg Leu Asn Gly Leu Asp
305                 310                 315                 320

Lys Thr Val Ser Asp Leu Arg Lys Glu Thr Arg Gln Gly Leu Ala Glu
                325                 330                 335

Gln Ala Ala Leu Ser Gly Leu Phe Gln Pro Tyr Asn Val Gly Gly Ser
            340                 345                 350

Gly Gly Gly Gly Ser Asp Leu Ala Asn Asp Ser Phe Ile Arg Gln Val
        355                 360                 365

Leu Asp Arg Gln His Phe Glu Pro Asp Gly Lys Tyr His Leu Phe Gly
        370                 375                 380

Ser Arg Gly Glu Leu Ala Glu Arg Ser Gly His Ile Gly Leu Gly Lys
385                 390                 395                 400

Ile Gln Ser His Gln Leu Gly Asn Leu Met Ile Gln Gln Ala Ala Ile
                405                 410                 415

Lys Gly Asn Ile Gly Tyr Ile Val Arg Phe Ser Asp His Gly His Glu
            420                 425                 430

Val His Ser Pro Phe Asp Asn His Ala Ser His Ser Asp Ser Asp Glu
        435                 440                 445

Ala Gly Ser Pro Val Asp Gly Phe Ser Leu Tyr Arg Ile His Trp Asp
450                 455                 460

Gly Tyr Glu His His Pro Ala Asp Gly Tyr Asp Gly Pro Gln Gly Gly
465                 470                 475                 480

Gly Tyr Pro Ala Pro Lys Gly Ala Arg Asp Ile Tyr Ser Tyr Asp Ile
                485                 490                 495

Lys Gly Val Ala Gln Asn Ile Arg Leu Asn Leu Thr Asp Asn Arg Ser
            500                 505                 510

Thr Gly Gln Arg Leu Ala Asp Arg Phe His Asn Ala Gly Ser Met Leu
        515                 520                 525

Thr Gln Gly Val Gly Asp Gly Phe Lys Arg Ala Thr Arg Tyr Ser Pro
        530                 535                 540

Glu Leu Asp Arg Ser Gly Asn Ala Ala Glu Ala Phe Asn Gly Thr Ala
545                 550                 555                 560

Asp Ile Val Lys Asn Ile Ile Gly Ala Ala Gly Glu Ile Val Gly Ala
                565                 570                 575

Gly Asp Ala Val Gln Gly Ile Ser Glu Gly Ser Asn Ile Ala Val Met
            580                 585                 590

His Gly Leu Gly Leu Leu Ser Thr Glu Asn Lys Met Ala Arg Ile Asn
        595                 600                 605
```

```
Asp Leu Ala Asp Met Ala Gln Leu Lys Asp Tyr Ala Ala Ala Ala Ile
            610                 615                 620

Arg Asp Trp Ala Val Gln Asn Pro Asn Ala Ala Gln Gly Ile Glu Ala
625                 630                 635                 640

Val Ser Asn Ile Phe Met Ala Ala Ile Pro Ile Lys Gly Ile Gly Ala
                645                 650                 655

Val Arg Gly Lys Tyr Gly Leu Gly Ile Thr Ala His Pro Ile Lys
            660                 665                 670

Arg Ser Gln Met Gly Ala Ile Ala Leu Pro Lys Gly Lys Ser Ala Val
            675                 680                 685

Ser Asp Asn Phe Ala Asp Ala Ala Tyr Ala Lys Tyr Pro Ser Pro Tyr
        690                 695                 700

His Ser Arg Asn Ile Arg Ser Asn Leu Glu Arg Tyr Gly Lys Glu
705                 710                 715                 720

Asn Ile Thr Ser Thr Val Pro Pro Ser Asn Gly Lys Asn Val Lys
                725                 730                 735

Leu Ala Asp Gln Arg His Pro Lys Thr Gly Val Pro Phe Asp Gly Lys
            740                 745                 750

Gly Phe Pro Asn Phe Glu Lys His Val Lys Tyr Asp Thr
        755                 760                 765

<210> SEQ ID NO 160
<211> LENGTH: 1839
<212> TYPE: DNA
<213> ORGANISM: Artificial Sequence
<220> FEATURE:
<223> OTHER INFORMATION: 961cL-741

<400> SEQUENCE: 160
atgaaacact ttccatccaa agtactgacc acagccatcc ttgccacttt ctgtagcggc      60
gcactggcag ccacaaacga cgacgatgtt aaaaaagctg ccactgtggc cattgctgct     120
gcctacaaca atggccaaga atcaacggt ttcaaagctg agagaccat ctacgacatt      180 gatgaagacg gcacaattac caaaaaagac gcaactgcag ccgatgttga agccgacgac     240
tttaaaggtc tgggtctgaa aaagtcgtg actaacctga ccaaaaccgt caatgaaaac     300
aaacaaaacg tcgatgccaa agtaaaagct gcagaatctg aaatagaaaa gttaacaacc     360
aagttagcag acactgatgc cgctttagca gatactgatg ccgctctgga tgcaaccacc     420
aacgccttga taaaattggg agaaaatata cgacatttg ctgaagagac taagacaaat     480
atcgtaaaaa ttgatgaaaa attagaagcc gtggctgata ccgtcgacaa gcatgccgaa     540
gcattcaacg tatcgccga ttcattggat gaaaccaaca ctaaggcaga cgaagccgtc     600
aaaaccgcca atgaagccaa acagacggcc gaagaaacca acaaaacgt cgatgccaaa     660 gtaaaagctg cagaaactgc agcaggcaaa gccgaagctg ccgctggcac agctaatact     720
gcagccgaca aggccgaagc tgtcgctgca aaagttaccg catcaaagc tgatatcgct     780 acgaacaaag ataatattgc taaaaaagca aacagtgccg acgtgtacac cagagaagag     840
tctgacagca aatttgtcag aattgatggt ctgaacgcta ctaccgaaaa attggacaca     900
cgcttggctt ctgctgaaaa atccattgcc gatcacgata tcgcctgaa cggtttggat     960 aaacagtgt cagacctgcg caagaaacc cgccaaggcc ttgcagaaca agccgcgctc    1020
tccggtctgt tccaacctta acgtgggt ggatccggag ggggtggtgt cgccgccgac    1080
atcggtgcgg ggcttgccga tgcactaacc gcaccgctcg accataaaga caaaggtttg    1140
cagtctttga cgctggatca gtccgtcagg aaaaacgaga aactgaagct ggcggcacaa    1200
```

```
ggtgcggaaa aaacttatgg aaacggtgac agcctcaata cgggcaaatt gaagaacgac    1260
aaggtcagcc gtttcgactt tatccgccaa atcgaagtgg acgggcagct cattaccttg    1320
gagagtggag agttccaagt atacaaacaa agccattccg ccttaaccgc ctttcagacc    1380
gagcaaatac aagattcgga gcattccggg aagatggttg cgaaacgcca gttcagaatc    1440
ggcgacatag cgggcgaaca tacatctttt gacaagcttc ccgaaggcgg cagggcgaca    1500
tatcgcggga cggcgttcgg ttcagacgat gccggcggaa aactgaccta caccatagat    1560
ttcgccgcca agcagggaaa cggcaaaatc gaacatttga atcgccaga actcaatgtc     1620 gacctggccg ccgccgatat caagccggat ggaaaacgcc atgccgtcat cagcggttcc    1680
gtcctttaca accaagccga gaaggcagt tactccctcg gtatctttgg cggaaaagcc     1740
caggaagttg ccggcagcgc ggaagtgaaa accgtaaacg gcatacgcca tatcggcctt    1800
gccgccaagc aactcgagca ccaccaccac caccactga                           1839
```

```
<210> SEQ ID NO 161
<211> LENGTH: 612
<212> TYPE: PRT
<213> ORGANISM: Artificial Sequence
<220> FEATURE:
<223> OTHER INFORMATION: 961cL-741

<400> SEQUENCE: 161

Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
            20                  25                  30

Ala Ala Thr Val Ala Ile Ala Ala Ala Tyr Asn Asn Gly Gln Glu Ile
        35                  40                  45

Asn Gly Phe Lys Ala Gly Glu Thr Ile Tyr Asp Ile Asp Glu Asp Gly
    50                  55                  60

Thr Ile Thr Lys Lys Asp Ala Thr Ala Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
        115                 120                 125

Leu Ala Asp Thr Asp Ala Ala Leu Asp Ala Thr Thr Asn Ala Leu Asn
    130                 135                 140

Lys Leu Gly Glu Asn Ile Thr Thr Phe Ala Glu Glu Thr Lys Thr Asn
145                 150                 155                 160

Ile Val Lys Ile Asp Glu Lys Leu Glu Ala Val Ala Asp Thr Val Asp
                165                 170                 175

Lys His Ala Glu Ala Phe Asn Asp Ile Ala Asp Ser Leu Asp Glu Thr
            180                 185                 190

Asn Thr Lys Ala Asp Glu Ala Val Lys Thr Ala Asn Glu Ala Lys Gln
        195                 200                 205

Thr Ala Glu Glu Thr Lys Gln Asn Val Asp Ala Lys Val Lys Ala Ala
    210                 215                 220

Glu Thr Ala Ala Gly Lys Ala Glu Ala Ala Gly Thr Ala Asn Thr
225                 230                 235                 240

Ala Ala Asp Lys Ala Glu Ala Val Ala Lys Val Thr Asp Ile Lys
                245                 250                 255
```

```
Ala Asp Ile Ala Thr Asn Lys Asp Asn Ile Ala Lys Lys Ala Asn Ser
            260                 265                 270

Ala Asp Val Tyr Thr Arg Glu Glu Ser Asp Ser Lys Phe Val Arg Ile
            275                 280                 285

Asp Gly Leu Asn Ala Thr Thr Glu Lys Leu Asp Thr Arg Leu Ala Ser
290                 295                 300

Ala Glu Lys Ser Ile Ala Asp His Asp Thr Arg Leu Asn Gly Leu Asp
305                 310                 315                 320

Lys Thr Val Ser Asp Leu Arg Lys Glu Thr Arg Gln Gly Leu Ala Glu
                325                 330                 335

Gln Ala Ala Leu Ser Gly Leu Phe Gln Pro Tyr Asn Val Gly Gly Ser
                340                 345                 350

Gly Gly Gly Gly Val Ala Ala Asp Ile Gly Ala Gly Leu Ala Asp Ala
            355                 360                 365

Leu Thr Ala Pro Leu Asp His Lys Asp Lys Gly Leu Gln Ser Leu Thr
370                 375                 380

Leu Asp Gln Ser Val Arg Lys Asn Glu Lys Leu Lys Leu Ala Ala Gln
385                 390                 395                 400

Gly Ala Glu Lys Thr Tyr Gly Asn Gly Asp Ser Leu Asn Thr Gly Lys
                405                 410                 415

Leu Lys Asn Asp Lys Val Ser Arg Phe Asp Phe Ile Arg Gln Ile Glu
                420                 425                 430

Val Asp Gly Gln Leu Ile Thr Leu Glu Ser Gly Glu Phe Gln Val Tyr
            435                 440                 445

Lys Gln Ser His Ser Ala Leu Thr Ala Phe Gln Thr Glu Gln Ile Gln
450                 455                 460

Asp Ser Glu His Ser Gly Lys Met Val Ala Lys Arg Gln Phe Arg Ile
465                 470                 475                 480

Gly Asp Ile Ala Gly Glu His Thr Ser Phe Asp Lys Leu Pro Glu Gly
                485                 490                 495

Gly Arg Ala Thr Tyr Arg Gly Thr Ala Phe Gly Ser Asp Asp Ala Gly
                500                 505                 510

Gly Lys Leu Thr Tyr Thr Ile Asp Phe Ala Ala Lys Gln Gly Asn Gly
            515                 520                 525

Lys Ile Glu His Leu Lys Ser Pro Glu Leu Asn Val Asp Leu Ala Ala
530                 535                 540

Ala Asp Ile Lys Pro Asp Gly Lys Arg His Ala Val Ile Ser Gly Ser
545                 550                 555                 560

Val Leu Tyr Asn Gln Ala Glu Lys Gly Ser Tyr Ser Leu Gly Ile Phe
                565                 570                 575

Gly Gly Lys Ala Gln Glu Val Ala Gly Ser Ala Glu Val Lys Thr Val
            580                 585                 590

Asn Gly Ile Arg His Ile Gly Leu Ala Ala Lys Gln Leu Glu His His
            595                 600                 605

His His His His
        610

<210> SEQ ID NO 162
<211> LENGTH: 4218
<212> TYPE: DNA
<213> ORGANISM: Artificial Sequence
<220> FEATURE:
<223> OTHER INFORMATION: 961cL-983

<400> SEQUENCE: 162
```

```
atgaaacact tttccatccaa agtactgacc acagccatcc ttgccacttt ctgtagcggc    60
gcactggcag ccacaaacga cgacgatgtt aaaaaagctg ccactgtggc cattgctgct   120
gcctacaaca atggccaaga atcaacggt ttcaaagctg agagaccat ctacgacatt    180
gatgaagacg gcacaattac caaaaaagac gcaactgcag ccgatgttga agccgacgac   240
tttaaaggtc tgggtctgaa aaaagtcgtg actaacctga ccaaaaccgt caatgaaaac   300
aaacaaaacg tcgatgccaa agtaaaagct gcagaatctg aaatagaaaa gttaacaacc   360
aagttagcag acactgatgc cgctttagca gatactgatg ccgctctgga tgcaaccacc   420
aacgccttga ataaattggg agaaaatata cgacatttg ctgaagagac taagacaaat    480
atcgtaaaaa ttgatgaaaa attagaagcc gtggctgata ccgtcgacaa gcatgccgaa   540
gcattcaacg atatcgccga ttcattggat gaaaccaaca ctaaggcaga cgaagccgtc   600
aaaaccgcca atgaagccaa acagacggcc gaagaaacca acaaaacgt cgatgccaaa    660
gtaaaagctg cagaaactgc agcaggcaaa gccgaagctg ccgctggcac agctaatact   720
gcagccgaca aggccgaagc tgtcgctgca aaagttaccg acatcaaagc tgatatcgct   780
acgaacaaag ataatattgc taaaaaagca aacagtgccg acgtgtacac cagagaagag   840
tctgacagca aatttgtcag aattgatggt ctgaacgcta ctaccgaaaa attggacaca   900
cgcttggctt ctgctgaaaa atccattgcc gatcacgata ctcgcctgaa cggtttggat   960
aaaacagtgt cagacctgcg caaagaaacc cgccaaggcc ttgcagaaca gccgcgctc   1020
tccggtctgt tccaacctta caacgtgggt ggatccggcg gaggcggcac ttctgcgccc  1080
gacttcaatg caggcggtac cggtatcggc agcaacagca gagcaacaac agcgaaatca  1140
gcagcagtat cttacgccgg tatcaagaac gaaatgtgca agacagaag catgctctgt   1200
gccggtcggg atgacgttgc ggttacagac agggatgcca aatcaatgc ccccccccg    1260
aatctgcata ccggagactt tccaaaccca aatgacgcat acaagaattt gatcaacctc  1320
aaacctgcaa ttgaagcagg ctatacagga cgcggggtag aggtaggtat cgtcgacaca  1380
ggcgaatccg tcggcagcat atcctttccc gaactgtatg cagaaaaga acacggctat   1440
aacgaaaatt acaaaaacta tacggcgtat atgcggaagg aagcgcctga agacggaggc  1500
ggtaaagaca ttgaagcttc tttcgacgat gaggccgtta tagagactga agcaaagccg  1560
acggatatcc gccacgtaaa agaaatcgga cacatcgatt ggtctcccta tattattggc  1620
gggcgttccg tggacggcag acctgcaggc ggtattgcgc ccgatgcgac gctacacata  1680
atgaatacga atgatgaaac caagaacgaa atgatggttg cagccatccg caatgcatgg  1740
gtcaagctgg gcgaacgtgg cgtgcgcatc gtcaataaca gttttggaac aacatcgagg  1800
gcaggcactg ccgacctttt ccaaatagcc aattcggagg agcagtaccg ccaagcgttg  1860
ctcgactatt ccggcggtga taaaacagac gagggtatcc gcctgatgca acagagcgat  1920
tacggcaacc tgtcctacca catccgtaat aaaaacatgc ttttcatctt ttcgacaggc  1980
aatgacgcac aagctcagcc caacacatat gccctattgc catttatga aaaagacgct   2040
caaaaaggca ttatcacagt cgcaggcgta gaccgcagtg agaaaagtt caaacgggaa   2100
atgtatggag aaccgggtac agaaccgctt gagtatggct ccaaccattg cggaattact  2160
gccatgtggt gcctgtcggc acccatgaa gcaagcgtcc gtttcacccg tacaaacccg   2220
attcaaattg ccggaacatc cttttccgca cccatcgtaa ccggcacggc ggctctgctg  2280
ctgcagaaat acccgtggat gagcaacgac aacctgcgta ccacgttgct gacgacggc   2340
caggacatcg gtgcagtcgg cgtggacagc aagttcggct ggggactgct ggatgcgggt  2400
```

```
aaggccatga acggacccgc gtcctttccg ttcggcgact ttaccgccga tacgaaaggt    2460
acatccgata ttgcctactc cttccgtaac gacatttcag gcacggggcgg cctgatcaaa    2520 aaaggcggca gccaactgca actgcacggc aacaacacct atacgggcaa accattatc     2580 gaaggcggtt cgctggtgtt gtacggcaac aacaaatcgg atatgcgcgt cgaaaccaaa    2640
ggtgcgctga tttataacgg ggcggcatcc ggcggcagcc tgaacagcga cggcattgtc    2700
tatctggcag ataccgacca atccggcgca acgaaaccg tacacatcaa aggcagtctg     2760
cagctggacg gcaaaggtac gctgtacaca cgtttgggca aactgctgaa agtggacggt    2820
acggcgatta tcggcggcaa gctgtacatg tcggcacgcg gcaaggggggc aggctatctc    2880 aacagtaccg gacgacgtgt tcccttcctg agtgccgcca aaatcgggca ggattattct    2940
ttcttcacaa acatcgaaac cgacggcggc ctgctggctt ccctcgacag cgtcgaaaaa    3000
acagcgggca gtgaaggcga cacgctgtcc tattatgtcc gtcgcggcaa tgcggcacgg    3060
actgcttcgg cagcggcaca ttccgcgccc gccggtctga acacgccgt agaacagggc    3120 ggcagcaatc tggaaaacct gatggtcgaa ctggatgcct ccgaatcatc cgcaacaccc    3180
gagacggttg aaactgcggc agccgaccgc acagatatgc cggcatccg ccctacggc     3240 gcaactttcc gcgcagcggc agccgtacag catgcgaatg ccgccgacgg tgtacgcatc    3300
ttcaacagtc tcgccgctac cgtctatgcc gacagtaccg ccgcccatgc cgatatgcag    3360
ggacgccgcc tgaaagccgt atcggacggg ttggaccaca acggcacggg tctgcgcgtc    3420
atcgcgcaaa cccaacagga cggtggaacg tgggaacagg gcggtgttga aggcaaaatg    3480
cgcggcagta cccaaaccgt cggcattgcc gcgaaaaccg gcgaaaatac gacagcagcc    3540 gcccacactgg gcatgggacg cagcacatgg agcgaaaaca gtgcaaatgc aaaaaccgac    3600
agcattagtc tgtttgcagg catacggcac gatgcgggcg atatcggcta tctcaaaggc    3660
ctgttctcct acggacgcta caaaaacagc atcagccgca gcaccggtgc ggacgaacat    3720
gcggaaggca gcgtcaacgg cacgctgatg cagctgggcg cactgggcgg tgtcaacgtt    3780
ccgtttgccg caacgggaga tttgacggtc gaaggcggtc tgcgctacga cctgctcaaa    3840
caggatgcat cgccgaaaaa aggcagtgct ttgggctgga gcggcaacag cctcactgaa    3900
ggcacgctgg tcggactcgc gggtctgaag ctgtcgcaac ccttgagcga taaagccgtc    3960
ctgtttgcaa cggcgggcgt ggaacgcgac ctgaacggac gcgactacac ggtaacgggc    4020
ggctttaccg gcgcgactgc agcaaccggc aagacggggg cacgcaatat gccgcacacc    4080
cgtctggttg ccgcctgggg cgcggatgtc gaattcggca acggctggaa cggcttggca    4140
cgttacagct acgccggttc caaacagtac ggcaaccaca gcggacgagt cggcgtaggc    4200
taccggttct gactcgag                                                  4218
```

<210> SEQ ID NO 163
<211> LENGTH: 1403
<212> TYPE: PRT
<213> ORGANISM: Artificial Sequence
<220> FEATURE:
<223> OTHER INFORMATION: 961cL-983

<400> SEQUENCE: 163

```
Met Lys His Phe Pro Ser Lys Val Leu Thr Thr Ala Ile Leu Ala Thr
  1               5                  10                  15

Phe Cys Ser Gly Ala Leu Ala Ala Thr Asn Asp Asp Val Lys Lys
                 20                  25                  30

Ala Ala Thr Val Ala Ile Ala Ala Tyr Asn Asn Gly Gln Glu Ile
         35                  40                  45
```

```
Asn Gly Phe Lys Ala Gly Glu Thr Ile Tyr Asp Ile Asp Glu Asp Gly
    50                  55                  60
Thr Ile Thr Lys Lys Asp Ala Thr Ala Asp Val Glu Ala Asp Asp
65                  70                  75                  80
Phe Lys Gly Leu Gly Leu Lys Lys Val Val Thr Asn Leu Thr Lys Thr
                    85                  90                  95
Val Asn Glu Asn Lys Gln Asn Val Asp Ala Lys Val Lys Ala Ala Glu
                100                 105                 110
Ser Glu Ile Glu Lys Leu Thr Thr Lys Leu Ala Asp Thr Asp Ala Ala
                115                 120                 125
Leu Ala Asp Thr Asp Ala Ala Leu Asp Ala Thr Thr Asn Ala Leu Asn
    130                 135                 140
Lys Leu Gly Glu Asn Ile Thr Thr Phe Ala Glu Glu Thr Lys Thr Asn
145                 150                 155                 160
Ile Val Lys Ile Asp Glu Lys Leu Glu Ala Val Ala Asp Thr Val Asp
                165                 170                 175
Lys His Ala Glu Ala Phe Asn Asp Ile Ala Asp Ser Leu Asp Glu Thr
                180                 185                 190
Asn Thr Lys Ala Asp Glu Ala Val Lys Thr Ala Asn Glu Ala Lys Gln
                195                 200                 205
Thr Ala Glu Glu Thr Lys Gln Asn Val Asp Ala Lys Val Lys Ala Ala
    210                 215                 220
Glu Thr Ala Ala Gly Lys Ala Glu Ala Ala Gly Thr Ala Asn Thr
225                 230                 235                 240
Ala Ala Asp Lys Ala Glu Ala Val Ala Lys Val Thr Asp Ile Lys
                245                 250                 255
Ala Asp Ile Ala Thr Asn Lys Asp Asn Ile Ala Lys Lys Ala Asn Ser
                260                 265                 270
Ala Asp Val Tyr Thr Arg Glu Glu Ser Asp Ser Lys Phe Val Arg Ile
                275                 280                 285
Asp Gly Leu Asn Ala Thr Thr Glu Lys Leu Asp Thr Arg Leu Ala Ser
    290                 295                 300
Ala Glu Lys Ser Ile Ala Asp His Asp Thr Arg Leu Asn Gly Leu Asp
305                 310                 315                 320
Lys Thr Val Ser Asp Leu Arg Lys Glu Thr Arg Gln Gly Leu Ala Glu
                325                 330                 335
Gln Ala Ala Leu Ser Gly Leu Phe Gln Pro Tyr Asn Val Gly Gly Ser
                340                 345                 350
Gly Gly Gly Gly Thr Ser Ala Pro Asp Phe Asn Ala Gly Gly Thr Gly
                355                 360                 365
Ile Gly Ser Asn Ser Arg Ala Thr Thr Ala Lys Ser Ala Ala Val Ser
    370                 375                 380
Tyr Ala Gly Ile Lys Asn Glu Met Cys Lys Asp Arg Ser Met Leu Cys
385                 390                 395                 400
Ala Gly Arg Asp Asp Val Ala Val Thr Asp Arg Asp Ala Lys Ile Asn
                405                 410                 415
Ala Pro Pro Pro Asn Leu His Thr Gly Asp Phe Pro Asn Pro Asn Asp
                420                 425                 430
Ala Tyr Lys Asn Leu Ile Asn Leu Lys Pro Ala Ile Glu Ala Gly Tyr
                435                 440                 445
Thr Gly Arg Gly Val Glu Val Gly Ile Val Asp Thr Gly Glu Ser Val
    450                 455                 460
Gly Ser Ile Ser Phe Pro Glu Leu Tyr Gly Arg Lys Glu His Gly Tyr
```

```
                465                 470                 475                 480
Asn Glu Asn Tyr Lys Asn Tyr Thr Ala Tyr Met Arg Lys Glu Ala Pro
                    485                 490                 495
Glu Asp Gly Gly Gly Lys Asp Ile Glu Ala Ser Phe Asp Asp Glu Ala
                500                 505                 510
Val Ile Glu Thr Glu Ala Lys Pro Thr Asp Ile Arg His Val Lys Glu
            515                 520                 525
Ile Gly His Ile Asp Leu Val Ser His Ile Ile Gly Gly Arg Ser Val
        530                 535                 540
Asp Gly Arg Pro Ala Gly Ile Ala Pro Asp Ala Thr Leu His Ile
545                 550                 555                 560
Met Asn Thr Asn Asp Glu Thr Lys Asn Glu Met Met Val Ala Ala Ile
                565                 570                 575
Arg Asn Ala Trp Val Lys Leu Gly Glu Arg Gly Val Arg Ile Val Asn
                580                 585                 590
Asn Ser Phe Gly Thr Thr Ser Arg Ala Gly Thr Ala Asp Leu Phe Gln
            595                 600                 605
Ile Ala Asn Ser Glu Glu Gln Tyr Arg Gln Ala Leu Leu Asp Tyr Ser
        610                 615                 620
Gly Gly Asp Lys Thr Asp Glu Gly Ile Arg Leu Met Gln Gln Ser Asp
625                 630                 635                 640
Tyr Gly Asn Leu Ser Tyr His Ile Arg Asn Lys Asn Met Leu Phe Ile
                645                 650                 655
Phe Ser Thr Gly Asn Asp Ala Gln Ala Gln Pro Asn Thr Tyr Ala Leu
                660                 665                 670
Leu Pro Phe Tyr Glu Lys Asp Ala Gln Lys Gly Ile Ile Thr Val Ala
            675                 680                 685
Gly Val Asp Arg Ser Gly Glu Lys Phe Lys Arg Glu Met Tyr Gly Glu
        690                 695                 700
Pro Gly Thr Glu Pro Leu Glu Tyr Gly Ser Asn His Cys Gly Ile Thr
705                 710                 715                 720
Ala Met Trp Cys Leu Ser Ala Pro Tyr Glu Ala Ser Val Arg Phe Thr
                725                 730                 735
Arg Thr Asn Pro Ile Gln Ile Ala Gly Thr Ser Phe Ser Ala Pro Ile
                740                 745                 750
Val Thr Gly Thr Ala Ala Leu Leu Leu Gln Lys Tyr Pro Trp Met Ser
            755                 760                 765
Asn Asp Asn Leu Arg Thr Thr Leu Leu Thr Thr Ala Gln Asp Ile Gly
        770                 775                 780
Ala Val Gly Val Asp Ser Lys Phe Gly Trp Gly Leu Leu Asp Ala Gly
785                 790                 795                 800
Lys Ala Met Asn Gly Pro Ala Ser Phe Pro Phe Gly Asp Phe Thr Ala
                805                 810                 815
Asp Thr Lys Gly Thr Ser Asp Ile Ala Tyr Ser Phe Arg Asn Asp Ile
                820                 825                 830
Ser Gly Thr Gly Gly Leu Ile Lys Lys Gly Gly Ser Gln Leu Gln Leu
            835                 840                 845
His Gly Asn Asn Thr Tyr Thr Gly Lys Thr Ile Ile Glu Gly Gly Ser
        850                 855                 860
Leu Val Leu Tyr Gly Asn Asn Lys Ser Asp Met Arg Val Glu Thr Lys
865                 870                 875                 880
Gly Ala Leu Ile Tyr Asn Gly Ala Ala Ser Gly Gly Ser Leu Asn Ser
                885                 890                 895
```

-continued

Asp Gly Ile Val Tyr Leu Ala Asp Thr Asp Gln Ser Gly Ala Asn Glu
            900                 905                 910
Thr Val His Ile Lys Gly Ser Leu Gln Leu Asp Gly Lys Gly Thr Leu
    915                 920                 925
Tyr Thr Arg Leu Gly Lys Leu Leu Lys Val Asp Gly Thr Ala Ile Ile
        930                 935                 940
Gly Gly Lys Leu Tyr Met Ser Ala Arg Gly Lys Gly Ala Gly Tyr Leu
945                 950                 955                 960
Asn Ser Thr Gly Arg Arg Val Pro Phe Leu Ser Ala Ala Lys Ile Gly
                965                 970                 975
Gln Asp Tyr Ser Phe Phe Thr Asn Ile Glu Thr Asp Gly Gly Leu Leu
            980                 985                 990
Ala Ser Leu Asp Ser Val Glu Lys Thr Ala Gly Ser Glu Gly Asp Thr
        995                 1000                1005
Leu Ser Tyr Tyr Val Arg Arg Gly Asn Ala Ala Arg Thr Ala Ser Ala
    1010                1015                1020
Ala Ala His Ser Ala Pro Ala Gly Leu Lys His Ala Val Glu Gln Gly
1025                1030                1035                1040
Gly Ser Asn Leu Glu Asn Leu Met Val Glu Leu Asp Ala Ser Glu Ser
                1045                1050                1055
Ser Ala Thr Pro Glu Thr Val Glu Thr Ala Ala Ala Asp Arg Thr Asp
            1060                1065                1070
Met Pro Gly Ile Arg Pro Tyr Gly Ala Thr Phe Arg Ala Ala Ala Ala
        1075                1080                1085
Val Gln His Ala Asn Ala Ala Asp Gly Val Arg Ile Phe Asn Ser Leu
    1090                1095                1100
Ala Ala Thr Val Tyr Ala Asp Ser Thr Ala Ala His Ala Asp Met Gln
1105                1110                1115                1120
Gly Arg Arg Leu Lys Ala Val Ser Asp Gly Leu Asp His Asn Gly Thr
                1125                1130                1135
Gly Leu Arg Val Ile Ala Gln Thr Gln Gln Asp Gly Gly Thr Trp Glu
            1140                1145                1150
Gln Gly Gly Val Glu Gly Lys Met Arg Gly Ser Thr Gln Thr Val Gly
        1155                1160                1165
Ile Ala Ala Lys Thr Gly Glu Asn Thr Thr Ala Ala Ala Thr Leu Gly
    1170                1175                1180
Met Gly Arg Ser Thr Trp Ser Glu Asn Ser Ala Asn Ala Lys Thr Asp
1185                1190                1195                1200
Ser Ile Ser Leu Phe Ala Gly Ile Arg His Asp Ala Gly Asp Ile Gly
                1205                1210                1215
Tyr Leu Lys Gly Leu Phe Ser Tyr Gly Arg Tyr Lys Asn Ser Ile Ser
            1220                1225                1230
Arg Ser Thr Gly Ala Asp Glu His Ala Glu Gly Ser Val Asn Gly Thr
        1235                1240                1245
Leu Met Gln Leu Gly Ala Leu Gly Gly Val Asn Val Pro Phe Ala Ala
    1250                1255                1260
Thr Gly Asp Leu Thr Val Glu Gly Gly Leu Arg Tyr Asp Leu Leu Lys
1265                1270                1275                1280
Gln Asp Ala Phe Ala Glu Lys Gly Ser Ala Leu Gly Trp Ser Gly Asn
                1285                1290                1295
Ser Leu Thr Glu Gly Thr Leu Val Gly Leu Ala Gly Leu Lys Leu Ser
            1300                1305                1310
Gln Pro Leu Ser Asp Lys Ala Val Leu Phe Ala Thr Ala Gly Val Glu
        1315                1320                1325

```
Arg Asp Leu Asn Gly Arg Asp Tyr Thr Val Thr Gly Gly Phe Thr Gly
         1330                1335                1340

Ala Thr Ala Ala Thr Gly Lys Thr Gly Ala Arg Asn Met Pro His Thr
1345                1350                1355                1360

Arg Leu Val Ala Gly Leu Gly Ala Asp Val Glu Phe Gly Asn Gly Trp
                1365                1370                1375

Asn Gly Leu Ala Arg Tyr Ser Tyr Ala Gly Ser Lys Gln Tyr Gly Asn
            1380                1385                1390

His Ser Gly Arg Val Gly Val Gly Tyr Arg Phe
        1395                1400

<210> SEQ ID NO 164
<211> LENGTH: 33
<212> TYPE: DNA
<213> ORGANISM: Artificial Sequence
<220> FEATURE:
<223> OTHER INFORMATION: Oligonucleotide

<400> SEQUENCE: 164
cgcggatccg ctagcaaaac aaccgacaaa cgg                           33

<210> SEQ ID NO 165
<211> LENGTH: 27
<212> TYPE: DNA
<213> ORGANISM: Artificial Sequence
<220> FEATURE:
<223> OTHER INFORMATION: Oligonucleotide

<400> SEQUENCE: 165
cccgctcgag ttaccagcgg tagccta                                 27

<210> SEQ ID NO 166
<211> LENGTH: 30
<212> TYPE: DNA
<213> ORGANISM: Artificial Sequence
<220> FEATURE:
<223> OTHER INFORMATION: Oligonucleotide

<400> SEQUENCE: 166
ctagctagcg gacacactta tttcggcatc                              30

<210> SEQ ID NO 167
<211> LENGTH: 32
<212> TYPE: DNA
<213> ORGANISM: Artificial Sequence
<220> FEATURE:
<223> OTHER INFORMATION: Oligonucleotide

<400> SEQUENCE: 167
cccgctcgag ttaccagcgg tagcctaatt tg                           32

<210> SEQ ID NO 168
<211> LENGTH: 10
<212> TYPE: DNA
<213> ORGANISM: Artificial Sequence
<220> FEATURE:
<223> OTHER INFORMATION: Oligonucleotide

<400> SEQUENCE: 168
cccgctcgag                                                    10

<210> SEQ ID NO 169
<211> LENGTH: 33
<212> TYPE: DNA
```

```
<213> ORGANISM: Artificial Sequence
<220> FEATURE:
<223> OTHER INFORMATION: Oligonucleotide

<400> SEQUENCE: 169
cgcggatccc atatgaaaac cttcttcaaa acc                                    33

<210> SEQ ID NO 170
<211> LENGTH: 28
<212> TYPE: DNA
<213> ORGANISM: Artificial Sequence
<220> FEATURE:
<223> OTHER INFORMATION: Oligonucleotide

<400> SEQUENCE: 170
cccgctcgag ttatttggct gcgccttc                                          28

<210> SEQ ID NO 171
<211> LENGTH: 35
<212> TYPE: DNA
<213> ORGANISM: Artificial Sequence
<220> FEATURE:
<223> OTHER INFORMATION: Oligonucleotide

<400> SEQUENCE: 171
gcggcattaa tatgttgaga aaattgttga aatgg                                  35

<210> SEQ ID NO 172
<211> LENGTH: 34
<212> TYPE: DNA
<213> ORGANISM: Artificial Sequence
<220> FEATURE:
<223> OTHER INFORMATION: Oligonucleotide

<400> SEQUENCE: 172
gcggcctcga gttattttt caaaatatat ttgc                                    34

<210> SEQ ID NO 173
<211> LENGTH: 33
<212> TYPE: DNA
<213> ORGANISM: Artificial Sequence
<220> FEATURE:
<223> OTHER INFORMATION: Oligonucleotide

<400> SEQUENCE: 173
gcggccatat gttacctaac cgtttcaaaa tgt                                    33

<210> SEQ ID NO 174
<211> LENGTH: 31
<212> TYPE: DNA
<213> ORGANISM: Artificial Sequence
<220> FEATURE:
<223> OTHER INFORMATION: Oligonucleotide

<400> SEQUENCE: 174
gcggcctcga gttatttccg aggttttcgg g                                      31

<210> SEQ ID NO 175
<211> LENGTH: 32
<212> TYPE: DNA
<213> ORGANISM: Artificial Sequence
<220> FEATURE:
<223> OTHER INFORMATION: Oligonucleotide

<400> SEQUENCE: 175
cgcggatccc atatgacacg cttcaaatat tc                                     32
```

```
<210> SEQ ID NO 176
<211> LENGTH: 31
<212> TYPE: DNA
<213> ORGANISM: Artificial Sequence
<220> FEATURE:
<223> OTHER INFORMATION: Oligonucleotide

<400> SEQUENCE: 176
cccgctcgag ttatttaaac cgataggtaa a                              31

<210> SEQ ID NO 177
<211> LENGTH: 31
<212> TYPE: DNA
<213> ORGANISM: Artificial Sequence
<220> FEATURE:
<223> OTHER INFORMATION: Oligonucleotide

<400> SEQUENCE: 177
cgcggatccc atatgggcag ggaagaaccg c                              31

<210> SEQ ID NO 178
<211> LENGTH: 28
<212> TYPE: DNA
<213> ORGANISM: Artificial Sequence
<220> FEATURE:
<223> OTHER INFORMATION: Oligonucleotide

<400> SEQUENCE: 178
gcccaagctt atcgatggaa tagccgcg                                  28

<210> SEQ ID NO 179
<211> LENGTH: 32
<212> TYPE: DNA
<213> ORGANISM: Artificial Sequence
<220> FEATURE:
<223> OTHER INFORMATION: Oligonucleotide

<400> SEQUENCE: 179
cgcggatccg ctagcaacgg tttggatgcc cg                             32

<210> SEQ ID NO 180
<211> LENGTH: 30
<212> TYPE: DNA
<213> ORGANISM: Artificial Sequence
<220> FEATURE:
<223> OTHER INFORMATION: Oligonucleotide

<400> SEQUENCE: 180
cccgctcgag tttgtctaag ttcctgatat                                30

<210> SEQ ID NO 181
<211> LENGTH: 26
<212> TYPE: DNA
<213> ORGANISM: Artificial Sequence
<220> FEATURE:
<223> OTHER INFORMATION: Oligonucleotide

<400> SEQUENCE: 181
cccgctcgag attcccacct gccatc                                    26

<210> SEQ ID NO 182
<211> LENGTH: 37
<212> TYPE: DNA
<213> ORGANISM: Artificial Sequence
<220> FEATURE:
<223> OTHER INFORMATION: Oligonucleotide
```

```
<400> SEQUENCE: 182
cgcggatccg ctagcatgaa tttgcctatt caaaaat                              37

<210> SEQ ID NO 183
<211> LENGTH: 29
<212> TYPE: DNA
<213> ORGANISM: Artificial Sequence
<220> FEATURE:
<223> OTHER INFORMATION: Oligonucleotide

<400> SEQUENCE: 183
cccgctcgag ttaattccca cctgccatc                                      29

<210> SEQ ID NO 184
<211> LENGTH: 37
<212> TYPE: DNA
<213> ORGANISM: Artificial Sequence
<220> FEATURE:
<223> OTHER INFORMATION: Oligonucleotide

<400> SEQUENCE: 184
cgcggatccg ctagcatgaa tttgcctatt caaaaat                              37

<210> SEQ ID NO 185
<211> LENGTH: 27
<212> TYPE: DNA
<213> ORGANISM: Artificial Sequence
<220> FEATURE:
<223> OTHER INFORMATION: Oligonucleotide

<400> SEQUENCE: 185
cccgctcgag ttggacgatg cccgcga                                        27

<210> SEQ ID NO 186
<211> LENGTH: 37
<212> TYPE: DNA
<213> ORGANISM: Artificial Sequence
<220> FEATURE:
<223> OTHER INFORMATION: Oligonucleotide

<400> SEQUENCE: 186
cgcggatccg ctagcatgaa tttgcctatt caaaaat                              37

<210> SEQ ID NO 187
<211> LENGTH: 28
<212> TYPE: DNA
<213> ORGANISM: Artificial Sequence
<220> FEATURE:
<223> OTHER INFORMATION: Oligonucleotide

<400> SEQUENCE: 187
cccgctcgag ttattggacg atgcccgc                                       28

<210> SEQ ID NO 188
<211> LENGTH: 32
<212> TYPE: DNA
<213> ORGANISM: Artificial Sequence
<220> FEATURE:
<223> OTHER INFORMATION: Oligonucleotide

<400> SEQUENCE: 188
cgcggatccc atatgtatcg caaactgatt gc                                  32

<210> SEQ ID NO 189
<211> LENGTH: 28
<212> TYPE: DNA
```

```
-continued

<213> ORGANISM: Artificial Sequence
<220> FEATURE:
<223> OTHER INFORMATION: Oligonucleotide

<400> SEQUENCE: 189
cccgctcgag ctaatcgatg gaatagcc                                      28

<210> SEQ ID NO 190
<211> LENGTH: 32
<212> TYPE: DNA
<213> ORGANISM: Artificial Sequence
<220> FEATURE:
<223> OTHER INFORMATION: Oligonucleotide

<400> SEQUENCE: 190
cgcggatccc atatgaaaca gacagtcaaa tg                                 32

<210> SEQ ID NO 191
<211> LENGTH: 28
<212> TYPE: DNA
<213> ORGANISM: Artificial Sequence
<220> FEATURE:
<223> OTHER INFORMATION: Oligonucleotide

<400> SEQUENCE: 191
cccgctcgag tcaataaccc gccttcag                                      28

<210> SEQ ID NO 192
<211> LENGTH: 45
<212> TYPE: DNA
<213> ORGANISM: Artificial Sequence
<220> FEATURE:
<223> OTHER INFORMATION: Oligonucleotide

<400> SEQUENCE: 192
cgcggatccc atatgttacg tttgactgct ttagccgtat gcacc                   45

<210> SEQ ID NO 193
<211> LENGTH: 40
<212> TYPE: DNA
<213> ORGANISM: Artificial Sequence
<220> FEATURE:
<223> OTHER INFORMATION: Oligonucleotide

<400> SEQUENCE: 193
cccgctcgag ttattttgcc gcgttaaaag cgtcggcaac                         40

<210> SEQ ID NO 194
<211> LENGTH: 32
<212> TYPE: DNA
<213> ORGANISM: Artificial Sequence
<220> FEATURE:
<223> OTHER INFORMATION: Oligonucleotide

<400> SEQUENCE: 194
cgcggatccc atatgaacaa aatataccgc at                                 32

<210> SEQ ID NO 195
<211> LENGTH: 28
<212> TYPE: DNA
<213> ORGANISM: Artificial Sequence
<220> FEATURE:
<223> OTHER INFORMATION: Oligonucleotide

<400> SEQUENCE: 195
cccgctcgag ttaccactga taaccgac                                      28
```

<210> SEQ ID NO 196
<211> LENGTH: 34
<212> TYPE: DNA
<213> ORGANISM: Artificial Sequence
<220> FEATURE:
<223> OTHER INFORMATION: Oligonucleotide

<400> SEQUENCE: 196
cgcggatccc atatgaccga tgacgacgat ttat                             34

<210> SEQ ID NO 197
<211> LENGTH: 28
<212> TYPE: DNA
<213> ORGANISM: Artificial Sequence
<220> FEATURE:
<223> OTHER INFORMATION: Oligonucleotide

<400> SEQUENCE: 197
gcccaagctt ccactgataa ccgacaga                                    28

<210> SEQ ID NO 198
<211> LENGTH: 32
<212> TYPE: DNA
<213> ORGANISM: Artificial Sequence
<220> FEATURE:
<223> OTHER INFORMATION: Oligonucleotide

<400> SEQUENCE: 198
cgcggatccc atatgaacaa aatataccgc at                               32

<210> SEQ ID NO 199
<211> LENGTH: 28
<212> TYPE: DNA
<213> ORGANISM: Artificial Sequence
<220> FEATURE:
<223> OTHER INFORMATION: Oligonucleotide

<400> SEQUENCE: 199
gcccaagctt ttaccactga taaccgac                                    28

<210> SEQ ID NO 200
<211> LENGTH: 34
<212> TYPE: DNA
<213> ORGANISM: Artificial Sequence
<220> FEATURE:
<223> OTHER INFORMATION: Oligonucleotide

<400> SEQUENCE: 200
gggaattcca tatgggcatt tcccgcaaaa tatc                             34

<210> SEQ ID NO 201
<211> LENGTH: 40
<212> TYPE: DNA
<213> ORGANISM: Artificial Sequence
<220> FEATURE:
<223> OTHER INFORMATION: Oligonucleotide

<400> SEQUENCE: 201
cccgctcgag ttatttactc ctataacgag gtctcttaac                       40

<210> SEQ ID NO 202
<211> LENGTH: 36
<212> TYPE: DNA
<213> ORGANISM: Artificial Sequence
<220> FEATURE:
<223> OTHER INFORMATION: Oligonucleotide -continued
<400> SEQUENCE: 202
gggaattcca tatgtcagat ttggcaaacg attctt    36

<210> SEQ ID NO 203
<211> LENGTH: 40
<212> TYPE: DNA
<213> ORGANISM: Artificial Sequence
<220> FEATURE:
<223> OTHER INFORMATION: Oligonucleotide
<400> SEQUENCE: 203
cccgctcgag ttatttactc ctataacgag gtctcttaac    40

<210> SEQ ID NO 204
<211> LENGTH: 34
<212> TYPE: DNA
<213> ORGANISM: Artificial Sequence
<220> FEATURE:
<223> OTHER INFORMATION: Oligonucleotide
<400> SEQUENCE: 204
gggaattcca tatgggcatt tcccgcaaaa tatc    34

<210> SEQ ID NO 205
<211> LENGTH: 32
<212> TYPE: DNA
<213> ORGANISM: Artificial Sequence
<220> FEATURE:
<223> OTHER INFORMATION: Oligonucleotide
<400> SEQUENCE: 205
cccgctcgag ttacgtatca tatttcacgt gc    32

<210> SEQ ID NO 206
<211> LENGTH: 35
<212> TYPE: DNA
<213> ORGANISM: Artificial Sequence
<220> FEATURE:
<223> OTHER INFORMATION: Oligonucleotide
<400> SEQUENCE: 206
gggaattcca tatgcacgtg aaatatgata cgaag    35

<210> SEQ ID NO 207
<211> LENGTH: 37
<212> TYPE: DNA
<213> ORGANISM: Artificial Sequence
<220> FEATURE:
<223> OTHER INFORMATION: Oligonucleotide
<400> SEQUENCE: 207
cccgctcgag tttactccta taacgaggtc tcttaac    37

<210> SEQ ID NO 208
<211> LENGTH: 36
<212> TYPE: DNA
<213> ORGANISM: Artificial Sequence
<220> FEATURE:
<223> OTHER INFORMATION: Oligonucleotide
<400> SEQUENCE: 208
gggaattcca tatgtcagat ttggcaaacg attctt    36

<210> SEQ ID NO 209
<211> LENGTH: 29
<212> TYPE: DNA

<213> ORGANISM: Artificial Sequence
<220> FEATURE:
<223> OTHER INFORMATION: Oligonucleotide

<400> SEQUENCE: 209
cccgctcgag cgtatcatat ttcacgtgc                             29

<210> SEQ ID NO 210
<211> LENGTH: 36
<212> TYPE: DNA
<213> ORGANISM: Artificial Sequence
<220> FEATURE:
<223> OTHER INFORMATION: Oligonucleotide

<400> SEQUENCE: 210
gggaattcca tatgtcagat ttggcaaacg attctt                     36

<210> SEQ ID NO 211
<211> LENGTH: 37
<212> TYPE: DNA
<213> ORGANISM: Artificial Sequence
<220> FEATURE:
<223> OTHER INFORMATION: Oligonucleotide

<400> SEQUENCE: 211
cccgctcgag tttactccta taacgaggtc tcttaac                    37

<210> SEQ ID NO 212
<211> LENGTH: 35
<212> TYPE: DNA
<213> ORGANISM: Artificial Sequence
<220> FEATURE:
<223> OTHER INFORMATION: Oligonucleotide

<400> SEQUENCE: 212
cgcggatccc atatgcaaaa tgcgttcaaa atccc                      35

<210> SEQ ID NO 213
<211> LENGTH: 32
<212> TYPE: DNA
<213> ORGANISM: Artificial Sequence
<220> FEATURE:
<223> OTHER INFORMATION: Oligonucleotide

<400> SEQUENCE: 213
cgcggatccc atatgaacaa aatataccgc at                         32

<210> SEQ ID NO 214
<211> LENGTH: 29
<212> TYPE: DNA
<213> ORGANISM: Artificial Sequence
<220> FEATURE:
<223> OTHER INFORMATION: Oligonucleotide

<400> SEQUENCE: 214
cccgctcgag tttgctttcg atagaacgg                             29

<210> SEQ ID NO 215
<211> LENGTH: 34
<212> TYPE: DNA
<213> ORGANISM: Artificial Sequence
<220> FEATURE:
<223> OTHER INFORMATION: Oligonucleotide

<400> SEQUENCE: 215
gcggccatat ggtcataaaa tatacaaatt tgaa                       34

<210> SEQ ID NO 216
<211> LENGTH: 34
<212> TYPE: DNA
<213> ORGANISM: Artificial Sequence
<220> FEATURE:
<223> OTHER INFORMATION: Oligonucleotide

<400> SEQUENCE: 216
gcggcctcga gttagcctga gacctttgca aatt                            34

<210> SEQ ID NO 217
<211> LENGTH: 30
<212> TYPE: DNA
<213> ORGANISM: Artificial Sequence
<220> FEATURE:
<223> OTHER INFORMATION: Oligonucleotide

<400> SEQUENCE: 217
gcggccatat gaaacagaaa aaaccgctg                                  30

<210> SEQ ID NO 218
<211> LENGTH: 32
<212> TYPE: DNA
<213> ORGANISM: Artificial Sequence
<220> FEATURE:
<223> OTHER INFORMATION: Oligonucleotide

<400> SEQUENCE: 218
gcggcctcga gttacggttt gacaccgttt tc                              32

<210> SEQ ID NO 219
<211> LENGTH: 30
<212> TYPE: DNA
<213> ORGANISM: Artificial Sequence
<220> FEATURE:
<223> OTHER INFORMATION: Oligonucleotide

<400> SEQUENCE: 219
cgcggatccc atatgaaaac cctgctcctc                                 30

<210> SEQ ID NO 220
<211> LENGTH: 27
<212> TYPE: DNA
<213> ORGANISM: Artificial Sequence
<220> FEATURE:
<223> OTHER INFORMATION: Oligonucleotide

<400> SEQUENCE: 220
cccgctcgag ttatcctcct ttgcggc                                    27

<210> SEQ ID NO 221
<211> LENGTH: 30
<212> TYPE: DNA
<213> ORGANISM: Artificial Sequence
<220> FEATURE:
<223> OTHER INFORMATION: Oligonucleotide

<400> SEQUENCE: 221
gcggccatat ggcaaaaatg atgaaatggg                                 30

<210> SEQ ID NO 222
<211> LENGTH: 29
<212> TYPE: DNA
<213> ORGANISM: Artificial Sequence
<220> FEATURE:
<223> OTHER INFORMATION: Oligonucleotide

```
<400> SEQUENCE: 222
gcggcctcga gttatcggcg cggcgggcc                              29

<210> SEQ ID NO 223
<211> LENGTH: 30
<212> TYPE: DNA
<213> ORGANISM: Artificial Sequence
<220> FEATURE:
<223> OTHER INFORMATION: Oligonucleotide

<400> SEQUENCE: 223
gcggccatat gaaaaaatcc tccctcatca                             30

<210> SEQ ID NO 224
<211> LENGTH: 32
<212> TYPE: DNA
<213> ORGANISM: Artificial Sequence
<220> FEATURE:
<223> OTHER INFORMATION: Oligonucleotide

<400> SEQUENCE: 224
gcggcctcga gttatttgcc gccgtttttg gc                          32

<210> SEQ ID NO 225
<211> LENGTH: 31
<212> TYPE: DNA
<213> ORGANISM: Artificial Sequence
<220> FEATURE:
<223> OTHER INFORMATION: Oligonucleotide

<400> SEQUENCE: 225
gcggccatat ggcccctgcc gacgcggtaa g                           31

<210> SEQ ID NO 226
<211> LENGTH: 33
<212> TYPE: DNA
<213> ORGANISM: Artificial Sequence
<220> FEATURE:
<223> OTHER INFORMATION: Oligonucleotide

<400> SEQUENCE: 226
gcggcctcga gtttgccgcc gtttttggct ttc                         33

<210> SEQ ID NO 227
<211> LENGTH: 30
<212> TYPE: DNA
<213> ORGANISM: Artificial Sequence
<220> FEATURE:
<223> OTHER INFORMATION: Oligonucleotide

<400> SEQUENCE: 227
gcggccatat gaaacacata ctccccctga                             30

<210> SEQ ID NO 228
<211> LENGTH: 32
<212> TYPE: DNA
<213> ORGANISM: Artificial Sequence
<220> FEATURE:
<223> OTHER INFORMATION: Oligonucleotide

<400> SEQUENCE: 228
gcggcctcga gttattcgcc tacggttttt tg                          32

<210> SEQ ID NO 229
<211> LENGTH: 30
<212> TYPE: DNA
```

```
<213> ORGANISM: Artificial Sequence
<220> FEATURE:
<223> OTHER INFORMATION: Oligonucleotide

<400> SEQUENCE: 229
gcggccatat gatttacatc gtactgtttc                                    30

<210> SEQ ID NO 230
<211> LENGTH: 32
<212> TYPE: DNA
<213> ORGANISM: Artificial Sequence
<220> FEATURE:
<223> OTHER INFORMATION: Oligonucleotide

<400> SEQUENCE: 230
gcggcctcga gttaggagaa caggcgcaat gc                                 32

<210> SEQ ID NO 231
<211> LENGTH: 32
<212> TYPE: DNA
<213> ORGANISM: Artificial Sequence
<220> FEATURE:
<223> OTHER INFORMATION: Oligonucleotide

<400> SEQUENCE: 231
gcggccatat gtacaacatg tatcaggaaa ac                                 32

<210> SEQ ID NO 232
<211> LENGTH: 31
<212> TYPE: DNA
<213> ORGANISM: Artificial Sequence
<220> FEATURE:
<223> OTHER INFORMATION: Oligonucleotide

<400> SEQUENCE: 232
gcggcctcga gggagaacag gcgcaatgcg g                                  31

<210> SEQ ID NO 233
<211> LENGTH: 29
<212> TYPE: DNA
<213> ORGANISM: Artificial Sequence
<220> FEATURE:
<223> OTHER INFORMATION: Oligonucleotide

<400> SEQUENCE: 233
cgcggatccg ctagctgcgg cacggcggg                                     29

<210> SEQ ID NO 234
<211> LENGTH: 28
<212> TYPE: DNA
<213> ORGANISM: Artificial Sequence
<220> FEATURE:
<223> OTHER INFORMATION: Oligonucleotide

<400> SEQUENCE: 234
cccgctcgag ataacggtat gccgccag                                      28

<210> SEQ ID NO 235
<211> LENGTH: 31
<212> TYPE: DNA
<213> ORGANISM: Artificial Sequence
<220> FEATURE:
<223> OTHER INFORMATION: Oligonucleotide

<400> SEQUENCE: 235
cgcggatccc atatggaatc aacactttca c                                  31
```

<210> SEQ ID NO 236
<211> LENGTH: 27
<212> TYPE: DNA
<213> ORGANISM: Artificial Sequence
<220> FEATURE:
<223> OTHER INFORMATION: Oligonucleotide

<400> SEQUENCE: 236
cccgctcgag ttacacgcgg ttgctgt                              27

<210> SEQ ID NO 237
<211> LENGTH: 31
<212> TYPE: DNA
<213> ORGANISM: Artificial Sequence
<220> FEATURE:
<223> OTHER INFORMATION: Oligonucleotide

<400> SEQUENCE: 237
cgcggatccc atatgaacaa cagacatttt g                         31

<210> SEQ ID NO 238
<211> LENGTH: 28
<212> TYPE: DNA
<213> ORGANISM: Artificial Sequence
<220> FEATURE:
<223> OTHER INFORMATION: Oligonucleotide

<400> SEQUENCE: 238
cccgctcgag ttacctgtcc ggtaaaag                             28

<210> SEQ ID NO 239
<211> LENGTH: 33
<212> TYPE: DNA
<213> ORGANISM: Artificial Sequence
<220> FEATURE:
<223> OTHER INFORMATION: Oligonucleotide

<400> SEQUENCE: 239
cgcggatccg ctagcaccgt catcaaacag gaa                       33

<210> SEQ ID NO 240
<211> LENGTH: 27
<212> TYPE: DNA
<213> ORGANISM: Artificial Sequence
<220> FEATURE:
<223> OTHER INFORMATION: Oligonucleotide

<400> SEQUENCE: 240
cccgctcgag tcaagattcg acgggga                              27

<210> SEQ ID NO 241
<211> LENGTH: 31
<212> TYPE: DNA
<213> ORGANISM: Artificial Sequence
<220> FEATURE:
<223> OTHER INFORMATION: Oligonucleotide

<400> SEQUENCE: 241
cgcggatccc atatgtccgc aaacgaatac g                         31

<210> SEQ ID NO 242
<211> LENGTH: 28
<212> TYPE: DNA
<213> ORGANISM: Artificial Sequence
<220> FEATURE:
<223> OTHER INFORMATION: Oligonucleotide

```
<400> SEQUENCE: 242
cccgctcgag tcagtgttct gccagttt                                    28

<210> SEQ ID NO 243
<211> LENGTH: 29
<212> TYPE: DNA
<213> ORGANISM: Artificial Sequence
<220> FEATURE:
<223> OTHER INFORMATION: Oligonucleotide

<400> SEQUENCE: 243
cgcggatccc atatgccgtc tgaaacacg                                   29

<210> SEQ ID NO 244
<211> LENGTH: 28
<212> TYPE: DNA
<213> ORGANISM: Artificial Sequence
<220> FEATURE:
<223> OTHER INFORMATION: Oligonucleotide

<400> SEQUENCE: 244
cccgctcgag ttagcggagc agttttc                                     28

<210> SEQ ID NO 245
<211> LENGTH: 28
<212> TYPE: DNA
<213> ORGANISM: Artificial Sequence
<220> FEATURE:
<223> OTHER INFORMATION: Oligonucleotide

<400> SEQUENCE: 245
cgcggatccc atatgaccgc catcagcc                                    28

<210> SEQ ID NO 246
<211> LENGTH: 27
<212> TYPE: DNA
<213> ORGANISM: Artificial Sequence
<220> FEATURE:
<223> OTHER INFORMATION: Oligonucleotide

<400> SEQUENCE: 246
cccgctcgag ttaaagccgg gtaacgc                                     27

<210> SEQ ID NO 247
<211> LENGTH: 31
<212> TYPE: DNA
<213> ORGANISM: Artificial Sequence
<220> FEATURE:
<223> OTHER INFORMATION: Oligonucleotide

<400> SEQUENCE: 247
gcggccatat ggaaacacag ctttacatcg g                                31

<210> SEQ ID NO 248
<211> LENGTH: 30
<212> TYPE: DNA
<213> ORGANISM: Artificial Sequence
<220> FEATURE:
<223> OTHER INFORMATION: Oligonucleotide

<400> SEQUENCE: 248
gcggcctcga gtcaataata atatcccgcg                                  30

<210> SEQ ID NO 249
<211> LENGTH: 30
<212> TYPE: DNA
```

```
<213> ORGANISM: Artificial Sequence
<220> FEATURE:
<223> OTHER INFORMATION: Oligonucleotide

<400> SEQUENCE: 249
gcggccatat gattaaaatc cgcaatatcc                                    30

<210> SEQ ID NO 250
<211> LENGTH: 36
<212> TYPE: DNA
<213> ORGANISM: Artificial Sequence
<220> FEATURE:
<223> OTHER INFORMATION: Oligonucleotide

<400> SEQUENCE: 250
gcggcctcga gttaaatctt ggtagattgg atttgg                             36

<210> SEQ ID NO 251
<211> LENGTH: 30
<212> TYPE: DNA
<213> ORGANISM: Artificial Sequence
<220> FEATURE:
<223> OTHER INFORMATION: Oligonucleotide

<400> SEQUENCE: 251
gcggccatat gactgacaac gcactgctcc                                    30

<210> SEQ ID NO 252
<211> LENGTH: 31
<212> TYPE: DNA
<213> ORGANISM: Artificial Sequence
<220> FEATURE:
<223> OTHER INFORMATION: Oligonucleotide

<400> SEQUENCE: 252
gcggcctcga gtcagaccgc gttgtcgaaa c                                  31

<210> SEQ ID NO 253
<211> LENGTH: 32
<212> TYPE: DNA
<213> ORGANISM: Artificial Sequence
<220> FEATURE:
<223> OTHER INFORMATION: Oligonucleotide

<400> SEQUENCE: 253
cgcggatccc atatggcgtt aaaaacatca aa                                 32

<210> SEQ ID NO 254
<211> LENGTH: 27
<212> TYPE: DNA
<213> ORGANISM: Artificial Sequence
<220> FEATURE:
<223> OTHER INFORMATION: Oligonucleotide

<400> SEQUENCE: 254
cccgctcgag tcagcccttc atacagc                                       27

<210> SEQ ID NO 255
<211> LENGTH: 32
<212> TYPE: DNA
<213> ORGANISM: Artificial Sequence
<220> FEATURE:
<223> OTHER INFORMATION: Oligonucleotide

<400> SEQUENCE: 255
gcggcattaa tggcacaaac tacactcaaa cc                                 32
```

```
<210> SEQ ID NO 256
<211> LENGTH: 33
<212> TYPE: DNA
<213> ORGANISM: Artificial Sequence
<220> FEATURE:
<223> OTHER INFORMATION: Oligonucleotide

<400> SEQUENCE: 256
gcggcctcga gttaaaactt cacgttcacg ccg                                    33

<210> SEQ ID NO 257
<211> LENGTH: 34
<212> TYPE: DNA
<213> ORGANISM: Artificial Sequence
<220> FEATURE:
<223> OTHER INFORMATION: Oligonucleotide

<400> SEQUENCE: 257
gcggcattaa tgcatgaaac tgagcaatcg gtgg                                   34

<210> SEQ ID NO 258
<211> LENGTH: 38
<212> TYPE: DNA
<213> ORGANISM: Artificial Sequence
<220> FEATURE:
<223> OTHER INFORMATION: Oligonucleotide

<400> SEQUENCE: 258
gcggcctcga gaaacttcac gttcacgccg ccggtaaa                               38

<210> SEQ ID NO 259
<211> LENGTH: 33
<212> TYPE: DNA
<213> ORGANISM: Artificial Sequence
<220> FEATURE:
<223> OTHER INFORMATION: Oligonucleotide

<400> SEQUENCE: 259
cgcggatccc atatgggcaa atccgaaaat acg                                    33

<210> SEQ ID NO 260
<211> LENGTH: 26
<212> TYPE: DNA
<213> ORGANISM: Artificial Sequence
<220> FEATURE:
<223> OTHER INFORMATION: Oligonucleotide

<400> SEQUENCE: 260
cccgctcgag ataatggcgg cggcgg                                            26

<210> SEQ ID NO 261
<211> LENGTH: 29
<212> TYPE: DNA
<213> ORGANISM: Artificial Sequence
<220> FEATURE:
<223> OTHER INFORMATION: Oligonucleotide

<400> SEQUENCE: 261
cgcggatccc atatgtttcc ccccgacaa                                         29

<210> SEQ ID NO 262
<211> LENGTH: 31
<212> TYPE: DNA
<213> ORGANISM: Artificial Sequence
<220> FEATURE:
<223> OTHER INFORMATION: Oligonucleotide
```

```
<400> SEQUENCE: 262
cccgctcgag tcattctgta aaaaaagtat g                              31

<210> SEQ ID NO 263
<211> LENGTH: 32
<212> TYPE: DNA
<213> ORGANISM: Artificial Sequence
<220> FEATURE:
<223> OTHER INFORMATION: Oligonucleotide

<400> SEQUENCE: 263
cgcggatccc atatgcttca aagcgacagc ag                             32

<210> SEQ ID NO 264
<211> LENGTH: 29
<212> TYPE: DNA
<213> ORGANISM: Artificial Sequence
<220> FEATURE:
<223> OTHER INFORMATION: Oligonucleotide

<400> SEQUENCE: 264
cccgctcgag ttcggatttt tgcgtactc                                 29

<210> SEQ ID NO 265
<211> LENGTH: 31
<212> TYPE: DNA
<213> ORGANISM: Artificial Sequence
<220> FEATURE:
<223> OTHER INFORMATION: Oligonucleotide

<400> SEQUENCE: 265
cgcggatccc atatggcaat ggcagaaaac g                              31

<210> SEQ ID NO 266
<211> LENGTH: 27
<212> TYPE: DNA
<213> ORGANISM: Artificial Sequence
<220> FEATURE:
<223> OTHER INFORMATION: Oligonucleotide

<400> SEQUENCE: 266
cccgctcgag ctatacaatc cgtgccg                                   27

<210> SEQ ID NO 267
<211> LENGTH: 32
<212> TYPE: DNA
<213> ORGANISM: Artificial Sequence
<220> FEATURE:
<223> OTHER INFORMATION: Oligonucleotide

<400> SEQUENCE: 267
cgcggatccc atatggattc tttttcaaa cc                              32

<210> SEQ ID NO 268
<211> LENGTH: 27
<212> TYPE: DNA
<213> ORGANISM: Artificial Sequence
<220> FEATURE:
<223> OTHER INFORMATION: Oligonucleotide

<400> SEQUENCE: 268
cccgctcgag tcagttcaga aagcggg                                   27

<210> SEQ ID NO 269
<211> LENGTH: 32
<212> TYPE: DNA
```

```
<213> ORGANISM: Artificial Sequence
<220> FEATURE:
<223> OTHER INFORMATION: Oligonucleotide

<400> SEQUENCE: 269
cgcggatccc atatgaaacc tttgatttta gg                          32

<210> SEQ ID NO 270
<211> LENGTH: 28
<212> TYPE: DNA
<213> ORGANISM: Artificial Sequence
<220> FEATURE:
<223> OTHER INFORMATION: Oligonucleotide

<400> SEQUENCE: 270
cccgctcgag ttatttgggc tgctcttc                               28

<210> SEQ ID NO 271
<211> LENGTH: 30
<212> TYPE: DNA
<213> ORGANISM: Artificial Sequence
<220> FEATURE:
<223> OTHER INFORMATION: Oligonucleotide

<400> SEQUENCE: 271
cgcggatccc atatggtaat cgtctggttg                             30

<210> SEQ ID NO 272
<211> LENGTH: 27
<212> TYPE: DNA
<213> ORGANISM: Artificial Sequence
<220> FEATURE:
<223> OTHER INFORMATION: Oligonucleotide

<400> SEQUENCE: 272
cccgctcgag ctacgacttg gttaccg                                27

<210> SEQ ID NO 273
<211> LENGTH: 33
<212> TYPE: DNA
<213> ORGANISM: Artificial Sequence
<220> FEATURE:
<223> OTHER INFORMATION: Oligonucleotide

<400> SEQUENCE: 273
gcggccatat gagacgtaaa atgctaaagc tac                         33

<210> SEQ ID NO 274
<211> LENGTH: 31
<212> TYPE: DNA
<213> ORGANISM: Artificial Sequence
<220> FEATURE:
<223> OTHER INFORMATION: Oligonucleotide

<400> SEQUENCE: 274
gcggcctcga gtcaaagtgt tctgtttgcg c                           31

<210> SEQ ID NO 275
<211> LENGTH: 30
<212> TYPE: DNA
<213> ORGANISM: Artificial Sequence
<220> FEATURE:
<223> OTHER INFORMATION: Oligonucleotide

<400> SEQUENCE: 275
gccgccatat gttgacttta acccgaaaaa                             30
```

<210> SEQ ID NO 276
<211> LENGTH: 34
<212> TYPE: DNA
<213> ORGANISM: Artificial Sequence
<220> FEATURE:
<223> OTHER INFORMATION: Oligonucleotide

<400> SEQUENCE: 276
gccgcctcga ggccggcggt caataccgcc cgaa                          34

<210> SEQ ID NO 277
<211> LENGTH: 32
<212> TYPE: DNA
<213> ORGANISM: Artificial Sequence
<220> FEATURE:
<223> OTHER INFORMATION: Oligonucleotide

<400> SEQUENCE: 277
cgcggatccc atatggcgca atgcgatttg ac                            32

<210> SEQ ID NO 278
<211> LENGTH: 27
<212> TYPE: DNA
<213> ORGANISM: Artificial Sequence
<220> FEATURE:
<223> OTHER INFORMATION: Oligonucleotide

<400> SEQUENCE: 278
cccgctcgag ttcggcggta aatgccg                                  27

<210> SEQ ID NO 279
<211> LENGTH: 28
<212> TYPE: DNA
<213> ORGANISM: Artificial Sequence
<220> FEATURE:
<223> OTHER INFORMATION: Oligonucleotide

<400> SEQUENCE: 279
gcggccatat ggcggggccg attttttgt                                28

<210> SEQ ID NO 280
<211> LENGTH: 33
<212> TYPE: DNA
<213> ORGANISM: Artificial Sequence
<220> FEATURE:
<223> OTHER INFORMATION: Oligonucleotide

<400> SEQUENCE: 280
gcggcctcga gttatttgct ttcagtatta ttg                           33

<210> SEQ ID NO 281
<211> LENGTH: 30
<212> TYPE: DNA
<213> ORGANISM: Artificial Sequence
<220> FEATURE:
<223> OTHER INFORMATION: Oligonucleotide

<400> SEQUENCE: 281
gcggccatat gaactttgct ttatccgtca                               30

<210> SEQ ID NO 282
<211> LENGTH: 32
<212> TYPE: DNA
<213> ORGANISM: Artificial Sequence
<220> FEATURE:
<223> OTHER INFORMATION: Oligonucleotide -continued

<400> SEQUENCE: 282
gcggcctcga gttaacggca gtatttgttt ac                          32

<210> SEQ ID NO 283
<211> LENGTH: 31
<212> TYPE: DNA
<213> ORGANISM: Artificial Sequence
<220> FEATURE:
<223> OTHER INFORMATION: Oligonucleotide

<400> SEQUENCE: 283
cgcggatccc atatgggttt gcgcttcggg c                           31

<210> SEQ ID NO 284
<211> LENGTH: 29
<212> TYPE: DNA
<213> ORGANISM: Artificial Sequence
<220> FEATURE:
<223> OTHER INFORMATION: Oligonucleotide

<400> SEQUENCE: 284
gcccaagctt ttttcctttg ccgtttccg                              29

<210> SEQ ID NO 285
<211> LENGTH: 32
<212> TYPE: DNA
<213> ORGANISM: Artificial Sequence
<220> FEATURE:
<223> OTHER INFORMATION: Oligonucleotide

<400> SEQUENCE: 285
cgcggatccc atatggccga cctttccgaa aa                          32

<210> SEQ ID NO 286
<211> LENGTH: 27
<212> TYPE: DNA
<213> ORGANISM: Artificial Sequence
<220> FEATURE:
<223> OTHER INFORMATION: Oligonucleotide

<400> SEQUENCE: 286
cccgctcgag gaagcgcgtt cccaagc                                27

<210> SEQ ID NO 287
<211> LENGTH: 29
<212> TYPE: DNA
<213> ORGANISM: Artificial Sequence
<220> FEATURE:
<223> OTHER INFORMATION: Oligonucleotide

<400> SEQUENCE: 287
cgcggatccc atatgcacga cacccgtac                              29

<210> SEQ ID NO 288
<211> LENGTH: 28
<212> TYPE: DNA
<213> ORGANISM: Artificial Sequence
<220> FEATURE:
<223> OTHER INFORMATION: Oligonucleotide

<400> SEQUENCE: 288
cccgctcgag ttagaagcgc gttcccaa                               28

<210> SEQ ID NO 289
<211> LENGTH: 34
<212> TYPE: DNA

```
<213> ORGANISM: Artificial Sequence
<220> FEATURE:
<223> OTHER INFORMATION: Oligonucleotide

<400> SEQUENCE: 289
ctagctagct ttaaacgcag cgtaatcgca atgg                          34

<210> SEQ ID NO 290
<211> LENGTH: 31
<212> TYPE: DNA
<213> ORGANISM: Artificial Sequence
<220> FEATURE:
<223> OTHER INFORMATION: Oligonucleotideucleotide

<400> SEQUENCE: 290
cccgctcgag tcaatcctgc tctttttgc c                              31

<210> SEQ ID NO 291
<211> LENGTH: 25
<212> TYPE: DNA
<213> ORGANISM: Artificial Sequence
<220> FEATURE:
<223> OTHER INFORMATION: Oligonucleotide

<400> SEQUENCE: 291
ctagctagcg ggggcggcgg tggcg                                    25

<210> SEQ ID NO 292
<211> LENGTH: 31
<212> TYPE: DNA
<213> ORGANISM: Artificial Sequence
<220> FEATURE:
<223> OTHER INFORMATION: Oligonucleotide

<400> SEQUENCE: 292
cccgctcgag tcaatcctgc tctttttgc c                              31

<210> SEQ ID NO 293
<211> LENGTH: 40
<212> TYPE: DNA
<213> ORGANISM: Artificial Sequence
<220> FEATURE:
<223> OTHER INFORMATION: Oligonucleotide

<400> SEQUENCE: 293
ctagctagcg ctcatcctcg ccgcctgcgg gggcggcggt                    40

<210> SEQ ID NO 294
<211> LENGTH: 31
<212> TYPE: DNA
<213> ORGANISM: Artificial Sequence
<220> FEATURE:
<223> OTHER INFORMATION: Oligonucleotide

<400> SEQUENCE: 294
cccgctcgag tcaatcctgc tctttttgc c                              31

<210> SEQ ID NO 295
<211> LENGTH: 25
<212> TYPE: DNA
<213> ORGANISM: Artificial Sequence
<220> FEATURE:
<223> OTHER INFORMATION: Oligonucleotide

<400> SEQUENCE: 295
cggggatccg ggggcggcgg tggcg                                    25
```

```
<210> SEQ ID NO 296
<211> LENGTH: 31
<212> TYPE: DNA
<213> ORGANISM: Artificial Sequence
<220> FEATURE:
<223> OTHER INFORMATION: Oligonucleotide

<400> SEQUENCE: 296
cccgctcgag tcaatcctgc tctttttgc c                              31

<210> SEQ ID NO 297
<211> LENGTH: 25
<212> TYPE: DNA
<213> ORGANISM: Artificial Sequence
<220> FEATURE:
<223> OTHER INFORMATION: Oligonucleotide

<400> SEQUENCE: 297
ctagctagcg ggggcggcgg tggcg                                    25

<210> SEQ ID NO 298
<211> LENGTH: 28
<212> TYPE: DNA
<213> ORGANISM: Artificial Sequence
<220> FEATURE:
<223> OTHER INFORMATION: Oligonucleotide

<400> SEQUENCE: 298
cccgctcgag atcctgctct ttttgcc                                  28

<210> SEQ ID NO 299
<211> LENGTH: 28
<212> TYPE: DNA
<213> ORGANISM: Artificial Sequence
<220> FEATURE:
<223> OTHER INFORMATION: Oligonucleotide

<400> SEQUENCE: 299
ctagctagct gcggggcgg cggtggcg                                  28

<210> SEQ ID NO 300
<211> LENGTH: 28
<212> TYPE: DNA
<213> ORGANISM: Artificial Sequence
<220> FEATURE:
<223> OTHER INFORMATION: Oligonucleotide

<400> SEQUENCE: 300
cccgctcgag atcctgctct ttttgcc                                  28

<210> SEQ ID NO 301
<211> LENGTH: 32
<212> TYPE: DNA
<213> ORGANISM: Artificial Sequence
<220> FEATURE:
<223> OTHER INFORMATION: Oligonucleotide

<400> SEQUENCE: 301
cgcggatccg ctagccccga tgttaaatcg gc                            32

<210> SEQ ID NO 302
<211> LENGTH: 32
<212> TYPE: DNA
<213> ORGANISM: Artificial Sequence
<220> FEATURE:
<223> OTHER INFORMATION: Oligonucleotide
```

```
<400> SEQUENCE: 302
cgcggatccg ctagccaaga tatggcggca gt                              32

<210> SEQ ID NO 303
<211> LENGTH: 32
<212> TYPE: DNA
<213> ORGANISM: Artificial Sequence
<220> FEATURE:
<223> OTHER INFORMATION: Oligonucleotide

<400> SEQUENCE: 303
cgcggatccg ctagcgccga atccgcaaat ca                              32

<210> SEQ ID NO 304
<211> LENGTH: 32
<212> TYPE: DNA
<213> ORGANISM: Artificial Sequence
<220> FEATURE:
<223> OTHER INFORMATION: Oligonucleotide

<400> SEQUENCE: 304
cgcgctagcg gaagggttga tttggctaat gg                              32

<210> SEQ ID NO 305
<211> LENGTH: 32
<212> TYPE: DNA
<213> ORGANISM: Artificial Sequence
<220> FEATURE:
<223> OTHER INFORMATION: Oligonucleotide

<400> SEQUENCE: 305
cgcgctagcg gaagggttga tttggctaat gg                              32

<210> SEQ ID NO 306
<211> LENGTH: 29
<212> TYPE: DNA
<213> ORGANISM: Artificial Sequence
<220> FEATURE:
<223> OTHER INFORMATION: Oligonucleotide

<400> SEQUENCE: 306
cgccatatgt ttaaacgcag cgtaatcgc                                  29

<210> SEQ ID NO 307
<211> LENGTH: 34
<212> TYPE: DNA
<213> ORGANISM: Artificial Sequence
<220> FEATURE:
<223> OTHER INFORMATION: Oligonucleotide

<400> SEQUENCE: 307
cccgctcgag aaaattgcta ccgccattcg cagg                            34

<210> SEQ ID NO 308
<211> LENGTH: 32
<212> TYPE: DNA
<213> ORGANISM: Artificial Sequence
<220> FEATURE:
<223> OTHER INFORMATION: Oligonucleotide

<400> SEQUENCE: 308
cgccatatgg gaagggttga tttggctaat gg                              32

<210> SEQ ID NO 309
<211> LENGTH: 38
<212> TYPE: DNA
```

```
<213> ORGANISM: Artificial Sequence
<220> FEATURE:
<223> OTHER INFORMATION: Oligonucleotide

<400> SEQUENCE: 309
cccgctcgag cttgtcttta taaatgatga catatttg                               38

<210> SEQ ID NO 310
<211> LENGTH: 40
<212> TYPE: DNA
<213> ORGANISM: Artificial Sequence
<220> FEATURE:
<223> OTHER INFORMATION: Oligonucleotide

<400> SEQUENCE: 310
cccgctcgag tttataaaag ataatatatt gattgattcc                             40

<210> SEQ ID NO 311
<211> LENGTH: 31
<212> TYPE: DNA
<213> ORGANISM: Artificial Sequence
<220> FEATURE:
<223> OTHER INFORMATION: Oligonucleotide

<400> SEQUENCE: 311
cgcgctagca tgccgctgat tcccgtcaat c                                      31

<210> SEQ ID NO 312
<211> LENGTH: 25
<212> TYPE: DNA
<213> ORGANISM: Artificial Sequence
<220> FEATURE:
<223> OTHER INFORMATION: Oligonucleotide

<400> SEQUENCE: 312
ctagctagcg ggggcggcgg tggcg                                             25

<210> SEQ ID NO 313
<211> LENGTH: 31
<212> TYPE: DNA
<213> ORGANISM: Artificial Sequence
<220> FEATURE:
<223> OTHER INFORMATION: Oligonucleotide

<400> SEQUENCE: 313
cccgctcgag tcaatcctgc tcttttttgc c                                      31

<210> SEQ ID NO 314
<211> LENGTH: 32
<212> TYPE: DNA
<213> ORGANISM: Artificial Sequence
<220> FEATURE:
<223> OTHER INFORMATION: Oligonucleotide

<400> SEQUENCE: 314
cgcggatccg ctagccccga tgttaaatcg gc                                     32

<210> SEQ ID NO 315
<211> LENGTH: 28
<212> TYPE: DNA
<213> ORGANISM: Artificial Sequence
<220> FEATURE:
<223> OTHER INFORMATION: Oligonucleotide

<400> SEQUENCE: 315
cccgctcgag atcctgctct tttttgcc                                          28
```

<210> SEQ ID NO 316
<211> LENGTH: 32
<212> TYPE: DNA
<213> ORGANISM: Artificial Sequence
<220> FEATURE:
<223> OTHER INFORMATION: Oligonucleotide

<400> SEQUENCE: 316
cgcggatccg ctagccccga tgttaaatcg gc                          32

<210> SEQ ID NO 317
<211> LENGTH: 31
<212> TYPE: DNA
<213> ORGANISM: Artificial Sequence
<220> FEATURE:
<223> OTHER INFORMATION: Oligonucleotide

<400> SEQUENCE: 317
cccgctcgag tcaatcctgc tcttttttgc c                            31

<210> SEQ ID NO 318
<211> LENGTH: 87
<212> TYPE: DNA
<213> ORGANISM: Artificial Sequence
<220> FEATURE:
<223> OTHER INFORMATION: Oligonucleotide

<400> SEQUENCE: 318
cgcggatccg ctagctttga acgcagtgtg attgcaatgg cttgtatttt tgcccttttca    60 gcctgttcgc ccgatgttaa atcggcg                                         87

<210> SEQ ID NO 319
<211> LENGTH: 31
<212> TYPE: DNA
<213> ORGANISM: Artificial Sequence
<220> FEATURE:
<223> OTHER INFORMATION: Oligonucleotide

<400> SEQUENCE: 319
cccgctcgag tcaatcctgc tcttttttgc c                            31

<210> SEQ ID NO 320
<211> LENGTH: 90
<212> TYPE: DNA
<213> ORGANISM: Artificial Sequence
<220> FEATURE:
<223> OTHER INFORMATION: Oligonucleotide

<400> SEQUENCE: 320
cgcggatccg ctagcaaaac cttcttcaaa acccttccg ccgccgcact cgcgctcatc      60
ctcgccgcct gctcgcccga tgttaaatcg                                      90

<210> SEQ ID NO 321
<211> LENGTH: 31
<212> TYPE: DNA
<213> ORGANISM: Artificial Sequence
<220> FEATURE:
<223> OTHER INFORMATION: Oligonucleotide

<400> SEQUENCE: 321
cccgctcgag tcaatcctgc tcttttttgc c                            31

<210> SEQ ID NO 322
<211> LENGTH: 33
<212> TYPE: DNA

<213> ORGANISM: Artificial Sequence
<220> FEATURE:
<223> OTHER INFORMATION: Oligonucleotide

<400> SEQUENCE: 322
cgcggatccc atatgaaaac caagttaatc aaa                    33

<210> SEQ ID NO 323
<211> LENGTH: 30
<212> TYPE: DNA
<213> ORGANISM: Artificial Sequence
<220> FEATURE:
<223> OTHER INFORMATION: Oligonucleotide

<400> SEQUENCE: 323
cccgctcgag ttattgattt ttgcggatga                        30

<210> SEQ ID NO 324
<211> LENGTH: 34
<212> TYPE: DNA
<213> ORGANISM: Artificial Sequence
<220> FEATURE:
<223> OTHER INFORMATION: Oligonucleotide

<400> SEQUENCE: 324
cgcggatccc atatgttaaa tcgggtattt tatc                   34

<210> SEQ ID NO 325
<211> LENGTH: 28
<212> TYPE: DNA
<213> ORGANISM: Artificial Sequence
<220> FEATURE:
<223> OTHER INFORMATION: Oligonucleotide

<400> SEQUENCE: 325
cccgctcgag ttaatccgcc attccctg                          28

<210> SEQ ID NO 326
<211> LENGTH: 30
<212> TYPE: DNA
<213> ORGANISM: Artificial Sequence
<220> FEATURE:
<223> OTHER INFORMATION: Oligonucleotide

<400> SEQUENCE: 326
gcggccatat gaaattacaa caattggctg                        30

<210> SEQ ID NO 327
<211> LENGTH: 31
<212> TYPE: DNA
<213> ORGANISM: Artificial Sequence
<220> FEATURE:
<223> OTHER INFORMATION: Oligonucleotide

<400> SEQUENCE: 327
gcggcctcga gttaccttac gtttttcaaa g                      31

<210> SEQ ID NO 328
<211> LENGTH: 29
<212> TYPE: DNA
<213> ORGANISM: Artificial Sequence
<220> FEATURE:
<223> OTHER INFORMATION: Oligonucleotide

<400> SEQUENCE: 328
cgcggatccc atatgcaagc acggctgct                         29

<210> SEQ ID NO 329
<211> LENGTH: 29
<212> TYPE: DNA
<213> ORGANISM: Artificial Sequence
<220> FEATURE:
<223> OTHER INFORMATION: Oligonucleotide

<400> SEQUENCE: 329
cccgctcgag tcaaggttgt ccttgtcta                    29

<210> SEQ ID NO 330
<211> LENGTH: 30
<212> TYPE: DNA
<213> ORGANISM: Artificial Sequence
<220> FEATURE:
<223> OTHER INFORMATION: Oligonucleotide

<400> SEQUENCE: 330
cgcggatccc atatgatgaa accgcacaac                   30

<210> SEQ ID NO 331
<211> LENGTH: 28
<212> TYPE: DNA
<213> ORGANISM: Artificial Sequence
<220> FEATURE:
<223> OTHER INFORMATION: Oligonucleotide

<400> SEQUENCE: 331
cccgctcgag tcagttgctc aacacgtc                     28

<210> SEQ ID NO 332
<211> LENGTH: 32
<212> TYPE: DNA
<213> ORGANISM: Artificial Sequence
<220> FEATURE:
<223> OTHER INFORMATION: Oligonucleotide

<400> SEQUENCE: 332
cgcggatccc atatggtaga cgcgcttaag ca                32

<210> SEQ ID NO 333
<211> LENGTH: 25
<212> TYPE: DNA
<213> ORGANISM: Artificial Sequence
<220> FEATURE:
<223> OTHER INFORMATION: Oligonucleotide

<400> SEQUENCE: 333
cccgctcgag agctgcatgg cggcg                        25

<210> SEQ ID NO 334
<211> LENGTH: 30
<212> TYPE: DNA
<213> ORGANISM: Artificial Sequence
<220> FEATURE:
<223> OTHER INFORMATION: Oligonucleotide

<400> SEQUENCE: 334
cgcggatccc atatggcacg gtcgttatac                   30

<210> SEQ ID NO 335
<211> LENGTH: 26
<212> TYPE: DNA
<213> ORGANISM: Artificial Sequence
<220> FEATURE:
<223> OTHER INFORMATION: Oligonucleotide -continued

<400> SEQUENCE: 335
cccgctcgag ctaccgcgca ttcctg                                          26

<210> SEQ ID NO 336
<211> LENGTH: 31
<212> TYPE: DNA
<213> ORGANISM: Artificial Sequence
<220> FEATURE:
<223> OTHER INFORMATION: Oligonucleotide

<400> SEQUENCE: 336
gcggccatat ggaattttc attatcttgt t                                     31

<210> SEQ ID NO 337
<211> LENGTH: 31
<212> TYPE: DNA
<213> ORGANISM: Artificial Sequence
<220> FEATURE:
<223> OTHER INFORMATION: Oligonucleotide

<400> SEQUENCE: 337
gcggcctcga gttatttggc ggttttgctg c                                    31

<210> SEQ ID NO 338
<211> LENGTH: 32
<212> TYPE: DNA
<213> ORGANISM: Artificial Sequence
<220> FEATURE:
<223> OTHER INFORMATION: Oligonucleotide

<400> SEQUENCE: 338
gcggccatat gaagtatgtc cggttatttt tc                                   32

<210> SEQ ID NO 339
<211> LENGTH: 30
<212> TYPE: DNA
<213> ORGANISM: Artificial Sequence
<220> FEATURE:
<223> OTHER INFORMATION: Oligonucleotide

<400> SEQUENCE: 339
gcggcctcga gttatcggct tgtgcaacgg                                      30

<210> SEQ ID NO 340
<211> LENGTH: 32
<212> TYPE: DNA
<213> ORGANISM: Artificial Sequence
<220> FEATURE:
<223> OTHER INFORMATION: Oligonucleotide

<400> SEQUENCE: 340
cgcggatccg ctagctccgg cagcaaaacc ga                                   32

<210> SEQ ID NO 341
<211> LENGTH: 28
<212> TYPE: DNA
<213> ORGANISM: Artificial Sequence
<220> FEATURE:
<223> OTHER INFORMATION: Oligonucleotide

<400> SEQUENCE: 341
gcccaagctt acgcagttcg gaatggag                                        28

<210> SEQ ID NO 342
<211> LENGTH: 35
<212> TYPE: DNA

```
<213> ORGANISM: Artificial Sequence
<220> FEATURE:
<223> OTHER INFORMATION: Oligonucleotide

<400> SEQUENCE: 342
gccgccatat gttgaatatt aaactgaaaa ccttg                        35

<210> SEQ ID NO 343
<211> LENGTH: 32
<212> TYPE: DNA
<213> ORGANISM: Artificial Sequence
<220> FEATURE:
<223> OTHER INFORMATION: Oligonucleotide

<400> SEQUENCE: 343
gccgcctcga gttatttctg atgcctttc cc                           32

<210> SEQ ID NO 344
<211> LENGTH: 29
<212> TYPE: DNA
<213> ORGANISM: Artificial Sequence
<220> FEATURE:
<223> OTHER INFORMATION: Oligonucleotide

<400> SEQUENCE: 344
gccgccatat ggacaataag accaaactg                              29

<210> SEQ ID NO 345
<211> LENGTH: 30
<212> TYPE: DNA
<213> ORGANISM: Artificial Sequence
<220> FEATURE:
<223> OTHER INFORMATION: Oligonucleotide

<400> SEQUENCE: 345
gccgcctcga gttaacggtg cggacgtttc                             30

<210> SEQ ID NO 346
<211> LENGTH: 32
<212> TYPE: DNA
<213> ORGANISM: Artificial Sequence
<220> FEATURE:
<223> OTHER INFORMATION: Oligonucleotide

<400> SEQUENCE: 346
cgcggatccc atatgaacaa actgtttctt ac                          32

<210> SEQ ID NO 347
<211> LENGTH: 28
<212> TYPE: DNA
<213> ORGANISM: Artificial Sequence
<220> FEATURE:
<223> OTHER INFORMATION: Oligonucleotide

<400> SEQUENCE: 347
cccgctcgag tcattccgcc ttcagaaa                               28

<210> SEQ ID NO 348
<211> LENGTH: 45
<212> TYPE: DNA
<213> ORGANISM: Artificial Sequence
<220> FEATURE:
<223> OTHER INFORMATION: Oligonucleotide

<400> SEQUENCE: 348
cgcggatccc atatgcaagg tatcgttgcc gacaaatccg cacct            45
```

<210> SEQ ID NO 349
<211> LENGTH: 42
<212> TYPE: DNA
<213> ORGANISM: Artificial Sequence
<220> FEATURE:
<223> OTHER INFORMATION: Oligonucleotide

<400> SEQUENCE: 349
cccgctcgag agctaattgt gcttggtttg cagataggag tt                        42

<210> SEQ ID NO 350
<211> LENGTH: 52
<212> TYPE: DNA
<213> ORGANISM: Artificial Sequence
<220> FEATURE:
<223> OTHER INFORMATION: Oligonucleotide

<400> SEQUENCE: 350
cgcggatccc atatgaaccg caccctgtac aaagttgtat ttaacaaaca tc              52

<210> SEQ ID NO 351
<211> LENGTH: 45
<212> TYPE: DNA
<213> ORGANISM: Artificial Sequence
<220> FEATURE:
<223> OTHER INFORMATION: Oligonucleotide

<400> SEQUENCE: 351
cccgctcgag ttaagctaat tgtgcttggt ttgcagatag gagtt                     45

<210> SEQ ID NO 352
<211> LENGTH: 46
<212> TYPE: DNA
<213> ORGANISM: Artificial Sequence
<220> FEATURE:
<223> OTHER INFORMATION: Oligonucleotide

<400> SEQUENCE: 352
cgcggatccc atatgacggg agaaaatcat gcggtttcac ttcatg                    46

<210> SEQ ID NO 353
<211> LENGTH: 42
<212> TYPE: DNA
<213> ORGANISM: Artificial Sequence
<220> FEATURE:
<223> OTHER INFORMATION: Oligonucleotide

<400> SEQUENCE: 353
cccgctcgag agctaattgt gcttggtttg cagataggag tt                        42

<210> SEQ ID NO 354
<211> LENGTH: 51
<212> TYPE: DNA
<213> ORGANISM: Artificial Sequence
<220> FEATURE:
<223> OTHER INFORMATION: Oligonucleotide

<400> SEQUENCE: 354
cgcggatccc atatggtttc agacggccta tacaaccaac atggtgaaat t              51

<210> SEQ ID NO 355
<211> LENGTH: 41
<212> TYPE: DNA
<213> ORGANISM: Artificial Sequence
<220> FEATURE:
<223> OTHER INFORMATION: Oligonucleotide -continued

<400> SEQUENCE: 355
cccgctcgag gcggtaactg ccgcttgcac tgaatccgta a    41

<210> SEQ ID NO 356
<211> LENGTH: 46
<212> TYPE: DNA
<213> ORGANISM: Artificial Sequence
<220> FEATURE:
<223> OTHER INFORMATION: Oligonucleotide

<400> SEQUENCE: 356
cgcggatccc atatgacggg agaaaatcat gcggtttcac ttcatg    46

<210> SEQ ID NO 357
<211> LENGTH: 41
<212> TYPE: DNA
<213> ORGANISM: Artificial Sequence
<220> FEATURE:
<223> OTHER INFORMATION: Oligonucleotide

<400> SEQUENCE: 357
cccgctcgag gcggtaactg ccgcttgcac tgaatccgta a    41

<210> SEQ ID NO 358
<211> LENGTH: 49
<212> TYPE: DNA
<213> ORGANISM: Artificial Sequence
<220> FEATURE:
<223> OTHER INFORMATION: Oligonucleotide

<400> SEQUENCE: 358
cgcggatccc atatgcaaag caaagtcaaa gcagaccatg cctccgtaa    49

<210> SEQ ID NO 359
<211> LENGTH: 56
<212> TYPE: DNA
<213> ORGANISM: Artificial Sequence
<220> FEATURE:
<223> OTHER INFORMATION: Oligonucleotide

<400> SEQUENCE: 359
cccgctcgag tcttttcctt tcaattataa ctttagtagg ttcaattttg gtcccc    56

<210> SEQ ID NO 360
<211> LENGTH: 51
<212> TYPE: DNA
<213> ORGANISM: Artificial Sequence
<220> FEATURE:
<223> OTHER INFORMATION: Oligonucleotide

<400> SEQUENCE: 360
cgcggatccc atatggtttc agacggccta tacaaccaac atggtgaaat t    51

<210> SEQ ID NO 361
<211> LENGTH: 56
<212> TYPE: DNA
<213> ORGANISM: Artificial Sequence
<220> FEATURE:
<223> OTHER INFORMATION: Oligonucleotide

<400> SEQUENCE: 361
cccgctcgag tcttttcctt tcaattataa ctttagtagg ttcaattttg gtcccc    56

<210> SEQ ID NO 362
<211> LENGTH: 27
<212> TYPE: DNA

```
<213> ORGANISM: Artificial Sequence
<220> FEATURE:
<223> OTHER INFORMATION: Oligonucleotide

<400> SEQUENCE: 362
gcggccatat gacccgtttg acccgcg                                          27

<210> SEQ ID NO 363
<211> LENGTH: 31
<212> TYPE: DNA
<213> ORGANISM: Artificial Sequence
<220> FEATURE:
<223> OTHER INFORMATION: Oligonucleotide

<400> SEQUENCE: 363
gcggcctcga gtcagcgggc gttcatttct t                                     31

<210> SEQ ID NO 364
<211> LENGTH: 33
<212> TYPE: DNA
<213> ORGANISM: Artificial Sequence
<220> FEATURE:
<223> OTHER INFORMATION: Oligonucleotide

<400> SEQUENCE: 364
cgcggatccc atatgaacac cattttcaaa atc                                   33

<210> SEQ ID NO 365
<211> LENGTH: 32
<212> TYPE: DNA
<213> ORGANISM: Artificial Sequence
<220> FEATURE:
<223> OTHER INFORMATION: Oligonucleotide

<400> SEQUENCE: 365
cccgctcgag ttaatttact tttttgatgt cg                                    32

<210> SEQ ID NO 366
<211> LENGTH: 28
<212> TYPE: DNA
<213> ORGANISM: Artificial Sequence
<220> FEATURE:
<223> OTHER INFORMATION: Oligonucleotide

<400> SEQUENCE: 366
gcggccatat ggattcgccc aaggtcgg                                         28

<210> SEQ ID NO 367
<211> LENGTH: 31
<212> TYPE: DNA
<213> ORGANISM: Artificial Sequence
<220> FEATURE:
<223> OTHER INFORMATION: Oligonucleotide

<400> SEQUENCE: 367
gcggcctcga gctacacttc ccccgaagtg g                                     31

<210> SEQ ID NO 368
<211> LENGTH: 31
<212> TYPE: DNA
<213> ORGANISM: Artificial Sequence
<220> FEATURE:
<223> OTHER INFORMATION: Oligonucleotide

<400> SEQUENCE: 368
cgcggatccc atatgatagt tgaccaaagc c                                     31
```

<210> SEQ ID NO 369
<211> LENGTH: 30
<212> TYPE: DNA
<213> ORGANISM: Artificial Sequence
<220> FEATURE:
<223> OTHER INFORMATION: Oligonucleotide

<400> SEQUENCE: 369
cccgctcgag ttatttttcc gattttcgg                                    30

<210> SEQ ID NO 370
<211> LENGTH: 28
<212> TYPE: DNA
<213> ORGANISM: Artificial Sequence
<220> FEATURE:
<223> OTHER INFORMATION: Oligonucleotide

<400> SEQUENCE: 370
gcggccatat gcttgaactg aacggact                                     28

<210> SEQ ID NO 371
<211> LENGTH: 30
<212> TYPE: DNA
<213> ORGANISM: Artificial Sequence
<220> FEATURE:
<223> OTHER INFORMATION: Oligonucleotide

<400> SEQUENCE: 371
gcggcctcga gtcagcggaa gcggacgatt                                   30

<210> SEQ ID NO 372
<211> LENGTH: 34
<212> TYPE: DNA
<213> ORGANISM: Artificial Sequence
<220> FEATURE:
<223> OTHER INFORMATION: Oligonucleotide

<400> SEQUENCE: 372
cgcggatccc atatgtccaa actcaaaacc atcg                              34

<210> SEQ ID NO 373
<211> LENGTH: 29
<212> TYPE: DNA
<213> ORGANISM: Artificial Sequence
<220> FEATURE:
<223> OTHER INFORMATION: Oligonucleotide

<400> SEQUENCE: 373
cccgctcgag gcttccaatc agtttgacc                                    29

<210> SEQ ID NO 374
<211> LENGTH: 32
<212> TYPE: DNA
<213> ORGANISM: Artificial Sequence
<220> FEATURE:
<223> OTHER INFORMATION: Oligonucleotide

<400> SEQUENCE: 374
gcggccatat gagcgcaatc gttgatattt tc                                32

<210> SEQ ID NO 375
<211> LENGTH: 34
<212> TYPE: DNA
<213> ORGANISM: Artificial Sequence
<220> FEATURE:
<223> OTHER INFORMATION: Oligonucleotide -continued

```
<400> SEQUENCE: 375
gcggcctcga gttatttgcc cagttggtag aatg                                34

<210> SEQ ID NO 376
<211> LENGTH: 32
<212> TYPE: DNA
<213> ORGANISM: Artificial Sequence
<220> FEATURE:
<223> OTHER INFORMATION: Oligonucleotide

<400> SEQUENCE: 376
gcggccatat ggtgatacat ccgcactact tc                                  32

<210> SEQ ID NO 377
<211> LENGTH: 32
<212> TYPE: DNA
<213> ORGANISM: Artificial Sequence
<220> FEATURE:
<223> OTHER INFORMATION: Oligonucleotide

<400> SEQUENCE: 377
gcggcctcga gtcaaaatcg agttttacac ca                                  32

<210> SEQ ID NO 378
<211> LENGTH: 31
<212> TYPE: DNA
<213> ORGANISM: Artificial Sequence
<220> FEATURE:
<223> OTHER INFORMATION: Oligonucleotide

<400> SEQUENCE: 378
gcggccatat gaccatctat ttcaaaaacg g                                   31

<210> SEQ ID NO 379
<211> LENGTH: 34
<212> TYPE: DNA
<213> ORGANISM: Artificial Sequence
<220> FEATURE:
<223> OTHER INFORMATION: Oligonucleotide

<400> SEQUENCE: 379
gcggcctcga gtcagccgat gtttagcgtc catt                                34

<210> SEQ ID NO 380
<211> LENGTH: 31
<212> TYPE: DNA
<213> ORGANISM: Artificial Sequence
<220> FEATURE:
<223> OTHER INFORMATION: Oligonucleotide

<400> SEQUENCE: 380
cgcggatccc atatgagcag cggaggggt g                                    31

<210> SEQ ID NO 381
<211> LENGTH: 27
<212> TYPE: DNA
<213> ORGANISM: Artificial Sequence
<220> FEATURE:
<223> OTHER INFORMATION: Oligonucleotide

<400> SEQUENCE: 381
cccgctcgag ttgcttggcg gcaaggc                                        27

<210> SEQ ID NO 382
<211> LENGTH: 31
<212> TYPE: DNA
```

```
<213> ORGANISM: Artificial Sequence
<220> FEATURE:
<223> OTHER INFORMATION: Oligonucleotide

<400> SEQUENCE: 382
cgcggatccc atatggtcgc cgccgacatc g                              31

<210> SEQ ID NO 383
<211> LENGTH: 27
<212> TYPE: DNA
<213> ORGANISM: Artificial Sequence
<220> FEATURE:
<223> OTHER INFORMATION: Oligonucleotide

<400> SEQUENCE: 383
cccgctcgag ttgcttggcg gcaaggc                                   27

<210> SEQ ID NO 384
<211> LENGTH: 31
<212> TYPE: DNA
<213> ORGANISM: Artificial Sequence
<220> FEATURE:
<223> OTHER INFORMATION: Oligonucleotide

<400> SEQUENCE: 384
cgcggatccc atatgggcgg ttcggaaggc g                              31

<210> SEQ ID NO 385
<211> LENGTH: 33
<212> TYPE: DNA
<213> ORGANISM: Artificial Sequence
<220> FEATURE:
<223> OTHER INFORMATION: Oligonucleotide

<400> SEQUENCE: 385
cccgctcgag ttgaacactg atgtcttttc cga                            33

<210> SEQ ID NO 386
<211> LENGTH: 35
<212> TYPE: DNA
<213> ORGANISM: Artificial Sequence
<220> FEATURE:
<223> OTHER INFORMATION: Oligonucleotide

<400> SEQUENCE: 386
cgcggatccg ctagcaaact gtcgttggtg ttaac                          35

<210> SEQ ID NO 387
<211> LENGTH: 26
<212> TYPE: DNA
<213> ORGANISM: Artificial Sequence
<220> FEATURE:
<223> OTHER INFORMATION: Oligonucleotide

<400> SEQUENCE: 387
cccgctcgag ttgacccgct ccacgg                                    26

<210> SEQ ID NO 388
<211> LENGTH: 31
<212> TYPE: DNA
<213> ORGANISM: Artificial Sequence
<220> FEATURE:
<223> OTHER INFORMATION: Oligonucleotide

<400> SEQUENCE: 388
gccgccatat ggcggacttg gcgcaagacc c                              31
```

<210> SEQ ID NO 389
<211> LENGTH: 39
<212> TYPE: DNA
<213> ORGANISM: Artificial Sequence
<220> FEATURE:
<223> OTHER INFORMATION: Oligonucleotide

<400> SEQUENCE: 389
gccgcctcga gatctcctaa acctgtttta acaatgccg           39

<210> SEQ ID NO 390
<211> LENGTH: 31
<212> TYPE: DNA
<213> ORGANISM: Artificial Sequence
<220> FEATURE:
<223> OTHER INFORMATION: Oligonucleotide

<400> SEQUENCE: 390
gccgccatat ggcggacttg gcgcaagacc c                   31

<210> SEQ ID NO 391
<211> LENGTH: 31
<212> TYPE: DNA
<213> ORGANISM: Artificial Sequence
<220> FEATURE:
<223> OTHER INFORMATION: Oligonucleotide

<400> SEQUENCE: 391
gcggcctcga gctccatgct gttgcccag c                    31

<210> SEQ ID NO 392
<211> LENGTH: 31
<212> TYPE: DNA
<213> ORGANISM: Artificial Sequence
<220> FEATURE:
<223> OTHER INFORMATION: Oligonucleotide

<400> SEQUENCE: 392
gccgccatat ggcggacttg gcgcaagacc c                   31

<210> SEQ ID NO 393
<211> LENGTH: 31
<212> TYPE: DNA
<213> ORGANISM: Artificial Sequence
<220> FEATURE:
<223> OTHER INFORMATION: Oligonucleotide

<400> SEQUENCE: 393
gcggcctcga gaaaatcccc gctaaccgca g                   31

<210> SEQ ID NO 394
<211> LENGTH: 31
<212> TYPE: DNA
<213> ORGANISM: Artificial Sequence
<220> FEATURE:
<223> OTHER INFORMATION: Oligonucleotide

<400> SEQUENCE: 394
cgcggatccc atatgagcag cggaggggt g                    31

<210> SEQ ID NO 395
<211> LENGTH: 27
<212> TYPE: DNA
<213> ORGANISM: Artificial Sequence
<220> FEATURE:
<223> OTHER INFORMATION: Oligonucleotide

```
<400> SEQUENCE: 395
cccgctcgag ttgcttggcg gcaaggc                                    27

<210> SEQ ID NO 396
<211> LENGTH: 31
<212> TYPE: DNA
<213> ORGANISM: Artificial Sequence
<220> FEATURE:
<223> OTHER INFORMATION: Oligonucleotide

<400> SEQUENCE: 396
cgcggatccc atatggtcgc cgccgacatc g                               31

<210> SEQ ID NO 397
<211> LENGTH: 27
<212> TYPE: DNA
<213> ORGANISM: Artificial Sequence
<220> FEATURE:
<223> OTHER INFORMATION: Oligonucleotide

<400> SEQUENCE: 397
cccgctcgag ttgcttggcg gcaaggc                                    27

<210> SEQ ID NO 398
<211> LENGTH: 33
<212> TYPE: DNA
<213> ORGANISM: Artificial Sequence
<220> FEATURE:
<223> OTHER INFORMATION: Oligonucleotide

<400> SEQUENCE: 398
cgcggatccc atatggacgg tgttgtgcct gtt                             33

<210> SEQ ID NO 399
<211> LENGTH: 29
<212> TYPE: DNA
<213> ORGANISM: Artificial Sequence
<220> FEATURE:
<223> OTHER INFORMATION: Oligonucleotide

<400> SEQUENCE: 399
cccgctcgag cttacggatc aaattgacg                                  29

<210> SEQ ID NO 400
<211> LENGTH: 33
<212> TYPE: DNA
<213> ORGANISM: Artificial Sequence
<220> FEATURE:
<223> OTHER INFORMATION: Oligonucleotide

<400> SEQUENCE: 400
cgcggatccc atatgggcag ccaatctgaa gaa                             33

<210> SEQ ID NO 401
<211> LENGTH: 28
<212> TYPE: DNA
<213> ORGANISM: Artificial Sequence
<220> FEATURE:
<223> OTHER INFORMATION: Oligonucleotide

<400> SEQUENCE: 401
cccgctcgag ctcagctttt gccgtcaa                                   28

<210> SEQ ID NO 402
<211> LENGTH: 33
<212> TYPE: DNA
```

```
<213> ORGANISM: Artificial Sequence
<220> FEATURE:
<223> OTHER INFORMATION: Oligonucleotide

<400> SEQUENCE: 402
cgcggatccg ctagctactc atccattgtc cgc                          33

<210> SEQ ID NO 403
<211> LENGTH: 29
<212> TYPE: DNA
<213> ORGANISM: Artificial Sequence
<220> FEATURE:
<223> OTHER INFORMATION: Oligonucleotide

<400> SEQUENCE: 403
cccgctcgag ccagttgtag cctattttg                                29

<210> SEQ ID NO 404
<211> LENGTH: 32
<212> TYPE: DNA
<213> ORGANISM: Artificial Sequence
<220> FEATURE:
<223> OTHER INFORMATION: Oligonucleotide

<400> SEQUENCE: 404
cgcggatccg ctagcatgcg cttcacacac ac                           32

<210> SEQ ID NO 405
<211> LENGTH: 30
<212> TYPE: DNA
<213> ORGANISM: Artificial Sequence
<220> FEATURE:
<223> OTHER INFORMATION: Oligonucleotide

<400> SEQUENCE: 405
cccgctcgag ttaccagttg tagcctattt                              30

<210> SEQ ID NO 406
<211> LENGTH: 32
<212> TYPE: DNA
<213> ORGANISM: Artificial Sequence
<220> FEATURE:
<223> OTHER INFORMATION: Oligonucleotide

<400> SEQUENCE: 406
gccgccatat ggcacaaacg gaaggtttgg aa                           32

<210> SEQ ID NO 407
<211> LENGTH: 36
<212> TYPE: DNA
<213> ORGANISM: Artificial Sequence
<220> FEATURE:
<223> OTHER INFORMATION: Oligonucleotide

<400> SEQUENCE: 407
gccgcctcga gaaaactgta acgcaggttt gccgtc                       36

<210> SEQ ID NO 408
<211> LENGTH: 32
<212> TYPE: DNA
<213> ORGANISM: Artificial Sequence
<220> FEATURE:
<223> OTHER INFORMATION: Oligonucleotide

<400> SEQUENCE: 408
gcggccatat ggaagaaaca ccgcgcgaac cg                           32
```

```
<210> SEQ ID NO 409
<211> LENGTH: 32
<212> TYPE: DNA
<213> ORGANISM: Artificial Sequence
<220> FEATURE:
<223> OTHER INFORMATION: Oligonucleotide

<400> SEQUENCE: 409
gcggcctcga ggaacgtttt attaaactcg ac                                32

<210> SEQ ID NO 410
<211> LENGTH: 32
<212> TYPE: DNA
<213> ORGANISM: Artificial Sequence
<220> FEATURE:
<223> OTHER INFORMATION: Oligonucleotide

<400> SEQUENCE: 410
gcggccatat gagaaaaccg accgataccc ta                                32

<210> SEQ ID NO 411
<211> LENGTH: 33
<212> TYPE: DNA
<213> ORGANISM: Artificial Sequence
<220> FEATURE:
<223> OTHER INFORMATION: Oligonucleotide

<400> SEQUENCE: 411
gcggcctcga gtcaacgcca ctgccagcgg ttg                               33

<210> SEQ ID NO 412
<211> LENGTH: 48
<212> TYPE: DNA
<213> ORGANISM: Artificial Sequence
<220> FEATURE:
<223> OTHER INFORMATION: Oligonucleotide

<400> SEQUENCE: 412
cgcggatccc atatgaagaa gaacatattg gaattttggg tcggactg               48

<210> SEQ ID NO 413
<211> LENGTH: 38
<212> TYPE: DNA
<213> ORGANISM: Artificial Sequence
<220> FEATURE:
<223> OTHER INFORMATION: Oligonucleotide

<400> SEQUENCE: 413
cccgctcgag ttattcggcg gcttttccg cattgccg                           38

<210> SEQ ID NO 414
<211> LENGTH: 103
<212> TYPE: DNA
<213> ORGANISM: Artificial Sequence
<220> FEATURE:
<223> OTHER INFORMATION: Oligonucleotide

<400> SEQUENCE: 414
gggaattcca tatgaaaaag acagctatcg cgattgcagt ggcactggct ggtttcgcta  60
ccgtagcgca ggccgctagc gctttccgcg tggccggcgg tgc                   103

<210> SEQ ID NO 415
<211> LENGTH: 38
<212> TYPE: DNA
<213> ORGANISM: Artificial Sequence
<220> FEATURE:
```

<223> OTHER INFORMATION: Oligonucleotide

<400> SEQUENCE: 415
cccgctcgag ttattcggcg gcttttttccg cattgccg                38

<210> SEQ ID NO 416
<211> LENGTH: 32
<212> TYPE: DNA
<213> ORGANISM: Artificial Sequence
<220> FEATURE:
<223> OTHER INFORMATION: Oligonucleotide

<400> SEQUENCE: 416
catgccatgg ctttccgcgt ggccggcggt gc                32

<210> SEQ ID NO 417
<211> LENGTH: 38
<212> TYPE: DNA
<213> ORGANISM: Artificial Sequence
<220> FEATURE:
<223> OTHER INFORMATION: Oligonucleotide

<400> SEQUENCE: 417
cccgctcgag ttattcggcg gcttttttccg cattgccg                38

<210> SEQ ID NO 418
<211> LENGTH: 31
<212> TYPE: DNA
<213> ORGANISM: Artificial Sequence
<220> FEATURE:
<223> OTHER INFORMATION: Oligonucleotide

<400> SEQUENCE: 418
cgcggatccc atatgtttgc cgaaacccgc c                31

<210> SEQ ID NO 419
<211> LENGTH: 28
<212> TYPE: DNA
<213> ORGANISM: Artificial Sequence
<220> FEATURE:
<223> OTHER INFORMATION: Oligonucleotide

<400> SEQUENCE: 419
cccgctcgag aggttgtgtt ccaggttg                28

<210> SEQ ID NO 420
<211> LENGTH: 31
<212> TYPE: DNA
<213> ORGANISM: Artificial Sequence
<220> FEATURE:
<223> OTHER INFORMATION: Oligonucleotide

<400> SEQUENCE: 420
cgcggatccc atatgaaaaa aaccgcctat g                31

<210> SEQ ID NO 421
<211> LENGTH: 28
<212> TYPE: DNA
<213> ORGANISM: Artificial Sequence
<220> FEATURE:
<223> OTHER INFORMATION: Oligonucleotide

<400> SEQUENCE: 421
cccgctcgag ttaaggttgt gttccagg                28

<210> SEQ ID NO 422

```
<211> LENGTH: 33
<212> TYPE: DNA
<213> ORGANISM: Artificial Sequence
<220> FEATURE:
<223> OTHER INFORMATION: Oligonucleotide

<400> SEQUENCE: 422
cgcggatccc atatgaaaaa atacctattc cgc                              33

<210> SEQ ID NO 423
<211> LENGTH: 27
<212> TYPE: DNA
<213> ORGANISM: Artificial Sequence
<220> FEATURE:
<223> OTHER INFORMATION: Oligonucleotide

<400> SEQUENCE: 423
cccgctcgag ttacgggcgg tattcgg                                     27

<210> SEQ ID NO 424
<211> LENGTH: 34
<212> TYPE: DNA
<213> ORGANISM: Artificial Sequence
<220> FEATURE:
<223> OTHER INFORMATION: Oligonucleotide

<400> SEQUENCE: 424
cgcggatccc atatgcaaag caagagcatc caaa                             34

<210> SEQ ID NO 425
<211> LENGTH: 27
<212> TYPE: DNA
<213> ORGANISM: Artificial Sequence
<220> FEATURE:
<223> OTHER INFORMATION: Oligonucleotide

<400> SEQUENCE: 425
cccgctcgag ttacgggcgg tattcgg                                     27

<210> SEQ ID NO 426
<211> LENGTH: 86
<212> TYPE: DNA
<213> ORGANISM: Artificial Sequence
<220> FEATURE:
<223> OTHER INFORMATION: Oligonucleotide

<400> SEQUENCE: 426
gggaattcca tatgaaaacc ttcttcaaaa ccctttccgc cgccgcgcta gcgctcatcc  60
tcgccgcctg ccaaagcaag agcatc                                      86

<210> SEQ ID NO 427
<211> LENGTH: 38
<212> TYPE: DNA
<213> ORGANISM: Artificial Sequence
<220> FEATURE:
<223> OTHER INFORMATION: Oligonucleotide

<400> SEQUENCE: 427
cccgctcgag ttacgggcgg tattcgggct tcataccg                         38

<210> SEQ ID NO 428
<211> LENGTH: 33
<212> TYPE: DNA
<213> ORGANISM: Artificial Sequence
<220> FEATURE:
<223> OTHER INFORMATION: Oligonucleotide
```

-continued

<400> SEQUENCE: 428
cgcggatccg tcgactgtgg gggcggcggt ggc                          33

<210> SEQ ID NO 429
<211> LENGTH: 31
<212> TYPE: DNA
<213> ORGANISM: Artificial Sequence
<220> FEATURE:
<223> OTHER INFORMATION: Oligonucleotide

<400> SEQUENCE: 429
cccgctcgag tcaatcctgc tcttttttgc c                           31

<210> SEQ ID NO 430
<211> LENGTH: 30
<212> TYPE: DNA
<213> ORGANISM: Artificial Sequence
<220> FEATURE:
<223> OTHER INFORMATION: Oligonucleotide

<400> SEQUENCE: 430
gcggccatat gaagaaaaca ttgacactgc                              30

<210> SEQ ID NO 431
<211> LENGTH: 32
<212> TYPE: DNA
<213> ORGANISM: Artificial Sequence
<220> FEATURE:
<223> OTHER INFORMATION: Oligonucleotide

<400> SEQUENCE: 431
gcggcctcga gttaatggtg cgaatgaccg at                           32

<210> SEQ ID NO 432
<211> LENGTH: 46
<212> TYPE: DNA
<213> ORGANISM: Artificial Sequence
<220> FEATURE:
<223> OTHER INFORMATION: Oligonucleotide

<400> SEQUENCE: 432
ggggacaagt ttgtacaaaa aagcaggctt gcggcaagga tgccgg            46

<210> SEQ ID NO 433
<211> LENGTH: 47
<212> TYPE: DNA
<213> ORGANISM: Artificial Sequence
<220> FEATURE:
<223> OTHER INFORMATION: Oligonucleotide

<400> SEQUENCE: 433
ggggaccact ttgtacaaga aagctgggtc taaagcaaca atgccgg           47

<210> SEQ ID NO 434
<211> LENGTH: 30
<212> TYPE: DNA
<213> ORGANISM: Artificial Sequence
<220> FEATURE:
<223> OTHER INFORMATION: Oligonucleotide

<400> SEQUENCE: 434
cgcggatccc atatgaaaca caccgtatcc                              30

<210> SEQ ID NO 435
<211> LENGTH: 26
<212> TYPE: DNA

<213> ORGANISM: Artificial Sequence
<220> FEATURE:
<223> OTHER INFORMATION: Oligonucleotide

<400> SEQUENCE: 435
cccgctcgag ttatctcgtg cgcgcc 26

<210> SEQ ID NO 436
<211> LENGTH: 30
<212> TYPE: DNA
<213> ORGANISM: Artificial Sequence
<220> FEATURE:
<223> OTHER INFORMATION: Oligonucleotide

<400> SEQUENCE: 436
cgcggatccc atatgagccc cgcgccgatt 30

<210> SEQ ID NO 437
<211> LENGTH: 28
<212> TYPE: DNA
<213> ORGANISM: Artificial Sequence
<220> FEATURE:
<223> OTHER INFORMATION: Oligonucleotide

<400> SEQUENCE: 437
cccgctcgag tttttgtgcg gtcaggcg 28

<210> SEQ ID NO 438
<211> LENGTH: 62
<212> TYPE: DNA
<213> ORGANISM: Artificial Sequence
<220> FEATURE:
<223> OTHER INFORMATION: Oligonucleotide

<400> SEQUENCE: 438
ggggacaagt ttgtacaaaa aagcaggctt gttcgtttgg gggatttaaa ccaaaccaaa 60
tc 62

<210> SEQ ID NO 439
<211> LENGTH: 30
<212> TYPE: DNA
<213> ORGANISM: Artificial Sequence
<220> FEATURE:
<223> OTHER INFORMATION: Oligonucleotide

<400> SEQUENCE: 439
cgcggatccc atatggcgga tgcgcccgcg 30

<210> SEQ ID NO 440
<211> LENGTH: 26
<212> TYPE: DNA
<213> ORGANISM: Artificial Sequence
<220> FEATURE:
<223> OTHER INFORMATION: Oligonucleotide

<400> SEQUENCE: 440
cccgctcgag aaaccgccaa tccgcc 26

<210> SEQ ID NO 441
<211> LENGTH: 61
<212> TYPE: DNA
<213> ORGANISM: Artificial Sequence
<220> FEATURE:
<223> OTHER INFORMATION: Oligonucleotide

<400> SEQUENCE: 441

-continued

```
ggggaccact tgtacaaga aagctgggtt cattttgttt ttccttcttc tcgaggccat    60
t                                                                  61

<210> SEQ ID NO 442
<211> LENGTH: 30
<212> TYPE: DNA
<213> ORGANISM: Artificial Sequence
<220> FEATURE:
<223> OTHER INFORMATION: Oligonucleotide

<400> SEQUENCE: 442
cgcggatccc atatgaaacc caaaccgcac                                   30

<210> SEQ ID NO 443
<211> LENGTH: 27
<212> TYPE: DNA
<213> ORGANISM: Artificial Sequence
<220> FEATURE:
<223> OTHER INFORMATION: Oligonucleotide

<400> SEQUENCE: 443
cccgctcgag tcagcgttgg acgtagt                                      27

<210> SEQ ID NO 444
<211> LENGTH: 33
<212> TYPE: DNA
<213> ORGANISM: Artificial Sequence
<220> FEATURE:
<223> OTHER INFORMATION: Oligonucleotide

<400> SEQUENCE: 444
gggaattcca tatgaaaaaa atcatcttcg ccg                               33

<210> SEQ ID NO 445
<211> LENGTH: 31
<212> TYPE: DNA
<213> ORGANISM: Artificial Sequence
<220> FEATURE:
<223> OTHER INFORMATION: Oligonucleotide

<400> SEQUENCE: 445
cccgctcgag ttattgtttg gctgcctcga t                                 31

<210> SEQ ID NO 446
<211> LENGTH: 33
<212> TYPE: DNA
<213> ORGANISM: Artificial Sequence
<220> FEATURE:
<223> OTHER INFORMATION: Oligonucleotide

<400> SEQUENCE: 446
gggaattcca tatggccacc tacaaagtgg acg                               33

<210> SEQ ID NO 447
<211> LENGTH: 30
<212> TYPE: DNA
<213> ORGANISM: Artificial Sequence
<220> FEATURE:
<223> OTHER INFORMATION: Oligonucleotide

<400> SEQUENCE: 447
cggggatcct tgtttggctg cctcgatttg                                   30

<210> SEQ ID NO 448
<211> LENGTH: 34
<212> TYPE: DNA
```

<213> ORGANISM: Artificial Sequence
<220> FEATURE:
<223> OTHER INFORMATION: Oligonucleotide

<400> SEQUENCE: 448
cgcggatccc atatgcaaga acaatcgcag aaag                           34

<210> SEQ ID NO 449
<211> LENGTH: 30
<212> TYPE: DNA
<213> ORGANISM: Artificial Sequence
<220> FEATURE:
<223> OTHER INFORMATION: Oligonucleotide

<400> SEQUENCE: 449
cccgctcgag ttttttcggc aaattggctt                                30

<210> SEQ ID NO 450
<211> LENGTH: 45
<212> TYPE: DNA
<213> ORGANISM: Artificial Sequence
<220> FEATURE:
<223> OTHER INFORMATION: Oligonucleotide

<400> SEQUENCE: 450
ggggacaagt ttgtacaaaa aagcaggctg ccgatgccgt tgcgg               45

<210> SEQ ID NO 451
<211> LENGTH: 47
<212> TYPE: DNA
<213> ORGANISM: Artificial Sequence
<220> FEATURE:
<223> OTHER INFORMATION: Oligonucleotide

<400> SEQUENCE: 451
ggggaccact ttgtacaaga aagctgggtt cagggtcgtt tgttgcg             47

<210> SEQ ID NO 452
<211> LENGTH: 30
<212> TYPE: DNA
<213> ORGANISM: Artificial Sequence
<220> FEATURE:
<223> OTHER INFORMATION: Oligonucleotide

<400> SEQUENCE: 452
cgcggatccc atatgaaaca ctttccatcc                                30

<210> SEQ ID NO 453
<211> LENGTH: 28
<212> TYPE: DNA
<213> ORGANISM: Artificial Sequence
<220> FEATURE:
<223> OTHER INFORMATION: Oligonucleotide

<400> SEQUENCE: 453
cccgctcgag ttaccactcg taattgac                                  28

<210> SEQ ID NO 454
<211> LENGTH: 30
<212> TYPE: DNA
<213> ORGANISM: Artificial Sequence
<220> FEATURE:
<223> OTHER INFORMATION: Oligonucleotide

<400> SEQUENCE: 454
cgcggatccc atatggccac aagcgacgac                                30

<210> SEQ ID NO 455
<211> LENGTH: 28
<212> TYPE: DNA
<213> ORGANISM: Artificial Sequence
<220> FEATURE:
<223> OTHER INFORMATION: Oligonucleotide

<400> SEQUENCE: 455
cccgctcgag ttaccactcg taattgac                                      28

<210> SEQ ID NO 456
<211> LENGTH: 28
<212> TYPE: DNA
<213> ORGANISM: Artificial Sequence
<220> FEATURE:
<223> OTHER INFORMATION: Oligonucleotide

<400> SEQUENCE: 456
cgcggatccc atatggccac aaacgacg                                      28

<210> SEQ ID NO 457
<211> LENGTH: 28
<212> TYPE: DNA
<213> ORGANISM: Artificial Sequence
<220> FEATURE:
<223> OTHER INFORMATION: Oligonucleotide

<400> SEQUENCE: 457
cccgctcgag acccacgttg taaggttg                                      28

<210> SEQ ID NO 458
<211> LENGTH: 32
<212> TYPE: DNA
<213> ORGANISM: Artificial Sequence
<220> FEATURE:
<223> OTHER INFORMATION: Oligonucleotide

<400> SEQUENCE: 458
cgcggatccc atatggccac aagcgacgac ga                                 32

<210> SEQ ID NO 459
<211> LENGTH: 28
<212> TYPE: DNA
<213> ORGANISM: Artificial Sequence
<220> FEATURE:
<223> OTHER INFORMATION: Oligonucleotide

<400> SEQUENCE: 459
cccgctcgag acccacgttg taaggttg                                      28

<210> SEQ ID NO 460
<211> LENGTH: 33
<212> TYPE: DNA
<213> ORGANISM: Artificial Sequence
<220> FEATURE:
<223> OTHER INFORMATION: Oligonucleotide

<400> SEQUENCE: 460
cgcggatccc atatgatgaa acactttcca tcc                                33

<210> SEQ ID NO 461
<211> LENGTH: 29
<212> TYPE: DNA
<213> ORGANISM: Artificial Sequence
<220> FEATURE:
<223> OTHER INFORMATION: Oligonucleotide

```
<400> SEQUENCE: 461
cccgctcgag ttaacccacg ttgtaaggt                              29

<210> SEQ ID NO 462
<211> LENGTH: 33
<212> TYPE: DNA
<213> ORGANISM: Artificial Sequence
<220> FEATURE:
<223> OTHER INFORMATION: Oligonucleotide

<400> SEQUENCE: 462
cgcggatccc atatgatgaa acactttcca tcc                          33

<210> SEQ ID NO 463
<211> LENGTH: 29
<212> TYPE: DNA
<213> ORGANISM: Artificial Sequence
<220> FEATURE:
<223> OTHER INFORMATION: Oligonucleotide

<400> SEQUENCE: 463
cccgctcgag ttaacccacg ttgtaaggt                              29

<210> SEQ ID NO 464
<211> LENGTH: 28
<212> TYPE: DNA
<213> ORGANISM: Artificial Sequence
<220> FEATURE:
<223> OTHER INFORMATION: Oligonucleotide

<400> SEQUENCE: 464
cgcggatccc atatggccac aaacgacg                               28

<210> SEQ ID NO 465
<211> LENGTH: 29
<212> TYPE: DNA
<213> ORGANISM: Artificial Sequence
<220> FEATURE:
<223> OTHER INFORMATION: Oligonucleotide

<400> SEQUENCE: 465
cccgctcgag gtctgacact gttttatcc                              29

<210> SEQ ID NO 466
<211> LENGTH: 33
<212> TYPE: DNA
<213> ORGANISM: Artificial Sequence
<220> FEATURE:
<223> OTHER INFORMATION: Oligonucleotide

<400> SEQUENCE: 466
cgcggatccc atatgatgaa acactttcca tcc                          33

<210> SEQ ID NO 467
<211> LENGTH: 29
<212> TYPE: DNA
<213> ORGANISM: Artificial Sequence
<220> FEATURE:
<223> OTHER INFORMATION: Oligonucleotide

<400> SEQUENCE: 467
cccgctcgag ttatgctttg gcggcaaag                              29

<210> SEQ ID NO 468
<211> LENGTH: 30
<212> TYPE: DNA
```

```
<213> ORGANISM: Artificial Sequence
<220> FEATURE:
<223> OTHER INFORMATION: Oligonucleotide

<400> SEQUENCE: 468
cgcggatccc atatggccac aaacgacgac                                  30

<210> SEQ ID NO 469
<211> LENGTH: 27
<212> TYPE: DNA
<213> ORGANISM: Artificial Sequence
<220> FEATURE:
<223> OTHER INFORMATION: Oligonucleotide

<400> SEQUENCE: 469
cgcggatccc cactcgtaat tgacgcc                                     27

<210> SEQ ID NO 470
<211> LENGTH: 30
<212> TYPE: DNA
<213> ORGANISM: Artificial Sequence
<220> FEATURE:
<223> OTHER INFORMATION: Oligonucleotide

<400> SEQUENCE: 470
cgcggatccc atatggccac aagcgacgac                                  30

<210> SEQ ID NO 471
<211> LENGTH: 27
<212> TYPE: DNA
<213> ORGANISM: Artificial Sequence
<220> FEATURE:
<223> OTHER INFORMATION: Oligonucleotide

<400> SEQUENCE: 471
cgcggatccc cactcgtaat tgacgcc                                     27

<210> SEQ ID NO 472
<211> LENGTH: 30
<212> TYPE: DNA
<213> ORGANISM: Artificial Sequence
<220> FEATURE:
<223> OTHER INFORMATION: Oligonucleotide

<400> SEQUENCE: 472
cgcggatccc atatggccac aaacgacgac                                  30

<210> SEQ ID NO 473
<211> LENGTH: 27
<212> TYPE: DNA
<213> ORGANISM: Artificial Sequence
<220> FEATURE:
<223> OTHER INFORMATION: Oligonucleotide

<400> SEQUENCE: 473
cgcggatcca cccacgttgt aaggttg                                     27

<210> SEQ ID NO 474
<211> LENGTH: 33
<212> TYPE: DNA
<213> ORGANISM: Artificial Sequence
<220> FEATURE:
<223> OTHER INFORMATION: Oligonucleotide

<400> SEQUENCE: 474
cgcggatccc atatgatgaa acactttcca tcc                              33
```

```
<210> SEQ ID NO 475
<211> LENGTH: 27
<212> TYPE: DNA
<213> ORGANISM: Artificial Sequence
<220> FEATURE:
<223> OTHER INFORMATION: Oligonucleotide

<400> SEQUENCE: 475
cgcggatcca cccacgttgt aaggttg                                           27

<210> SEQ ID NO 476
<211> LENGTH: 25
<212> TYPE: DNA
<213> ORGANISM: Artificial Sequence
<220> FEATURE:
<223> OTHER INFORMATION: Oligonucleotide

<400> SEQUENCE: 476
cgcggatccg gagggggtgg tgtcg                                             25

<210> SEQ ID NO 477
<211> LENGTH: 27
<212> TYPE: DNA
<213> ORGANISM: Artificial Sequence
<220> FEATURE:
<223> OTHER INFORMATION: Oligonucleotide

<400> SEQUENCE: 477
cccgctcgag ttgcttggcg gcaaggc                                           27

<210> SEQ ID NO 478
<211> LENGTH: 25
<212> TYPE: DNA
<213> ORGANISM: Artificial Sequence
<220> FEATURE:
<223> OTHER INFORMATION: Oligonucleotide

<400> SEQUENCE: 478
cgcggatccg gcggaggcgg cactt                                             25

<210> SEQ ID NO 479
<211> LENGTH: 26
<212> TYPE: DNA
<213> ORGANISM: Artificial Sequence
<220> FEATURE:
<223> OTHER INFORMATION: Oligonucleotide

<400> SEQUENCE: 479
cccgctcgag gaaccggtag cctacg                                            26

<210> SEQ ID NO 480
<211> LENGTH: 41
<212> TYPE: DNA
<213> ORGANISM: Artificial Sequence
<220> FEATURE:
<223> OTHER INFORMATION: Oligonucleotide

<400> SEQUENCE: 480
cgcggatccg gtggtggtgg ttcagatttg gcaaacgatt c                           41

<210> SEQ ID NO 481
<211> LENGTH: 29
<212> TYPE: DNA
<213> ORGANISM: Artificial Sequence
<220> FEATURE:
<223> OTHER INFORMATION: Oligonucleotide
```

```
<400> SEQUENCE: 481
cccgctcgag cgtatcatat ttcacgtgc                                     29

<210> SEQ ID NO 482
<211> LENGTH: 25
<212> TYPE: DNA
<213> ORGANISM: Artificial Sequence
<220> FEATURE:
<223> OTHER INFORMATION: Oligonucleotide

<400> SEQUENCE: 482
cgcggatccg gagggggtgg tgtcg                                         25

<210> SEQ ID NO 483
<211> LENGTH: 28
<212> TYPE: DNA
<213> ORGANISM: Artificial Sequence
<220> FEATURE:
<223> OTHER INFORMATION: Oligonucleotide

<400> SEQUENCE: 483
cccgctcgag ttattgcttg gcggcaag                                      28

<210> SEQ ID NO 484
<211> LENGTH: 25
<212> TYPE: DNA
<213> ORGANISM: Artificial Sequence
<220> FEATURE:
<223> OTHER INFORMATION: Oligonucleotide

<400> SEQUENCE: 484
cgcggatccg gcggaggcgg cactt                                         25

<210> SEQ ID NO 485
<211> LENGTH: 28
<212> TYPE: DNA
<213> ORGANISM: Artificial Sequence
<220> FEATURE:
<223> OTHER INFORMATION: Oligonucleotide

<400> SEQUENCE: 485
cccgctcgag tcagaaccgg tagcctac                                      28

<210> SEQ ID NO 486
<211> LENGTH: 41
<212> TYPE: DNA
<213> ORGANISM: Artificial Sequence
<220> FEATURE:
<223> OTHER INFORMATION: Oligonucleotide

<400> SEQUENCE: 486
cgcggatccg gtggtggtgg ttcagatttg gcaaacgatt c                       41

<210> SEQ ID NO 487
<211> LENGTH: 32
<212> TYPE: DNA
<213> ORGANISM: Artificial Sequence
<220> FEATURE:
<223> OTHER INFORMATION: Oligonucleotide

<400> SEQUENCE: 487
cccgctcgag ttacgtatca tatttcacgt gc                                 32

<210> SEQ ID NO 488
<211> LENGTH: 31
<212> TYPE: DNA
```

```
<213> ORGANISM: Artificial Sequence
<220> FEATURE:
<223> OTHER INFORMATION: Oligonucleotide

<400> SEQUENCE: 488
cgcggatccc atatggccac aagcgacgac g                                  31

<210> SEQ ID NO 489
<211> LENGTH: 28
<212> TYPE: DNA
<213> ORGANISM: Artificial Sequence
<220> FEATURE:
<223> OTHER INFORMATION: Oligonucleotide

<400> SEQUENCE: 489
cccgctcgag ccactcgtaa ttgacgcc                                      28

<210> SEQ ID NO 490
<211> LENGTH: 30
<212> TYPE: DNA
<213> ORGANISM: Artificial Sequence
<220> FEATURE:
<223> OTHER INFORMATION: Oligonucleotide

<400> SEQUENCE: 490
cgcggatccc atatggccac aaacgacgac                                    30

<210> SEQ ID NO 491
<211> LENGTH: 28
<212> TYPE: DNA
<213> ORGANISM: Artificial Sequence
<220> FEATURE:
<223> OTHER INFORMATION: Oligonucleotide

<400> SEQUENCE: 491
cccgctcgag tgctttggcg gcaaagtt                                      28

<210> SEQ ID NO 492
<211> LENGTH: 30
<212> TYPE: DNA
<213> ORGANISM: Artificial Sequence
<220> FEATURE:
<223> OTHER INFORMATION: Oligonucleotide

<400> SEQUENCE: 492
cgcggatccc atatggccac aaacgacgac                                    30

<210> SEQ ID NO 493
<211> LENGTH: 37
<212> TYPE: DNA
<213> ORGANISM: Artificial Sequence
<220> FEATURE:
<223> OTHER INFORMATION: Oligonucleotide

<400> SEQUENCE: 493
cccgctcgag tttagcaata ttatctttgt tcgtagc                            37

<210> SEQ ID NO 494
<211> LENGTH: 32
<212> TYPE: DNA
<213> ORGANISM: Artificial Sequence
<220> FEATURE:
<223> OTHER INFORMATION: Oligonucleotide

<400> SEQUENCE: 494
cgcggatccc atatgaaagc aaaccgtgcc ga                                 32
```

<210> SEQ ID NO 495
<211> LENGTH: 28
<212> TYPE: DNA
<213> ORGANISM: Artificial Sequence
<220> FEATURE:
<223> OTHER INFORMATION: Oligonucleotide

<400> SEQUENCE: 495
cccgctcgag ccactcgtaa ttgacgcc                              28

<210> SEQ ID NO 496
<211> LENGTH: 61
<212> TYPE: DNA
<213> ORGANISM: Artificial Sequence
<220> FEATURE:
<223> OTHER INFORMATION: Oligonucleotide

<400> SEQUENCE: 496
ggggacaagt ttgtacaaaa aagcaggctg cagccacaaa cgacgacgat gttaaaaaag    60
c                                                                   61

<210> SEQ ID NO 497
<211> LENGTH: 61
<212> TYPE: DNA
<213> ORGANISM: Artificial Sequence
<220> FEATURE:
<223> OTHER INFORMATION: Oligonucleotide

<400> SEQUENCE: 497
ggggaccact ttgtacaaga aagctgggtt taccactcgt aattgacgcc gacatggtag    60
g                                                                   61

<210> SEQ ID NO 498
<211> LENGTH: 31
<212> TYPE: DNA
<213> ORGANISM: Artificial Sequence
<220> FEATURE:
<223> OTHER INFORMATION: Oligonucleotide

<400> SEQUENCE: 498
gcggccatat ggcagcaaaa gacgtacagt t                          31

<210> SEQ ID NO 499
<211> LENGTH: 33
<212> TYPE: DNA
<213> ORGANISM: Artificial Sequence
<220> FEATURE:
<223> OTHER INFORMATION: Oligonucleotide

<400> SEQUENCE: 499
gcggcctcga gttacatcat gccgcccata cca                        33

<210> SEQ ID NO 500
<211> LENGTH: 31
<212> TYPE: DNA
<213> ORGANISM: Artificial Sequence
<220> FEATURE:
<223> OTHER INFORMATION: Oligonucleotide

<400> SEQUENCE: 500
cgcggatccg ctagcttagg cggcggcgga g                          31

<210> SEQ ID NO 501
<211> LENGTH: 26
<212> TYPE: DNA

<213> ORGANISM: Artificial Sequence
<220> FEATURE:
<223> OTHER INFORMATION: Oligonucleotide

<400> SEQUENCE: 501
cccgctcgag gaaccggtag cctacg                            26

<210> SEQ ID NO 502
<211> LENGTH: 29
<212> TYPE: DNA
<213> ORGANISM: Artificial Sequence
<220> FEATURE:
<223> OTHER INFORMATION: Oligonucleotide

<400> SEQUENCE: 502
cccctagcta gcacttctgc gcccgactt                         29

<210> SEQ ID NO 503
<211> LENGTH: 26
<212> TYPE: DNA
<213> ORGANISM: Artificial Sequence
<220> FEATURE:
<223> OTHER INFORMATION: Oligonucleotide

<400> SEQUENCE: 503
cccgctcgag gaaccggtag cctacg                            26

<210> SEQ ID NO 504
<211> LENGTH: 31
<212> TYPE: DNA
<213> ORGANISM: Artificial Sequence
<220> FEATURE:
<223> OTHER INFORMATION: Oligonucleotide

<400> SEQUENCE: 504
cgcggatccg ctagcttagg cggcggcgga g                      31

<210> SEQ ID NO 505
<211> LENGTH: 26
<212> TYPE: DNA
<213> ORGANISM: Artificial Sequence
<220> FEATURE:
<223> OTHER INFORMATION: Oligonucleotide

<400> SEQUENCE: 505
cccgctcgag gaaccggtag cctacg                            26

<210> SEQ ID NO 506
<211> LENGTH: 32
<212> TYPE: DNA
<213> ORGANISM: Artificial Sequence
<220> FEATURE:
<223> OTHER INFORMATION: Oligonucleotide

<400> SEQUENCE: 506
cgcggatccg ctagcacttc tgcgcccgac tt                     32

<210> SEQ ID NO 507
<211> LENGTH: 26
<212> TYPE: DNA
<213> ORGANISM: Artificial Sequence
<220> FEATURE:
<223> OTHER INFORMATION: Oligonucleotide

<400> SEQUENCE: 507
cccgctcgag gaaccggtag cctacg                            26

```
<210> SEQ ID NO 508
<211> LENGTH: 50
<212> TYPE: DNA
<213> ORGANISM: Artificial Sequence
<220> FEATURE:
<223> OTHER INFORMATION: Oligonucleotide

<400> SEQUENCE: 508
cgcggatccg ctagccgaac gaccccaacc ttccctacaa aaactttcaa                50

<210> SEQ ID NO 509
<211> LENGTH: 35
<212> TYPE: DNA
<213> ORGANISM: Artificial Sequence
<220> FEATURE:
<223> OTHER INFORMATION: Oligonucleotide

<400> SEQUENCE: 509
cccgctcgag tcagaaccga cgtgccaagc cgttc                                35

<210> SEQ ID NO 510
<211> LENGTH: 32
<212> TYPE: DNA
<213> ORGANISM: Artificial Sequence
<220> FEATURE:
<223> OTHER INFORMATION: Oligonucleotide

<400> SEQUENCE: 510
gccgccatat gccccactg gaagaacgga cg                                    32

<210> SEQ ID NO 511
<211> LENGTH: 35
<212> TYPE: DNA
<213> ORGANISM: Artificial Sequence
<220> FEATURE:
<223> OTHER INFORMATION: Oligonucleotide

<400> SEQUENCE: 511
gccgcctcga gtaataaacc ttctatgggc agcag                                35

<210> SEQ ID NO 512
<211> LENGTH: 31
<212> TYPE: DNA
<213> ORGANISM: Artificial Sequence
<220> FEATURE:
<223> OTHER INFORMATION: Oligonucleotide

<400> SEQUENCE: 512
cgcggatccc atatgtccgt ccacgcatcc g                                    31

<210> SEQ ID NO 513
<211> LENGTH: 31
<212> TYPE: DNA
<213> ORGANISM: Artificial Sequence
<220> FEATURE:
<223> OTHER INFORMATION: Oligonucleotide

<400> SEQUENCE: 513
cccgctcgag tttgaatttg taggtgtatt g                                    31

<210> SEQ ID NO 514
<211> LENGTH: 29
<212> TYPE: DNA
<213> ORGANISM: Artificial Sequence
<220> FEATURE:
<223> OTHER INFORMATION: Oligonucleotide
```

```
<400> SEQUENCE: 514
cgcggatccc atatgacccc ttccgcact                                    29

<210> SEQ ID NO 515
<211> LENGTH: 32
<212> TYPE: DNA
<213> ORGANISM: Artificial Sequence
<220> FEATURE:
<223> OTHER INFORMATION: Oligonucleotide

<400> SEQUENCE: 515
cccgctcgag ttatttgaat ttgtaggtgt at                                32

<210> SEQ ID NO 516
<211> LENGTH: 33
<212> TYPE: DNA
<213> ORGANISM: Artificial Sequence
<220> FEATURE:
<223> OTHER INFORMATION: Oligonucleotide

<400> SEQUENCE: 516
cgcggatccc atatgaaaac caattcagaa gaa                               33

<210> SEQ ID NO 517
<211> LENGTH: 28
<212> TYPE: DNA
<213> ORGANISM: Artificial Sequence
<220> FEATURE:
<223> OTHER INFORMATION: Oligonucleotide

<400> SEQUENCE: 517
cccgctcgag tccacagaga ttgtttcc                                     28

<210> SEQ ID NO 518
<211> LENGTH: 17
<212> TYPE: DNA
<213> ORGANISM: Artificial Sequence
<220> FEATURE:
<223> OTHER INFORMATION: Oligonucleotide

<400> SEQUENCE: 518
gatgcccgaa gggcggg                                                 17

<210> SEQ ID NO 519
<211> LENGTH: 29
<212> TYPE: DNA
<213> ORGANISM: Artificial Sequence
<220> FEATURE:
<223> OTHER INFORMATION: Oligonucleotide

<400> SEQUENCE: 519
gcccaagctt tcagaagaag acttcacgc                                    29

<210> SEQ ID NO 520
<211> LENGTH: 36
<212> TYPE: DNA
<213> ORGANISM: Artificial Sequence
<220> FEATURE:
<223> OTHER INFORMATION: Oligonucleotide

<400> SEQUENCE: 520
cgcggatccc atatgcaaac ccataaatac gctatt                            36

<210> SEQ ID NO 521
<211> LENGTH: 29
<212> TYPE: DNA
```

```
<213> ORGANISM: Artificial Sequence
<220> FEATURE:
<223> OTHER INFORMATION: Oligonucleotide

<400> SEQUENCE: 521
gcccaagctt gaagaagact tcacgccag                              29

<210> SEQ ID NO 522
<211> LENGTH: 35
<212> TYPE: DNA
<213> ORGANISM: Artificial Sequence
<220> FEATURE:
<223> OTHER INFORMATION: Oligonucleotide

<400> SEQUENCE: 522
cgcggatccc atatggtctt tttcgacaat accga                       35

<210> SEQ ID NO 523
<211> LENGTH: 10
<212> TYPE: DNA
<213> ORGANISM: Artificial Sequence
<220> FEATURE:
<223> OTHER INFORMATION: Oligonucleotide

<400> SEQUENCE: 523
gcccaagctt                                                   10

<210> SEQ ID NO 524
<211> LENGTH: 36
<212> TYPE: DNA
<213> ORGANISM: Artificial Sequence
<220> FEATURE:
<223> OTHER INFORMATION: Oligonucleotide

<400> SEQUENCE: 524
cgcggatccc atatgaataa aactttaaaa aggcgg                      36

<210> SEQ ID NO 525
<211> LENGTH: 29
<212> TYPE: DNA
<213> ORGANISM: Artificial Sequence
<220> FEATURE:
<223> OTHER INFORMATION: Oligonucleotide

<400> SEQUENCE: 525
gcccaagctt tcagaagaag acttcacgc                              29

<210> SEQ ID NO 526
<211> LENGTH: 35
<212> TYPE: DNA
<213> ORGANISM: Artificial Sequence
<220> FEATURE:
<223> OTHER INFORMATION: Oligonucleotide

<400> SEQUENCE: 526
cgcgaatccc atatgttcga tcttgattct gtcga                       35

<210> SEQ ID NO 527
<211> LENGTH: 28
<212> TYPE: DNA
<213> ORGANISM: Artificial Sequence
<220> FEATURE:
<223> OTHER INFORMATION: Oligonucleotide

<400> SEQUENCE: 527
cccgctcgag tcgcacaggc tgttggcg                               28
```

```
<210> SEQ ID NO 528
<211> LENGTH: 32
<212> TYPE: DNA
<213> ORGANISM: Artificial Sequence
<220> FEATURE:
<223> OTHER INFORMATION: Oligonucleotide

<400> SEQUENCE: 528
cgcgaatccc atatgttggg cggaggcggc ag                                    32

<210> SEQ ID NO 529
<211> LENGTH: 28
<212> TYPE: DNA
<213> ORGANISM: Artificial Sequence
<220> FEATURE:
<223> OTHER INFORMATION: Oligonucleotide

<400> SEQUENCE: 529
cccgctcgag tcgcacaggc tgttggcg                                         28

<210> SEQ ID NO 530
<211> LENGTH: 32
<212> TYPE: DNA
<213> ORGANISM: Artificial Sequence
<220> FEATURE:
<223> OTHER INFORMATION: Oligonucleotide

<400> SEQUENCE: 530
cgcgaatccc atatgttggg cggaggcggc ag                                    32

<210> SEQ ID NO 531
<211> LENGTH: 28
<212> TYPE: DNA
<213> ORGANISM: Artificial Sequence
<220> FEATURE:
<223> OTHER INFORMATION: Oligonucleotide

<400> SEQUENCE: 531
cccgctcgag tcgcacaggc tgttggcg                                         28

<210> SEQ ID NO 532
<211> LENGTH: 33
<212> TYPE: DNA
<213> ORGANISM: Artificial Sequence
<220> FEATURE:
<223> OTHER INFORMATION: Oligonucleotide

<400> SEQUENCE: 532
cgcggatccc atatggcaaa tttggaggtg cgc                                   33

<210> SEQ ID NO 533
<211> LENGTH: 27
<212> TYPE: DNA
<213> ORGANISM: Artificial Sequence
<220> FEATURE:
<223> OTHER INFORMATION: Oligonucleotide

<400> SEQUENCE: 533
cccgctcgag ttcggagcgg ttgaagc                                          27

<210> SEQ ID NO 534
<211> LENGTH: 34
<212> TYPE: DNA
<213> ORGANISM: Artificial Sequence
<220> FEATURE:
<223> OTHER INFORMATION: Oligonucleotide
```

```
<400> SEQUENCE: 534
cgcggatccc atatgcaacg tcgtattata accc                                   34

<210> SEQ ID NO 535
<211> LENGTH: 29
<212> TYPE: DNA
<213> ORGANISM: Artificial Sequence
<220> FEATURE:
<223> OTHER INFORMATION: Oligonucleotide

<400> SEQUENCE: 535
cccgctcgag ttattcggag cggttgaag                                         29

<210> SEQ ID NO 536
<211> LENGTH: 42
<212> TYPE: DNA
<213> ORGANISM: Artificial Sequence
<220> FEATURE:
<223> OTHER INFORMATION: Oligonucleotide

<400> SEQUENCE: 536
cgcggatccc atatgggcat caaagtcgcc atcaacggct ac                          42

<210> SEQ ID NO 537
<211> LENGTH: 35
<212> TYPE: DNA
<213> ORGANISM: Artificial Sequence
<220> FEATURE:
<223> OTHER INFORMATION: Oligonucleotide

<400> SEQUENCE: 537
cccgctcgag tttgagcggg cgcacttcaa gtccg                                  35

<210> SEQ ID NO 538
<211> LENGTH: 33
<212> TYPE: DNA
<213> ORGANISM: Artificial Sequence
<220> FEATURE:
<223> OTHER INFORMATION: Oligonucleotide

<400> SEQUENCE: 538
cgcggatccc atatgggcgg cagcgaaaaa aac                                    33

<210> SEQ ID NO 539
<211> LENGTH: 28
<212> TYPE: DNA
<213> ORGANISM: Artificial Sequence
<220> FEATURE:
<223> OTHER INFORMATION: Oligonucleotide

<400> SEQUENCE: 539
cccgctcgag gttggtgccg actttgat                                          28

<210> SEQ ID NO 540
<211> LENGTH: 31
<212> TYPE: DNA
<213> ORGANISM: Artificial Sequence
<220> FEATURE:
<223> OTHER INFORMATION: Oligonucleotide

<400> SEQUENCE: 540
cgcggatccc atatgggcgg cggaagcgat a                                      31

<210> SEQ ID NO 541
<211> LENGTH: 27
<212> TYPE: DNA
```

```
<213> ORGANISM: Artificial Sequence
<220> FEATURE:
<223> OTHER INFORMATION: Oligonucleotide

<400> SEQUENCE: 541
cccgctcgag tttgcccgct ttgagcc                                       27

<210> SEQ ID NO 542
<211> LENGTH: 33
<212> TYPE: DNA
<213> ORGANISM: Artificial Sequence
<220> FEATURE:
<223> OTHER INFORMATION: Oligonucleotide

<400> SEQUENCE: 542
cgcggatccc atatgggcaa atccgaaaat acg                                33

<210> SEQ ID NO 543
<211> LENGTH: 27
<212> TYPE: DNA
<213> ORGANISM: Artificial Sequence
<220> FEATURE:
<223> OTHER INFORMATION: Oligonucleotide

<400> SEQUENCE: 543
cccgctcgag catcccgtac tgtttcg                                       27

<210> SEQ ID NO 544
<211> LENGTH: 62
<212> TYPE: DNA
<213> ORGANISM: Artificial Sequence
<220> FEATURE:
<223> OTHER INFORMATION: Oligonucleotide

<400> SEQUENCE: 544
ggggacaagt ttgtacaaaa aagcaggctc cgacattacc gtgtacaacg gccaacaaag   60
aa                                                                  62

<210> SEQ ID NO 545
<211> LENGTH: 61
<212> TYPE: DNA
<213> ORGANISM: Artificial Sequence
<220> FEATURE:
<223> OTHER INFORMATION: Oligonucleotide

<400> SEQUENCE: 545
ggggaccact ttgtacaaga aagctgggtc ttatttcata ccggcttgct caagcagccg   60
g                                                                   61

<210> SEQ ID NO 546
<211> LENGTH: 61
<212> TYPE: DNA
<213> ORGANISM: Artificial Sequence
<220> FEATURE:
<223> OTHER INFORMATION: Oligonucleotide

<400> SEQUENCE: 546
ggggacaagt ttgtacaaaa aagcaggctg atacggtgtt ttcctgtaaa acggacaaca   60
a                                                                   61

<210> SEQ ID NO 547
<211> LENGTH: 60
<212> TYPE: DNA
<213> ORGANISM: Artificial Sequence
<220> FEATURE:
```

-continued

<223> OTHER INFORMATION: Oligonucleotide

<400> SEQUENCE: 547
ggggaccact ttgtacaaga aagctgggtc taggaaaaat cgtcatcgtt gaaattcgcc    60

<210> SEQ ID NO 548
<211> LENGTH: 47
<212> TYPE: DNA
<213> ORGANISM: Artificial Sequence
<220> FEATURE:
<223> OTHER INFORMATION: Oligonucleotide

<400> SEQUENCE: 548
ggggacaagt ttgtacaaaa aagcaggcta tgcaccccat cgaaacc    47

<210> SEQ ID NO 549
<211> LENGTH: 47
<212> TYPE: DNA
<213> ORGANISM: Artificial Sequence
<220> FEATURE:
<223> OTHER INFORMATION: Oligonucleotide

<400> SEQUENCE: 549
ggggaccact ttgtacaaga aagctgggtc tagtcttgca gtgcctc    47

<210> SEQ ID NO 550
<211> LENGTH: 41
<212> TYPE: DNA
<213> ORGANISM: Artificial Sequence
<220> FEATURE:
<223> OTHER INFORMATION: Oligonucleotide

<400> SEQUENCE: 550
cgcggatccc atatgggaaa tttcttatat agaggcatta g    41

<210> SEQ ID NO 551
<211> LENGTH: 40
<212> TYPE: DNA
<213> ORGANISM: Artificial Sequence
<220> FEATURE:
<223> OTHER INFORMATION: Oligonucleotide

<400> SEQUENCE: 551
cccgctcgag gttaatttct atcaactctt tagcaataat    40

<210> SEQ ID NO 552
<211> LENGTH: 31
<212> TYPE: DNA
<213> ORGANISM: Artificial Sequence
<220> FEATURE:
<223> OTHER INFORMATION: Oligonucleotide

<400> SEQUENCE: 552
cgcggatccc atatggcctg ccaagacgac a    31

<210> SEQ ID NO 553
<211> LENGTH: 26
<212> TYPE: DNA
<213> ORGANISM: Artificial Sequence
<220> FEATURE:
<223> OTHER INFORMATION: Oligonucleotide

<400> SEQUENCE: 553
cccgctcgag ccgcctcctg ccgaaa    26

<210> SEQ ID NO 554

```
<211> LENGTH: 34
<212> TYPE: DNA
<213> ORGANISM: Artificial Sequence
<220> FEATURE:
<223> OTHER INFORMATION: Oligonucleotide

<400> SEQUENCE: 554
cgcggatccc atatggcaga gatctgtttg ataa                    34

<210> SEQ ID NO 555
<211> LENGTH: 27
<212> TYPE: DNA
<213> ORGANISM: Artificial Sequence
<220> FEATURE:
<223> OTHER INFORMATION: Oligonucleotide

<400> SEQUENCE: 555
cccgctcgag cggtttccg cccaatg                             27

<210> SEQ ID NO 556
<211> LENGTH: 30
<212> TYPE: DNA
<213> ORGANISM: Artificial Sequence
<220> FEATURE:
<223> OTHER INFORMATION: Oligonucleotide

<400> SEQUENCE: 556
cgcggatccc atatgcagcc ggatacggtc                         30

<210> SEQ ID NO 557
<211> LENGTH: 30
<212> TYPE: DNA
<213> ORGANISM: Artificial Sequence
<220> FEATURE:
<223> OTHER INFORMATION: Oligonucleotide

<400> SEQUENCE: 557
cccgctcgag aatcacttcc aacacaaaat                         30

<210> SEQ ID NO 558
<211> LENGTH: 33
<212> TYPE: DNA
<213> ORGANISM: Artificial Sequence
<220> FEATURE:
<223> OTHER INFORMATION: Oligonucleotide

<400> SEQUENCE: 558
cgcggatccc atatgtggtt gctgatgaag ggc                     33

<210> SEQ ID NO 559
<211> LENGTH: 28
<212> TYPE: DNA
<213> ORGANISM: Artificial Sequence
<220> FEATURE:
<223> OTHER INFORMATION: Oligonucleotide

<400> SEQUENCE: 559
cccgctcgag gactgcttca tcttctgc                           28

<210> SEQ ID NO 560
<211> LENGTH: 34
<212> TYPE: DNA
<213> ORGANISM: Artificial Sequence
<220> FEATURE:
<223> OTHER INFORMATION: Oligonucleotide

<400> SEQUENCE: 560
```

```
cgcggatccc atatggaact gatgactgtt ttgc                                    34
```

<210> SEQ ID NO 561
<211> LENGTH: 29
<212> TYPE: DNA
<213> ORGANISM: Artificial Sequence
<220> FEATURE:
<223> OTHER INFORMATION: Oligonucleotide

<400> SEQUENCE: 561

```
cccgctcgag tcagactgct tcatcttct                                          29
```

<210> SEQ ID NO 562
<211> LENGTH: 45
<212> TYPE: DNA
<213> ORGANISM: Artificial Sequence
<220> FEATURE:
<223> OTHER INFORMATION: Oligonucleotide

<400> SEQUENCE: 562

```
cgcggatccc atatgagcat taaagtagcg attaacggtt tcggc                        45
```

<210> SEQ ID NO 563
<211> LENGTH: 40
<212> TYPE: DNA
<213> ORGANISM: Artificial Sequence
<220> FEATURE:
<223> OTHER INFORMATION: Oligonucleotide

<400> SEQUENCE: 563

```
cccgctcgag gattttgcct gcgaagtatt ccaaagtgcg                              40
```

<210> SEQ ID NO 564
<211> LENGTH: 32
<212> TYPE: DNA
<213> ORGANISM: Artificial Sequence
<220> FEATURE:
<223> OTHER INFORMATION: Oligonucleotide

<400> SEQUENCE: 564

```
cgcggatccg ctagccccga tgttaaatcg gc                                      32
```

<210> SEQ ID NO 565
<211> LENGTH: 29
<212> TYPE: DNA
<213> ORGANISM: Artificial Sequence
<220> FEATURE:
<223> OTHER INFORMATION: Oligonucleotide

<400> SEQUENCE: 565

```
cggggatcca tcctgctctt ttttgccgg                                          29
```

<210> SEQ ID NO 566
<211> LENGTH: 42
<212> TYPE: DNA
<213> ORGANISM: Artificial Sequence
<220> FEATURE:
<223> OTHER INFORMATION: Oligonucleotide

<400> SEQUENCE: 566

```
cgcggatccg gtggtggtgg tcaaagcaag agcatccaaa cc                           42
```

<210> SEQ ID NO 567
<211> LENGTH: 30
<212> TYPE: DNA
<213> ORGANISM: Artificial Sequence
<220> FEATURE:

<223> OTHER INFORMATION: Oligonucleotide

<400> SEQUENCE: 567
cccaagcttt tcgggcggta ttcgggcttc　　　　　　　　　　　　　　　　　　30

<210> SEQ ID NO 568
<211> LENGTH: 39
<212> TYPE: DNA
<213> ORGANISM: Artificial Sequence
<220> FEATURE:
<223> OTHER INFORMATION: Oligonucleotide

<400> SEQUENCE: 568
cgcggatccg gtggtggtgg tgccacctac aaagtggac　　　　　　　　　　　　　39

<210> SEQ ID NO 569
<211> LENGTH: 28
<212> TYPE: DNA
<213> ORGANISM: Artificial Sequence
<220> FEATURE:
<223> OTHER INFORMATION: Oligonucleotide

<400> SEQUENCE: 569
gcccaagctt ttgtttggct gcctcgat　　　　　　　　　　　　　　　　　　28

<210> SEQ ID NO 570
<211> LENGTH: 34
<212> TYPE: DNA
<213> ORGANISM: Artificial Sequence
<220> FEATURE:
<223> OTHER INFORMATION: Oligonucleotide

<400> SEQUENCE: 570
cgcggatccg gtggtggtgg tacaagcgac gacg　　　　　　　　　　　　　　　34

<210> SEQ ID NO 571
<211> LENGTH: 28
<212> TYPE: DNA
<213> ORGANISM: Artificial Sequence
<220> FEATURE:
<223> OTHER INFORMATION: Oligonucleotide

<400> SEQUENCE: 571
gcccaagctt ccactcgtaa ttgacgcc　　　　　　　　　　　　　　　　　　28

<210> SEQ ID NO 572
<211> LENGTH: 41
<212> TYPE: DNA
<213> ORGANISM: Artificial Sequence
<220> FEATURE:
<223> OTHER INFORMATION: Oligonucleotide

<400> SEQUENCE: 572
cgcggatccg gtggtggtgg ttcagatttg gcaaacgatt c　　　　　　　　　　　41

<210> SEQ ID NO 573
<211> LENGTH: 28
<212> TYPE: DNA
<213> ORGANISM: Artificial Sequence
<220> FEATURE:
<223> OTHER INFORMATION: Oligonucleotide

<400> SEQUENCE: 573
cccaagcttc gtatcatatt tcacgtgc　　　　　　　　　　　　　　　　　　28

<210> SEQ ID NO 574

```
<211> LENGTH: 44
<212> TYPE: DNA
<213> ORGANISM: Artificial Sequence
<220> FEATURE:
<223> OTHER INFORMATION: Oligonucleotide

<400> SEQUENCE: 574
cccaagcttg gtggtggtgg tggttcagat ttggcaaacg attc            44

<210> SEQ ID NO 575
<211> LENGTH: 29
<212> TYPE: DNA
<213> ORGANISM: Artificial Sequence
<220> FEATURE:
<223> OTHER INFORMATION: Oligonucleotide

<400> SEQUENCE: 575
cccgctcgag cgtatcatat ttcacgtgc                             29

<210> SEQ ID NO 576
<211> LENGTH: 45
<212> TYPE: DNA
<213> ORGANISM: Artificial Sequence
<220> FEATURE:
<223> OTHER INFORMATION: Oligonucleotide

<400> SEQUENCE: 576
cccaagcttg gtggtggtgg tggtcaaagc aagagcatcc aaacc           45

<210> SEQ ID NO 577
<211> LENGTH: 28
<212> TYPE: DNA
<213> ORGANISM: Artificial Sequence
<220> FEATURE:
<223> OTHER INFORMATION: Oligonucleotide

<400> SEQUENCE: 577
cccgctcgag cgggcggtat tcgggctt                              28

<210> SEQ ID NO 578
<211> LENGTH: 32
<212> TYPE: DNA
<213> ORGANISM: Artificial Sequence
<220> FEATURE:
<223> OTHER INFORMATION: Oligonucleotide

<400> SEQUENCE: 578
cgcggatccg ctagccccga tgttaaatcg gc                         32

<210> SEQ ID NO 579
<211> LENGTH: 29
<212> TYPE: DNA
<213> ORGANISM: Artificial Sequence
<220> FEATURE:
<223> OTHER INFORMATION: Oligonucleotide

<400> SEQUENCE: 579
cggggatcca tcctgctctt ttttgccgg                             29

<210> SEQ ID NO 580
<211> LENGTH: 36
<212> TYPE: DNA
<213> ORGANISM: Artificial Sequence
<220> FEATURE:
<223> OTHER INFORMATION: Oligonucleotide

<400> SEQUENCE: 580
```

```
cgcggatccg ctagcggaca cacttatttc ggcatc                               36
```

<210> SEQ ID NO 581
<211> LENGTH: 30
<212> TYPE: DNA
<213> ORGANISM: Artificial Sequence
<220> FEATURE:
<223> OTHER INFORMATION: Oligonucleotide

<400> SEQUENCE: 581

```
cgcggatccc cagcggtagc ctaatttgat                                      30
```

<210> SEQ ID NO 582
<211> LENGTH: 41
<212> TYPE: DNA
<213> ORGANISM: Artificial Sequence
<220> FEATURE:
<223> OTHER INFORMATION: Oligonucleotide

<400> SEQUENCE: 582

```
cgcggatccg gtggtggtgg ttcagatttg gcaaacgatt c                         41
```

<210> SEQ ID NO 583
<211> LENGTH: 28
<212> TYPE: DNA
<213> ORGANISM: Artificial Sequence
<220> FEATURE:
<223> OTHER INFORMATION: Oligonucleotide

<400> SEQUENCE: 583

```
cccaagcttc gtatcatatt tcacgtgc                                        28
```

<210> SEQ ID NO 584
<211> LENGTH: 36
<212> TYPE: DNA
<213> ORGANISM: Artificial Sequence
<220> FEATURE:
<223> OTHER INFORMATION: Oligonucleotide

<400> SEQUENCE: 584

```
gcggcgtcga cggtggcgga ggcactggat cctcag                               36
```

<210> SEQ ID NO 585
<211> LENGTH: 35
<212> TYPE: DNA
<213> ORGANISM: Artificial Sequence
<220> FEATURE:
<223> OTHER INFORMATION: Oligonucleotide

<400> SEQUENCE: 585

```
ggaggcactg gatcctcaga tttggcaaac gattc                                35
```

<210> SEQ ID NO 586
<211> LENGTH: 29
<212> TYPE: DNA
<213> ORGANISM: Artificial Sequence
<220> FEATURE:
<223> OTHER INFORMATION: Oligonucleotide

<400> SEQUENCE: 586

```
cccgctcgag cgtatcatat ttcacgtgc                                       29
```

<210> SEQ ID NO 587
<211> LENGTH: 33
<212> TYPE: DNA
<213> ORGANISM: Artificial Sequence
<220> FEATURE:

<223> OTHER INFORMATION: Oligonucleotide

<400> SEQUENCE: 587
ggaattccat atgtcagatt tggcaaacga ttc    33

<210> SEQ ID NO 588
<211> LENGTH: 28
<212> TYPE: DNA
<213> ORGANISM: Artificial Sequence
<220> FEATURE:
<223> OTHER INFORMATION: Oligonucleotide

<400> SEQUENCE: 588
cgcggatccc gtatcatatt tcacgtgc    28

<210> SEQ ID NO 589
<211> LENGTH: 25
<212> TYPE: DNA
<213> ORGANISM: Artificial Sequence
<220> FEATURE:
<223> OTHER INFORMATION: Oligonucleotide

<400> SEQUENCE: 589
cggggatccg ggggcggcgg tggcg    25

<210> SEQ ID NO 590
<211> LENGTH: 30
<212> TYPE: DNA
<213> ORGANISM: Artificial Sequence
<220> FEATURE:
<223> OTHER INFORMATION: Oligonucleotide

<400> SEQUENCE: 590
cccaagctta tcctgctctt ttttgccggc    30

<210> SEQ ID NO 591
<211> LENGTH: 42
<212> TYPE: DNA
<213> ORGANISM: Artificial Sequence
<220> FEATURE:
<223> OTHER INFORMATION: Oligonucleotide

<400> SEQUENCE: 591
cgcggatccg gtggtggtgg tcaaagcaag agcatccaaa cc    42

<210> SEQ ID NO 592
<211> LENGTH: 28
<212> TYPE: DNA
<213> ORGANISM: Artificial Sequence
<220> FEATURE:
<223> OTHER INFORMATION: Oligonucleotide

<400> SEQUENCE: 592
cccaagcttc gggcggtatt cgggcttc    28

<210> SEQ ID NO 593
<211> LENGTH: 26
<212> TYPE: DNA
<213> ORGANISM: Artificial Sequence
<220> FEATURE:
<223> OTHER INFORMATION: Oligonucleotide

<400> SEQUENCE: 593
ccccaagctt gggggcggcg gtggcg    26

<210> SEQ ID NO 594

<211> LENGTH: 31
<212> TYPE: DNA
<213> ORGANISM: Artificial Sequence
<220> FEATURE:
<223> OTHER INFORMATION: Oligonucleotide

<400> SEQUENCE: 594
cccgctcgag atcctgctct tttttgccgg c                              31

<210> SEQ ID NO 595
<211> LENGTH: 45
<212> TYPE: DNA
<213> ORGANISM: Artificial Sequence
<220> FEATURE:
<223> OTHER INFORMATION: Oligonucleotide

<400> SEQUENCE: 595
cccaagcttg gtggtggtgg tggtcaaagc aagagcatcc aaacc               45

<210> SEQ ID NO 596
<211> LENGTH: 28
<212> TYPE: DNA
<213> ORGANISM: Artificial Sequence
<220> FEATURE:
<223> OTHER INFORMATION: Oligonucleotide

<400> SEQUENCE: 596
cccgctcgag cgggcggtat tcgggctt                                  28

<210> SEQ ID NO 597
<211> LENGTH: 35
<212> TYPE: DNA
<213> ORGANISM: Artificial Sequence
<220> FEATURE:
<223> OTHER INFORMATION: Oligonucleotide

<400> SEQUENCE: 597
ggaggcactg gatccgcagc cacaaacgac gacga                          35

<210> SEQ ID NO 598
<211> LENGTH: 36
<212> TYPE: DNA
<213> ORGANISM: Artificial Sequence
<220> FEATURE:
<223> OTHER INFORMATION: Oligonucleotide

<400> SEQUENCE: 598
gcggcctcga gggtggcgga ggcactggat ccgcag                         36

<210> SEQ ID NO 599
<211> LENGTH: 28
<212> TYPE: DNA
<213> ORGANISM: Artificial Sequence
<220> FEATURE:
<223> OTHER INFORMATION: Oligonucleotide

<400> SEQUENCE: 599
cccgctcgag acccagcttg taaggttg                                  28

<210> SEQ ID NO 600
<211> LENGTH: 35
<212> TYPE: DNA
<213> ORGANISM: Artificial Sequence
<220> FEATURE:
<223> OTHER INFORMATION: Oligonucleotide

<400> SEQUENCE: 600
ggaggcactg gatccgcagc cacaaacgac gacga    35

<210> SEQ ID NO 601
<211> LENGTH: 36
<212> TYPE: DNA
<213> ORGANISM: Artificial Sequence
<220> FEATURE:
<223> OTHER INFORMATION: Oligonucleotide

<400> SEQUENCE: 601
gcggcctcga gggtggcgga ggcactggat ccgcag    36

<210> SEQ ID NO 602
<211> LENGTH: 28
<212> TYPE: DNA
<213> ORGANISM: Artificial Sequence
<220> FEATURE:
<223> OTHER INFORMATION: Oligonucleotide

<400> SEQUENCE: 602
cccgctcgag ccactcgtaa ttgacgcc    28

<210> SEQ ID NO 603
<211> LENGTH: 38
<212> TYPE: DNA
<213> ORGANISM: Artificial Sequence
<220> FEATURE:
<223> OTHER INFORMATION: Oligonucleotide

<400> SEQUENCE: 603
gcggcctcga gggatccggc ggaggcggca cttctgcg    38

<210> SEQ ID NO 604
<211> LENGTH: 26
<212> TYPE: DNA
<213> ORGANISM: Artificial Sequence
<220> FEATURE:
<223> OTHER INFORMATION: Oligonucleotide

<400> SEQUENCE: 604
cccgctcgag gaaccggtag cctacg    26

<210> SEQ ID NO 605
<211> LENGTH: 35
<212> TYPE: DNA
<213> ORGANISM: Artificial Sequence
<220> FEATURE:
<223> OTHER INFORMATION: Oligonucleotide

<400> SEQUENCE: 605
ggaggcactg gatcctcaga tttggcaaac gattc    35

<210> SEQ ID NO 606
<211> LENGTH: 37
<212> TYPE: DNA
<213> ORGANISM: Artificial Sequence
<220> FEATURE:
<223> OTHER INFORMATION: Oligonucleotide

<400> SEQUENCE: 606
gcggcgtcga cggtggcgga ggcactggat cctcaga    37

<210> SEQ ID NO 607
<211> LENGTH: 29
<212> TYPE: DNA
<213> ORGANISM: Artificial Sequence
<220> FEATURE:

<223> OTHER INFORMATION: Oligonucleotide

<400> SEQUENCE: 607
cccgctcgag cgtatcatat ttcacgtgc                                  29

<210> SEQ ID NO 608
<211> LENGTH: 35
<212> TYPE: DNA
<213> ORGANISM: Artificial Sequence
<220> FEATURE:
<223> OTHER INFORMATION: Oligonucleotide

<400> SEQUENCE: 608
gcggcctcga gggatccgga gggggtggtg tcgcc                           35

<210> SEQ ID NO 609
<211> LENGTH: 25
<212> TYPE: DNA
<213> ORGANISM: Artificial Sequence
<220> FEATURE:
<223> OTHER INFORMATION: Oligonucleotide

<400> SEQUENCE: 609
cccgctcgag ttgcttggcg gcaag                                      25

<210> SEQ ID NO 610
<211> LENGTH: 35
<212> TYPE: DNA
<213> ORGANISM: Artificial Sequence
<220> FEATURE:
<223> OTHER INFORMATION: Oligonucleotide

<400> SEQUENCE: 610
ggaggcactg gatccgcagc cacaaacgac gacga                           35

<210> SEQ ID NO 611
<211> LENGTH: 36
<212> TYPE: DNA
<213> ORGANISM: Artificial Sequence
<220> FEATURE:
<223> OTHER INFORMATION: Oligonucleotide

<400> SEQUENCE: 611
gcggcctcga gggtggcgga ggcactggat ccgcag                          36

<210> SEQ ID NO 612
<211> LENGTH: 28
<212> TYPE: DNA
<213> ORGANISM: Artificial Sequence
<220> FEATURE:
<223> OTHER INFORMATION: Oligonucleotide

<400> SEQUENCE: 612
cccgctcgag acccagcttg taaggttg                                   28

<210> SEQ ID NO 613
<211> LENGTH: 35
<212> TYPE: DNA
<213> ORGANISM: Artificial Sequence
<220> FEATURE:
<223> OTHER INFORMATION: Oligonucleotide

<400> SEQUENCE: 613
ggaggcactg gatccgcagc cacaaacgac gacga                           35

<210> SEQ ID NO 614

```
<211> LENGTH: 36
<212> TYPE: DNA
<213> ORGANISM: Artificial Sequence
<220> FEATURE:
<223> OTHER INFORMATION: Oligonucleotide

<400> SEQUENCE: 614
gcggcctcga gggtggcgga ggcactggat ccgcag                                  36

<210> SEQ ID NO 615
<211> LENGTH: 28
<212> TYPE: DNA
<213> ORGANISM: Artificial Sequence
<220> FEATURE:
<223> OTHER INFORMATION: Oligonucleotide

<400> SEQUENCE: 615
cccgctcgag ccactcgtaa ttgacgcc                                           28

<210> SEQ ID NO 616
<211> LENGTH: 35
<212> TYPE: DNA
<213> ORGANISM: Artificial Sequence
<220> FEATURE:
<223> OTHER INFORMATION: Oligonucleotide

<400> SEQUENCE: 616
ggaggcactg gatcctcaga tttggcaaac gattc                                   35

<210> SEQ ID NO 617
<211> LENGTH: 37
<212> TYPE: DNA
<213> ORGANISM: Artificial Sequence
<220> FEATURE:
<223> OTHER INFORMATION: Oligonucleotide

<400> SEQUENCE: 617
gcggcgtcga cggtggcgga ggcactggat cctcaga                                 37

<210> SEQ ID NO 618
<211> LENGTH: 29
<212> TYPE: DNA
<213> ORGANISM: Artificial Sequence
<220> FEATURE:
<223> OTHER INFORMATION: Oligonucleotide

<400> SEQUENCE: 618
cccgctcgag cgtatcatat ttcacgtgc                                          29

<210> SEQ ID NO 619
<211> LENGTH: 488
<212> TYPE: PRT
<213> ORGANISM: Artificial Sequence
<220> FEATURE:
<223> OTHER INFORMATION: MC58

<400> SEQUENCE: 619

Met Phe Lys Arg Ser Val Ile Ala Met Ala Cys Ile Phe Ala Leu Ser
1               5                   10                  15

Ala Cys Gly Gly Gly Gly Gly Gly Ser Pro Asp Val Lys Ser Ala Asp
                20                  25                  30

Thr Leu Ser Lys Pro Ala Ala Pro Val Val Ser Glu Lys Glu Thr Glu
        35                  40                  45

Ala Lys Glu Asp Ala Pro Gln Ala Gly Ser Gln Gly Gln Gly Ala Pro
    50                  55                  60
```

-continued

```
Ser Ala Gln Gly Ser Gln Asp Met Ala Ala Val Ser Glu Glu Asn Thr
 65                  70                  75                  80

Gly Asn Gly Gly Ala Val Thr Ala Asp Asn Pro Lys Asn Glu Asp Glu
                 85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
        115                 120                 125

Asn Gln Ala Thr Asp Ala Gly Glu Ser Ser Gln Pro Ala Asn Gln Pro
    130                 135                 140

Asp Met Ala Asn Ala Ala Asp Gly Met Gln Gly Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
        195                 200                 205

Asn Gly Val Leu Ile Asp Gly Pro Ser Gln Asn Ile Thr Leu Thr His
210                 215                 220

Cys Lys Gly Asp Ser Cys Ser Gly Asn Asn Phe Leu Asp Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
        275                 280                 285

Pro Lys Pro Thr Ser Phe Ala Arg Phe Arg Arg Ser Ala Arg Ser Arg
    290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
        355                 360                 365

Ala Lys Gly Glu Met Leu Ala Gly Ala Val Tyr Asn Gly Glu Val
    370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415

Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
        435                 440                 445

Asp Val Ser Gly Lys Phe Tyr Gly Pro Ala Gly Glu Glu Val Ala Gly
    450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
                485
```

<210> SEQ ID NO 620
<211> LENGTH: 427
<212> TYPE: PRT
<213> ORGANISM: Artificial Sequence
<220> FEATURE:
<223> OTHER INFORMATION: 2996

<400> SEQUENCE: 620

```
Met Phe Glu Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ala Glu Lys Glu Thr Glu
        35                  40                  45

Val Lys Glu Asp Ala Pro Gln Ala Gly Ser Gln Gly Gln Gly Ala Pro
    50                  55                  60

Ser Thr Gln Gly Ser Gln Asp Met Ala Ala Val Ser Ala Glu Asn Thr
65                  70                  75                  80

Gly Asn Gly Gly Ala Ala Thr Thr Asp Lys Pro Lys Asn Glu Asp Glu
                85                  90                  95

Gly Pro Gln Asn Asp Met Pro Gln Asn Ser Ala Glu Ser Ala Asn Gln
            100                 105                 110

Thr Gly Asn Asn Gln Pro Ala Asp Ser Ser Asp Ser Ala Pro Ala Ser
        115                 120                 125

Asn Pro Ala Pro Ala Asn Gly Gly Ser Asn Phe Gly Arg Val Asp Leu
    130                 135                 140

Ala Asn Gly Val Leu Ile Asp Gly Pro Ser Gln Asn Ile Thr Leu Thr
145                 150                 155                 160

His Cys Lys Gly Asp Ser Cys Asn Gly Asp Asn Leu Leu Asp Glu Glu
                165                 170                 175

Ala Pro Ser Lys Ser Glu Phe Glu Asn Leu Asn Glu Ser Glu Arg Ile
            180                 185                 190

Glu Lys Tyr Lys Lys Asp Gly Lys Ser Asp Lys Phe Thr Asn Leu Val
        195                 200                 205

Ala Thr Ala Val Gln Ala Asn Gly Thr Asn Lys Tyr Val Ile Ile Tyr
    210                 215                 220

Lys Asp Lys Ser Ala Ser Ser Ser Ala Arg Phe Arg Arg Ser Ala
225                 230                 235                 240

Arg Ser Arg Arg Ser Leu Pro Ala Glu Met Pro Leu Ile Pro Val Asn
                245                 250                 255

Gln Ala Asp Thr Leu Ile Val Asp Gly Glu Ala Val Ser Leu Thr Gly
            260                 265                 270

His Ser Gly Asn Ile Phe Ala Pro Glu Gly Asn Tyr Arg Tyr Leu Thr
        275                 280                 285

Tyr Gly Ala Glu Lys Leu Pro Gly Gly Ser Tyr Ala Leu Arg Val Gln
    290                 295                 300

Gly Glu Pro Ala Lys Gly Glu Met Leu Ala Gly Thr Ala Val Tyr Asn
305                 310                 315                 320

Gly Glu Val Leu His Phe His Thr Glu Asn Gly Arg Pro Tyr Pro Thr
                325                 330                 335

Arg Gly Arg Phe Ala Ala Lys Val Asp Phe Gly Ser Lys Ser Val Asp
            340                 345                 350

Gly Ile Ile Asp Ser Gly Asp Asp Leu His Met Gly Thr Gln Lys Phe
        355                 360                 365
```

-continued

```
Lys Ala Ala Ile Asp Gly Asn Gly Phe Lys Gly Thr Trp Thr Glu Asn
            370                 375                 380
Gly Gly Gly Asp Val Ser Gly Arg Phe Tyr Gly Pro Ala Gly Glu Glu
385                 390                 395                 400
Val Ala Gly Lys Tyr Ser Tyr Arg Pro Thr Asp Ala Glu Lys Gly Gly
                405                 410                 415
Phe Gly Val Phe Ala Gly Lys Lys Glu Gln Asp
            420                 425

<210> SEQ ID NO 621
<211> LENGTH: 9
<212> TYPE: PRT
<213> ORGANISM: artificial sequence
<220> FEATURE:
<223> OTHER INFORMATION: replacement leader peptide

<400> SEQUENCE: 621

Met Lys Lys Tyr Leu Phe Ser Ala Ala
1               5

<210> SEQ ID NO 622
<211> LENGTH: 6
<212> TYPE: PRT
<213> ORGANISM: artificial sequence
<220> FEATURE:
<223> OTHER INFORMATION: sample poly-glycine stretch

<400> SEQUENCE: 622

Cys Gly Gly Gly Gly Ser
1               5

<210> SEQ ID NO 623
<211> LENGTH: 5
<212> TYPE: PRT
<213> ORGANISM: artificial sequence
<220> FEATURE:
<223> OTHER INFORMATION: deletion example

<400> SEQUENCE: 623

Cys Gly Gly Gly Ser
1               5

<210> SEQ ID NO 624
<211> LENGTH: 4
<212> TYPE: PRT
<213> ORGANISM: artificial sequence
<220> FEATURE:
<223> OTHER INFORMATION: deletion example

<400> SEQUENCE: 624

Cys Gly Gly Ser
1

<210> SEQ ID NO 625
<211> LENGTH: 6
<212> TYPE: PRT
<213> ORGANISM: artificial sequence
<220> FEATURE:
<223> OTHER INFORMATION: substitution example
<220> FEATURE:
<221> NAME/KEY: misc_feature
<222> LOCATION: 3)..(3)
<223> OTHER INFORMATION: Xaa can be any naturally occurring amino acid

<400> SEQUENCE: 625

Cys Gly Xaa Gly Gly Ser
1               5
```

<210> SEQ ID NO 626
<211> LENGTH: 6
<212> TYPE: PRT
<213> ORGANISM: artificial sequence
<220> FEATURE:
<223> OTHER INFORMATION: substitution example
<220> FEATURE:
<221> NAME/KEY: misc_feature
<222> LOCATION: (3)..(4)
<223> OTHER INFORMATION: Xaa can be any naturally occurring amino acid

<400> SEQUENCE: 626

Cys Gly Xaa Xaa Gly Ser
1               5

<210> SEQ ID NO 627
<211> LENGTH: 6
<212> TYPE: PRT
<213> ORGANISM: artificial sequence
<220> FEATURE:
<223> OTHER INFORMATION: substitution example
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 627

Cys Gly Xaa Gly Xaa Ser
1               5

<210> SEQ ID NO 628
<211> LENGTH: 7
<212> TYPE: PRT
<213> ORGANISM: artificial sequence
<220> FEATURE:
<223> OTHER INFORMATION: insertion example
<220> FEATURE:
<221> NAME/KEY: misc_feature
<222> LOCATION: (4)..(4)
<223> OTHER INFORMATION: Xaa can be any naturally occurring amino acid

<400> SEQUENCE: 628

Cys Gly Gly Xaa Gly Gly Ser
1               5

<210> SEQ ID NO 629
<211> LENGTH: 7
<212> TYPE: PRT
<213> ORGANISM: artificial sequence
<220> FEATURE:
<223> OTHER INFORMATION: insertion example
<220> FEATURE:
<221> NAME/KEY: misc_feature
<222> LOCATION: (3)..(3)
<223> OTHER INFORMATION: Xaa can be any naturally occurring amino acid

<400> SEQUENCE: 629

Cys Gly Xaa Gly Gly Gly Ser
1               5

<210> SEQ ID NO 630
<211> LENGTH: 19
<212> TYPE: PRT
<213> ORGANISM: artificial sequence
<220> FEATURE:
<223> OTHER INFORMATION: leader peptide from ORF4

```
<400> SEQUENCE: 630

Met Lys Thr Phe Phe Lys Thr Leu Ser Ala Ala Ala Leu Ala Leu Ile
1               5                   10                  15

Leu Ala Ala

<210> SEQ ID NO 631
<211> LENGTH: 7
<212> TYPE: PRT
<213> ORGANISM: artificial sequence
<220> FEATURE:
<223> OTHER INFORMATION: short N-terminal deletion

<400> SEQUENCE: 631

Gly Gly Gly Gly Gly Gly Ser
1               5

<210> SEQ ID NO 632
<211> LENGTH: 6
<212> TYPE: PRT
<213> ORGANISM: artificial sequence
<220> FEATURE:
<223> OTHER INFORMATION: deletion sequence

<400> SEQUENCE: 632

Gly Gly Gly Gly Gly Gly
1               5

<210> SEQ ID NO 633
<211> LENGTH: 20
<212> TYPE: PRT
<213> ORGANISM: artificial sequence
<220> FEATURE:
<223> OTHER INFORMATION: 20mer leader peptide from 919

<400> SEQUENCE: 633

Met Lys Lys Tyr Leu Phe Arg Ala Ala Leu Tyr Gly Ile Ala Ala Ala
1               5                   10                  15

Ile Leu Ala Ala
            20
```